(12) United States Patent
Beaton et al.

(10) Patent No.: US 6,924,284 B2
(45) Date of Patent: Aug. 2, 2005

(54) PARP INHIBITORS

(75) Inventors: Graham Beaton, Poway, CA (US);
Wilna J. Moree, San Diego, CA (US);
Jaimie K. Rueter, San Diego, CA (US); Russell S. Dahl, Carlsbad, CA (US); David L. McElligott, Bothell, WA (US); Phyllis Goldman, Bothell, WA (US); Anthony J. Demaggio, Kenmore, WA (US); Erik Christenson, Bellevue, WA (US); Dan Herendeen, Kirkland, WA (US); Kerry W. Fowler, Seattle, WA (US); Danwen Huang, Sammamish, WA (US); Jaimie E. Bertino, Guilderland, NY (US); Lisa H. Bourdon, Latham, NY (US); David J. Fairfax, Delmar, NY (US); Qin Jiang, Latham, NY (US); Helge A. Reisch, Rensselaer, NY (US); Ren Hua Song, Latham, NY (US); Pavel E. Zhichkin, Latham, NY (US)

(73) Assignees: ICOS Corporation, Bothell, WA (US); Deltagen Research Labs, LLC, San Diego, CA (US)

( * ) Notice: Subject to any disclaimer, the term of this patent is extended or adjusted under 35 U.S.C. 154(b) by 184 days.

(21) Appl. No.: 10/222,749

(22) Filed: Aug. 15, 2002

(65) Prior Publication Data
US 2004/0087588 A1 May 6, 2004

Related U.S. Application Data

(60) Provisional application No. 60/312,540, filed on Aug. 15, 2001.

(51) Int. Cl.$^7$ .............. C07D 413/14; C07D 413/12; C07D 237/52; A61K 31/5377; A61K 31/502
(52) U.S. Cl. .............. 514/234.5; 514/248; 544/116; 544/235; 544/236; 544/237
(58) Field of Search .............. 544/116, 281, 544/350, 354, 235, 236, 237; 514/234.8, 249, 234.5, 248

(56) References Cited

U.S. PATENT DOCUMENTS

| 4,371,540 A | 2/1983 | Lee et al. |
|---|---|---|
| 4,992,433 A | 2/1991 | Stokbroekx et al. |
| 5,032,617 A | 7/1991 | Lee et al. |
| 5,041,653 A | 8/1991 | Lee et al. |
| 5,106,973 A | 4/1992 | Stokbroekx et al. |
| 5,177,075 A | 1/1993 | Suto et al. |
| 5,215,738 A | 6/1993 | Lee et al. |
| 5,231,184 A | 7/1993 | Stokbroekx et al. |
| 5,587,384 A | 12/1996 | Zhang et al. |
| 5,756,510 A | 5/1998 | Griffin et al. |
| 5,874,444 A | 2/1999 | West |
| 6,015,827 A | 1/2000 | Griffin et al. |

FOREIGN PATENT DOCUMENTS

| EP | 0 320 032 B1 | 1/1995 |
|---|---|---|
| WO | WO 99/11622 | 3/1999 |
| WO | WO 00/42040 | 7/2000 |

OTHER PUBLICATIONS

Virag L, Szabo C., Pharmacol Rev. Sep. 2002;54(3):375–429.*
West, Anthony R., Solid State Chemistry and its Applications, Wiley, New York, 1988, pp. 358 & 365.*
Wolff, Manfred E. "Burger's Medicinal Chemistry, 5ed, Part I", John Wiley & Sons, 1995, pp. 975–977.*
Banker, G.S. et al, "Modern Pharmaceutics, 3ed.", Marcel Dekker, New York, 1996, pp. 451 and 596.*
Draetta, G. and Pagano, M. in "Annual Reports in Medicinal Chemistry, vol. 31", 1996, Academic Press, San Diego, p 241–246.*

* cited by examiner

Primary Examiner—Thomas C. McKenzie
(74) Attorney, Agent, or Firm—Townsend and Townsend and Crew LLP

(57) ABSTRACT

The present invention provides compounds comprising a bicyclic aryl moiety, such as 2H-phthalazin-1-one or derivatives thereof, compositions comprising the same, and methods for producing and using the same. In particular, the present invention provides compounds of the formula:

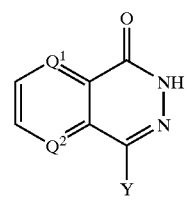

I or a pharmaceutically acceptable salt, a hydrate, a solvate, or a prodrug thereof; where $Q^1$, $Q^2$ and Y are those defined herein.

55 Claims, No Drawings

PARP INHIBITORS

CROSS-REFERENCE TO RELATED APPLICATIONS

This application claims the priority benefit of U.S. Provisional Application No. 60/312,540, filed Aug. 15, 2001, which is incorporated herein by reference in its entirety.

FIELD OF THE INVENTION

This invention relates to 2H-phthalazin-1-one compounds, compositions comprising the same, and methods for producing and using the same.

BACKGROUND OF THE INVENTION

Regulation of gene function occurs by several mechanisms in eukaryotic cells. Amongst these mechanisms are gene transcription regulation, mRNA translation regulation, and post-translation modification of proteins. The term "post-translation modification of proteins" includes several processes whereby proteins are structurally modified which may result in alterations in cellular, sub-cellular localization, stability, transport, interaction specificity, enzymatic activity, and numerous other characteristics.

Common and extensively studied post-translational modification processes include acetylation, glycosylation, and phosphorylation. Less well characterized is a process that involves the covalent addition of polymers of ADP-ribose to protein targets. The polymer is termed Poly (ADP-ribose) and the enzyme(s) responsible for this activity have been variously called Poly(ADP-ribose) Polymerase (PARP1), Poly(ADP-ribose) Synthetase (PARS), or ADP-Ribosyl Transferase (ADPRT), hereinafter called "PARP1". PARP1 is an enzyme located in the nuclei of cells of various organs, including muscle, heart and brain cells. PARP1 plays a physiological role in the repair of strand breaks in DNA. Once activated by damaged DNA fragments, PARP1 catalyzes the attachment of up to 100 ADP-ribose units to a variety of nuclear proteins, including histones and PARP1 itself. While the exact range of functions of PARP1 has not been fully established, this enzyme is thought to play a role in enhancing DNA repair. At least three members of a structurally related set of gene products have been shown to catalyze poly-ADP-ribosylation. Currently, the most studied member of this gene family is PARP1. The PARP1 gene product is expressed at high levels in the nuclei of cells and is dependent upon DNA damage for activation. Without being bound by any theory, it is believed that PARP1 binds to DNA single or double stranded breaks through an amino terminal DNA binding domain. The binding activates the carboxy terminal catalytic domain and results in the formation of polymers of ADP-ribose on target molecules. PARP1 is itself a target of poly ADP-ribosylation by virtue of a centrally located automodification domain. The ribosylation of PARP1 causes dissociation of the PARP1 molecules from the DNA. The entire process of binding, ribosylation, and dissociation occurs very rapidly. It has been suggested that this transient binding of PARP1 to sites of DNA damage result in the recruitment of DNA repair machinery or may act to suppress to recombination long enough for the recruitment of repair machinery.

The source of ADP-ribose for the PARP reaction is nicotinamide adenosine dinucleotide (NAD). NAD is synthesized in cells from cellular ATP stores and thus high levels of activation of PARP activity can rapidly lead to depletion of cellular energy stores. It has been demonstrated that induction of PARP activity can lead to cell death that is correlated with depletion of cellular NAD and ATP pools. PARP activity is induced in many instances of oxidative stress or during inflammation. For example, during reperfusion of ischemic tissues reactive nitric oxide is generated and nitric oxide results in the generation of additional reactive oxygen species including hydrogen peroxide, peroxynitrate and hydroxyl radical. These latter species can directly damage DNA and the resulting damage induces activation of PARP activity. Frequently, it appears that sufficient activation of PARP activity occurs such that the cellular energy stores are depleted and the cell dies. A similar mechanism is believe to operate during inflammation when endothelial cells and pro-inflammatory cells synthesize nitric oxide which results in oxidative DNA damage in surrounding cells and the subsequent activation of PARP activity. The cell death that results from PARP activation is believed to be a major contributing factor in the extent of tissue damage that results from ischemia-reperfusion injury or from inflammation.

Two lines of evidence suggest that PARP activity is a critical element in those processes. First, chemical inhibitors of PARP activity have been successfully utilized to reduce tissue damage resulting in animal models of ischemia-reperfusion injury or inflammation. Secondly, mice in which both alleles of PARP1 have been disabled (PARP1 knockout mice or PARP1 mutant mice) are resistant to numerous forms of ischemia-reperfusion injury and detrimental effects of inflammation.

Inhibition of PARP activity has also been shown to be potentially useful in the treatment of human cancer. PARP small molecule inhibitors sensitize treated tumor cell lines to killing by ionizing radiation and by some DNA damaging chemotherapeutic drugs. While the PARP inhibitors by themselves generally do not have significant anti-tumor effect, when combined with a chemotherapeutic they can induce tumor regression at concentrations of the chemotherapeutic that are ineffective by themselves. Further, PARP1 mutant mice and PARP1 mutant cell lines are sensitive to radiation and similar types of chemotherapeutic drugs.

Currently known PARP inhibiting compounds are not approved for clinical use in treating a variety of diseases. Therefore, there is a need for PARP inhibitors which are clinically useful.

SUMMARY OF THE INVENTION

The present invention provides bicyclic aryl compounds, such as 2H-phthalazin-1-one and derivatives thereof, compositions comprising the same, and methods for producing and using the same. In particular, the present invention provides bicyclic compounds of the formula:

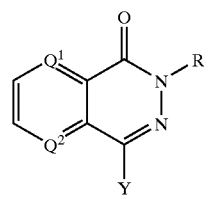

a pharmaceutically acceptable salt, a hydrate, a solvate, or a prodrug thereof;
wherein
each of $Q_1$ and $Q_2$ is independently N or $CR^a$, where $R^a$ is hydrogen, halo, nitro, or alkyl;

R is hydrogen, alkyl, or a nitrogen protecting group; and

Y is -(alkylene)$_x$-NR$^{11}$-R$^{12}$-NR$^{13}$-[C(=X$^3$)]$_c$-[NR$^{14}$]$_d$-[C(=X$^4$)]$_f$-R$^{16}$, wherein x is 0 or 1;

R$^{11}$ is selected from the group consisting of hydrogen, alkyl and optionally substituted heteroaralkyl; or R$^{11}$ together with the nitrogen atom to which it is attached to and at least a portion of R$^{12}$ form an optionally substituted heterocyclyl;

R$^{12}$ is selected from the group consisting of:
  (a) alkylene,
  (b) cycloalkylene,
  (c) heteroalkylene,
  (d) aralkylene, and
  (e) arylene;

c is 0, 1, or 2;

each of d, e, and f is independently 0 or 1;

each of X$^3$ and X$^4$ is independently selected from the group consisting of O and S;

R$^{13}$ is selected from the group consisting of hydrogen, alkyl, a moiety
of the formula
-(alkylene)-[C(=O)NR$^{40}$]$_y$-Ar$^4$, where y is 0 or 1, R$^{40}$ is hydrogen or alkyl, and Ar$^4$ is optionally substituted aryl or optionally substituted heteroaryl; or R$^{11}$ and R$^{13}$ together with the nitrogen atoms to which they are attached to and R$^{12}$ form an optionally substituted heterocyclyl; or R$^{13}$ together with the nitrogen atom to which it is attached to and at least a portion of R$^{12}$ form an optionally substituted heterocyclyl; or R$^{13}$ and R$^{16}$ together with atoms to which they are attached to form an optionally substituted heterocylic ring;

R$^{14}$ is hydrogen or alkyl;

R$^{15}$ is selected from the group consisting of:
  (a) optionally substituted alkylene,
  (b) optionally substituted heteroalkylene, and
  (c) optionally substituted alkenylene, R$^{16}$ is selected from the group consisting of:
  (a) hydrogen
  (b) optionally substituted heteroaryl,
  (c) optionally substituted aryl,
  (d) optionally substituted heteroalkyl,
  (e) alkoxy,
  (f) optionally substituted cycloalkyl,
  (g) optionally substituted alkyl,
  (h) optionally substituted aryloxy,
  (i) substituted aralkoxy,
  (j) heterocycloalkyl,
  (k) arylsulfonylalkyl,
  (l) —NR$^{50}$R$^{51}$, where R$^{50}$ is hydrogen or alkyl and R$^{51}$ is optionally substituted aryl, optionally substituted cycloalkyl, optionally substituted aralkyl, optionally substituted heteroaryl, optionally substituted heteroaralkyl, or optionally substituted heteroalkyl,
  (m) —NHPO$_3$R$^{17}$R$^{18}$, where R$^{17}$ and R$^{18}$ are alkyl,
  (n) —NHSO$_2$Ar$^2$, where Ar$^2$ is substituted aryl or aralkenyl,
  (o) alkylcarbamate;
  (p) —SO$_2$R$^{19}$, where R$^{19}$ is optionally substituted aryl, substituted heteroaryl, optionally substituted heteroaralkyl, alkyl, aralkenyl, substituted heterocycloalkylalkyl, or substituted heteroaryl,
  (q) alkylsulfonylalkyl,
  (r) heterocyclyl, and
  (s) a moiety of the formula -(alkylene)-[C(=O) NR$^{40}$]$_y$-Ar$^5$, where y is 0 or 1, R$^{40}$ is hydrogen or alkyl, and Ar$^5$ is optionally substituted aryl or optionally substituted heteroaryl.

DEFINITIONS

Unless otherwise stated, the following terms used in the specification and claims have the meanings given below:

"Alkenylene" means a linear or branched divalent hydrocarbon moiety of two to twenty, preferably two to ten, and more preferably two to six, carbon atoms comprising at least one carbon-carbon double bond. Alkenylene groups can be attached via a carbon atom that contains the carbon-carbon double bond and/or via a saturated carbon atom. Alkenylene groups can be optionally substituted with one or more halogen substituents.

"Alkenyl" means a linear or branched monovalent hydrocarbon moiety of two to twenty, preferably two to ten, and more preferably two to six, carbon atoms comprising at least one carbon-carbon double bond. Alkenyl groups can be attached via a carbon atom that contains the carbon-carbon double bond or via a saturated carbon atom. Alkenyl groups optionally can be substituted with one or more halogen substituents. Exemplary alkenyl groups include ethenyl, 1-propenyl, 2-propenyl, 2-butenyl, 3-butenyl, pentenyl, 5-hexenyl, dodecenyl, and the like.

"Alkoxy", "cycloalkoxy", "heterocyclyloxy", "heterocycloalkoxy", "aryloxy", and "heteroaryloxy" refer to a moiety of the formula —OR$^a$, wherein R$^a$ is alkyl, cycloalkyl, heterocyclyl, heterocycloalkyl, aryl, and heteroaryl, as defined herein, respectively.

"Alkyl" means a linear or branched saturated monovalent hydrocarbon moiety of one to twenty, preferably one to ten, and more preferably one to six, carbon atoms. Alkyl groups optionally can be substituted with one or more halogen substituents. Exemplary alkyl groups include methyl, ethyl, propyl, 2-propyl, n-butyl, iso-butyl, tert-butyl, pentyl, hexyl, dodecyl, fluoromethyl, difluoromethyl, trifluoromethyl, chloromethyl, dichloromethyl, trichloromethyl, iodomethyl, bromomethyl, and the like.

"Alkylcarbamate" means a moiety of the formula —NR$^a$—C(=O)—OR$^b$, wherein R$^a$ is hydrogen or alkyl, and R$^b$ is alkyl as defined herein.

"Alkylene" means a linear or branched saturated divalent hydrocarbon moiety of one to twenty, preferably one to ten, and more preferably one to six, carbon atoms. Alkylene groups optionally can be substituted with one or more halogen substituents. Exemplary alkyl groups include methylene, ethylene, propylene, butylene, and the like.

"Alkylsulfonylalkyl" means a moiety of the formula —R$^a$—SO$_2$—R$^b$, wherein R$^a$ and R$^b$ are alkyl as defined herein.

"Alkynyl" means a linear or branched monovalent hydrocarbon moiety of two to twenty carbon atoms, preferably two to ten, and more preferably two to six, comprising at least one carbon-carbon triple bond. Alkynyl groups can be attached via a carbon atom that contains the carbon-carbon triple bond or via a saturated carbon atom. Alkynyl groups can be optionally substituted with one or more halogen substituents.

"Alkynylene" means a divalent alkynyl as defined herein, e.g., a moiety containing a —C≡C— group.

"Amino" refers to a moiety of the formula —NR$^h$R$^i$, where each R$^h$ and R$^i$ is independently hydrogen, alkyl, cycloalkyl, aryl, aralkyl, heteroalkyl, or —C(=O)R$^j$, where R$^j$ is alkyl, aralkyl, aryl, cycloalkyl, hydrogen, or heteroalkyl.

"Aralkenyl" means a moiety of the formula —R$^a$R$^b$ wherein R$^a$ is alkenylene and R$^b$ is aryl as defined herein.

"Aralkyl" means a moiety of the formula —R$^a$R$^b$ wherein R$^a$ is alkenylene and R$^b$ is aryl as defined herein.

"Aralkynyl" means a moiety of the formula —R$^a$R$^b$ wherein R$^a$ is alkynylene and R$^b$ is aryl as defined herein.

"Aralkylene" means a divalent moiety of the formula —R$^a$—R$^b$—, wherein R$^a$ is alkylene and R$^b$ is arylene as defined herein.

"Aryl" means a monovalent monocyclic, bicyclic or tricyclic aromatic hydrocarbon moiety having six to twenty, preferably six to twelve, ring atoms. The aromatic portion of the aryl groups contain only carbon atoms. Exemplary aryl gruops include phenyl, naphthalenyl, and fluorenyl.

"Arylene" means a divalent monocyclic or bicyclic aromatic hydrocarbon moiety.

"Arylsulfonylalkyl" means a moiety of the formula —R$^a$—SO$_2$—Ar, wherein R$^a$ is alkylene and Ar is aryl as defined herein.

"Cycloalkyl" means a saturated or unsaturated non-aromatic monovalent monocyclic, bicyclic or tricyclic hydrocarbon moiety of three to ten ring carbons, e.g., cyclopropyl, cyclobutyl, cyclopentyl, cyclopentenyl, cyclohexyl, cyclohexenyl, cycloheptyl, cyclooctyl, decahydronaphthalenyl, adamantyl, norbornyl (i.e., bicyclo[2.2.1]hept-5-enyl), and the like.

"Cycloalkylalkyl" means a moiety of the formula —R$^a$R$^b$, where R$^a$ is alkylene and R$^b$ is cycloalkyl as defined herein.

"Halide" or "halo" are used interchangeably herein and refer to fluoro, chloro, bromo, or iodo, preferably fluoro or chloro.

"Heteroalkyl" means an alkyl moiety as defined herein wherein one or more hydrogen atoms have been replaced with a non-hydrogen atom or a moiety. Preferably, one or two carbon atoms is substituted with a carbonyl oxygen, and/or one or more (preferably one, two, or three) hydrogen atoms have been independently replaced with a substituent selected from the group consisting of —OR$^a$, —NR$^b$R$^c$, —C≡N and —S(O)$_n$R$^d$ (where n is an integer from 0 to 2, preferably 2), with the understanding that the point of attachment of the heteroalkyl moiety is through a carbon atom, wherein R$^a$ is hydrogen, alkyl, aryl, or aralkyl; R$^b$ and R$^c$ are independently of each other hydrogen, alkyl, optionally substituted aryl, optionally substituted aralkyl, optionally substituted heteroaryl, or optionally substituted heteroaralkyl; and R$^d$ is alkyl, optionally substituted aryl, optionally substituted aralkyl, optionally substituted heteroaryl, or optionally substituted heteroaralkyl.

"Heteroalkylene" means an alkylene moiety as defined herein wherein one or more hydrogen atoms have been replaced with a non-hydrogen atom or a moiety. Preferably, one or two carbon atoms is substituted with a carbonyl oxygen, and/or one or more (preferably one, two, or three) hydrogen atoms have been replaced with a substituent independently selected from the group consisting of —OR$^a$, —NR$^b$R$^c$, —C≡N and —S(O)$_n$R$^d$ (where n is an integer from 0 to 2, preferably 2), with the understanding that the point of attachment of the heteroalkylene moiety is through a carbon atom, wherein R$^a$ is hydrogen, alkyl, aryl, or aralkyl; R$^b$ and R$^c$ are independently of each other hydrogen, alkyl, optionally substituted aryl, optionally substituted aralkyl, optionally substituted heteroaryl, or optionally substituted heteroaralkyl; and R$^d$ is alkyl, heteroalkyl, optionally substituted aryl, optionally substituted aralkyl, optionally substituted heteroaryl, or optionally substituted heteroaralkyl.

"Heteroalkenyl" means alkenyl moiety as defined herein wherein one or more (preferably one, two, or three) hydrogen atoms have been replaced with a substituent independently selected from the group consisting of —OR$^a$, —NR$^b$R$^c$, —C≡N and —S(O)$_n$R$^d$ (where n is an integer from 0 to 2, preferably 2), with the understanding that the point of attachment of the heteroalkyl moiety is through a carbon atom, wherein R$^a$ is hydrogen, alkyl, aryl, or aralkyl; R$^b$ and R$^c$ are independently of each other hydrogen, alkyl, optionally substituted aryl, optionally substituted aralkyl, optionally substituted heteroaryl, or optionally substituted heteroaralkyl; and R$^d$ is alkyl, optionally substituted aryl, optionally substituted aralkyl, optionally substituted heteroaryl, or optionally substituted heteroaralkyl.

"Heteroaralkenyl" means a moiety of the formula —R$^a$R$^b$ wherein R$^a$ is alkenylene and R$^b$ is heteroaryl as defined herein.

"Heteroaralkyl" means a moiety of the formula —R$^a$R$^b$ wherein R$^a$ is alkylene and R$^b$ is heteroaryl as defined herein.

"Heteroaryl" means a monovalent monocyclic, bicyclic or tricyclic heteroaromatic moiety, e.g., an aryl group as defined herein in which at least one aromatic carbon ring atom is replaced with O, N, NH, or S group. The heteroaryl group can be attached through a heteroatom or a carbon atom of the aromatic ring system. Preferred heteroaryl groups include pyridinyl, furyl, thienyl, imidazo[2,1-b]thiazolyl, thiazolyl, oxadiazolyl, pyridinyl, pyrimidinyl, triazinyl, furanyl, thienyl, thiadiazolyl, pyrrolyl, pyrazolyl, dibenzofuranyl, pyrazolopyrimidinyl, 4-oxo-1H-[1,8]naphthyridinyl, 3-oxo-dihydro-pyrazolyl, imidazolyl, isoimidazolyl, oxazolyl, isoxazolyl, triazolyl, tetrazolyl, benzofuranyl, benzooxadiazolyl, benzothiofuranyl, indolyl, benzoimidazolyl, 1H-indazolyl, oxazolidinyl, isoxazolidinyl, benzotriazolyl, benzisoxazolyl, oxindolyl, benzoxazolinyl, quinolinyl, isoquinolinyl, 4-oxo-3,4-dihydro-phthalazinyl, tetrazolyl, and the like. More preferred heteroaryl groups are oxadiazolyl, furyl, 4-oxo-3,4-dihydro-phthalazinyl, thienyl, pyridinyl, imidazolyl, thiazolyl, tetrazolyl, pyrazolyl, indolyl, benzo[1,2,5]oxadiazolyl, pyrazolo[1,5-a]pyrimidinyl, isoxazolyl, pyrazinyl, pyrrolyl, [1,2,4]oxadiazolyl, oxazolyl, benzoimidazolyl, [1,3,4]thiadiazolyl, isoimidazolyl, isoxazolyl, 1,2,3-triazolyl, 4-oxo-1H-[1,8]naphthyridinyl, 1,2-dihydro-3-oxo-pyrazolyl, benzofuranyl, quinolinyl, pyrimidinyl, benzothiofuranyl, and dibenzofuranyl.

"Heterocycloalkyl" means a saturated or unsaturated non-aromatic monocyclic, bicyclic or tricyclic moiety of 3 to 8 ring atoms in which one or more ring atoms are heteroatoms selected from NR$^a$ (where R$^a$ is hydrogen, alkyl, an amine protecting group, or a moiety of the formula —S(O)$_m$R$^b$, where m is an integer from 0 to 2, and R$^b$ is hydrogen or alkyl), O, or S(O)$_n$ (where n is an integer from 0 to 2), the remaining ring atoms being C, with the understanding that the point of attachment of the heterocycloalkyl moiety is through a carbon atom of the ring system. Alternatively, or in addition, one, two, or three ring carbon atoms of the heterocycloalkyl moiety can be substituted with a carbonyl oxygen. Preferred heterocycloalkyl groups are piperidinyl, 2-oxo-tetrahydrofuranyl, pyrrolidinyl, piperazinyl, morpholino, diazepinyl, 7,7-dimethyl-2-oxo-bicyclo[2.2.1]

heptyl, tetrahydrofuranyl, thiazolidinyl, 2,3-dihydro-4-oxo-1H-pyridinyl, and oxazolidinyl. More preferred heterocycloalkyl group are piperidinyl, 2-oxo-tetrahydrofuranyl, pyrrolidinyl, 7,7-dimethyl-2-oxo-bicyclo[2.2.1]heptyl, tetrahydrofuranyl, thiazolidinyl, 2,3-dihydro-4-oxo-1H-pyridinyl, and oxazolidinyl.

"Heterocycloalkylalkyl" means a moiety of the formula —$R^aR^b$, where $R^a$ is alkylene and $R^b$ is heterocycloalkyl as defined herein, with the understanding that the point of attachment of $R^b$ to $R^a$ is through a carbon atom, preferably a nitrogen atom when present.

"Heterocyclyl" means a saturated or unsaturated non-aromatic monocyclic, bicyclic or tricyclic moiety of 3 to 8 ring atoms in which one or more ring atoms are heteroatoms selected from N, $NR^a$, O or $S(O)_n$ (where n is an integer from 0 to 2, and $R^a$ is hydrogen, alkyl, an amine protecting group or a moiety of the formula —$S(O)_mR^b$, where m is an integer from 0 to 2, and $R^b$ is hydrogen or alkyl), the remaining ring atoms being C, with the understanding that the point of attachment of the heterocyclyl moiety is through a heteroatom of the ring system, preferably a nitrogen atom when present. In addition, one or two ring carbon atoms of the heterocyclyl moiety can also be substituted with a carbonyl oxygen. Preferred heterocyclyl groups are piperidinyl, pyrrolidinyl, piperazinyl, morpholino, diazepinyl, thiazolidinyl, 2,3-dihydro-4-oxo-1H-pyridinyl, and oxazolidinyl.

"Heterocyclylalkyl" means a moiety of the formula —$R^aR^b$, where $R^a$ is alkylene and $R^b$ is heterocyclyl as defined herein, with the understanding that the point of attachment of $R^b$ to $R^a$ is through a heteroatom, preferably a nitrogen atom when present.

"Optionally substituted aralkyl" means an aralkyl or a substituted aralkyl as defined herein.

"Optionally substituted aryl" means an aryl or a substituted aryl as defined herein.

"Optionally substituted cycloalkylalkyl" means cycloalkylalkyl or substituted cycloalkylalkyl as defined herein.

"Optionally substituted heteroalkyl" means a heteroalkyl or substituted heteroalkyl as defined herein.

"Optionally substituted heteroaralkyl" means heteroaralkyl or substituted heteroaralkyl as defined herein.

"Optionally substituted heteroaryl" means a heteroaryl or a substituted heteroaryl as defined herein.

"Optionally substituted heterocyclyl" means a heterocyclyl or a substituted heterocyclyl as defined herein.

"Optionally substituted heterocyclylalkyl" means a heterocyclylalkyl or a substituted heterocyclylalkyl as defined herein.

"Substituted alkyl," "substituted alkylene", and "substituted alkenyl" means alkyl, alkylene, and alkenyl groups, respectively, as defined herein, wherein one or more (preferably one or two) hydrogen atoms have been replaced by a non-hydrogen, or a non-halide moiety. Preferably one or more, and more preferably one or two, hydrogen atoms have been replaced by optionally substituted aryl, optionally substituted heteroaryl, optionally substituted aryloxy, optionally substituted heteroaryloxy, optionally substituted heterocyclyl, optionally substituted heterocycloalkyl, or optionally substituted cycloalkyl.

"Substituted aralkenyl" means a moiety of the formula —$R^aR^b$ wherein $R^a$ is alkenylene and $R^b$ is substituted aryl as defined herein.

"Substituted aralkyl" means a moiety of the formula —$R^aR^b$ wherein $R^a$ is alkylene and $R^b$ is substituted aryl as defined herein.

"Substituted aryl" means an aryl moiety as defined herein wherein one or more (preferably one, two or three) hydrogen atoms of the aryl moiety have been replaced by a non-hydrogen moiety. Preferably, one or more hydrogen atoms of the aryl moiety have been replaced by halide, hydroxy, —$NR^aR^b$ (where $R^a$ and $R^b$ are independently hydrogen, alkyl, heteroalkyl, or —$SO_2R^c$, where $R^c$ is alkyl), nitro, nitroso, —C(=O)$R^a$ (where $R^a$ is alkyl, alkoxy or hydroxy), optionally substituted alkylthiol (i.e., —$SR^d$, where $R^d$ is optionally substituted alkyl), —$NR^eC(=O)R^f$ (where $R^e$ is hydrogen or alkyl and $R^f$ is hydrogen, optionally substituted aryl, optionally substituted cycloalkyl, or preferably optionally substituted alkyl or alkoxide), optionally substituted heteroalkyl, optionally substituted alkyl, optionally substituted alkoxide, alkynyl, optionally substituted aralkynyl, optionally substituted aralkenyl, —$X_m$-(alkylene)$_n$-$Ar^z$ (where X is O or $S(O)_p$, m and n is independently 0 or 1, p is 0, 1, or 2, and $Ar^z$ is optionally substituted aryl or optionally substituted heteroaryl), optionally substituted cycloalkyl, optionally substituted cycloalkylalkyl, optionally substituted heterocyclyl, —$S(O)_nR^b$ (where n is 0, 1 or 2 and $R^b$ is, alkyl, heteroaralkyl, or —$NR^eR^f$, where $R^e$ and $R^f$ are independently hydrogen or alkyl), nitrile, —OC(=O)NH—$Ar^a$ (where $Ar^a$ is optionally substituted aryl) or heteroalkenyl. In addition, the "substituted aryl" also includes an aryl group which is fused to one or more other ring moiety defined herein, such as optionally substituted heterocycloalkyl, optionally substituted heterocyclyl, or optionally substituted cycloalkyl group, with the understanding that the point of attachment is through the aromatic carbon ring atom. Exemplary substituted aryls include, but are not limited to, chlorophenyl, fluorophenyl, dichlorophenyl, difluorophenyl, (2-diethylaminoethyl) phenyl, (2-hydroxyethyl)phenyl, aminophenyl, hydroxyphenyl, benzo[1,3]dioxolyl, 2,3-dihydrobenzofuranyl, dibenzofuranyl, derivatives thereof, and the like.

"Substituted cycloalkyl" means a cycloalkyl moiety as defined herein wherein one or more hydrogen atoms have been replaced with a non-hydrogen moiety. Preferably, one or more (preferably one, two or three) hydrogen atoms of the cycloalkyl moiety have been independently replaced by amino, hydroxy, optionally substituted alkoxy, halide, optionally substituted alkyl, optionally substituted heteroalkyl, optionally substituted heterocycloalkyl, optionally substituted heterocyclyl, optionally substituted aryl, or optionally substituted heteroaryl. In addition, substituted cycloalkyl includes cycloalkyl groups having a fused ring system with one or more other ring moiety defined herein, such as optionally substituted aryl, optionally substituted heteroaryl, optionally substituted heterocycloalkyl, optionally substituted heterocyclyl or optionally substituted cycloalkenyl, etc., with the understanding that the point of attachment of a substituted cycloalkyl group is through a carbon atom of the cycloalkyl moiety. Exemplary substituted cycloalkyl groups which are fused to another ring system include bicyclo[4.2.0]octa-1,3,5-trienyl, bicyclo[4.3.0]-nona-1,3,5trienyl (i.e., indanyl).

"Substituted cycloalkylalkyl" means a moiety of the formula —$R^aR^b$, where $R^a$ is alkylene and $R^b$ is substituted cycloalkyl as defined herein.

"Substituted heteroalkyl" means a heteroalkyl moiety as defined herein wherein one or more hydrogen atoms have been replaced with a non-hydrogen moiety. Preferably, one or more (preferably one, two or three) hydrogen atoms of the heteroalkyl moiety have been independently replaced by halo, optionally substituted heterocycloalkyl, optionally subsituted heterocyclyl, optionally substituted aryl, optionally substituted heteroaryl, optionally substituted aralkenyl, optionally substituted heterocycloalkoxy, optionally substituted aryloxy, or optionally substituted heteroaryloxy. Alternatively, or in addition, one, two, or three carbon atoms of the substituted heteroalkyl moiety can be substituted with a carbonyl oxygen.

"Substituted heteroaralkenyl" means a moiety of the formula —$R^aR^b$ wherein $R^a$ is alkenylene and $R^b$ is substituted heteroaryl as defined herein.

"Substituted heteroaralkyl" means a moiety of the formula —$R^aR^b$ wherein $R^a$ is alkylene and $R^b$ is substituted heteroaryl as defined herein.

"Substituted heteroaryl" means a heteroaryl moiety as defined herein wherein one or more hydrogen atoms have been replaced with a non-hydrogen moiety. Preferably, one or more (preferably one, two or three) hydrogen atoms of the heteroaryl moiety have been replaced by halide, hydroxy, nitro, nitroso, nitrile, optionally substituted alkoxy, optionally substituted alkyl, optionally substituted heteroalkyl, optionally substituted aralkenyl, amine, optionally substituted aryl, optionally substituted aryloxy optionally substituted aralkyl, optionally substituted heteroaryl, optionally substituted cycloalkyl, optionally substituted heterocycloalkyl, optionally substituted heterocyclyl, —C(=O)$R^a$ (where $R^a$ is alkyl, alkoxy, amino or hydroxy), —S(O)$_n$R (where n is 0, 1 or 2 and R is alkyl), —X-(alkylene)$_n$-Ar (where X is O or S, n is 0 or 1, and Ar is optionally substituted aryl) or combinations thereof. In addition, substituted heteroaryl includes heteroaryl groups having a fused ring system with one or more other ring moiety defined herein, such as optionally substituted aryl, optionally substituted cyclyl, optionally substituted heterocycloalkyl, optionally substituted heterocyclyl or optionally substituted cycloalkenyl, etc.

"Substituted heterocycloalkyl" means heterocycloalkyl moiety as defined herein wherein one or more hydrogen atoms have been replaced with a non-hydrogen moiety. Preferably, one or more (preferably one, two or three) hydrogen atoms of the heterocycloalkyl moiety have been replaced by a substituent independently selected from the group consisting of halide, hydroxy, optionally substituted alkyl, amino, sulfonyl, optionally substituted heteroalkyl, optionally substituted aryl, optionally substituted heteroaryl, optionally substituted cycloalkyl, optionally substituted heterocycloalkyl, optionally substituted heterocyclyl, —C(=O)R (where R is alkyl, alkoxy), —S(O)$_n$R (where n is 0, 1 or 2, and R is alkyl), optionally substituted aryloxy, optionally substituted alkoxy, and optionally substituted heteroaryloxy.

"Substituted heterocyclyl" means heterocyclyl moiety as defined herein wherein one or more hydrogen atoms have been replaced with a non-hydrogen moiety. Preferably, one or more (preferably one, two or three) hydrogen atoms of the heterocyclyl moiety have been replaced by a substituent independently selected from the group consisting of halide, hydroxy, alkyl, amino, sulfonyl, optionally substituted heteroalkyl, optionally substituted aryl, optionally substituted aralkenyl, optionally substituted heteroaryl, optionally substituted cycloalkyl, optionally substituted heterocycloalkyl, optionally substituted heterocyclyl, —C(=O)R (where R is alkyl, alkoxy), —S(O)$_n$R (where n is 0, 1 or 2, and R is alkyl), optionally substituted aryloxy, optionally substituted alkoxy, and optionally substituted heteroaryloxy.

"Substituted heterocyclylalkyl" means a moiety of the formula —$R^aR^b$, where $R^a$ is alkylene and $R^b$ is substituted heterocyclyl as defined herein.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1–8 (John Wiley and Sons, 1971–1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom to which it is attached.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as wll as human pharmaceutical use. A "pharmaceutically acceptable excipient" as used in the specification and claims includes both one or more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzyol)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) can be cleaved in vivo to release the parent compound. Prodrugs include compounds of Formula I wherein a hydroxy, amino, or sulfhydryl group in a compound of Formula I is bonded to any group that can be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that when administered to a mammal for treating a disease, is sufficient to effect such treatment for the disease. The "therapeutically effective amount" will vary depending on the compound, the disease and its severity and the age, weight, etc., of the mammal to be treated.

"Nervous tissue" refers to the various components that make up the nervous system including, without limitation, neurons, neural support cells, glia, Schwann cells, vasculature contained within and supplying these structures, the central nervous system, the brain, the brain stem, the spinal cord, the junction of the central nervous system with the peripheral nervous system, the peripheral nervous system, and allied structures.

"Ischemia" refers to localized tissue anemia due to obstruction of the inflow of arterial blood. Global ischemia occurs when blood flow to the entire brain ceases for a period of time. Global ischemia can result from cardiac arrest. Focal ischemica occurs when a portion of the brain is deprived of its normal blood supply. Focal ischemia can result from thromboembolytic occlusion of a cerebral vessel, traumatic head injury, edema or brain tumor. Both global and focal ischemia can cause widespread neuronal damage. Although nerve tissue damage occurs over hours or even days following the onset of ischemia, some permanent nerve tissue damage can develop in the initial minutes following the cessation of blood flow to the brain. Ischemia can also occur in the heart in myocardial infarction and other cardiovascular disorders in which the coronary arteries have been obstructed as a result of atherosclerosis, thrombi, or spasm and in the eyes in retinal ischemia.

"Neural tissue damage resulting from ischemia and reperfusion injury and neurodegenerative diseases" include neurotoxicity, such as seen in vascular stroke and global and focal ischemia, as well as retinal ischemia.

"Neurodegenerative diseases" includes Alzheimer's disease, Parkinson's disease, Huntington's disease and amyotrophic lateral sclerosis (i.e., ALS).

"Nervous insult" refers to any damage to nervous tissue and any disability or death resulting therefrom. The cause of nervous insult can be metabolic, toxic, neurotoxic, iatrogenic, thermal or chemical, and includes, but not limited to, ischemia, hypoxia, cerebrovascular accident trauma, surgery, pressure, mass effect, hemorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

"Neuroprotective" refers to the effect of reducing, arresting or ameliorating nervous insult, and protecting, resuscitating, or reviving nervous tissue that has suffered nervous insult.

"Preventing neurodegeneration" includes the ability to prevent neurodegeneration in patients diagnosed with a neurodegenerative disease or who are at risk of developing a neurodegenerative disease. The term also encompasses preventing further neurodegeneration in patients who are already suffering from or have symptoms of a neurodegenerative disease.

"Radiosensitizer" refers to a compound, in particular a compound of the present invention, which when administered to a patient in therapeutically effective amounts increases the sensitivity of the cells to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention.

The terms "electromagnetic radiation" and "radiation" are used interchangeably herein and includes, but is not limited to, radiation having the wavelength of $10^{-20}$ to $10^0$ meters. Preferred embodiments of the present invention employ the electromagnetic radiation of: gamma-radiation ($10^{-11}$ to $10^{-4}$ nm) x-ray radiation ($10^{-5}$ to $10^0$ nm), ultraviolet light (10 nm to 400 nm), visible light (400 nm to 700 nm), infrared radiation (700 nm to 1.0 mm), and microwave radiation (1 mm to 30 cm).

"Chemosensitizer" refers to a compound, in particular a compound of the present invention, which when administered to a patient in therapeutically effective amounts increases the sensitivity of the cells to chemotherapy compounds and/or to promote the treatment of diseases which are treatable with chemotherapy treatment. Diseases which are treatable with chemotherapy include neoplastic diseases, benign and malignant tumors, and cancerous cells. Chemotherapy treatment of other diseases not listed herein are also contemplated by the present invention.

As used herein, the terms "as defined herein", "those defined above" and "those defined herein" when referring to a variable incorporates by reference the broad definition of the variable as well as preferred, more preferred and most preferred definitions, if any.

The terms "contacting" and "reacting" when referring to a chemical synthesis are used interchangeably herein and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

DETAILED DESCRIPTION

The present invention provides bicyclic aryl compounds, compositions comprising the same, and methods for producing and using the same. In particular, the present invention provides 2H-phthalazin-1-one compounds and derivatives thereof. Specifically, the bicyclic aryl compounds of the present invention are of the formula:

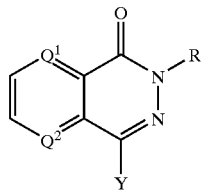

I a pharmaceutically acceptable salt, a hydrate, a solvate, or a prodrug thereof; wherein each of $Q_1$ and $Q_2$ is independently N or $CR^a$, where $R^a$ is hydrogen, halo, nitro, or alkyl, preferably $R^a$ is hydrogen or methyl, preferably $R^a$ is hydrogen, halo, or alkyl, and more preferably $R^a$ is hydrogen;

R is hydrogen, alkyl, or a nitrogen protecting group, preferably R is hydrogen; and Y is -(alkylene)$_x$-NR$^{11}$—R$^{12}$—NR$^{13}$—[C(=X$^3$)]$_c$—[NR$^{14}$]$_d$—[R$^{15}$]$_e$—[C(=X$^4$)]$_f$—R$^{16}$, wherein x is 0 or 1;

$R^{11}$ is selected from the group consisting of hydrogen, alkyl and optionally substituted heteroaralkyl; or $R^{11}$ together with the nitrogen atom to which it is attached to and at least a portion of $R^{12}$ form an optionally substituted heterocyclyl;

$R^{12}$ is selected from the group consisting of:
(a) alkylene,
(b) cycloalkylene,
(c) heteroalkylene,
(d) aralkylene, and
(e) arylene;

c is 0, 1, or 2;

each of d, e, and f is independently 0 or 1;

each of $X^3$ and $X^4$ is independently selected from the group consisting of O and S;

$R^{13}$ is selected from the group consisting of hydrogen, alkyl, a moiety of the formula
-(alkylene)-[C(=O)NR$^{40}$]$_y$—Ar$^4$, where y is 0 or 1, $R^{40}$ is hydrogen or alkyl, and Ar$^4$ is optionally substituted aryl or preferably optionally substituted heteroaryl; or $R^{11}$ and $R^{13}$ together with the nitrogen atoms to which they are attached to and $R^{12}$ form an optionally substituted heterocyclyl; or $R^{13}$ together with the nitrogen atom to which it is attached to and at least a portion of $R^{12}$ form an optionally substituted heterocyclyl; or $R^{13}$ and $R^{16}$ together with atoms to which they are attached to form an optionally substituted heterocylic ring;

$R^{14}$ is hydrogen or alkyl;

$R^{15}$ is selected from the group consisting of:
(a) optionally substituted alkylene,
(b) optionally substituted heteroalkylene, and
(c) optionally substituted alkenylene;

$R^{16}$ is selected from the group consisting of:
(a) hydrogen
(b) optionally substituted heteroaryl,
(c) optionally substituted aryl,
(d) optionally substituted heteroalkyl,
(e) alkoxy,
(f) optionally substituted cycloalkyl,
(g) optionally substituted alkyl,
(h) optionally substituted aryloxy,
(i) substituted aralkoxy,
(j) heterocycloalkyl,
(k) arylsulfonylalkyl,
(l) —NR$^{50}$R$^{51}$, where $R^{50}$ is hydrogen or alkyl and $R^{51}$ is optionally substituted aryl, optionally substituted cycloalkyl, optionally substituted aralkyl, optionally substituted heteroaryl, optionally substituted heteroaralkyl, or optionally substituted heteroalkyl,
(m) —NHPO$_3$R$^{17}$R$^{18}$, where $R^{17}$ and $R^{18}$ are alkyl,
(n) —NHSO$_2$Ar$^2$, where Ar$^2$ is substituted aryl or aralkenyl,
(o) alkylcarbamate;
(p) —SO$_2$R$^{19}$, where $R^{19}$ is optionally substituted aryl, substituted heteroaryl, optionally substituted heteroaralkyl, alkyl, aralkenyl, substituted heterocycloalkylalkyl, or substituted heteroaryl,
(q) alkylsulfonylalkyl,
(r) heterocyclyl, and
(s) a moiety of the formula -(alkylene)-[C(=O)NR$^{40}$]$_y$—Ar$^5$, where y is 0 or 1, $R^{40}$ is hydrogen or alkyl, and Ar$^5$ is optionally substituted aryl or preferably optionally substituted heteroaryl.

The compounds of the present invention can exist in unsolvated forms as well as solvated forms, including hydrated forms. In general, the solvated forms, including hydrated forms, are equivalent to unsolvated forms and are intended to be encompassed within the scope of the present invention. Furthermore, the present invention also includes all pharmaceutically acceptable salts of those compounds along with prodrug forms of the compounds and all stereoisomers whether in a pure chiral form or a racemic mixture or other form of mixture.

The compounds of Formula I are capable of further forming pharmaceutically acceptable acid addition salts. All of these forms are within the scope of the present Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge et al., "Pharmaceutical Salts," *J. of Pharmaceutical Science,* 1977, 66 1–19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms somewhat in certain physical properties such as solubility in polar solvents, but otherwise the salts are equivalent to their respective free base for purposes of the present invention.

Pharmaceutically acceptable base addition salts can be formed with metal ions or amines, such as alkali and alkaline earth metal ions or organic amines. Examples of metal ions which are used as cations include sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge et al, "Pharmaceutical Salts," *J. of Pharmaceutical Science*, 1977, 66, 1–19).

The base addition salts of acidic compounds can be prepared by contacting the free acid form with a sufficient amount of the desired base to produce the salt in the conventional manner. The free acid form can be regenerated by contacting the salt form with an acid and isolating the free acid in the conventional manner. The free acid forms may differ from their respective salt forms somewhat in certain physical properties such as solubility in polar solvents, but otherwise the salts are equivalent to their respective free acid for purposes of the present invention.

With respect to the compounds of Formula I, in one particular embodiment, x is 0.

In another embodiment, $R^{12}$ is selected from the group consisting of alkylene, cycloalkylene, heteroalkylene, aralkylene, and arylene. Preferably, $R^{12}$ is selected from the group consisting of propylene, 2,2-dimethylpropylene, ethylene, 1,3-cyclohexylene, 2-hydroxypropylene, 1,3-phenylene, butylene, and benz-3-ylene.

In another embodiment, $R^{13}$ together with the nitrogen atom to which it is attached to and at least a portion of $R^{12}$ form an optionally substituted heterocyclyl. Preferably, $R^{13}$ together with the nitrogen atom to which it is attached to and at least a portion of $R^{12}$ form piperidinyl.

Yet in another embodiment, $R^{11}$ together with the nitrogen atom to which it is attached to and at least a portion of $R^{12}$ form an optionally substituted heterocyclyl. Preferably, $R^{11}$ together with the nitrogen atom to which it is attached to and at least a portion of $R^{12}$ form piperidinyl.

Still in another embodiment, $R^{11}$ and $R^{13}$ together with the nitrogen atoms to which they are attached to and $R^{12}$ form an optionally substituted heterocyclyl. Preferably, $R^{11}$ and $R^{13}$ together with the nitrogen atoms to which they are attached to and $R^{12}$ form piperazinyl or diazepinyl.

In another embodiment, $R^{11}$ is hydrogen or alkyl. Preferably, $R^{11}$ is hydrogen or methyl.

Yet still in another embodiment, $R^{11}$ is optionally substituted heteroaralkyl. Preferably, $R^{11}$ is (4-oxo-3,4-dihydro-phthalazin-1-yl)methyl.

In one embodiment, $R^{13}$ is hydrogen or alkyl. Preferably, $R^{13}$ is hydrogen or methyl.

Still in another embodiment, $R^{14}$ is hydrogen.

In another embodiment, c and e are 1, and d and f are 0, i.e., Y is a moiety of the formula -(alkylene)$_x$-NR$^{11}$—R$^{12}$—NR$^{13}$—C(=X$^3$)—R$^{15}$—R$^{16}$, wherein x, R$^{11}$, R$^{12}$, R$^{13}$, X$^3$, R$^{15}$, and R$^{16}$ are as defined herein.

In some embodiments, $R^{15}$ is ethylene or propylene.

Still in other embodiments, $R^{16}$ is selected from the group consisting of hydrogen, optionally substituted heteroaryl, optionally substituted aryl, alkoxy, optionally substituted cycloalkyl, optionally substituted aryloxy, substituted aralkoxy, alkenyl, optionally substituted aralkenyl, optionally substituted heterocycloalkyl, arylsulfonylalkyl, a moiety of the formula —NR$^{50}$R$^{51}$, (where R$^{50}$ is hydrogen or alkyl and R$^{51}$ is optionally substituted aryl, optionally substituted cycloalkyl, optionally substituted heteroaryl, heteroaralkyl, or optionally substituted aralkyl), a moiety of the formula —NHPO$_3$R$^{17}$R$^{18}$ (where R$^{17}$ and R$^{18}$ are alkyl), a moiety of the formula —NHSO$_2$Ar$^2$ (where Ar$^2$ is substituted aryl or aralkenyl), and alkylcarbamate. In one particular embodiment, $R^{16}$ is preferably substituted heteroaryl.

In one particular embodiment, compounds of Formula I are of the formula:

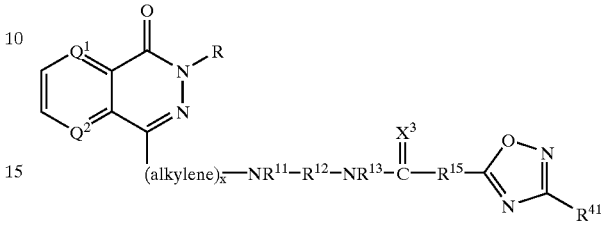

wherein $Q^1$, $Q^2$, R, x, $X^3$, $R^{11}$, $R^{12}$, $R^{13}$, and $R^{15}$ are as defined in above; and $R^{41}$ is optionally substituted aryl, optionally substituted aralkyl, optionally substituted heteroaryl, optionally substituted heterocycloalkyl, or optionally substituted heterocyclylalkyl. Preferably, x is 0. Preferably, $R^{41}$ is selected from the group consisting of optionally substituted pyrrolyl; optionally substituted thienyl; optionally substituted furyl; optionally substituted phenyl; optionally substituted imidazolyl; optionally substituted thiazolyl; optionally substituted pyrazolyl; optionally substituted indolyl; optionally substituted benzo[1,2,5]oxadiazolyl; optionally substituted pyridinyl; optionally substituted piperidinyl; optionally substituted pyrazolo[1,5-a]pyrimidinyl; optionally substituted pyrrolidinyl; optionally substituted (piperidin-1-yl)methyl; optionally substituted isoxazolyl; optionally substituted (morpholin-4-yl) methyl; optionally substituted benzyl; and optionally substituted pyrazinyl.

In another embodiment, c, d, e, and f are 0, i.e., Y is a moiety of the formula -(alkylene)$_x$-NR$^{11}$—R$^{12}$—NR$^{13}$—R$^{16}$. In this embodiment, x is preferably 0, i.e., Y is a moiety of the formula —NR$^{11}$—R$^{12}$—NR$^{13}$—R$^{16}$, where $R^{16}$ is perferably selected from the group consisting of hydrogen, optionally substituted heteroaralkyl, —SO$_2$R$^{19}$ (where $R^{19}$ is optionally substituted aryl, substituted heteroaryl, optionally substituted heteroaralkyl, alkyl, aralkenyl, substituted heterocycloalkylalkyl, or substituted heteroaryl), optionally substituted cycloalkylalkyl, alkyl, optionally substituted heteroalkyl, alkenyl, optionally substituted aralkyl, and optionally substituted heterocycloalkylalkyl. More preferably, $R^{16}$ is selected from the group consisting of —SO$_2$R$^{19}$ (where $R^{19}$ is optionally substituted aryl, substituted heteroaryl, optionally substituted heteroaralkyl, alkyl, aralkenyl, substituted heterocycloalkylalkyl, or substituted heteroaryl), optionally substituted cycloalkylalkyl, optionally substituted heteroalkyl, alkenyl, substituted heterocycloalkylalkyl, and optionally substituted heteroaralkyl.

In another embodiment of Compounds of Formula I, x is 0 and c and d are 1, i.e., Y=—NR$^{11}$—R$^{12}$NR$^{13}$—C(=X$^3$)—NR$^{14}$—[R$^{15}$]$_e$—[C(=X$^4$)]$_f$—R$^{16}$. In this embodiment, $R^{16}$ is preferably selected from the group consisting of optionally substituted aryl, cycloalkylalkyl, cycloalkyl, heteroaryl, heterocycloalkylalkyl, optionally substituted aralkyl, heteroaralkyl, heteroalkyl, alkyl, alkylsulfonylalkyl, heterocycloalkyl, aralkenyl, alkoxy, and alkenyl.

In another embodiment of Compounds of Formula I, x is 0, c and d are 1, e and f are 0, i.e., Y=—NR$^{11}$—R$^{12}$—NR$^{13}$—C(=X$^3$)—NR$^{14}$—R$^{16}$. In this embodiment, $R^{16}$ is preferably selected from the group consisting of optionally substituted aryl, cycloalkylalkyl, cycloalkyl, heteroaryl, heterocycloalkylalkyl, optionally substituted aralkyl, heteroarylalkyl, heteroalkyl, alkyl, alkylsulfonylalkyl, and heterocycloalkyl.

In another embodiment of Compounds of Formula I, x and e are 0, and c, d and f are 1, i.e., Y=—$NR^{11}$—$R^{12}$—$NR^{13}$—$C(=X^3)$—$NR^{14}$—$C(=X^4)$—$R^{16}$. In this embodiment, $R^{16}$ is preferably selected from the group consisting of substituted aryl, aralkenyl, and alkoxy.

Yet in another embodiment, $X^3$ is S.

In another embodiment of Compounds of Formula I, x is 0, c, d, e and f are 1, i.e., Y=—$NR^{11}$—$R^{12}$—$NR^{13}$—$C(=X^3)$—$NR^{14}$—$R^{15}$—$C(=X^4)$—$R^{16}$. In this embodiment, $R^{16}$ is preferably selected from the group consisting of alkoxy, and alkenyl.

In another embodiment of Compounds of Formula I, x, d and f are 0, and c and e are 1, i.e., Y=—$NR^{11}$—$R^{12}$—$NR^{13}$—$C(=X^3)$—$R^{15}$—$R^{16}$. In this embodiment, $R^{16}$ is optionally substituted heteroaryl.

Still in another embodiment, c, e, and f are 1, and d and x are 0, i.e., Y=—$NR^{11}$—$R^{12}$—$NR^{13}$—$C(=X^3)$—$R^{15}$—$C(=X^4)$—$R^{16}$. In this embodiment, $R^{16}$ is preferably selected from the group consisting of —$NR^{50}R^{51}$ (where $R^{50}$ is hydrogen or alkyl and $R^{51}$ is optionally substituted aryl, optionally substituted aralkyl, optionally substituted heteroaryl, or optionally substituted heteroalkyl), aryl, heteroaryl, alkoxy, and alkyl.

In another embodiment, $X^3$ is O.

Still further, combinations of the preferred groups described above can also form other preferred embodiments. For example, in one particularly preferred embodiment x, d and f are 0, c and e are 1, $R^{11}$, $R^{13}$ and $R^{14}$ are hydrogen, $R^{12}$ is propylene, 2-hydroxypropylene or 2,2-dimethylpropylene, $X^3$ is O, $R^{15}$ is ethylene and $R^{16}$ is substituted heteroaryl. In this manner, a variety of preferred compounds are embodied within the present invention.

Another aspect of the present invention provides a composition comprising a pharmaceutically acceptable excipient; and a compound of Formula I. Preferred compounds of Formula I in the composition are also the preferred compounds described above in addition to other preferred compounds of Formula I described below. Furthermore, preferred compounds of Formula I above includes those that are preferred in the composition which are described below.

Thus, in one embodiment, compounds of Formula I in the composition are ones in which x is 0.

In another preferred composition, $R^{16}$ of Compounds of Formula I is substituted heteroaryl. More preferably, $R^{16}$ is substituted [1,2,4]-oxadiazolyl. Still more preferably, $R^{16}$ is 3-(optionally substituted phenyl)-substituted [1,2,4]-oxadiazol-5-yl or 3-(optionally substituted heteroaryl)-substituted [1,2,4]-oxadiazol-5-yl.

Still in another embodiment, the compound of Formula I has $IC_{50}$ of 10 µM or less for inhibiting poly(ADP-ribose) polymerase in vitro.

Yet in another embodiment, the compound of Formula I has $IC_{50}$ of 10 µM or less for inhibiting poly(ADP-ribose) polymerase in vivo.

Another aspect of the present invention provides a method for inhibiting PARP activity comprising the steps of administering an effective amount of a compound of Formula I.

Yet another aspect of the present invention provides a method for radiosensitizing tumor cells comprising the steps of administering an effective amount of a compound of Formula I to the tumor cells.

Still yet another aspect of the present invention provides a method for chemosensitizing tumor cells comprising the steps of administering an effective amount of a compound of Formula I to the tumor cells.

Another aspect of the present invention provides a method for treating cancer in an animal comprising administering a therapeutically effective amount of a compound of Formula I to said animal in need of such a treatment. In one embodiment, the method further comprises administering a chemotherapy agent in combination with the compound of Formula I to said animal. In another embodiment, the method further comprises administering radiation in combination with the compound of Formula I to said animal.

Representative compounds of the present invention are shown in Tables 1 and 2 below.

TABLE 1

Representative compounds of Formula I.

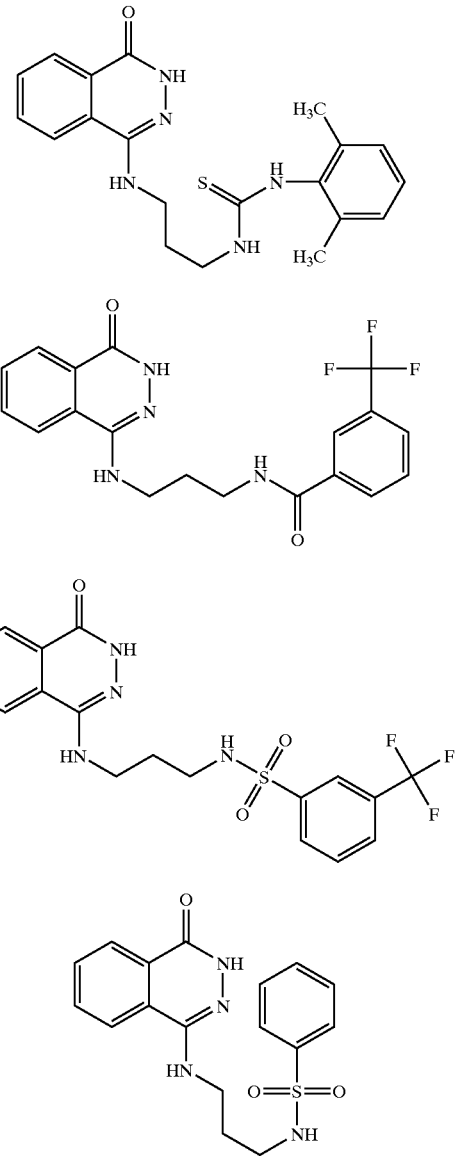

TABLE 1-continued
Representative compounds of Formula I.
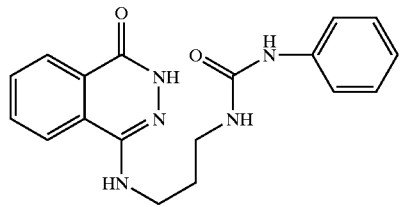
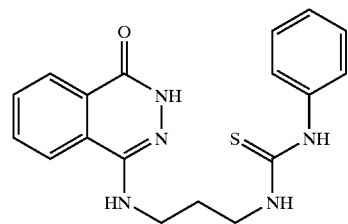
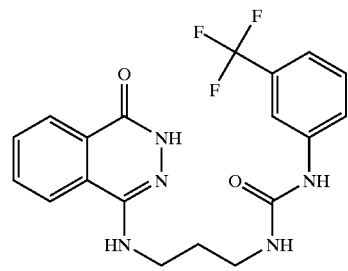
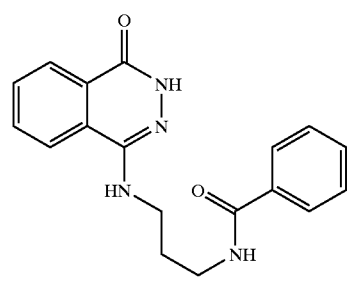
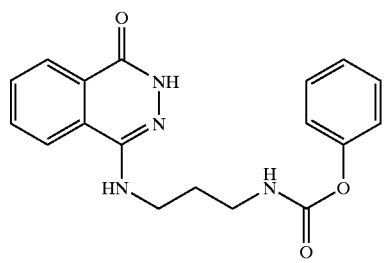
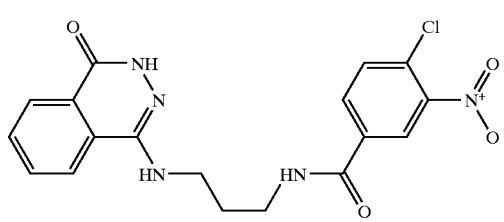
TABLE 1-continued
Representative compounds of Formula I.
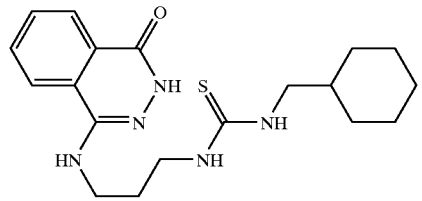
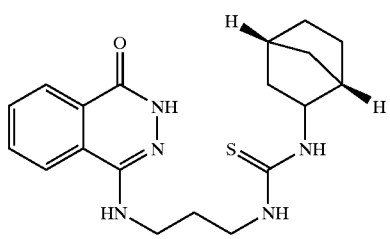
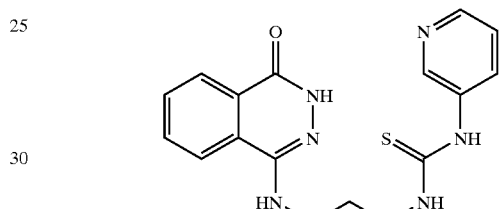
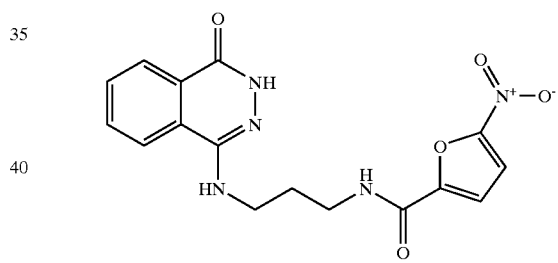
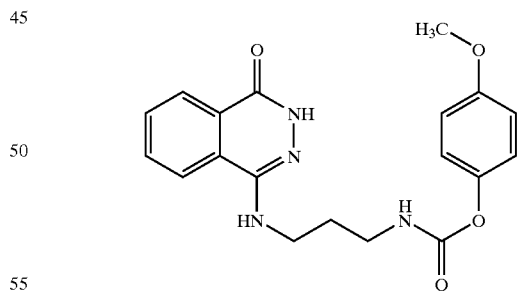
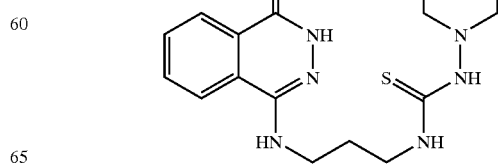

TABLE 1-continued

Representative compounds of Formula I.

TABLE 1-continued
Representative compounds of Formula I.
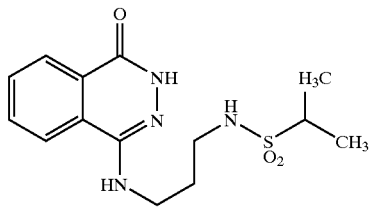
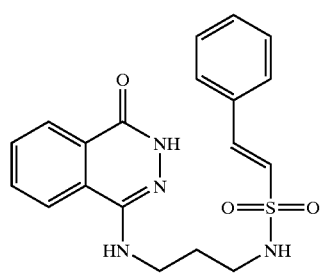
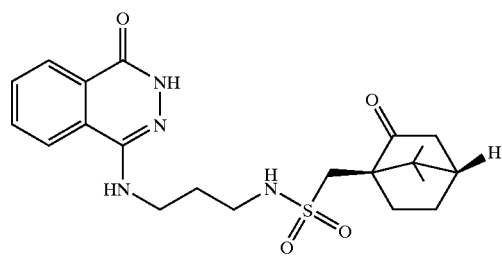
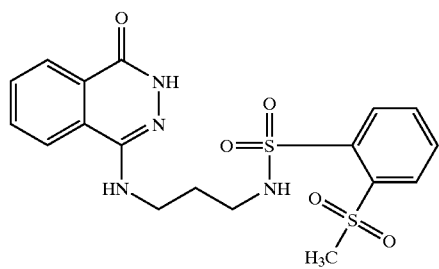
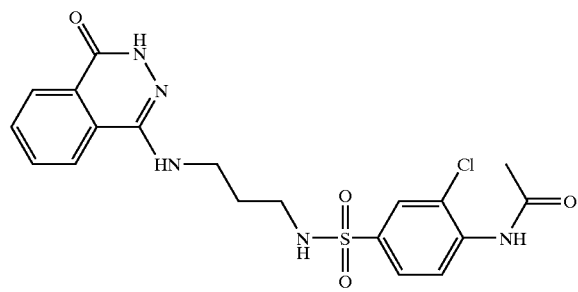
TABLE 1-continued
Representative compounds of Formula I.
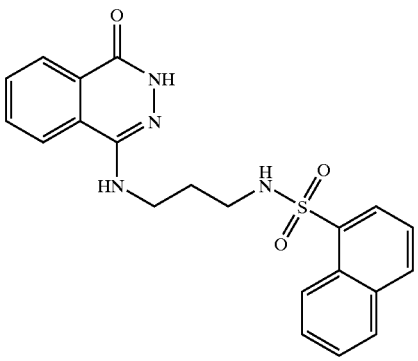
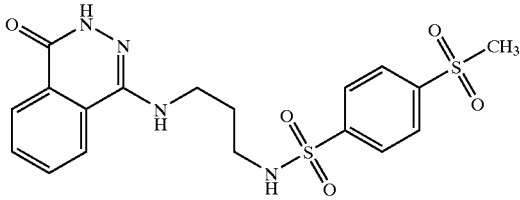
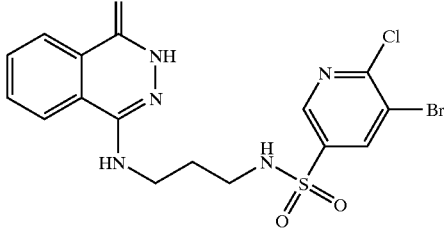
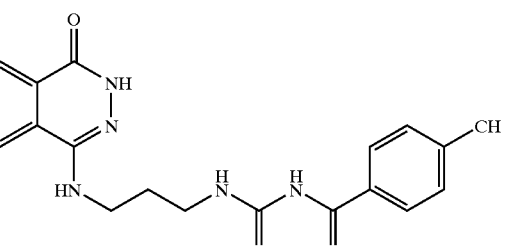
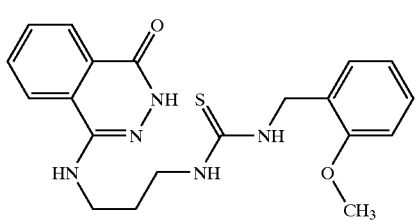

TABLE 1-continued
Representative compounds of Formula I.
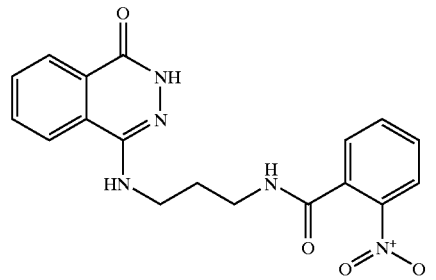
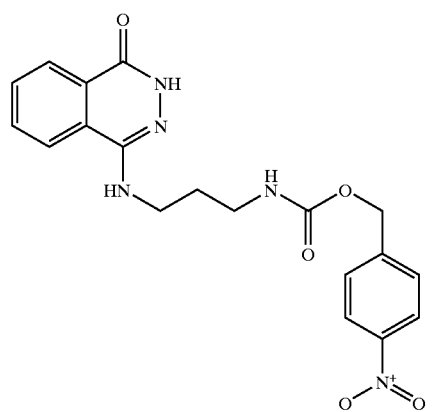
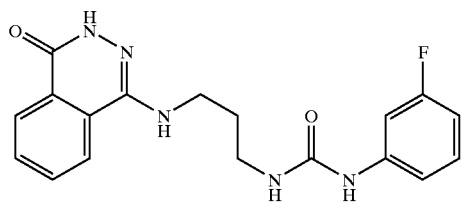
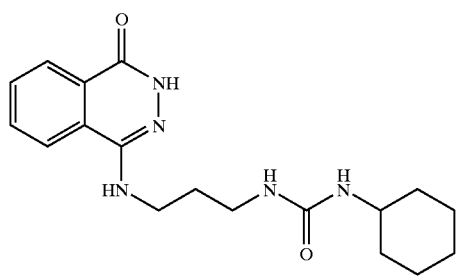
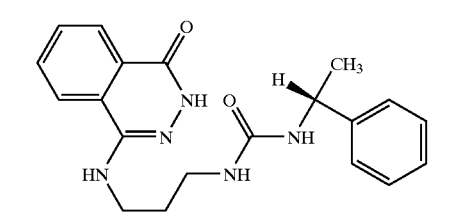
TABLE 1-continued
Representative compounds of Formula I.
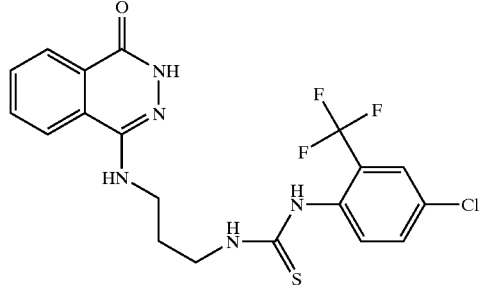
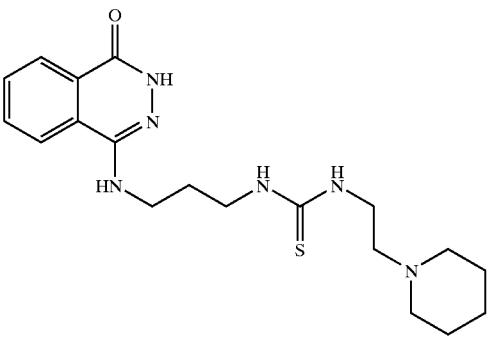
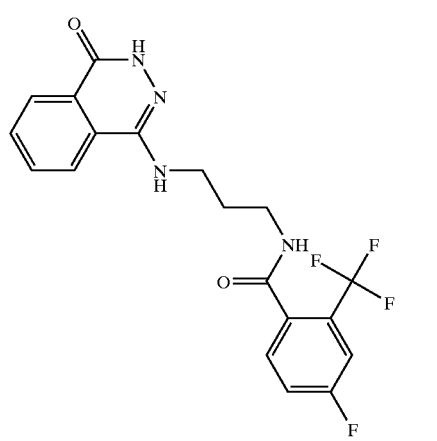
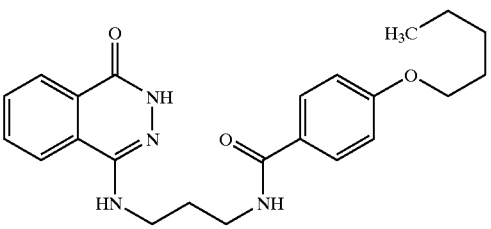
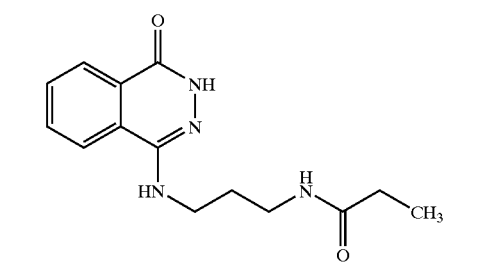

TABLE 1-continued
Representative compounds of Formula I.
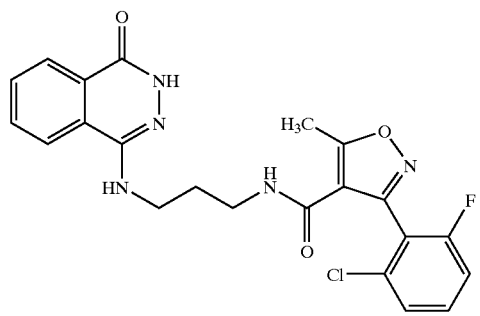
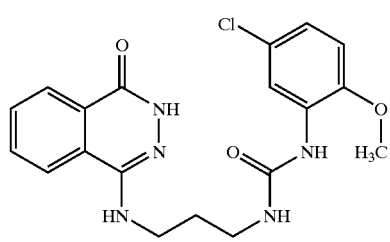
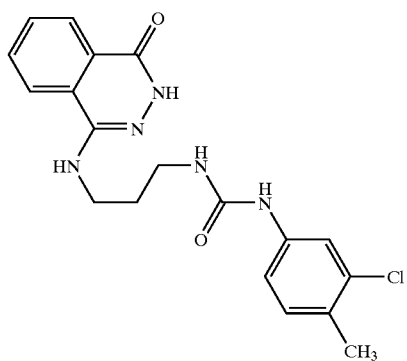
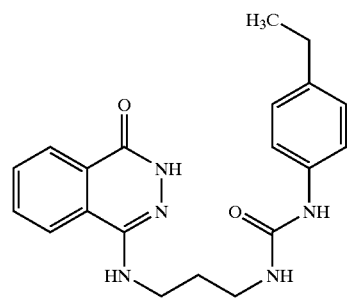
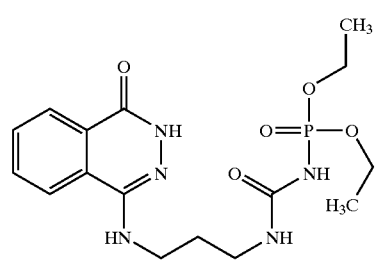
TABLE 1-continued
Representative compounds of Formula I.
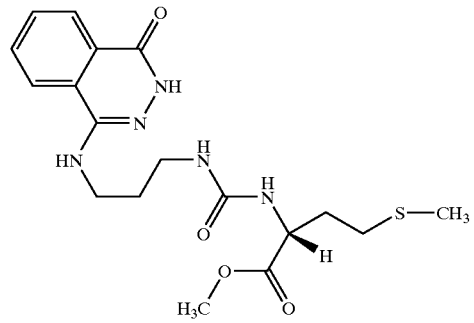
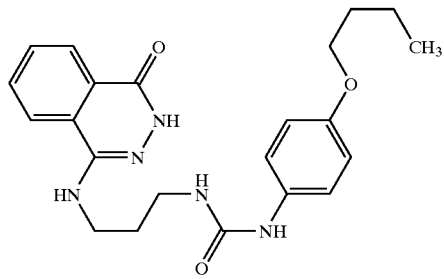
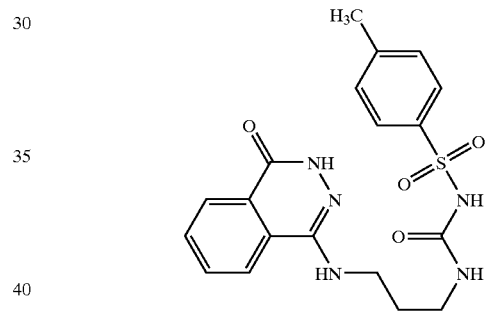
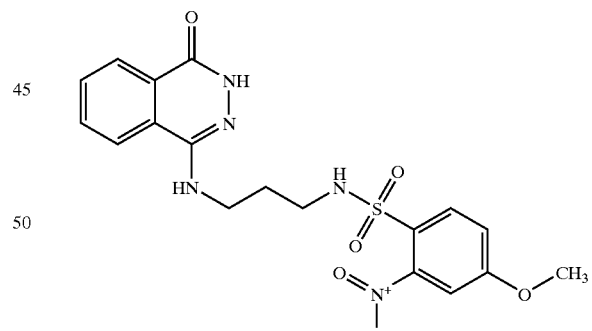
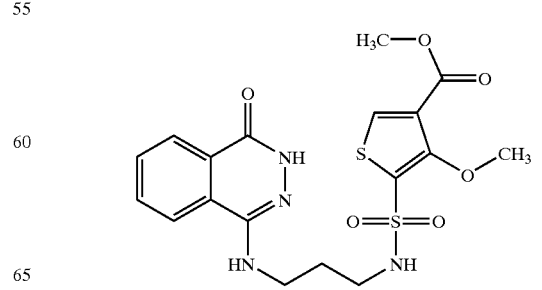

TABLE 1-continued
Representative compounds of Formula I.
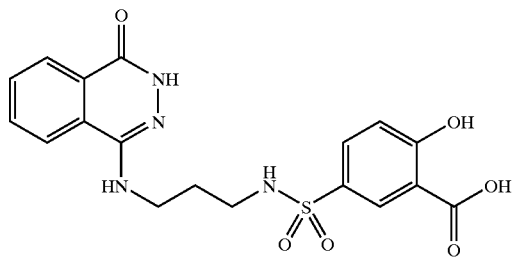
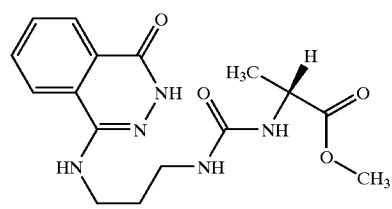
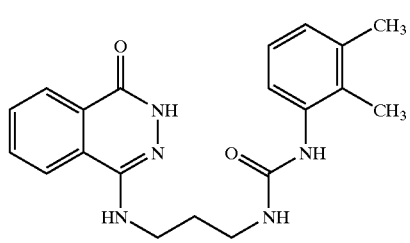
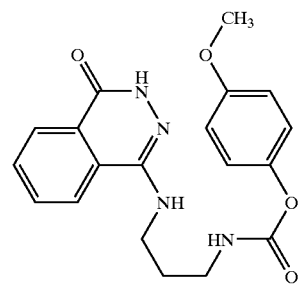
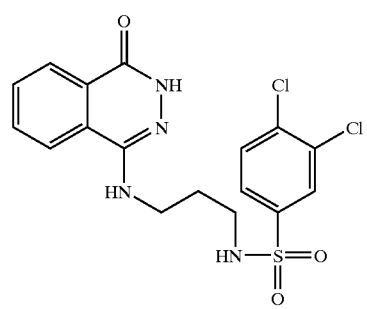
TABLE 1-continued
Representative compounds of Formula I.
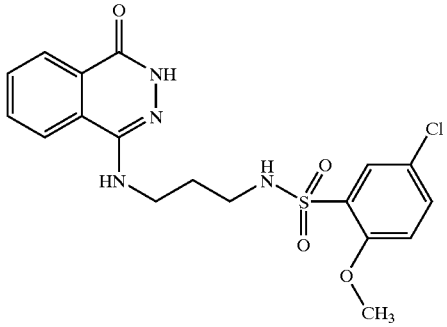
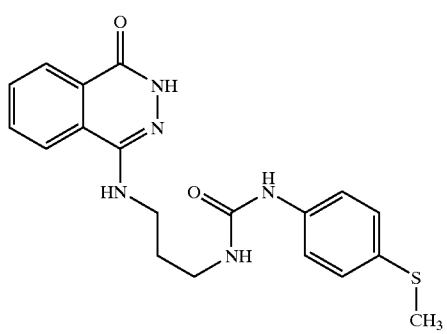
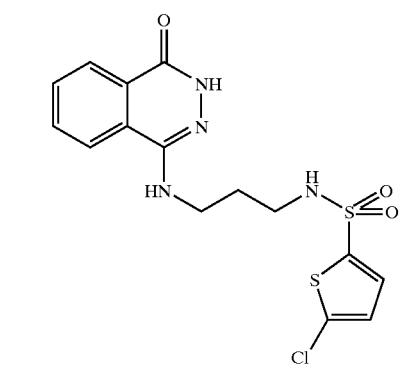
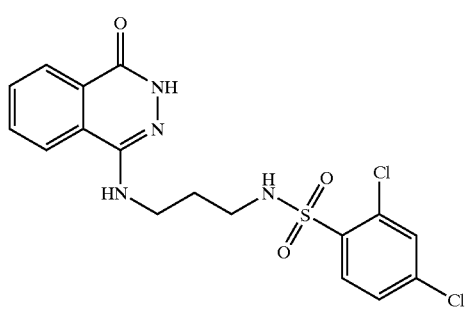

TABLE 1-continued
Representative compounds of Formula I.
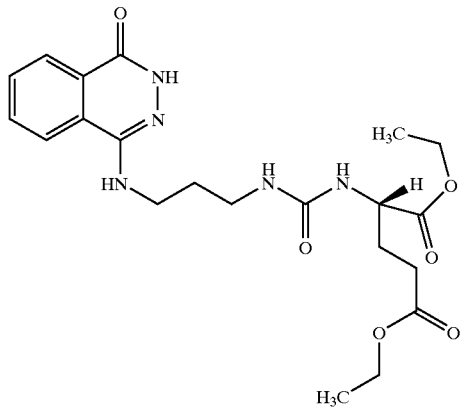
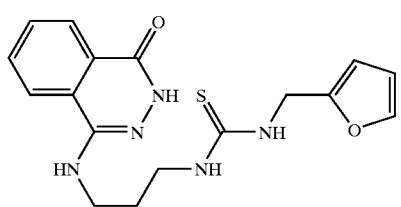
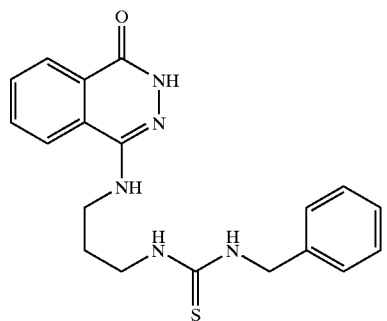
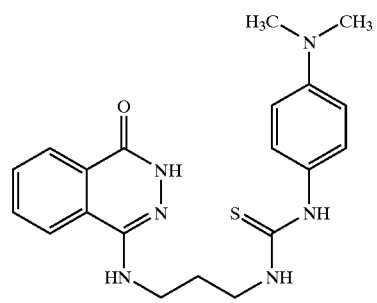
TABLE 1-continued
Representative compounds of Formula I.

TABLE 1-continued
Representative compounds of Formula I.
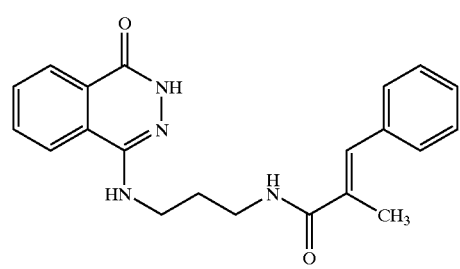
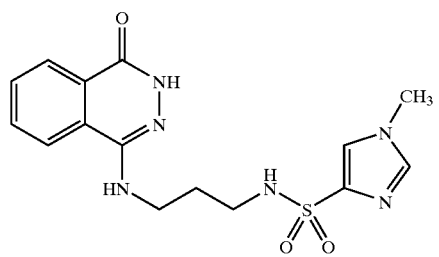
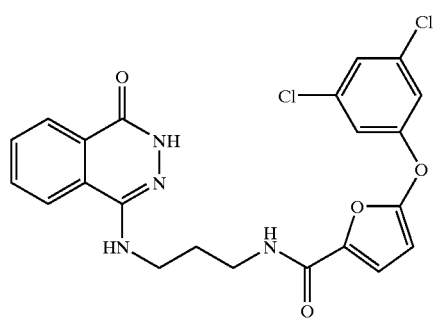
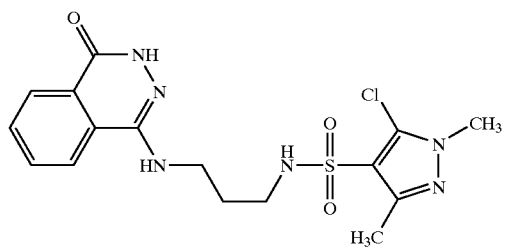
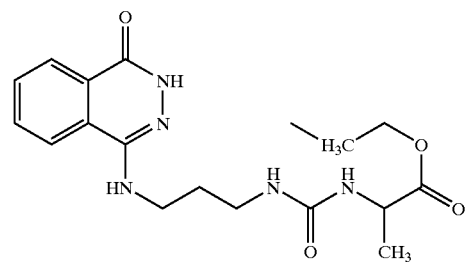
TABLE 1-continued
Representative compounds of Formula I.
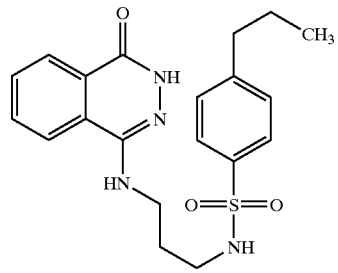
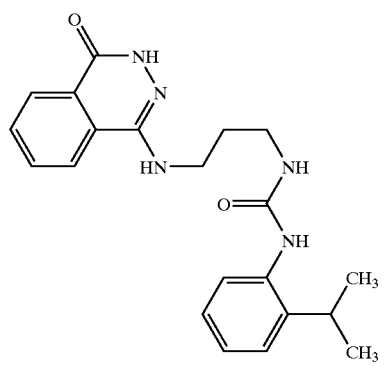
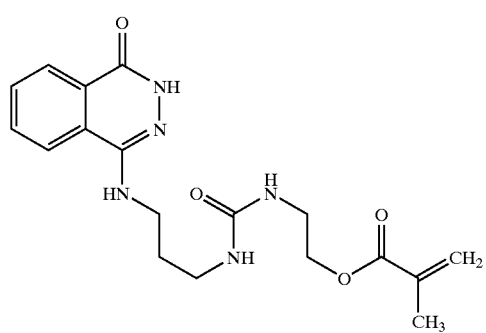
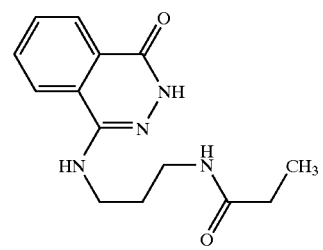
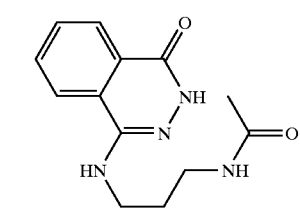

TABLE 1-continued
Representative compounds of Formula I.
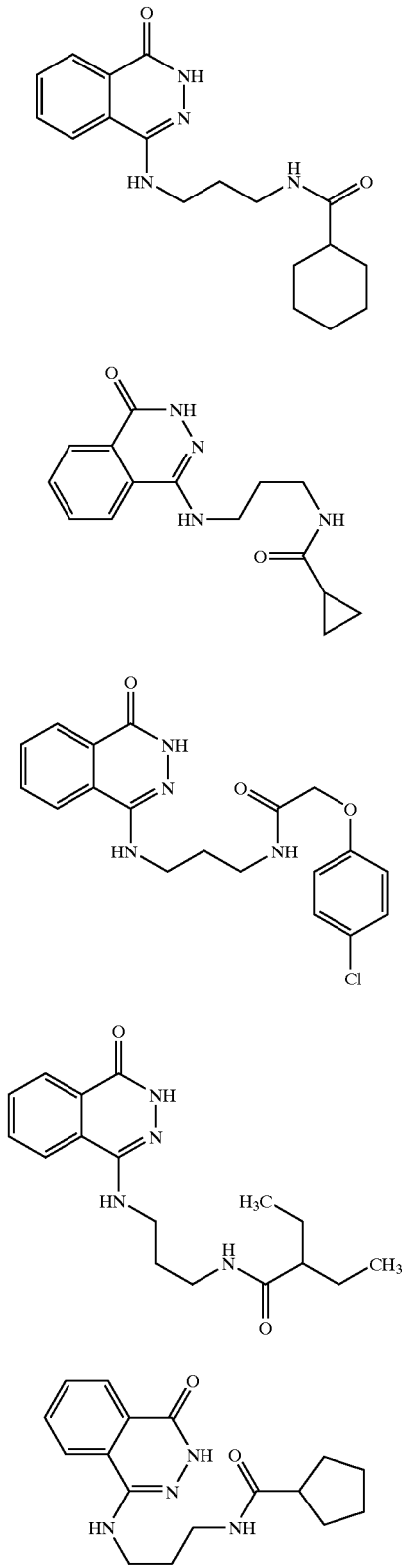
TABLE 1-continued
Representative compounds of Formula I.
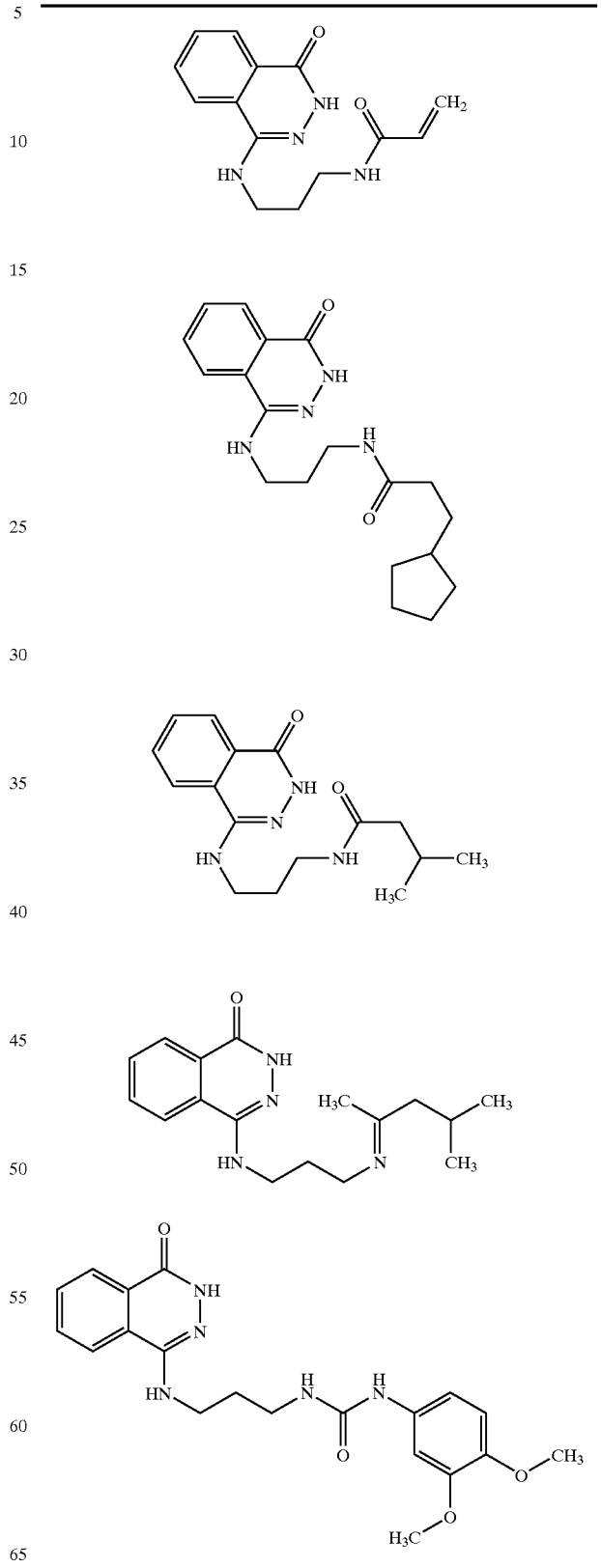

TABLE 1-continued

Representative compounds of Formula I.

TABLE 1-continued

Representative compounds of Formula I.

TABLE 1-continued
Representative compounds of Formula I.
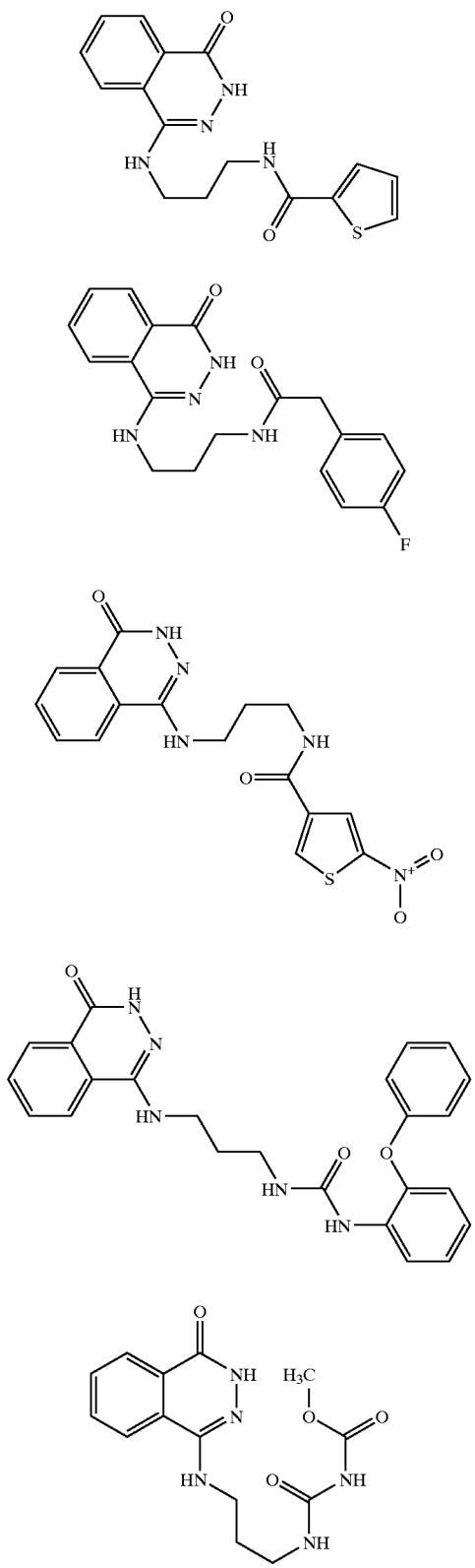
TABLE 1-continued
Representative compounds of Formula I.
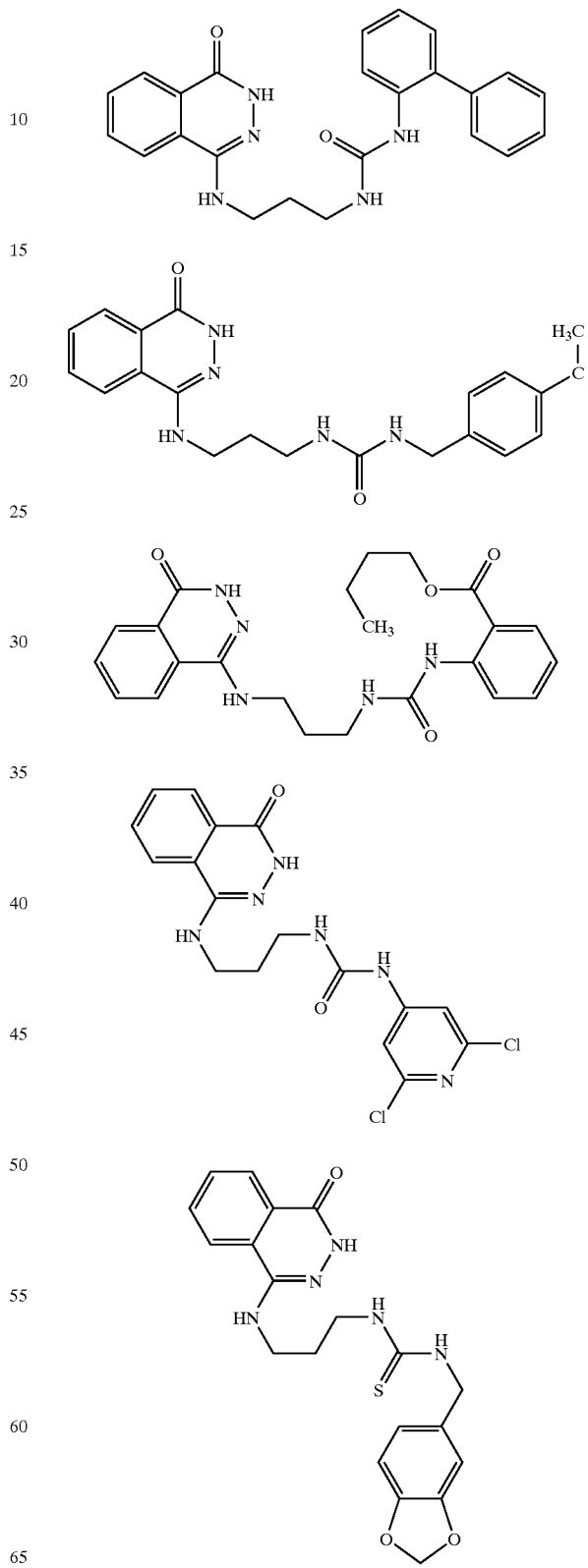

TABLE 1-continued
Representative compounds of Formula I.
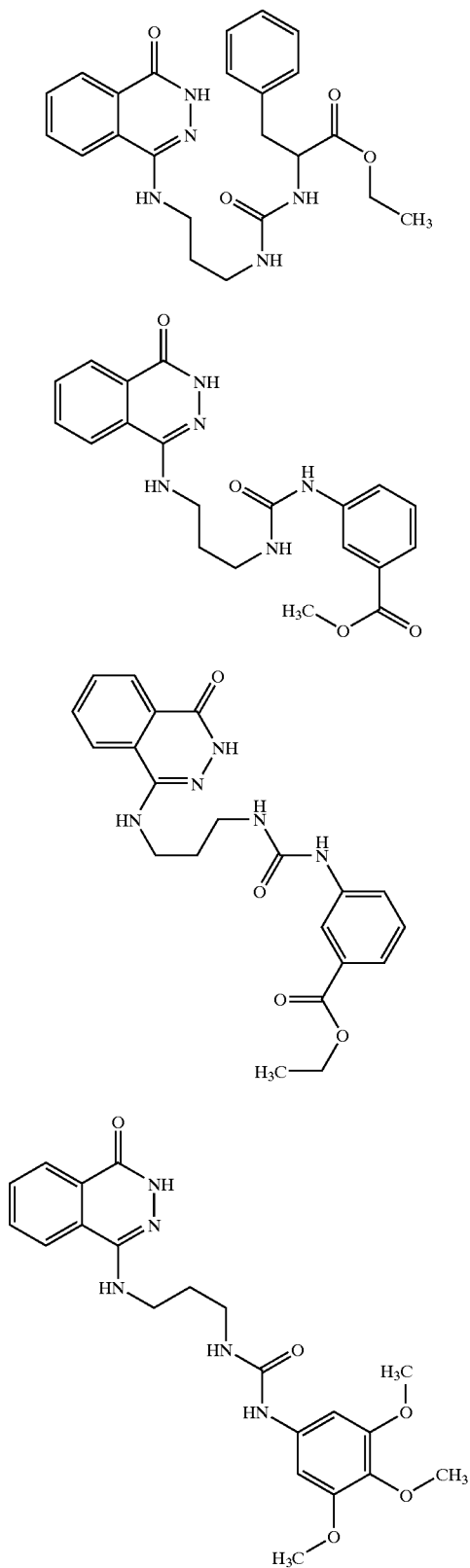
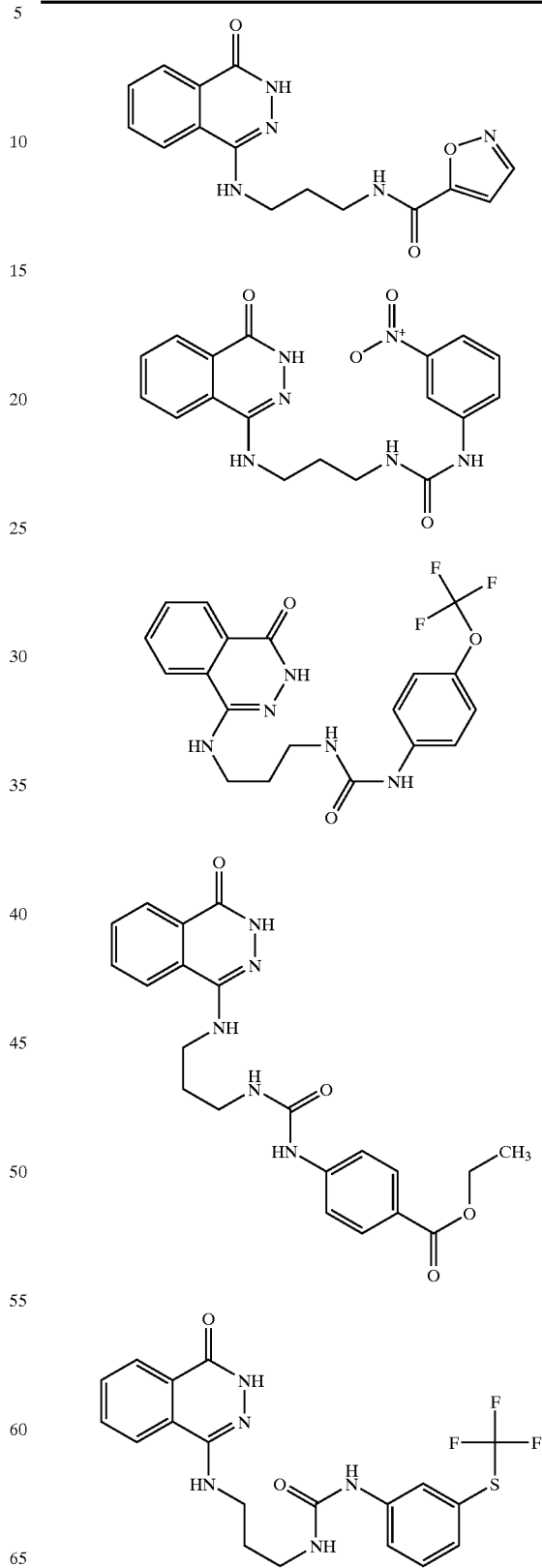

TABLE 1-continued
Representative compounds of Formula I.
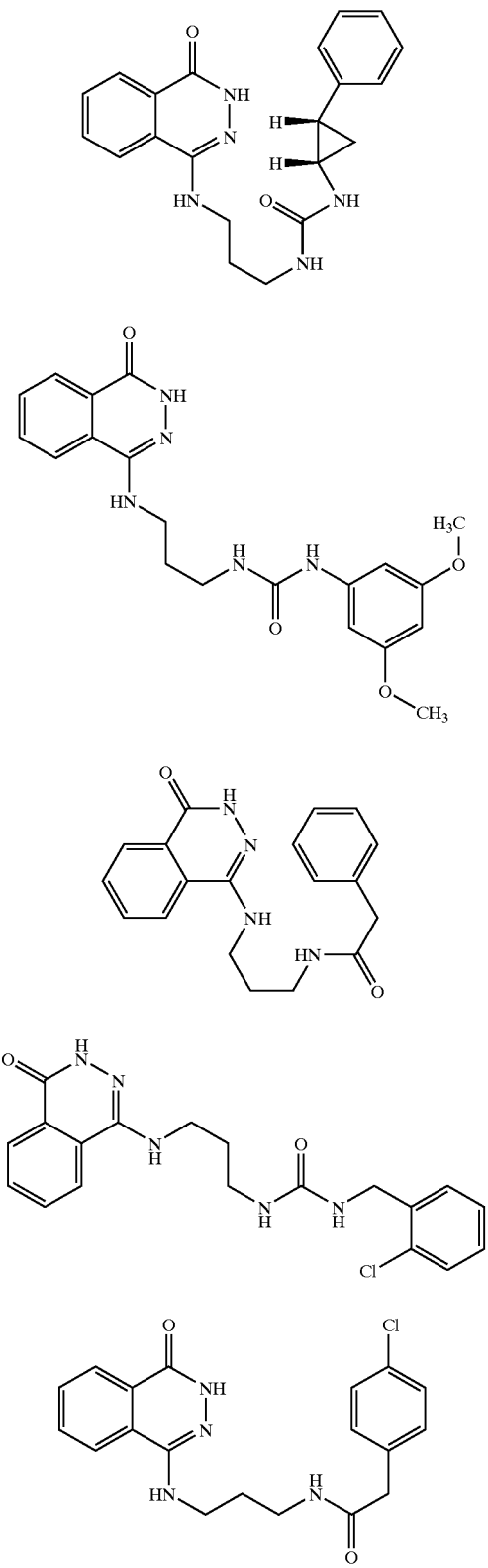
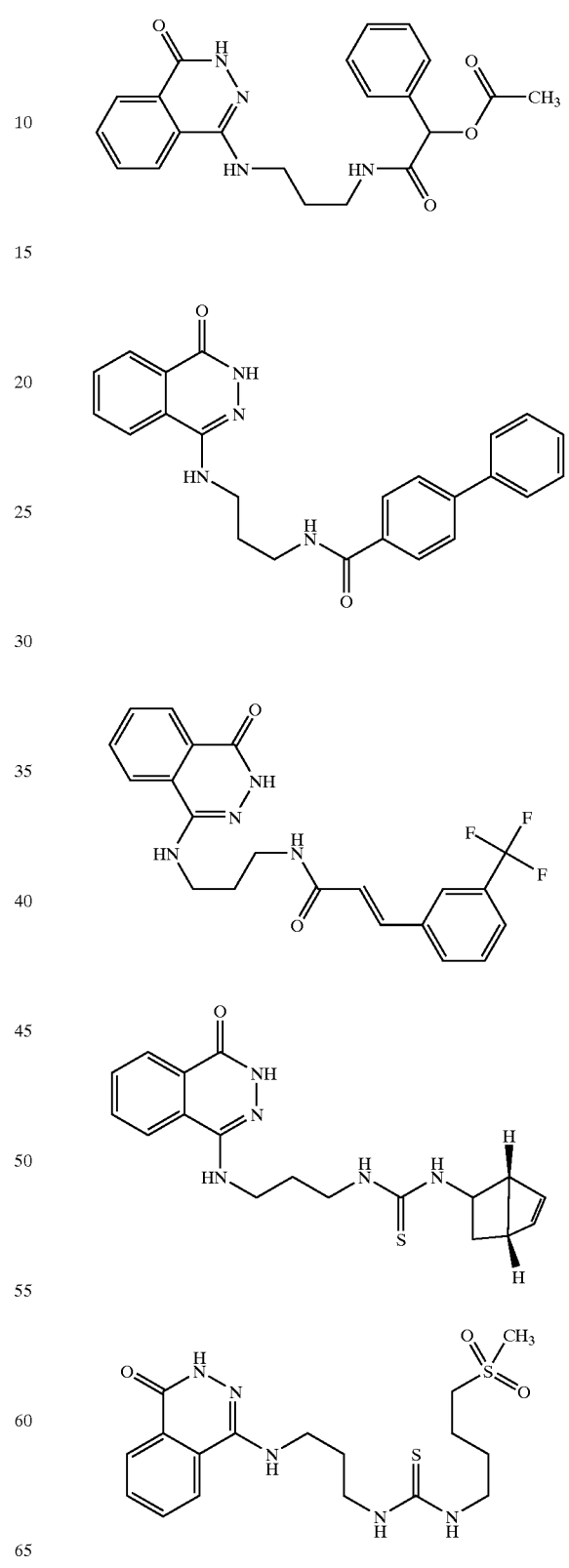

TABLE 1-continued
Representative compounds of Formula I.
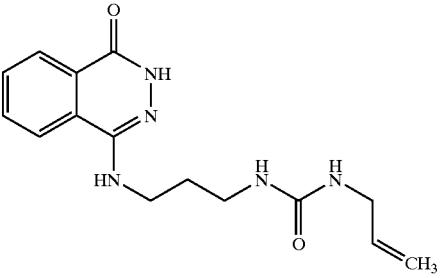
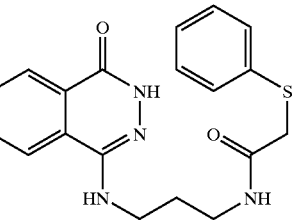
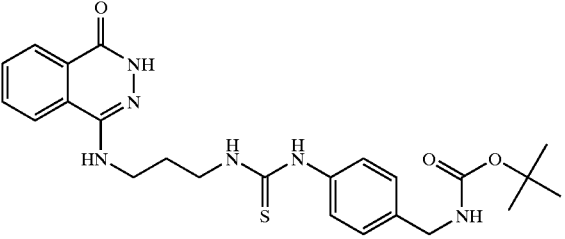
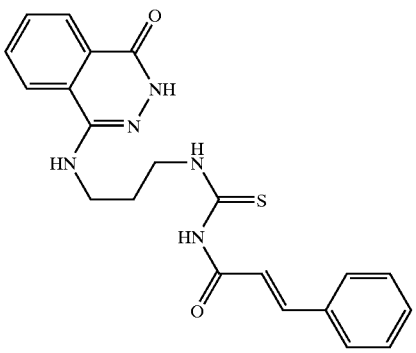
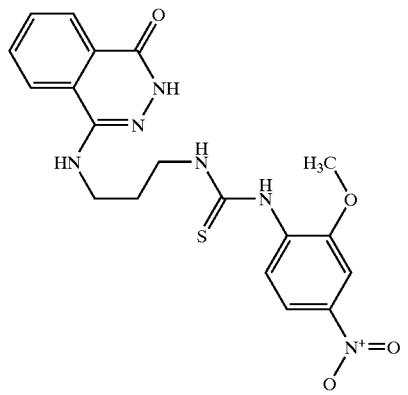
TABLE 1-continued
Representative compounds of Formula I.
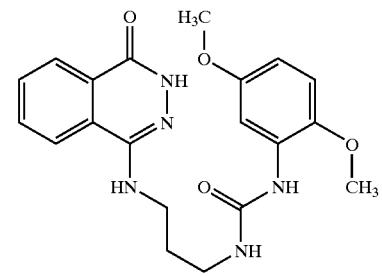
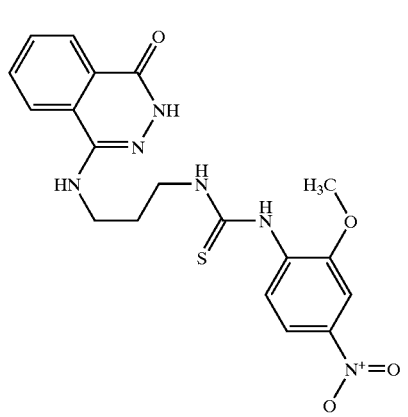
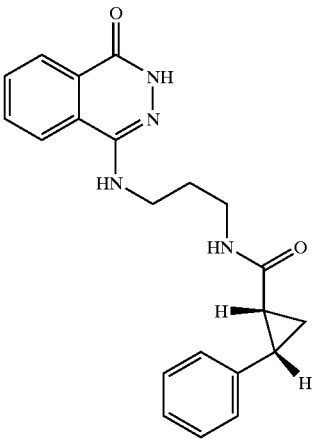
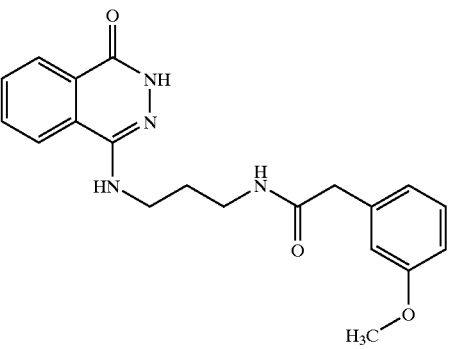

TABLE 1-continued

Representative compounds of Formula I.

TABLE 1-continued
Representative compounds of Formula I.
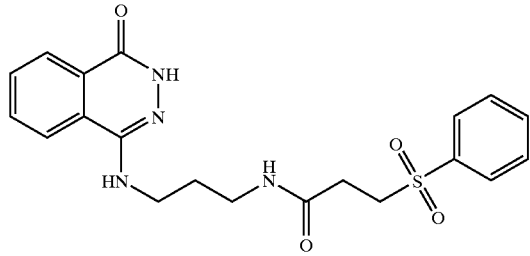
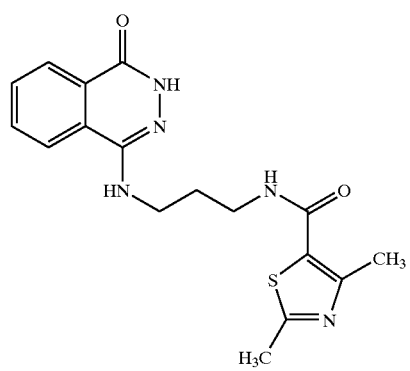
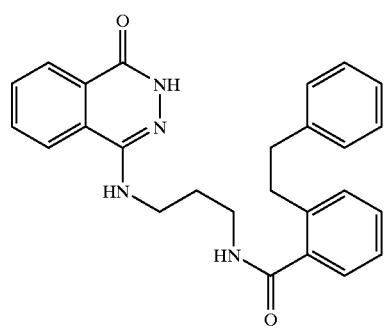
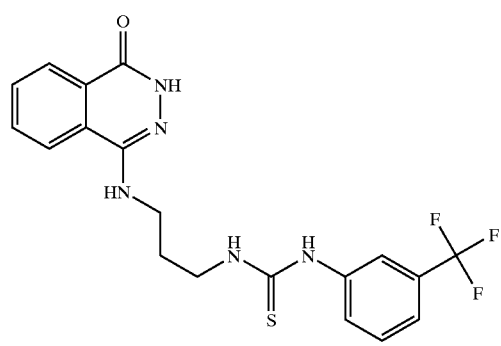
TABLE 1-continued
Representative compounds of Formula I.
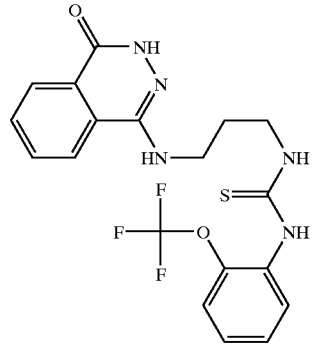
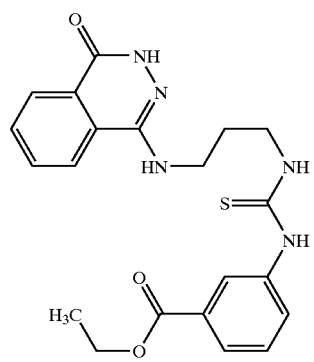
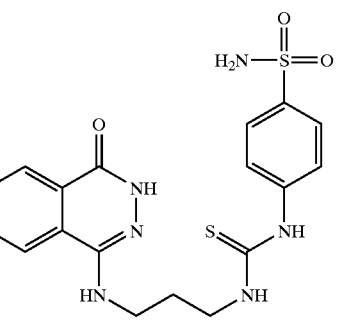
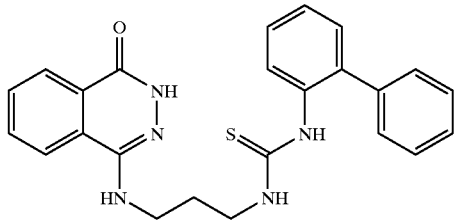
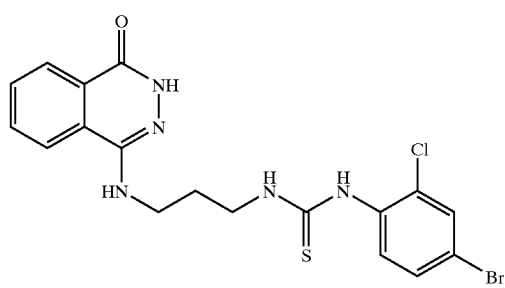

TABLE 1-continued
Representative compounds of Formula I.
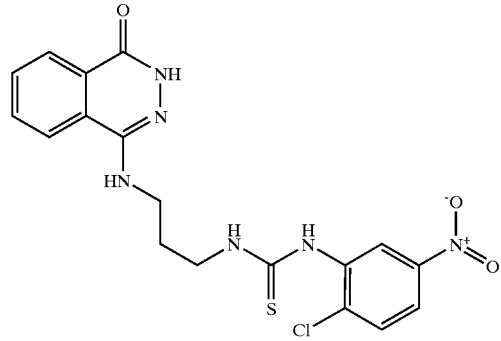
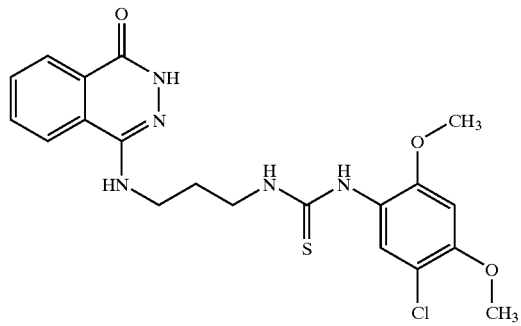
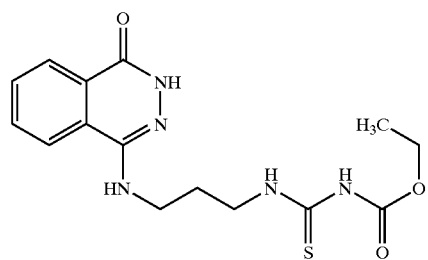
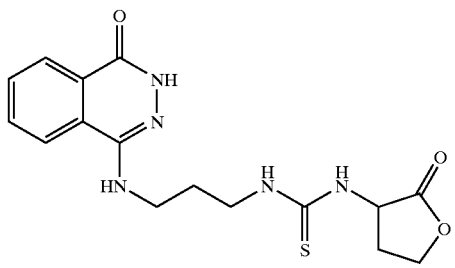
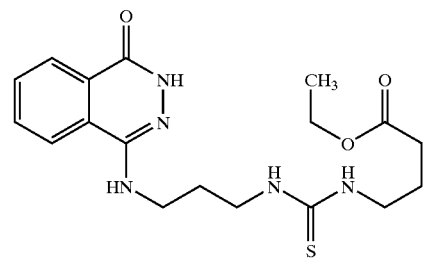
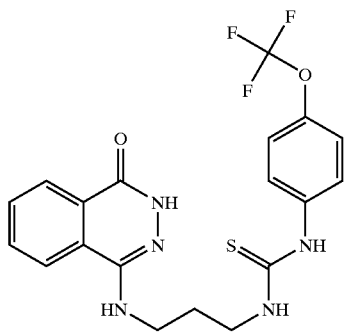
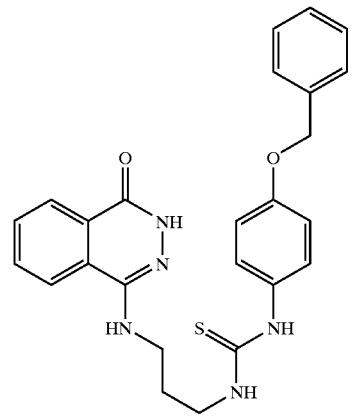
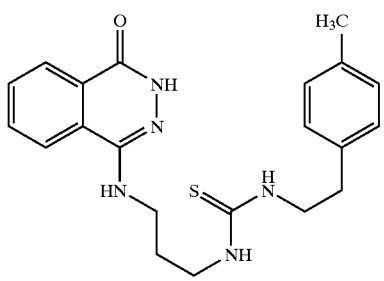
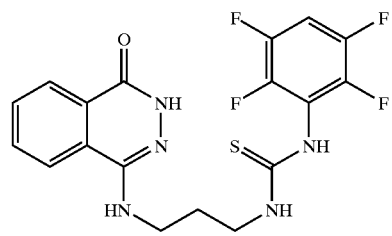
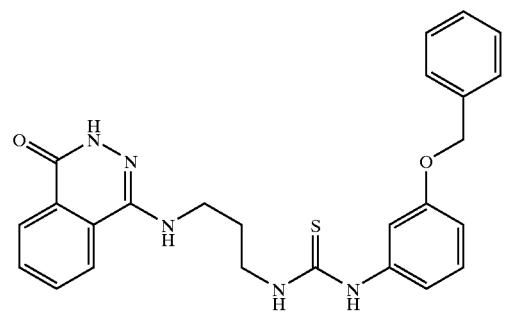

TABLE 1-continued
Representative compounds of Formula I.
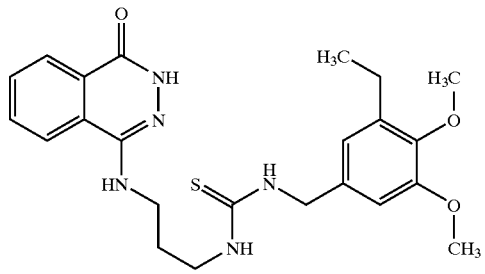
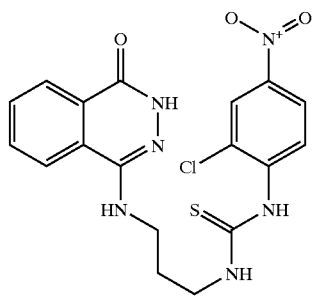
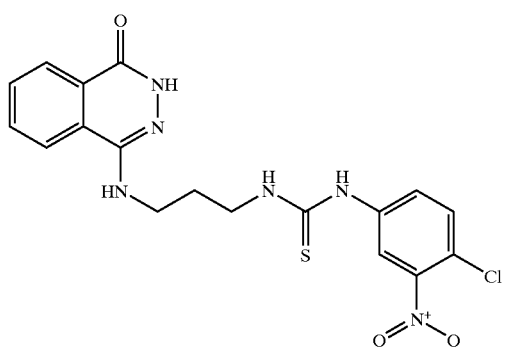
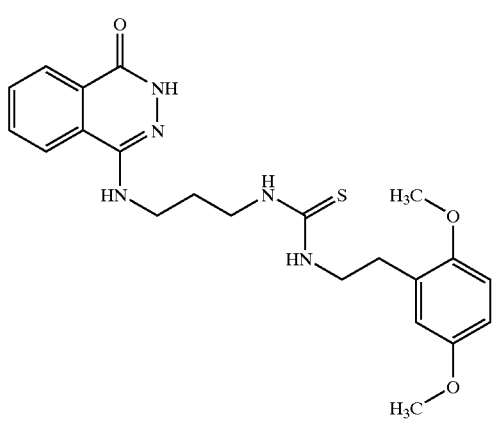
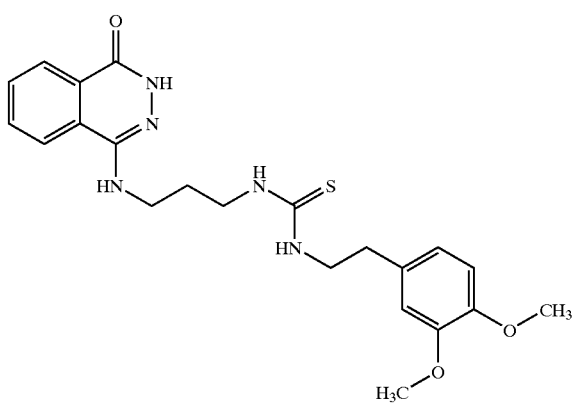
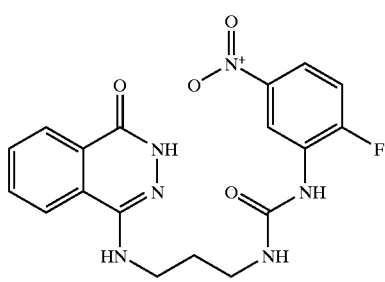
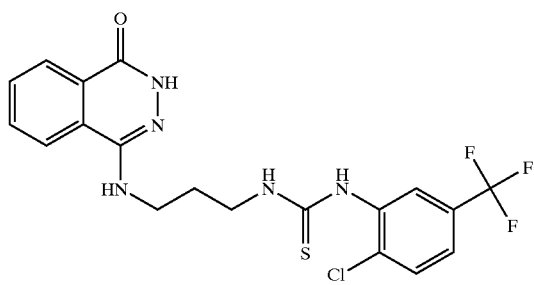
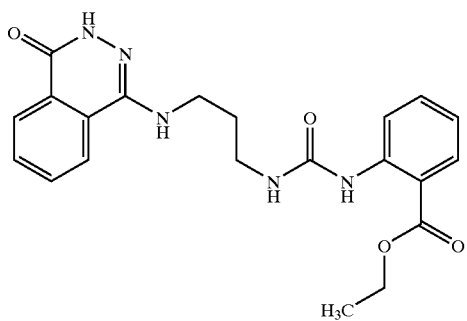

TABLE 1-continued
Representative compounds of Formula I.
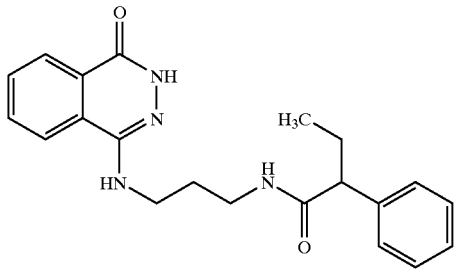
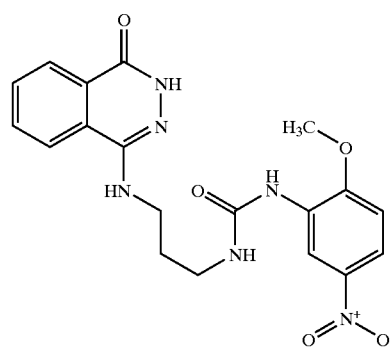
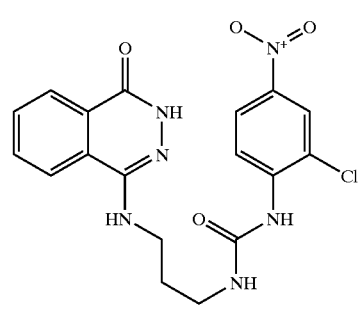
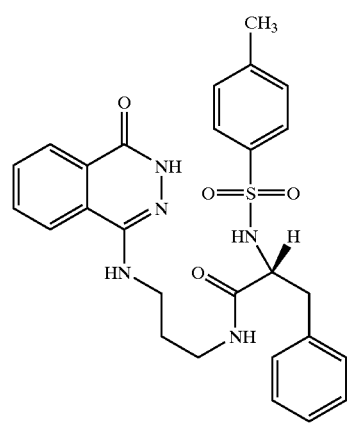
TABLE 1-continued
Representative compounds of Formula I.
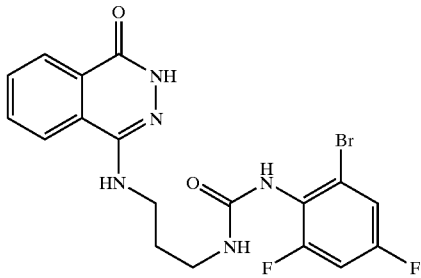
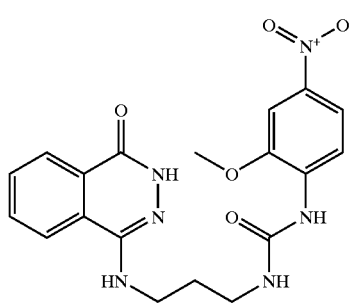
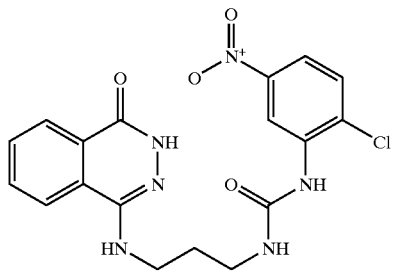
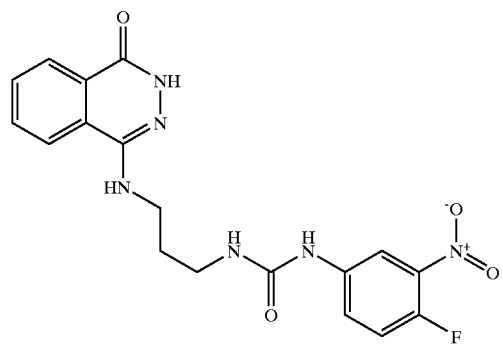
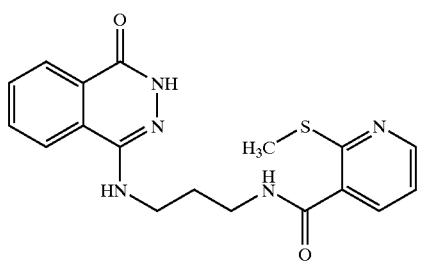

TABLE 1-continued
Representative compounds of Formula I.
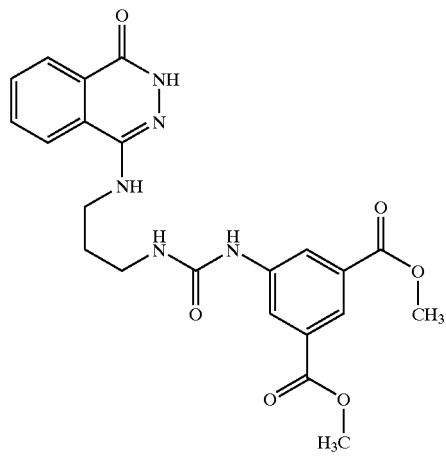
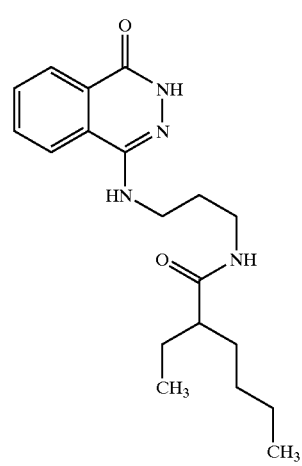
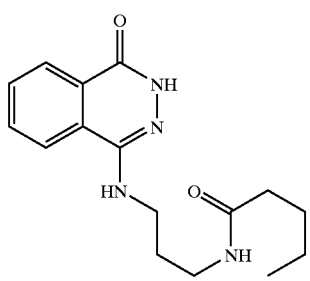
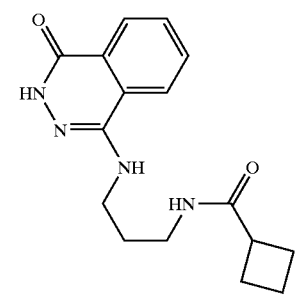
TABLE 1-continued
Representative compounds of Formula I.
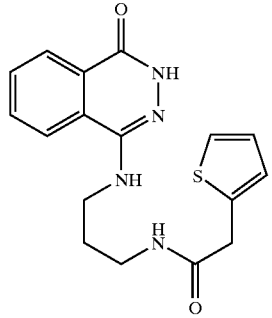
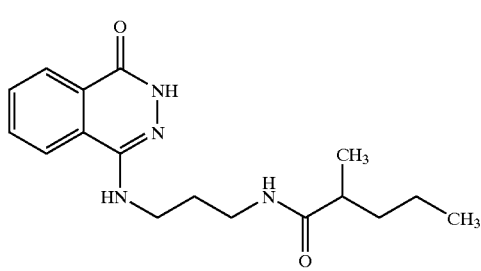
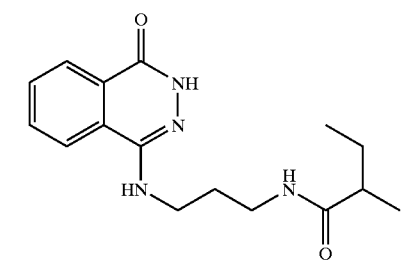
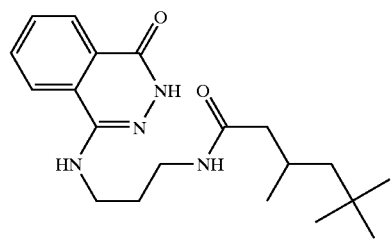
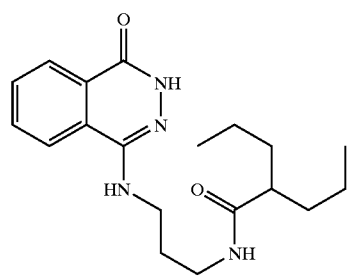

TABLE 1-continued
Representative compounds of Formula I.
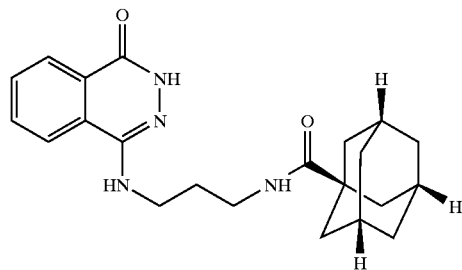
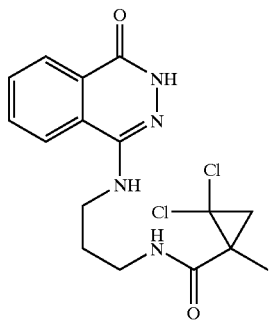
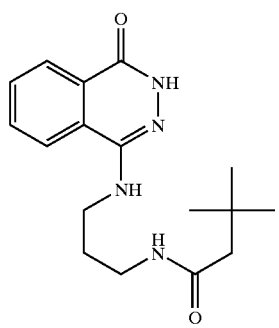
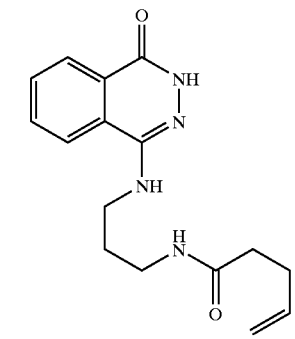
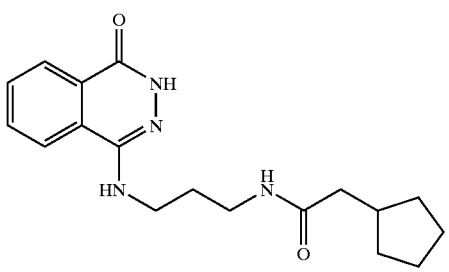
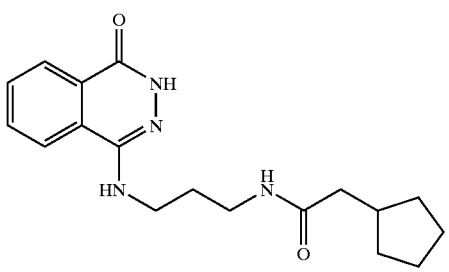
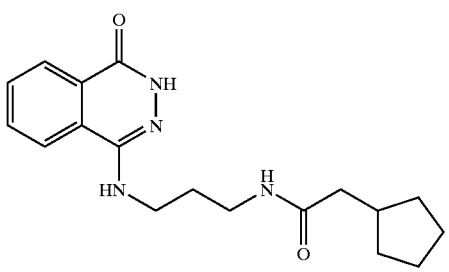
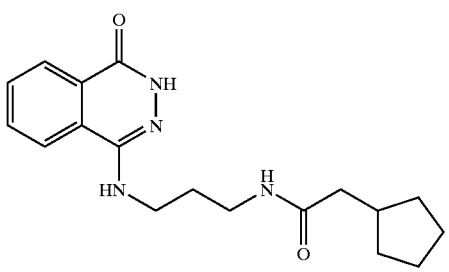
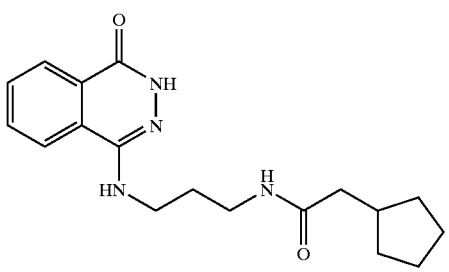
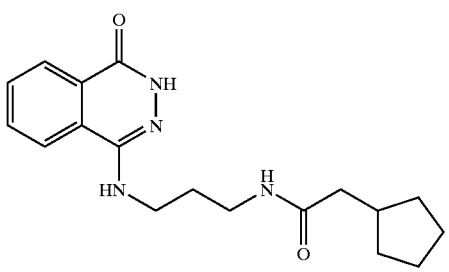

TABLE 1-continued
Representative compounds of Formula I.
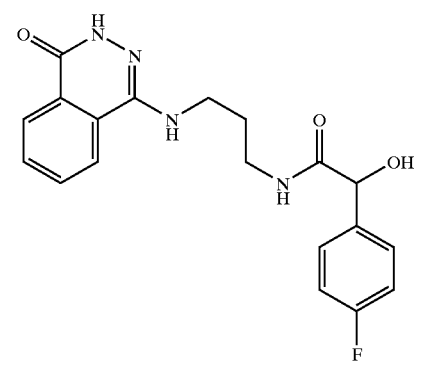
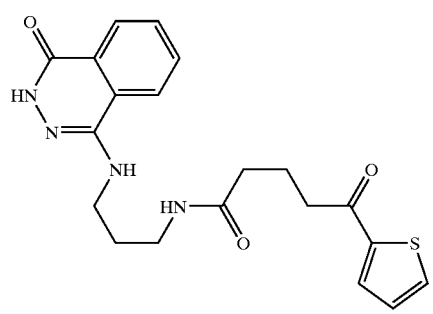
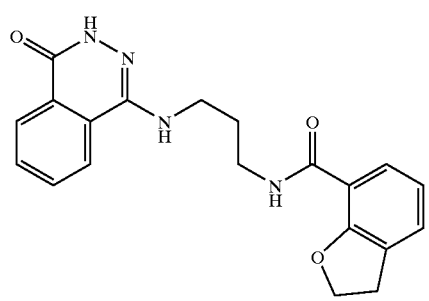
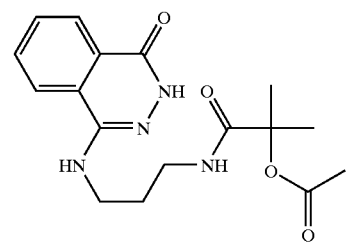
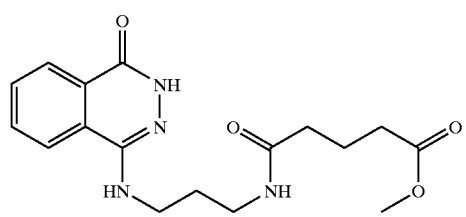
TABLE 1-continued
Representative compounds of Formula I.
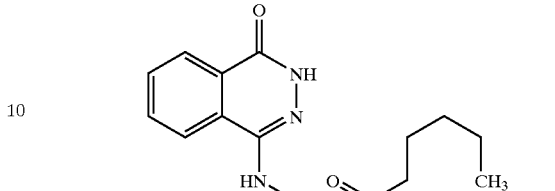
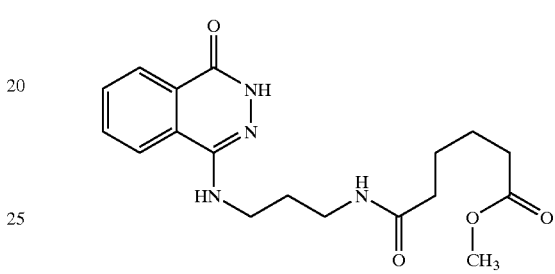
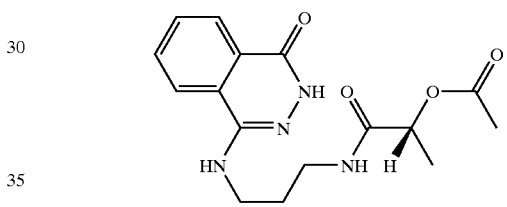
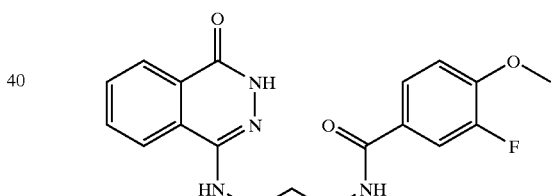
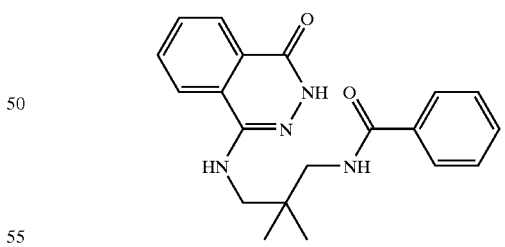
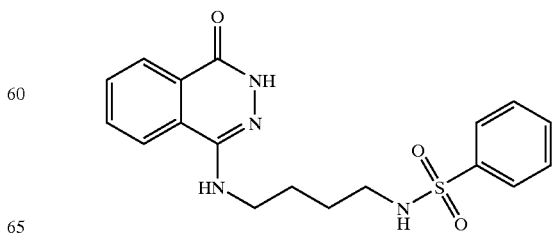

TABLE 1-continued
Representative compounds of Formula I.
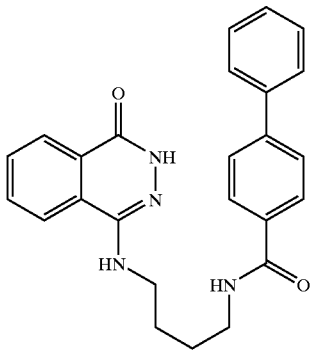
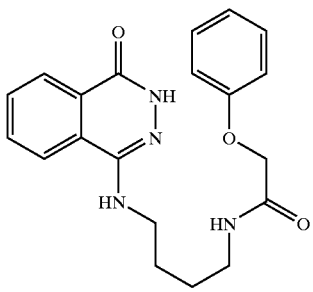
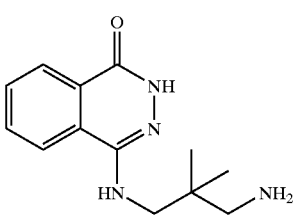
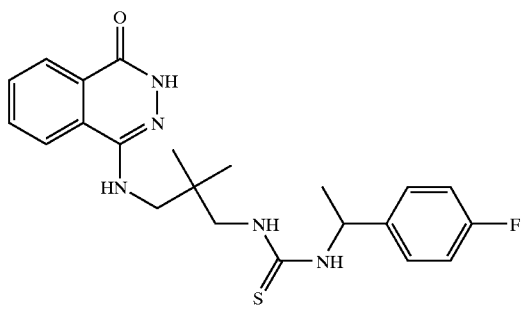
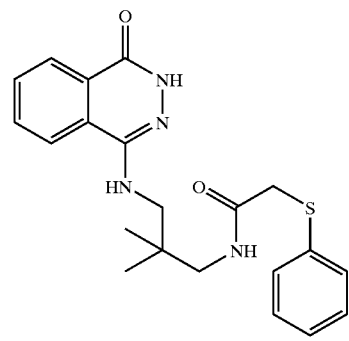
TABLE 1-continued
Representative compounds of Formula I.
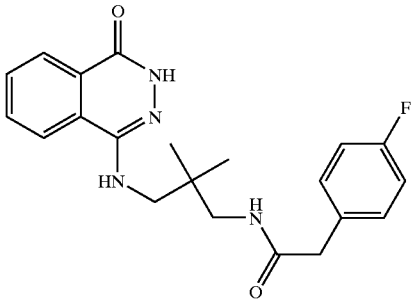
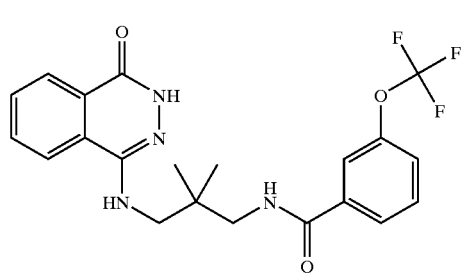
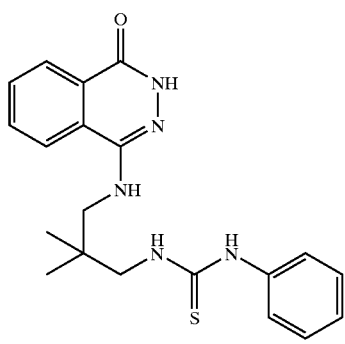
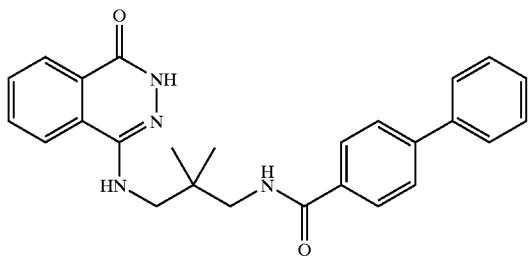
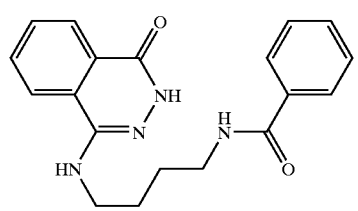

TABLE 1-continued
Representative compounds of Formula I.
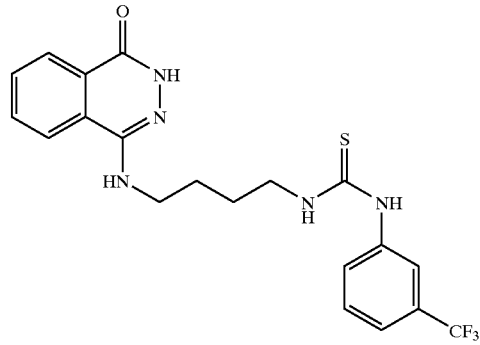
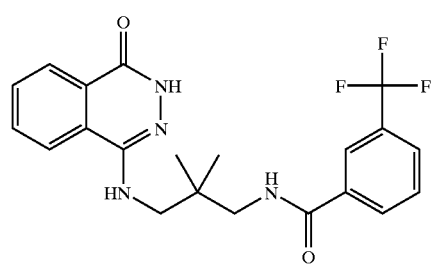
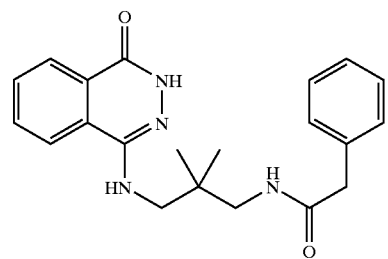
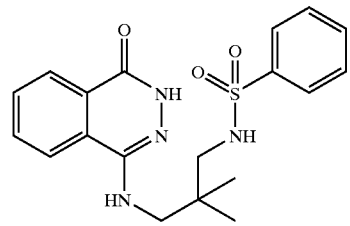
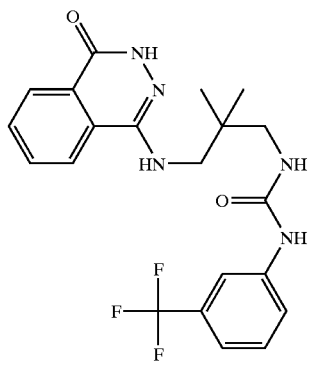
TABLE 1-continued
Representative compounds of Formula I.
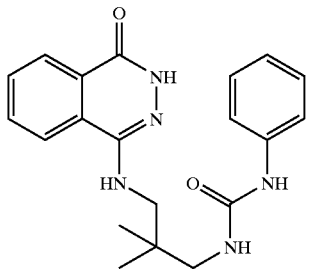
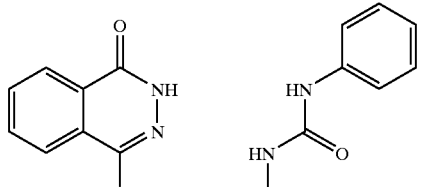
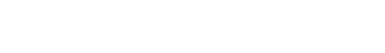
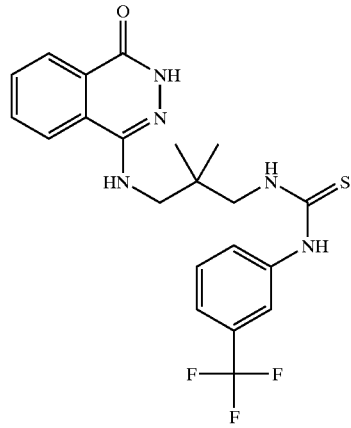
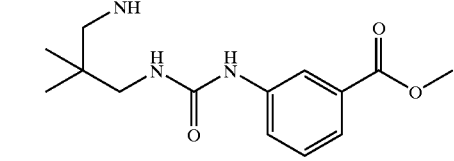

TABLE 1-continued
Representative compounds of Formula I.
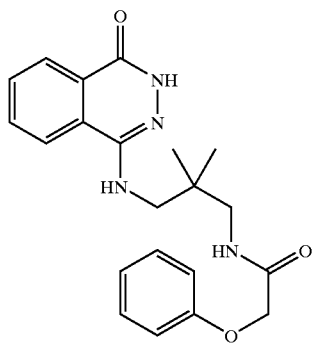
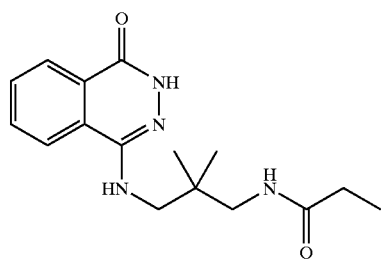
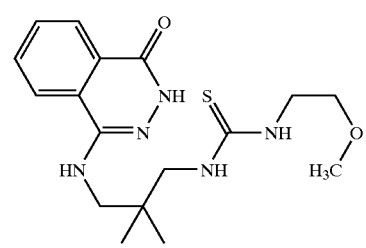
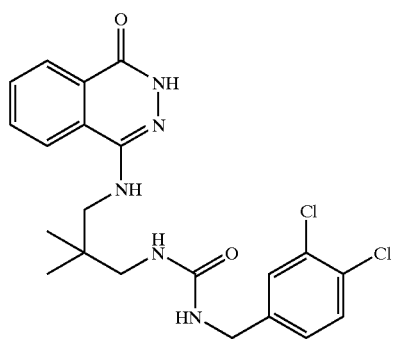
TABLE 1-continued
Representative compounds of Formula I.
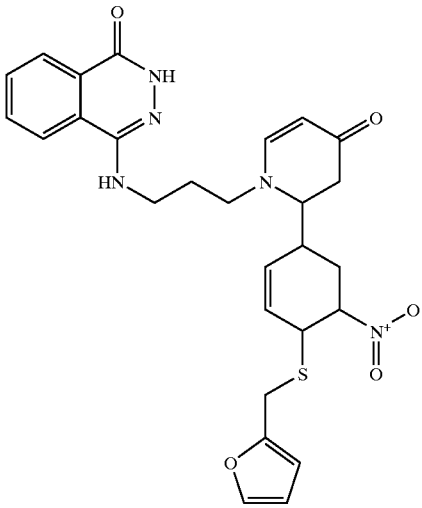
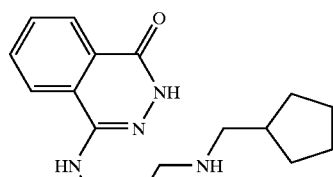
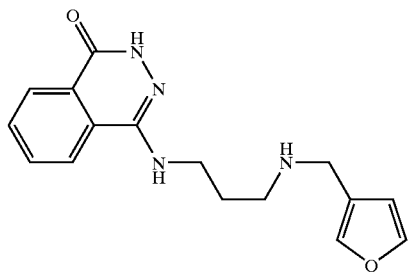
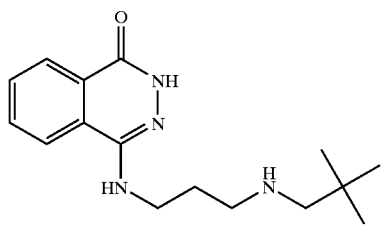
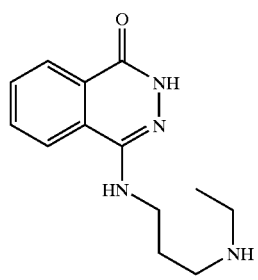

TABLE 1-continued

Representative compounds of Formula I.

TABLE 1-continued
Representative compounds of Formula I.
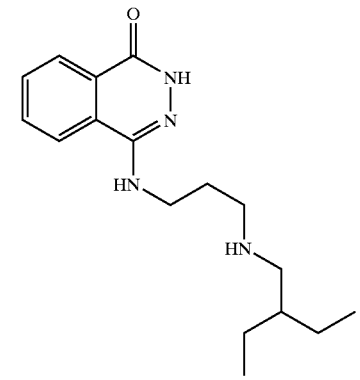
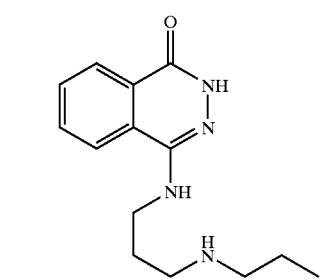
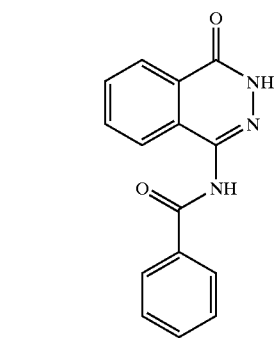
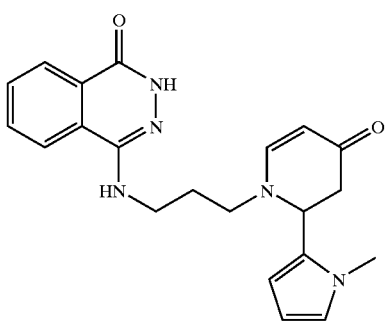
TABLE 1-continued
Representative compounds of Formula I.
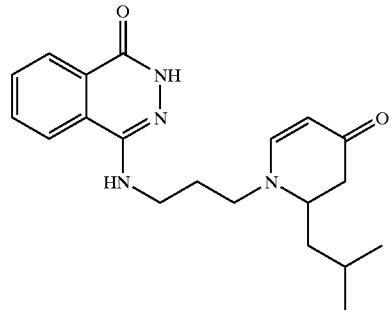
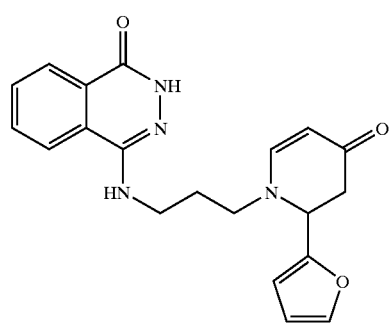
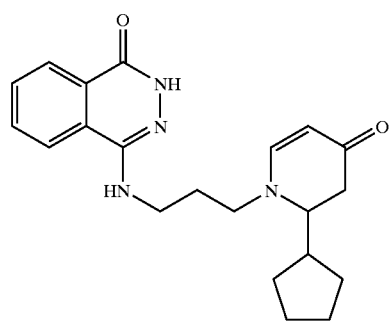
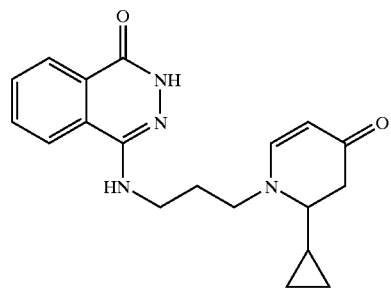
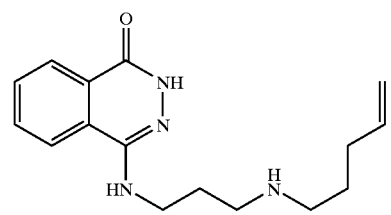

TABLE 1-continued
Representative compounds of Formula I.
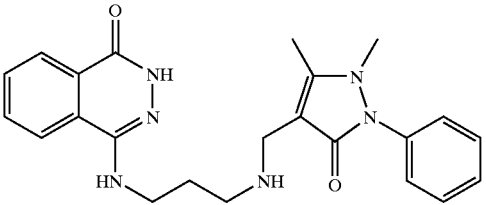
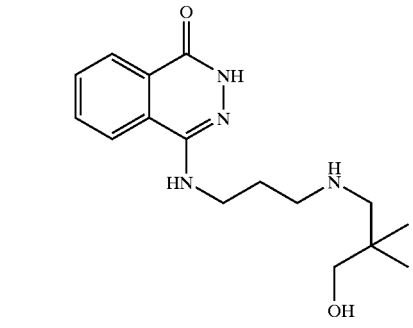
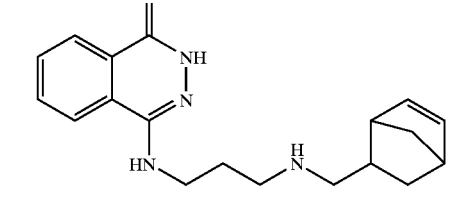
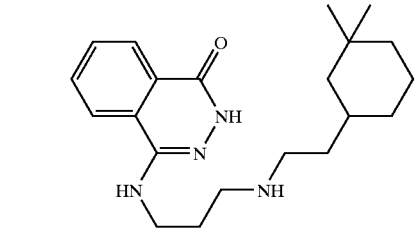
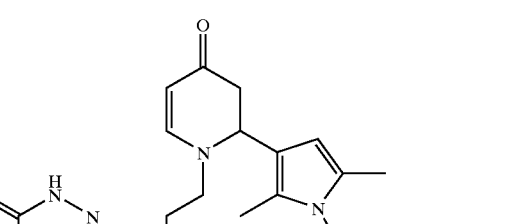
TABLE 1-continued
Representative compounds of Formula I.
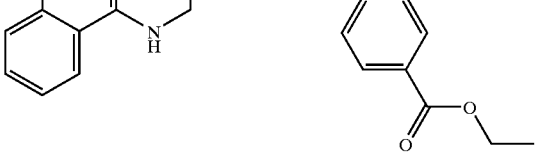
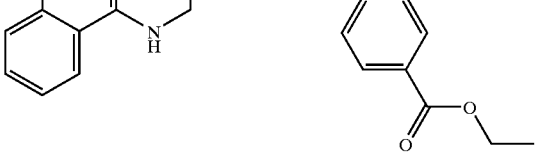
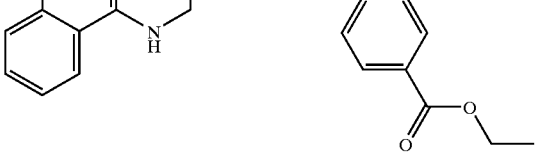
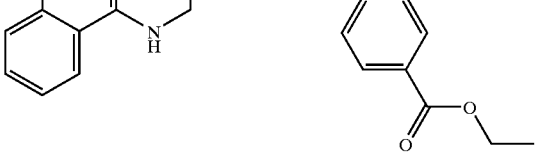
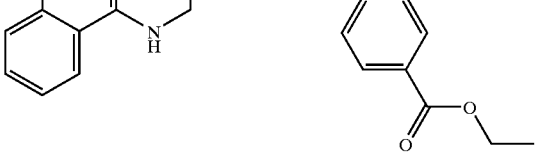

TABLE 1-continued
Representative compounds of Formula I.
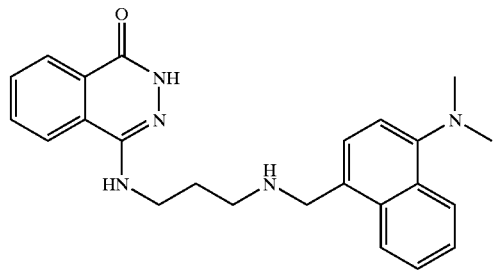
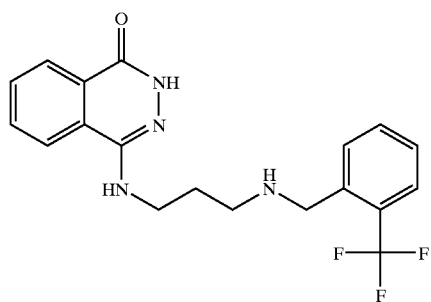
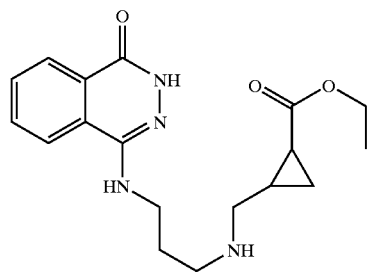
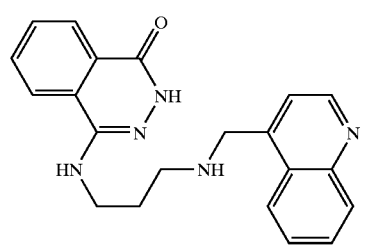
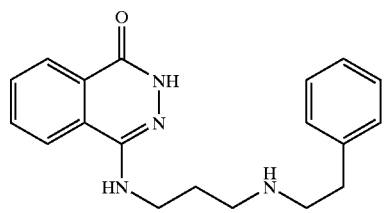
TABLE 1-continued
Representative compounds of Formula I.
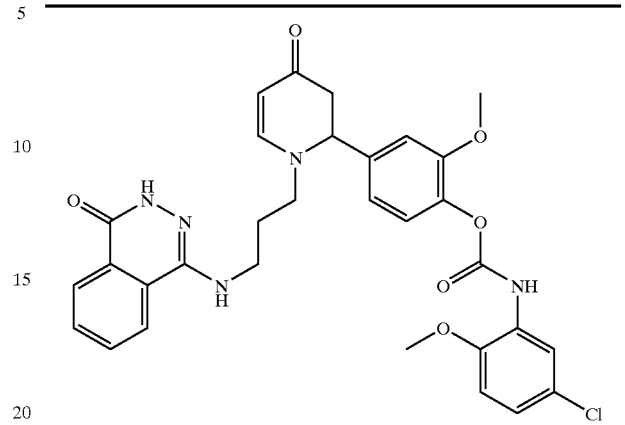
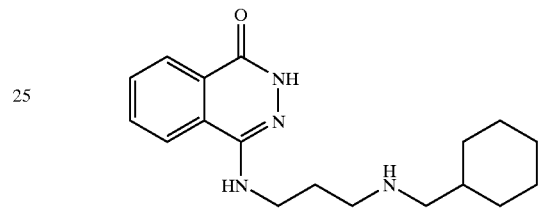
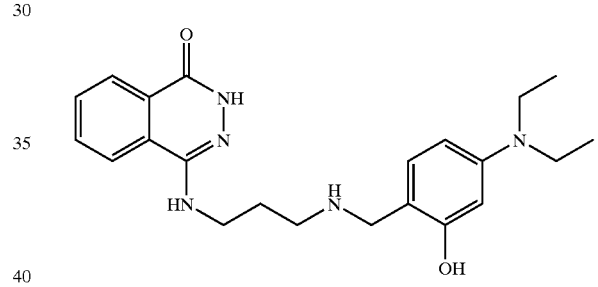
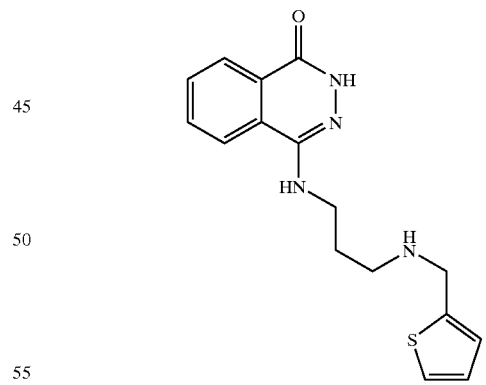
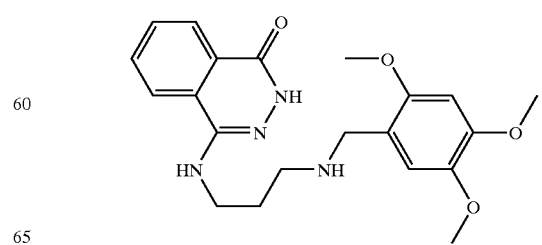

TABLE 1-continued
Representative compounds of Formula I.
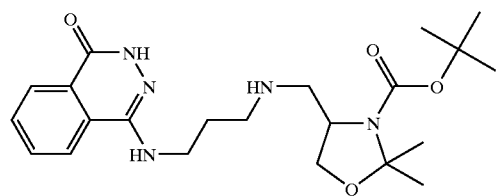
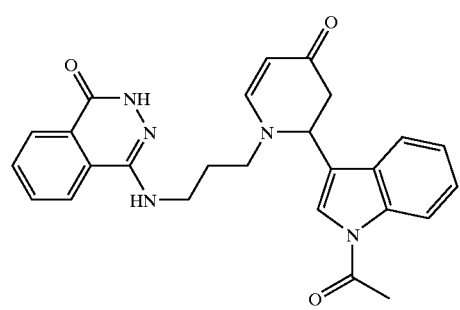
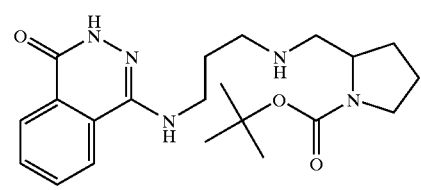
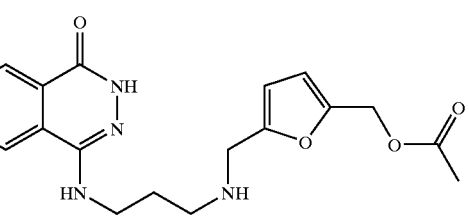
TABLE 1-continued
Representative compounds of Formula I.
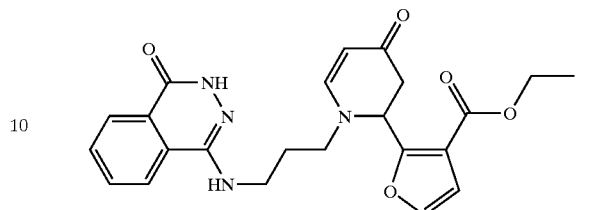
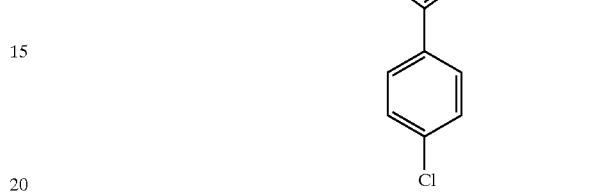
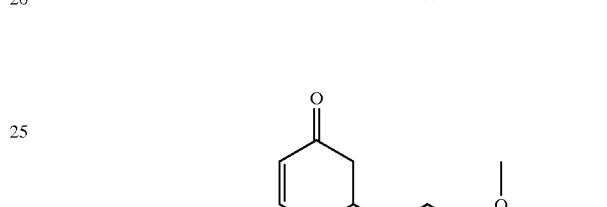
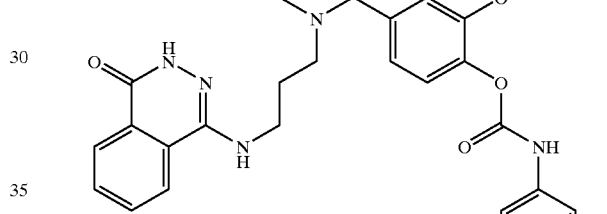
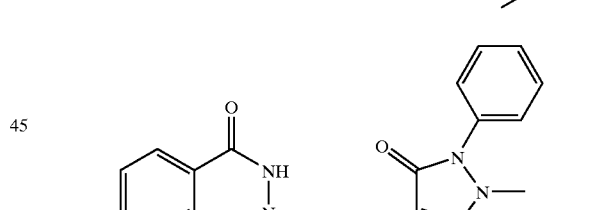
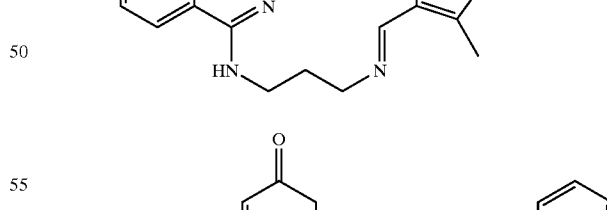
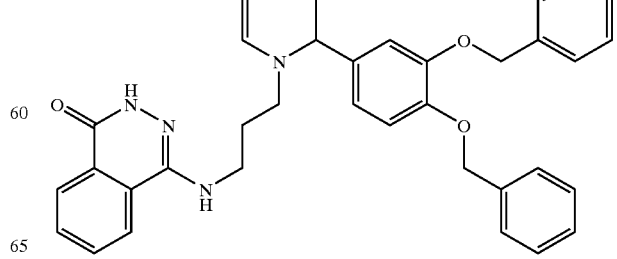

TABLE 1-continued
Representative compounds of Formula I.
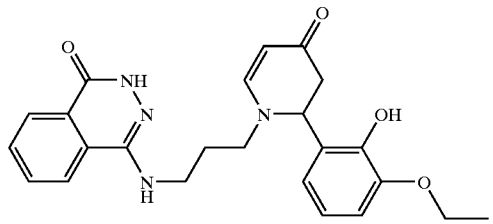
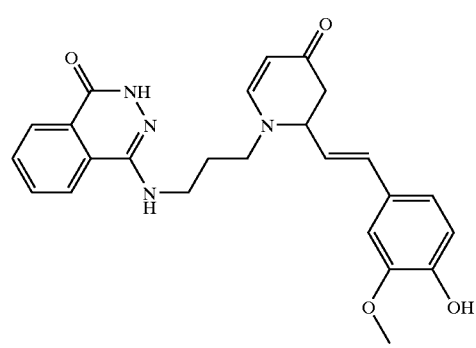
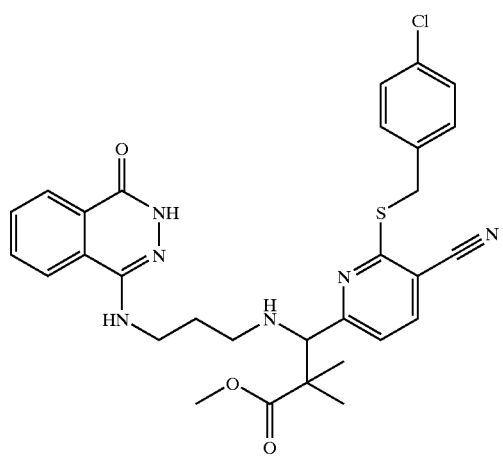
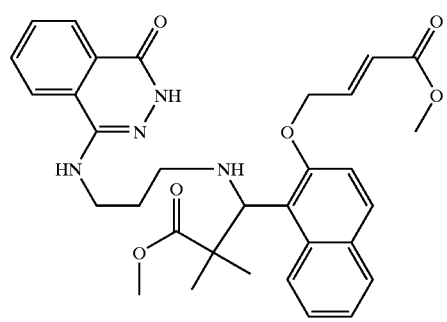
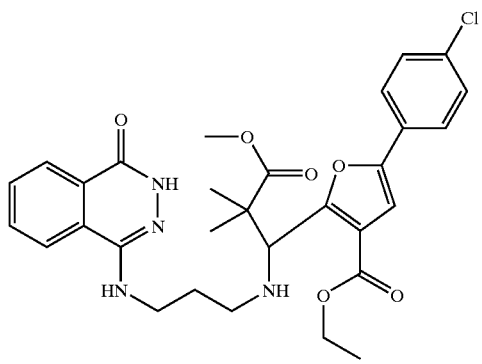
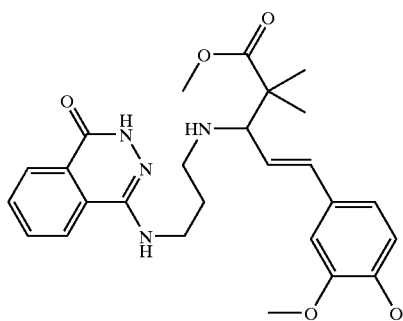
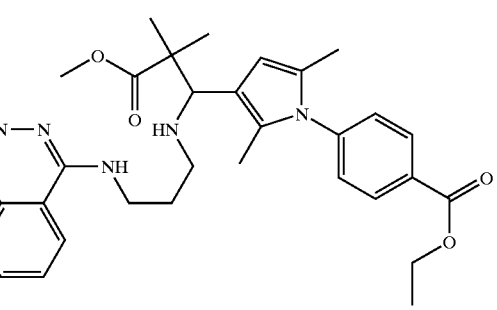

TABLE 1-continued
Representative compounds of Formula I.
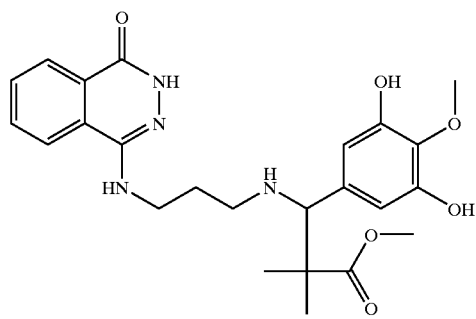
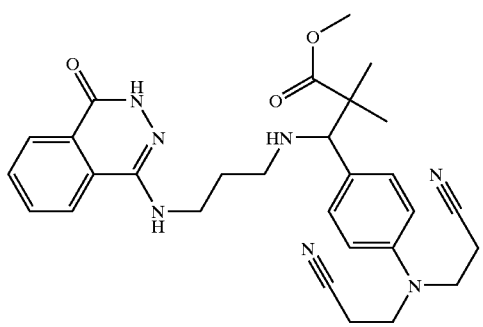
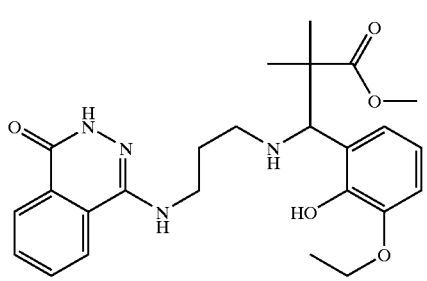
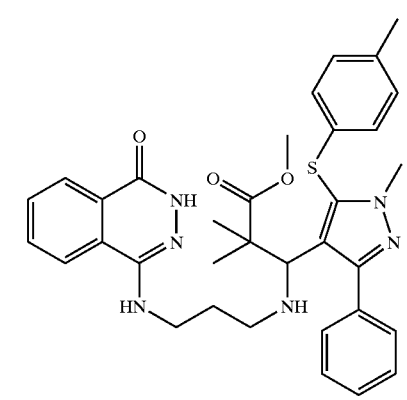
TABLE 1-continued
Representative compounds of Formula I.
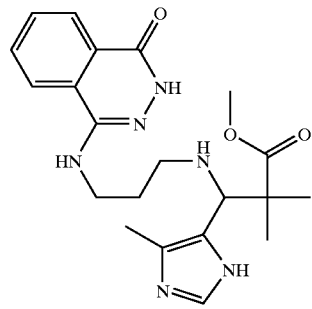
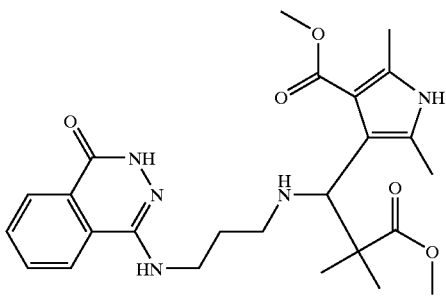
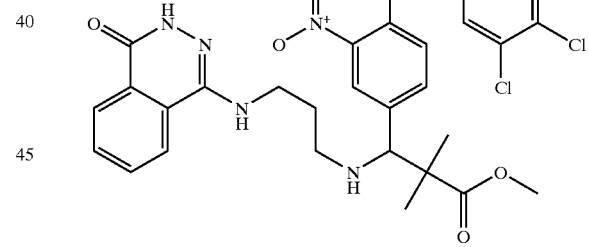
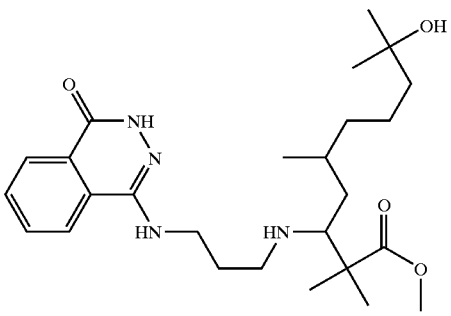

TABLE 1-continued

Representative compounds of Formula I.

TABLE 1-continued
Representative compounds of Formula I.
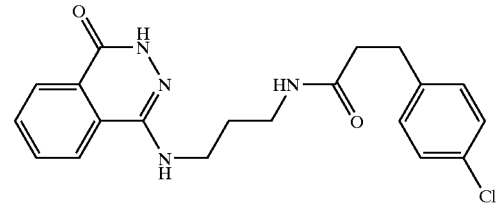
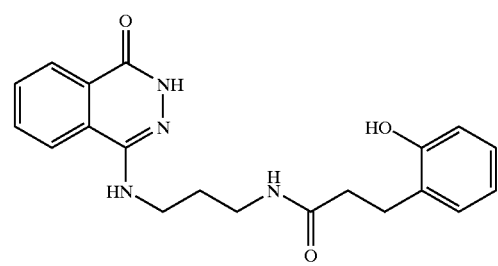
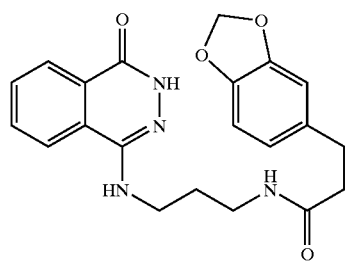
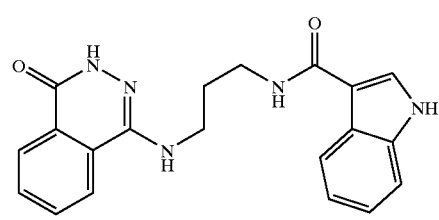
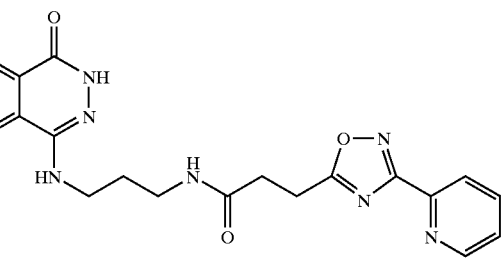
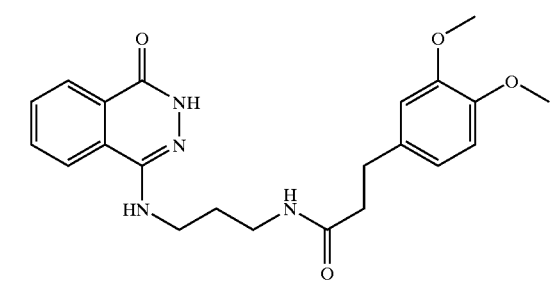
TABLE 1-continued
Representative compounds of Formula I.
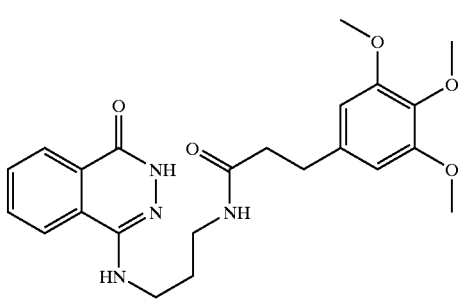
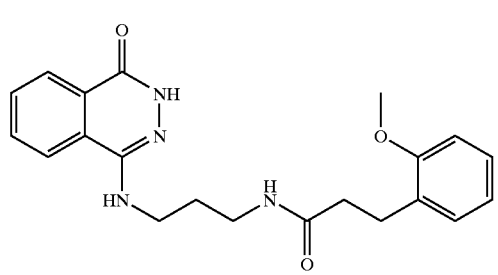
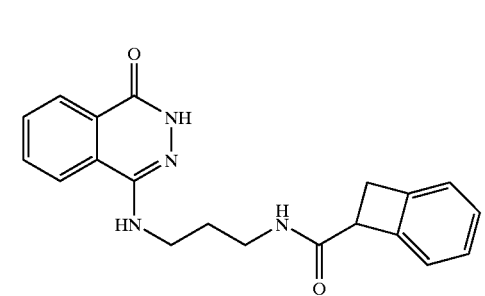
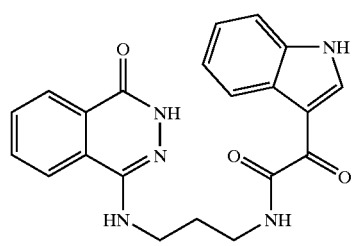
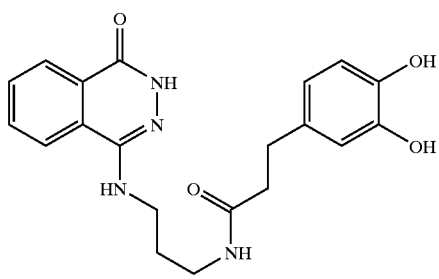

TABLE 1-continued
Representative compounds of Formula I.
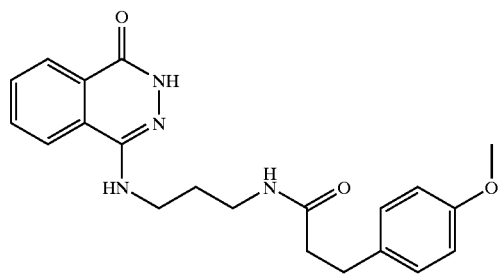
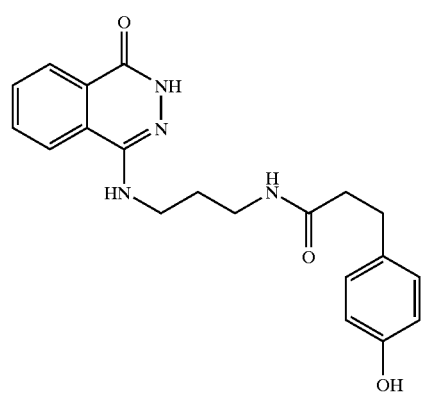
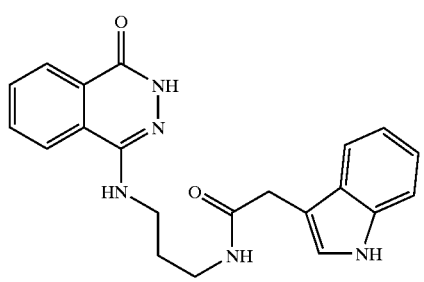
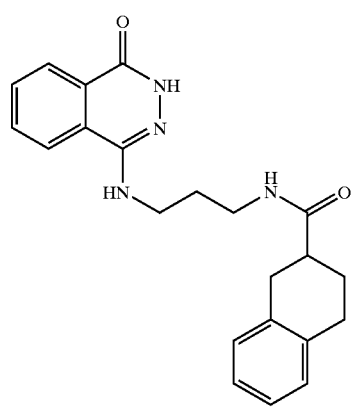

TABLE 1-continued
Representative compounds of Formula I.
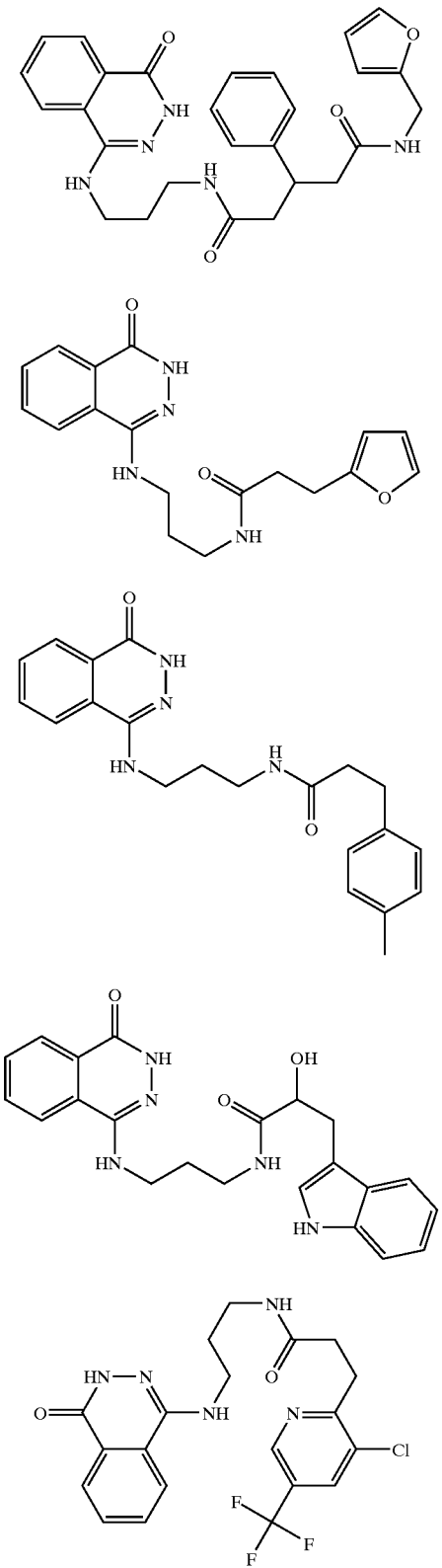
TABLE 1-continued
Representative compounds of Formula I.
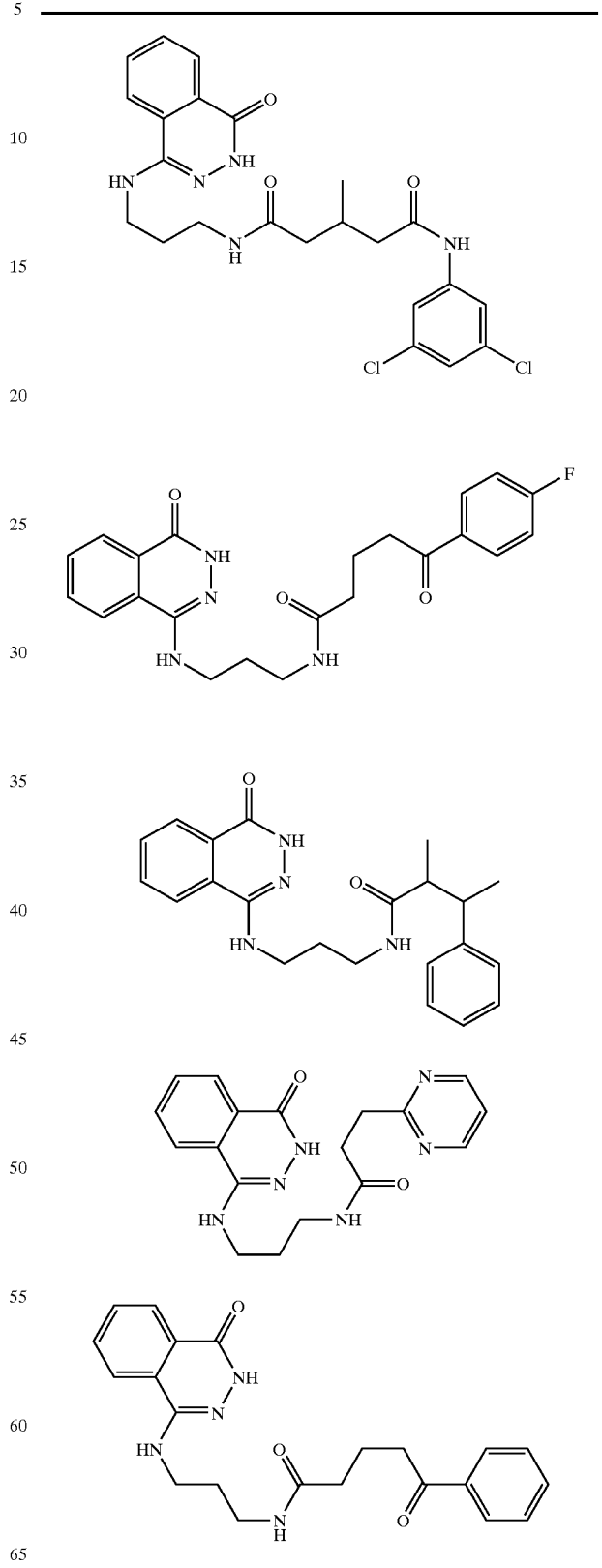

TABLE 1-continued

Representative compounds of Formula I.

TABLE 1-continued

Representative compounds of Formula I.

TABLE 1-continued
Representative compounds of Formula I.
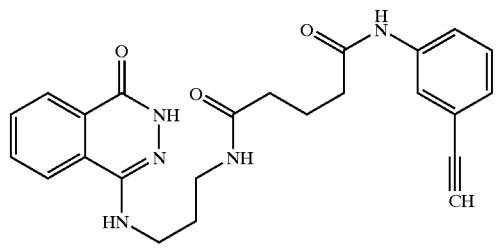
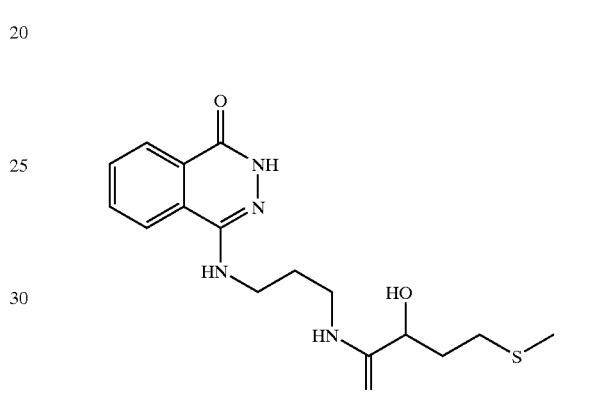
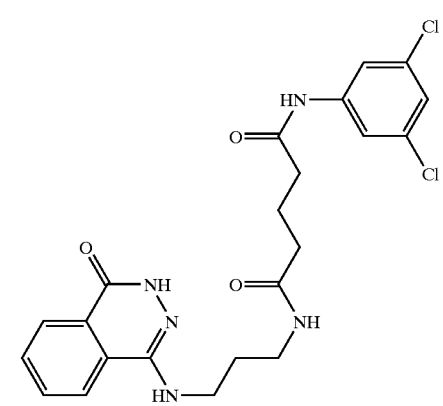
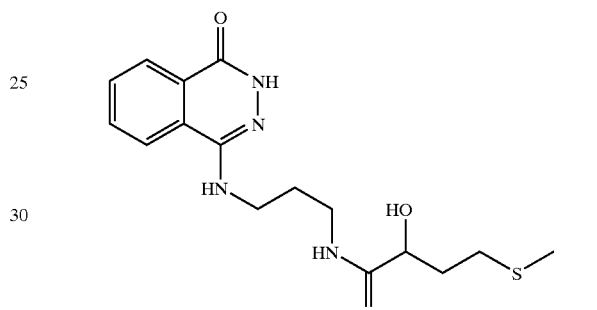
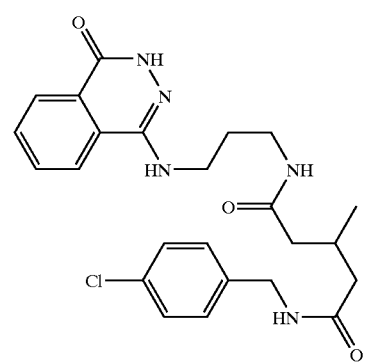
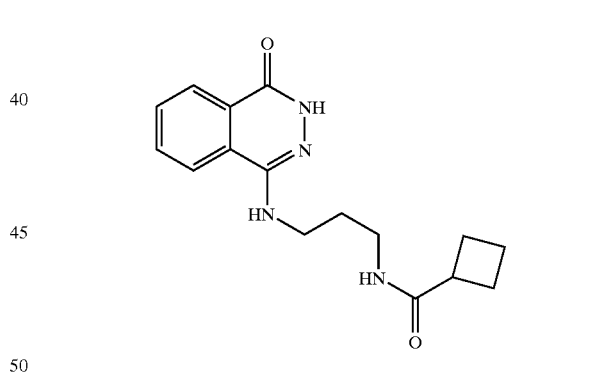
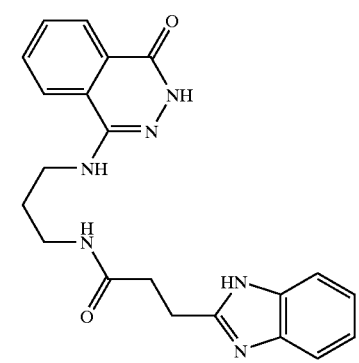
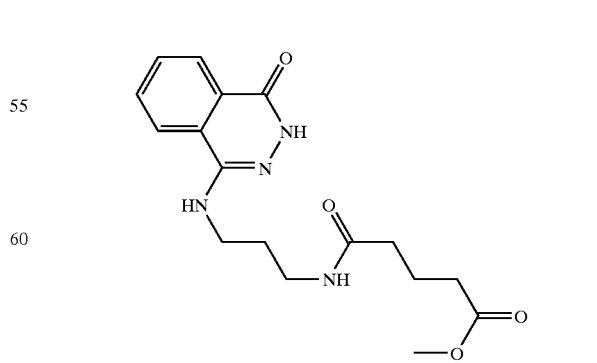

TABLE 1-continued
Representative compounds of Formula I.
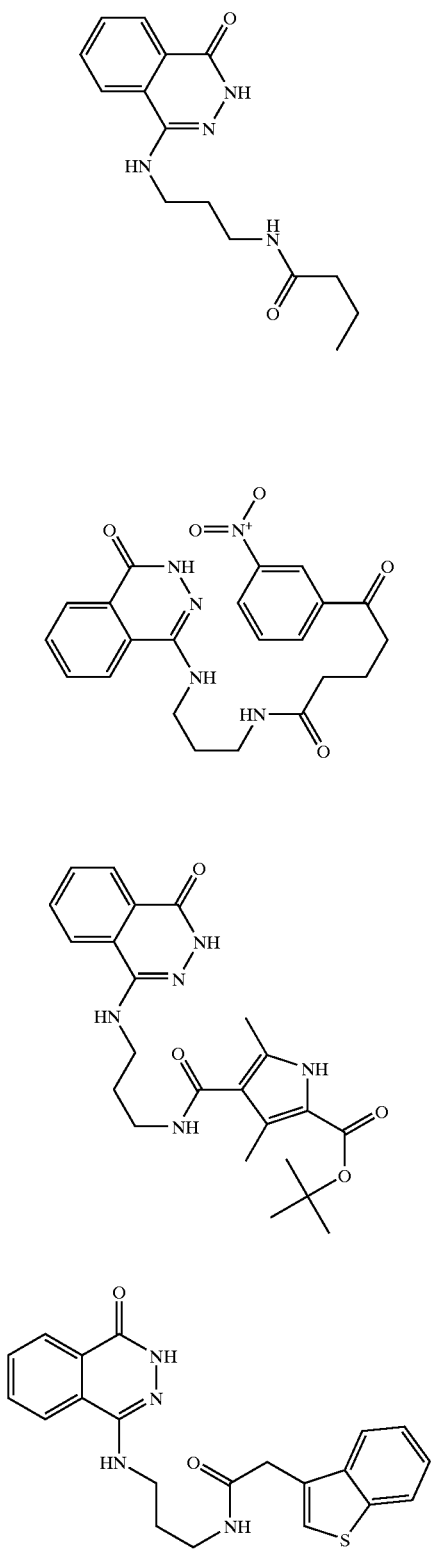
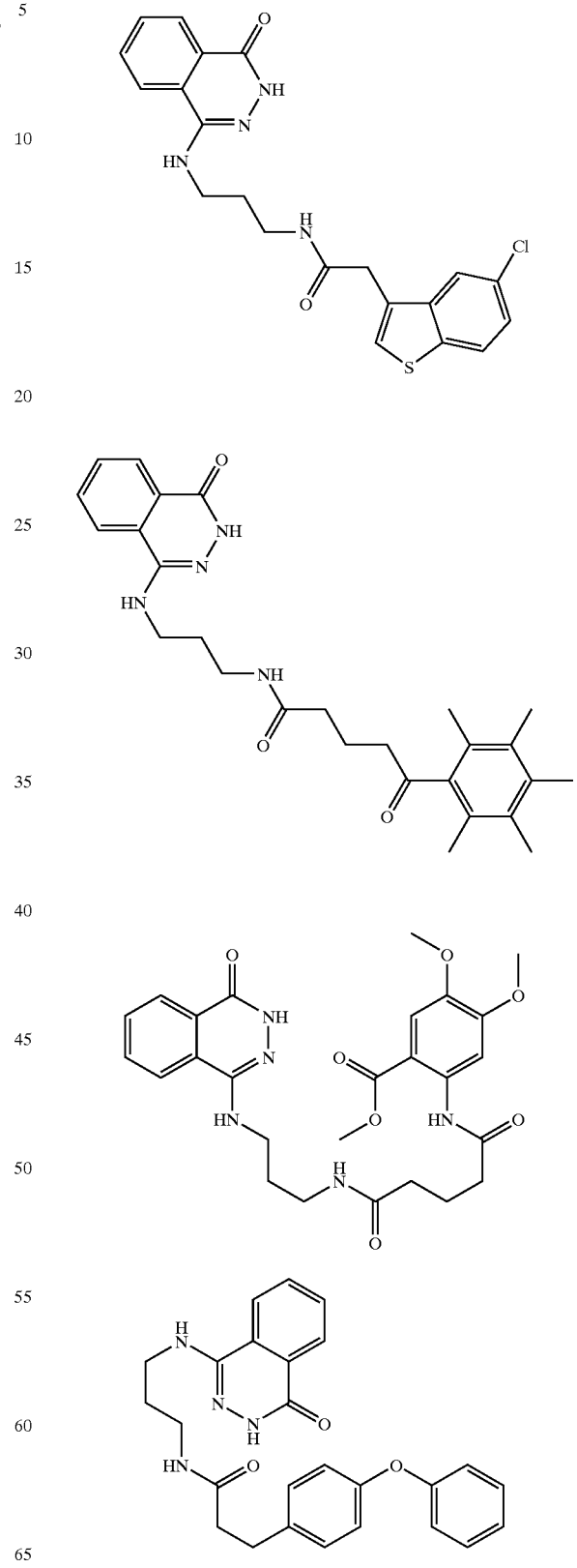

TABLE 1-continued
Representative compounds of Formula I.
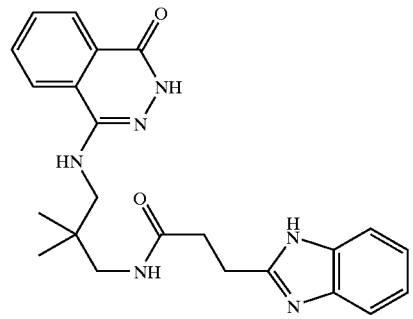
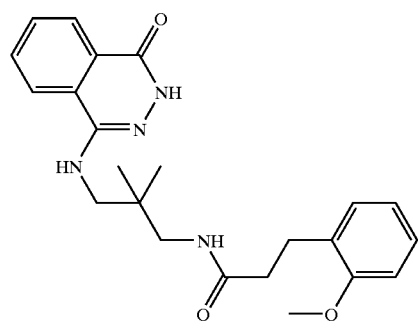
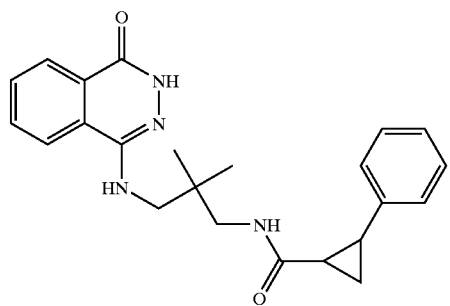
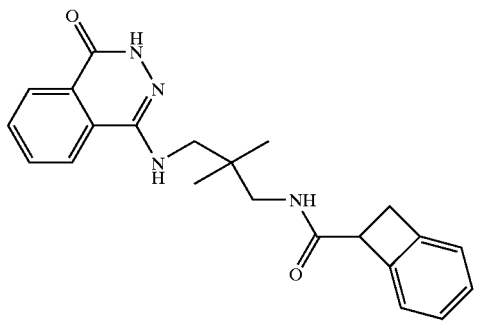
TABLE 1-continued
Representative compounds of Formula I.
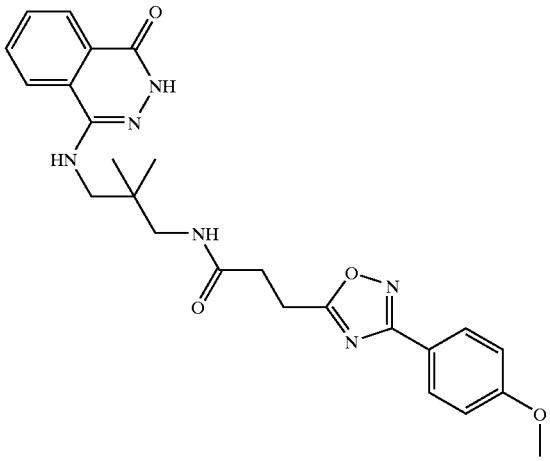
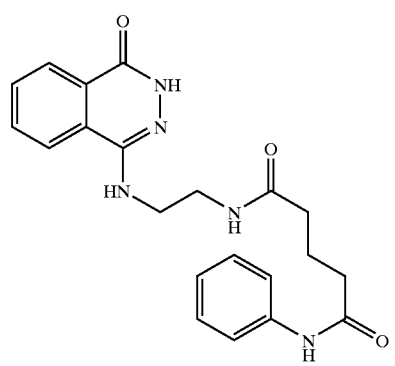
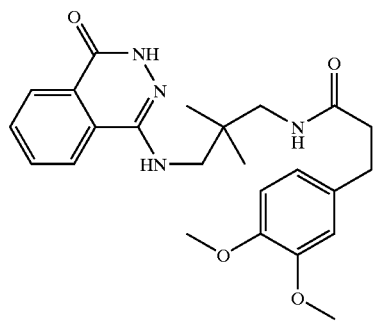
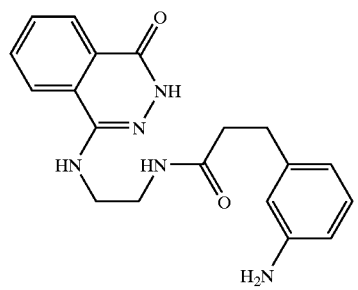

TABLE 1-continued
Representative compounds of Formula I.
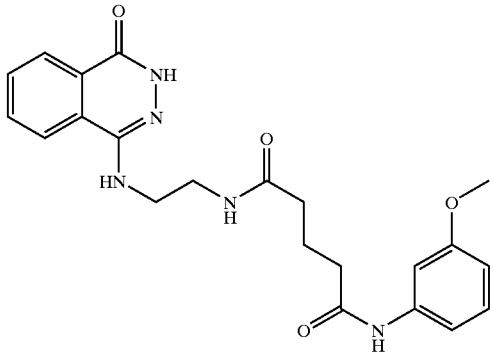
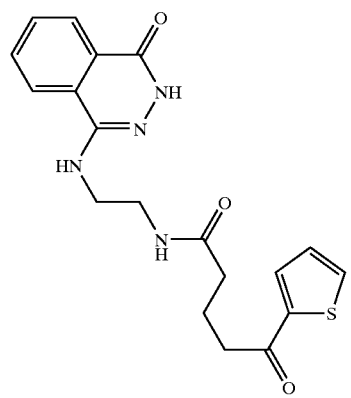
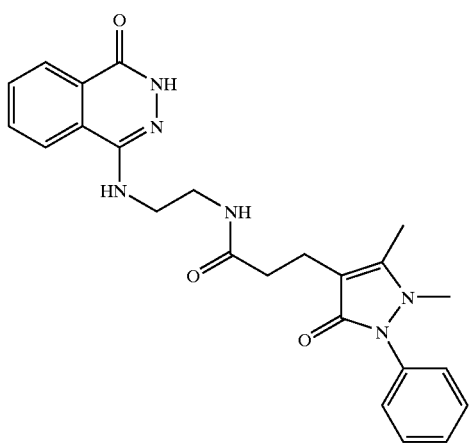
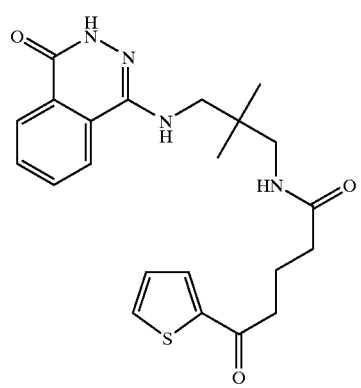
TABLE 1-continued
Representative compounds of Formula I.
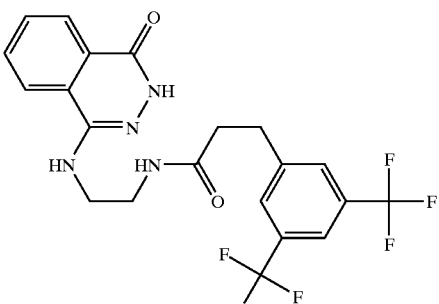
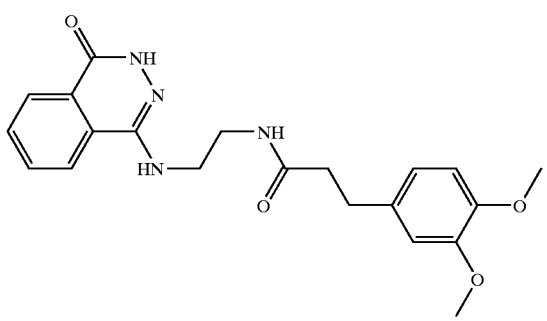
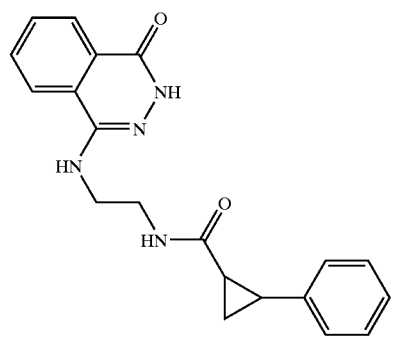
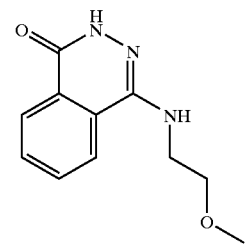
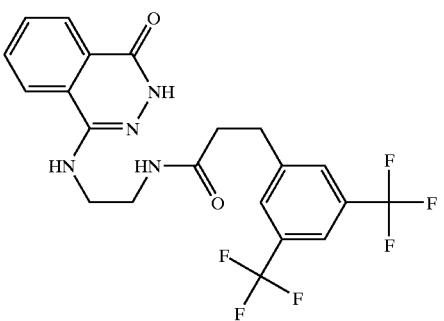

TABLE 1-continued
Representative compounds of Formula I.
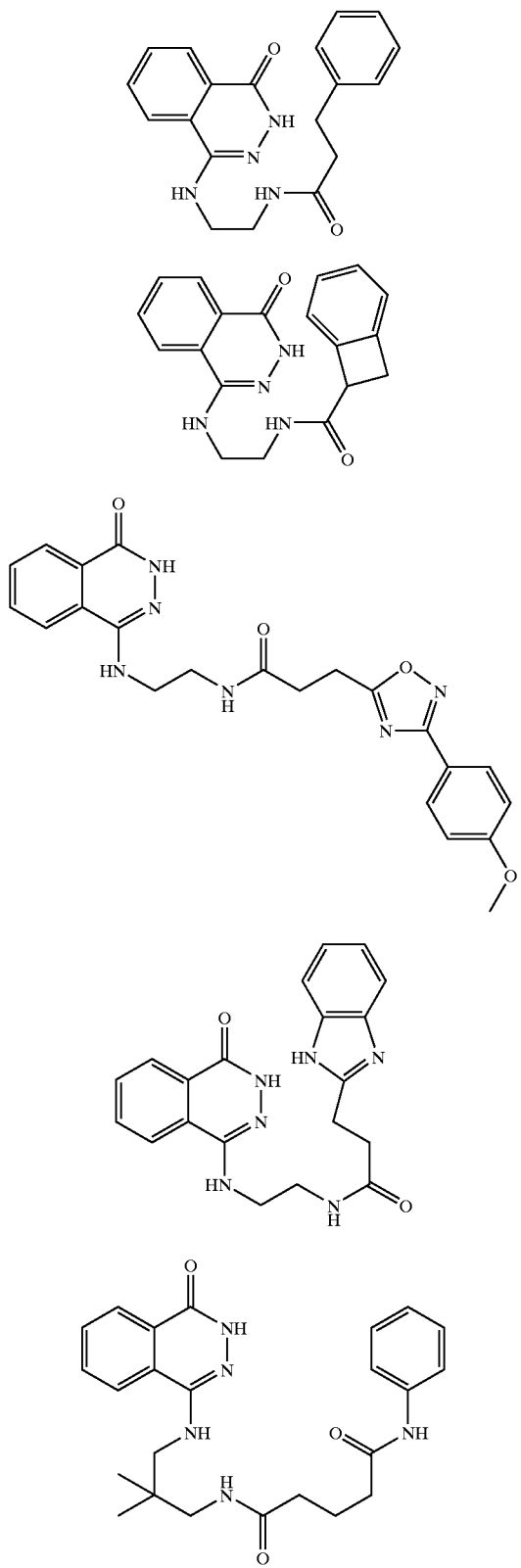
TABLE 1-continued
Representative compounds of Formula I.
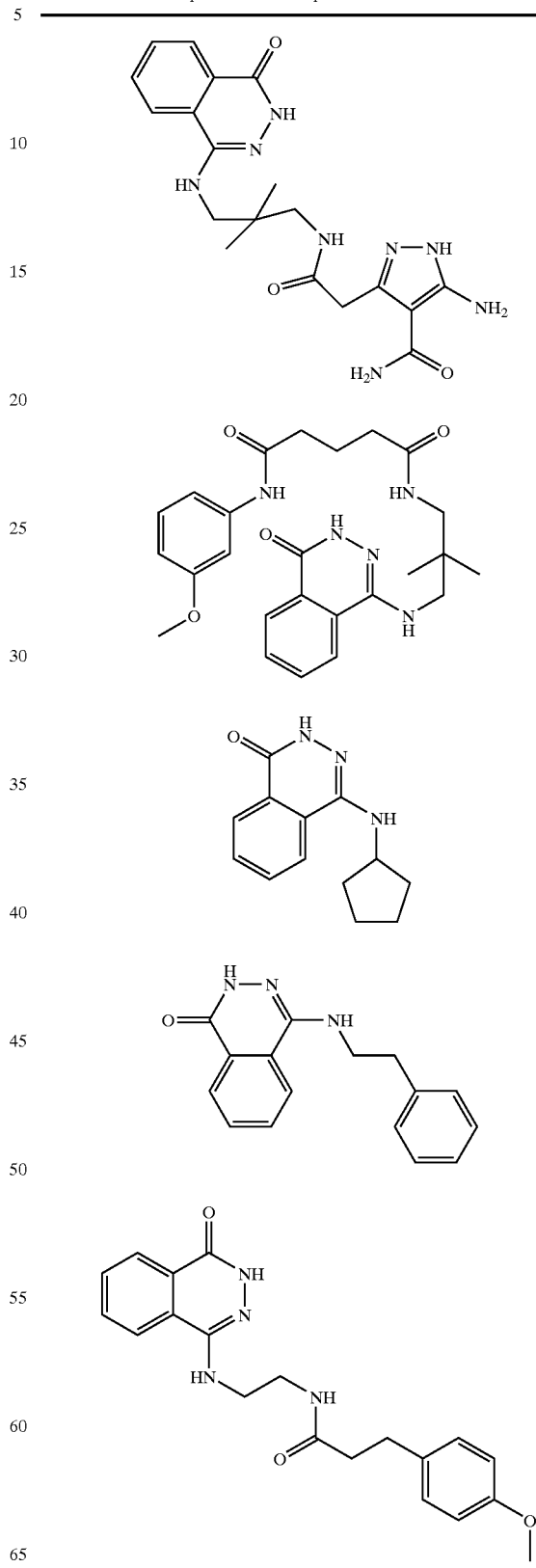

TABLE 1-continued
Representative compounds of Formula I.
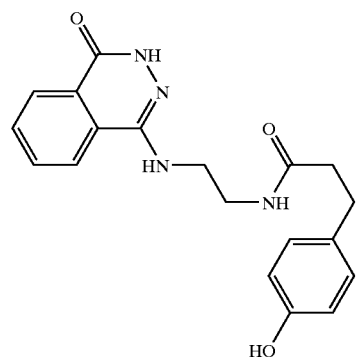
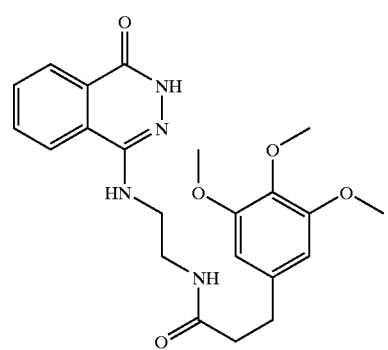
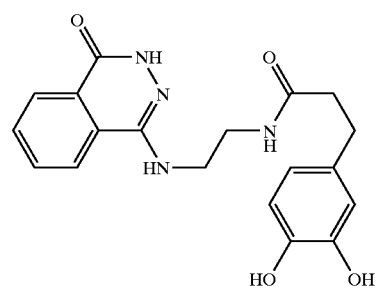
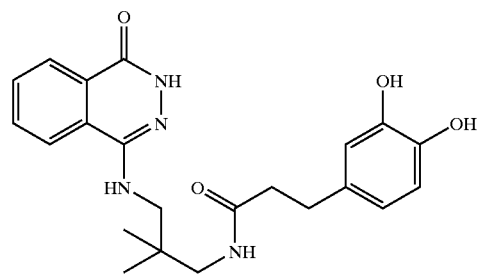
TABLE 1-continued
Representative compounds of Formula I.
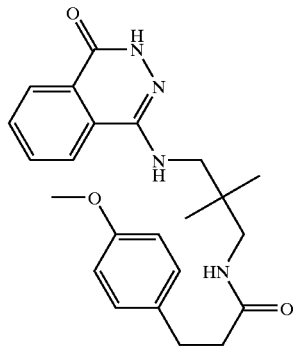
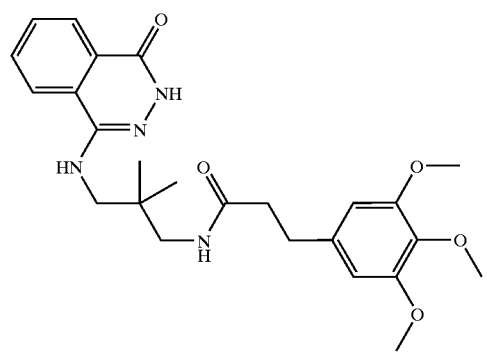
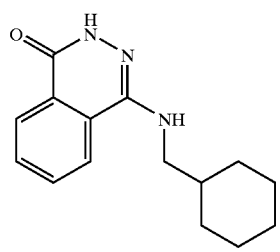
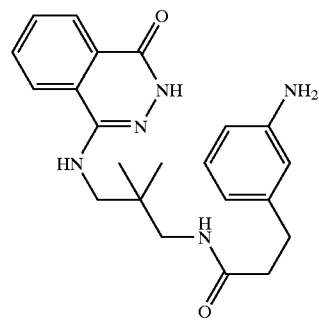

TABLE 1-continued
Representative compounds of Formula I.
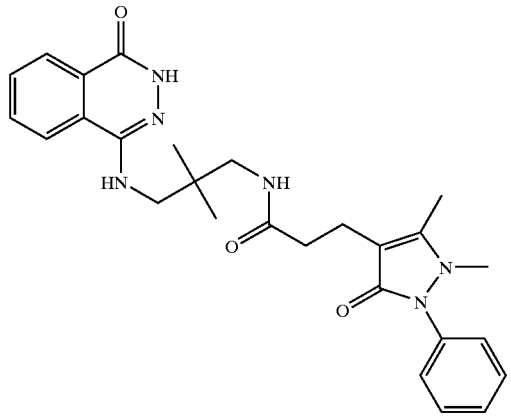
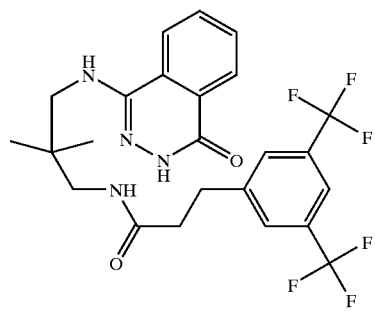
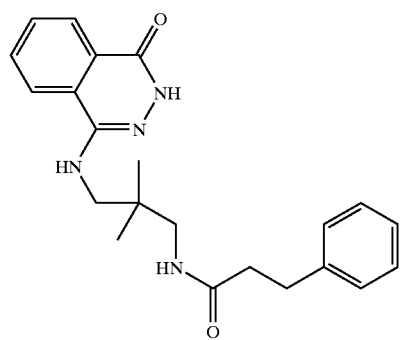
TABLE 1-continued
Representative compounds of Formula I.
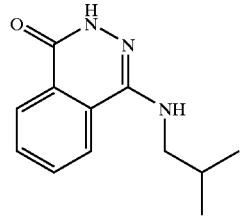
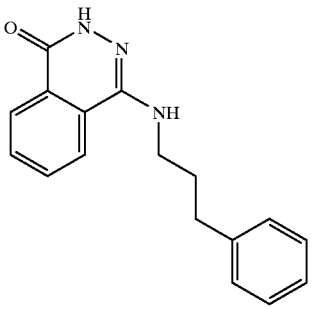
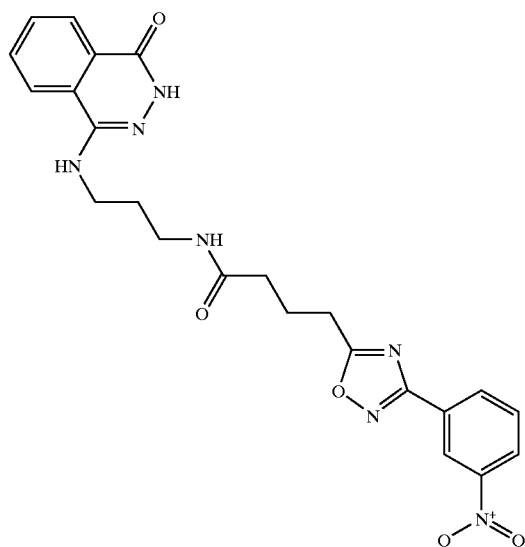
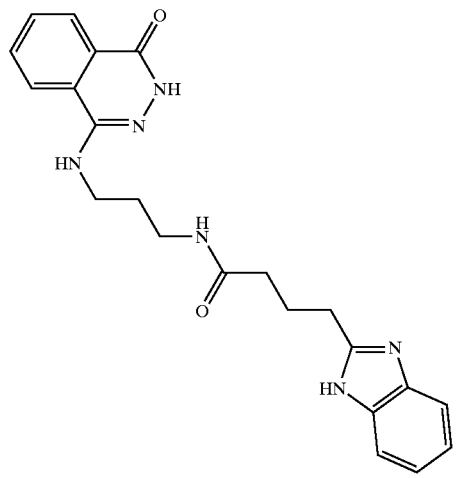

TABLE 1-continued
Representative compounds of Formula I.
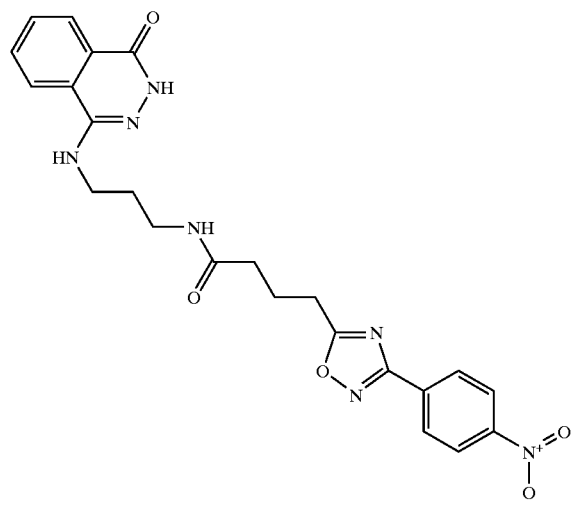
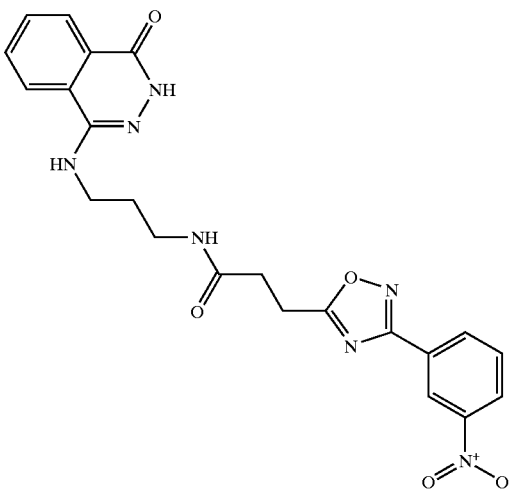
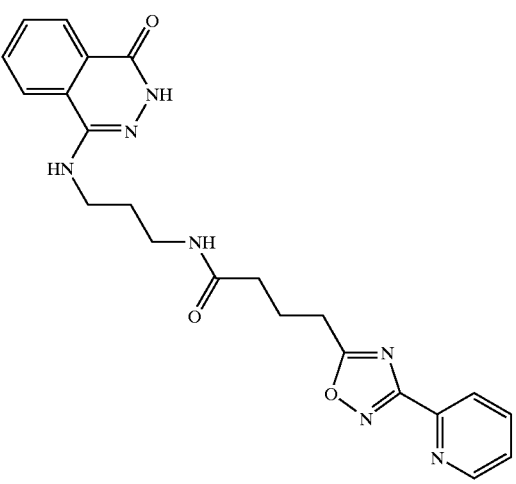
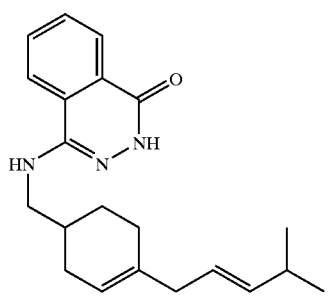

TABLE 1-continued
Representative compounds of Formula I.
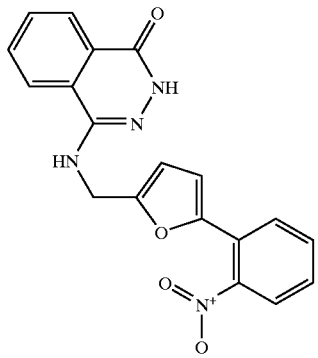
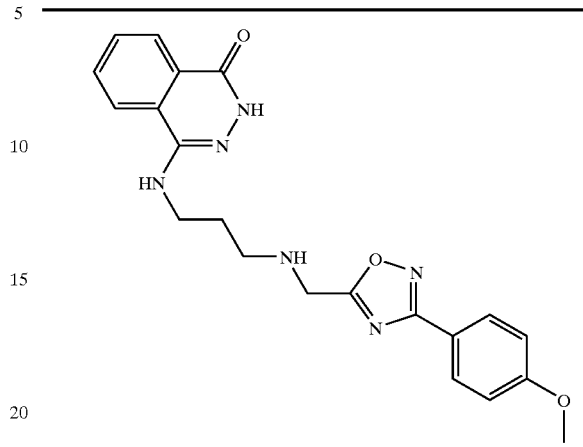
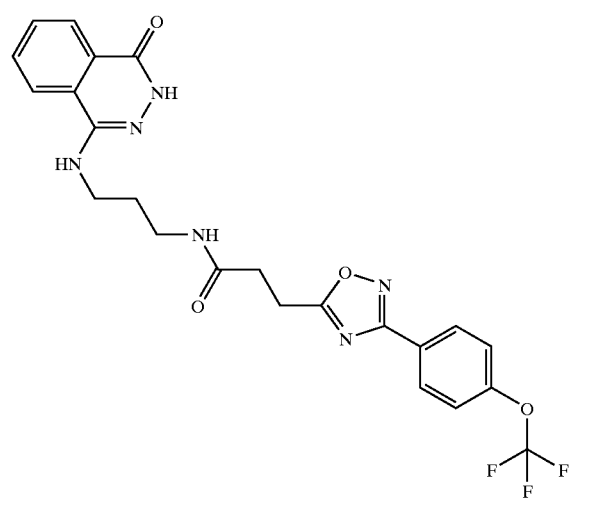
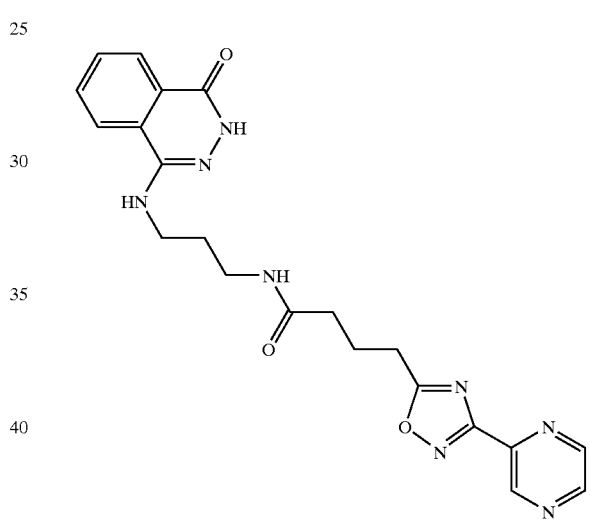
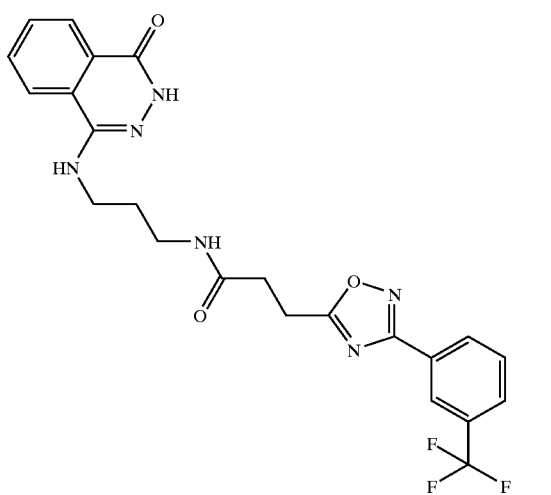
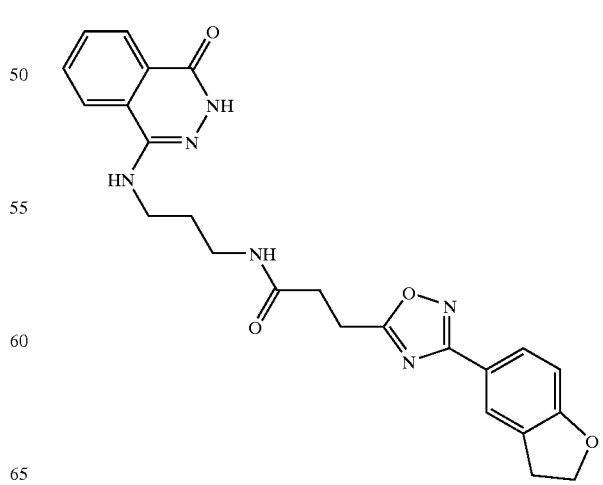

TABLE 1-continued
Representative compounds of Formula I.
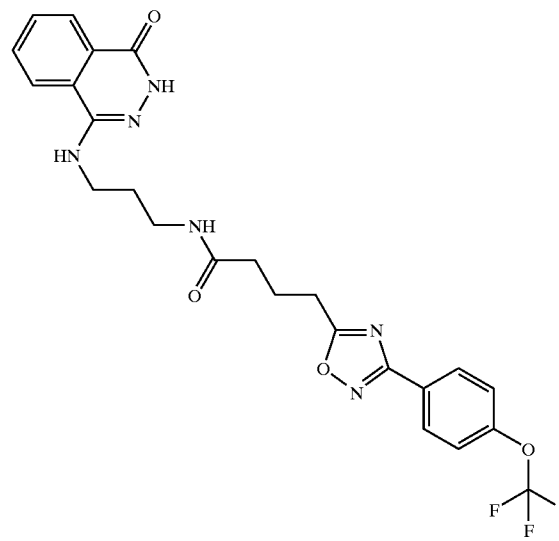
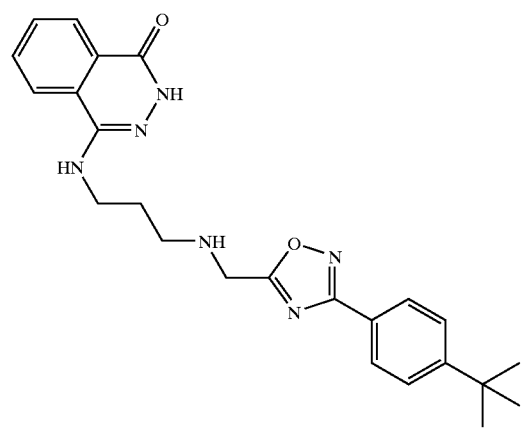
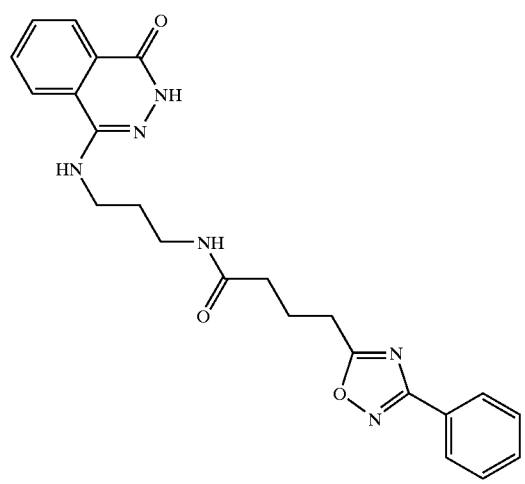
TABLE 1-continued
Representative compounds of Formula I.
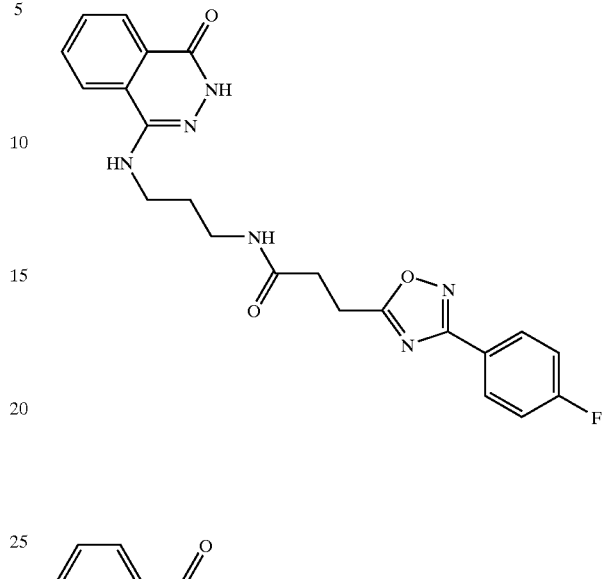
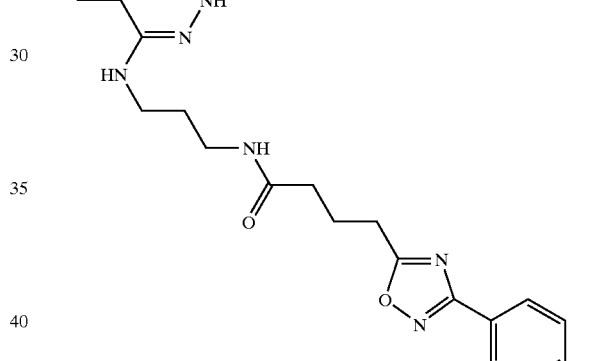
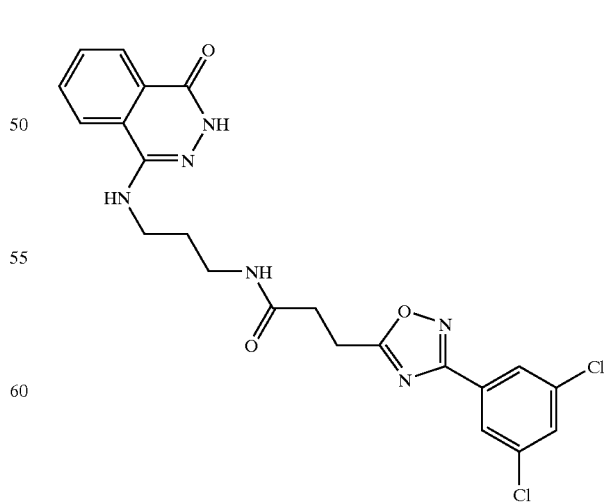

TABLE 1-continued
Representative compounds of Formula I.
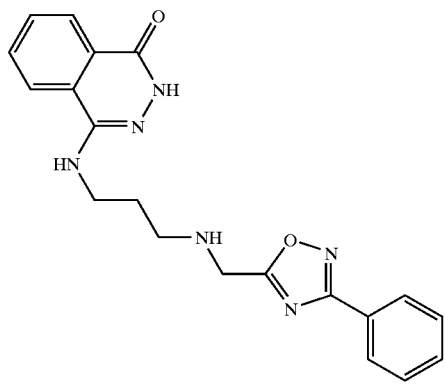
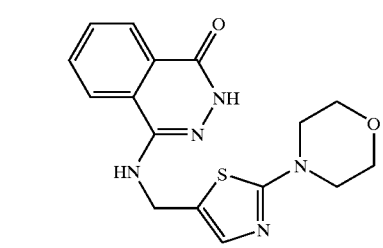
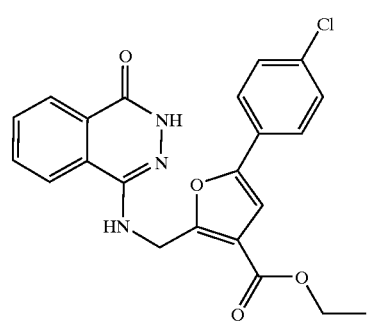
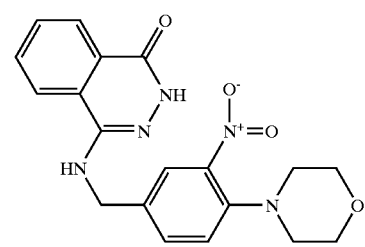
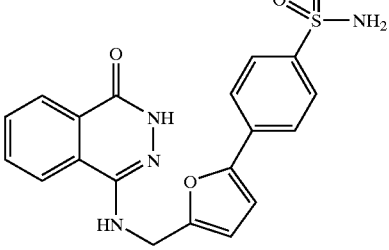
TABLE 1-continued
Representative compounds of Formula I.
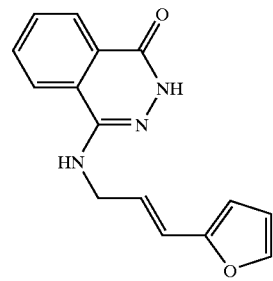
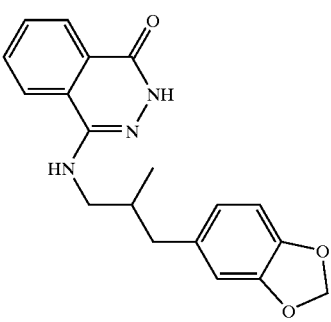
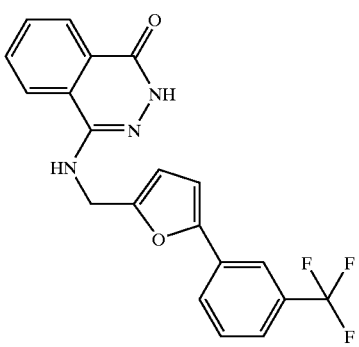
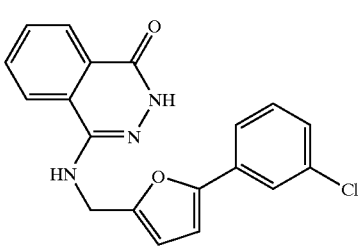
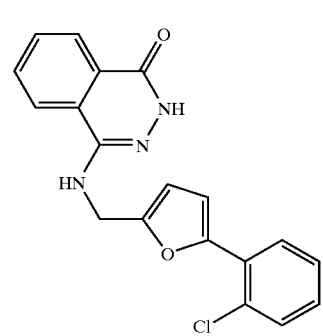

TABLE 1-continued
Representative compounds of Formula I.
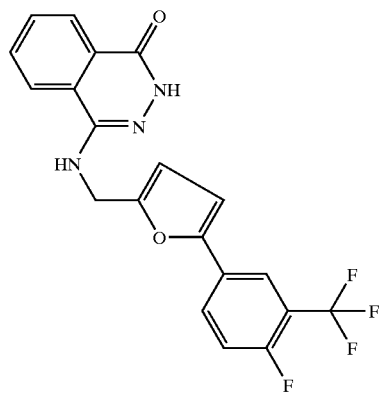
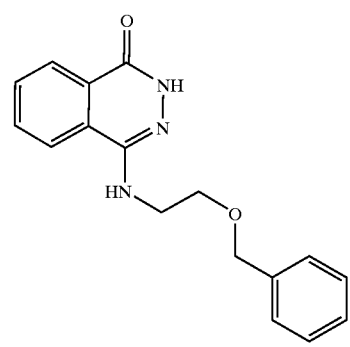
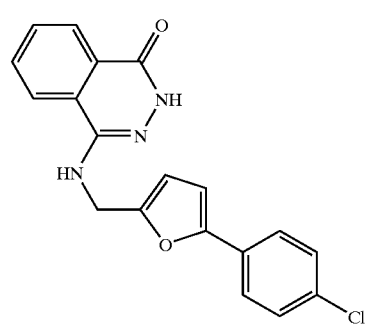
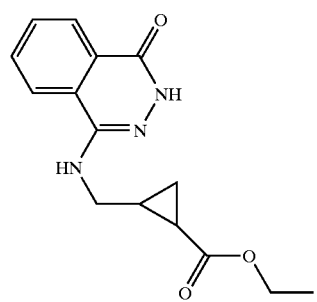
TABLE 1-continued
Representative compounds of Formula I.
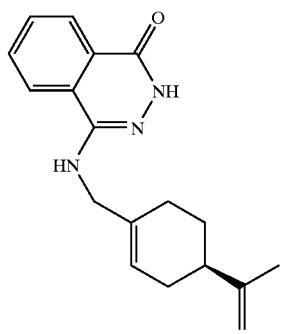
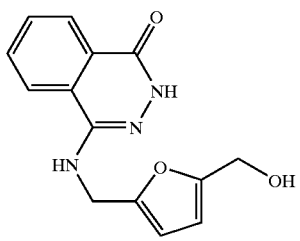
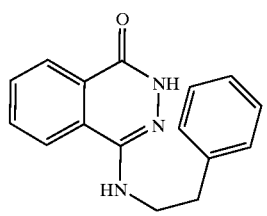
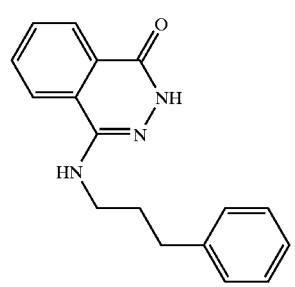
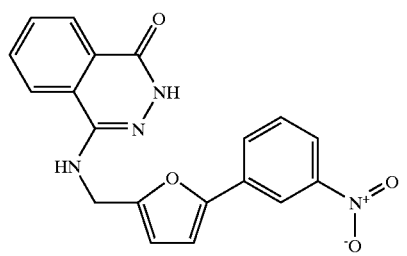

TABLE 1-continued
Representative compounds of Formula I.
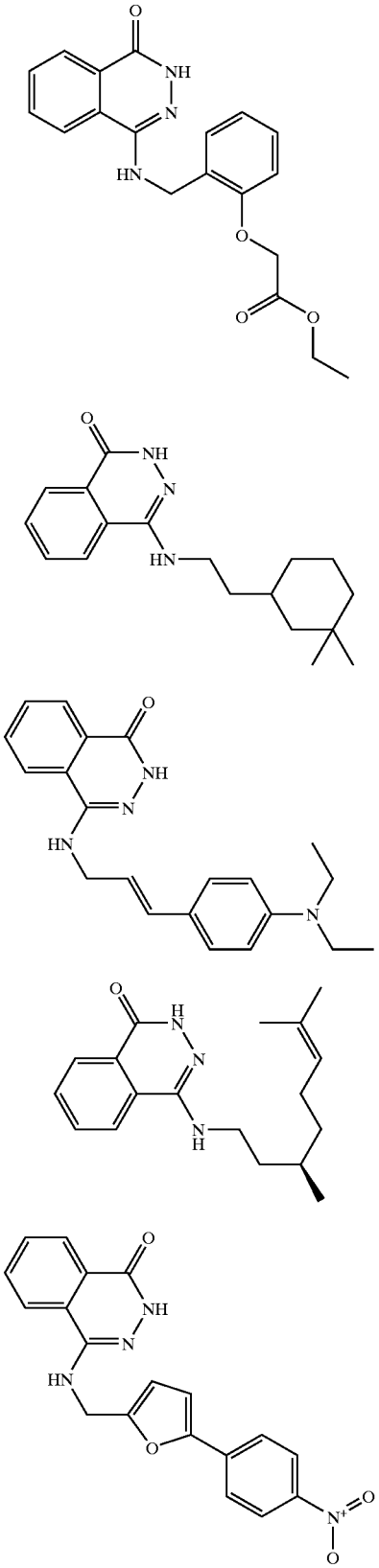
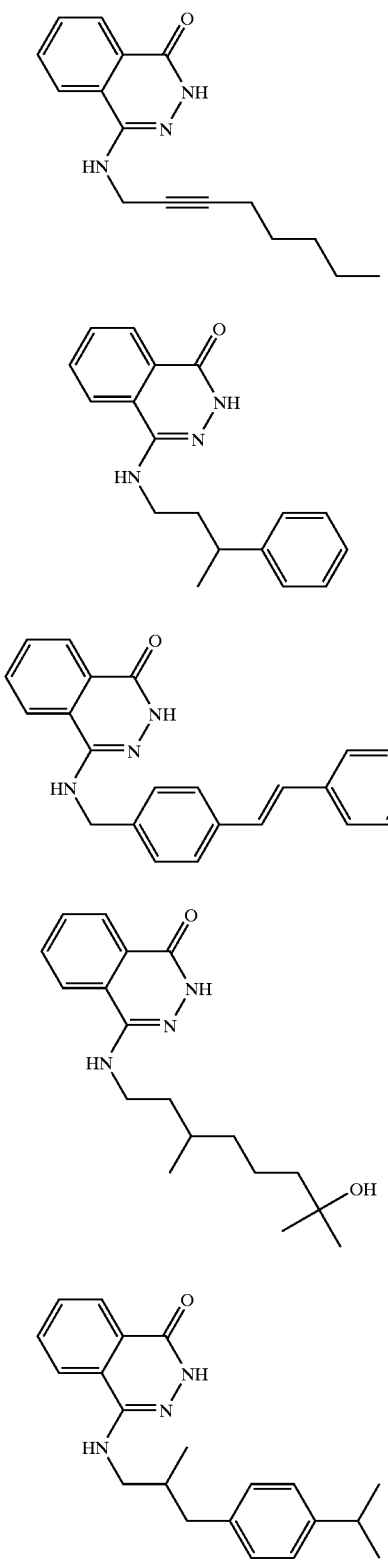

TABLE 1-continued
Representative compounds of Formula I.
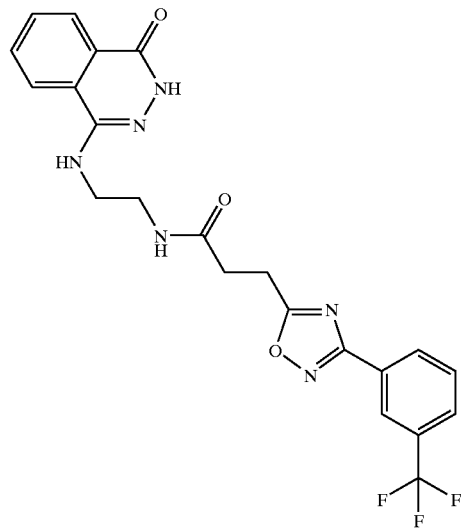
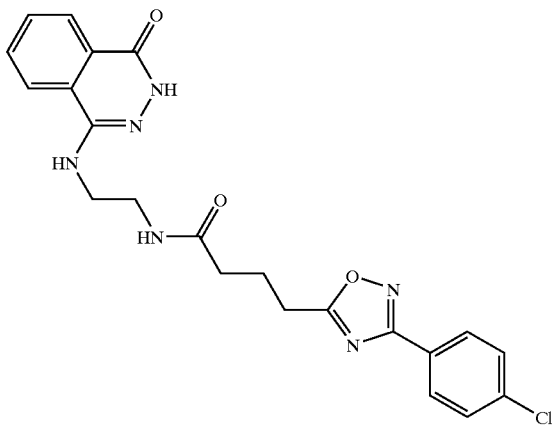
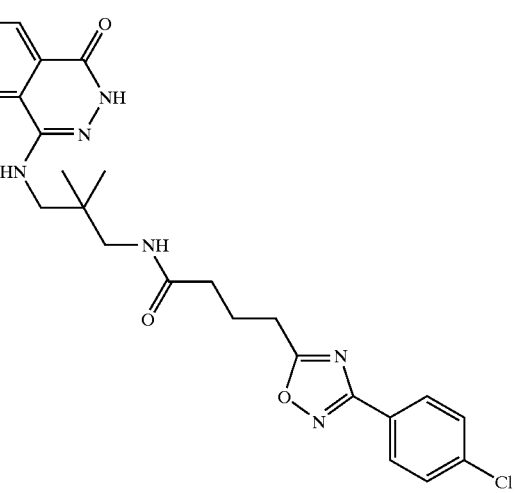

TABLE 1-continued

Representative compounds of Formula I.

TABLE 1-continued
Representative compounds of Formula I.
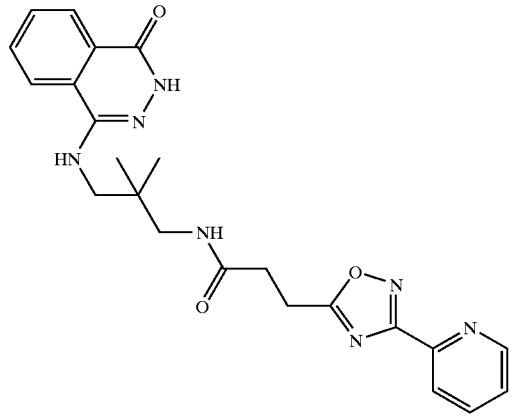
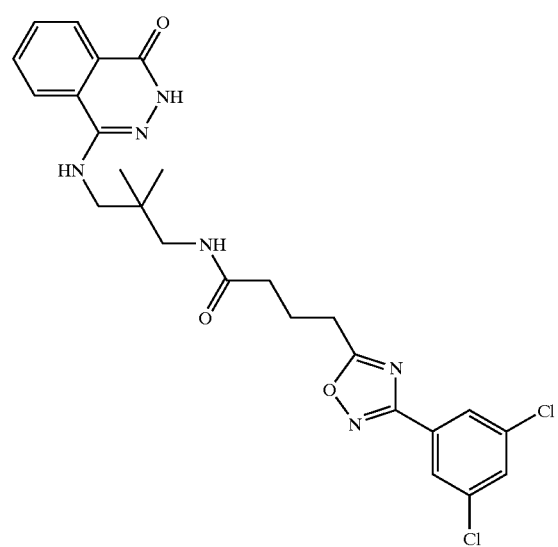
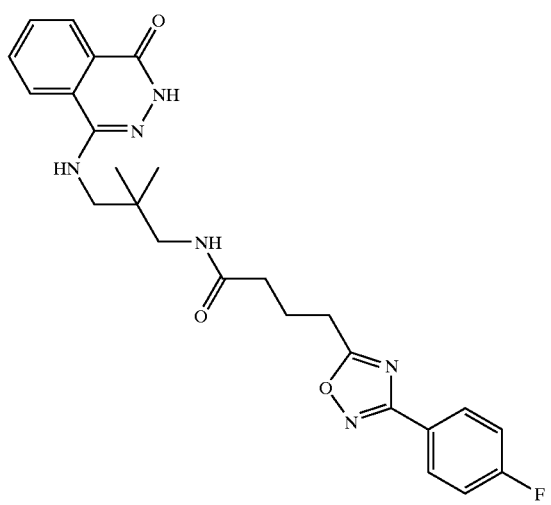
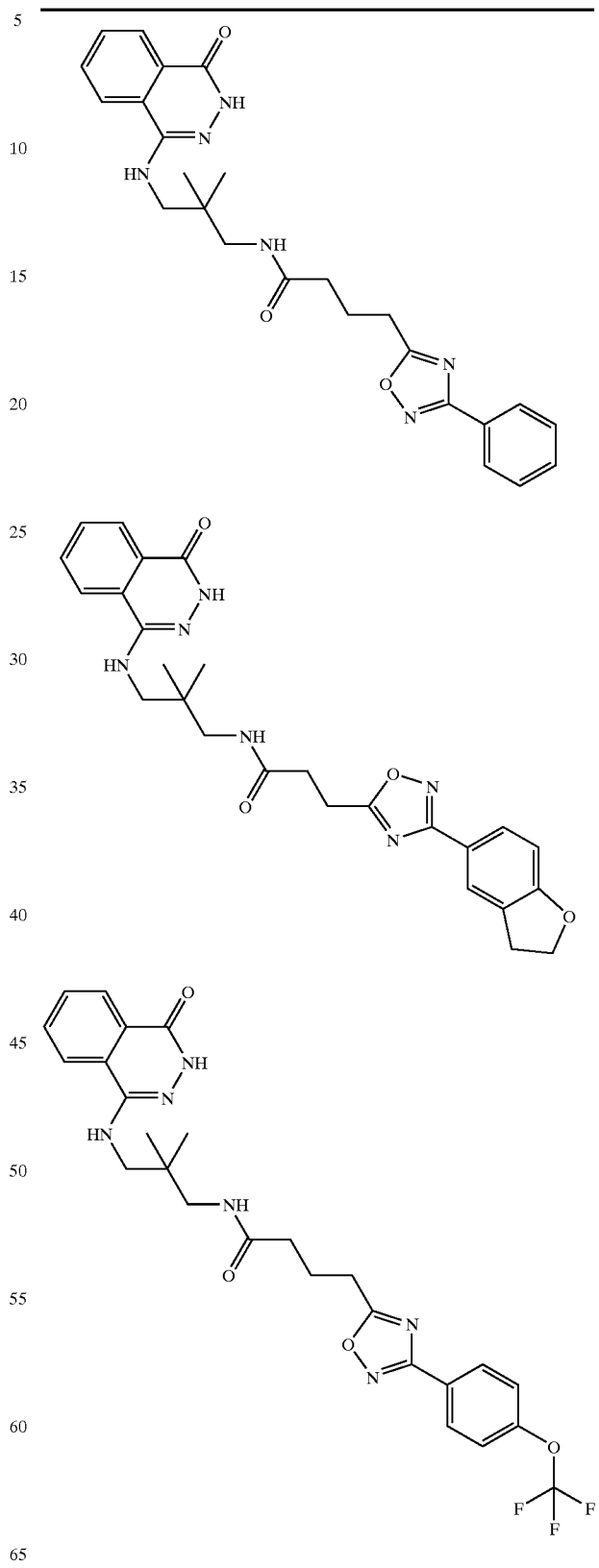

TABLE 1-continued
Representative compounds of Formula I.
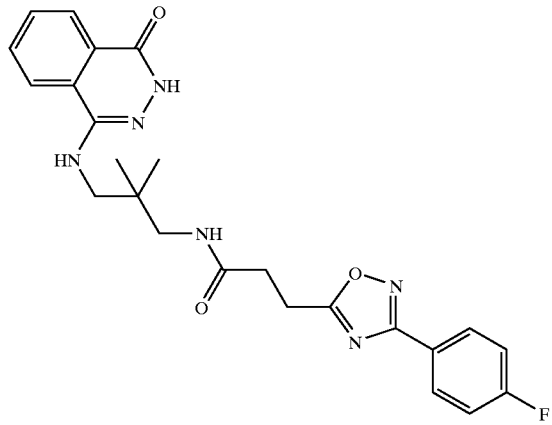
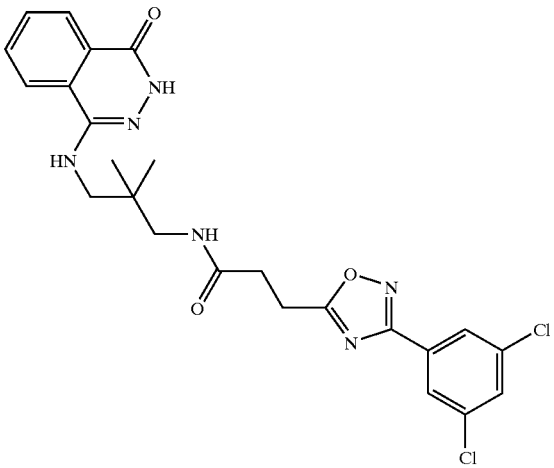
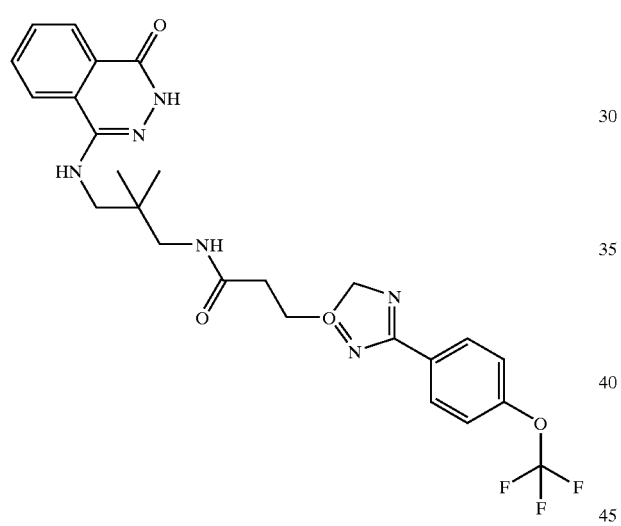
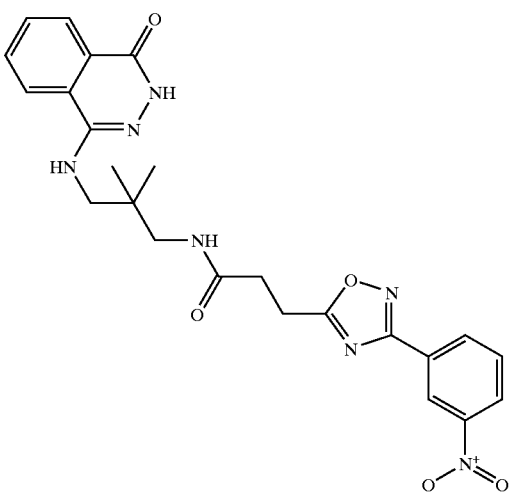
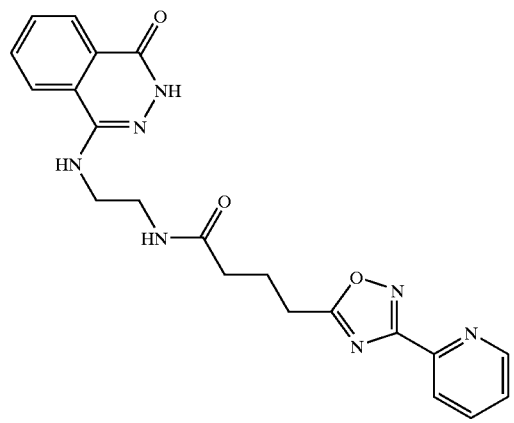
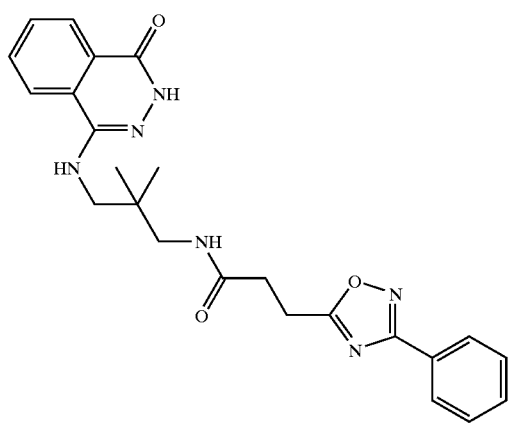

TABLE 1-continued
Representative compounds of Formula I.
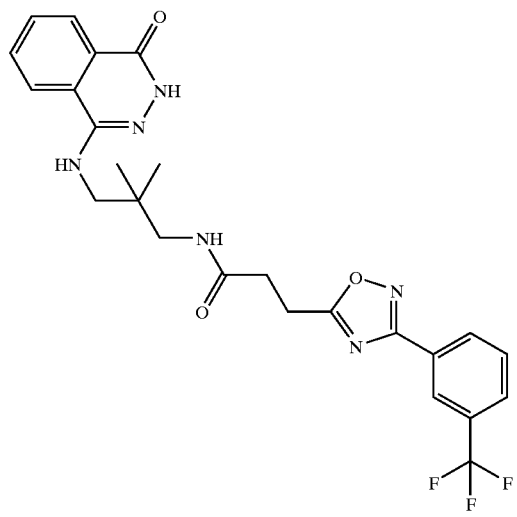
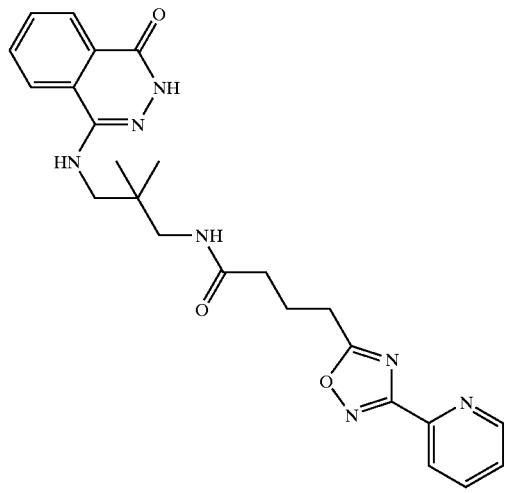
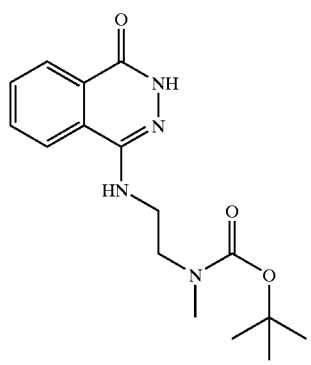

TABLE 1-continued
Representative compounds of Formula I.
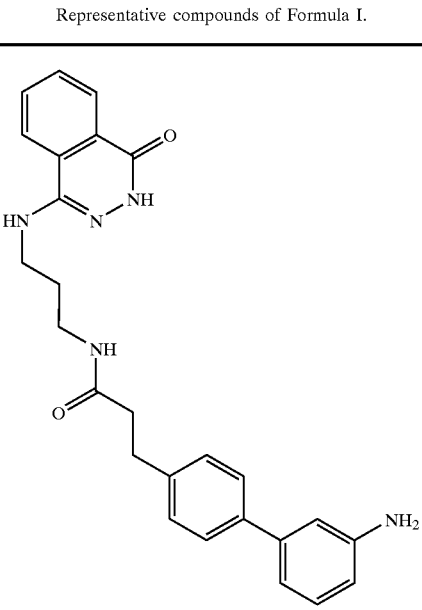
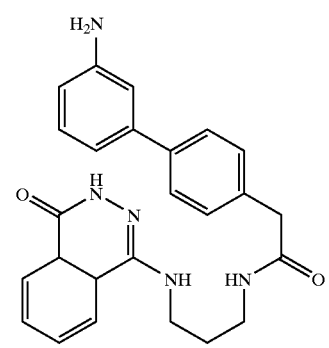
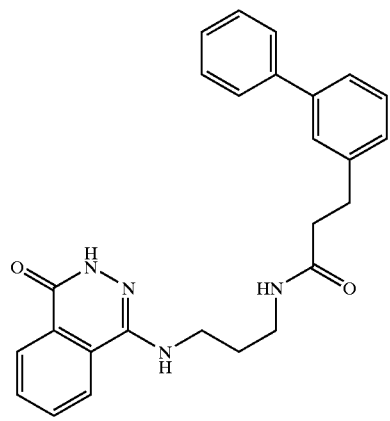
TABLE 1-continued
Representative compounds of Formula I.
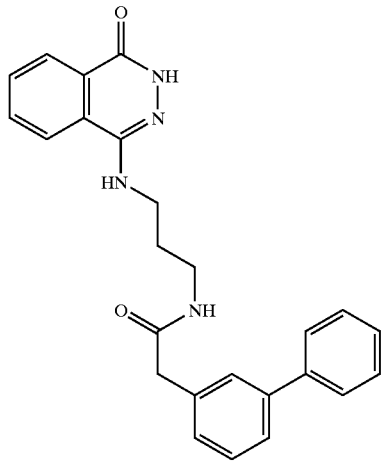
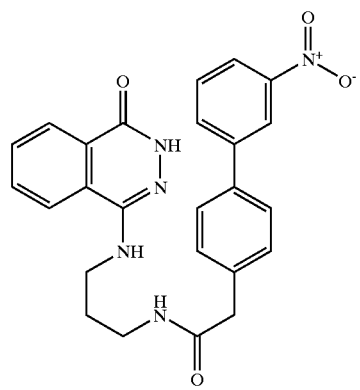
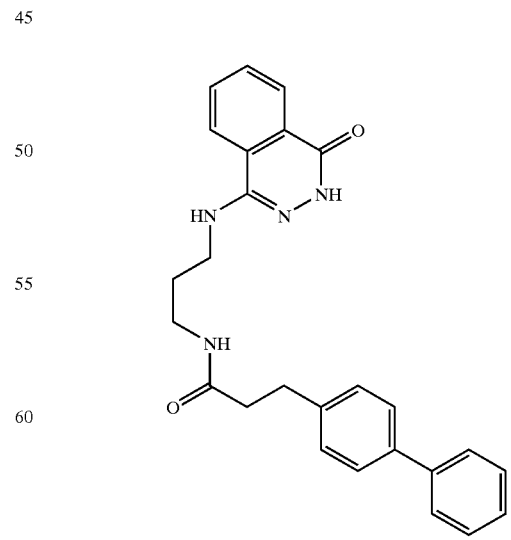

TABLE 1-continued
Representative compounds of Formula I.
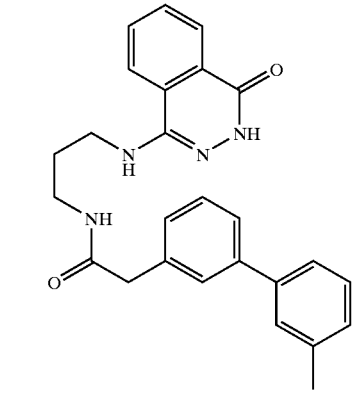
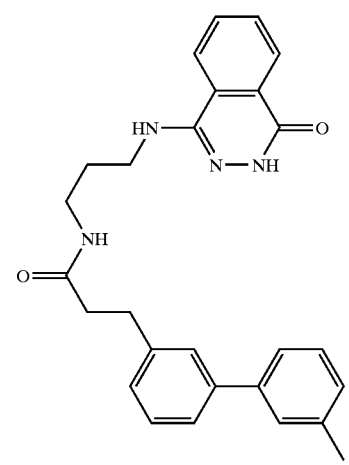
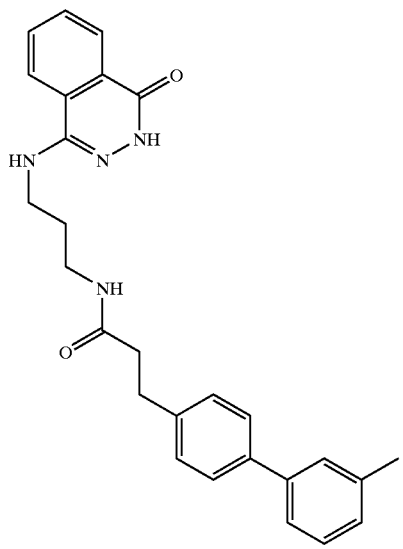
TABLE 1-continued
Representative compounds of Formula I.
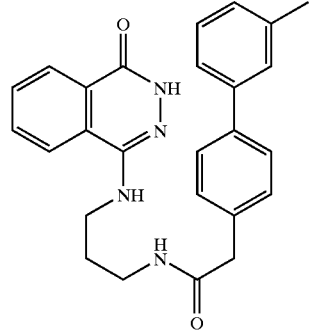
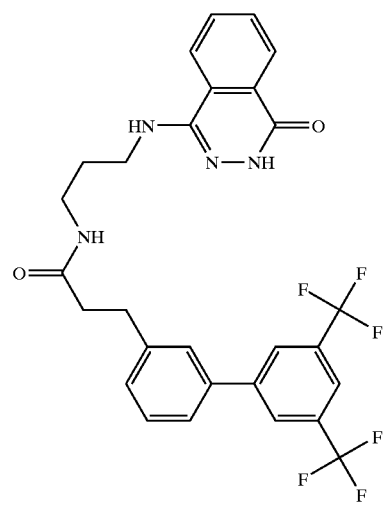
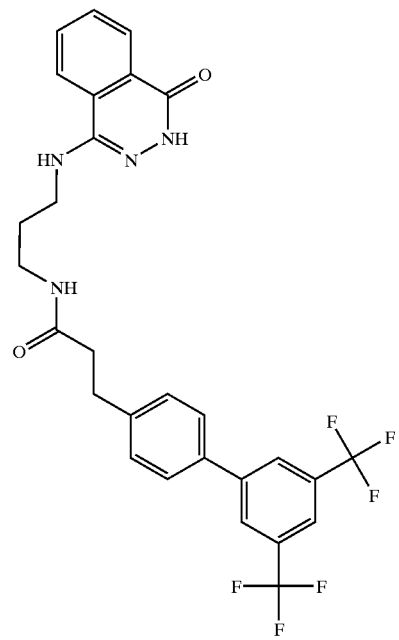

TABLE 1-continued
Representative compounds of Formula I.
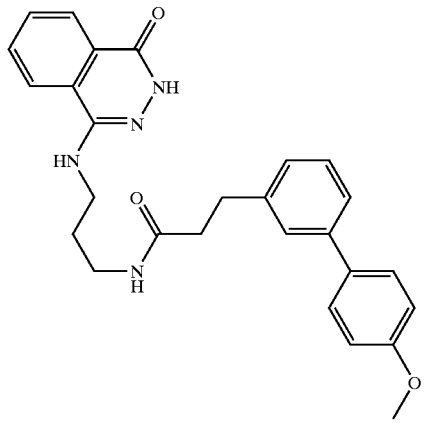
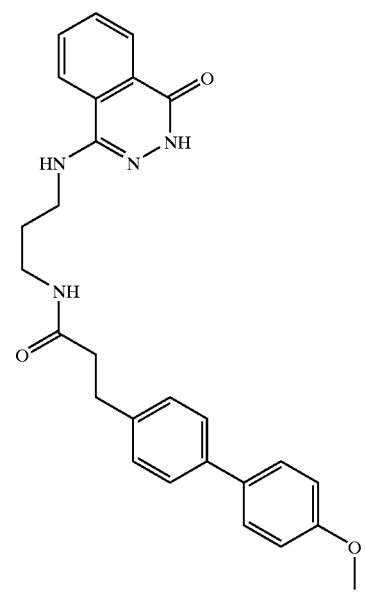
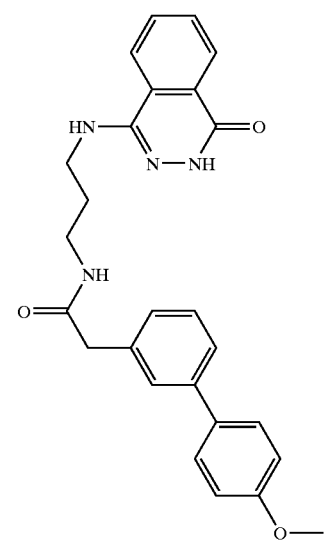
TABLE 1-continued
Representative compounds of Formula I.
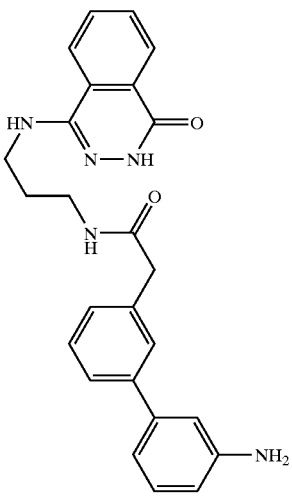
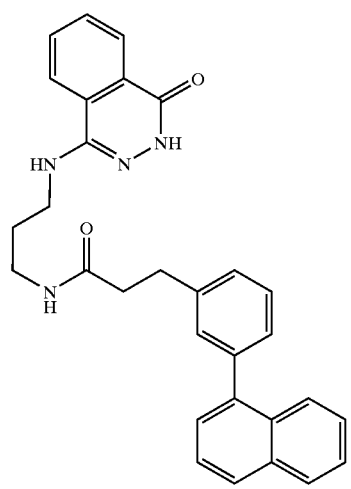
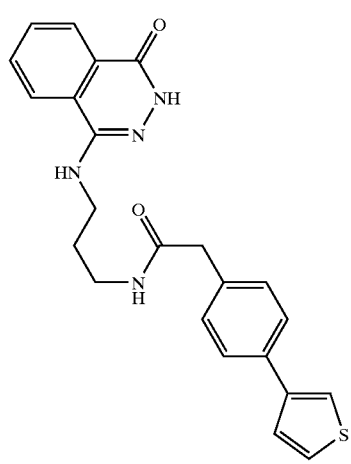

TABLE 1-continued
Representative compounds of Formula I.
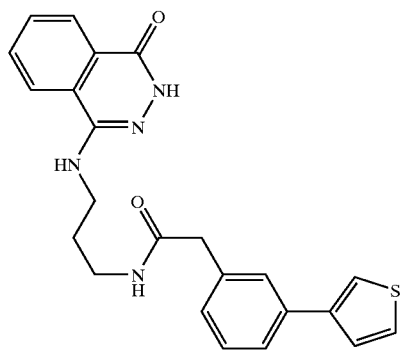
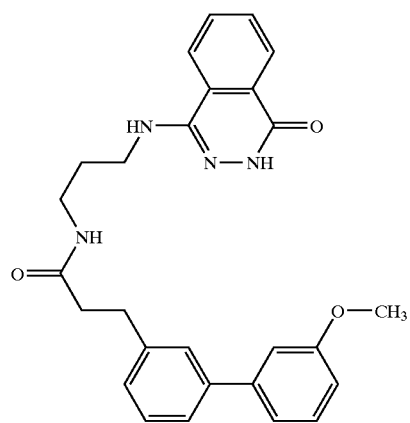
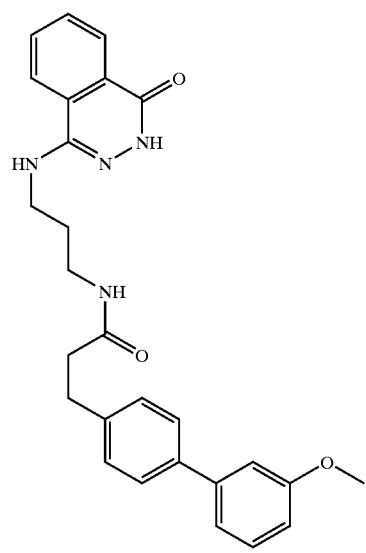
TABLE 1-continued
Representative compounds of Formula I.
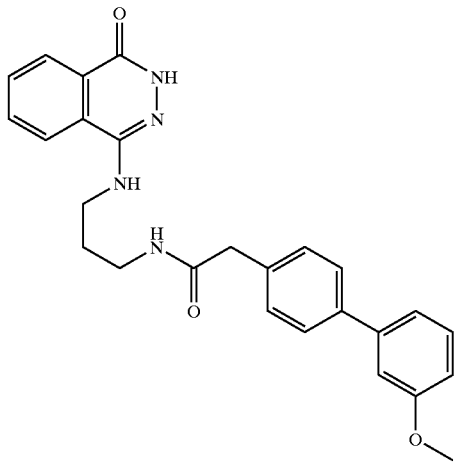
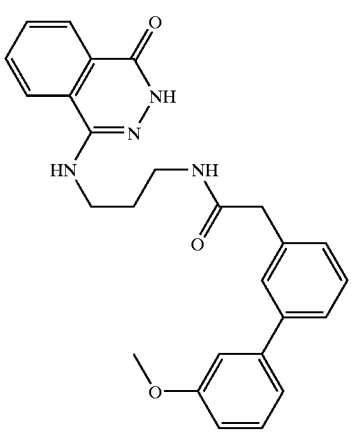
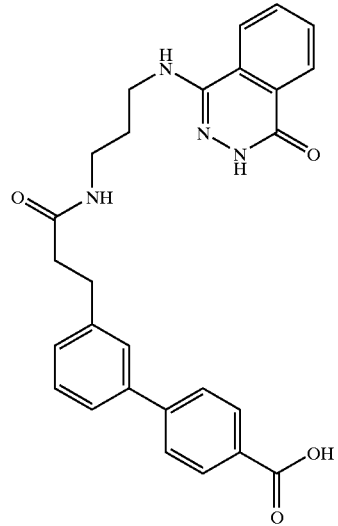

TABLE 1-continued
Representative compounds of Formula I.
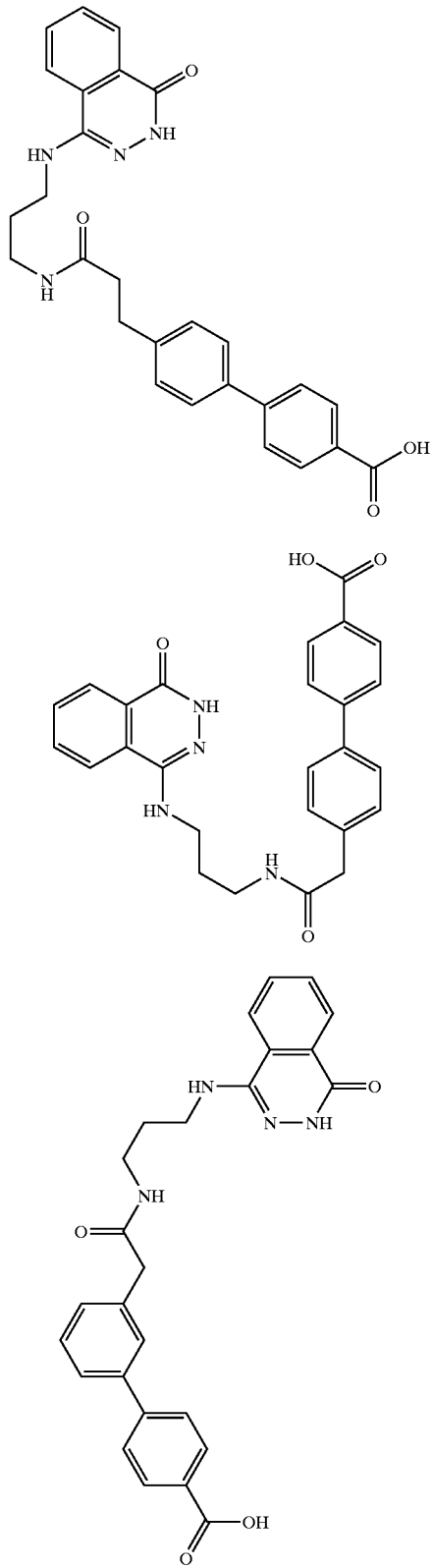
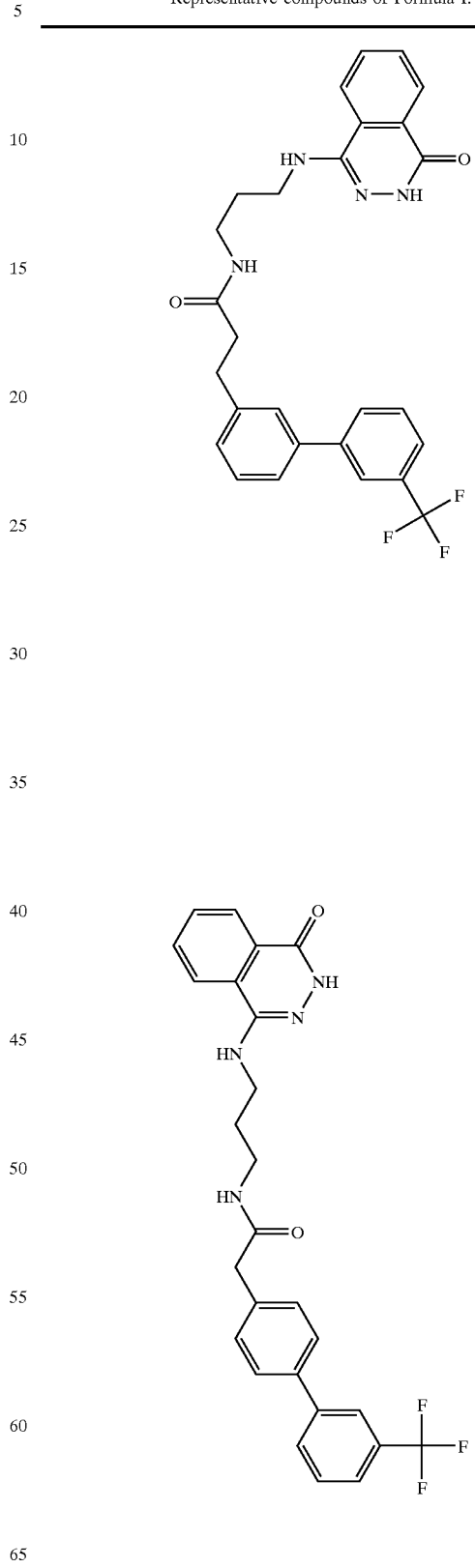

TABLE 1-continued
Representative compounds of Formula I.
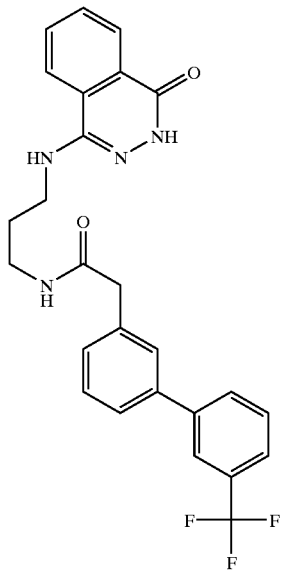
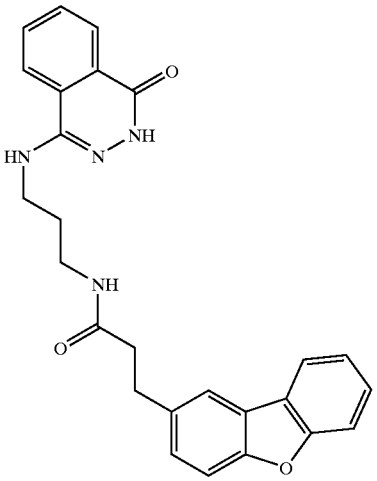
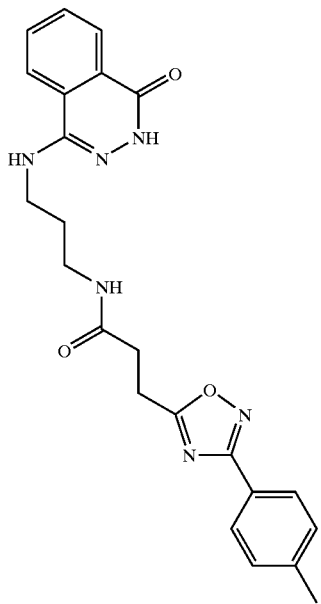
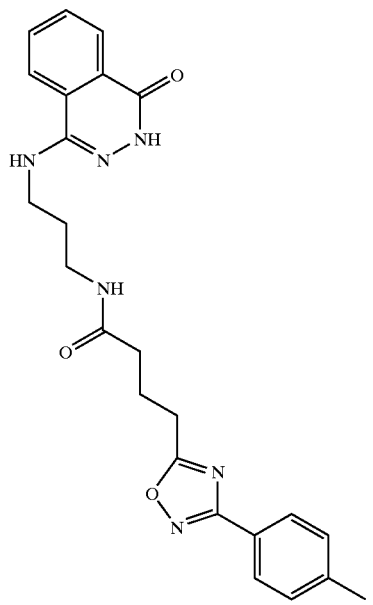

TABLE 1-continued
Representative compounds of Formula I.
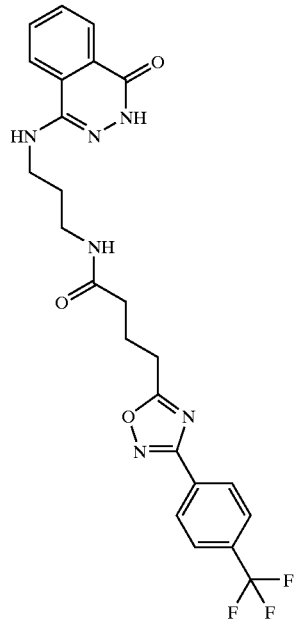
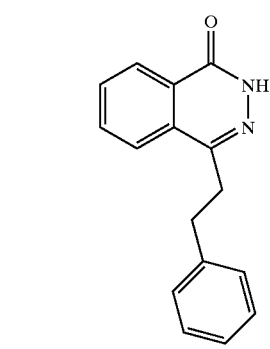
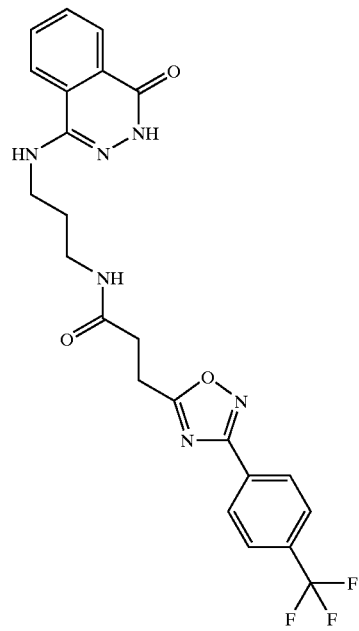
TABLE 1-continued
Representative compounds of Formula I.
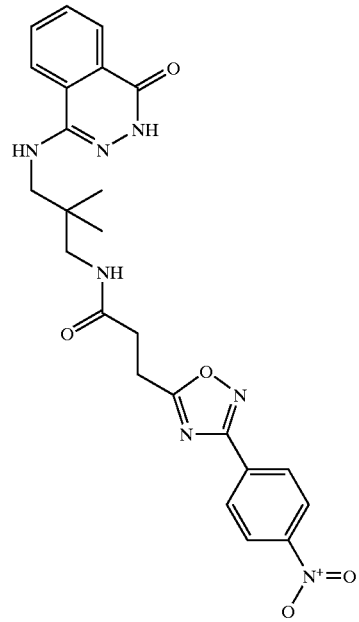
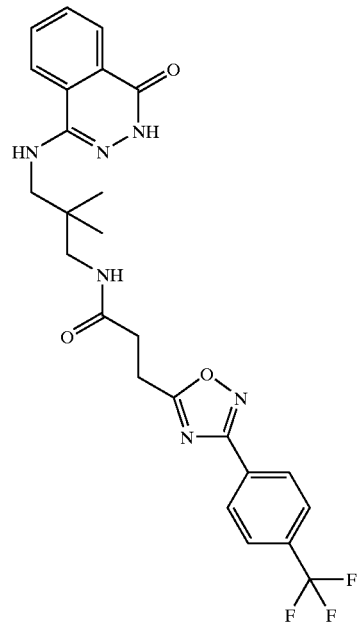

TABLE 1-continued
Representative compounds of Formula I.
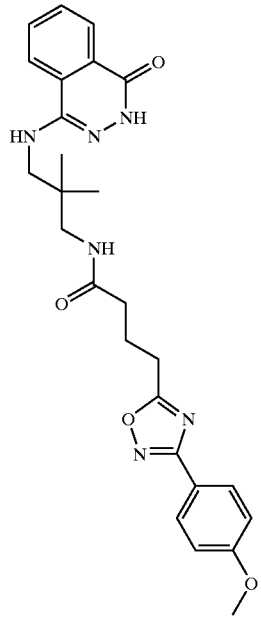
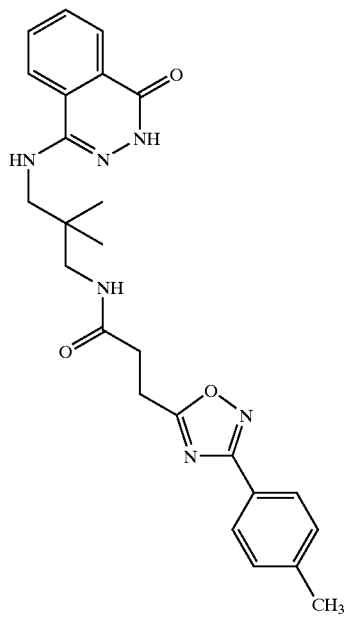
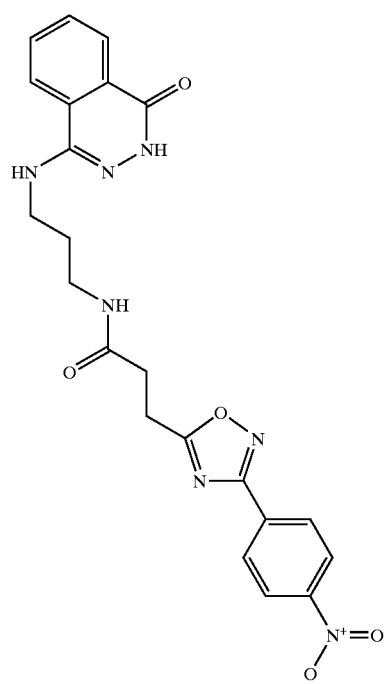
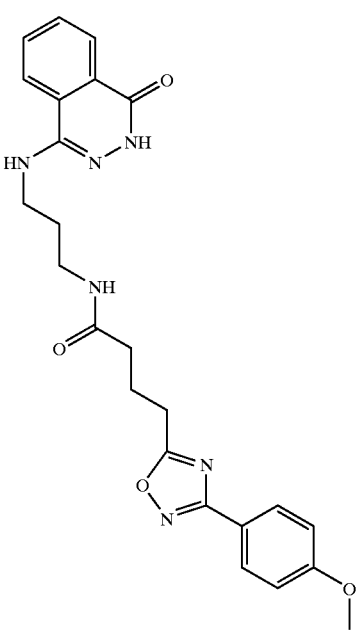

TABLE 1-continued
Representative compounds of Formula I.
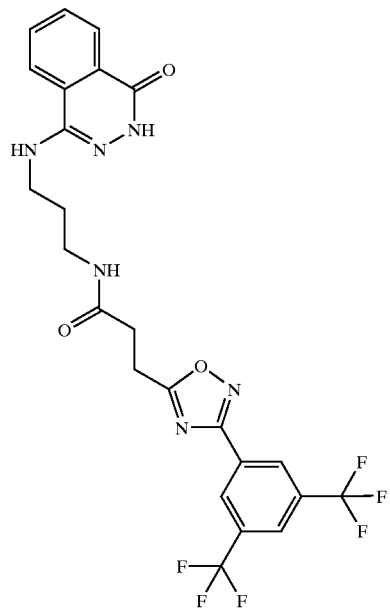
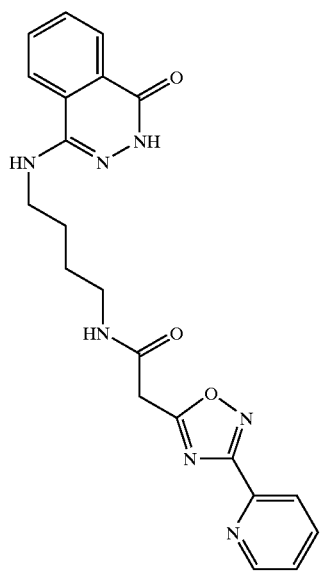

TABLE 1-continued
Representative compounds of Formula I.
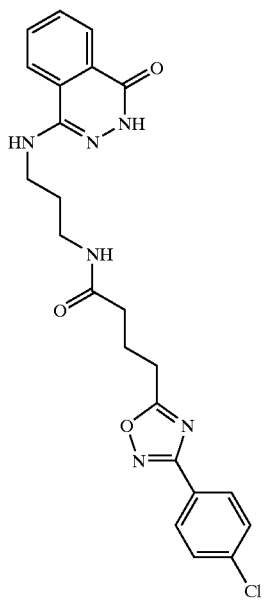
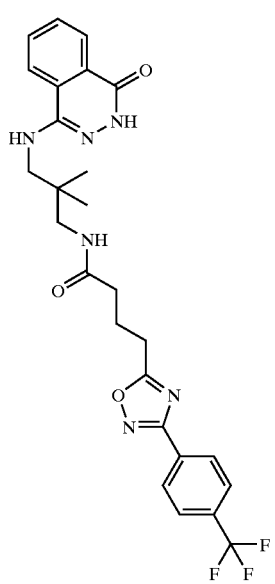
TABLE 1-continued
Representative compounds of Formula I.
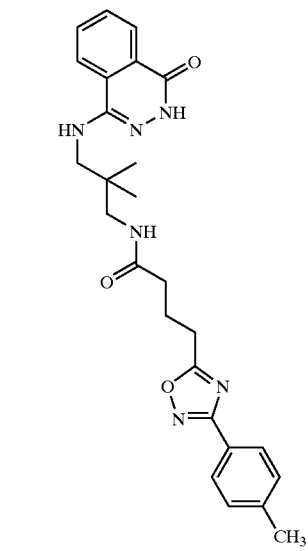
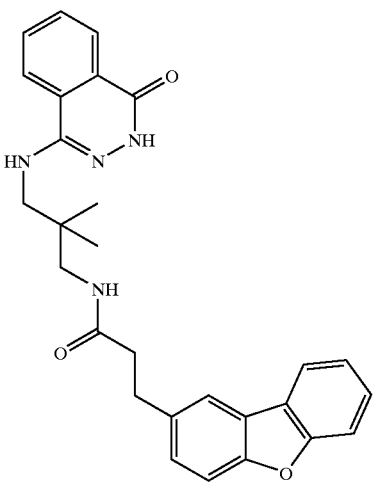
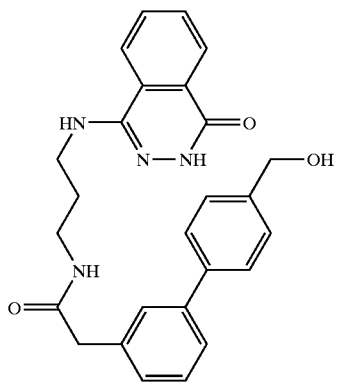

TABLE 1-continued
Representative compounds of Formula I.
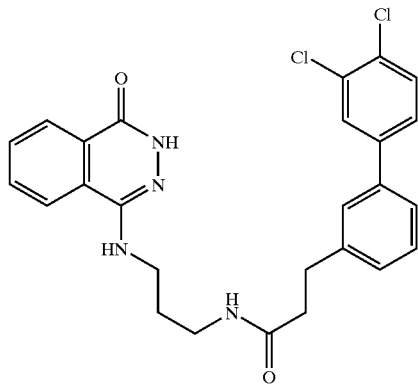
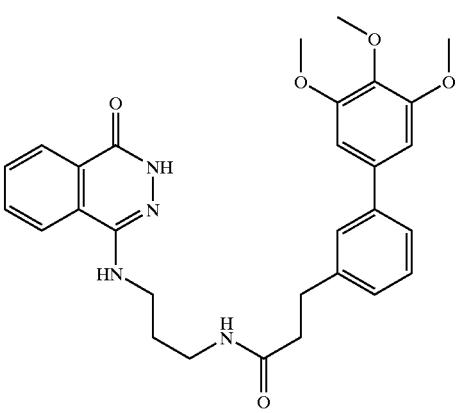
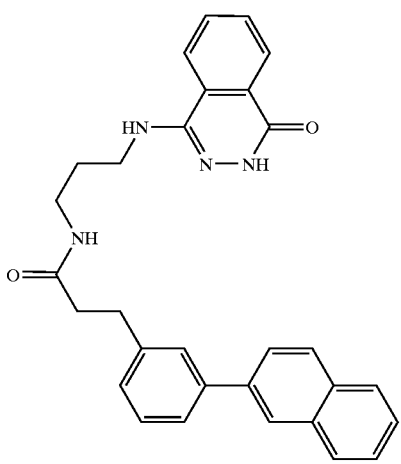
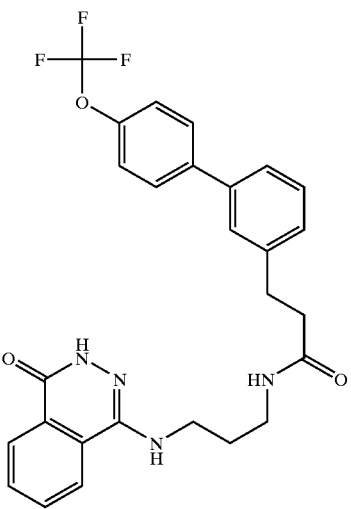

TABLE 1-continued
Representative compounds of Formula I.
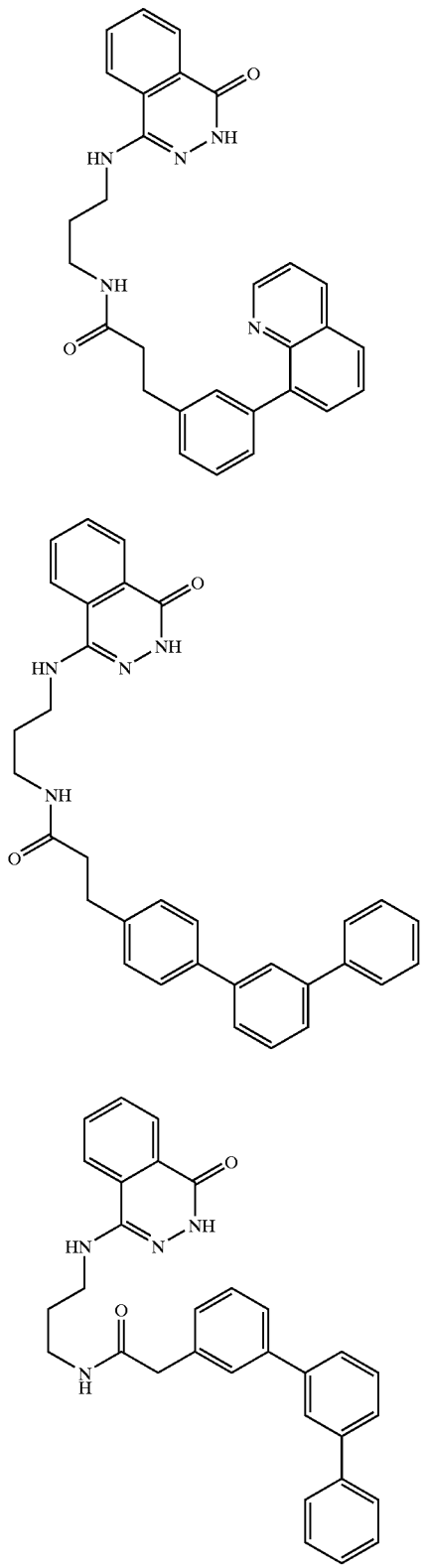
TABLE 1-continued
Representative compounds of Formula I.
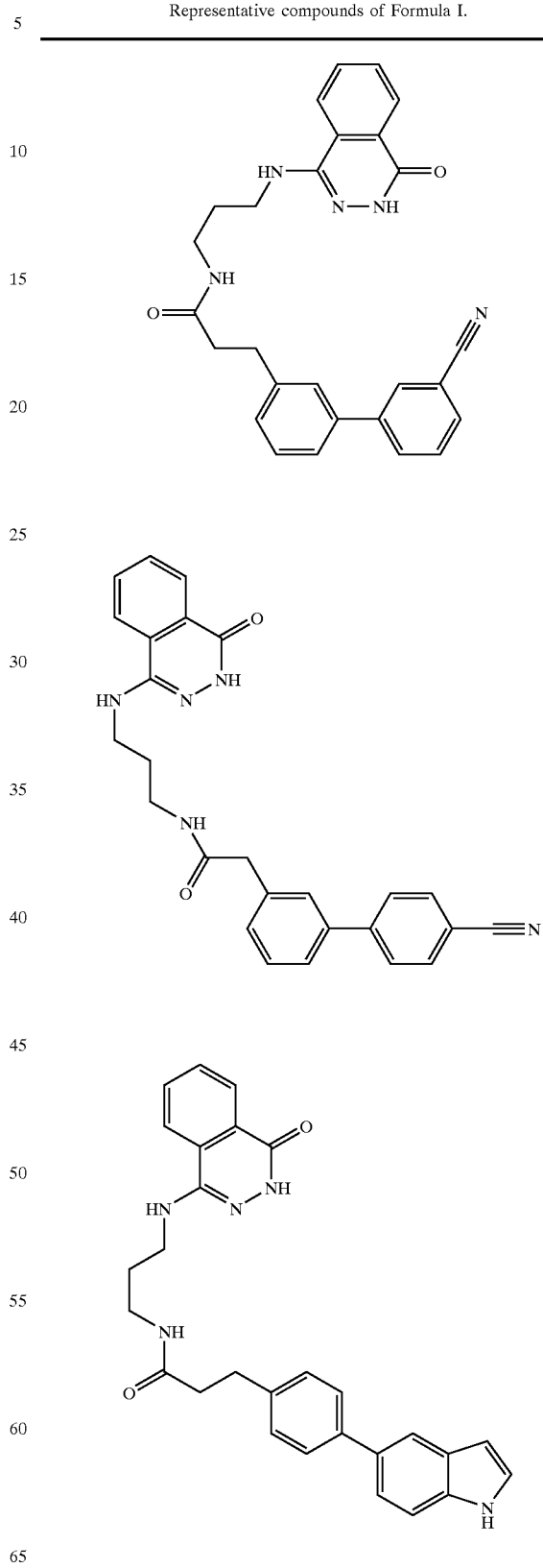

TABLE 1-continued
Representative compounds of Formula I.
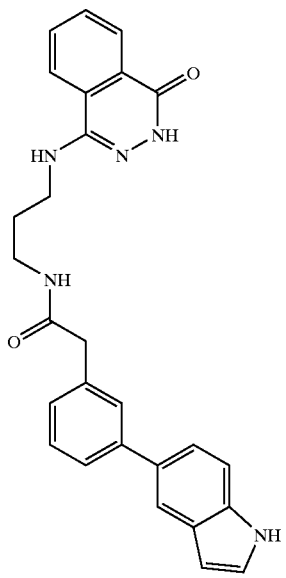
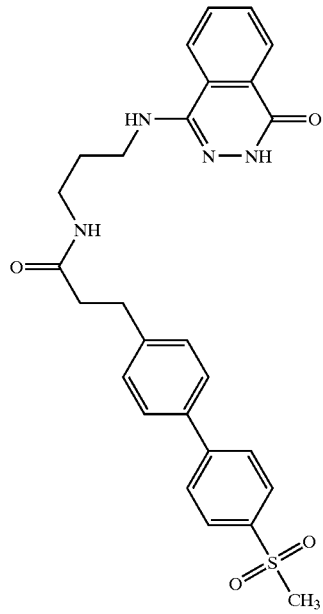
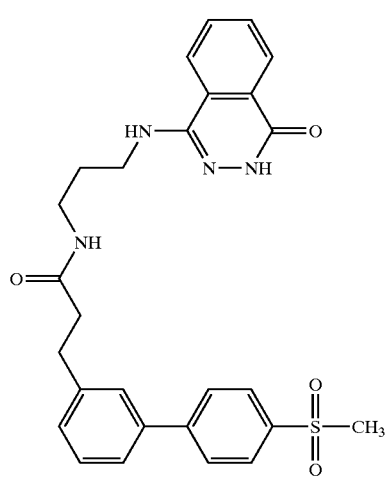
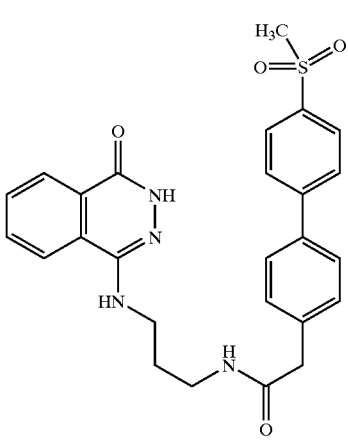

TABLE 1-continued
Representative compounds of Formula I.
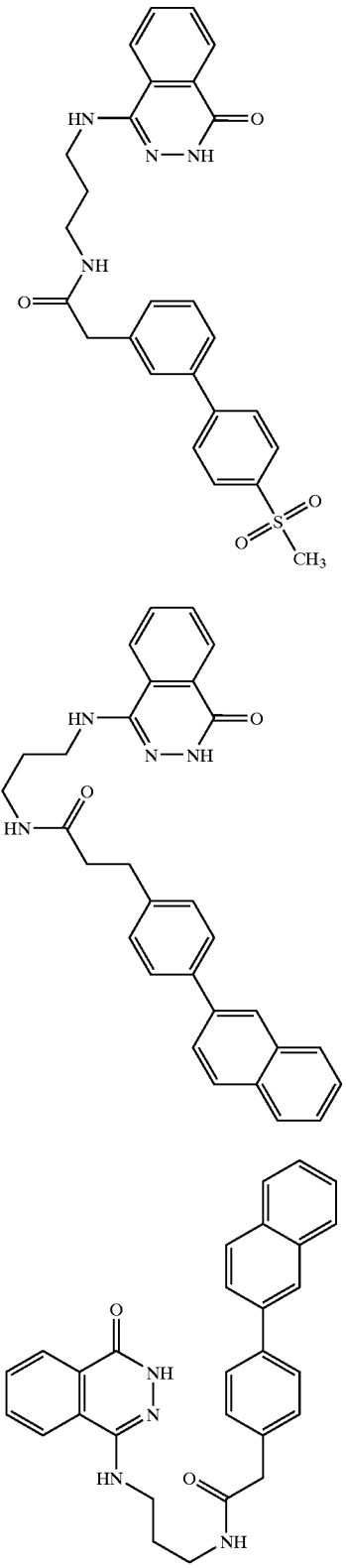
TABLE 1-continued
Representative compounds of Formula I.
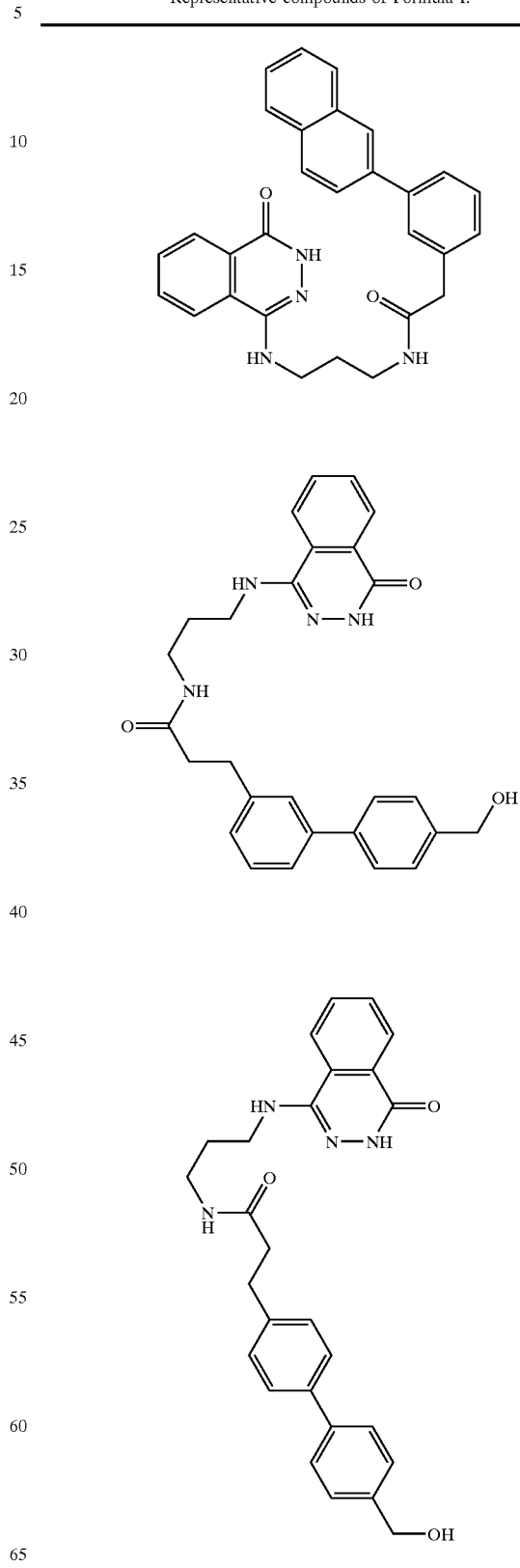

TABLE 1-continued
Representative compounds of Formula I.
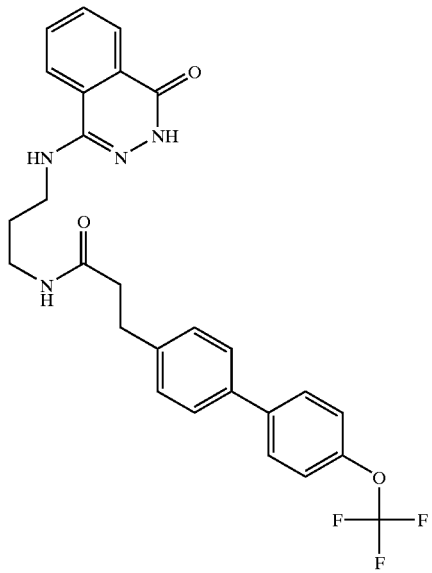
TABLE 1-continued
Representative compounds of Formula I.
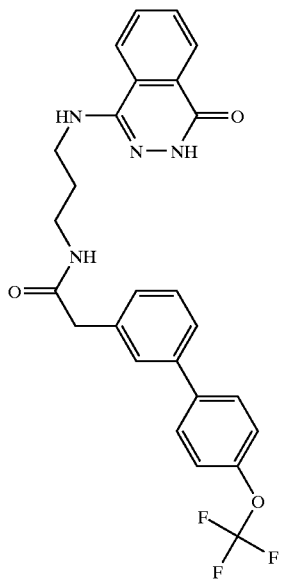
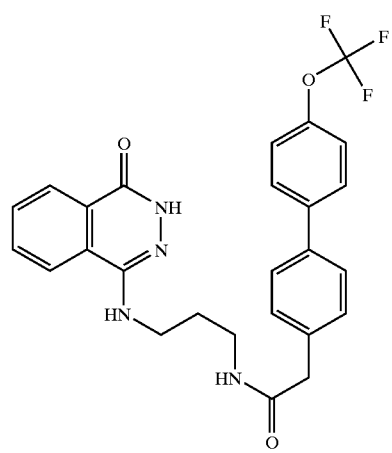
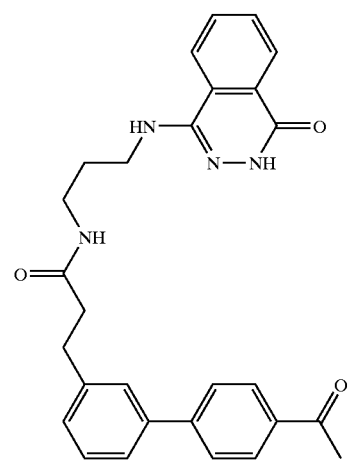

TABLE 1-continued
Representative compounds of Formula I.
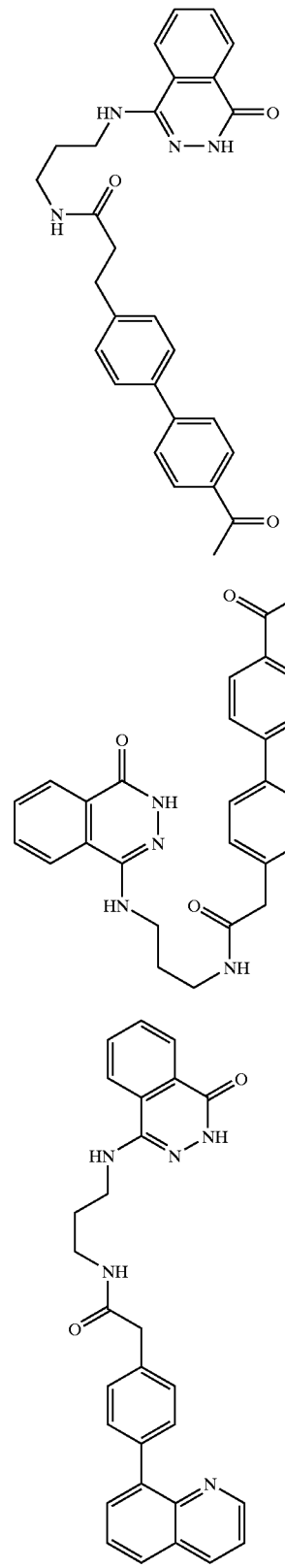
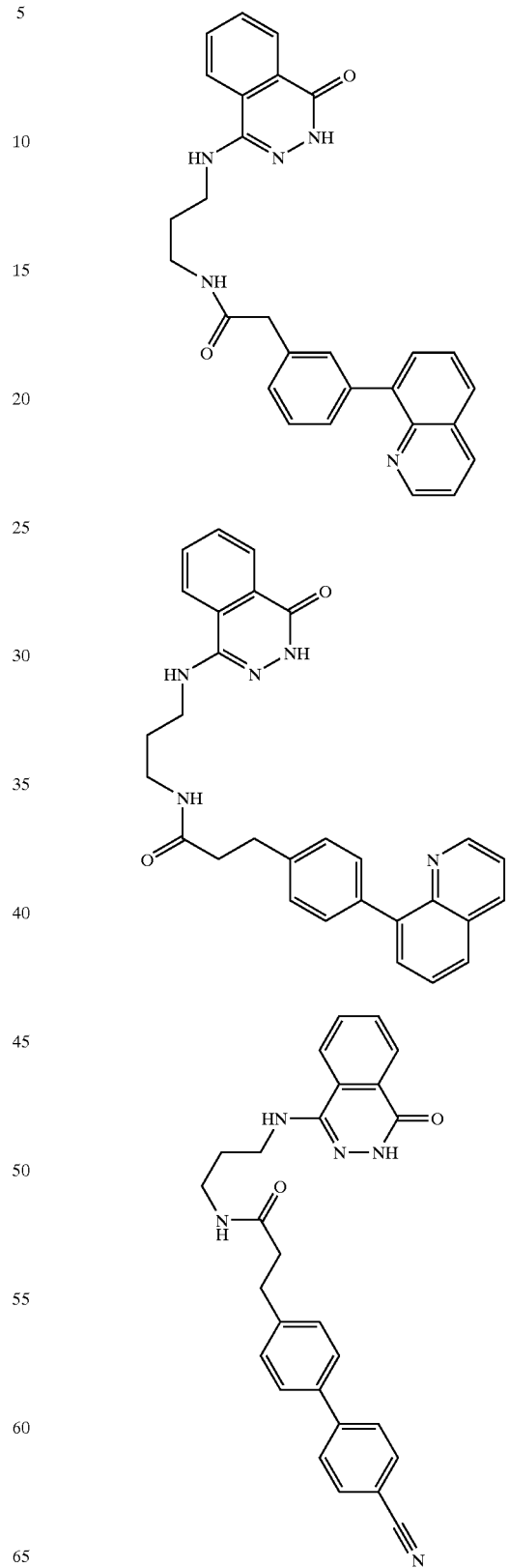

TABLE 1-continued
Representative compounds of Formula I.
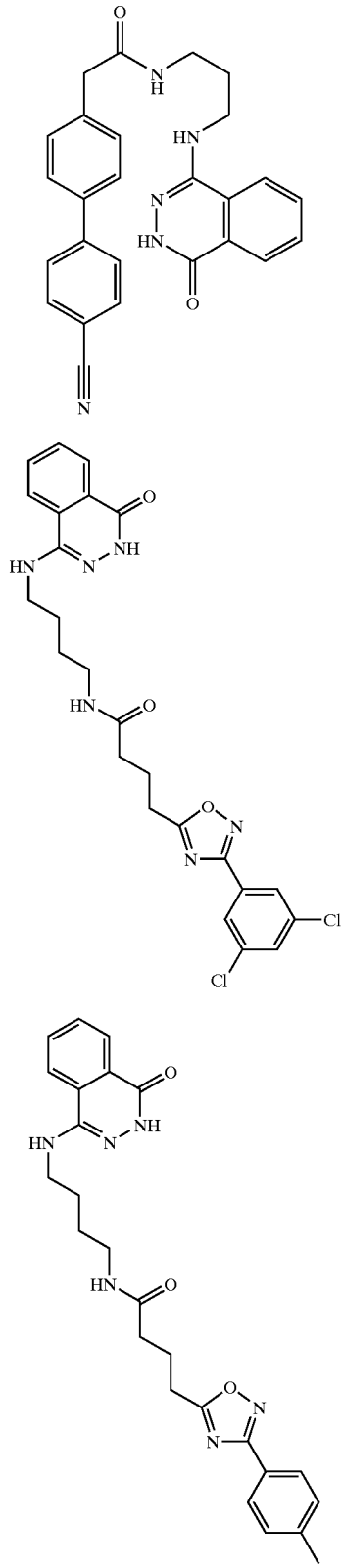
TABLE 1-continued
Representative compounds of Formula I.
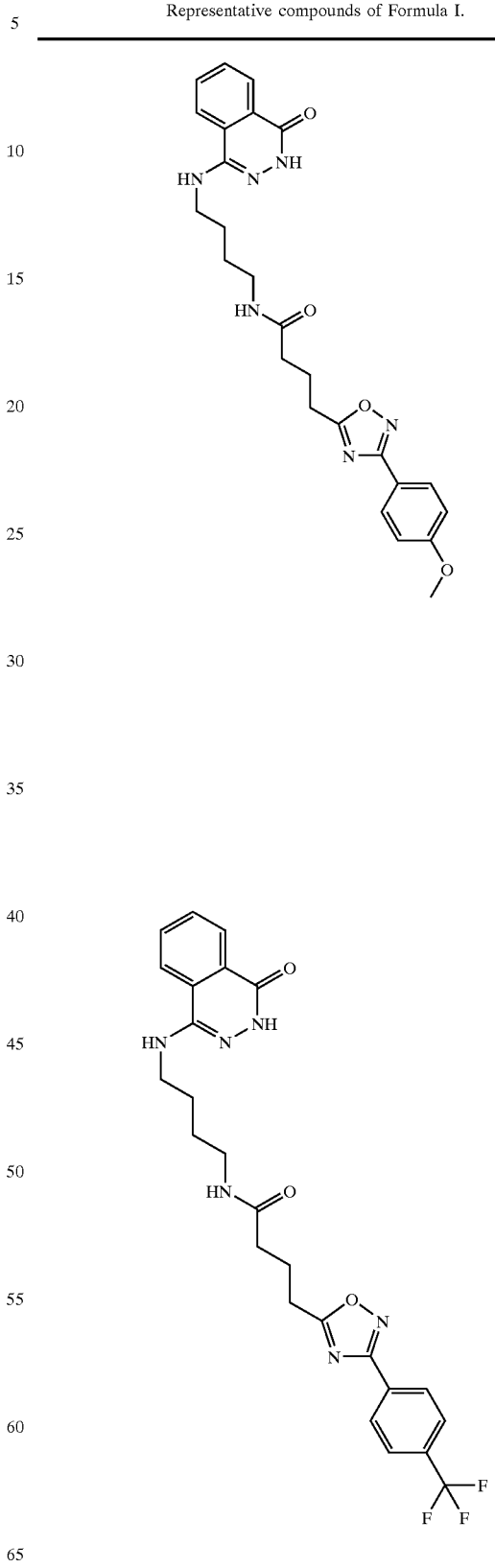

TABLE 1-continued
Representative compounds of Formula I.
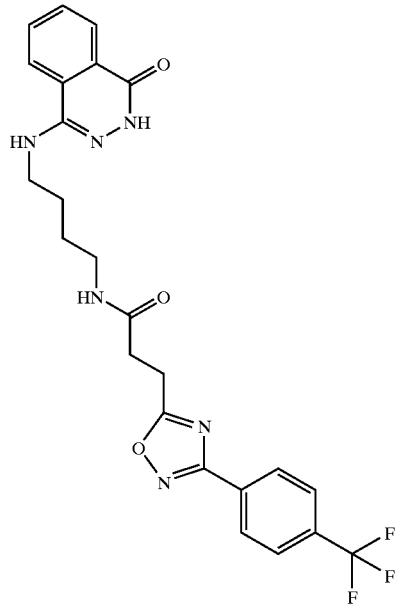
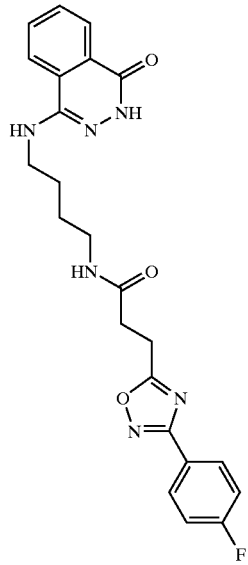
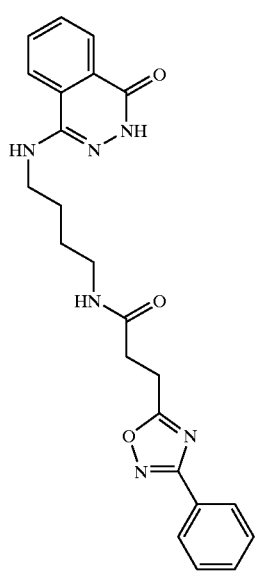
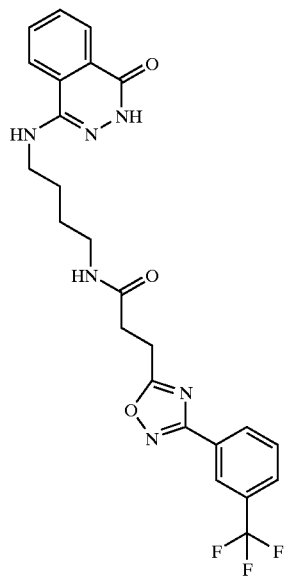

TABLE 1-continued
Representative compounds of Formula I.
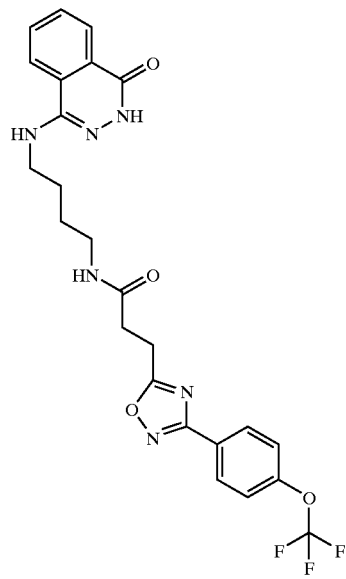
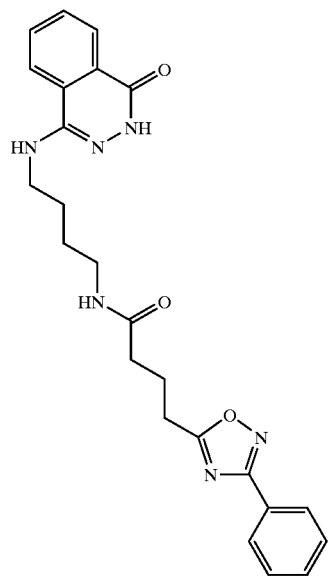
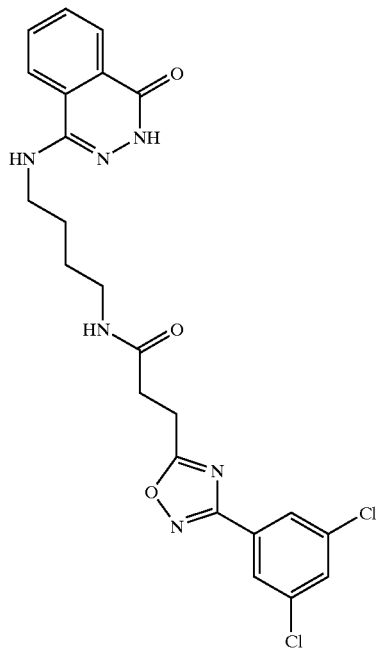

TABLE 1-continued
Representative compounds of Formula I.
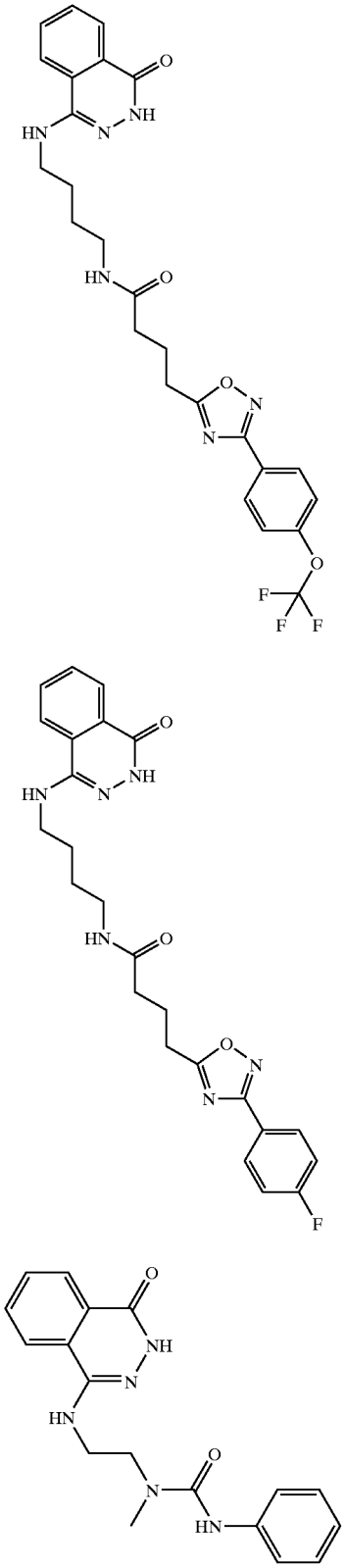
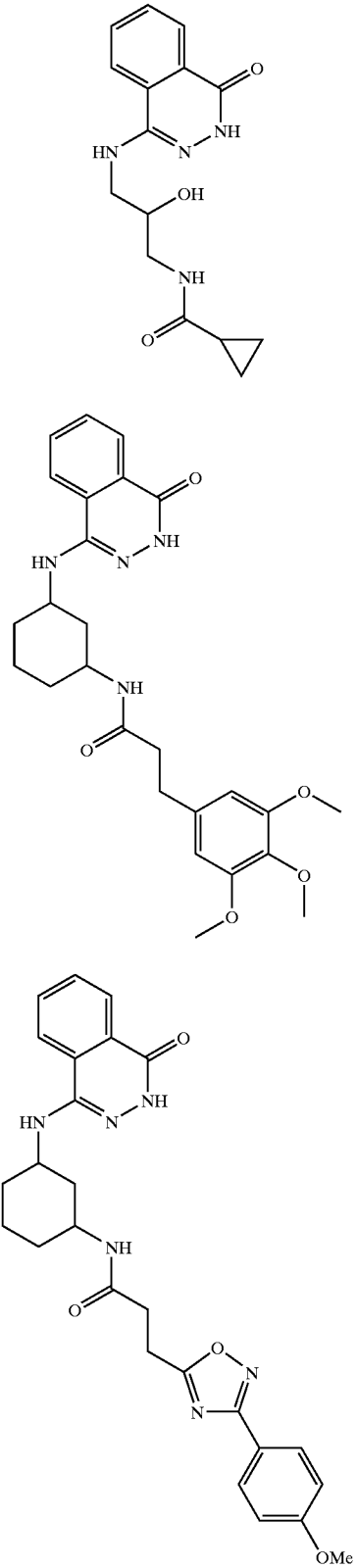

TABLE 1-continued
Representative compounds of Formula I.
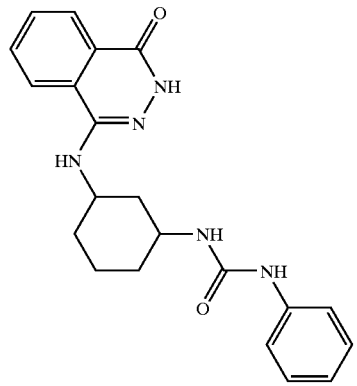
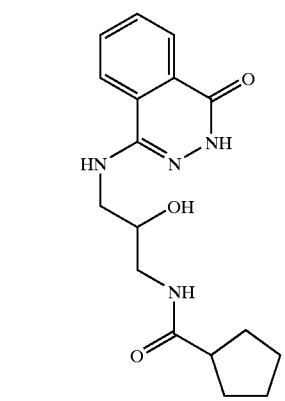
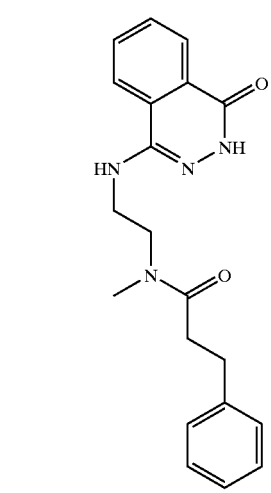
TABLE 1-continued
Representative compounds of Formula I.
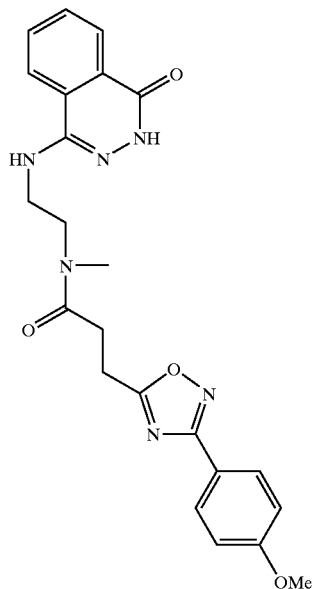
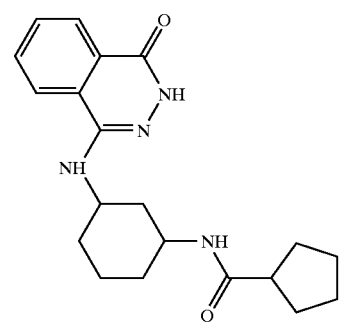
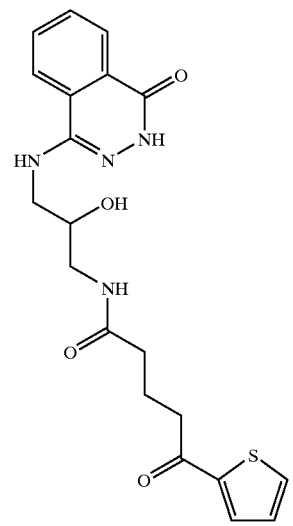

TABLE 1-continued
Representative compounds of Formula I.
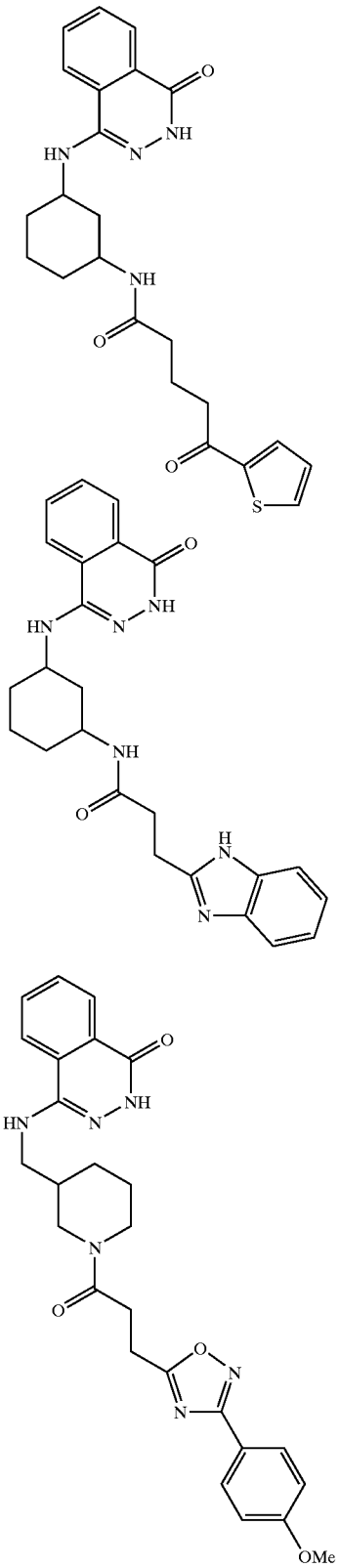
TABLE 1-continued
Representative compounds of Formula I.
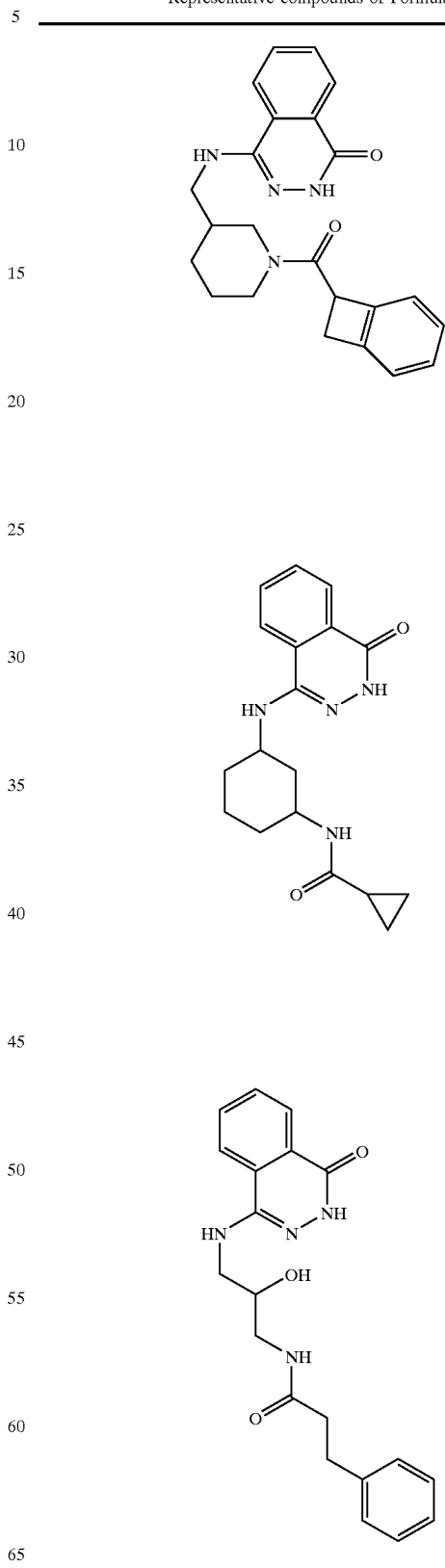

TABLE 1-continued
Representative compounds of Formula I.
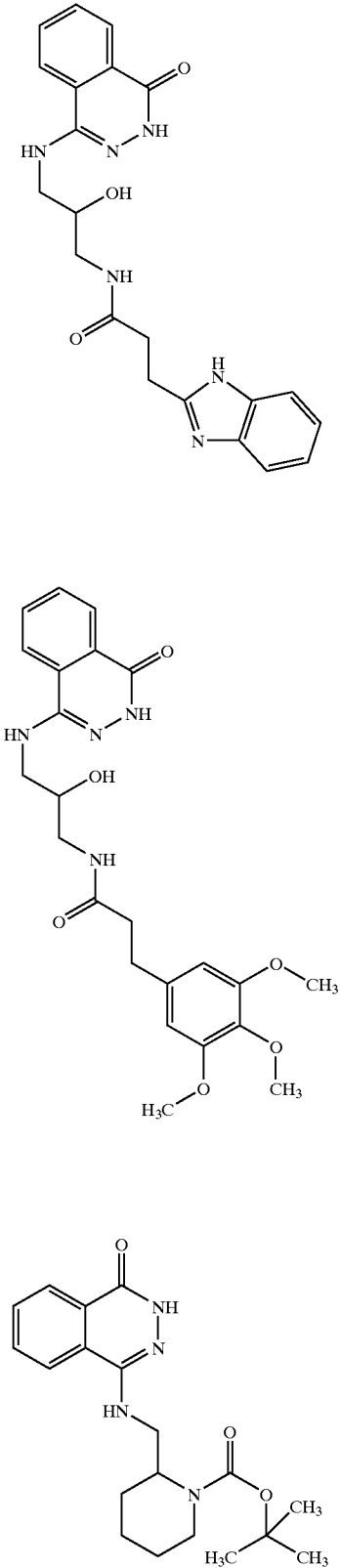
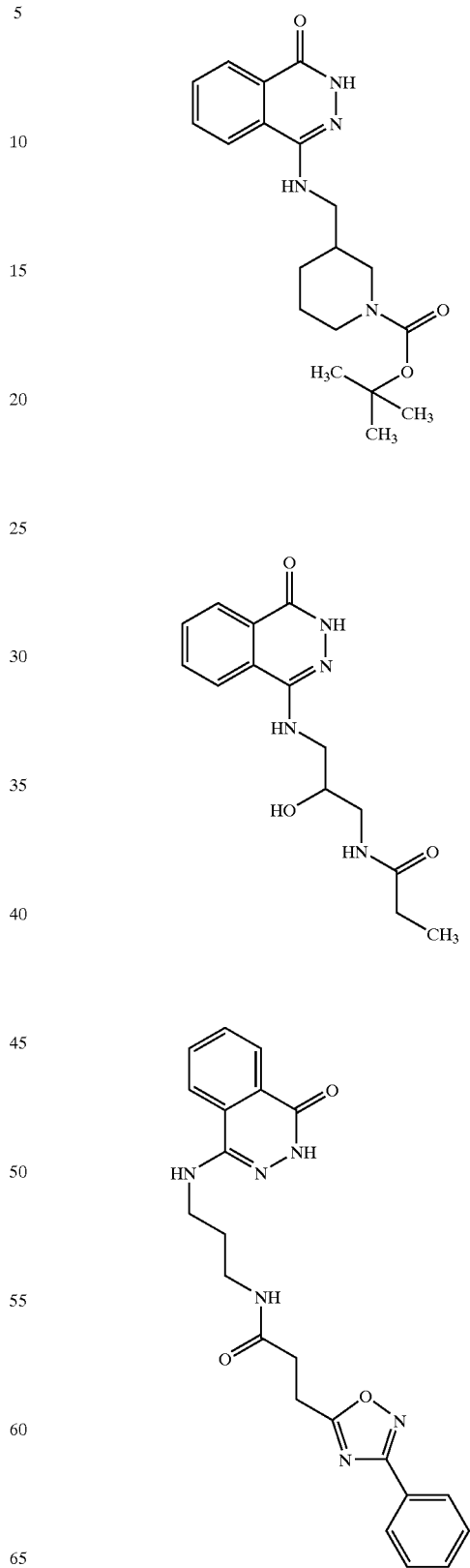

TABLE 1-continued
Representative compounds of Formula I.
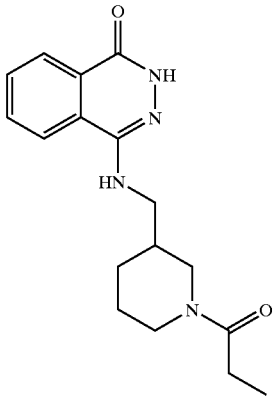
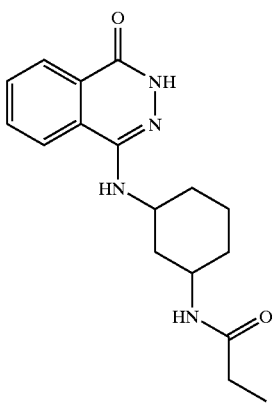
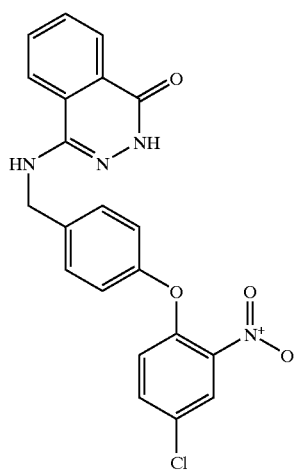
TABLE 1-continued
Representative compounds of Formula I.
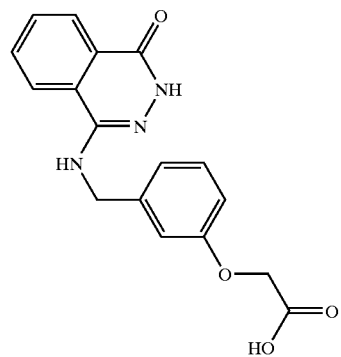
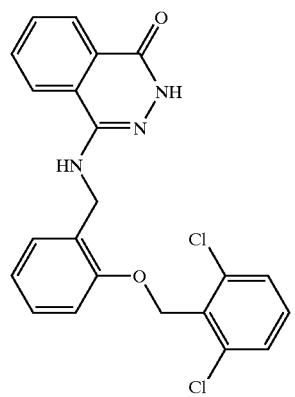
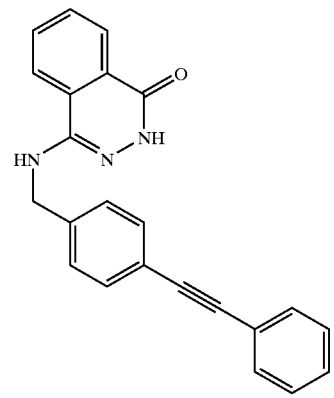
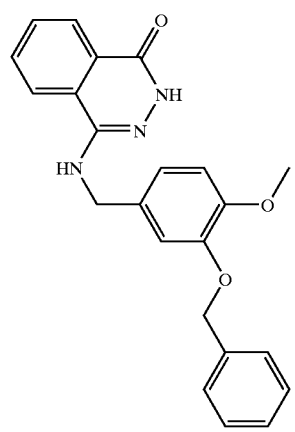

TABLE 1-continued
Representative compounds of Formula I.
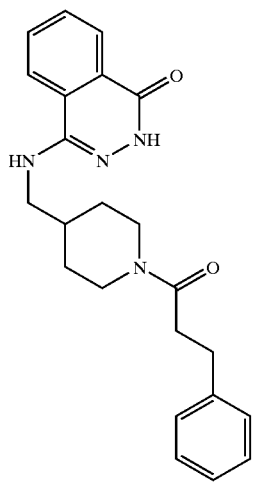
TABLE 1-continued
Representative compounds of Formula I.
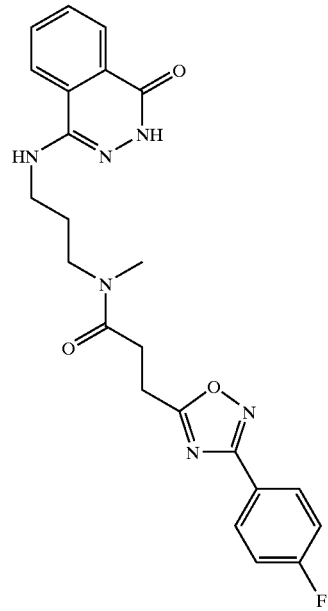
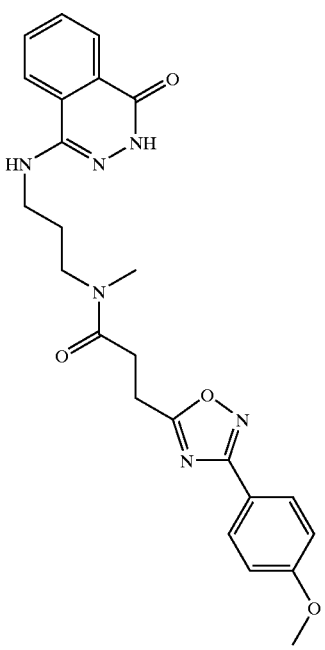
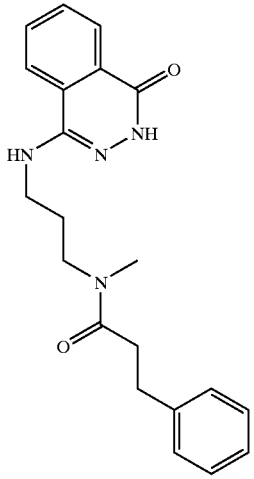

TABLE 1-continued
Representative compounds of Formula I.
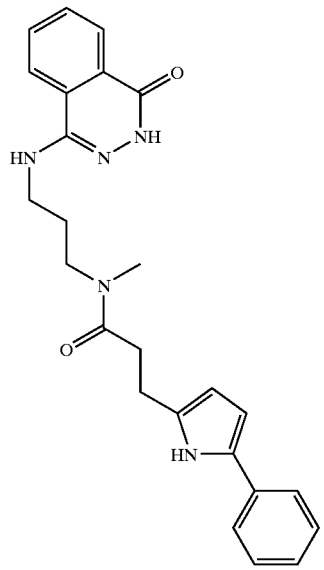
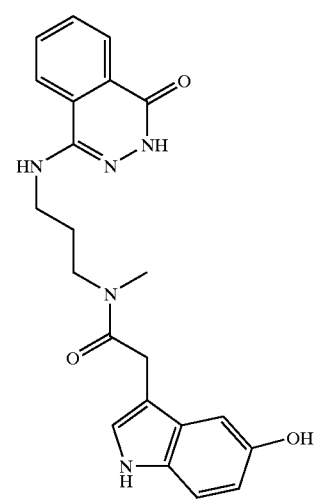
TABLE 1-continued
Representative compounds of Formula I.
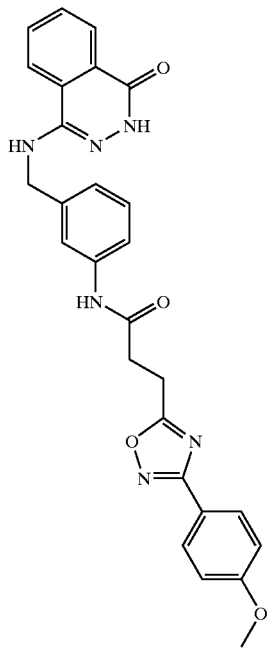
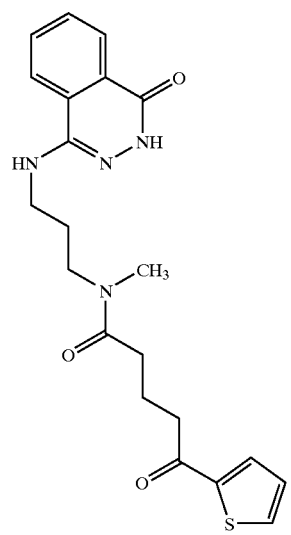

TABLE 1-continued
Representative compounds of Formula I.
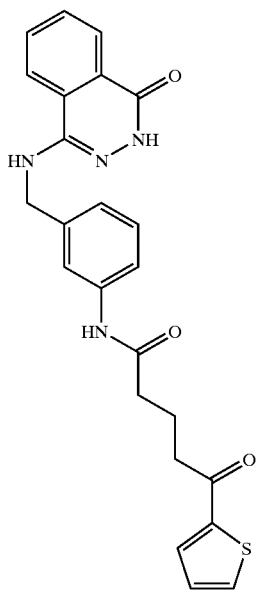
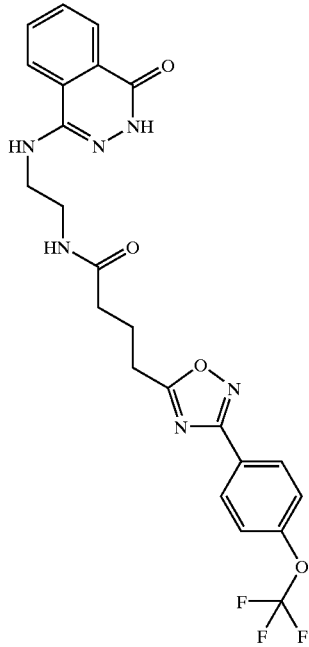
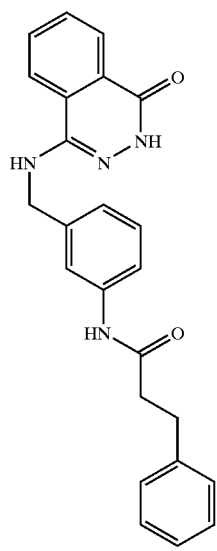
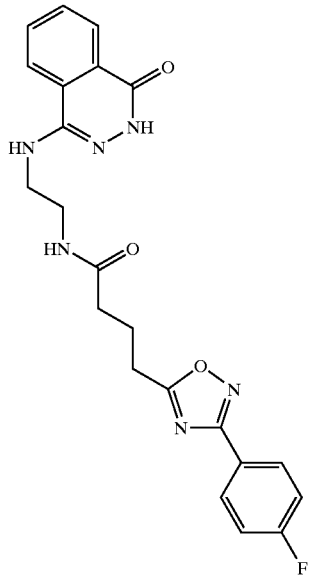

TABLE 1-continued
Representative compounds of Formula I.
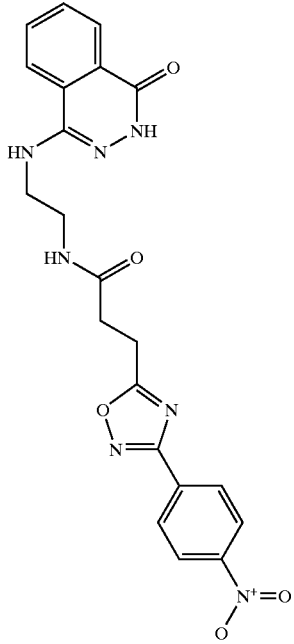
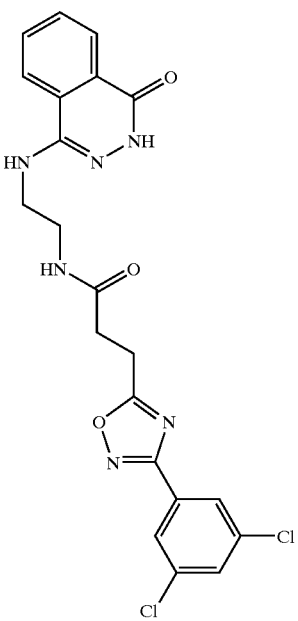
TABLE 1-continued
Representative compounds of Formula I.
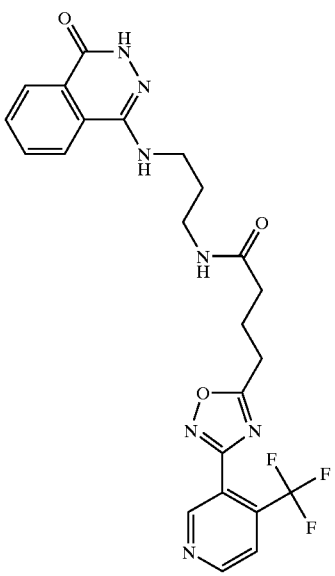
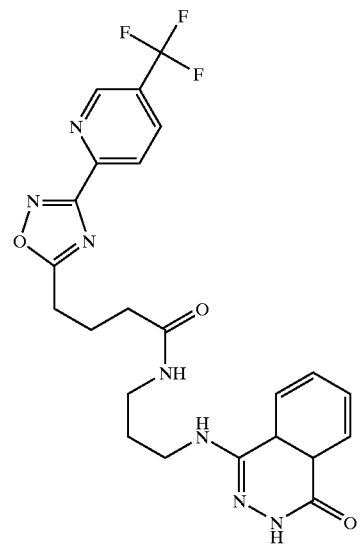

TABLE 1-continued
Representative compounds of Formula I.
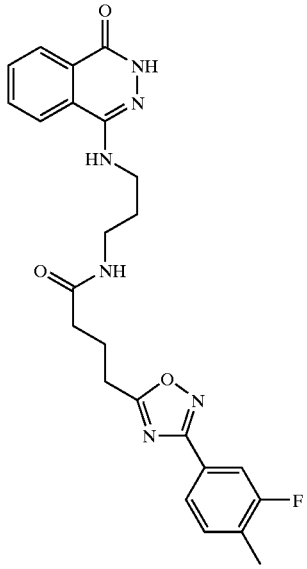
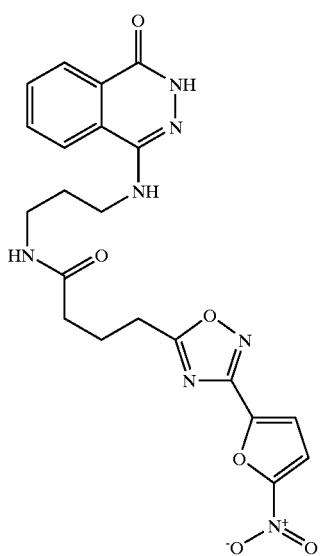
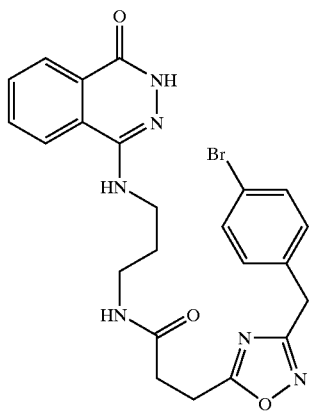
TABLE 1-continued
Representative compounds of Formula I.
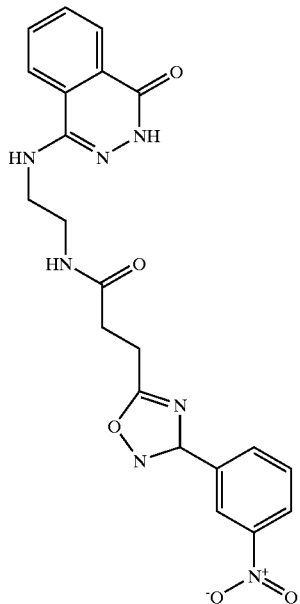
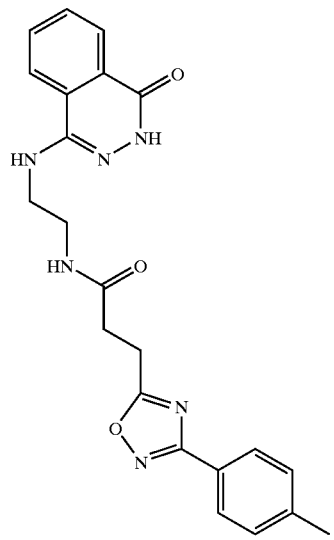

TABLE 1-continued
Representative compounds of Formula I.
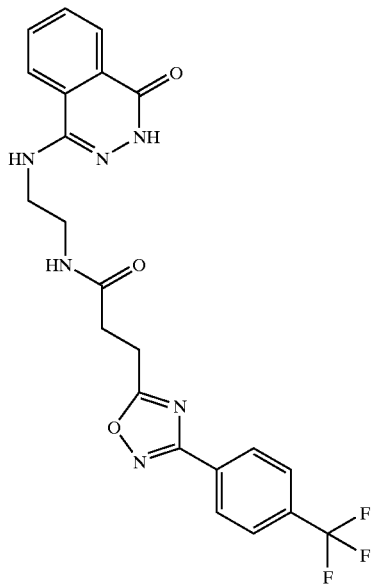
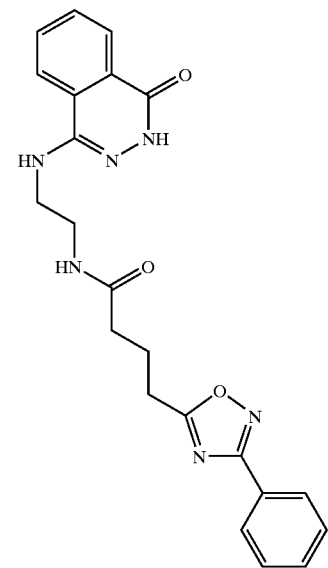
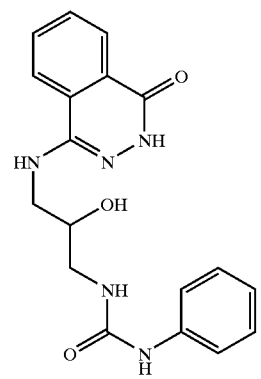
TABLE 1-continued
Representative compounds of Formula I.
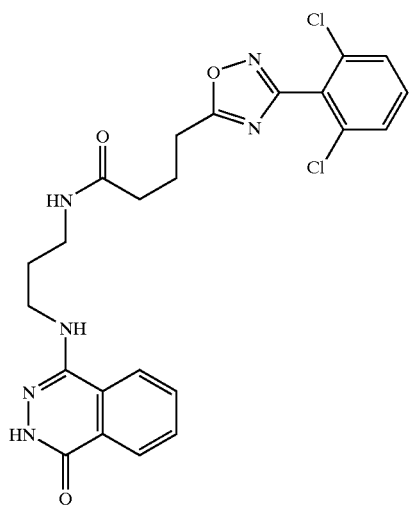
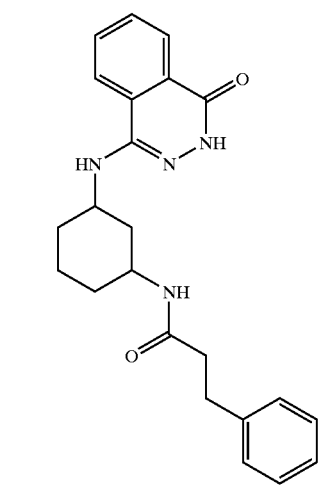
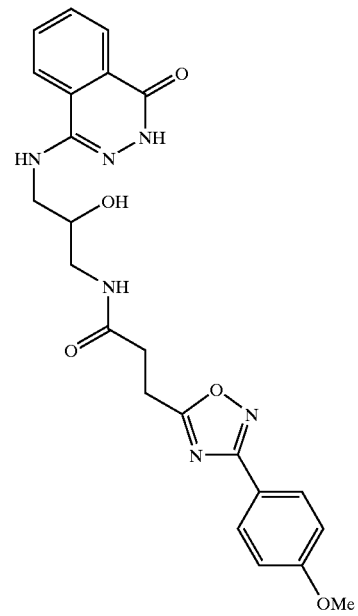

TABLE 1-continued
Representative compounds of Formula I.
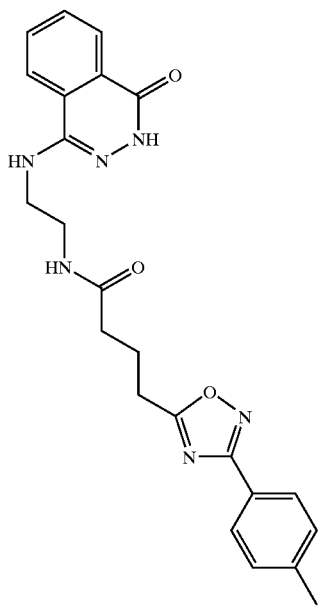
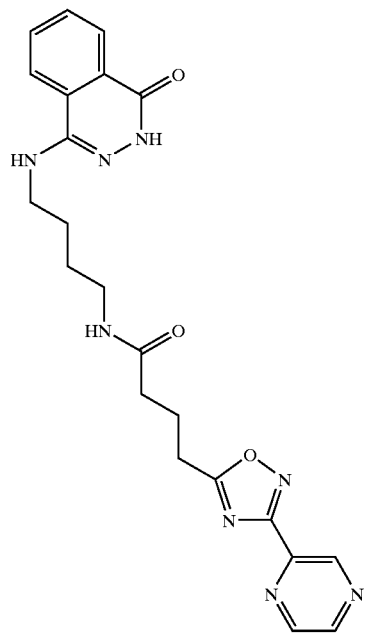
TABLE 1-continued
Representative compounds of Formula I.
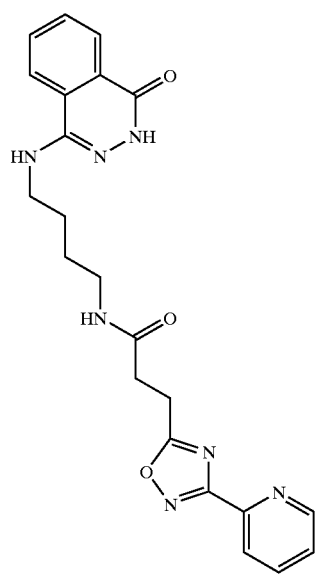
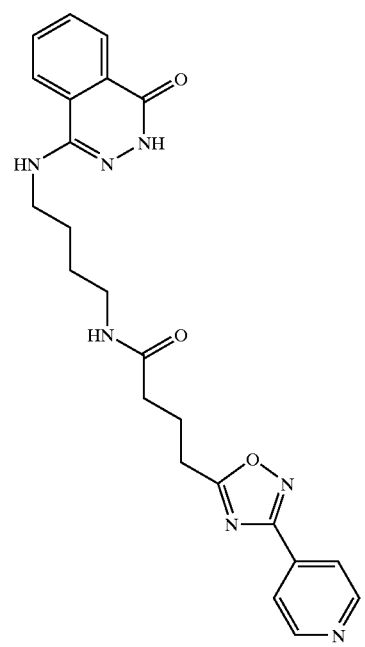

TABLE 1-continued
Representative compounds of Formula I.
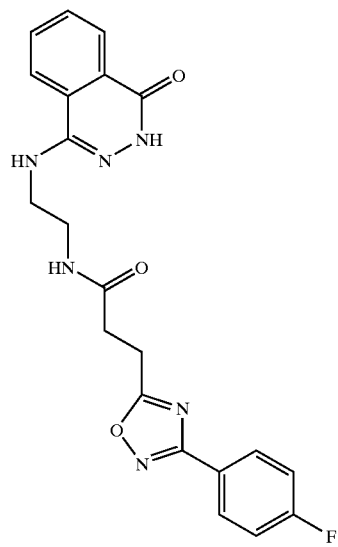
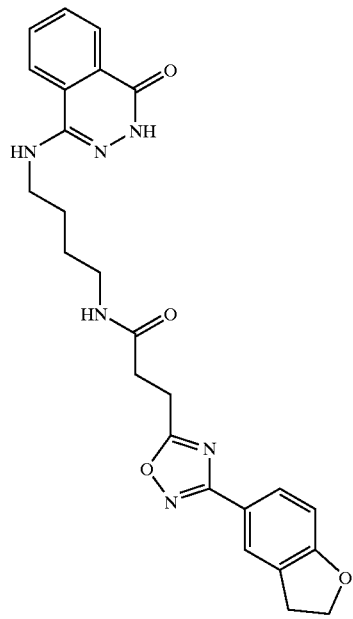
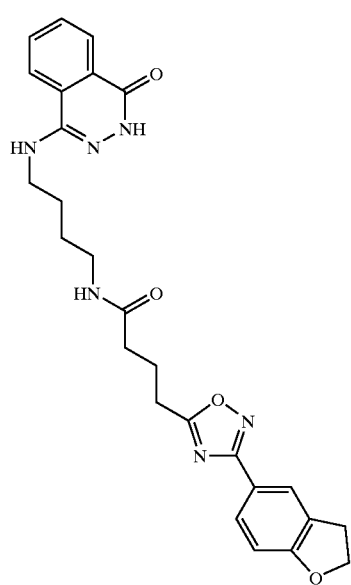
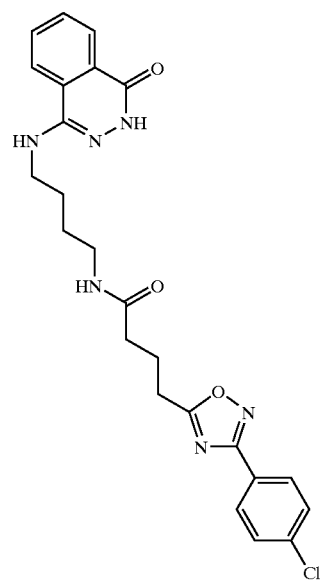

TABLE 1-continued

Representative compounds of Formula I.

TABLE 1-continued
Representative compounds of Formula I.
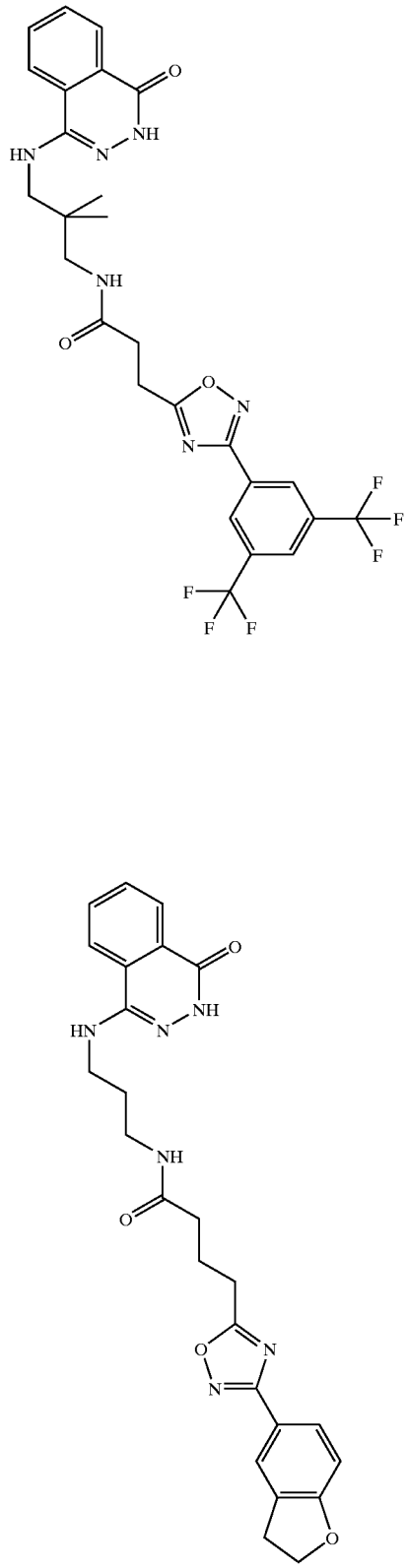
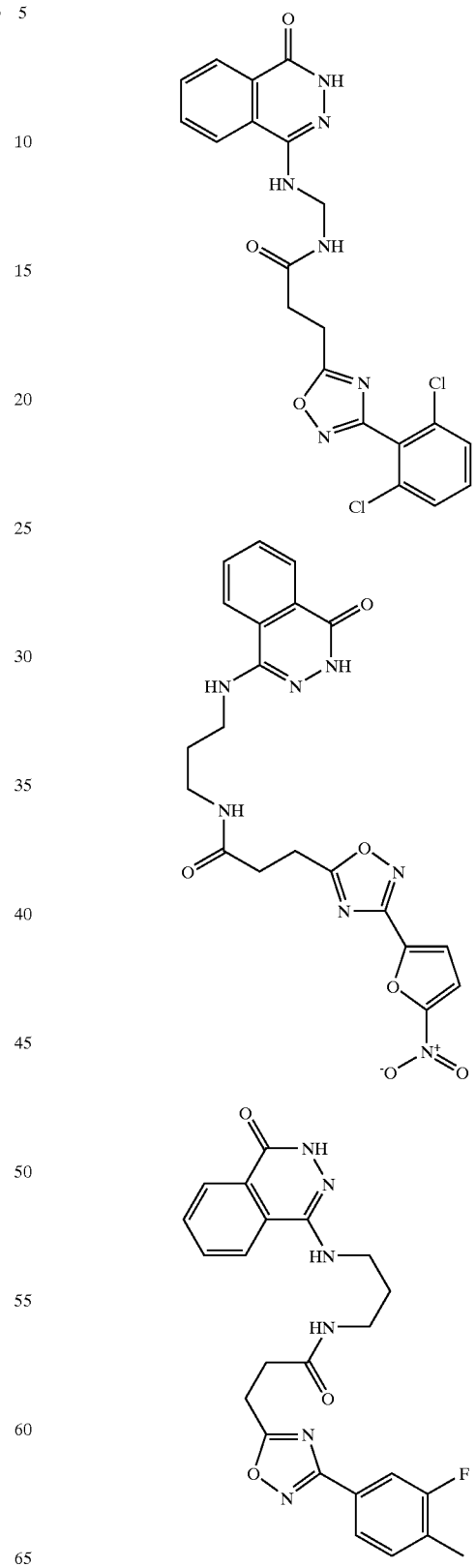

TABLE 1-continued
Representative compounds of Formula I.
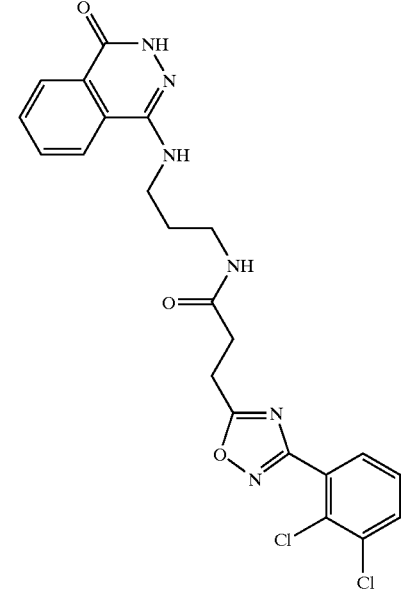
TABLE 1-continued
Representative compounds of Formula I.
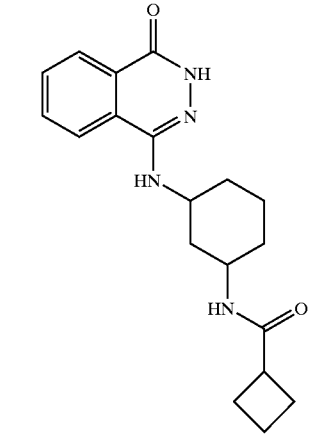

TABLE 1-continued
Representative compounds of Formula I.
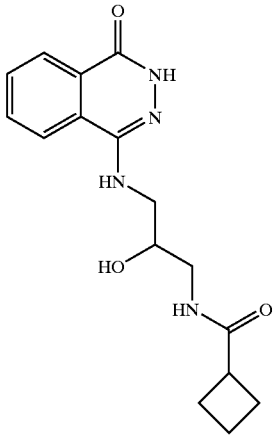
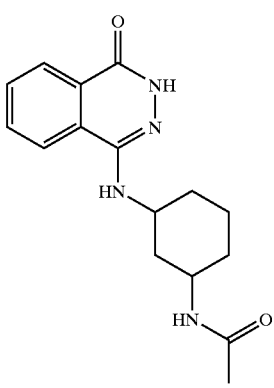
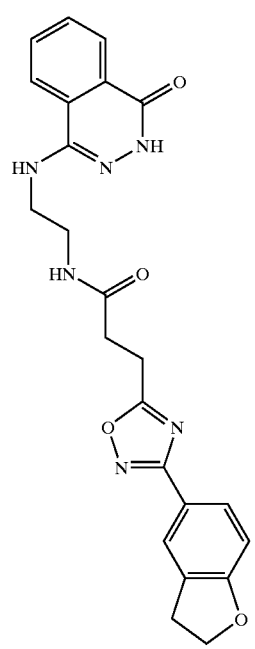
TABLE 1-continued
Representative compounds of Formula I.
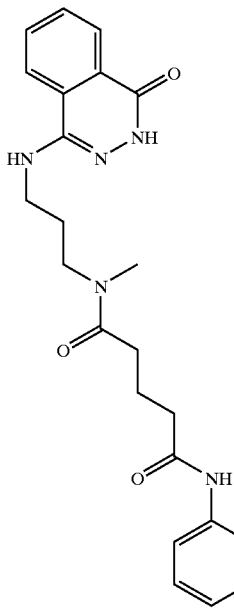
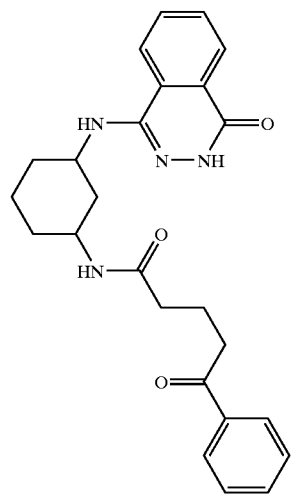
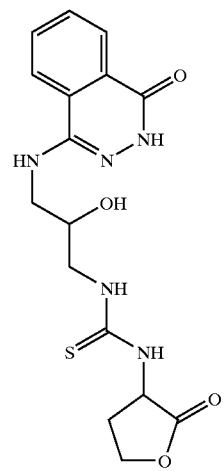

TABLE 1-continued
Representative compounds of Formula I.
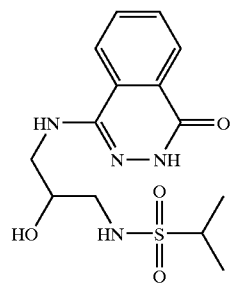
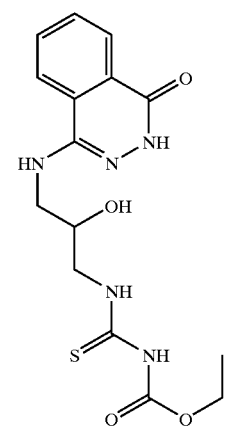
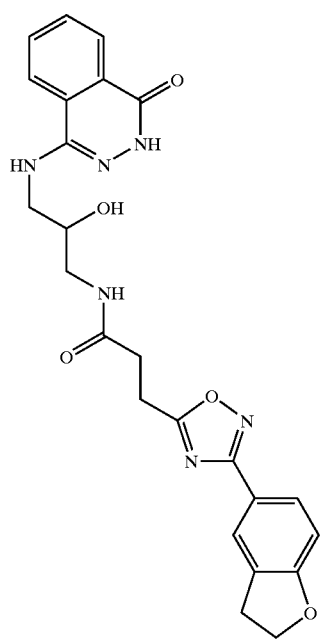
TABLE 1-continued
Representative compounds of Formula I.
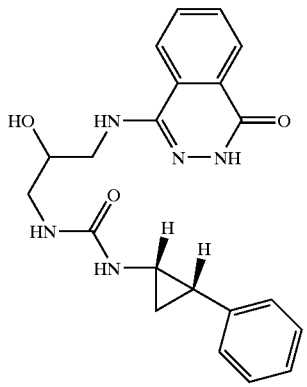
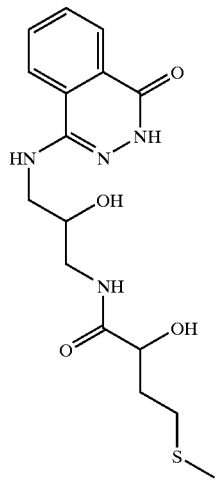
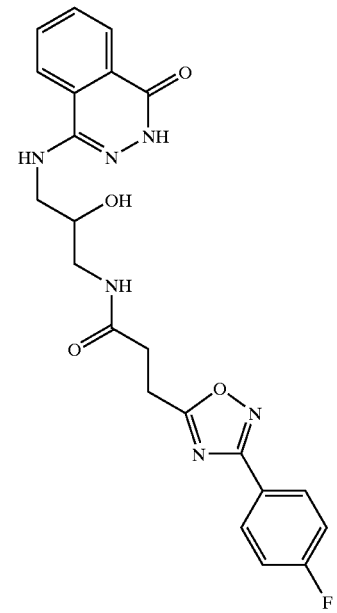

TABLE 1-continued
Representative compounds of Formula I.
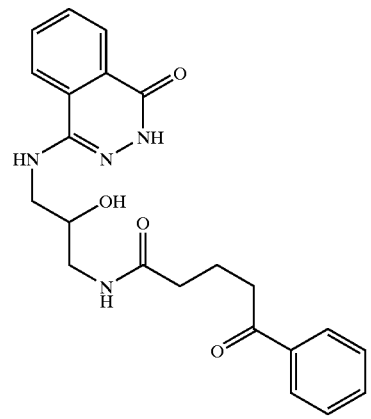
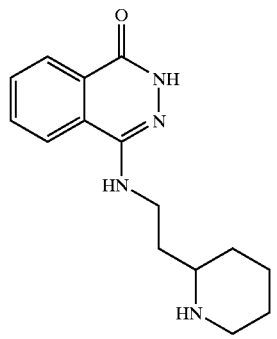
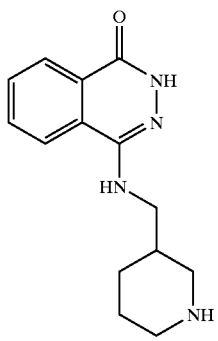
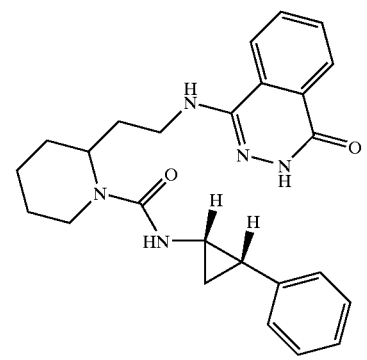
TABLE 1-continued
Representative compounds of Formula I.
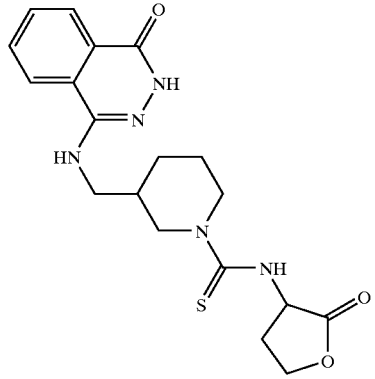
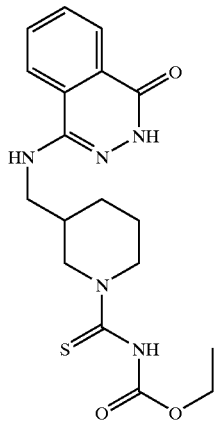
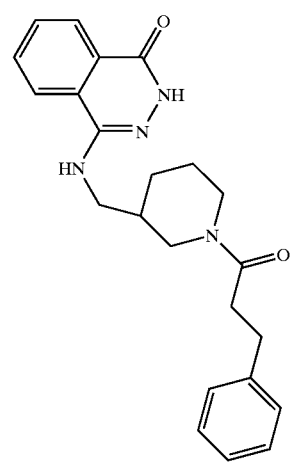

TABLE 1-continued
Representative compounds of Formula I.
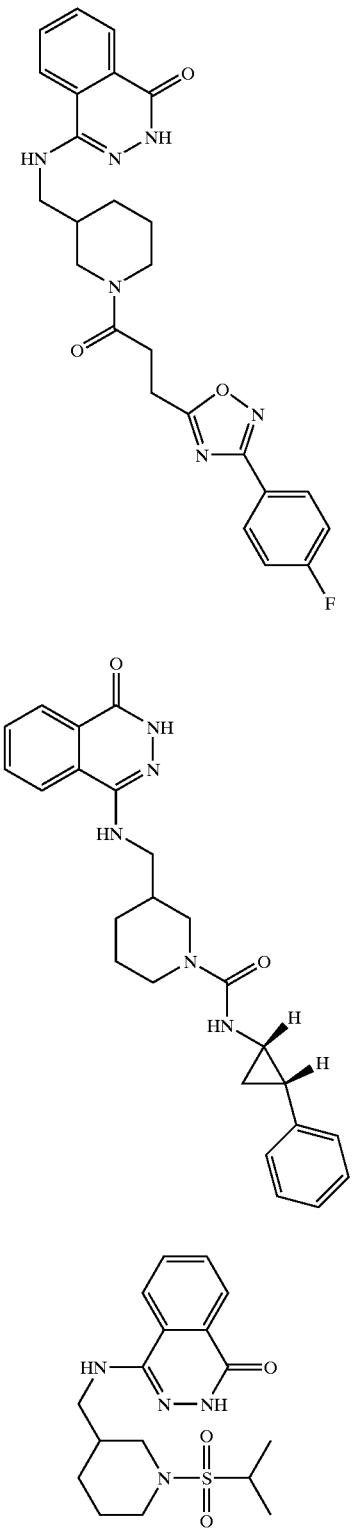
TABLE 1-continued
Representative compounds of Formula I.
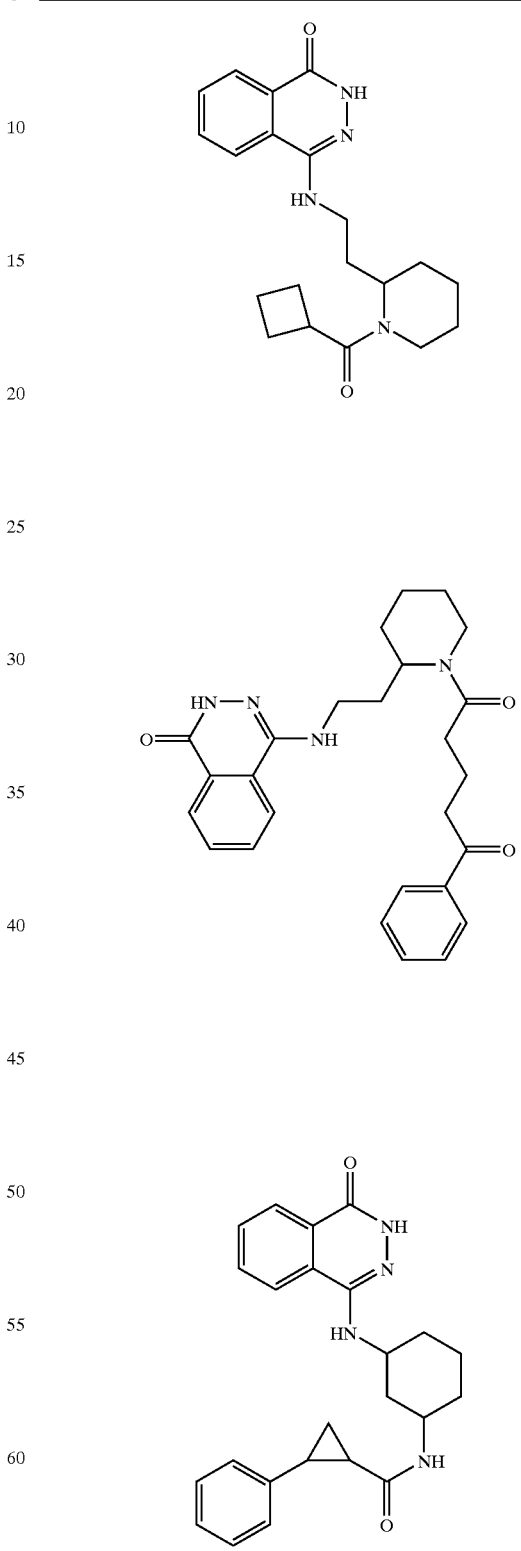

TABLE 1-continued
Representative compounds of Formula I.
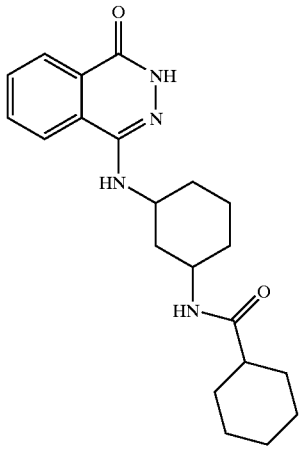
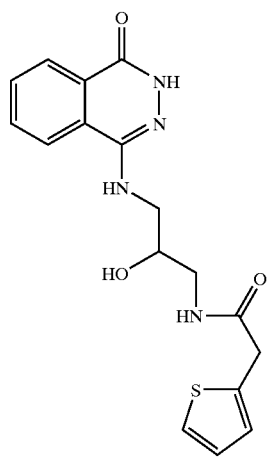
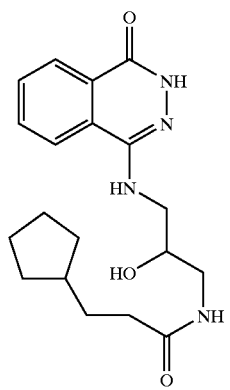
TABLE 1-continued
Representative compounds of Formula I.
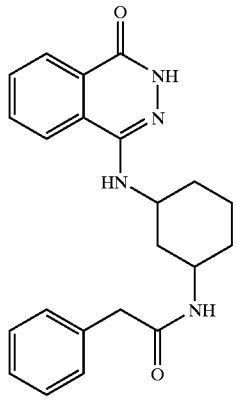
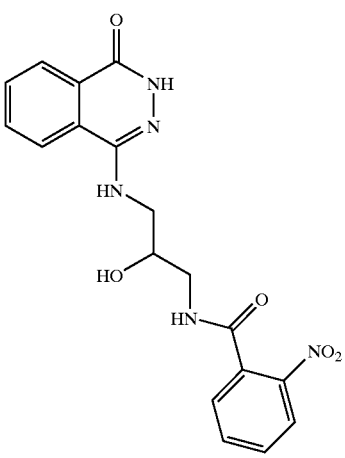
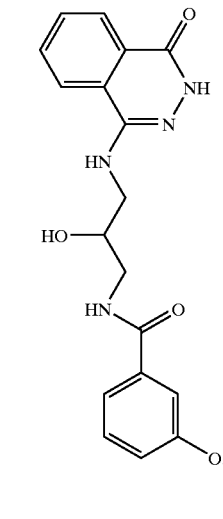

TABLE 1-continued
Representative compounds of Formula I.
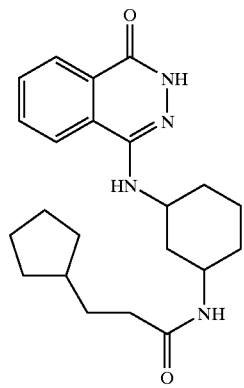
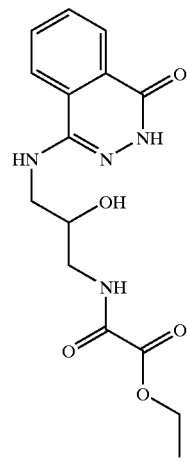
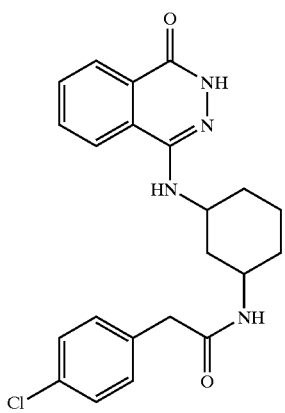
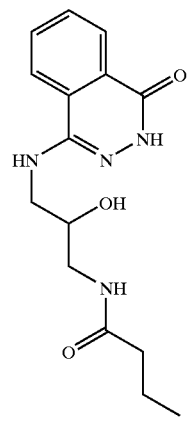
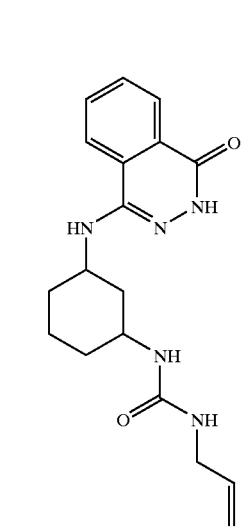
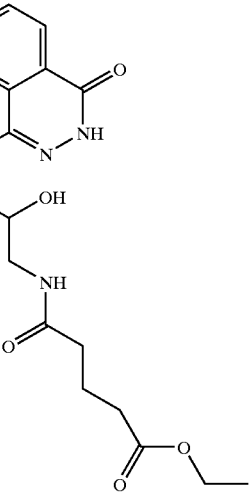

TABLE 1-continued
Representative compounds of Formula I.
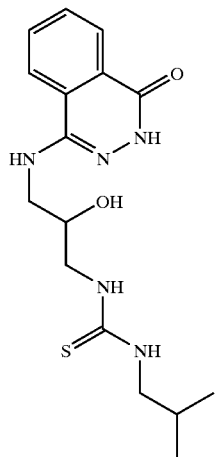
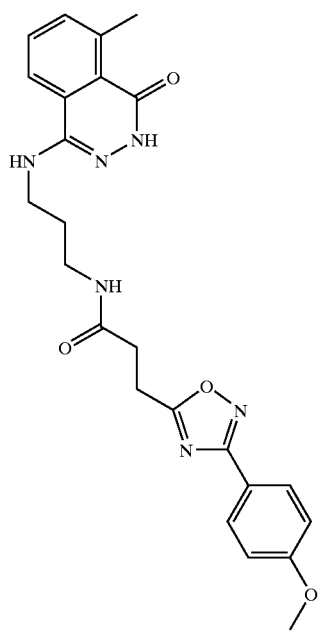
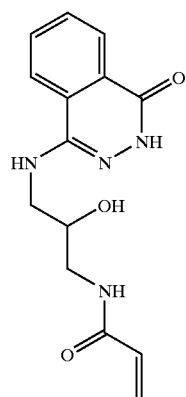
TABLE 1-continued
Representative compounds of Formula I.
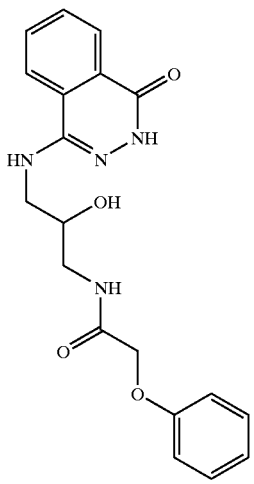
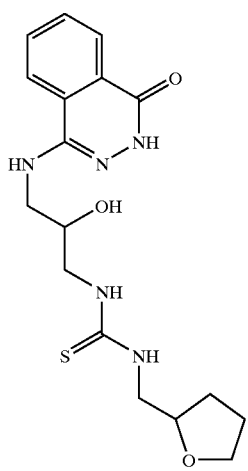
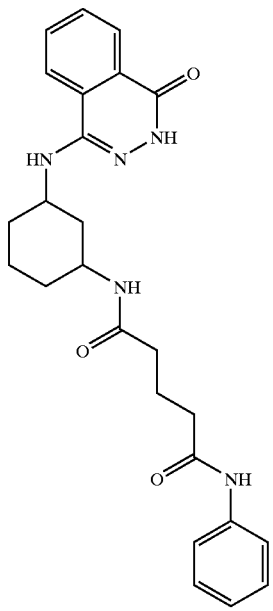

TABLE 1-continued
Representative compounds of Formula I.
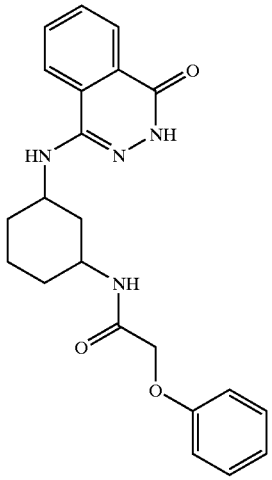
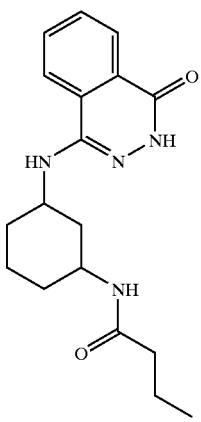
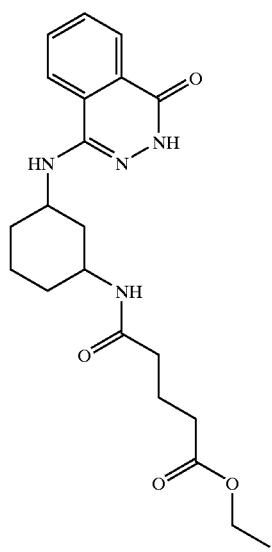
TABLE 1-continued
Representative compounds of Formula I.
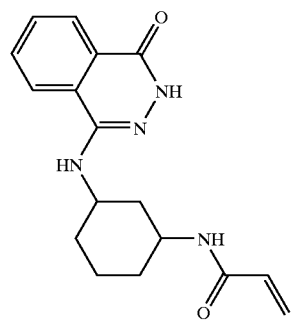
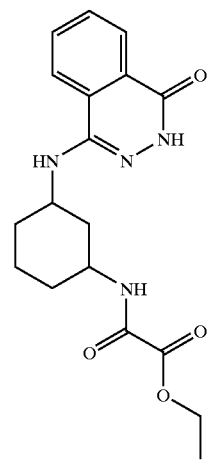
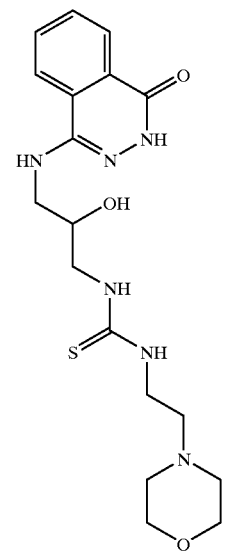

TABLE 1-continued
Representative compounds of Formula I.
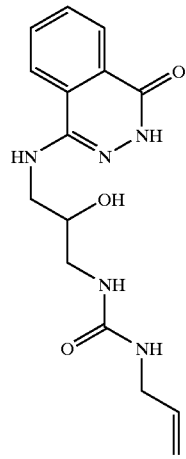
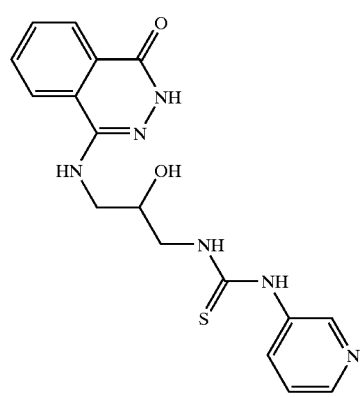
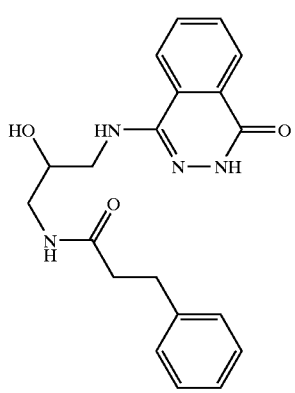
TABLE 1-continued
Representative compounds of Formula I.
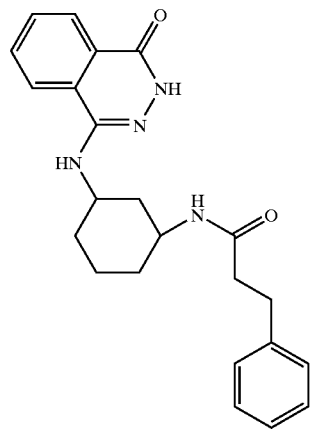
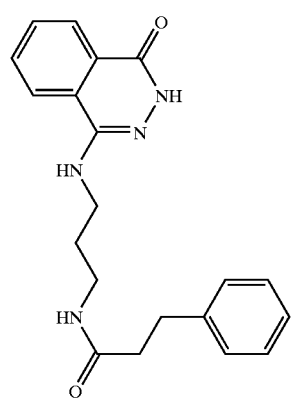
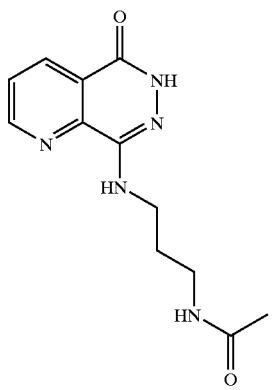

TABLE 1-continued
Representative compounds of Formula I.
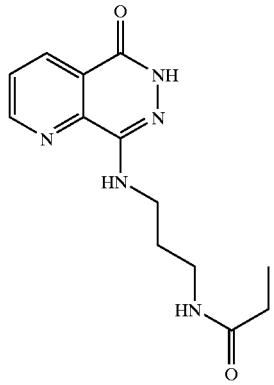
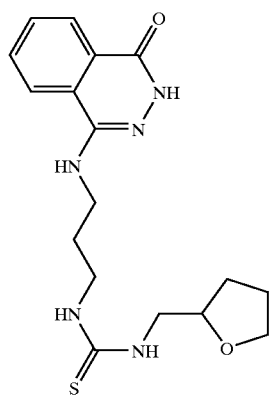
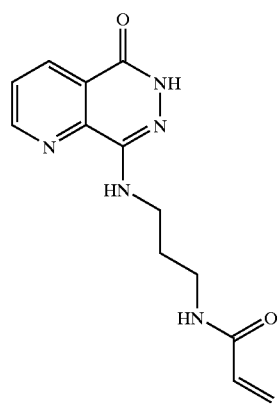
TABLE 1-continued
Representative compounds of Formula I.
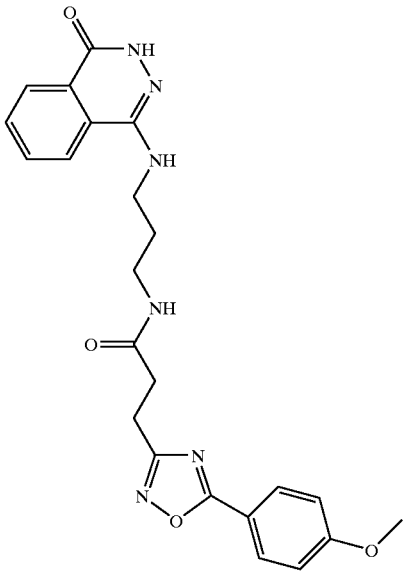
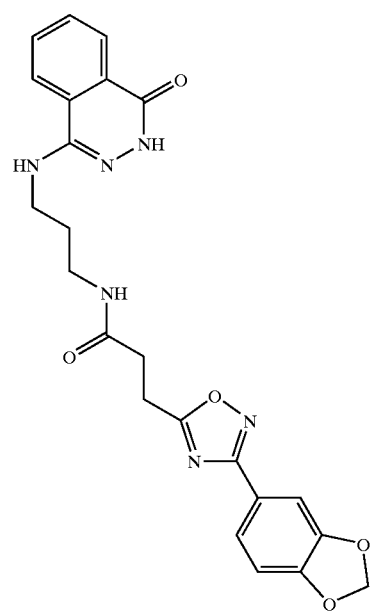

TABLE 1-continued
Representative compounds of Formula I.
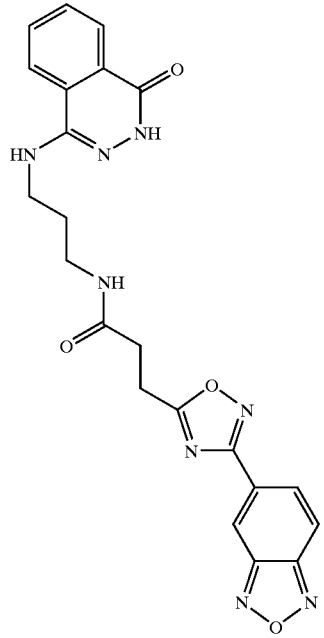
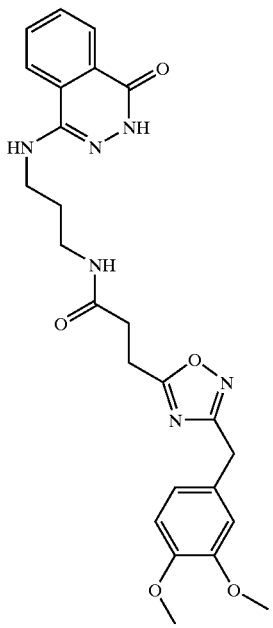
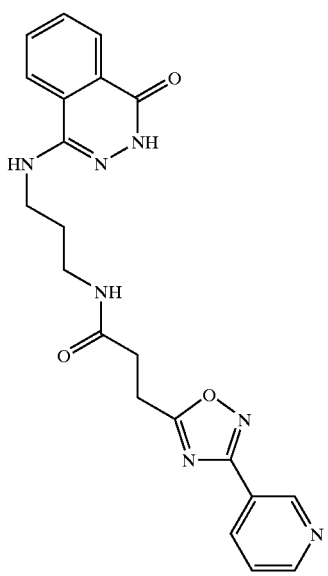
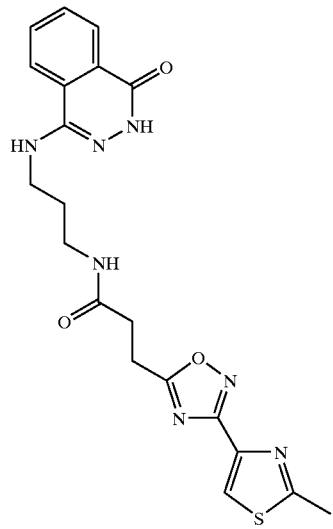

TABLE 1-continued
Representative compounds of Formula I.
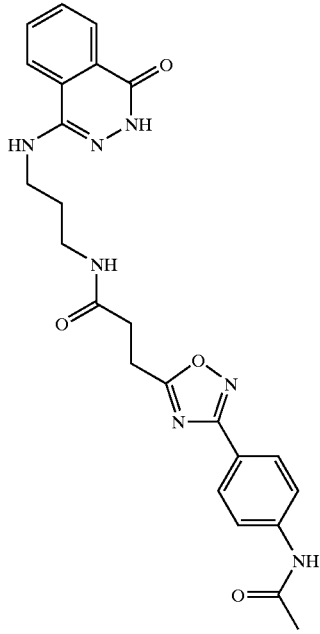
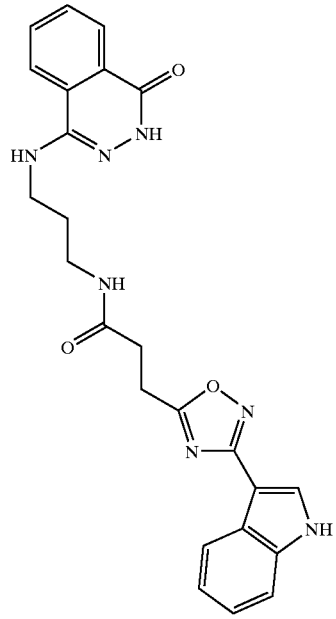
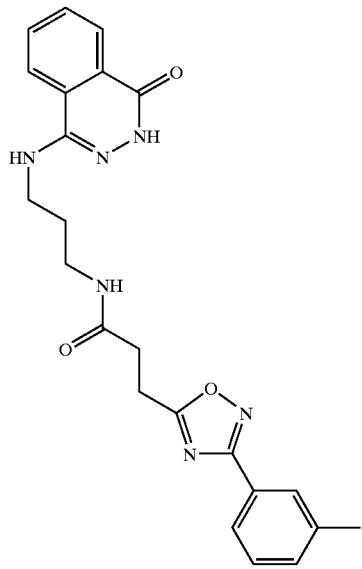
TABLE 1-continued
Representative compounds of Formula I.
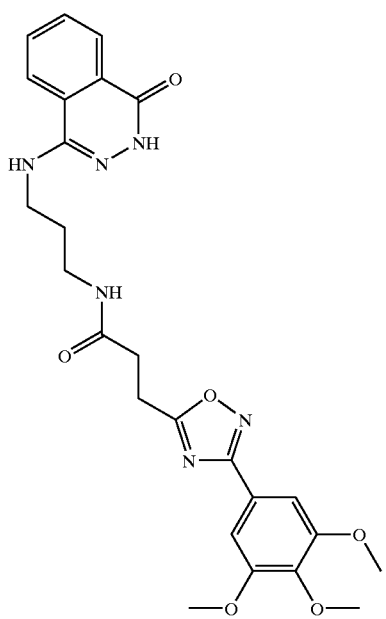

TABLE 1-continued

Representative compounds of Formula I.

TABLE 1-continued
Representative compounds of Formula I.
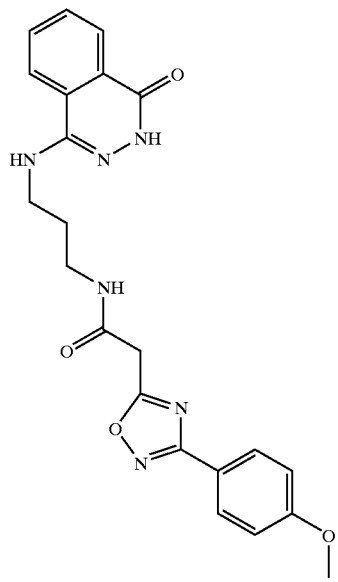
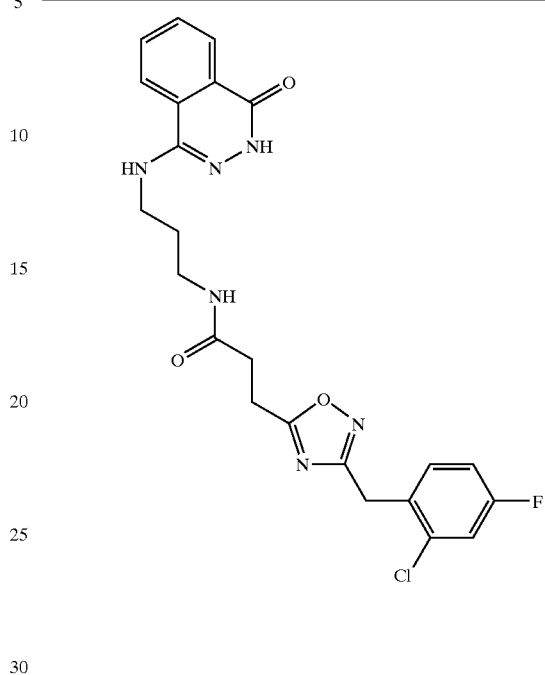
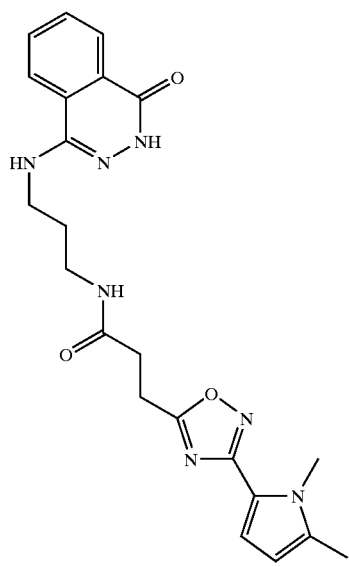
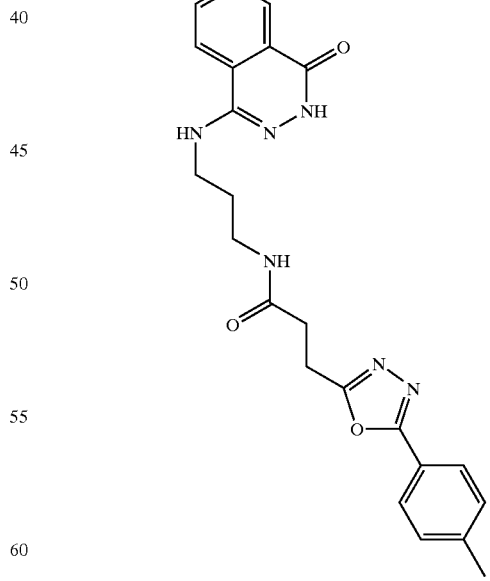

TABLE 1-continued
Representative compounds of Formula I.
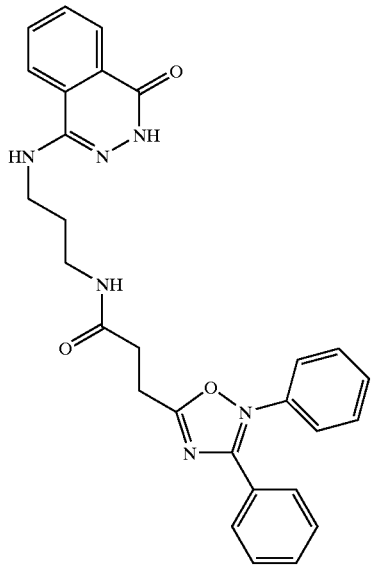
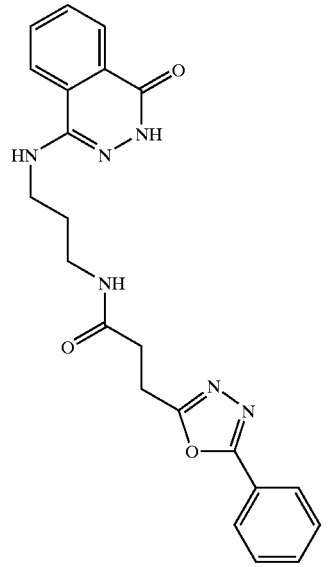
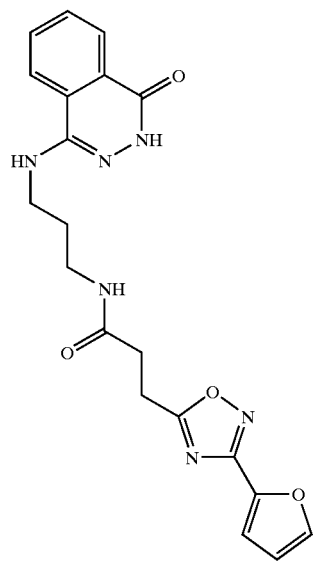
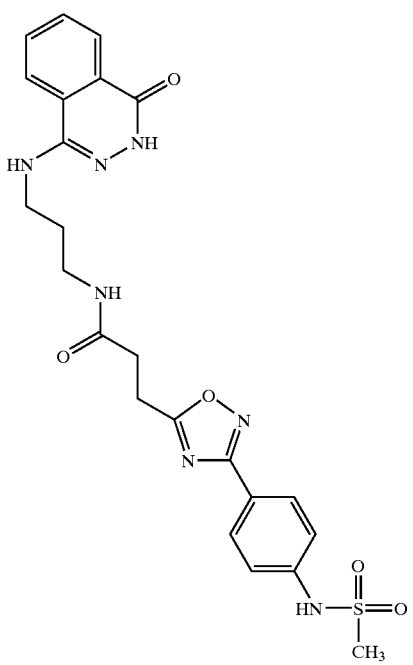

TABLE 1-continued
Representative compounds of Formula I.
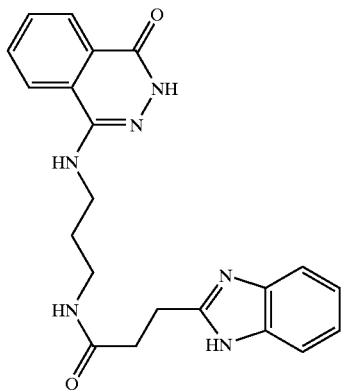
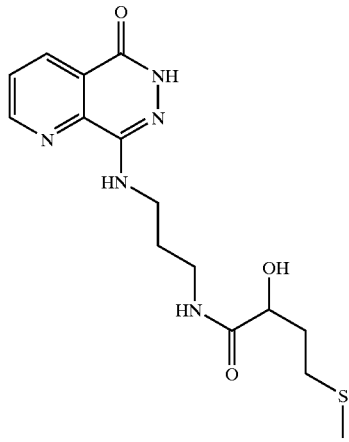

TABLE 1-continued
Representative compounds of Formula I.
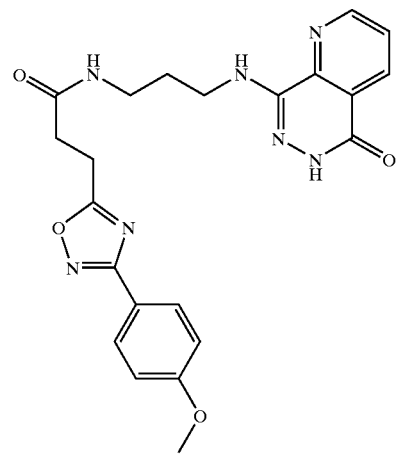
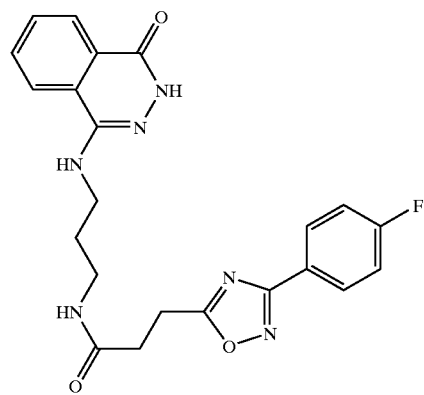
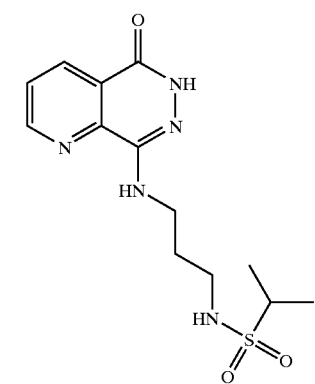
TABLE 1-continued
Representative compounds of Formula I.
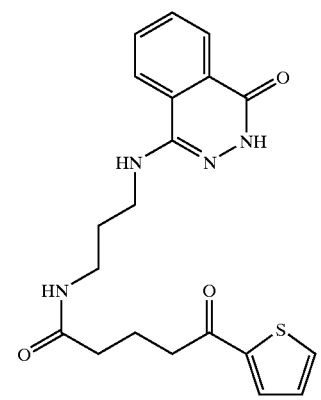
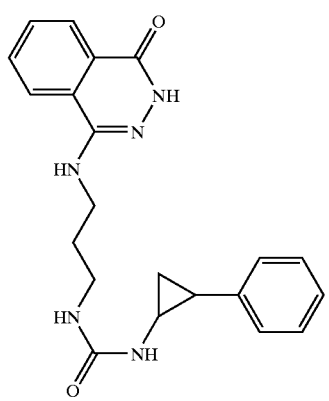
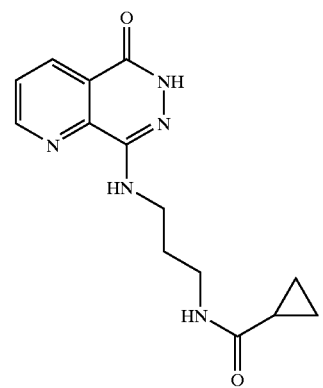
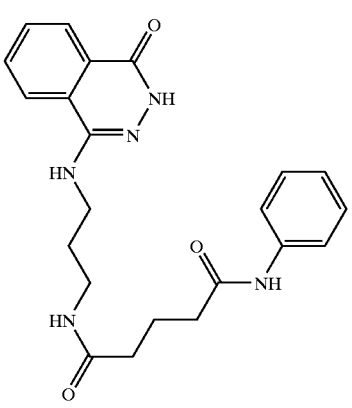

TABLE 1-continued
Representative compounds of Formula I.
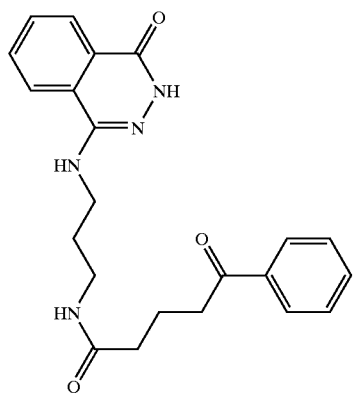
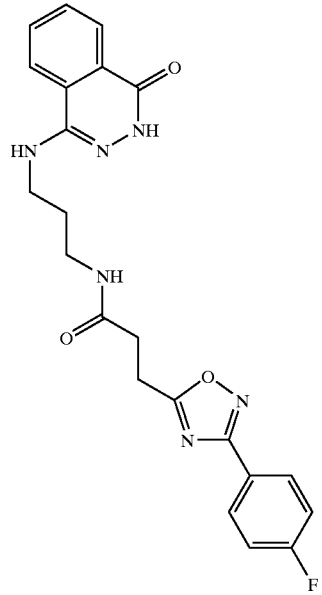
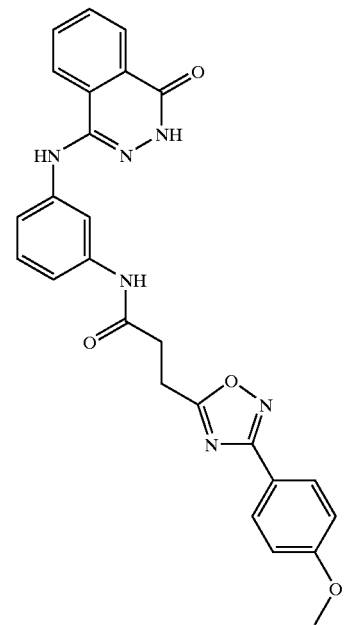
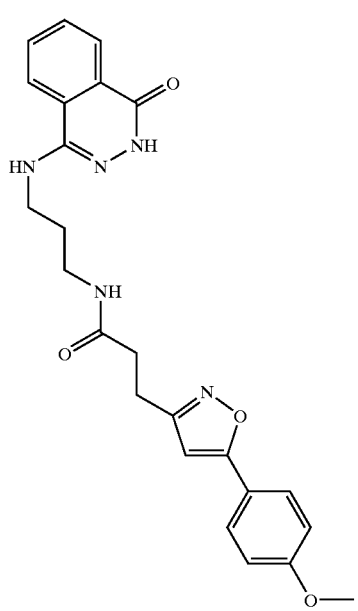

TABLE 1-continued
Representative compounds of Formula I.
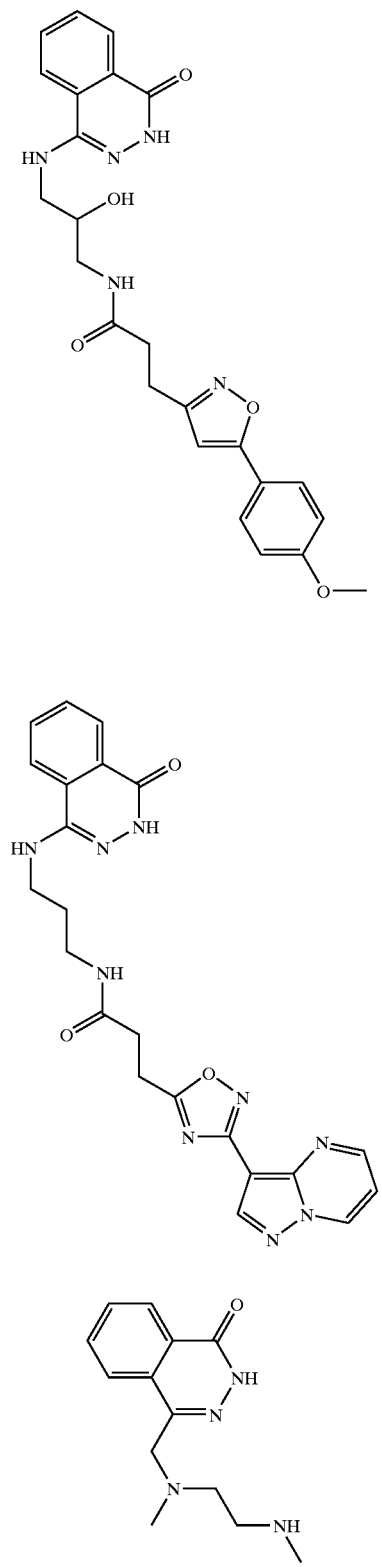
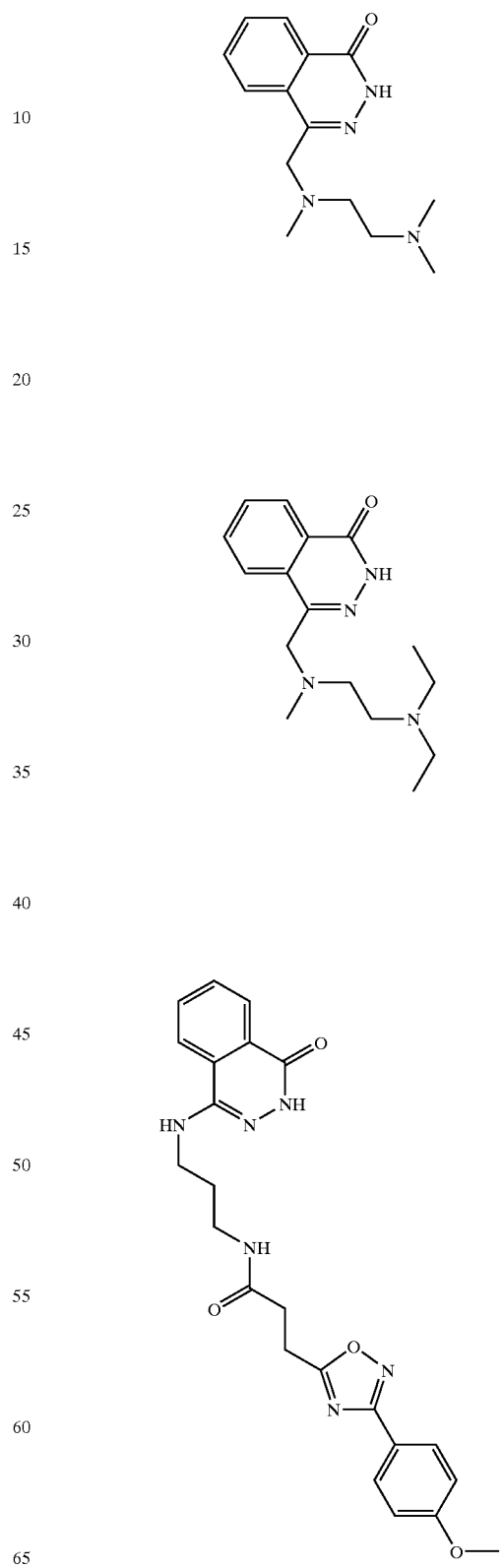

TABLE 1-continued
Representative compounds of Formula I.
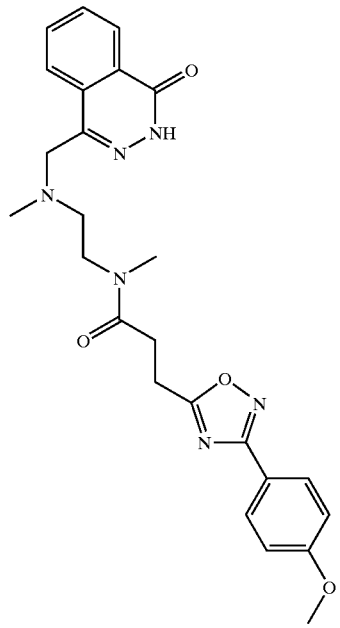
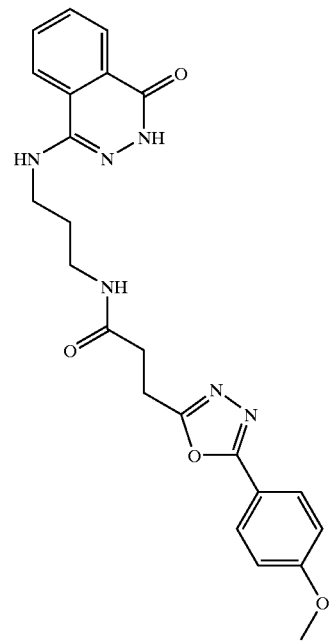
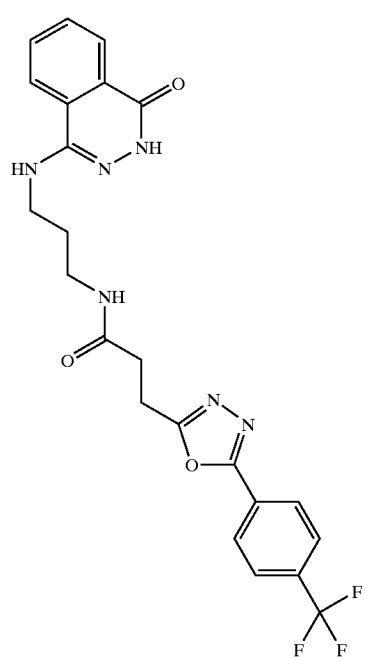
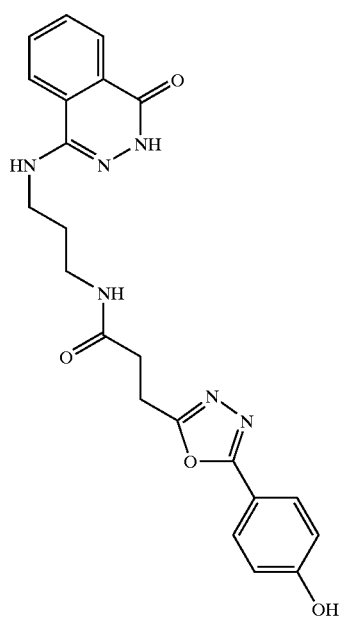

TABLE 1-continued
Representative compounds of Formula I.
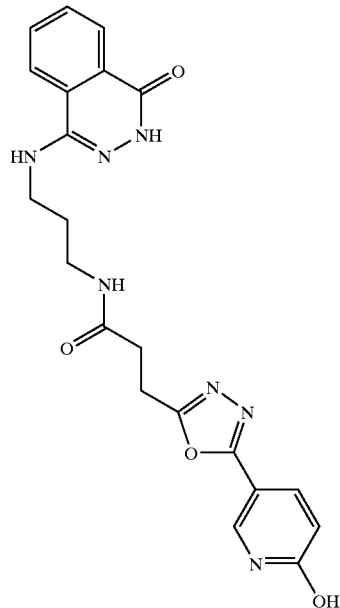
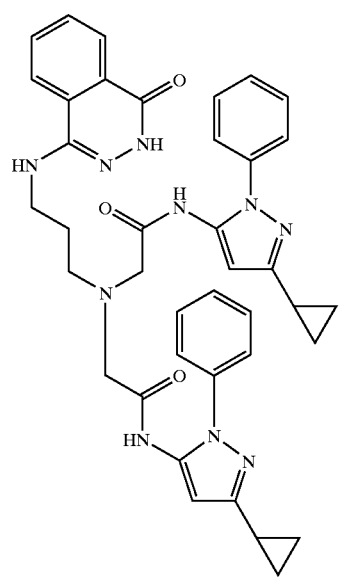
TABLE 1-continued
Representative compounds of Formula I.
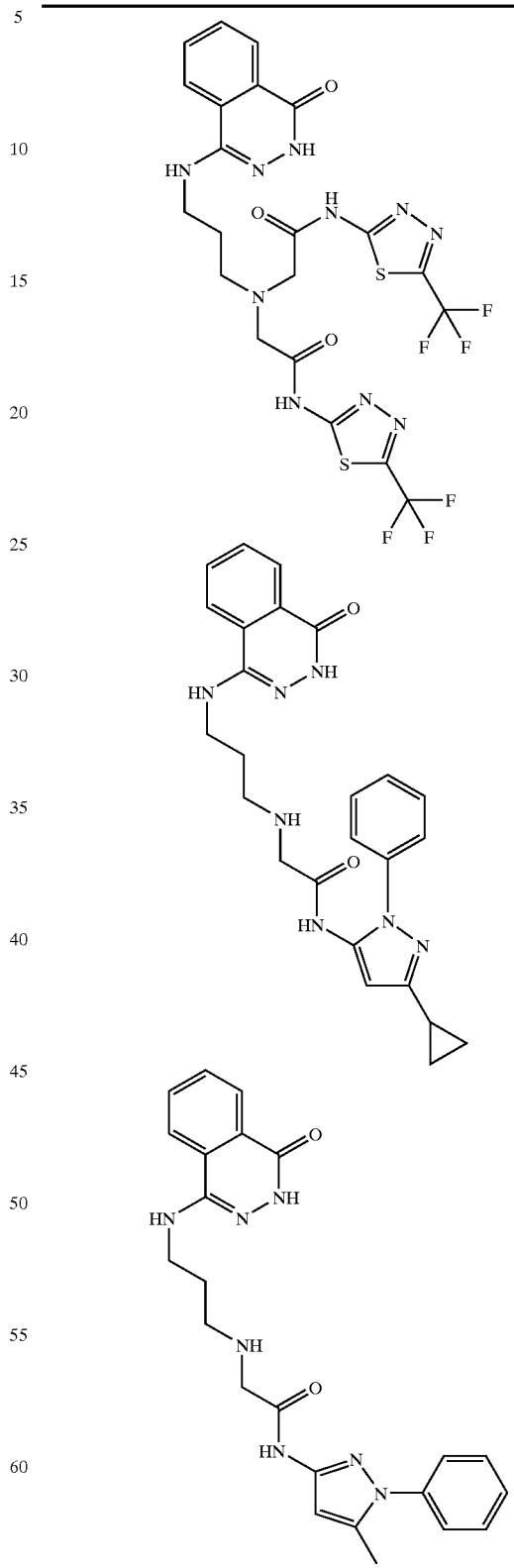

TABLE 1-continued
Representative compounds of Formula I.
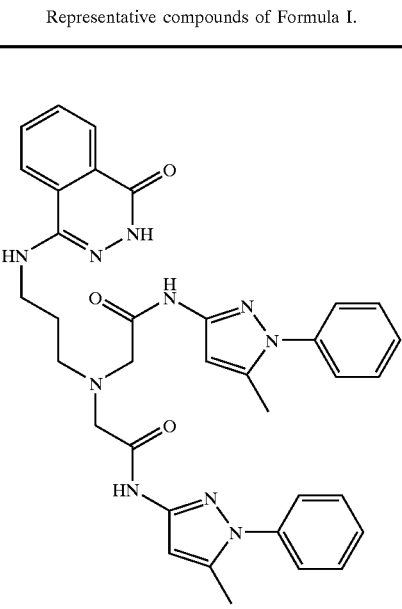
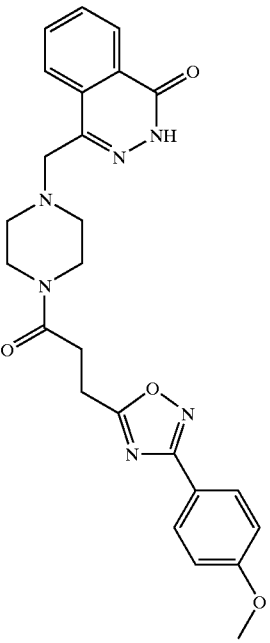
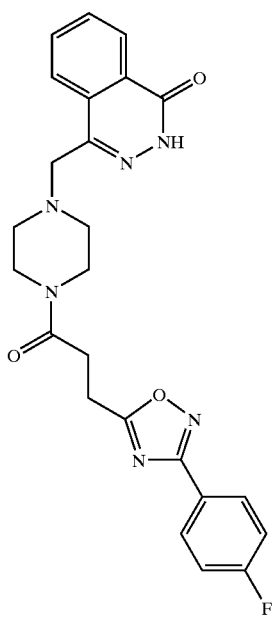
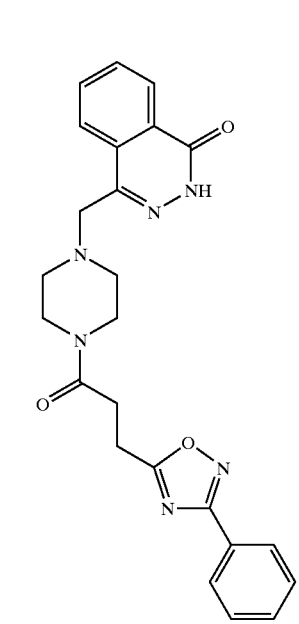

TABLE 1-continued
Representative compounds of Formula I.
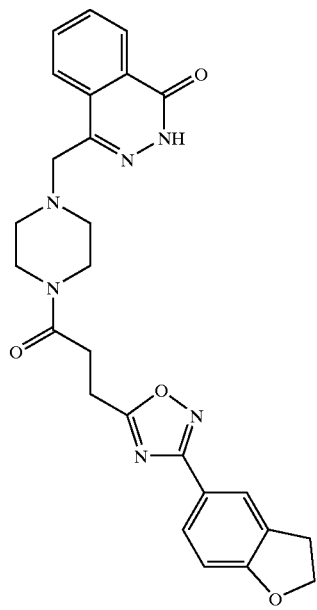
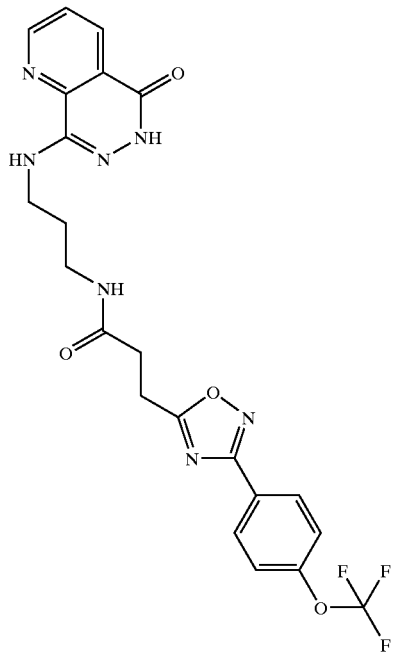

TABLE 1-continued
Representative compounds of Formula I.
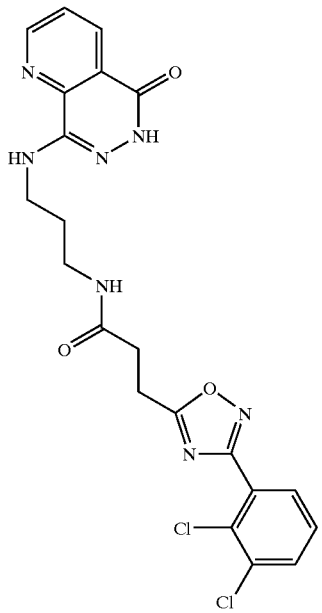
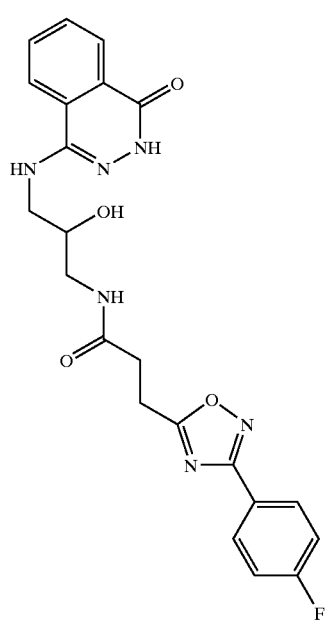
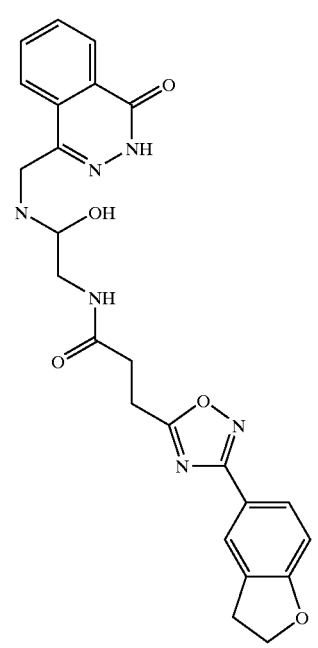
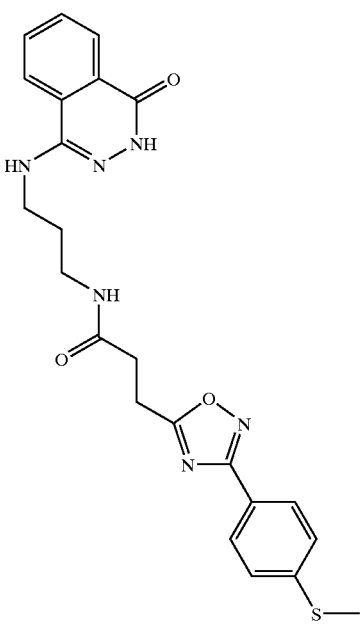

TABLE 1-continued
Representative compounds of Formula I.
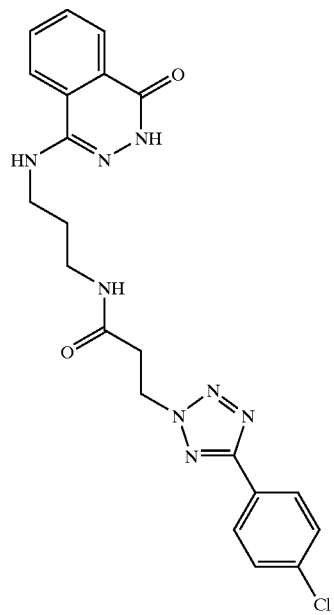
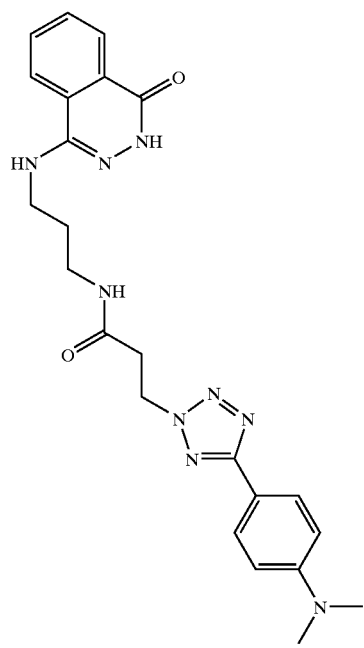
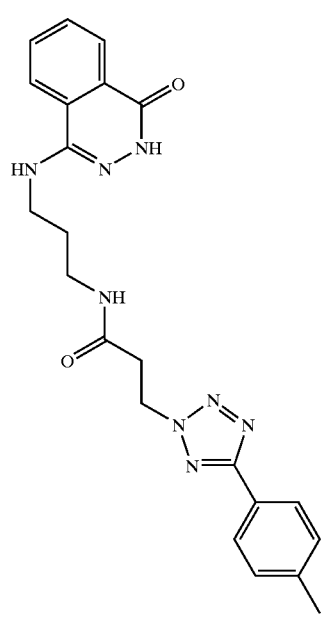
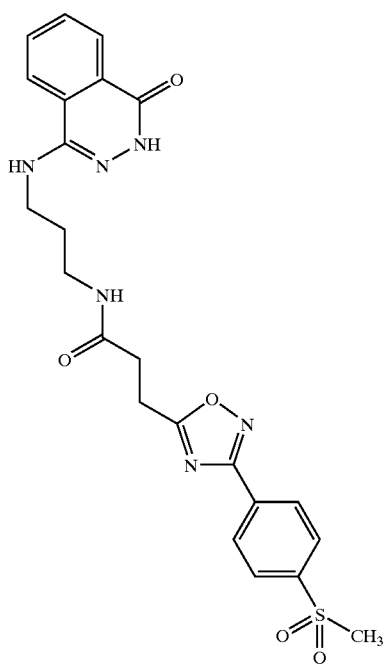

TABLE 1-continued
Representative compounds of Formula I.
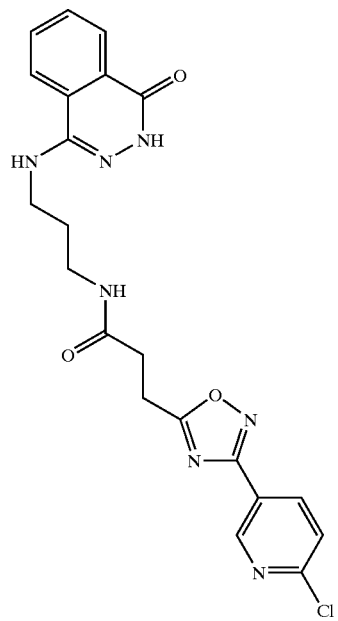
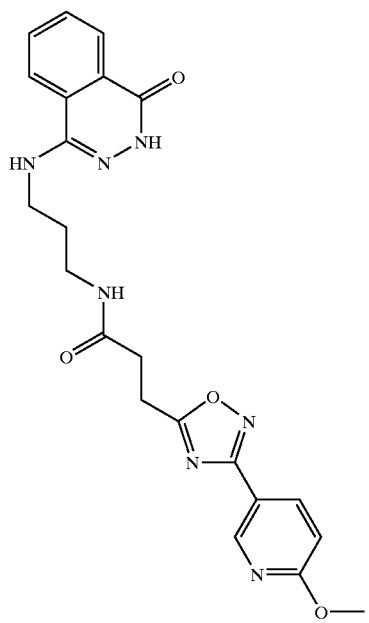
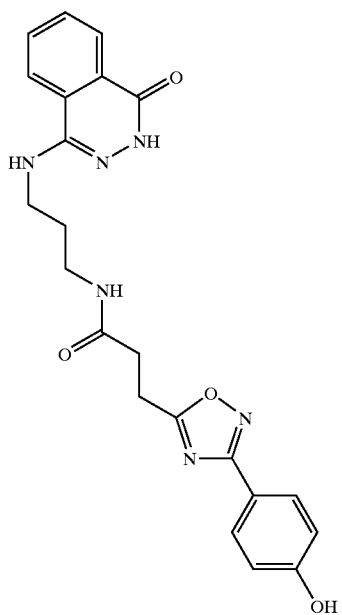
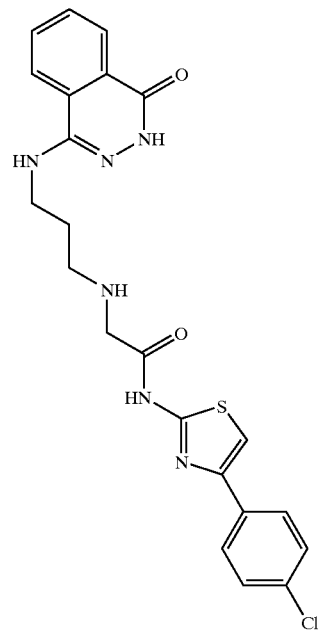

TABLE 1-continued
Representative compounds of Formula I.
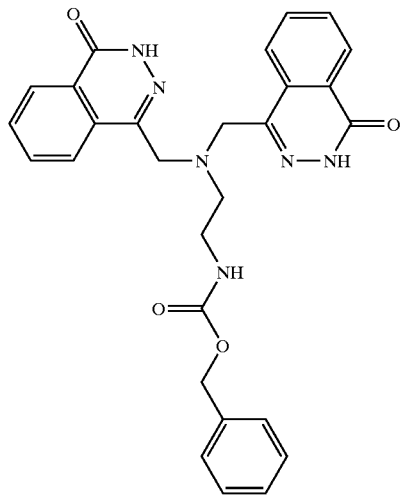
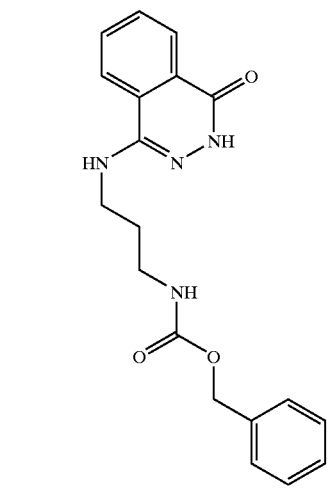
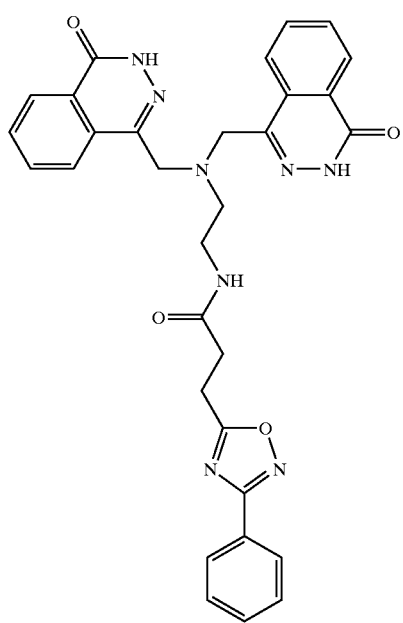
TABLE 1-continued
Representative compounds of Formula I.
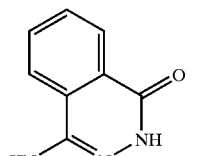
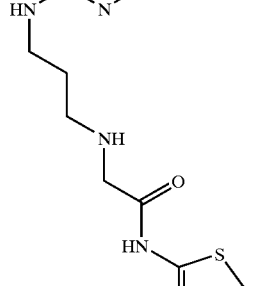
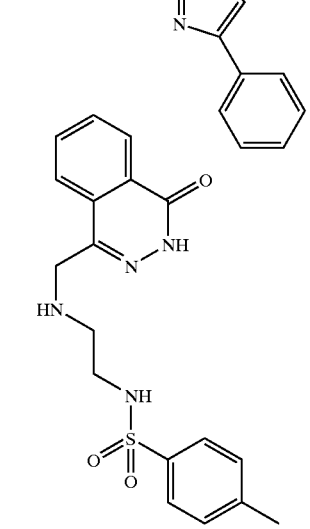
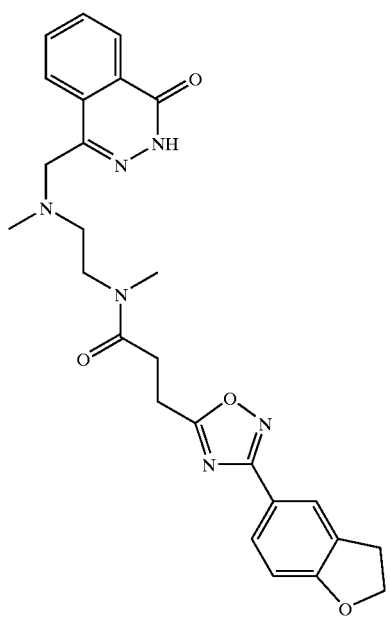

TABLE 1-continued
Representative compounds of Formula I.
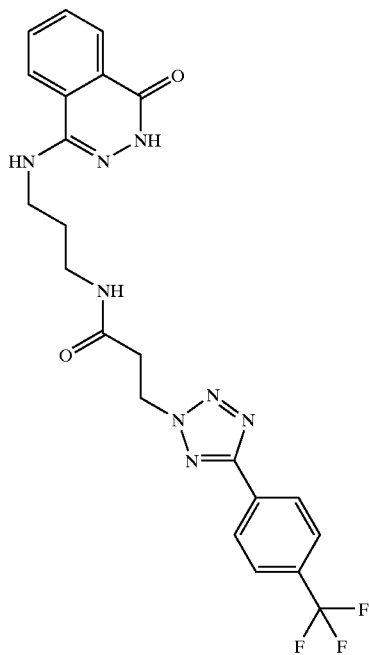
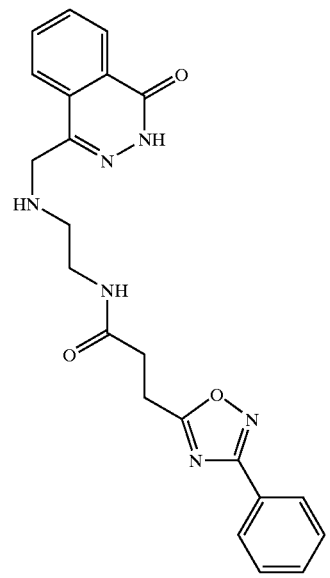
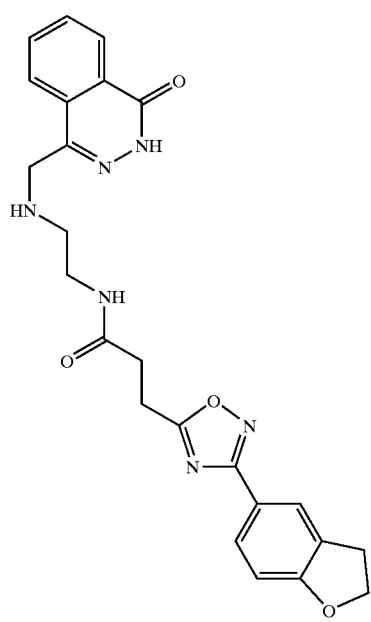
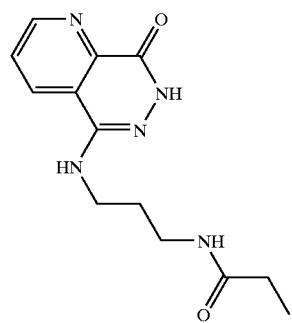

TABLE 1-continued
Representative compounds of Formula I.
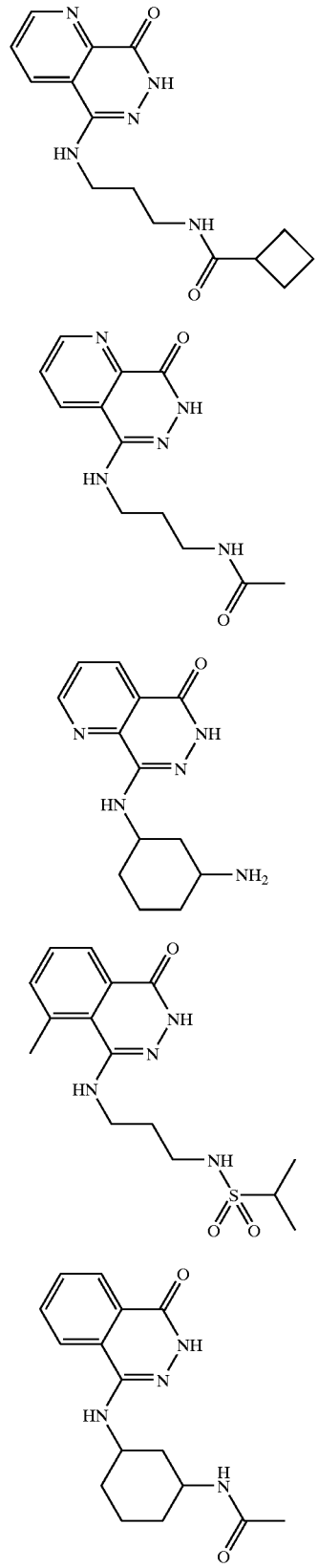
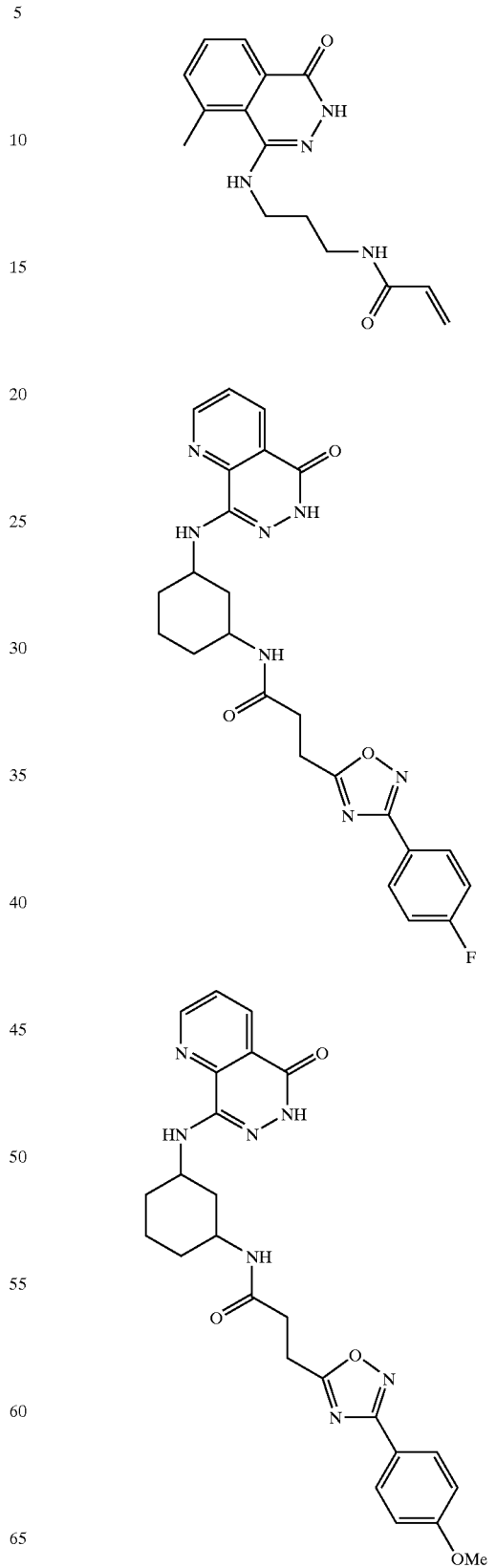

TABLE 1-continued
Representative compounds of Formula I.
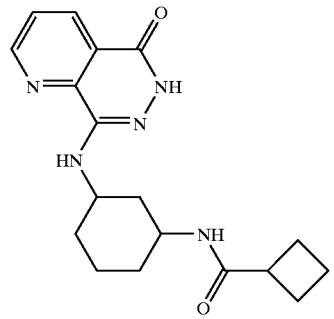
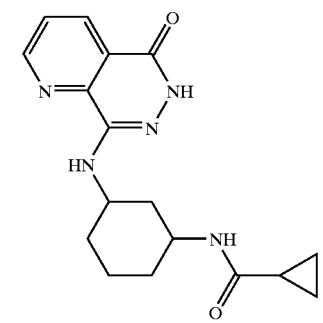
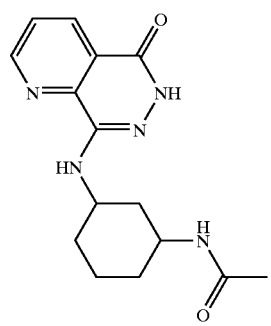
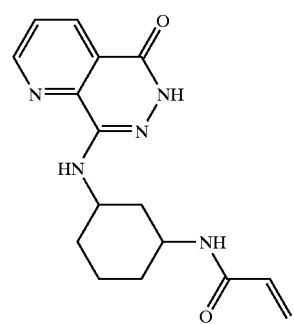
TABLE 1-continued
Representative compounds of Formula I.
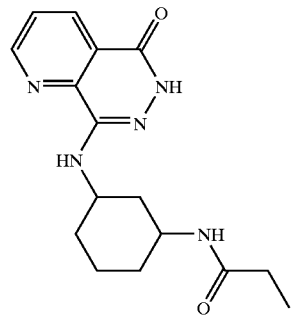
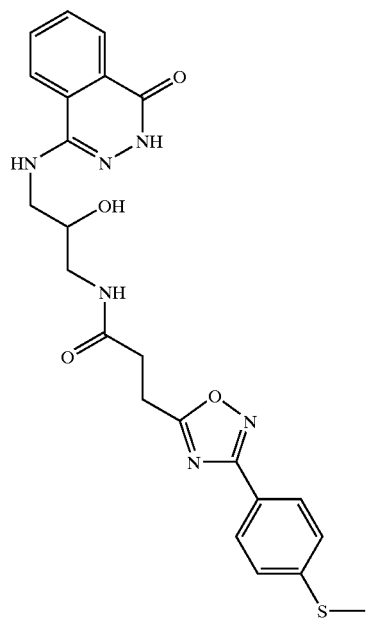
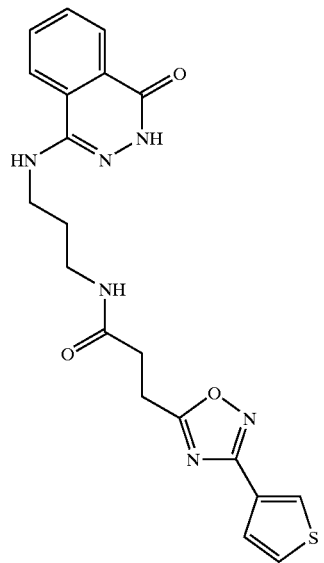

TABLE 1-continued
Representative compounds of Formula I.
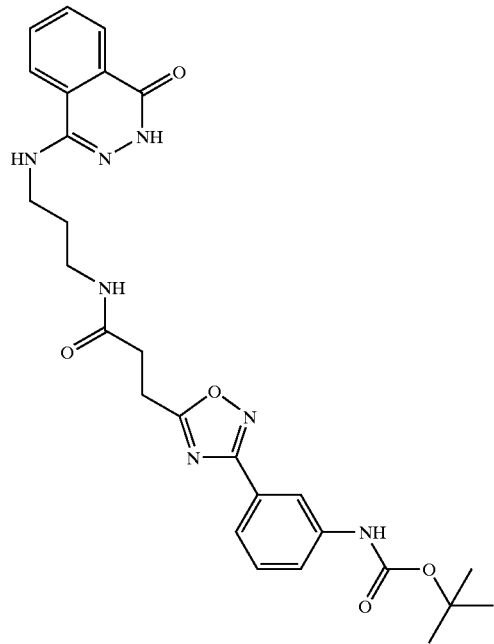
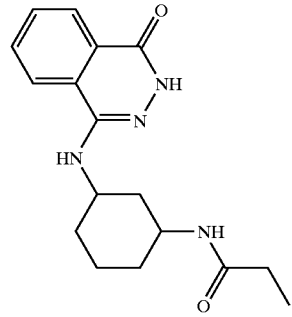
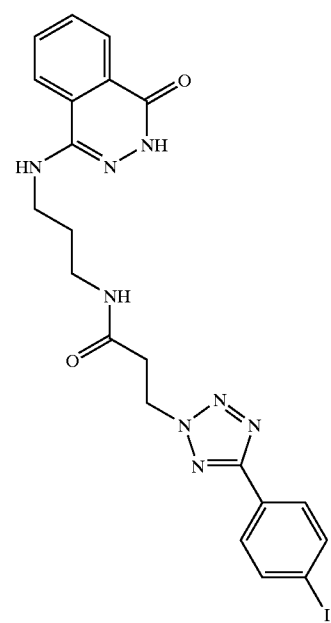
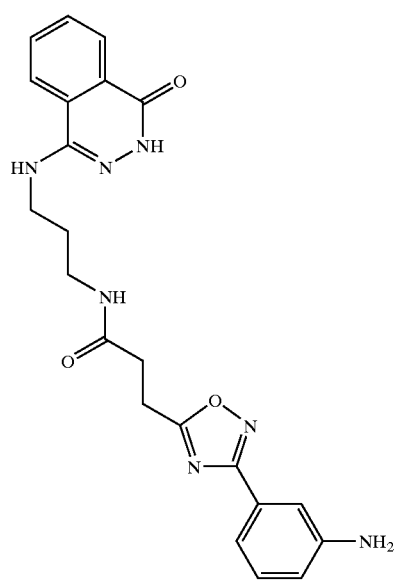
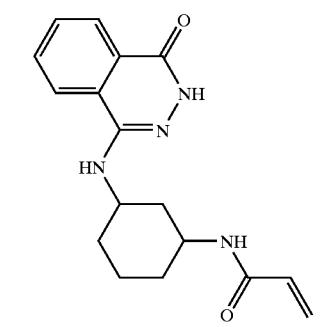
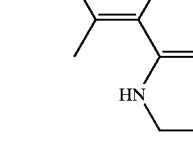

TABLE 1-continued
Representative compounds of Formula I.
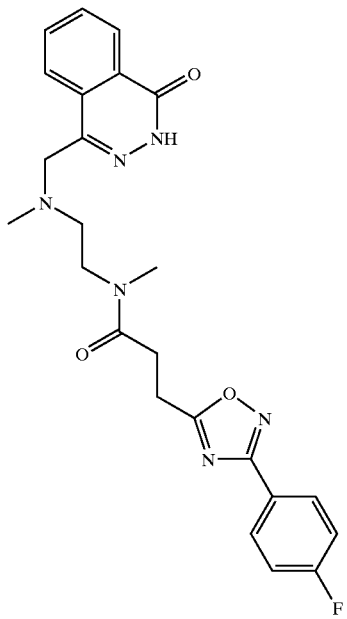
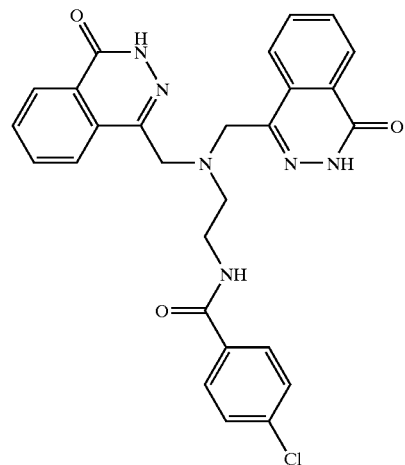
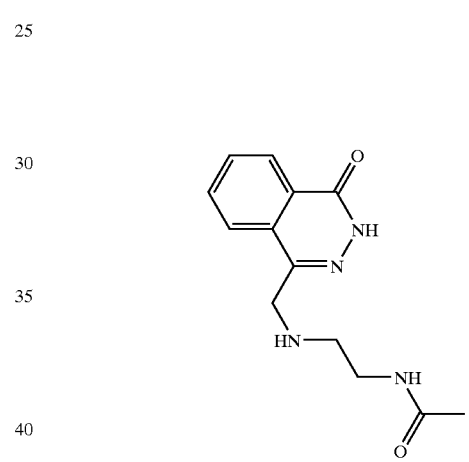
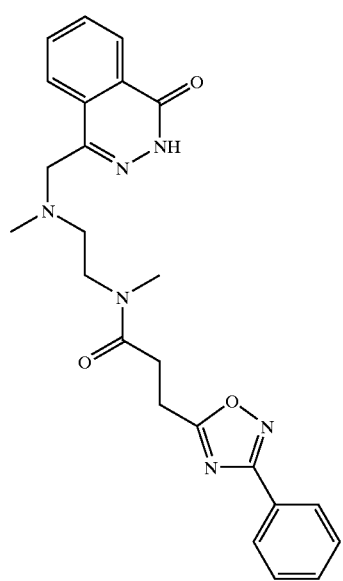
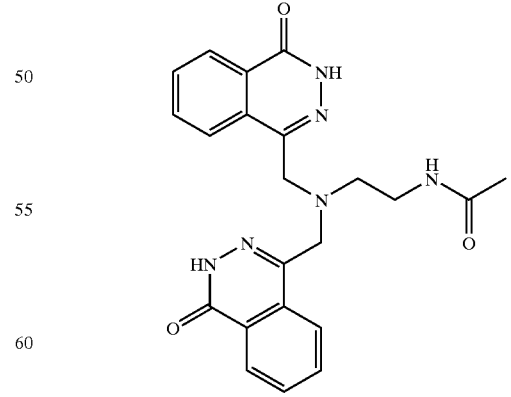

TABLE 1-continued
Representative compounds of Formula I.
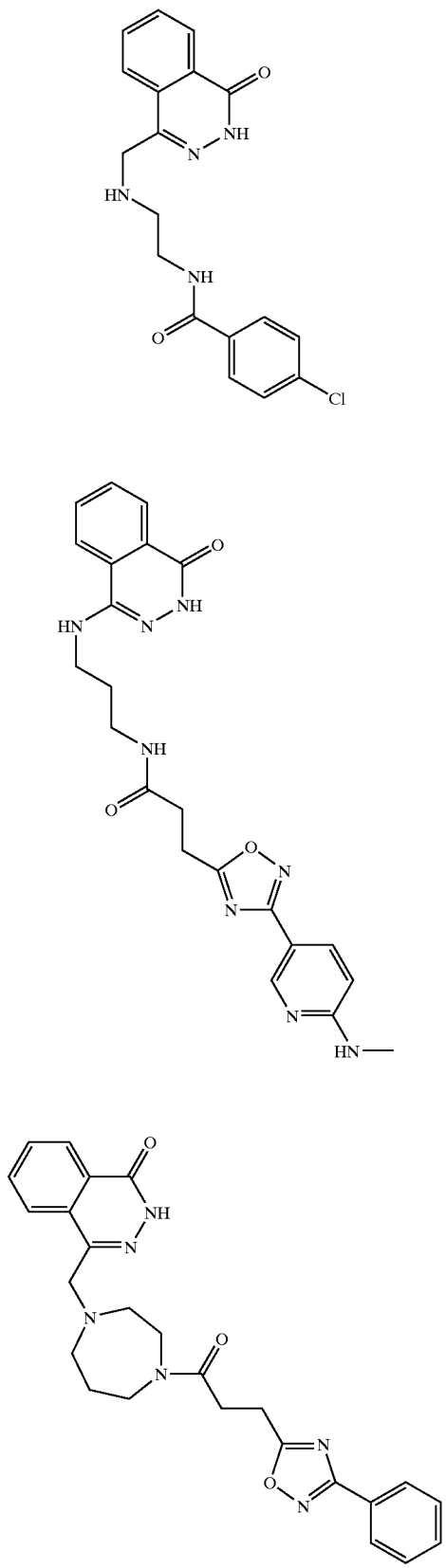
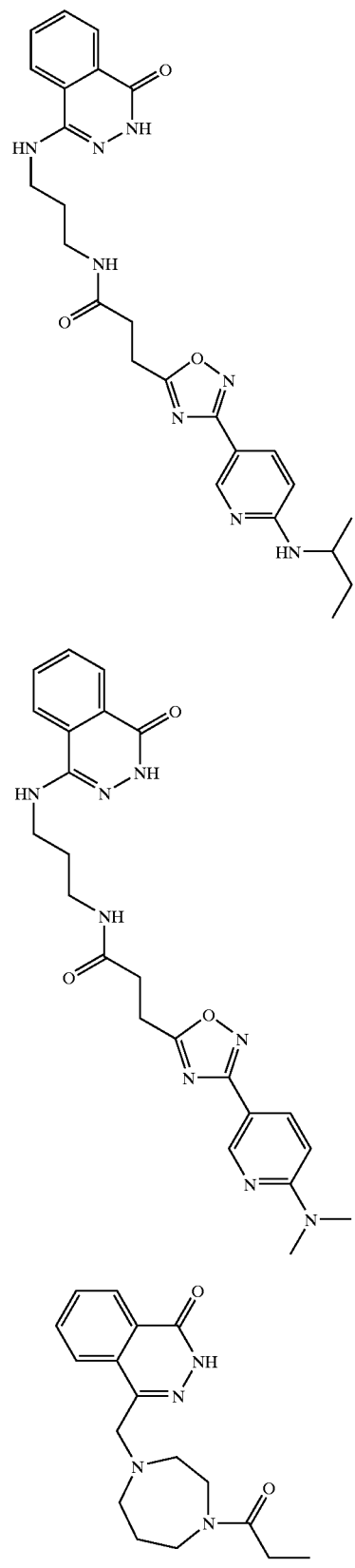

TABLE 1-continued
Representative compounds of Formula I.
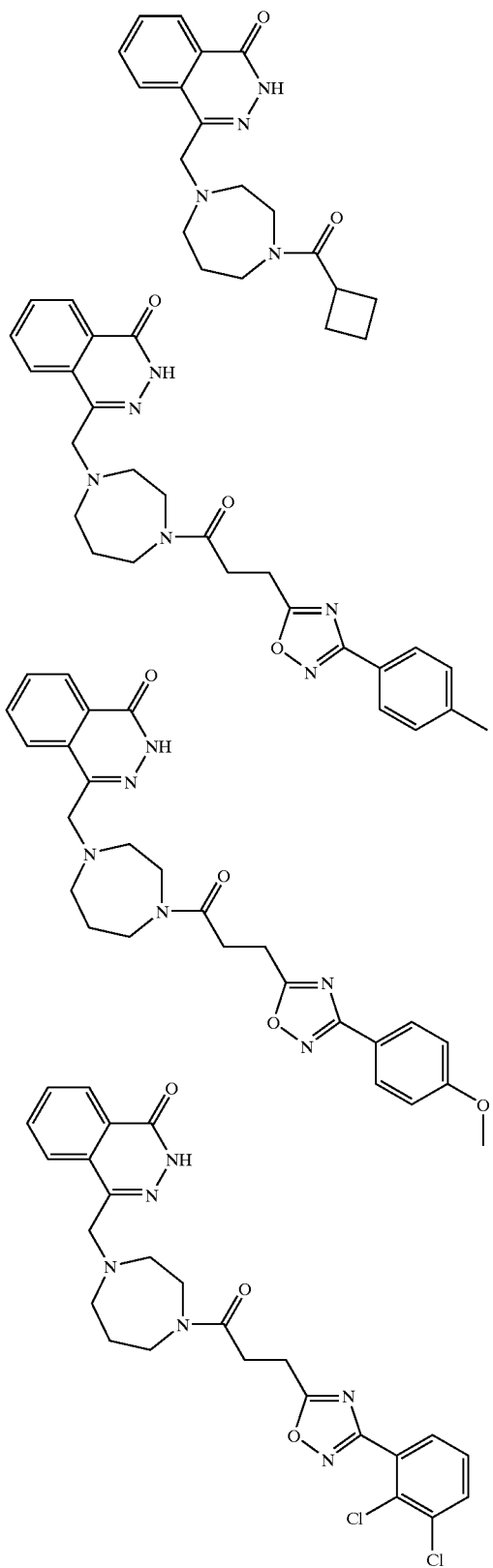
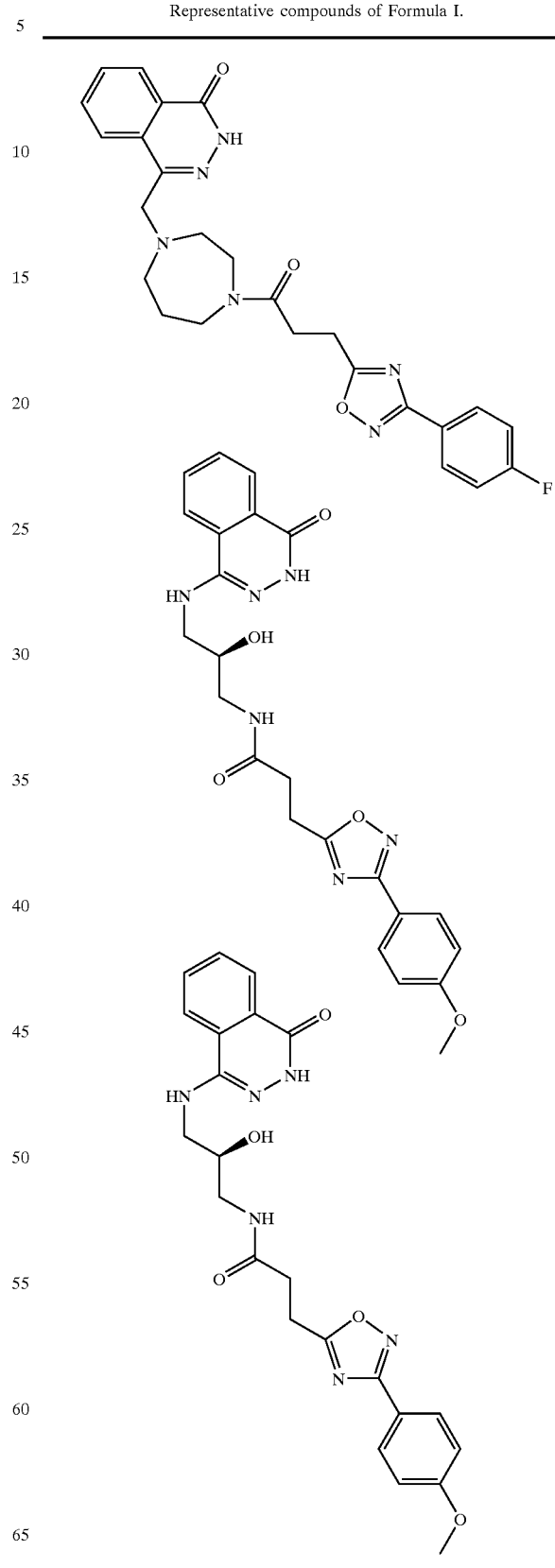

TABLE 2

Representative compounds of Formula I along with some nomenclatures.

| Structure | NAME |
|---|---|
| 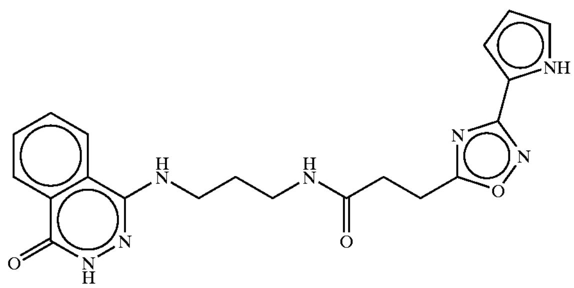 | N-[3-(4-Oxo-3,4-dihydro-phthalazin-1-ylamino)-propyl]-3-[3-(1H-pyrrol-2-yl)-[1,2,4]oxadiaol-5-yl]-propionamide |
| 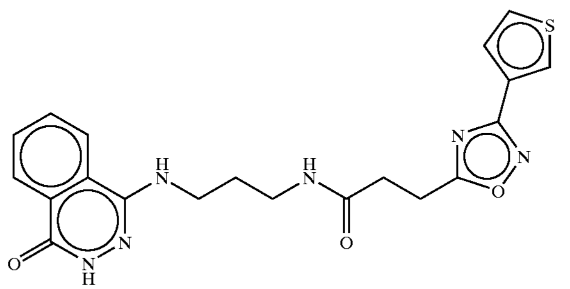 | N-[3-(4-Oxo-3,4-dihydro-phthalazin-1-ylamino)-propyl]-3-(3-thiophen-3-yl-[1,2,4]oxadiazol-5-yl)-propionamide |
| 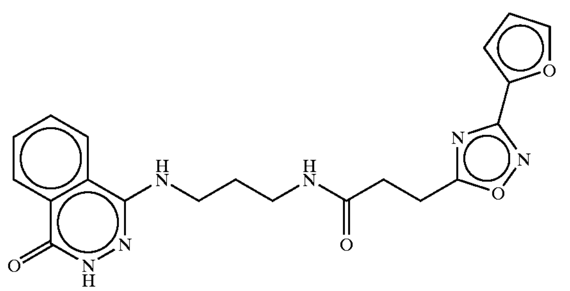 | 3-(3-Furan-2-yl-[1,2,4]oxadiazol-5-yl)-N-[3-(4-oxo-3,4-dihydro-phthalazin-1-ylamino)-propyl]-propionamide |
| 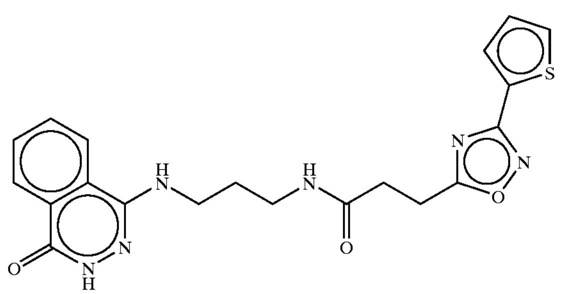 | N-[3-(4-Oxo-3,4-dihydro-phthalazin-1-ylamino)-propyl]-3-(3-thiophen-2-yl-[1,2,4]oxadiazol-5-yl)-propionamide |
| 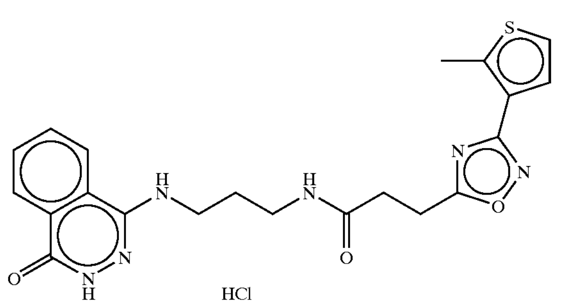 | 3-[3-(2-Methyl-thiophen-3-yl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 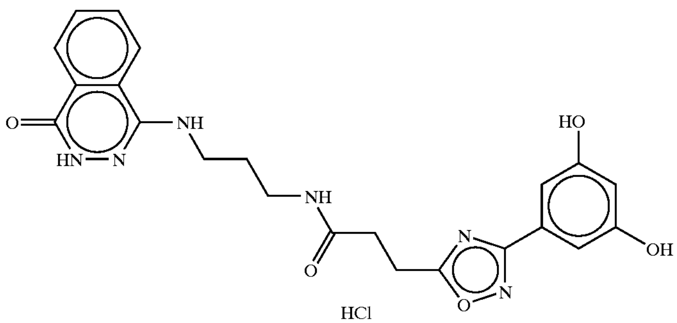 | 3-[3-(3,5-Dihydroxy-phenyl)-[1,2,4]oxadiazol-5-yl]-N-[3-(4-oxo-3,4-dihydro-phthalazin-1-ylamino)-propyl]-propionamide |
| 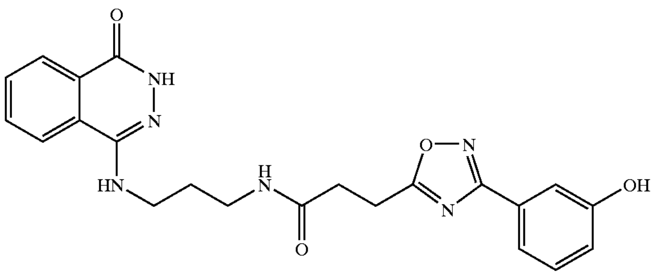 | 3-[3-(3-Hydroxy-phenyl)-[1,2,4]oxadiazol-5-yl]-N-[3-(4-oxo-3,4-dihydro-phthalazin-1-ylamino)-propyl]-propionamide |
| 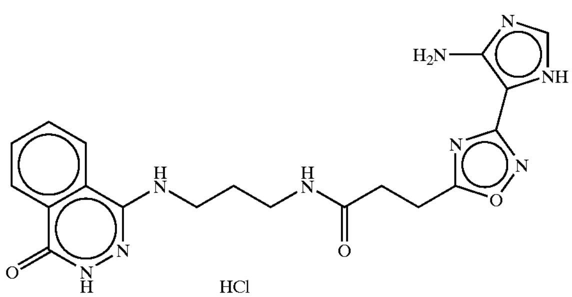 | 3-[3-(5-Amino-3H-imidazol-4-yl)-[1,2,4]oxadiazol-5-yl]-N-[3-(4-oxo-3,4-dihydro-phthalazin-1-ylamino)-propyl]-propionamide |
| 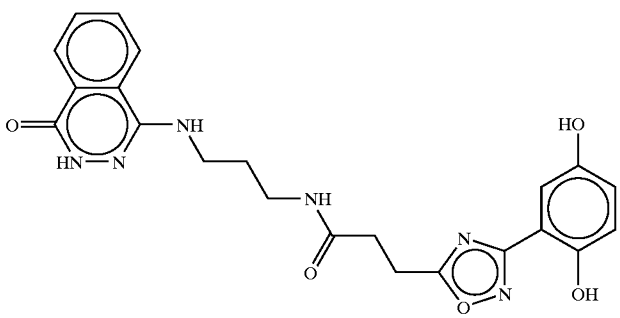 | 3-[3-(2,5-Dihydroxy-phenyl)-[1,2,4]oxadiazol-5-yl]-N-[3-(4-oxo-3,4-dihydro-phthalazin-1-ylamino)-propyl]-propionamide |
| 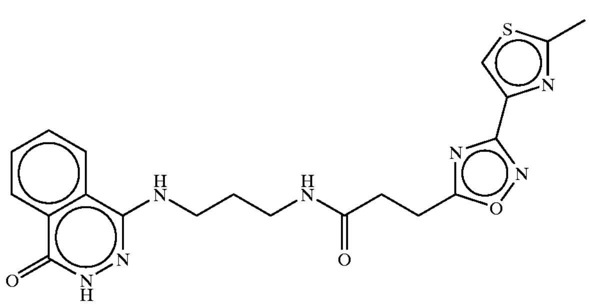 | 3-[3-(2-Methyl-thiazol-4-yl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 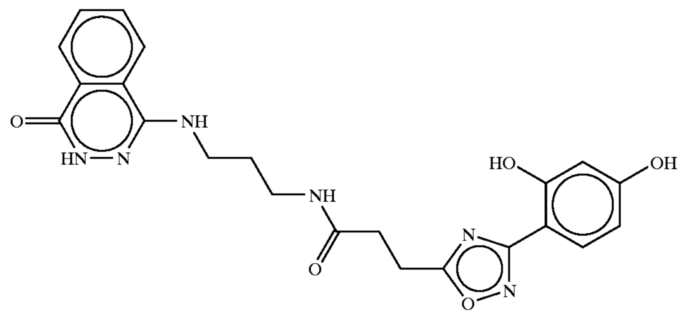 | 3-[3-(2,4-Dihydroxy-phenyl)-[1,2,4]oxadiazol-5-yl]-N-[3-(4-oxo-3,4-dihydro-phthalazin-1-ylamino)-propyl]-propionamide |
| 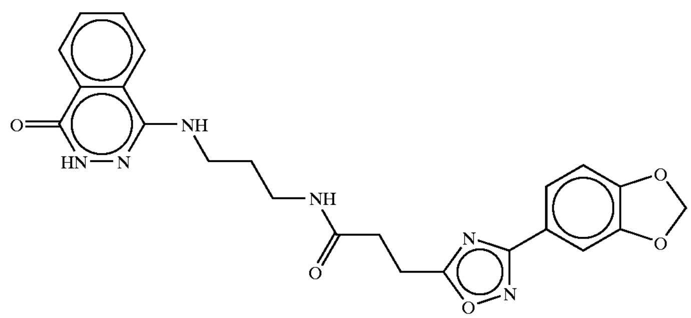 | 3-(3-Benzo[1,3]dioxol-5-yl-[1,2,4]oxadiazol-5-yl)-N-[3-(4-oxo-3,4-dihydro-phthalazin-1-ylamino)-propyl]-propionamide |
| 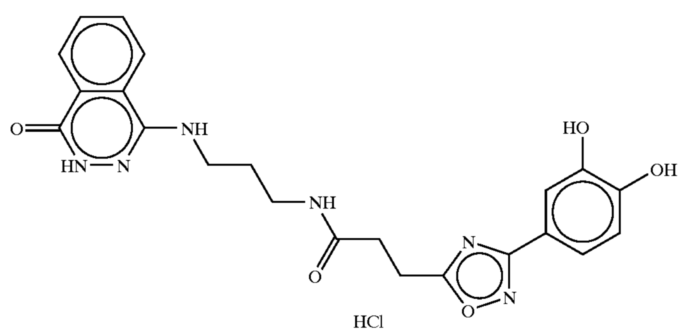 | 3-[3-(3,4-Dihydroxy-phenyl)-[1,2,4]oxadiazol-5-yl]-N-[3-(4-oxo-3,4-dihydro-phthalazin-1-ylamino)-propyl]-propionamide |
| 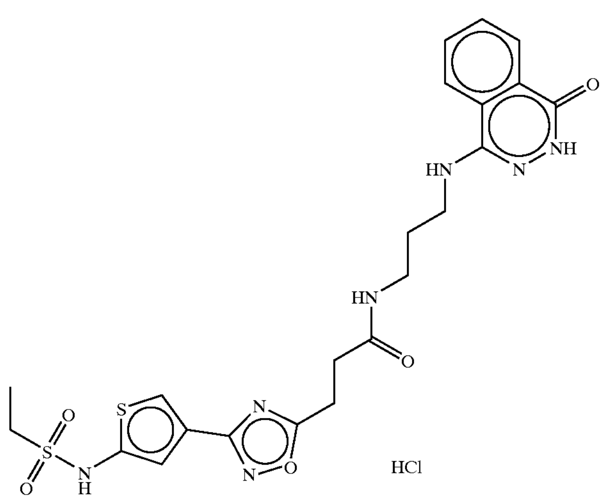 | 3-[3-(5-Ethanesulfonylamino-thiophen-3-yl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 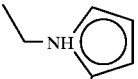 | 3-[3-(1-Ethyl-1H-pyrrol-2-yl)-[1,2,4]oxadiazol-5-yl]-N-[3-(4-oxo-3,4-dihydro-phthalazin-1-ylamino)-propyl]-propionamide |
| 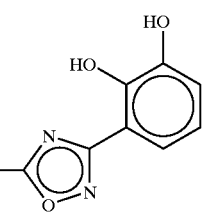 | 3-[3-(2,3-Dihydroxy-phenyl)-[1,2,4]oxadiazol-5-yl]-N-[3-(4-oxo-3,4-dihydro-phthalazin-1-ylamino)-propyl]-propionamide |
| 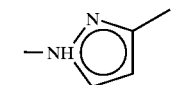 | 3-[3-(2,5-Dimethyl-2H-pyrazol-3-yl)-[1,2,4]oxadiazol-5-yl]-N-[3-(4-oxo-3,4-dihydro-phthalazin-1-ylamino)-propyl]-propionamide |
| 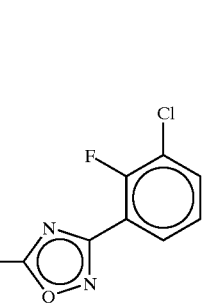 | 3-[3-(3-Chloro-2-fluoro-phenyl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| (structure) HCl | 3-{3-[1-(2-Hydroxy-ethyl)-1H-pyrrol-2-yl]-[1,2,4]oxadiazol-5-yl}-N-[3-(4-oxo-3,4-dihydro-phthalazin-1-ylamino)-propyl]-propionamide |
| (structure) | 3-[3-(2,6-Dihydroxy-phenyl)-[1,2,4]oxadiazol-5-yl]-N-[3-(4-oxo-3,4-dihydro-phthalazin-1-ylamino)-propyl]-propionamide |
| (structure) HCl | 3-[3-(3,4-Difluoro-phenyl)-[1,2,4]oxadiazol-5-yl]-N-[3-(4-oxo-3,4-dihydro-phthalazin-1-ylamino)-propyl]-propionamide |
| (structure) | 3-[3-(4-Methanesulfonylamino-phenyl)-[1,2,4]oxadiazol-5-yl]-N-[3-(4-oxo-3,4-dihydro-phthalazin-1-ylamino)-propyl]-propionamide |
| (structure) | 3-[3-(2,3-Dihydro-benzofuran-5-yl)-[1,2,4]oxadiazol-5-yl]-N-[3-(5-oxo-5,6-dihydro-pyrido[2,3-d]pyridazin-8-ylamino)-propyl]-propionamide |

TABLE 2-continued

Representative compounds of Formula I along with some nomenclatures.

| Structure | NAME |
| --- | --- |
| 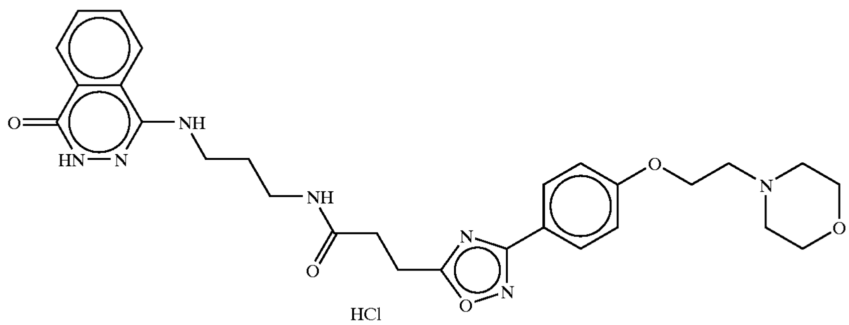 | 3-{3-[4-(2-Morpholin-4-yl-ethoxy)-phenyl]-[1,2,4]oxadiazol-5-yl}-N-[3-(4-oxo-3,4-dihydro-phthalazin-1-ylamino)-propyl]-propionamide |
| 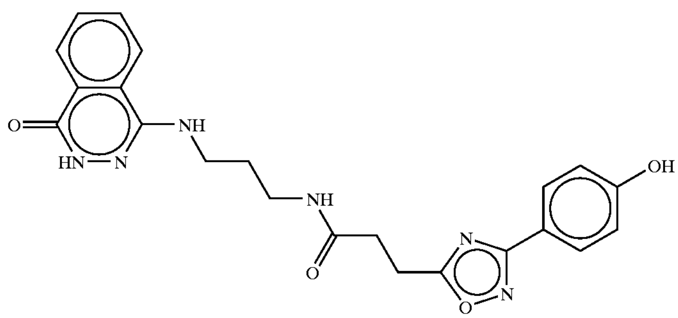 | 3-[3-(4-Hydroxy-phenyl)-[1,2,4]oxadiazol-5-yl]-N-[3-(4-oxo-3,4-dihydro-phthalazin-1-ylamino)-propyl]-propionamide |
| 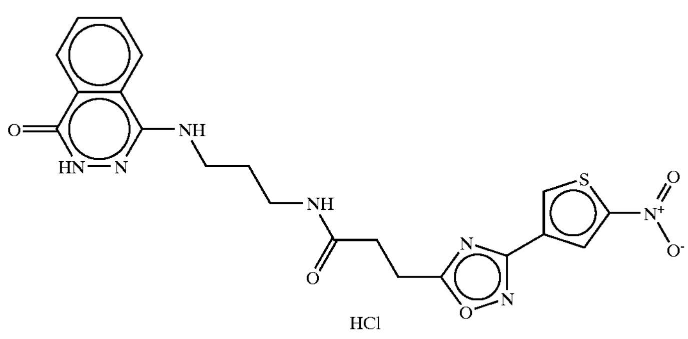 | 3-[3-(5-Nitro-thiophen-3-yl)-[1,2,4]oxadiazol-5-yl]-N-[3-(4-oxo-3,4-dihydro-phthalazin-1-ylamino)-propyl]-propionamide |
| 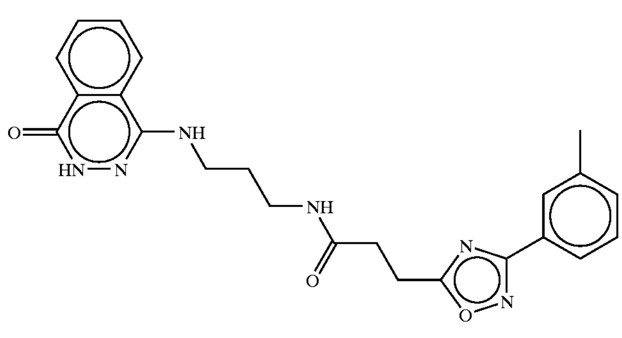 | N-[3-(4-Oxo-3,4-dihydro-phthalazin-1-ylamino)-propyl]-3-(3-m-tolyl-[1,2,4]oxadiazol-5-yl)-propionamide |

TABLE 2-continued

Representative compounds of Formula I along with some nomenclatures.

| Structure | NAME |
|---|---|
| 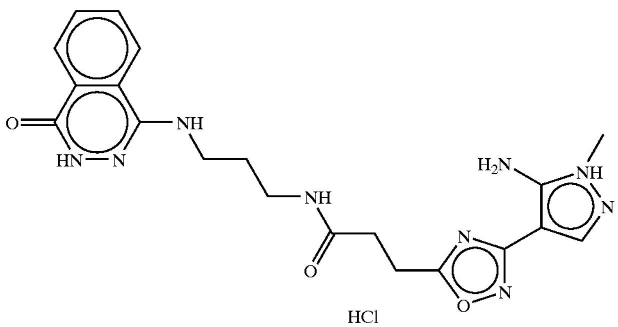 | 3-[3-(5-Amino-1-methyl-1H-pyrazol-4-yl)-[1,2,4]oxadiazol-5-yl]-N-[3-(4-oxo-3,4-dihydro-phthalazin-1-ylamino)-propyl]-propionamide |
| 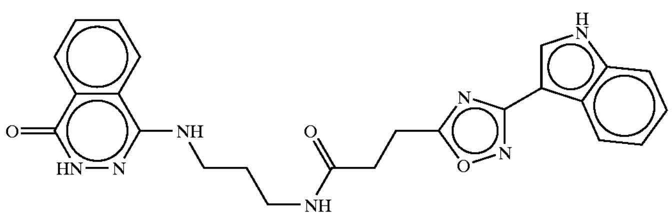 | 3-[3-(1H-Indol-3-yl)-[1,2,4]oxadiazol-5-yl]-N-[3-(4-oxo-3,4-dihydro-phthalazin-1-ylamino)-propyl]-propionamide |
| 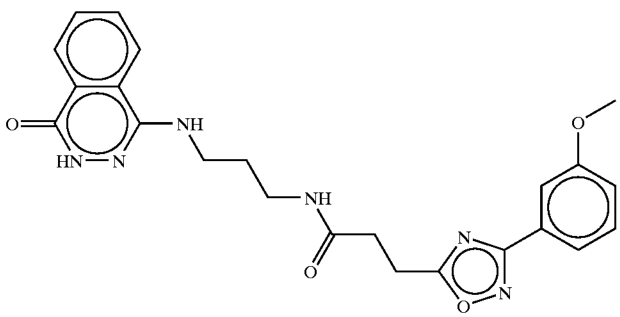 | 3-[3-(3-Methoxy-phenyl)-[1,2,4]oxadiazol-5-yl]-N-[3-(4-oxo-3,4-dihydro-phthalazin-1-ylamino)-propyl]-propionamide |
| 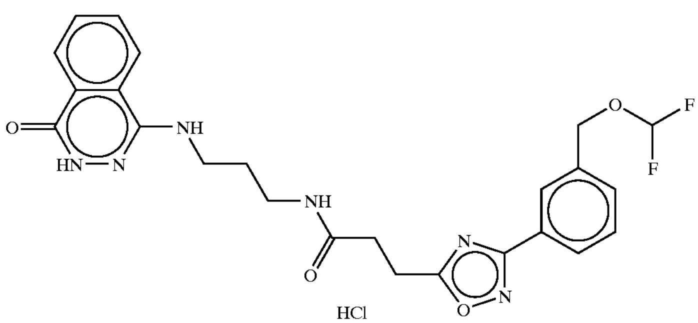 | 3-[3-(3-Difluoromethoxymethyl-phenyl)-[1,2,4]oxadiazol-5-yl]-N-[3-(4-oxo-3,4-dihydro-phthalazin-1-ylamino)-propyl]-propionamide |
| 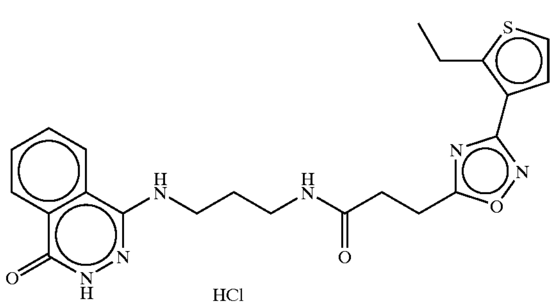 | 3-[3-(2-Ethyl-thiophen-3-yl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 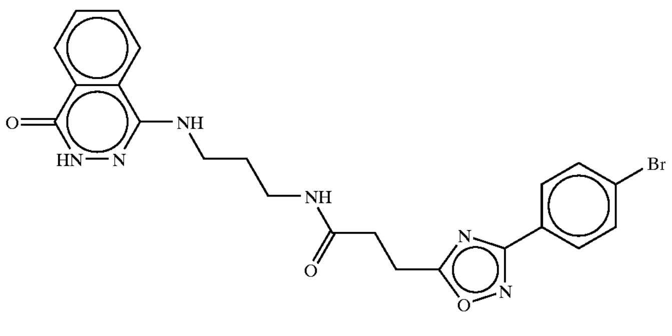 | 3-[3-(4-Bromo-phenyl)-[1,2,4]oxadiazol-5-yl]-N-[3-(4-oxo-3,4-dihydro-phthalazin-1-ylamino)-propyl]-propionamide |
| 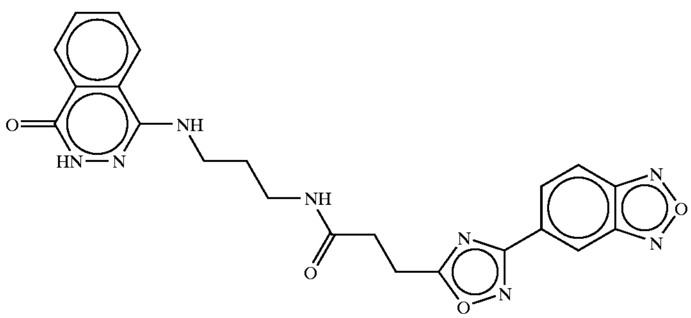 | 3-(3-Benzo[1,2,5]oxadiazol-5-yl-[1,2,4]oxadiazol-5-yl)-N-[3-(4-oxo-3,4-dihydro-phthalazin-1-ylamino)-propyl]-propionamide |
| 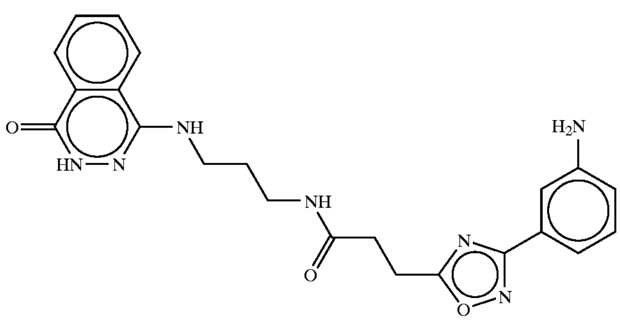 | 3-[3-(3-Amino-phenyl)-[1,2,4]oxadiazol-5-yl]-N-[3-(4-oxo-3,4-dihydro-phthalazin-1-ylamino)-propyl]-propionamide |
| 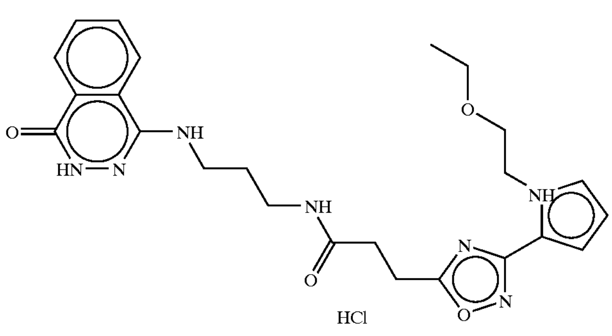 | 3-{3-[1-(2-Ethoxy-ethyl)-1H-pyrrol-2-yl]-[1,2,4]oxadiazol-5-yl}-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 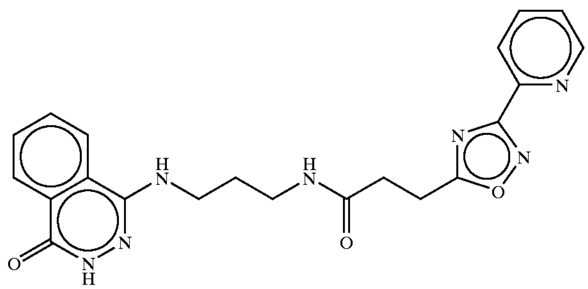 | N-[3-(4-Oxo-3,4-dihydro-phthalazin-1-ylamino)-propyl]-3-(3-pyridin-2-yl-[1,2,4]oxadiazol-5-yl)-propionamide |
| 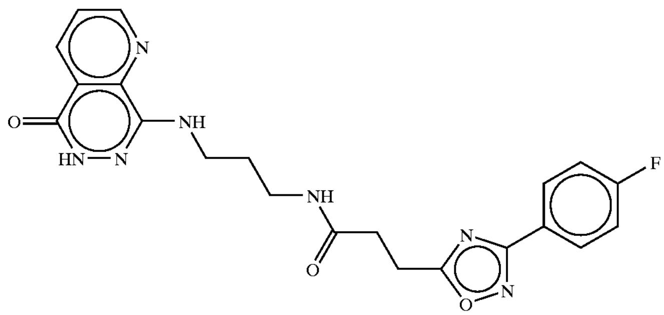 | 3-[3-(4-Fluoro-phenyl)-[1,2,4]oxadiazol-5-yl]-N-[3-(5-oxo-5,6-dihydro-pyrido[2,3-d]pyridazin-8-ylamino)-propyl]-propionamide |
| 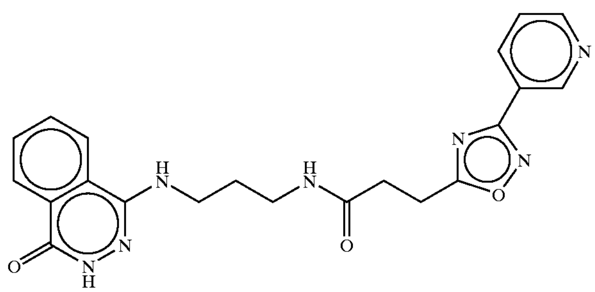 | N-[3-(4-Oxo-3,4-dihydro-phthalazin-1-ylamino)-propyl]-3-(3-pyridin-3-yl-[1,2,4]oxadiazol-5-yl)-propionamide |
| 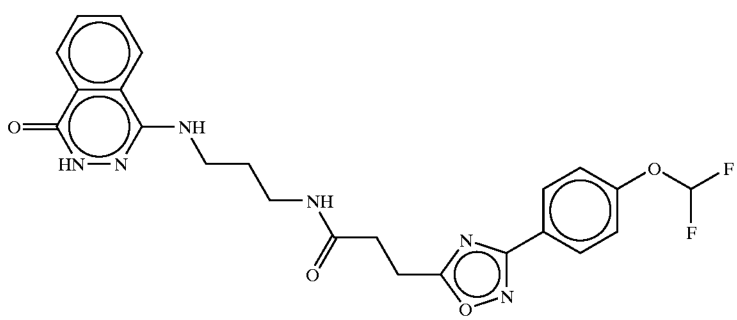 | 3-[3-(4-Difluoromethoxy-phenyl)-[1,2,4]oxadiazol-5-yl]-N-[3-(4-oxo-3,4-dihydro-phthalazin-1-ylamino)-propyl]-propionamide |
| 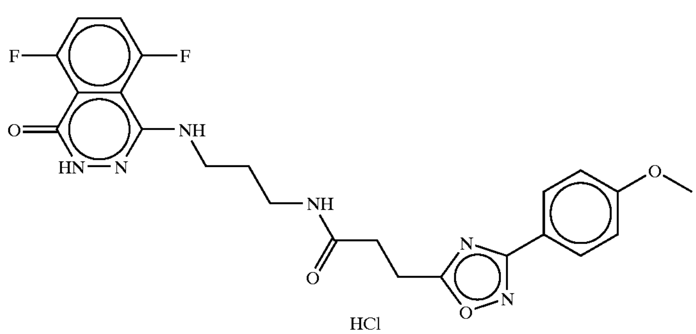 | N-[3-(5,8-Difluoro-4-oxo-3,4-dihydro-phthalazin-1-ylamino)-propyl]-3-[3-(4-methoxy-phenyl)-[1,2,4]oxadiazol-5-yl]-propionamide |

TABLE 2-continued

Representative compounds of Formula I along with some nomenclatures.

| Structure | NAME |
|---|---|
| 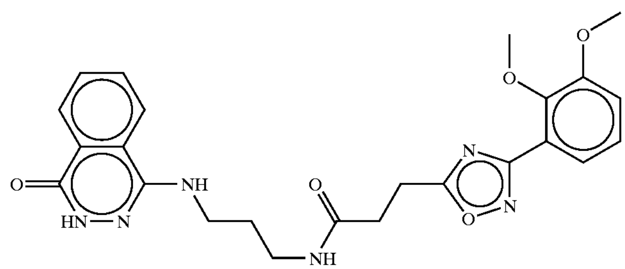 | 3-[3-(2,3-Dimethoxy-phenyl)-[1,2,4]oxadiazol-5-yl]-N-[3-(4-oxo-3,4-dihydro-phthalazin-1-ylamino)-propyl]-propionamide |
| 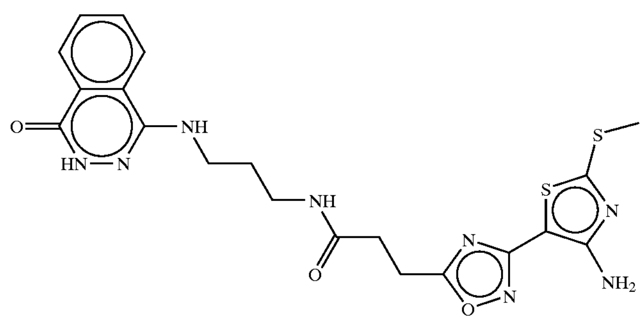 | 3-[3-(4-Amino-2-methylsulfanyl-thiazol-5-yl)-[1,2,4]oxadiazol-5-yl]-N-[3-(4-oxo-3,4-dihydro-phthalazin-1-ylamino)-propyl]-propionamide |
| 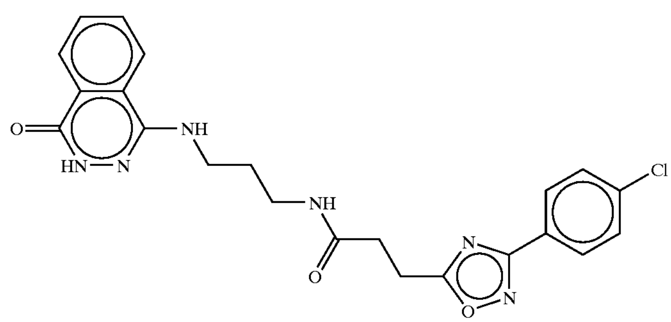 | 3-[3-(4-Chloro-phenyl)-[1,2,4]oxadiazol-5-yl]-N-[3-(4-oxo-3,4-dihydro-phthalazin-1-ylamino)-propyl]-propionamide |
| 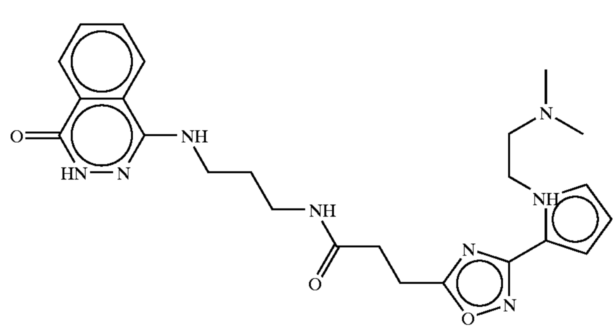 | 3-{3-[1-(2-Dimethylamino-ethyl)-1H-pyrrol-2-yl]-[1,2,4]oxadiazol-5-yl}-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 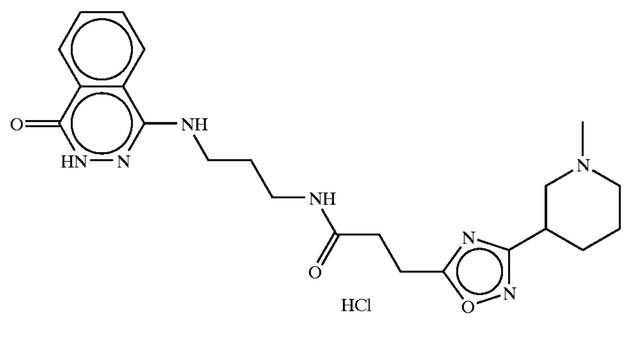 | 3-[3-(1-Methyl-piperidin-3-yl)-[1,2,4]oxadiazol-5-yl]-N-[3-(4-oxo-3,4-dihydro-phthalazin-1-ylamino)-propyl]-propionamide |
| 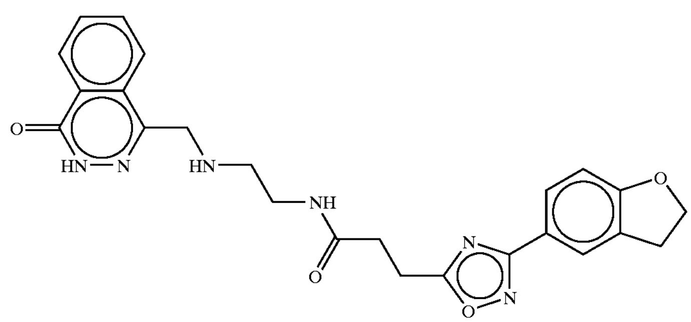 | 3-[3-(2,3-Dihydro-benzofuran-5-yl)-[1,2,4]oxadiazol-5-yl]-N-{2-[(4-oxo-3,4-dihydro-phthalazin-1-ylmethyl)-amino]-ethyl}-propionamide |
| 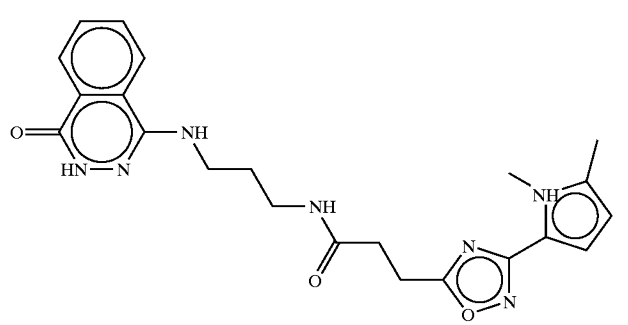 | 3-[3-(1,5-Dimethyl-1H-pyrrol-2-yl)-[1,2,4]oxadiazol-5-yl]-N-[3-(4-oxo-3,4-dihydro-phthalazin-1-ylamino)-propyl]-propionamide |
| 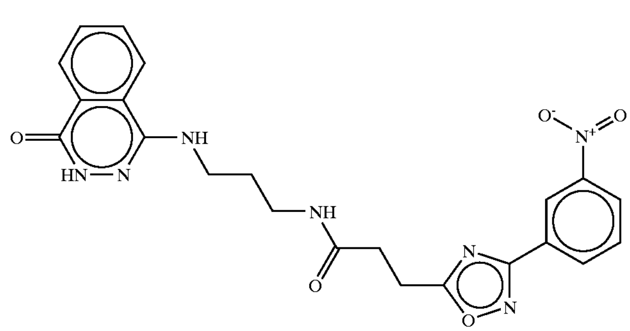 | 3-[3-(3-Nitro-phenyl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 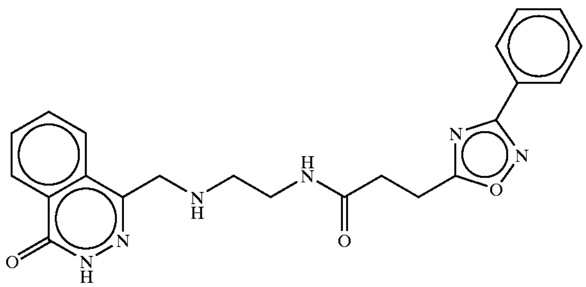 | N-{2-[(4-Oxo-3,4-dihydro-phthalazin-1-ylmethyl)-amino]-ethyl}-3-(3-phenyl-[1,2,4]oxadiazol-5-yl)-propionamide |
| 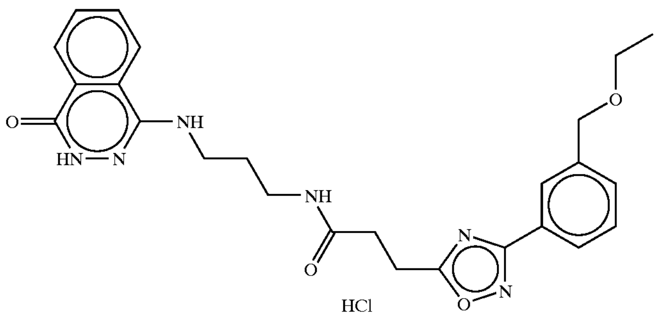 | 3-[3-(3-Ethoxymethyl-phenyl)-[1,2,4]oxadiazol-5-yl]-N-[3-(4-oxo-3,4-dihydro-phthalazin-1-ylamino)-propyl]-propionamide |
| 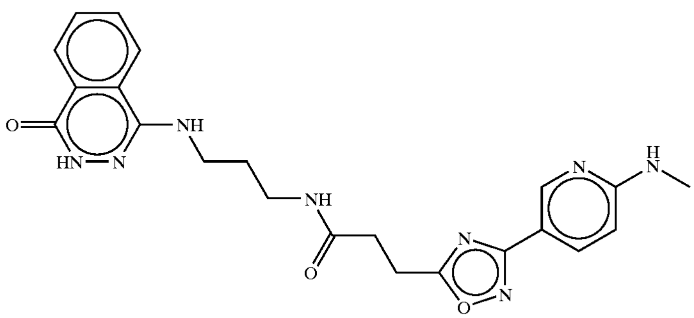 | 3-[3-(6-Methylamino-pyridin-3-yl)-[1,2,4]oxadiazol-5-yl]-N-[3-(4-oxo-3,4-dihydro-phthalazin-1-ylamino)-propyl]-propionamide |
| 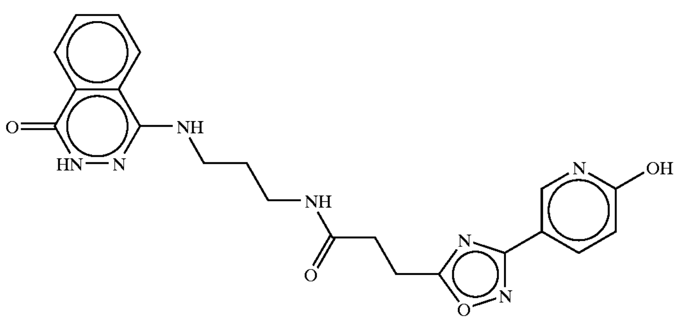 | 3-[3-(6-Hydroxy-pyridin-3-yl)-[1,2,4]pxadiazol-5-yl]-N-[3-(4-oxo-3,4-dihydro-phthalazin-1-ylamino)-propyl]-propionamide |
| 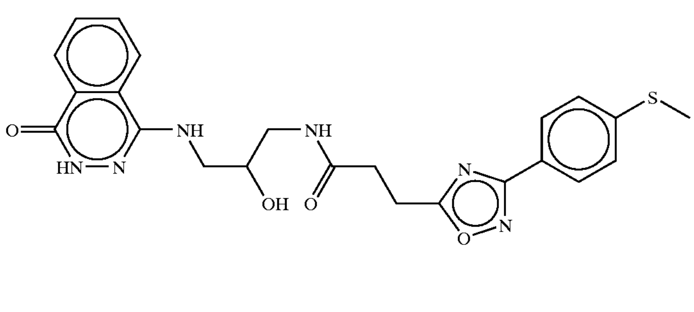 | N-[2-Hydroxy-3-(4-oxo-3,4-dihydro-phthalazin-1-ylamino)-propyl]-3-[3-(4-methylsulfanyl-phenyl)-[1,2,4]oxadiazol-5-yl]-propionamide |

TABLE 2-continued

Representative compounds of Formula I along with some nomenclatures.

| Structure | NAME |
|---|---|
| 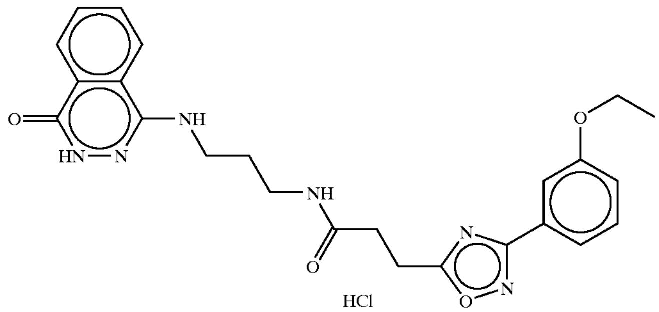 | 3-[3-(3-Ethoxy-phenyl)-[1,2,4]oxadiazol-5-yl]-N-[3-(4-oxo-3,4-dihydro-phthalazin-1-ylamino)-propyl]-propionamide |
| 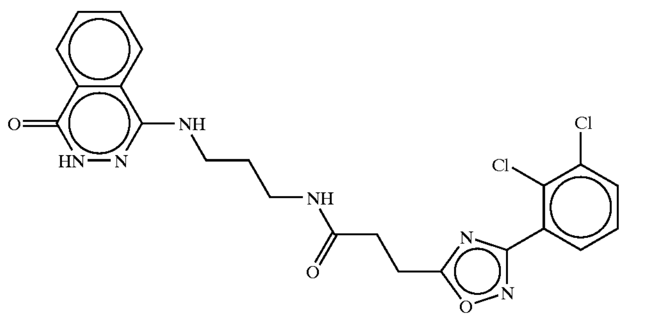 | 3-[3-(2,3-Dichloro-phenyl)-[1,2,4]oxadiazol-5-yl]-N-[3-(4-oxo-3,4-dihydro-phthalazin-1-ylamino)-propyl]-propionamide |
| 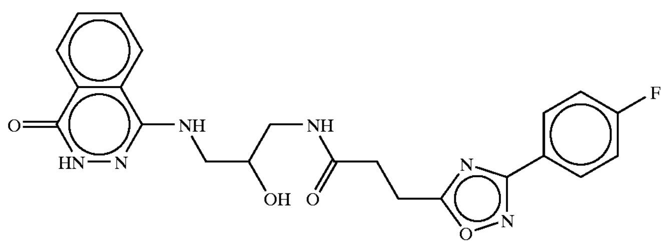 | 3-[3-(4-Fluoro-phenyl)-[1,2,4]oxadiazol-5-yl]-N-[2-hydroxy-3-(4-oxo-3,4-dihydro-phthalazin-1-ylamino)-propyl]-propionamide |
| 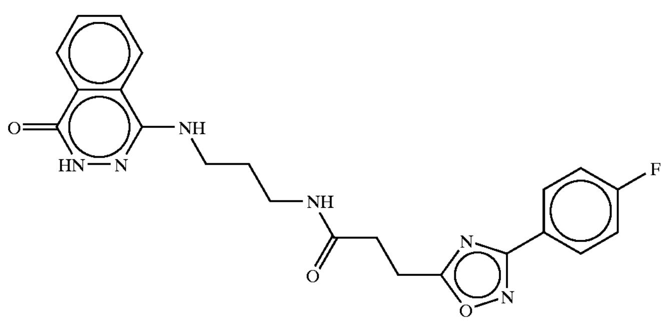 | 3-[3-(4-Fluoro-phenyl)-[1,2,4]oxadiazol-5-yl]-N-[3-(4-oxo-3,4-dihydro-phthalazin-1-ylamino)-propyl]-propionamide |
| 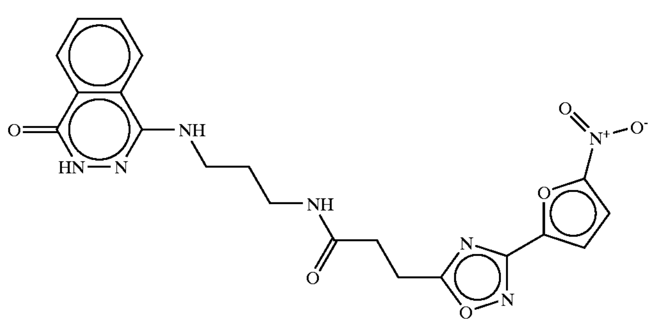 | 3-[3-(5-Nitro-furan-2-yl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
| --- | --- |
| 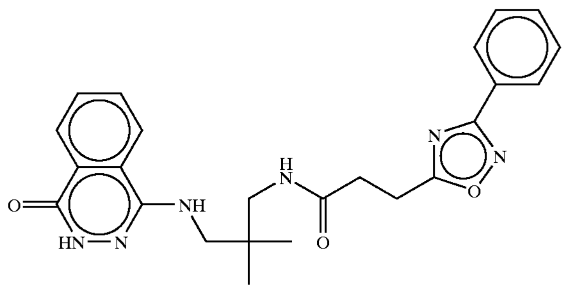 | N-[2,2-Dimethyl-3-(4-oxo-3,4-dihydro-phthalazin-1-ylamino)-propyl]-3-(3-phenyl-[1,2,4]oxadiazol-5-yl)-propionamide |
| 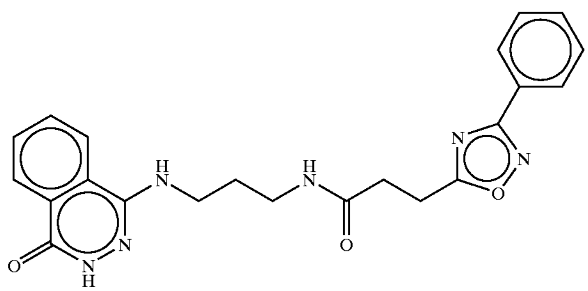 | N-[3-(4-Oxo-3,4-dihydro-phthalazin-1-ylamino)-propyl]-3-(3-phenyl-[1,2,4]oxadiazol-5-yl)-propionamide |
| 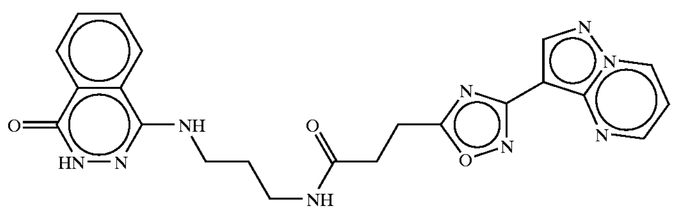 | N-[3-(4-Oxo-3,4-dihydro-phthalazin-1-ylamino)-propyl]-3-(3-pyrazolo[1,5-a]pyrimidin-3-yl-[1,2,4]oxadiazol-5-yl)-propionamide |
| 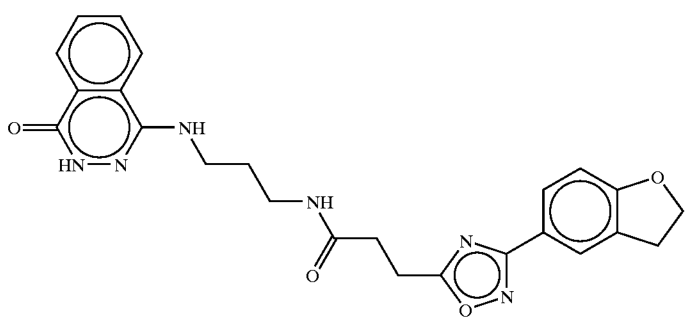 | 3-[3-(2,3-Dihydro-benzofuran-5-yl)-[1,2,4]oxadiazol-5-yl]-N-[3-(4-oxo-3,4-dihydro-phthalazin-1-ylamino)-propyl]-propionamide |
| 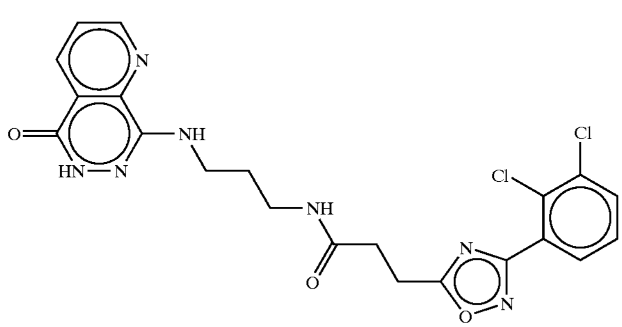 | 3-[3-(2,3-Dichloro-phenyl)-[1,2,4]oxadiazol-5-yl]-N-[3-(5-oxo-5,6-dihydro-pyrido[2,3-d]pyridazin-8-ylamino)-propyl]-propionamide |

TABLE 2-continued

Representative compounds of Formula I along with some nomenclatures.

| Structure | NAME |
|---|---|
| 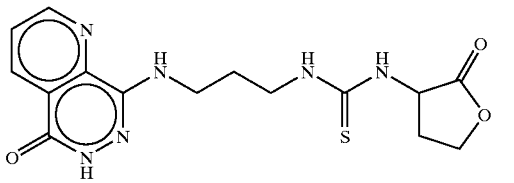 | 1-[3-(5-Oxo-5,6-dihydro-pyrido[2,3-d]pyridazin-8-ylamino)-propyl]-3-(2-oxo-tetrahydro-furan-3-yl)-thiourea |
| 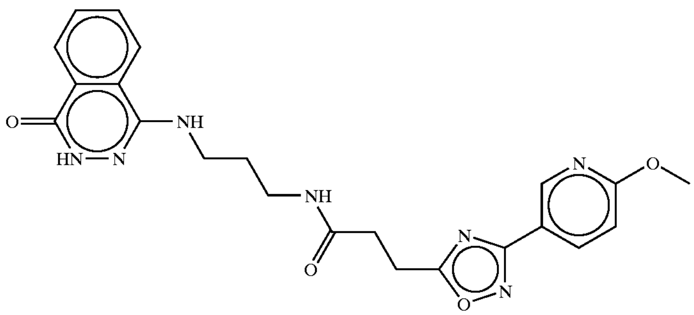 | 3-[3-(6-Methoxy-pyridin-3-yl)-[1,2,4]oxadiazol-5-yl]-N-[3-(4-oxo-3,4-dihydro-phthalazin-1-ylamino)-propyl]-propionamide |
| 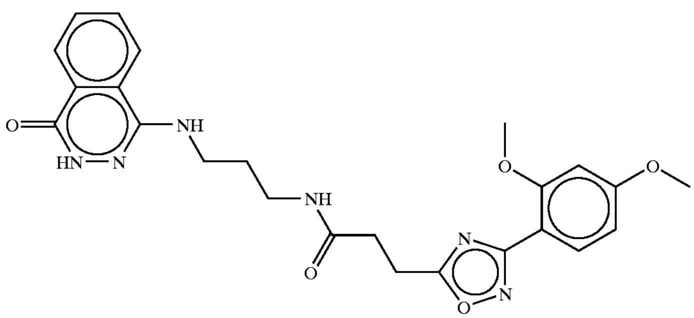 | 3-[3-(2,4-Dimethoxy-phenyl)-[1,2,4]oxadiazol-5-yl]-N-[3-(4-oxo-3,4-dihydro-phthalazin-1-ylamino)-propyl]-propionamide |
| 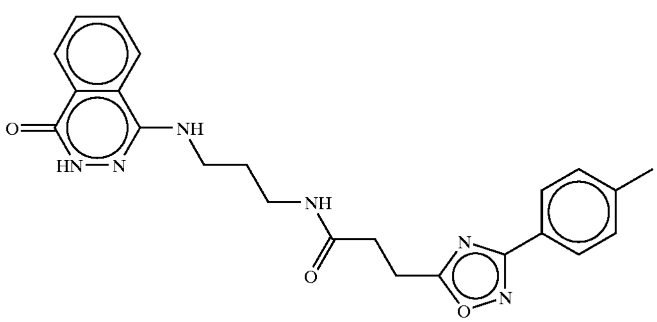 | N-[3-(4-Oxo-3,4-dihydro-phthalazin-1-ylamino)-propyl]-3-(3-p-tolyl-[1,2,4]oxadiazol-5-yl)-propionamide |
| 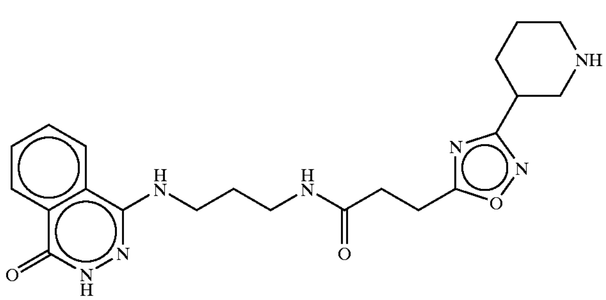 | N-[3-(4-Oxo-3,4-dihydro-phthalazin-1-ylamino)-propyl]-3-(3-piperidin-3-yl-[1,2,4]oxadiazol-5-yl)-propionamide |

TABLE 2-continued

Representative compounds of Formula I along with some nomenclatures.

| Structure | NAME |
|---|---|
| 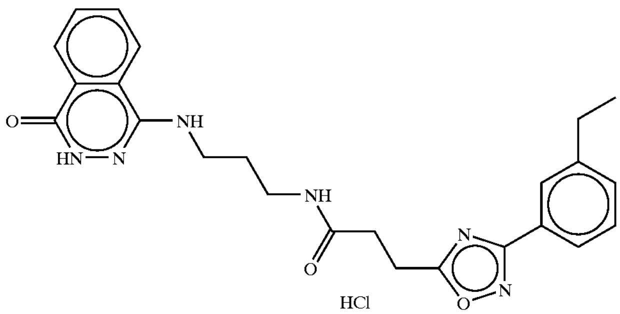 | 3-[3-(3-Ethyl-phenyl)-[1,2,4]oxadiazol-5-yl]-N-[3-(4-oxo-3,4-dihydro-phthalazin-1-ylamino)-propyl]-propionamide |
| 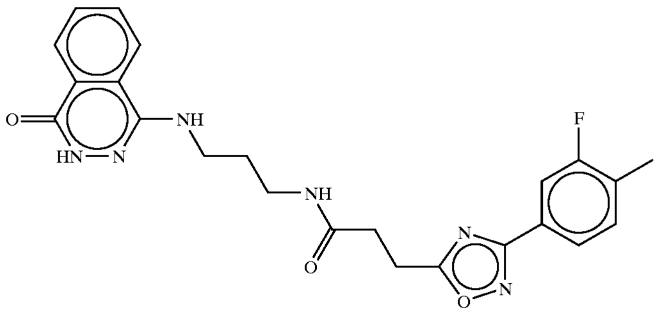 | 3-[3-(3-Fluoro-4-methyl-phenyl)-[1,2,4]oxadiazol-5-yl]-N-[3-(4-oxo-3,4-dihydro-phthalazin-1-ylamino)-propyl]-propionamide |
| 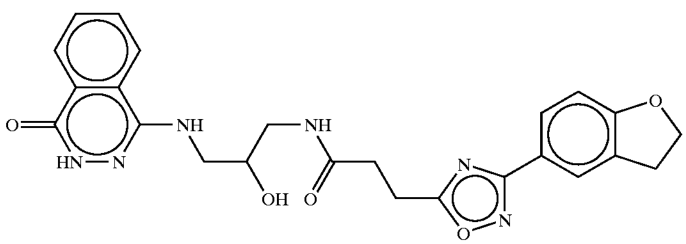 | 3-[3-(2,3-Dihydro-benzofuran-5-yl)-[1,2,4]oxadiazol-5-yl]-N-[2-hydroxy-3-(4-oxo-3,4-dihydro-phthalazin-1-ylamino)-propyl]-propionamide |
| 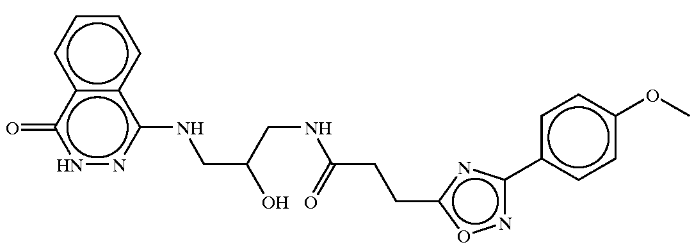 | N-[2-Hydroxy-3-(4-oxo-3,4-dihydro-phthalazin-1-ylamino)-propyl]-3-[3-(4-methoxy-phenyl)-[1,2,4]oxadiazol-5-yl]-propionamide |
| 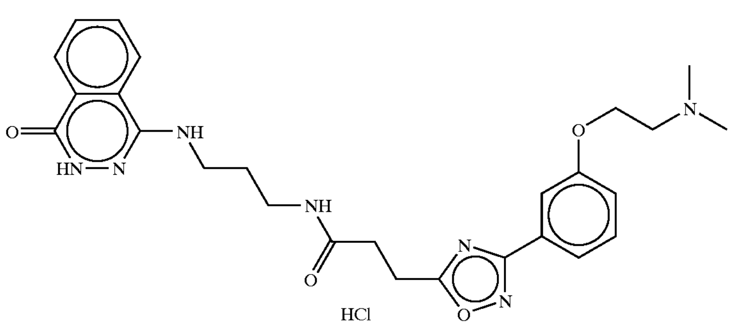 | 3-{3-[3-(2-Dimethylamino-ethoxy)-phenyl]-[1,2,4]oxadiazol-5-yl}-N-]3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 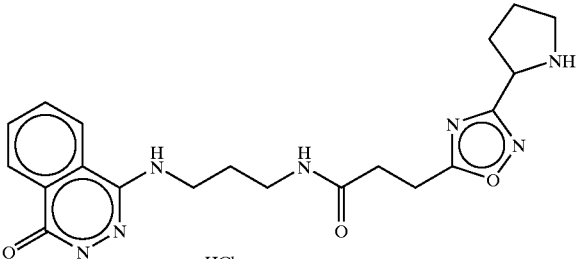 | N-[3-(4-Oxo-3,4-dihydro-phthalazin-1-ylamino)-propyl]-3-(3-pyrrolidin-2-yl-[1,2,4]oxadiazol-5-yl)-propionamide |
| 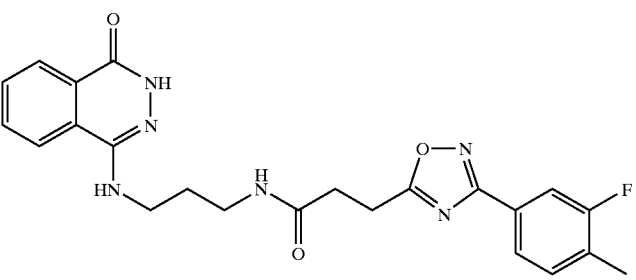 | 3-[3-(3-Fluoro-4-methyl-phenyl)-[1,2,4]oxadiazol-5-yl]-N-[3-(4-oxo-3,4-dihydro-phthalazin-1-ylamino)-propyl]-propionamide |
| 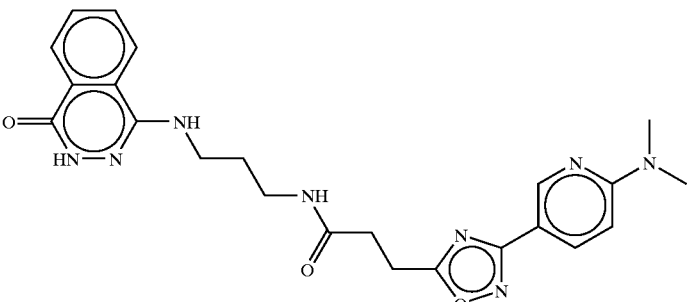 | 3-[3-(6-Dimethylamino-pyridin-3-yl)-[1,2,4]oxadiazol-5-yl]-N-[3-(4-oxo-3,4-dihydro-phthalazin-1-ylamino)-propyl]-propionamide |
| 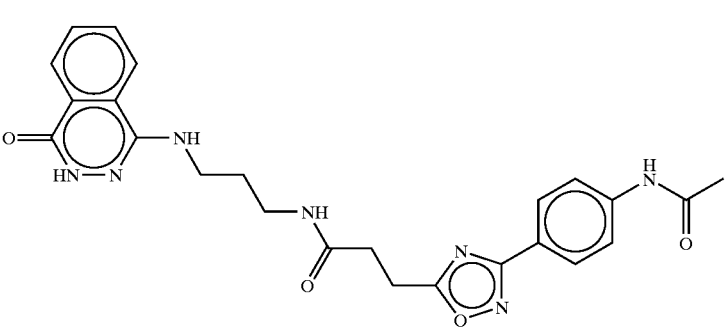 | 3-[3-(4-Acetylamino-phenyl)-[1,2,4]oxadiazol-5-yl]-N-[3-(4-oxo-3,4-dihydro-phthalazin-1-ylamino)-propyl]-propionamide |
| 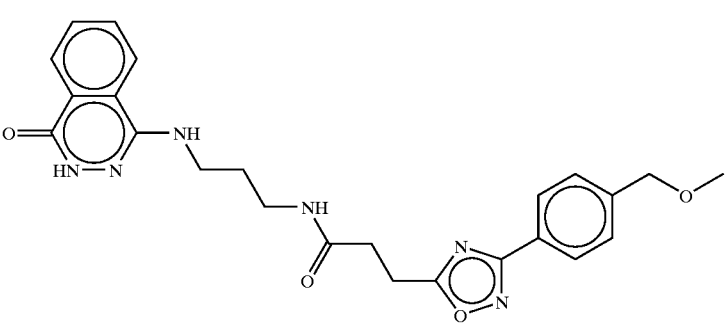 | 3-[3-(4-Methoxymethyl-phenyl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 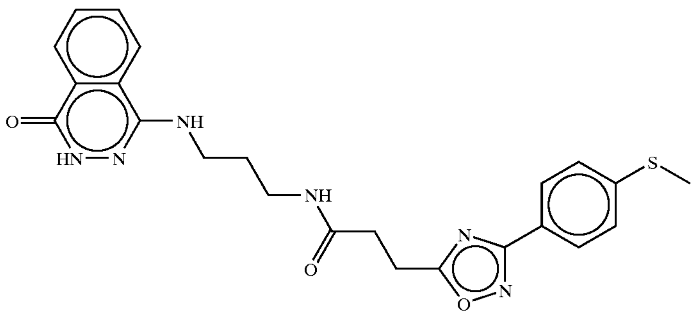 | 3-[3-(4-Methylsulfanyl-phenyl)-[1,2,4]oxadiazol-5-yl]-N-[3-(4-oxo-3,4-dihydro-phthalazin-1-ylamino)-propyl]-propionamide |
| 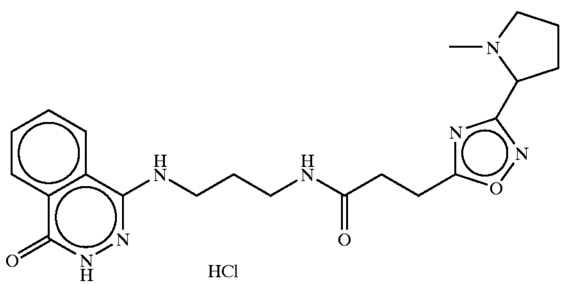 | 3-[3-(1-Methyl-pyrrolidin-2-yl)-[1,2,4]oxadiazol-5-yl]-N-[3-(4-oxo-3,4-dihydro-phthahzin-1-ylamino)-propyl]-propionamide |
| 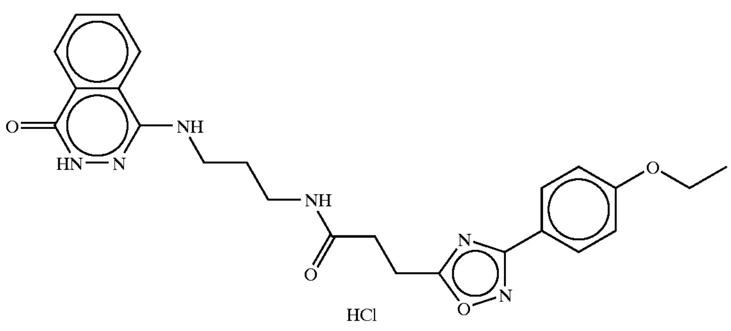 | 3-[3-(4-Ethoxy-phenyl)-[1,2,4]oxadiazol-5-yl]-N-[3-(4-oxo-3,4-dihydro-phthalazin-1-ylamino)-propyl]-propionamide |
| 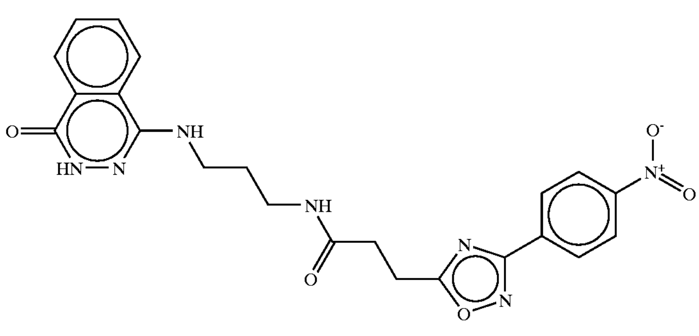 | 3-[3-(4-Nitro-phenyl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
| --- | --- |
| 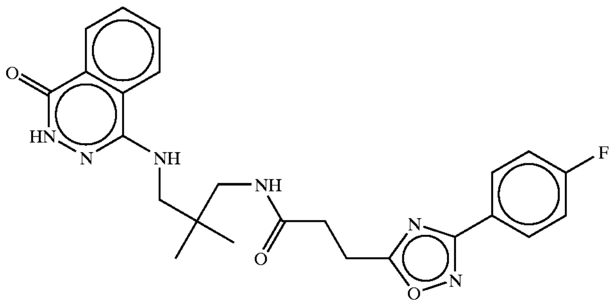 | N-[2,2-Dimethyl-3-(4-oxo-3,4-dihydro-phthalazin-1-ylamino)-propyl]-3-[3-(4-fluoro-phenyl)-[1,2,4]oxadiazol-5-yl]-propionamide |
| 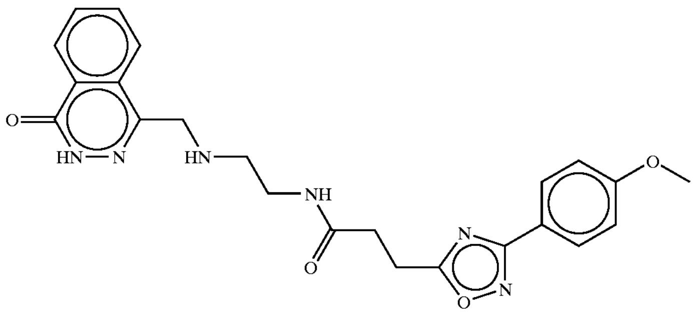 | 3-[3-(4-Methoxy-phenyl)-[1,2,4]oxadiazol-5-yl]-N-{2-[(4-oxo-3,4-dihydro-phthalazin-1-ylmethyl)-amino]-ethyl}-propionamide |
| 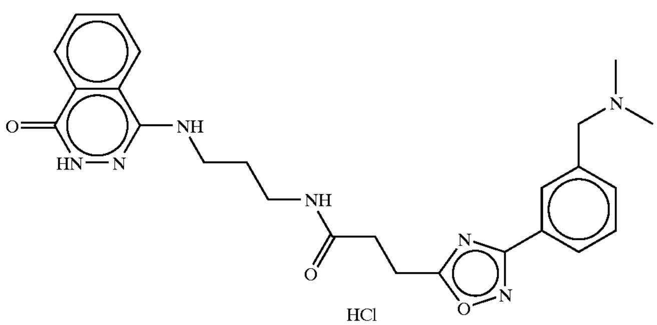 | 3-[3-(3-Dimethylaminomethyl-phenyl)-[1,2,4]oxadiazol-5-yl]-N-[3-(4-oxo-3,4-dihydro-phthalazin-1-ylamino)-propyl]-propionamide |
| 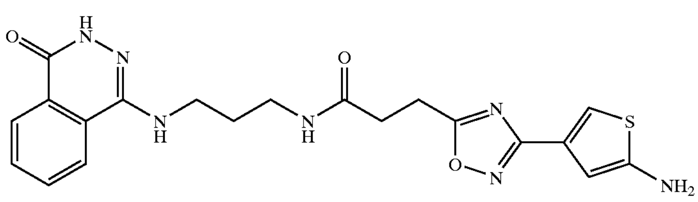 | 3-[3-(5-Amino-thiophen-3-yl)-[1,2,4]oxadiazol-5-yl]-N-[3-(4-oxo-3,4-dihydro-phthalazin-1-ylamino)-propyl]-propionamide |
| 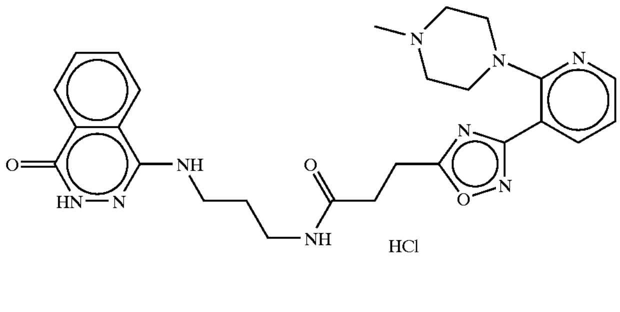 | 3-{3-[2-(4-Methyl-piperazin-1-yl)-pyridin-3-yl]-[1,2,4]oxadiazol-5-yl}-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 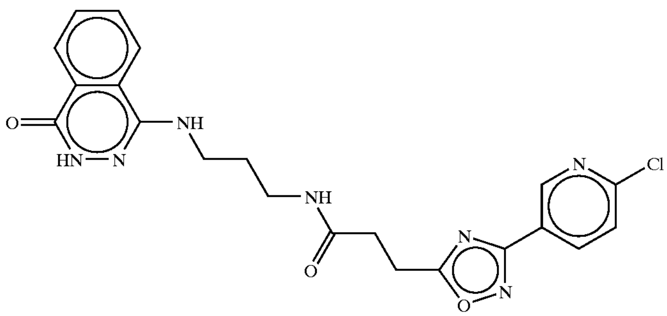 | 3-[3-(6-Chloro-pyridin-3-yl)-[1,2,4]oxadiazol-5-yl]-N-[3-(4-oxo-3,4-dihydro-phthalazin-1-ylamino)-propyl]-propionamide |
| 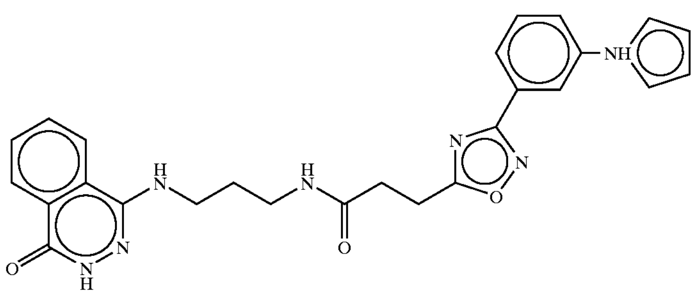 | N-[3-(4-Oxo-3,4-dihydro-phthalazin-1-ylamino)-propyl]-3-[3-(3-pyrrol-1-yl-phenyl)-[1,2,4]oxadiazol-5-yl]-propionamide |
| 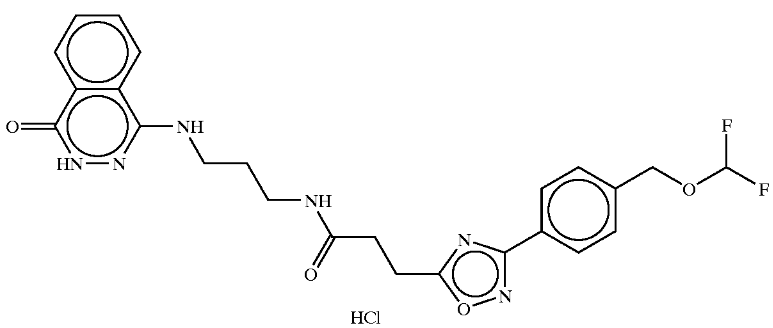 | 3-[3-(4-Difluoromethoxymethyl-phenyl)-[1,2,4]oxadiazol-5-yl]-N-[3-(4-oxo-3,4-dihydro-phthalazin-1-ylamino)-propyl]-propionamide |
| 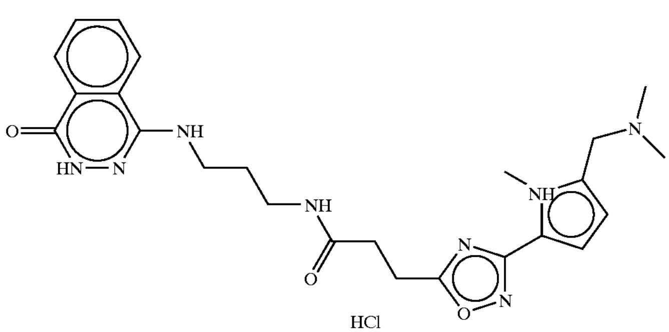 | 3-[3-(5-Dimethylaminomethyl-1-methyl-1H-pyrrol-2-yl)-[1,2,4]oxadiazol-5-yl]-N-[3-(4-oxo-3,4-dihydro-phthalazin-1-ylamino)-propyl]-propionamide |

TABLE 2-continued

*Representative compounds of Formula I along with some nomenclatures.*

| Structure | NAME |
|---|---|
| 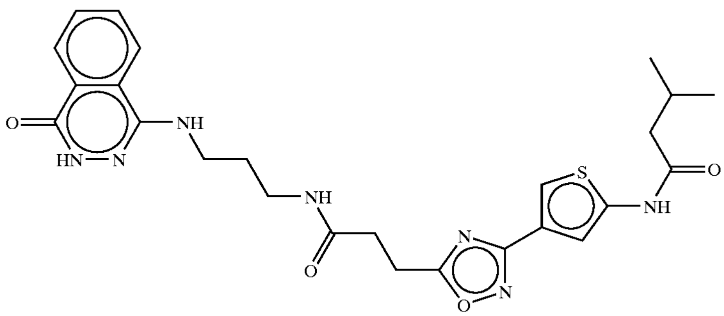 | 3-Methyl-N-[4-(5-{2-[3-(4-oxo-3,4-dihydro-phthalazin-1-ylamino)-propylcarbamoyl]-ethyl}-[1,2,4]oxadiazol-3-yl)-thiophen-2-yl]-butyramide |
| 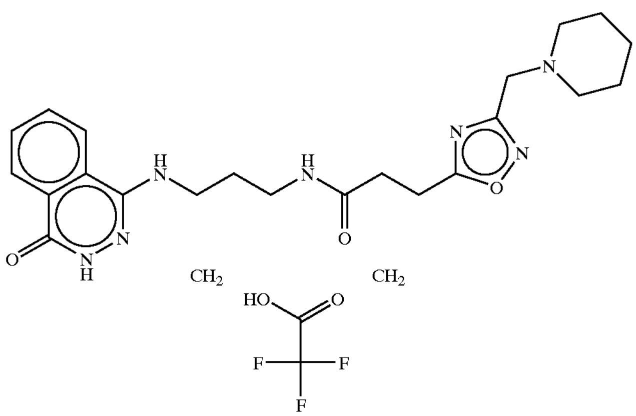 | N-[3-(4-Oxo-3,4-dihydro-phthalazin-1-ylamino)-propyl]-3-(3-piperidin-1-yl-[1,2,4]oxadiazol-5-yl)-propionamide |
| 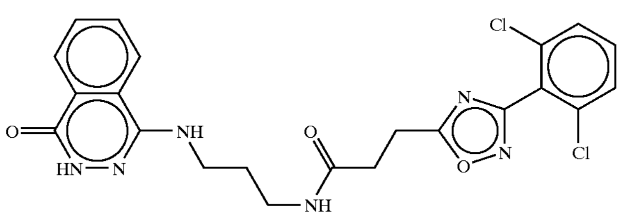 | 3-[3-(2,6-Dichloro-phenyl)-[1,2,4]oxadiazol-5-yl]-N-[3-(4-oxo-3,4-dihydro-phthalazin-1-ylamino)-propyl]-propionamide |
| 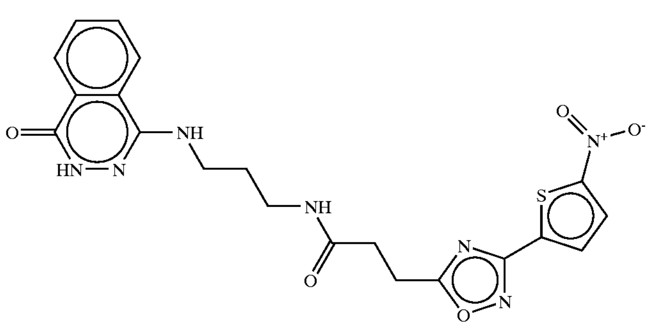 | 3-[3-(5-Nitro-thiophen-2-yl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 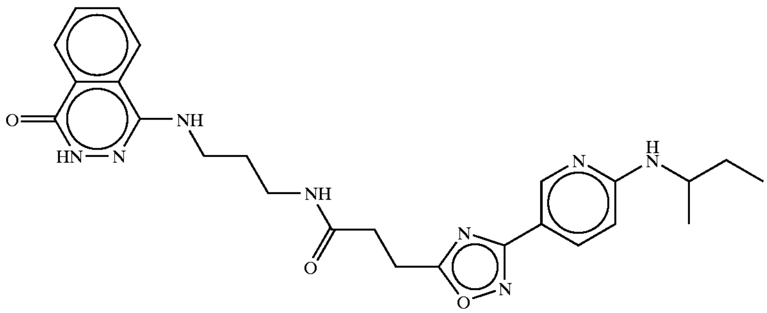 | 3-[3-(6-sec-Butylamino-pyridin-3-yl)-[1,2,4]oxadiazol-5-yl]-N-[3-(4-oxo-3,4-dihydro-phthalazin-1-ylamino)-propyl]-propionamide |
| 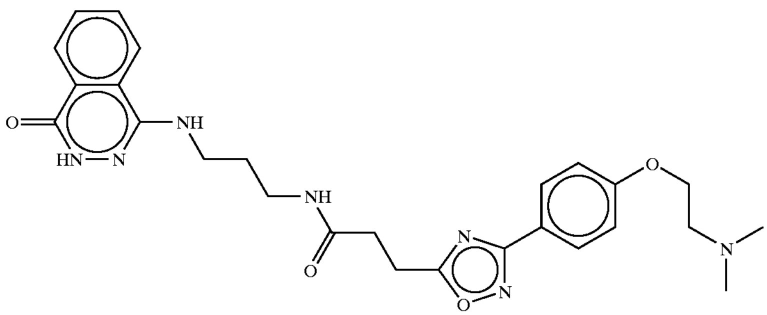 | 3-{3-[4-(2-Dimethylamino-ethoxy)-phenyl]-[1,2,4]oxadiazol-5-yl}-N-[3-(4-oxo-3,4-dihydro-phthalazin-1-ylamino)-propyl]-propionamide |
| 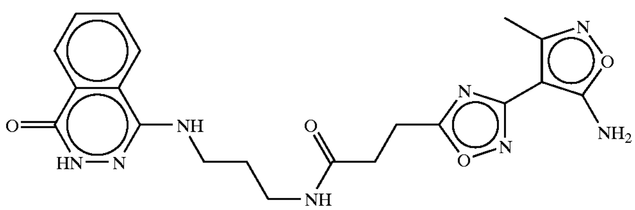 | 3-[3-(5-Amino-3-methyl-isoxazol-4-yl)-[1,2,4]oxadiazol-5-yl]-N-[3-(4-oxo-3,4-dihydro-phthalazin-1-ylamino)-propyl]-propionamide |
| 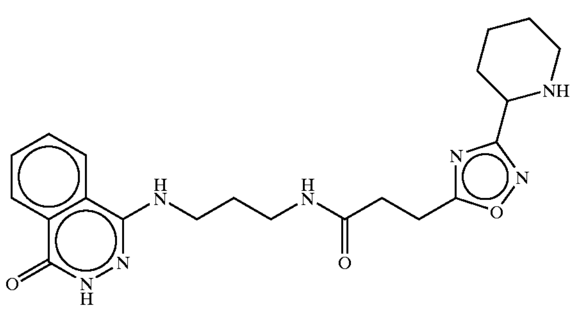 | N-[3-(4-Oxo-3,4-dihydro-phthalazin-1-ylamino)-propyl]-3-(3-piperidin-2-yl-[1,2,4]oxadiazol-5-yl)-propionamide |
| 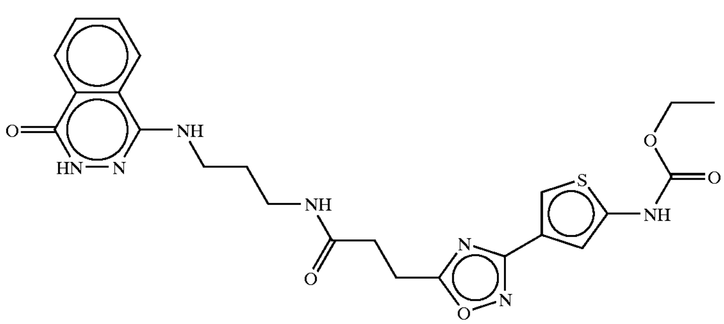 | [4-(5-{2-[3-(4-Oxo-3,4-dihydro-phthalazin-1-ylamino)-propylcarbamoyl]-ethyl}-[1,2,4]oxadiazol-3-yl)-thiophen-2-yl]-carbamic acid ethyl ester |

TABLE 2-continued

Representative compounds of Formula I along with some nomenclatures.

| Structure | NAME |
|---|---|
| 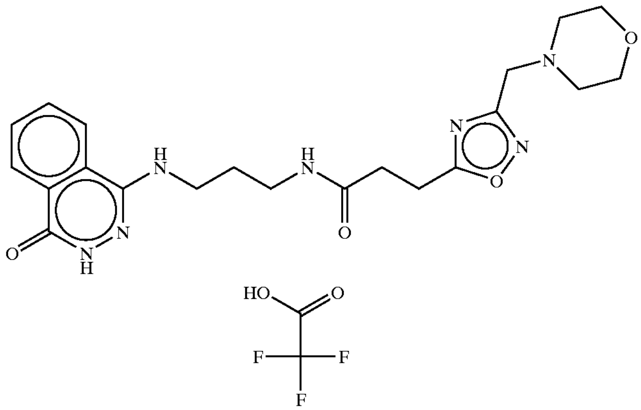 | 3-(3-Morpholin-4-yl-[1,2,4]oxadiazol-5-yl)-N-[3-(4-oxo-3,4-dihydro-phthalazin-1-ylamino)-propyl]-propionamide |
| 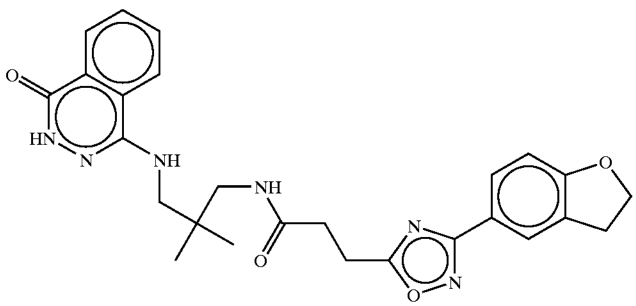 | 3-[3-(2,3-Dihydro-benzofuran-5-yl)-[1,2,4]oxadiazol-5-yl]-N-[2,2-dimethyl-3-(4-oxo-3,4-dihydro-phthalazin-1-ylamino)-propyl]-propionamide |
| 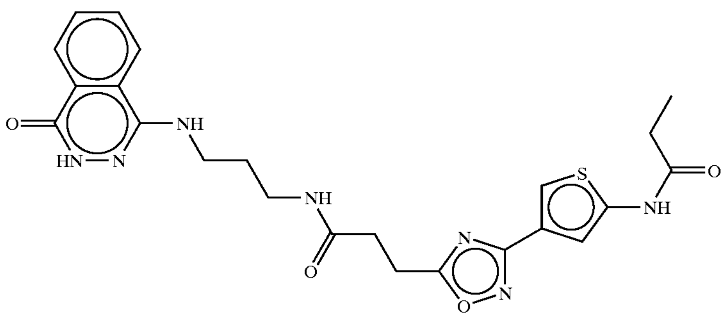 | N-[3-(4-Oxo-3,4-dihydro-phthalazin-1-ylamino)-propyl]-3-[3-(5-propionylamino-thiophen-3-yl)-[1,2,4]oxadiazol-5-yl]-propionamide |
| 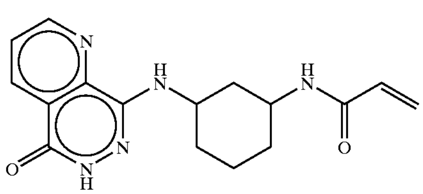 | N-[3-(5-Oxo-5,6-dihydro-pyrido[2,3-d]pyridazin-8-ylamino)-cyclohexyl]-acrylamide |
| 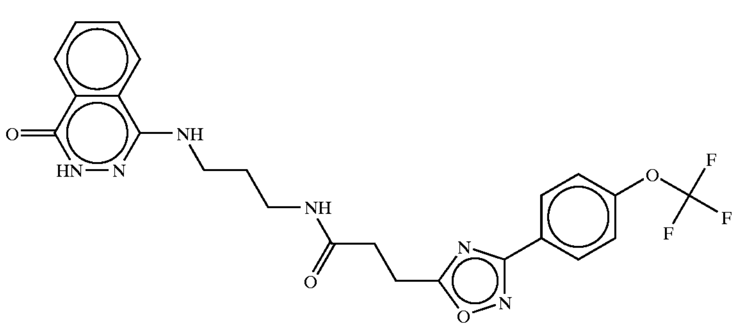 | N-[3-(4-Oxo-3,4-dihydro-phthalazin-1-ylamino)-propyl]-3-[3-(4-trifluoromethoxy-phenyl)-[1,2,4]oxadiazol-5-yl]-propionamide |

TABLE 2-continued

Representative compounds of Formula I along with some nomenclatures.

| Structure | NAME |
|---|---|
| 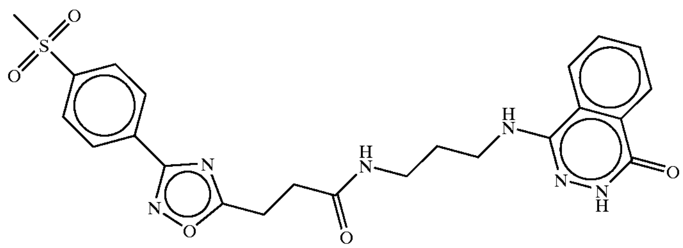 | 3-[3-(4-Methanesulfonyl-phenyl)-[1,2,4]oxadiazol-5-yl]-N-[3-(4-oxo-3,4-dihydro-phthalazin-1-ylamino)-propyl]-propionamide |
| 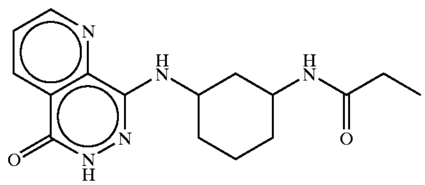 | N-[3-(5-Oxo-5,6-dihydro-pyrido[2,3-d]pyridazin-8-ylamino)-cyclohexyl]-propionamide |
| 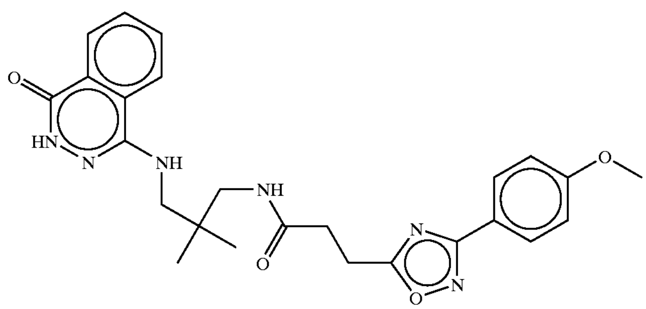 | N-[2,2-Dimethyl-3-(4-oxo-3,4-dihydro-phthalazin-1-ylamino)-propyl]-3-[3-(4-methoxy-phenyl)-[1,2,4]oxadiazol-5-yl]-propionamide |
| 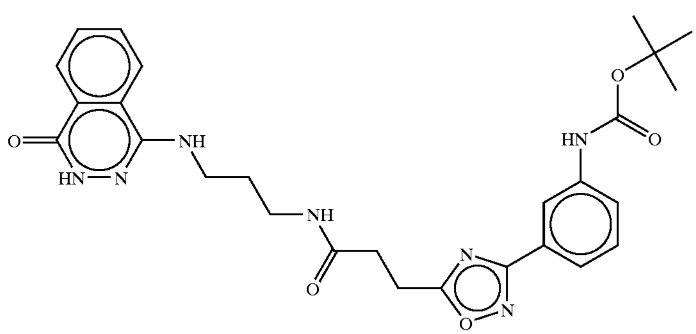 | [3-(5-{2-[3-(4-Oxo-3,4-dihydro-phthalazin-1-ylamino)-propylcarbamoyl]-ethyl}-[1,2,4]oxadiazol-3-yl)-phenyl]-carbamic acid tert-butyl ester |
| 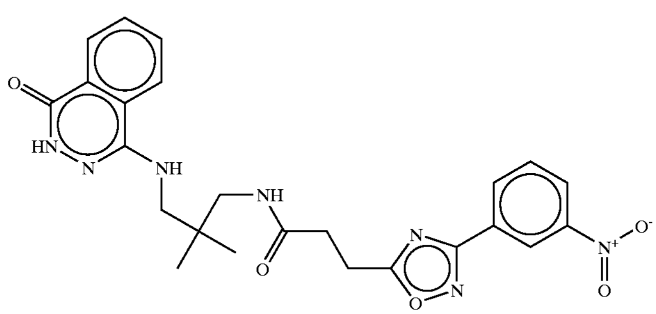 | N-[2,2-Dimethyl-3-(4-oxo-3,4-dihydro-phthalazin-1-ylamino)-propyl]-3-[3-(3-nitro-phenyl)-[1,2,4]oxadiazol-5-yl]-propionamide |

TABLE 2-continued

Representative compounds of Formula I along with some nomenclatures.

| Structure | NAME |
|---|---|
| 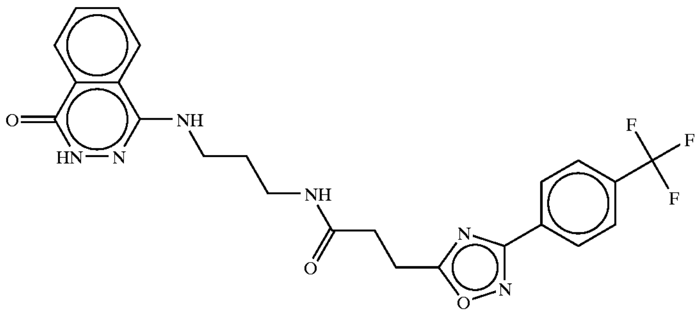 | N-[3-(4-Oxo-3,4-dihydro-phthalazin-1-ylamino)-propyl]-3-[3-(4-trifluoromethyl-phenyl)-[1,2,4]oxadiazol-5-yl]-propionamide |
| 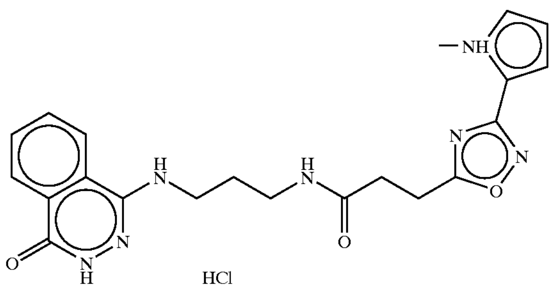 | 3-[3-(1-Methyl-1H-pyrrol-2-yl)-[1,2,4]oxadiazol-5-yl]-N-[3-(4-oxo-3,4-dihydro-phthalazin-1-ylamino)-propyl]-propionamide |
| 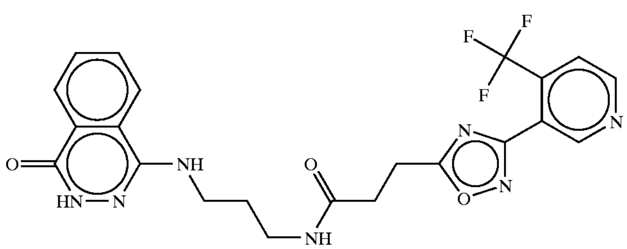 | N-[3-(4-Oxo-3,4-dihydro-phthalazin-1-ylamino)-propyl]-3-[3-(4-trifluoromethyl-pyridin-3-yl)-[1,2,4]oxadiazol-5-yl]-propionamide |
| 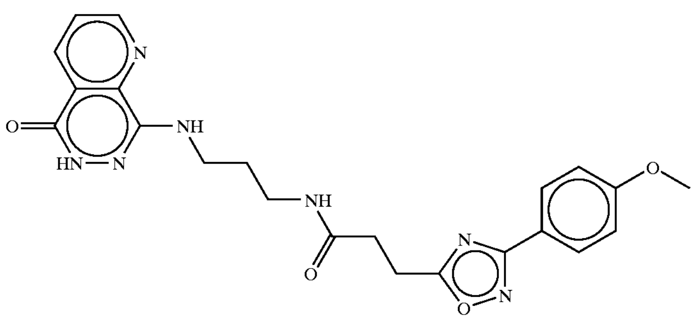 | 3-[3-(4-Methoxy-phenyl)-[1,2,4]oxadiazol-5-yl]-N-[3-(5-oxo-5,6-dihydro-pyridol[2,3-d]pyridazin-8-ylamino)-propyl]-propionamide |
| 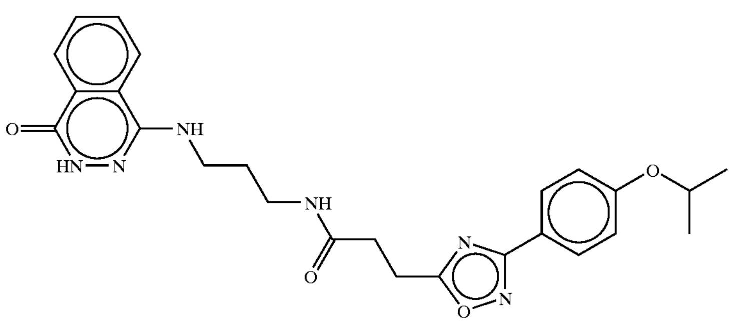 | 3-[3-(4-Isopropoxy-phenyl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 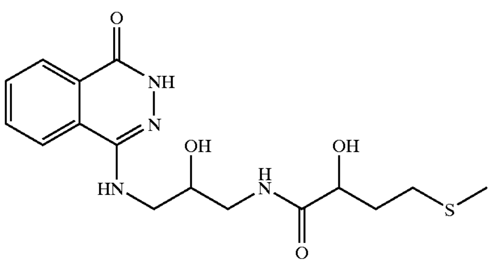 | 2-Hydroxy-N-[2-hydroxy-3-(4-oxo-3,4-dihydro-phthalazin-1-ylamino)-propyl]-4-methylsulfanyl-butyramide |
| 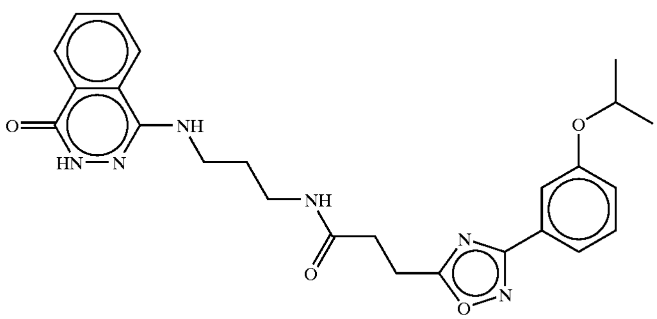 | 3-[3-(3-Isopropoxy-phenyl)-[1,2,4]oxadiazol-5-yl]-N-[3-(4-oxo-3,4-dihydro-phihalazin-1-ylamino)-propyl]-propionamide |
| 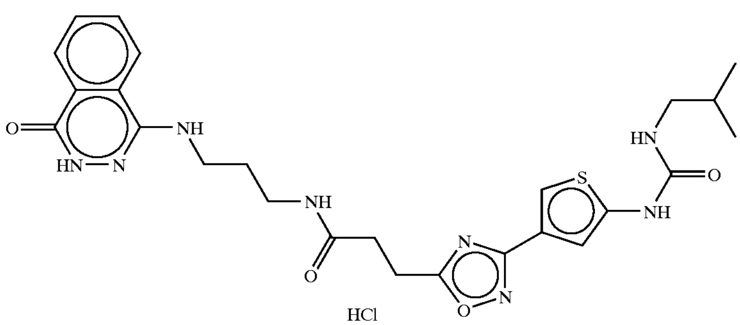 | 3-{3-[5-(3-Isobutyl-ureido)-thiophen-3-yl]-[1,2,4]oxadiazol-5-yl}-N-[3-(4-oxo-3,4-dihydro-phthalazin-1-ylamino)-propyl]-propionamide |
| 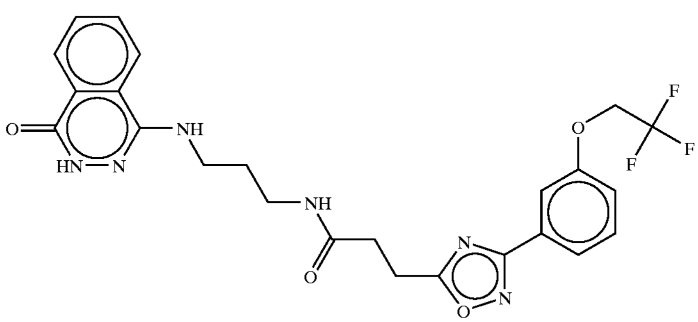 | N-[3-(4-Oxo-3,4-dihydro-phthalazin-1-ylamino)-propyl]-3-{3-[3-(2,2,2-trifluoro-ethoxy)-phenyl]-[1,2,4]oxadiazol-5-yl}-propionamide |
| 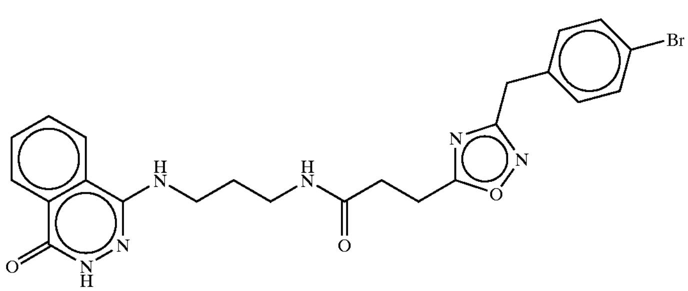 | 3-[3-(4-Bromo-benzyl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
| --- | --- |
| 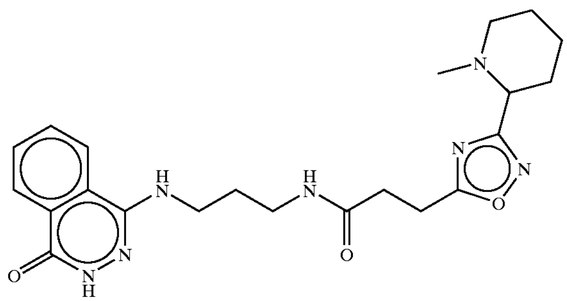 | 3-[3-(1-Methyl-piperidin-2-yl)-[1,2,4]oxadiazol-5-yl]-N-[3-(4-oxo-3,4-dihydro-phthalazin-1-ylamino)-propyl]-propionamide |
| 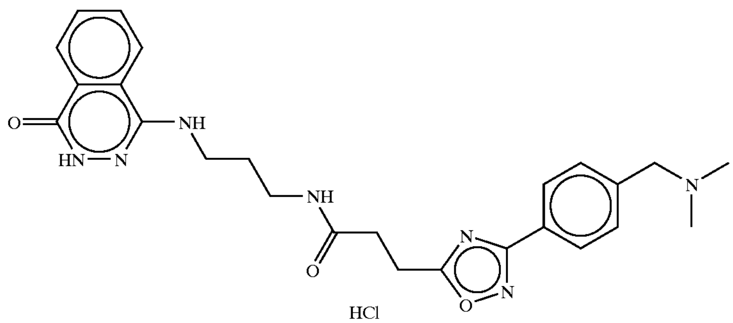 | 3-[3-(4-Dimethylaminomethyl-phenyl)-[1,2,4]oxadiazol-5-yl]-N-[3-(4-oxo-3,4-dihydro-phthalazin-1-ylamino)-propyl]-propionamide |
| 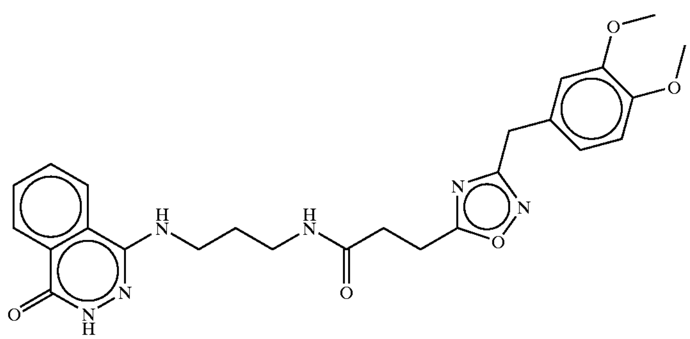 | 3-[3-(3,4-Dimethoxy-benzyl)-[1,2,4]oxadiazol-5-yl]-N-[3-(4-oxo-3,4-dihydro-phthalazin-1-ylamino)-propyl]-propionamide |
| 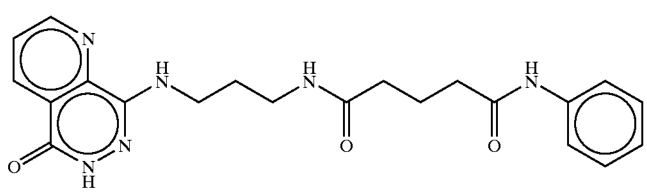 | Pentanedioic acid [3-(5-oxo-5,6-dihydro-pyrido[2,3-d]pyridazin-8-ylamino)-propyl]-amide phenylamide |
| 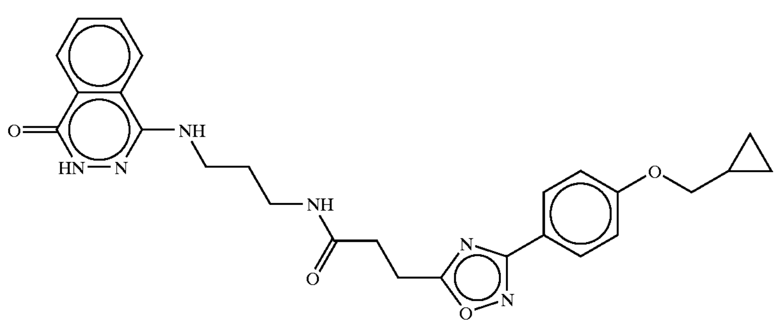 | 3-[3-(4-Cyclopropylmethoxy-phenyl)-[1,2,4]oxadiazol-5-yl]-N-[3-(4-oxo-3,4-dihydro-phthalazin-1-ylamino)-propyl]-propionamide |

TABLE 2-continued

*Representative compounds of Formula I along with some nomenclatures.*

| Structure | NAME |
|---|---|
| 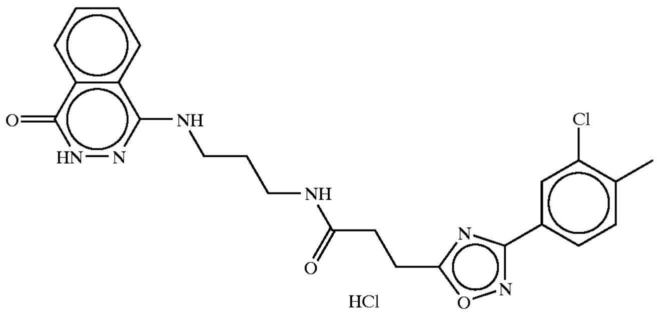 | 3-[3-(3-Chloro-4-methyl-phenyl)-[1,2,4]oxadiazol-5-yl]-N-[3-(4-oxo-3,4-dihydro-phihalazin-1-ylamino)-propyl]-propionamide |
| 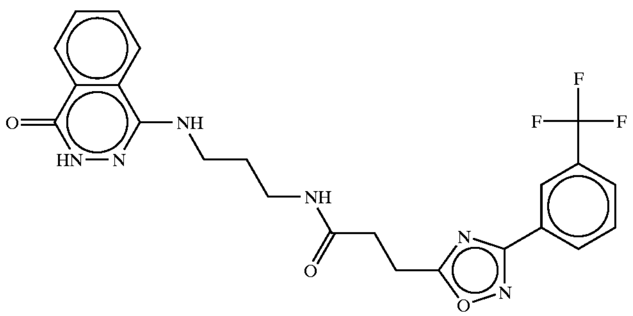 | N-[3-(4-Oxo-3,4-dihydro-phthalazin-1-ylamino)-propyl]-3-[3-(3-trifluoromethyl-phenyl)-[1,2,4]oxadiazol-5-yl]-propionamide |
| 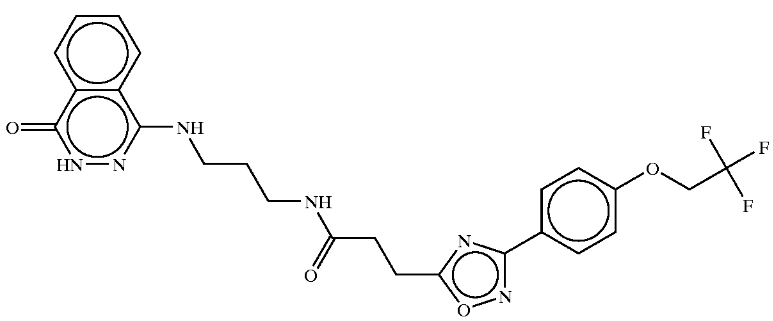 | N-[3-(4-Oxo-3,4-dihydro-phthalazin-1-ylamino)-propyl]-3-{3-[4-(2,2,2-trifluoro-ethoxy)-phenyl]-[1,2,4]oxadiazol-5-yl}-propionamide |
| 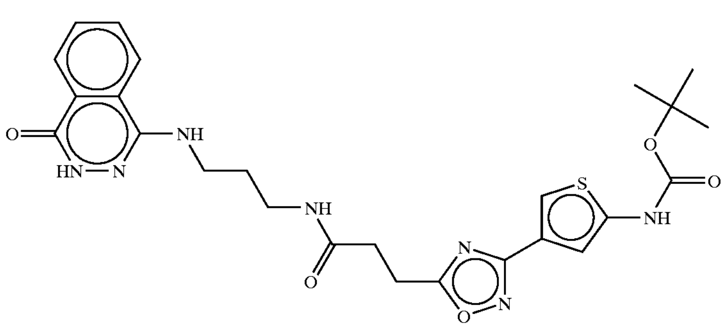 | [4-(5-{2-[3-(4-Oxo-3,4-dihydro-phthalazin-1-ylamino)-propylcarbamoyl]-ethyl}-[1,2,4]oxadiazol-3-yl)-thiophen-2-yl]-carbamic acid tert-butyl ester |

TABLE 2-continued

Representative compounds of Formula I along with some nomenclatures.

| Structure | NAME |
|---|---|
| 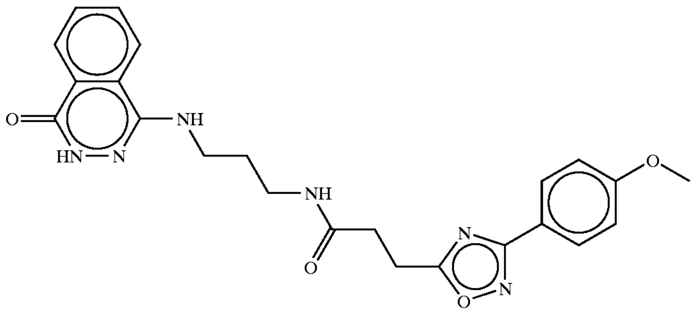 | 3-[3-(4-Methoxy-phenyl)-[1,2,4]oxadiazol-5-yl]-N-[3-(4-oxo-3,4-dihydro-phthalazin-1-ylamino)-propyl]-propionamide |
| 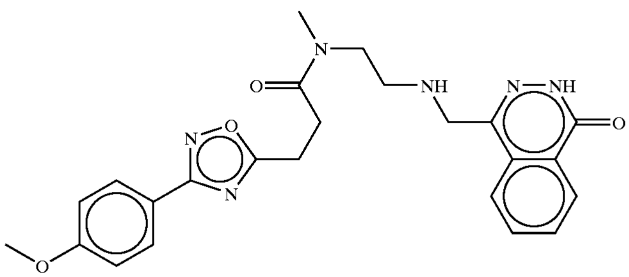 | 3-[3-(4-Methoxy-phenyl)-[1,2,4]oxadiazol-5-yl]-N-methyl-N-{2-[(4-oxo-3,4-dihydro-phthalazin-1-ylmethyl)-amino]-ethyl}-propionamide |
| 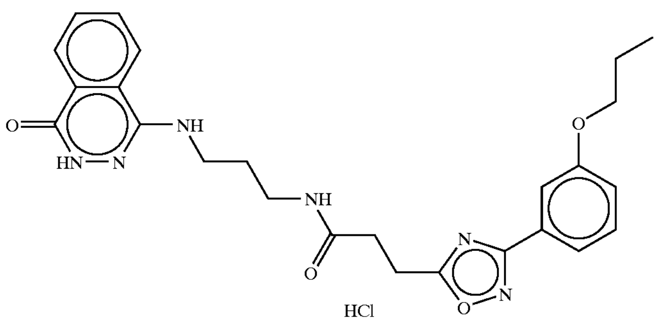 | N-[3-(4-Oxo-3,4-dihydro-phthalazin-1-ylamino)-propyl]-3-[3-(3-propoxy-phenyl)-[1,2,4]oxadiazol-5-yl]-propionamide |
| 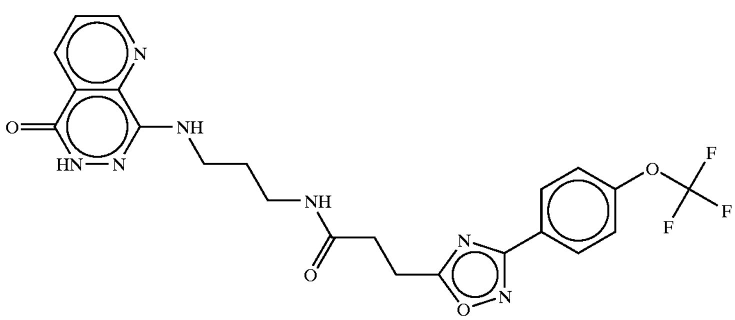 | N-[3-(5-Oxo-5,6-dihydro-pyrido[2,3-d]pyridazin-8-ylamino)-propyl]-3-[3-(4-trifluoromethoxy-phenyl)-[1,2,4]oxadiazol-5-yl]-propionamide |
| 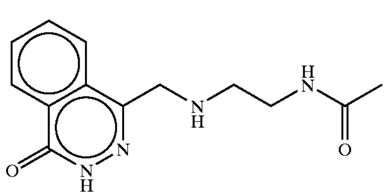 | N-{2-[(4-Oxo-3,4-dihydro-phthalazin-1-ylmethyl)-amino]-ethyl}-acetamide |

TABLE 2-continued

Representative compounds of Formula I along with some nomenclatures.

| Structure | NAME |
| --- | --- |
| 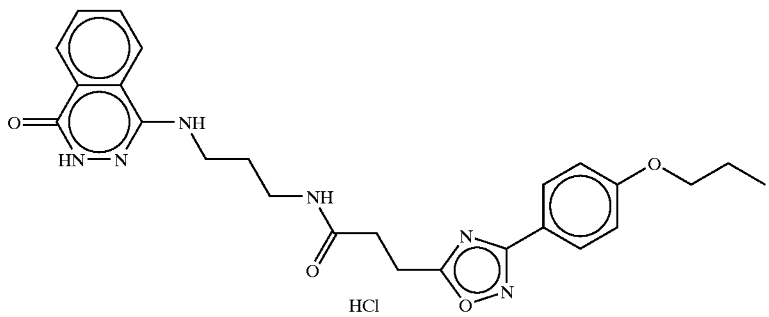 | N-[3-(4-Oxo-3,4-dihydro-phthalazin-1-ylamino)-propyl]-3-[3-(4-propoxy-phenyl)-[1,2,4]oxadiazol-5-yl]-propionamide |
| 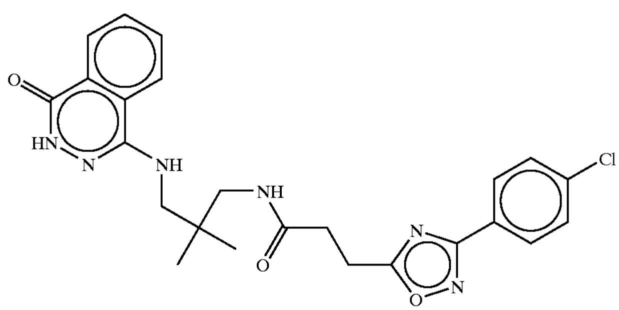 | 3-[3-(4-Chloro-phenyl)-[1,2,4]oxadiazol-5-yl]-N-[2,2-dimethyl-3-(4-oxo-3,4-dihydro-phthalazin-1-ylamino)-propyl]-propionamide |
| 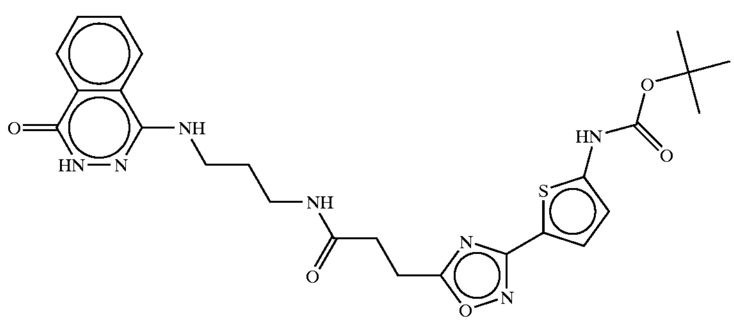 | [5-(5-{2-[3-(4-Oxo-3,4-dihydro-phthalazin-1-ylamino)-propylcarbamoyl]-ethyl}-[1,2,4]oxadiazol-3-yl)-thiophen-2-yl]-carbamic acid tert-butyl ester |
| 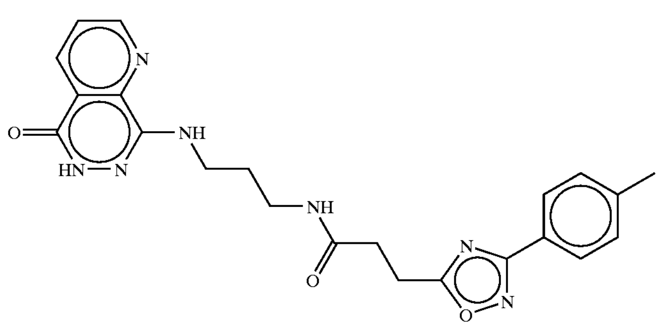 | N-[3-(5-Oxo-5,6-dihydro-pyrido[2,3-d]pyridazin-8-ylamino)-propyl]-3-(3-p-tolyl-[1,2,4]oxadiazol-5-yl)-propionamide |

TABLE 2-continued

Representative compounds of Formula I along with some nomenclatures.

| Structure | NAME |
|---|---|
| 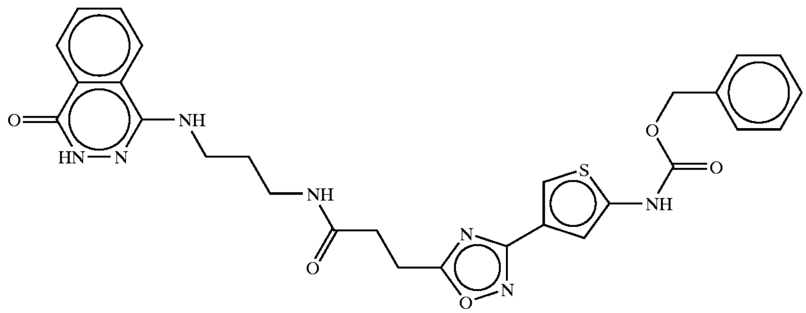 | [4-(5-{2-[3-(4-Oxo-3,4-dihydro-phthalazin-1-ylamino)-propylcarbamoyl]-ethyl}-[1,2,4]oxadiazol-3-yl)-thiophen-2-yl]-carbamic acid benzyl ester |
| 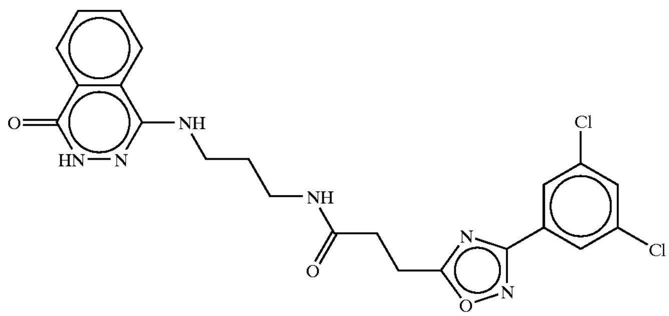 | 3-[3-(3,5-Dichloro-phenyl)-[1,2,4]oxadiazol-5-yl]-N-[3-(4-oxo-3,4-dihydro-phthalazin-1-ylamino)-propyl]-propionamide |
| 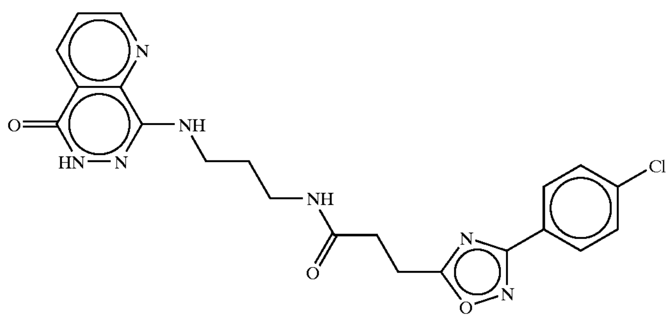 | 3-[3-(4-Chloro-phenyl)-[1,2,4]oxadiazol-5-yl]-N-[3-(5-oxo-5,6-dihydro-pyrido[2,3-d]pyridazin-8-ylamino)-propyl]-propionamide |
| 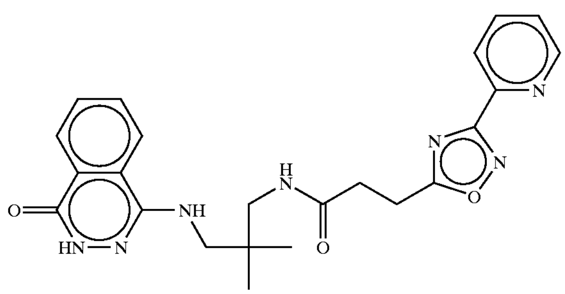 | N-[2,2-Dimethyl-3-(4-oxo-3,4-dihydro-phthalazin-1-ylamino)-propyl]-3-(3-pyridin-2-yl-[1,2,4]oxadiazol-5-yl)-propionamide |
| 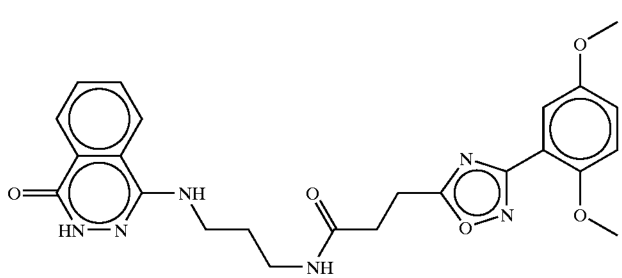 | 3-[3-(2,5-Dimethoxy-phenyl)-[1,2,4]oxadiazol-5-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 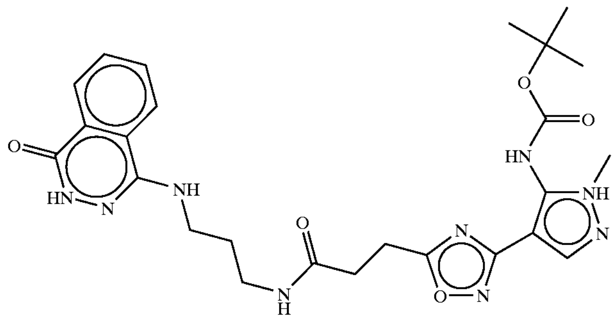 | [2-Methyl-4-(5-{2-[3-(4-oxo-3,4-dihydro-phthalazin-1-ylamino)-propylcarbamoyl]-ethyl}-[1,2,4]oxadiazol-3-yl)-2H-pyrazol-3-yl]-carbamic acid tert-butyl ester |
| 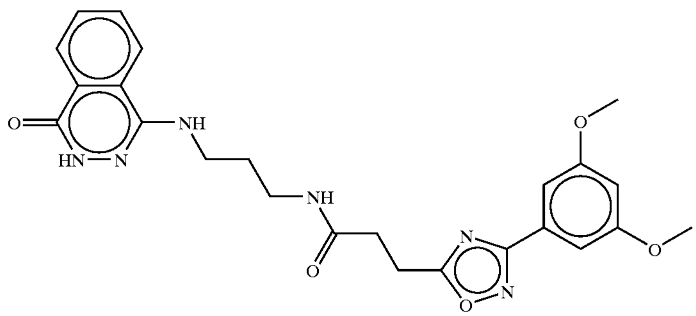 | 3-[3-(3,5-Dimethoxy-phenyl)-[1,2,4]oxadiazol-5-yl]-N-[3-(4-oxo-3,4-dihydro-phthalazin-1-ylamino)-propyl]-propionamide |
| 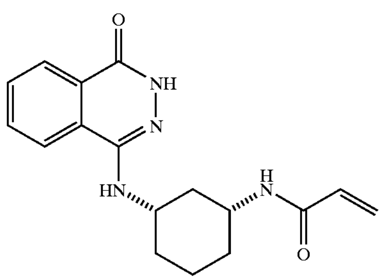 | N-[3-(4-Oxo-3,4-dihydro-phthalazin-1-ylamino)-cyclohexyl]-acrylamide |
| 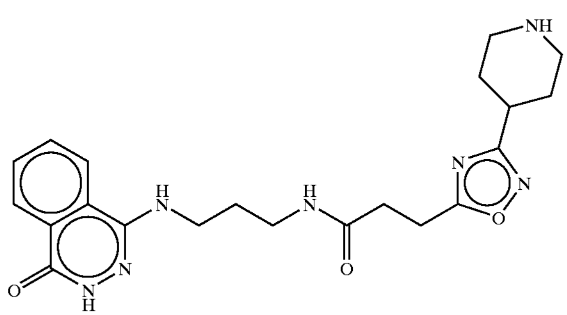 | 3-[3-(1-Methyl-piperidin-4-yl)-[1,2,4]oxadiazol-5-yl]-N-[3-(4-oxo-3,4-dihydro-phthalazin-1-ylamino)-propyl]-propionamide |
| 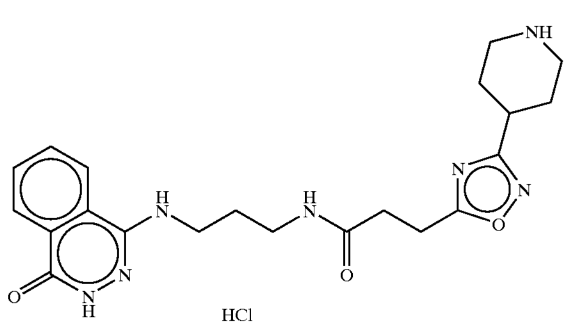 | N-[3-(4-Oxo-3,4-dihydro-phthalazin-1-ylamino)-propyl]-3-(3-piperidin-4-yl-[1,2,4]oxadiazol-5-yl)-propionamide |

TABLE 2-continued

Representative compounds of Formula I along with some nomenclatures.

| Structure | NAME |
|---|---|
| 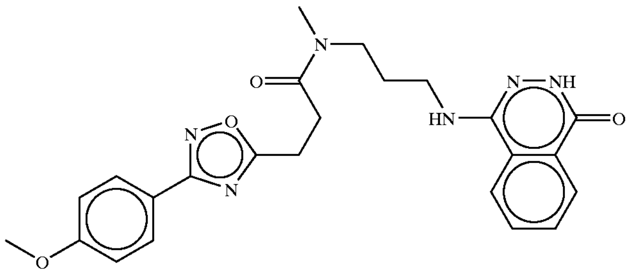 | 3-[3-(4-Methoxy-phenyl)-[1,2,4]oxadiazol-5-yl]-N-methyl-N-[3-(4-oxo-3,4-dihydro-phthalazin-1-ylamino)-propyl]-propionamide |
| 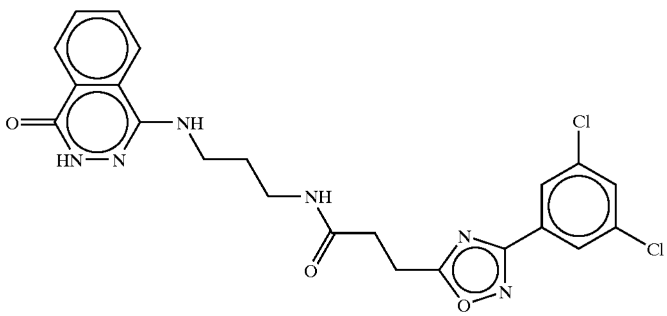 | 3-[3-(3,5-Dichloro-phenyl)-[1,2,4]oxadiazol-5-yl]-N-[3-(4-oxo-3,4-dihydro-phthalazin-1-ylamino)-propyl]-propionamide |
| 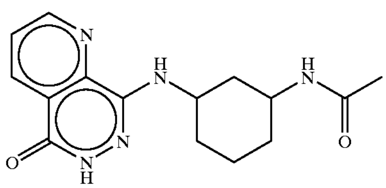 | N-[3-(5-Oxo-5,6-dihydro-pyrido[2,3-d]pyridazin-8-ylamino)-cyclohexyl]-acetamide |
| 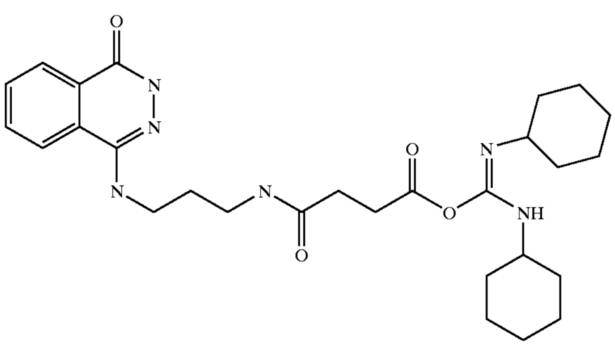 | 4-(N,N'-Dicyclohexyl-carbamimidoyloxy)-4-oxo-N-[3-(4-oxo-3,4-dihydro-phthalazin-1-ylamino)-propyl]-butyramide |
| 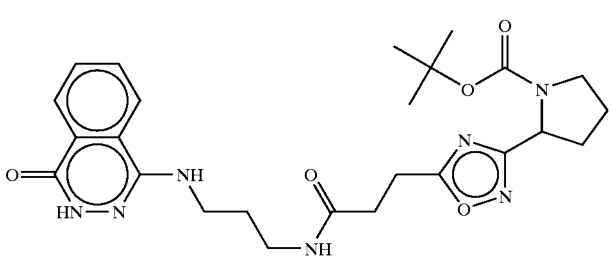 | 2-(5-{2-[3-(4-Oxo-3,4-dihydro-phthalazin-1-ylamino)-propylcarbamoyl]-ethyl}-[1,2,4]oxadiazol-3-yl)-pyrrolidine-1-carboxylic acid tert-butyl ester |

TABLE 2-continued

Representative compounds of Formula I along with some nomenclatures.

| Structure | NAME |
|---|---|
| 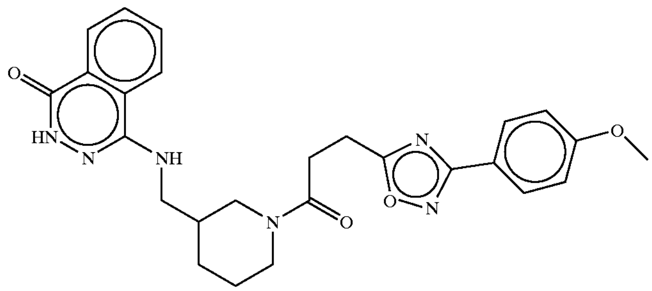 | 4-[(1-3-{3-[3-(4-Methoxy-phenyl)-[1,2,4]oxadiazol-5-yl]-propionyl}-piperidin-3-ylmethyl)-amino]-2lambda3-phthalazin-1-one |
| 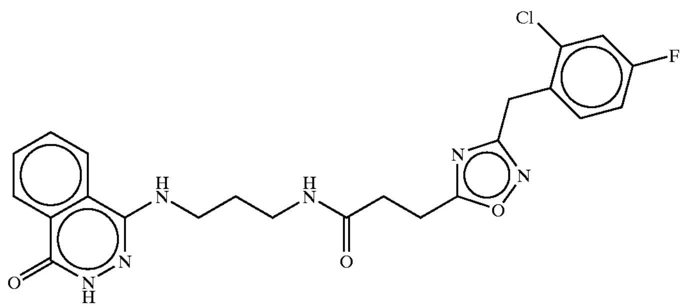 | 3-[3-(2-Chloro-4-fluoro-benzyl)-[1,2,4]oxadiazol-5-yl]-N-[3-(4-oxo-3,4-dihydro-phthalazin-1-ylamino)-propyl]-propionamide |
| 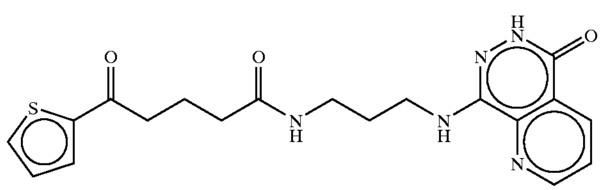 | 5-Oxo-5-thiophen-2-yl-pentanoic acid [3-(5-oxo-5,6-dihydro-pyrido[2,3-d]pyridazin-8-ylamino)-propyl]-amide |
| 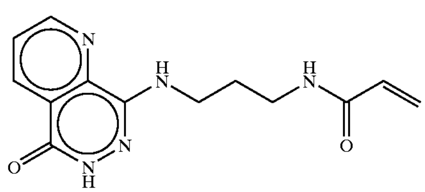 | N-[3-(5-Oxo-5,6-dihydro-pyrido[2,3-d]pyridazin-8-ylamino)-propyl]-acrylamide |
| 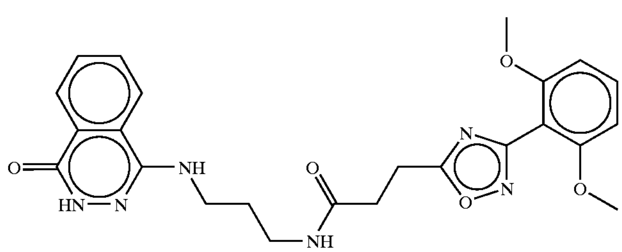 | 3-[3-(2,6-Dimethoxy-phenyl)-[1,2,4]oxadiazol-5-yl]-N-[3-(4-oxo-3,4-dihydro-phlhalazin-1-ylamino)-propyl]-propionamide |
| 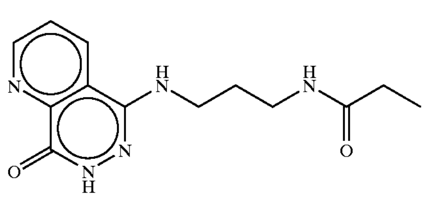 | N-[3-(8-Oxo-7,8-dihydro-pyrido[2,3-d]pyridazin-5-ylamino)-propyl]-propionamide |

TABLE 2-continued

Representative compounds of Formula I along with some nomenclatures.

| Structure | NAME |
|---|---|
| 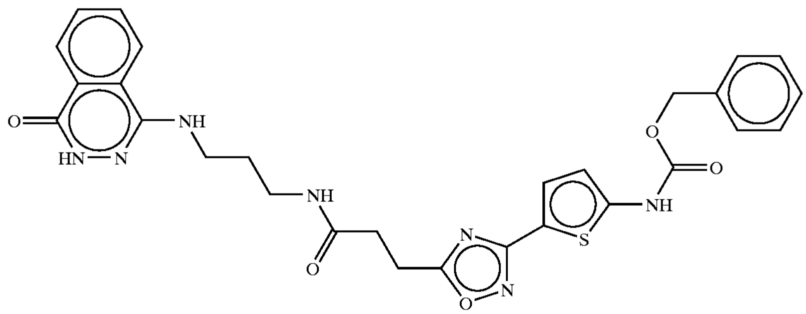 | [5-(5-{2-[3-(4-Oxo-3,4-dihydro-phthalazin-1-ylamino)-propylcarbamoyl]-ethyl}-[1,2,4]oxadiazol-3-yl)-thiophen-2-yl]-carbamic acid benzyl ester |
| 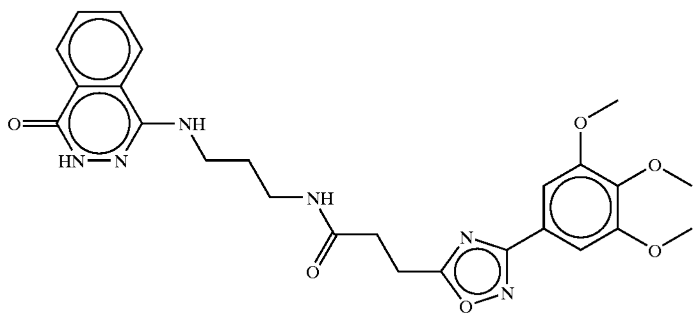 | N-[3-(4-Oxo-3,4-dihydro-phthalazin-1-ylamino)-propyl]-3-[3-(3,4,5-trimethoxy-phenyl)-[1,2,4]oxadiazol-5-yl]-propionamide |
| 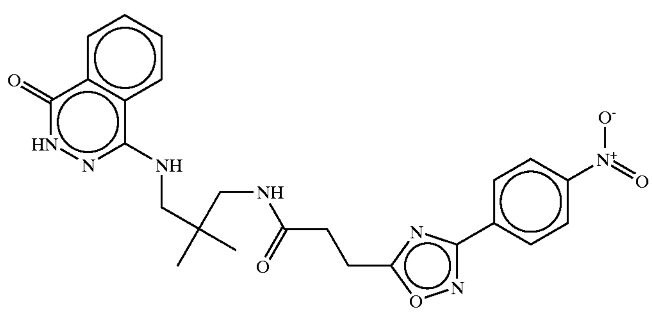 | N-[2,2-Dimethyl-3-(4-oxo-3,4-dihydro-phthalazin-1-ylamino)-propyl]-3-[3-(4-nitro-phenyl)-[1,2,4]oxadiazol-5-yl]-propionamide |
| 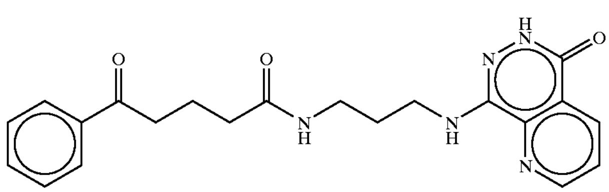 | 5-Oxo-5-phenyl-pentanoic acid [3-(5-oxo-5,6-dihydro-pyrido[2,3-d]pyridazin-8-ylamino)-propyl]-amide |
| 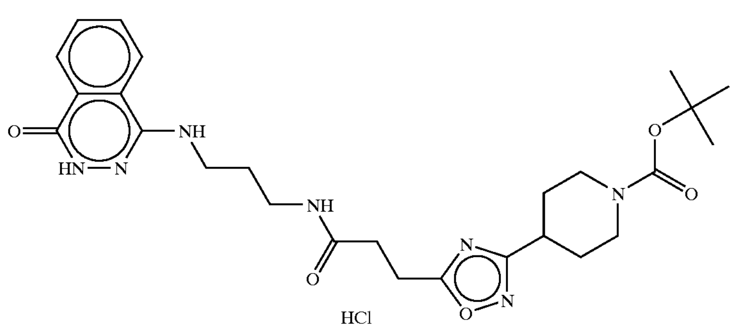 | 4-(5-{2-[3-(4-Oxo-3,4-dihydro-phthalazin-1-ylamino)-propylcarbamoyl]-ethyl}-[1,2,4]oxadiazol-3-yl)-piperidine-1-carboxylic acid tert-butyl ester |

TABLE 2-continued

Representative compounds of Formula I along with some nomenclatures.

| Structure | NAME |
|---|---|
| 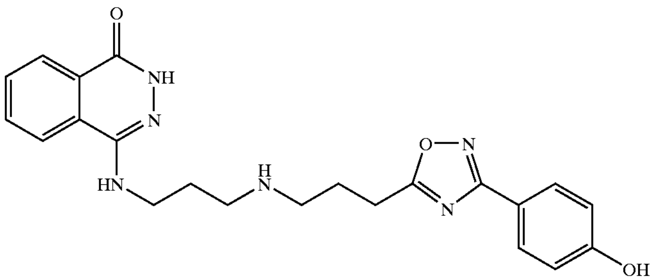 | 4-(3-{3-[3-(4-Hydroxy-phenyl)-[1,2,4]oxadiazol-5-yl]-propylamino}-propylamino)-2H-phthalazin-1-one |
| 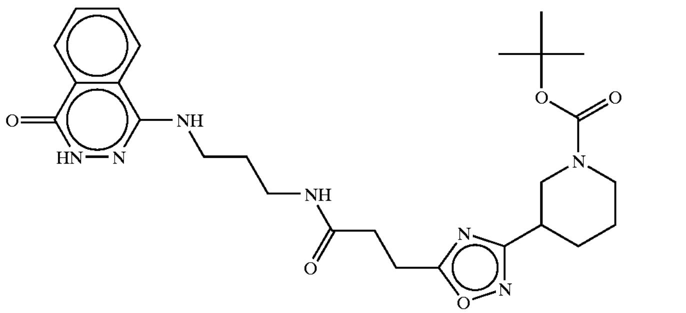 | 3-(5-{2-[3-(4-Oxo-3,4-dihydro-phthalazin-1-ylamino)-propylcarbamoyl]-ethyl}-[1,2,4]oxadiazol-3-yl)-piperidine-1-carboxylic acid tert-butyl ester |
| 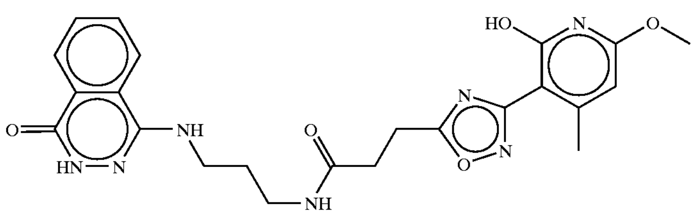 | 3-[3-(2-Hydroxy-6-methoxy-4-methyl-pyridin-3-yl)-[1,2,4]oxadiazol-5-yl]-N-[3-(4-oxo-3,4-dihydro-phthalazin-1-ylamino)-propyl]-propionamide |
| 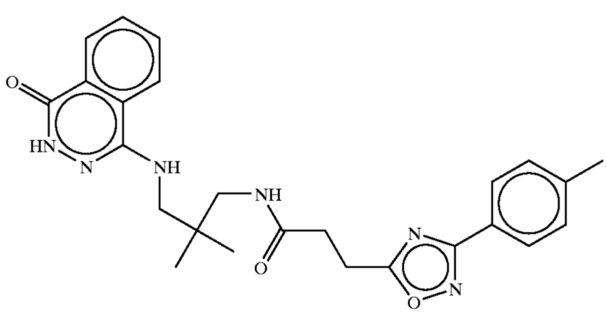 | N-[2,2-Dimethyl-3-(4-oxo-3,4-dihydro-phthalazin-1-ylamino)-propyl]-3-(3-p-tolyl-[1,2,4]oxadiazol-5-yl)-propionamide |
| 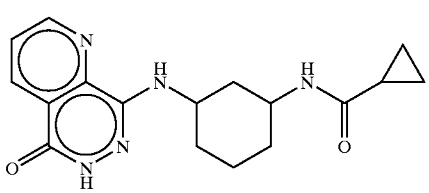 | Cyclopropanecarboxylic acid [3-(5-oxo-5,6-dihydro-pyrido[2,3-d]pyridazin-8-ylamino)-cyclohexyl]-amide |

TABLE 2-continued

Representative compounds of Formula I along with some nomenclatures.

| Structure | NAME |
|---|---|
| 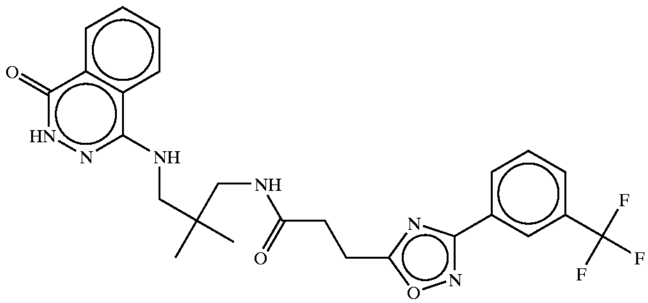 | N-[2,2-Dimethyl-3-(4-oxo-3,4-dihydro-phthalazin-1-ylamino)-propyl]-3-[3-(3-trifluoromethyl-phenyl)-[1,2,4]oxadiazol-5-yl]-propionamide |
| 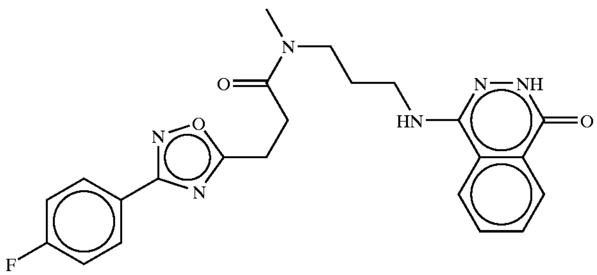 | 3-[3-(4-Fluoro-phenyl)-[1,2,4]oxadiazol-5-yl]-N-methyl-N-[3-(4-oxo-3,4-dihydro-phthalazin-1-ylamino)-propyl]-propionamide |
| 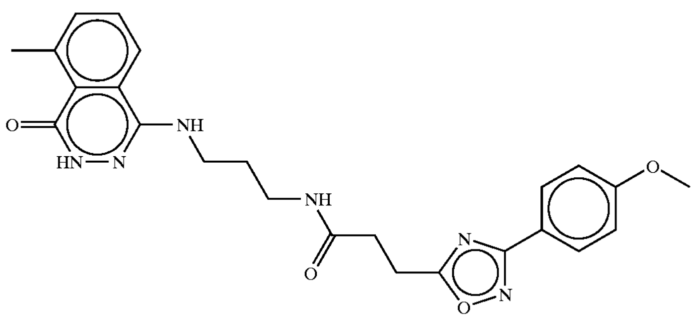 | 3-[3-(4-Methoxy-phenyl)-[1,2,4]oxadiazol-5-yl]-N-[3-(5-methyl-4-oxo-3,4-dihydro-phthalazin-1-ylamino)-propyl]-propionamide |
| 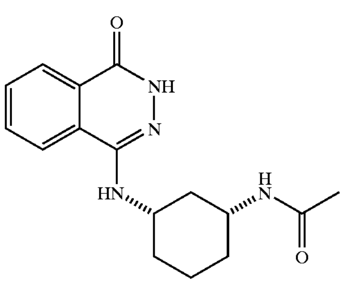 | N-[3-(4-Oxo-3,4-dihydro-phthalazin-1-ylamino)-cyclohexyl]-acetamide |
| 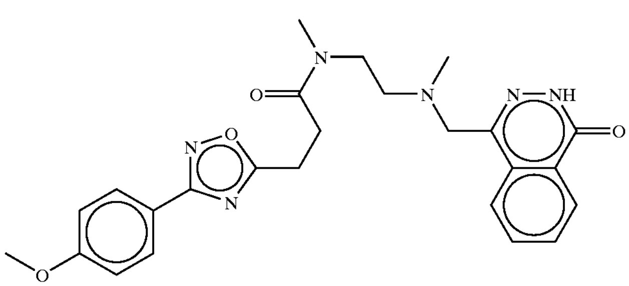 | 3-[3-(4-Methoxy-phenyl)-[1,2,4]oxadiazol-5-yl]-N-methyl-N-{2-[methyl-(4-oxo-3,4-dihydro-phthalazin-1-ylmethyl)-amino]-ethyl}-propionamide |

TABLE 2-continued

Representative compounds of Formula I along with some nomenclatures.

| Structure | NAME |
|---|---|
| 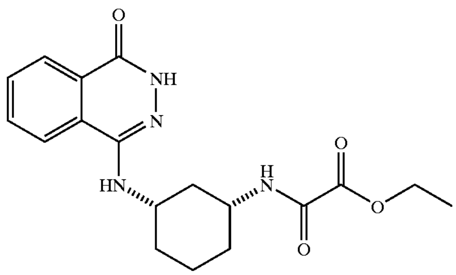 | N-[3-(4-Oxo-3,4-dihydro-phthalazin-1-ylamino)-cyclohexyl]-oxalamic acid ethyl ester |
| 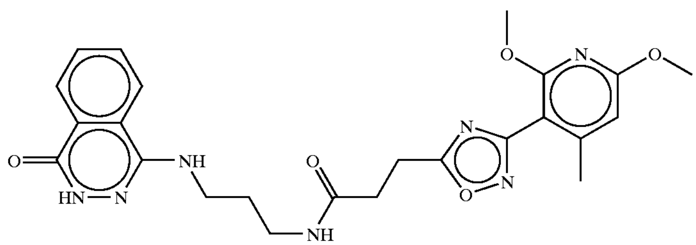 | 3-[3-(2,6-Dimethoxy-4-methyl-pyridin-3-yl)-[1,2,4]oxadiazol-5-yl]-N-[3-(4-oxo-3,4-dihydro-phthalazin-1-ylamino)-propyl]-propionamide |
| 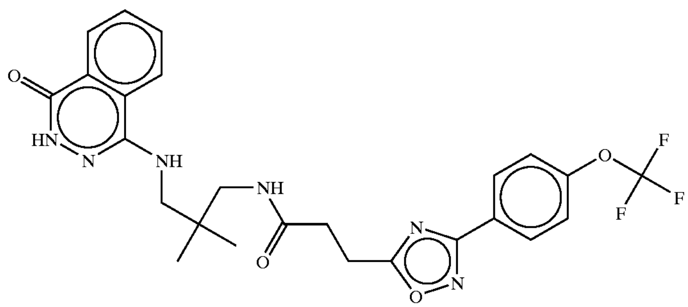 | N-[2,2-Dimethyl-3-(4-oxo-3,4-dihydro-phthalazin-1-ylamino)-propyl]-3-[3-(4-trifluoromethoxy-phenyl)-[1,2,4]oxadiazol-5-yl]-propionamide |
| 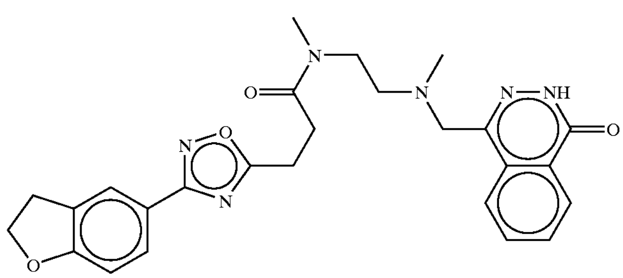 | 3-[3-(2,3-Dihydro-benzofuran-5-yl)-[1,2,4]oxadiazol-5-yl]-N-methyl-N-{2-[methyl-4-oxo-3,4-dihydro-phthalazin-1-ylmethyl)-amino]-ethyl}-propionamide |
| 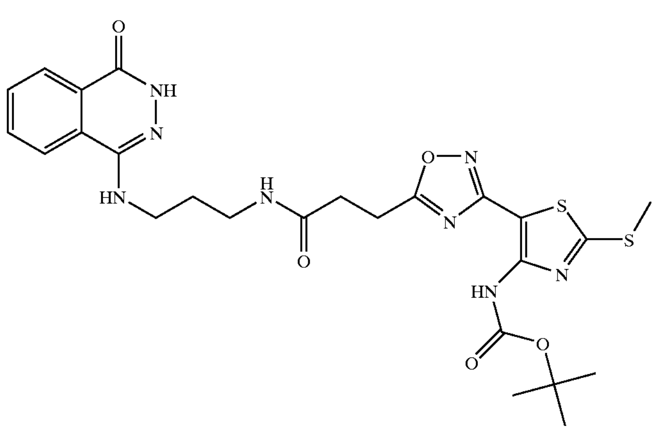 | [2-Methylsulfanyl-5-(5-{2-[3-(4-oxo-3,4-dihydro-phthalazin-1-ylamino)-propylcarbamoyl]-ethyl}-[1,2,4]oxadiazol-3-yl)-thiazol-4-yl]-carbamic acid tert-butyl ester |

TABLE 2-continued

Representative compounds of Formula I along with some nomenclatures.

| Structure | NAME |
|---|---|
| 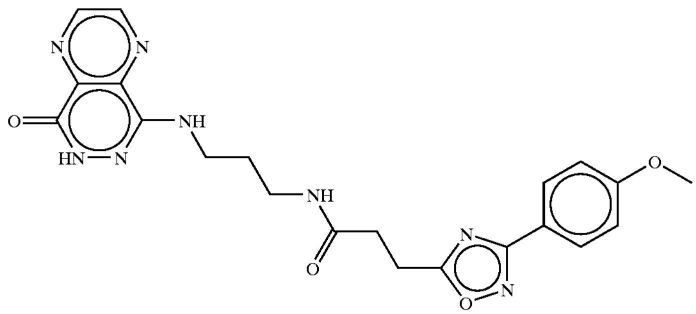 | 3-[3-(4-Methoxy-phenyl)-[1,2,4]oxadiazol-5-yl]-N-[3-(8-oxo-7,8-dihydro-pyrazino[2,3-d]pyridazin-5-ylamino)-propyl]-propionamide |
| 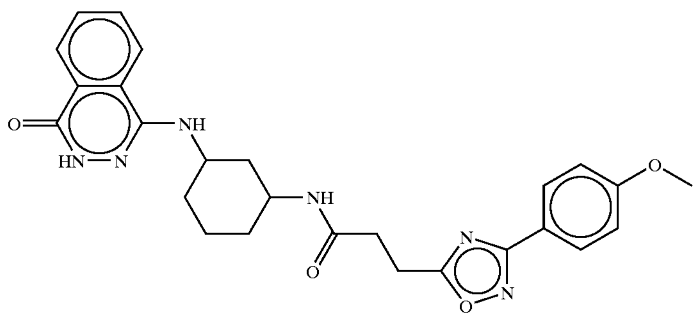 | 3-[3-(4-Methoxy-phenyl)-[1,2,4]oxadiazol-5-yl]-N-[3-(4-oxo-3,4-dihydro-phthalazin-1-ylamino)-cyclohexyl]-propionamide |
| 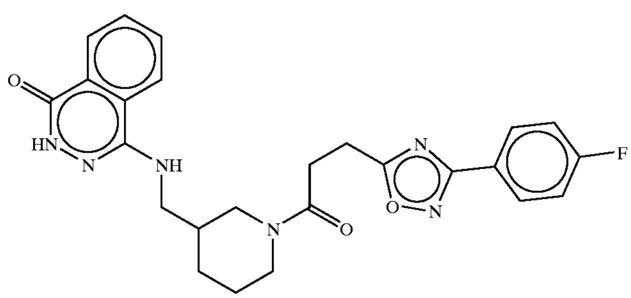 | 4-[(1-{3-[3-(4-Fluoro-phenyl)-[1,2,4]oxadiazol-5-yl]-propionyl}-piperidin-3-ylmethyl)-amino]-2H-phthalazin-1-one |
| 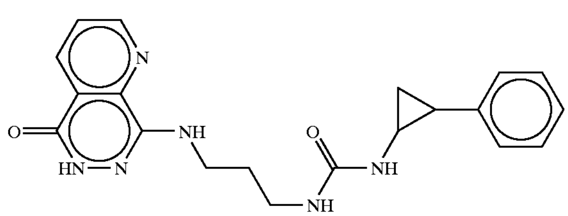 | 1-[3-(5-Oxo-5,6-dihydro-pyrido[2,3-d]pyridazin-8-ylamino)-propyl]-3-(2-phenyl-cyclopropyl)-urea |
| 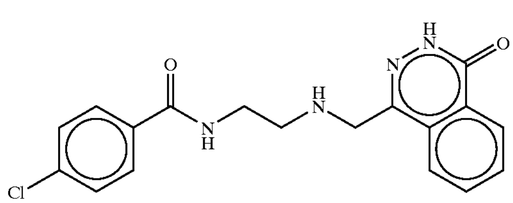 | 4-Chloro-N-{2-[(4-oxo-3,4-dihydro-phthalazin-1-ylmethyl)-amino]-ethyl}-benzamide |

TABLE 2-continued

Representative compounds of Formula I along with some nomenclatures.

| Structure | NAME |
|---|---|
| 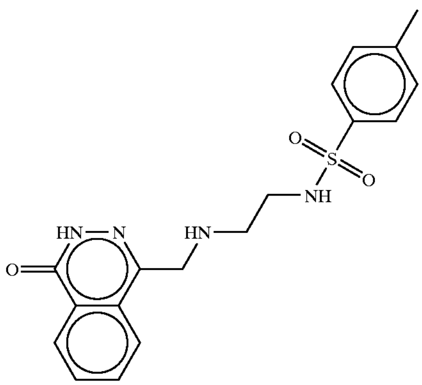 | 4-Methyl-N-{2-[(4-oxo-3,4-dihydro-phthalazin-1-ylmethyl)-amino]-ethyl}-benzenesulfonamide |
| | |
| 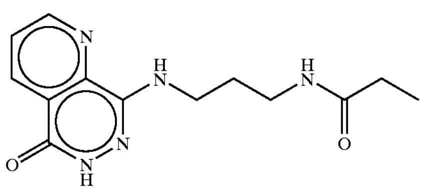 | N-[3-(5-Oxo-5,6-dihydro-pyrido[2,3-d]pyridazin-8-ylamino)-propyl]-propionamide |
| 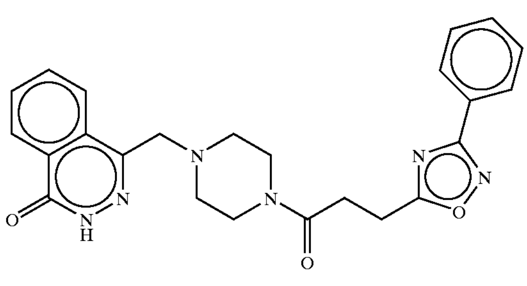 | 4-{4-[3-(3-Phenyl-[1,2,4]oxadiazol-5-yl)-propionyl]-piperazin-1-ylmethyl}-2H-phthalazin-1-one |
| 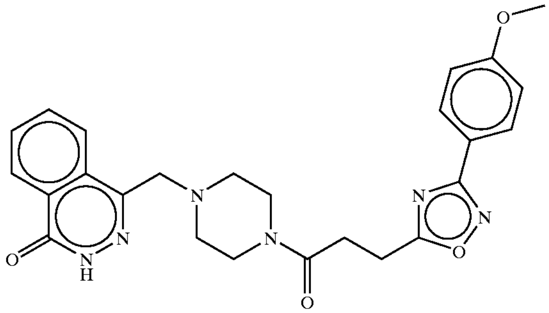 | 4-(4-{3-[3-(4-Methoxy-phenyl)-[1,2,4]oxadiazol-5-yl]-propionyl}-piperazin-1-ylmethyl)-2H-phthalazin-1-one |

TABLE 2-continued

Representative compounds of Formula I along with some nomenclatures.

| Structure | NAME |
|---|---|
| 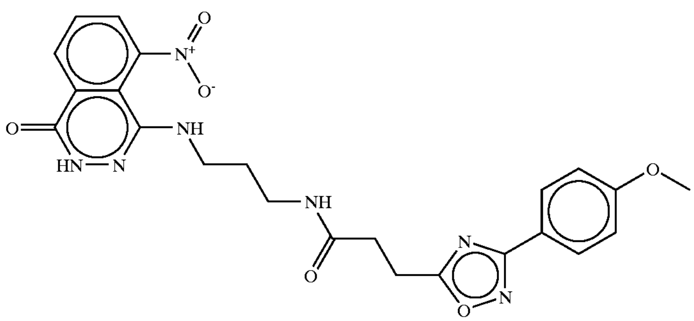 | 3-[3-(4-Methoxy-phenyl)-[1,2,4]oxadiazol-5-yl]-N-[3-(8-nitro-4-oxo-3,4-dihydro-phthalazin-1-ylamino)-propyl]-propionamide |
| 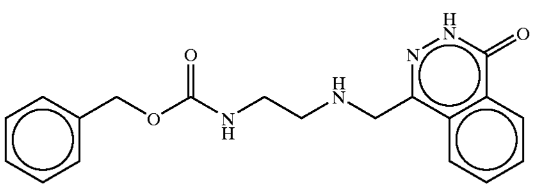 | {2-[(4-Oxo-3,4-dihydro-phthalazin-1-ylmethyl)-amino]-ethyl}-carbamic acid benzyl ester |
| 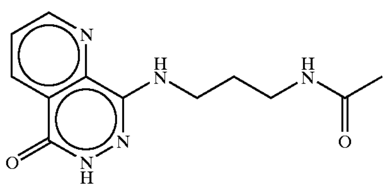 | N-[3-(5-Oxo-5,6-dihydro-pyrido[2,3-d]pyridazin-8-ylamino)-propyl]-acetamide |
| 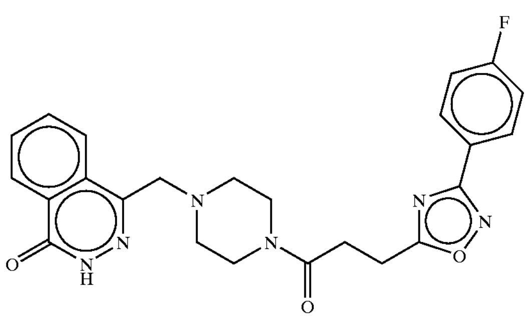 | 4-(4-{3-[3-(4-Fluoro-phenyl)-[1,2,4]oxadiazol-5-yl]-propionyl}-piperazin-1-ylmethyl)-2H-phthalazin-1-one |
| 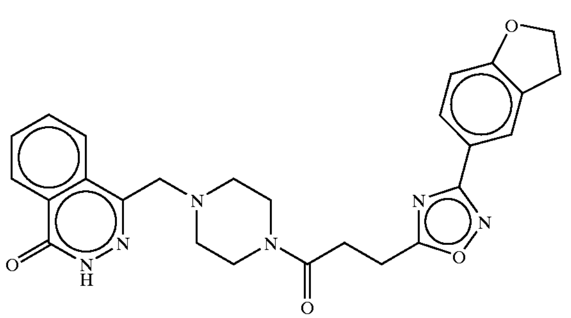 | 4-(4-{3-[3-(2,3-Dihydro-benzofuran-5-yl)-[1,2,4]oxadiazol-5-yl]-propionyl}-piperazin-1-ylmethyl)-2H-phthalazin-1-one |

TABLE 2-continued

Representative compounds of Formula I along with some nomenclatures.

| Structure | NAME |
|---|---|
| 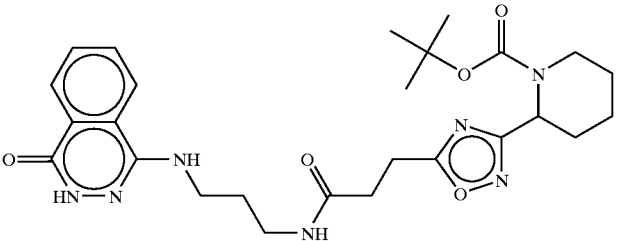 | 2-(5-{2-[3-(4-Oxo-3,4-dihydro-phthalazin-1-ylamino)-propylcarbamoyl]-ethyl}-[1,2,4]oxadiazol-3-yl)-piperidine-1-carboxylic acid tert-butyl ester |
| 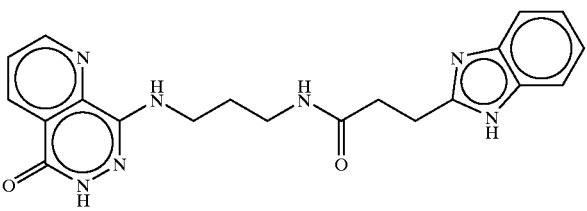 | 3-(1H-Benzoimidazol-2-yl)-N-[3-(5-oxo-5,6-dihydro-pyrido[2,3-d]pyridazin-8-ylamino)-propyl]-propionamide |
| 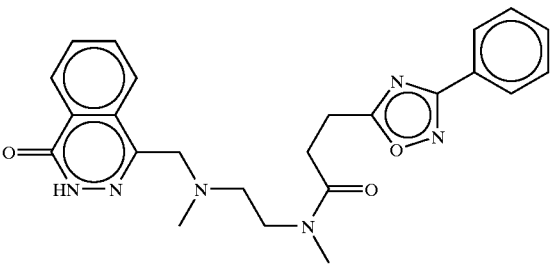 | N-Methyl-N-{2-[methyl-(4-oxo-3,4-dihydro-phthalazin-1-ylmethyl)-amino]-ethyl}-3-(3-phenyl-[1,2,4]oxadiazol-5-yl)-propionamide |
| 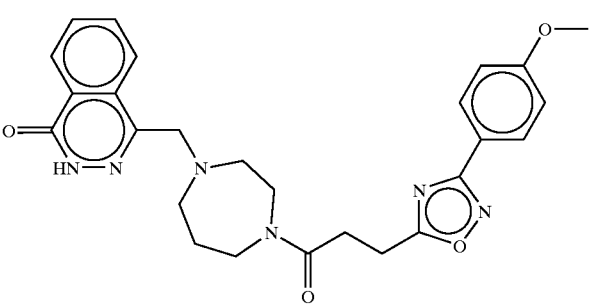 | 4-(4-{3-[3-(4-Methoxy-phenyl)-[1,2,4]oxadiazol-5-yl]-propionyl}-[1,4]diazepan-1-ylmethyl)-2H-phthalazin-1-one |
| 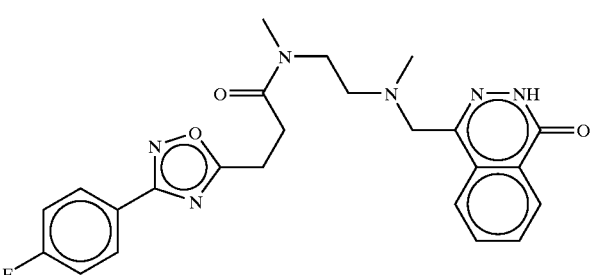 | 3-[3-(4-Fluoro-phenyl)-[1,2,4]oxadiazol-5-yl]-N-methyl-N-{2-[methyl-(4-oxo-3,4-dihydro-phthalazin-1-ylmethyl)-amino]-ethyl}-propionamide |
| 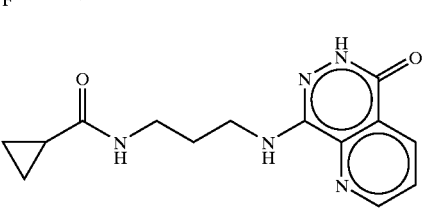 | Cyclopropanecarboxylic acid [3-(5-oxo-5,6-dihydro-pyrido[2,3-d]pyridazin-8-ylamino)-propyl]-amide |

TABLE 2-continued

Representative compounds of Formula I along with some nomenclatures.

| Structure | NAME |
|---|---|
| 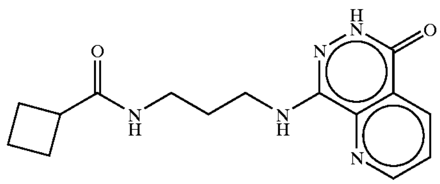 | Cyclobutanecarboxylic acid [3-(5-oxo-5,6-dihydro-pyrido[2,3-d]pyridazin-8-ylamino)-propyl]-amide |
| 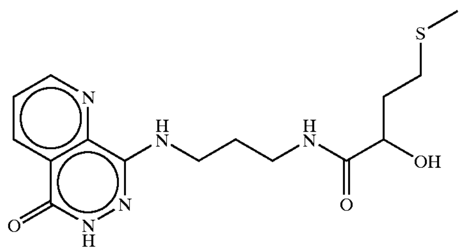 | 2-Hydroxy-4-methylsulfanyl-N-[3-(5-oxo-5,6-dihydro-pyrido[2,3-d]pyridazin-8-ylamino)-propyl]-butyramide |
| 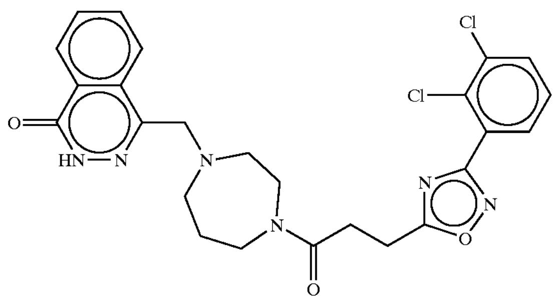 | 4-(4-{3-[3-(2,3-Dichloro-phenyl)-[1,2,4]oxadiazol-5-yl]-propionyl}-[1,4]diazepan-1-ylmethyl)-2H-phthalazin-1-one |
| 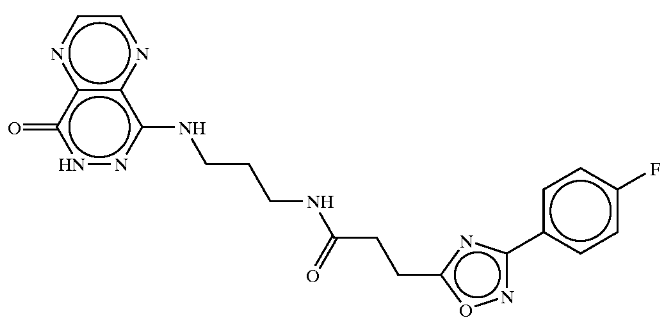 | 3-[3-(4-Fluoro-phenyl)-[1,2,4]oxadiazol-5-yl]-N-[3-(8-oxo-7,8-dihydro-pyrazino[2,3-d]pyridazin-5-ylamino)-propyl]-propionamide |
| 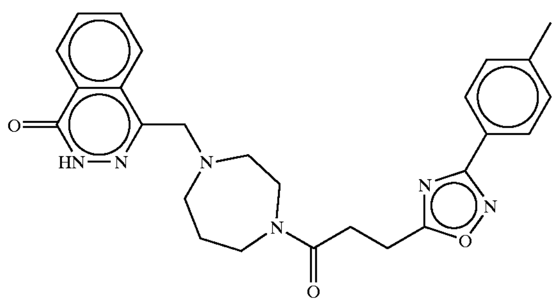 | 4-{4-[3-(3-p-Tolyl-[1,2,4]oxadiazol-5-yl)-propionyl]-[1,4]diazepan-1-ylmethyl}-2H-phthalazin-1-one |

TABLE 2-continued

Representative compounds of Formula I along with some nomenclatures.

| Structure | NAME |
|---|---|
| 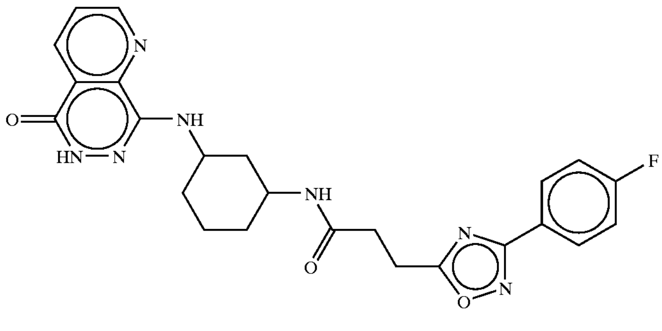 | 3-[3-(4-Fluoro-phenyl)-[1,2,4]oxadiazol-5-yl]-N-[3-(5-oxo-5,6-dihydro-pyrido[2,3-d]pyridazin-8-ylamino)-cyclohexyl]-propionamide |
| 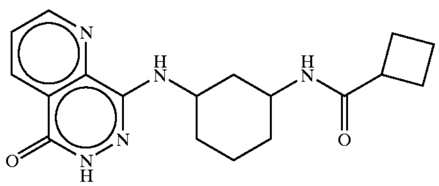 | Cyclobutanecarboxylic acid [3-(5-oxo-5,6-dihydro-pyrido[2,3-d]pyridazin-8-ylamino)-cyclohexyl]-amide |
| 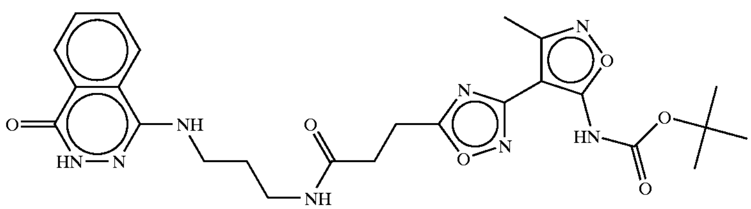 | [3-Methyl-4-(5-{2-[3-(4-oxo-3,4-dihydro-phthalazin-1-ylamino)-propylcarbamoyl]-ethyl}-[1,2,4]oxadiazol-3-yl)-isoxazol-5-yl]-carbamic acid tert-butyl ester |
| 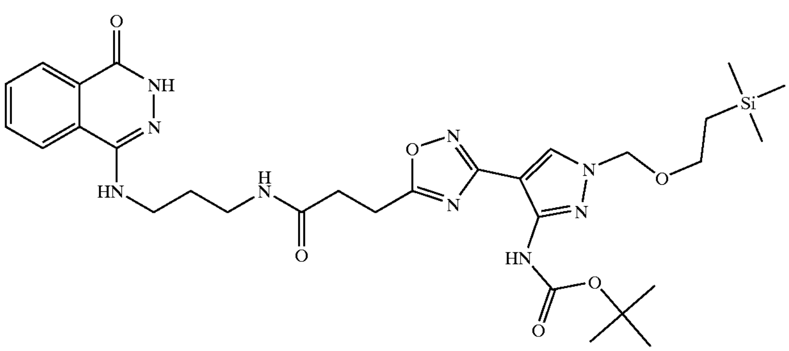 | [4-(5-{2-[3-(4-Oxo-3,4-dihydro-phthalazin-1-ylamino)-propylcarbamoyl]-ethyl}-[1,2,4]oxadiazol-3-yl)-1-(2-trimethylsilanyl-ethoxymethyl)-1H-pyrazol-3-yl]-carbamic acid tert-butyl ester |
| 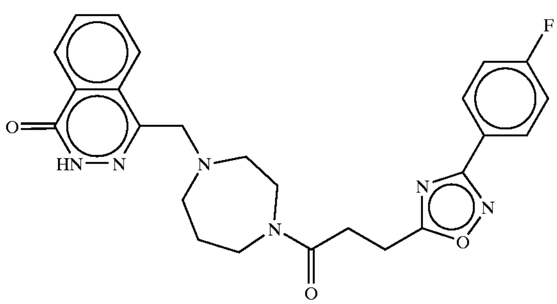 | 4-(4-{3-[3-(4-Fluoro-phenyl)-[1,2,4]oxadiazol-5-yl]-propionyl}-[1,4]diazepan-1-ylmethyl)-2H-phthalazin-1-one |

TABLE 2-continued

Representative compounds of Formula I along with some nomenclatures.

| Structure | NAME |
|---|---|
| 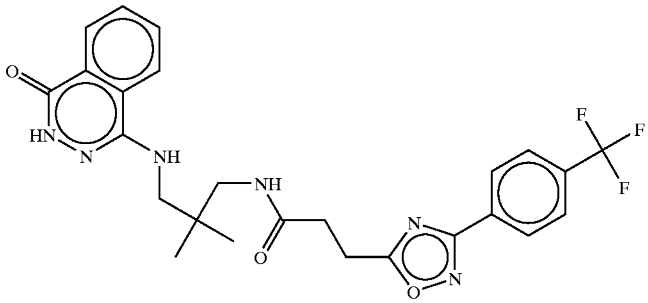 | N-[2,2-Dimethyl-3-(4-oxo-3,4-dihydro-phthalazin-1-ylamino)-propyl]-3-[3-(4-trifluoromethyl-phenyl)-[1,2,4]oxadiazol-5-yl]-propionamide |
| 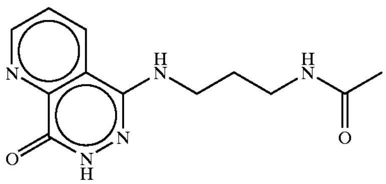 | N-[3-(8-Oxo-7,8-dihydro-pyrido[2,3-d]pyridazin-5-ylamino)-propyl]-acetamide |
| | 3-[3-(4-Methoxy-phenyl)-[1,2,4]oxadiazol-5-yl]-N-[3-(5-oxo-5,6-dihydro-pyrido[2,3-d]pyridazin-8-ylamino)-cyclohexyl]-propionamide |
| 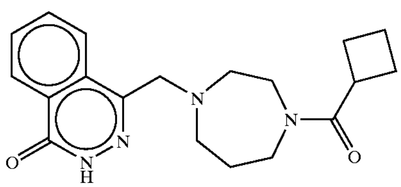 | 4-(4-Cyclobutanecarbonyl-[1,4]diazepan-1-ylmethyl)-2H-phthalazin-1-one |
| 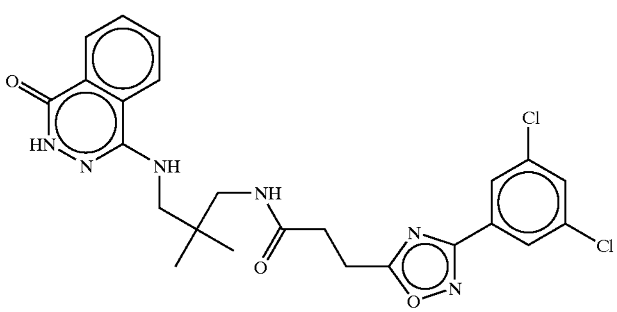 | 3-[3-(3,5-Dichloro-phenyl)-[1,2,4]oxadiazol-5-yl]-N-[2,2-dimethyl-3-(4-oxo-3,4-dihydro-phthalazin-1-ylamino)-propyl]-propionamide |
| 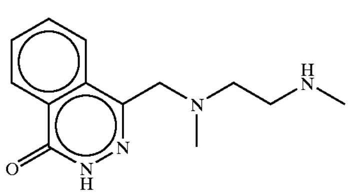 | 4-{[Methyl-(2-methylamino-ethyl)-amino]-methyl}-2H-phthalazin-1-one |

TABLE 2-continued

Representative compounds of Formula I along with some nomenclatures.

| Structure | NAME |
|---|---|
| 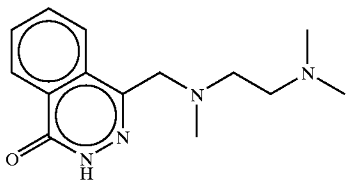 | 4-{[(2-Dimethylamino-ethyl)-methyl-amino]-methyl}-2H-phthalazin-1-one |
| 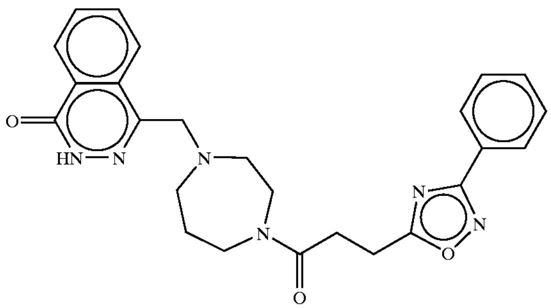 | 4-{4-[3-(3-Phenyl-[1,2,4]oxadiazol-5-yl)-propionyl]-[1,4]diazepan-1-ylmethyl}-2H-phthalazin-1-one |
| 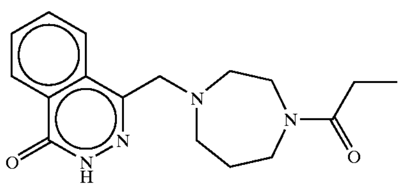 | 4-(4-Propionyl-[1,4]diazepan-1-ylmethyl)-2H-phthalazin-1-one |
| 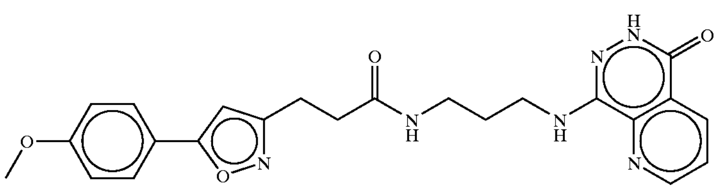 | 3-[5-(4-Methoxy-phenyl)-isoxazol-3-yl]-N-[3-(5-oxo-5,6-dihydro-pyrido[2,3-d]pyridazin-8-ylamino)-propyl]-propionamide |
| 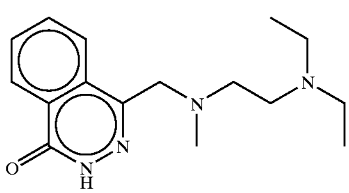 | 4-{[(2-Diethylamino-ethyl)-methyl-amino]-methyl}-2H-phthalazin-1-one |
| | 8-(3-Amino-cyclohexylamino)-6H-pyrido[2,3-d]pyridazin-5-one |
| 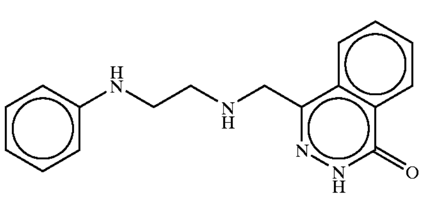 | 4-[(2-Phenylamino-ethylamino)-methyl]-2H-phthalazin-1-one |

TABLE 2-continued

Representative compounds of Formula I along with some nomenclatures.

| Structure | NAME |
|---|---|
| 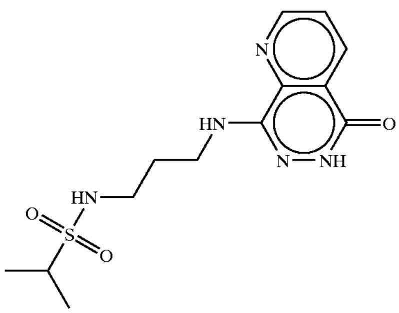 | Propane-2-sulfonic acid [3-(5-oxo-5,6-dihydro-pyrido[2,3-d]pyridazin-8-ylamino)-propyl]-amide |
| 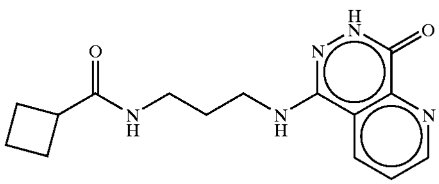 | Cyclobutanecarboxylic acid [3-(8-oxo-7,8-dihydro-pyrido[2,3-d]pyridazin-5-ylamino)-propyl]-amide |
| 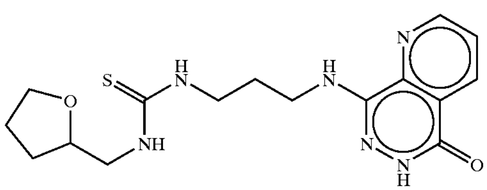 | 1-[3-(5-Oxo-5,6-dihydro-pyrido[2,3-d]pyridazin-8-ylamino)-propyl]-3-(tetrahydro-furan-2-ylmethyl)-thiourea |
| 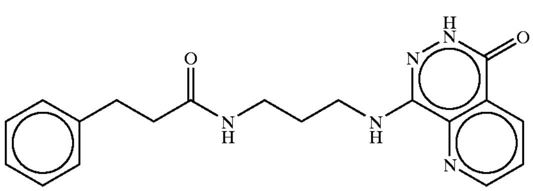 | N-[3-(5-Oxo-5,6-dihydro-pyrido[2,3-d]pyridazin-8-ylamino)-propyl]-3-phenyl-propionamide |
| 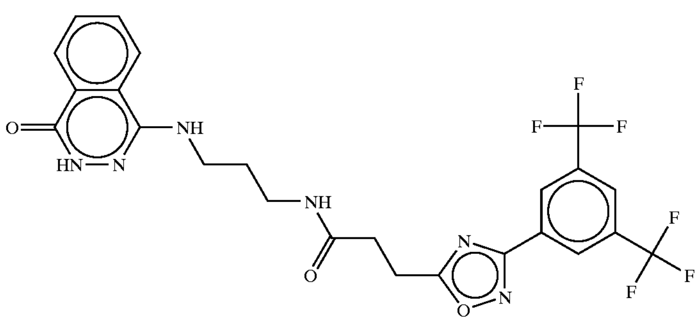 | 3-[3-(3,5-Bis-trifluoromethyl-phenyl)-[1,2,4]oxadiazol-5-yl]-N-[3-(4-oxo-3,4-dihydro-phthalazin-1-ylamino)-propyl]-propionamide |
| | |

TABLE 2-continued

Representative compounds of Formula I along with some nomenclatures.

| Structure | NAME |
|---|---|
| 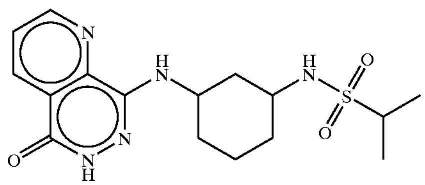 | Propane-2-sulfonic acid [3-(5-oxo-5,6-dihydro-pyrido[2,3-d]pyridazin-8-ylamino)-cyclohexyl]-amide |
| 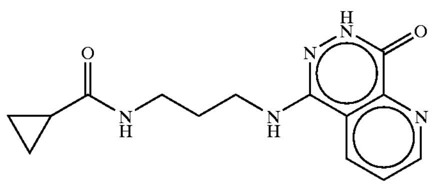 | Cyclopropanecarboxylic acid [3-(8-oxo-7,8-dihydro-pyrido[2,3-d]pyridazin-5-ylamino)-propyl]-amide |
| 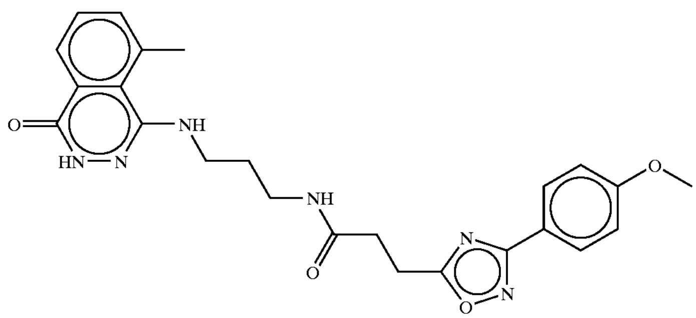 | 3-[3-(4-Methoxy-phenyl)-[1,2,4]oxadiazol-5-yl]-N-[3-(8-methyl-4-oxo-3,4-dihydro-phthalazin-1-ylamino)-propyl]-propionamide |
| 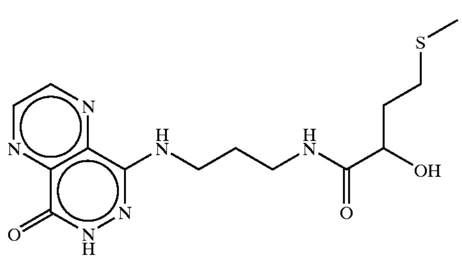 | 2-Hydroxy-4-methylsulfanyl-N-[3-(8-oxo-7,8-dihydro-pyrazino[2,3-d]pyridazin-5-ylamino)-propyl]-butyramide |
| 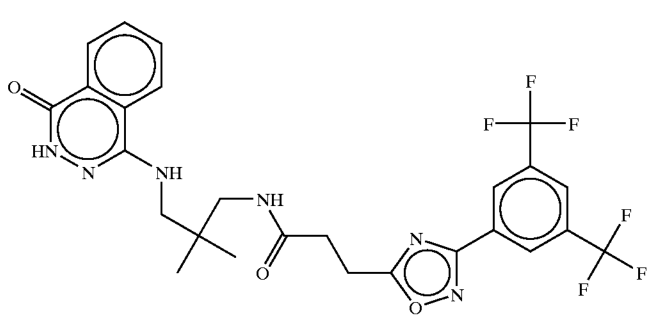 | 3-[3-(3,5-Bis-trifluoromethyl-phenyl)-[1,2,4]oxadiazol-5-yl]-N-[2,2-dimethyl-3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 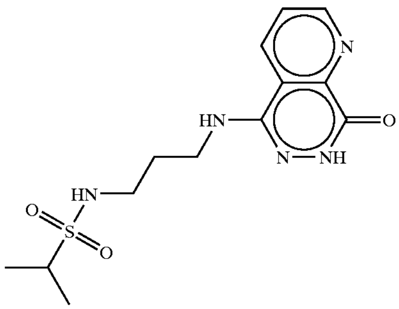 | Propane-2-sulfonic acid [3-(8-oxo-7,8-dihydro-pyrido[2,3-d]pyridazin-5-ylamino)-propyl]-amide |
| HCl | 3-[3-(4-Hydroxy-phenyl)-[1,2,4]oxadiazol-5-yl]-N-[3-(5-oxo-5,6-dihydro-pyrido[2,3-d]pyridazin-8-ylamino)-cyclohexyl]-propionamide |
| 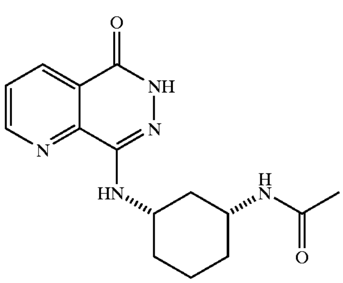 | N-[3-(5-Oxo-5,6-dihydro-pyrido[2,3-d]pyridazin-8-ylamino)-cyclohexyl]-acetamide |
| 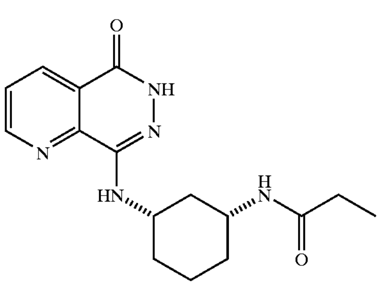 | N-[3-(5-Oxo-5,6-dihydro-pyrido[2,3-d]pyridazin-8-ylamino)-cyclohexyl]-propionamide |
| 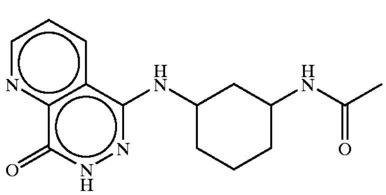 | N-[3-(8-Oxo-7,8-dihydro-pyrido[2,3-d]pyridazin-5-ylamino)-cyclohexyl]-acetamide |

TABLE 2-continued

Representative compounds of Formula I along with some nomenclatures.

| Structure | NAME |
|---|---|
| 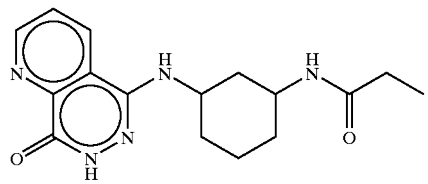 | N-[3-(8-Oxo-7,8-dihydro-pyrido[2,3-d]pyridazin-5-ylamino)-cyclohexyl]-propionamide |
| 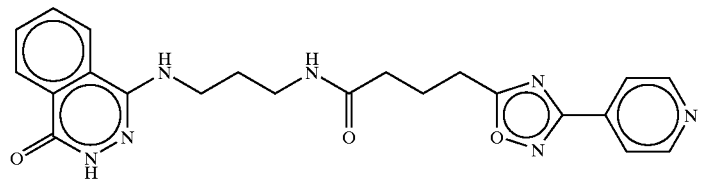 | N-[3-(4-Oxo-3,4-dihydro-phthalazin-1-ylamino)-propyl]-4-(3-pyridin-4-yl-[1,2,4]oxadiazol-5-yl)-butyramide |
| 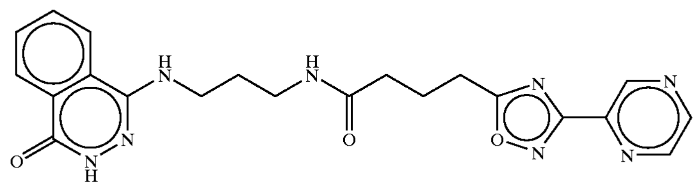 | N-[3-(4-Oxo-3,4-dihydro-phthalazin-1-ylamino)-propyl]-4-(3-pyrazin-2-yl-[1,2,4]oxadiazol-5-yl)-butyramide |
| 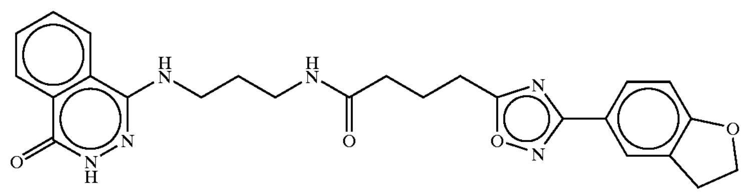 | 4-[3-(2,3-Dihydro-benzofuran-5-yl)-[1,2,4]oxadiazol-5-yl]-N-[3-(4-oxo-3,4-dihydro-phthalazin-1-ylamino)-propyl]-butyramide |
| 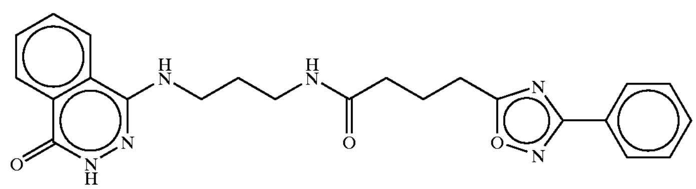 | N-[3-(4-Oxo-3,4-dihydro-phthalazin-1-ylamino)-propyl]-4-(3-phenyl-[1,2,4]oxadiazol-5-yl)-butyramide |
| 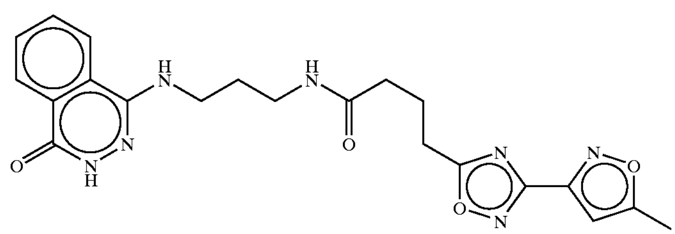 | 4-[3-(5-Methyl-isoxazol-3-yl)-[1,2,4]oxadiazol-5-yl]-N-[3-(4-oxo-3,4-dihydro-phthalazin-1-ylamino)-propyl]-butyramide |
| 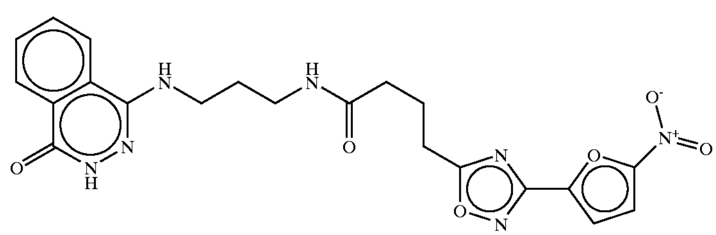 | 4-[3-(5-Nitro-furan-2-yl)-[1,2,4]oxadiazol-5-yl]-N-[3-(4-oxo-3,4-dihydro-phthalazin-1-ylamino)-propyl]-butyramide |

TABLE 2-continued

Representative compounds of Formula I along with some nomenclatures.

| Structure | NAME |
|---|---|
| 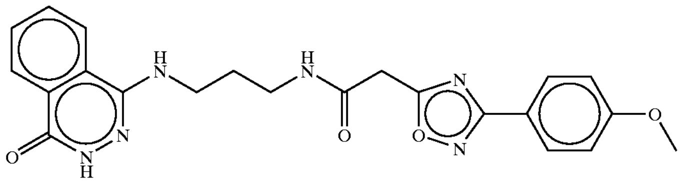 | 2-[3-(4-Methoxy-phenyl)-[1,2,4]oxadiazol-5-yl]-N-[3-(4-oxo-3,4-dihydro-phthalazin-1-ylamino)-propyl]-acetamide |
| 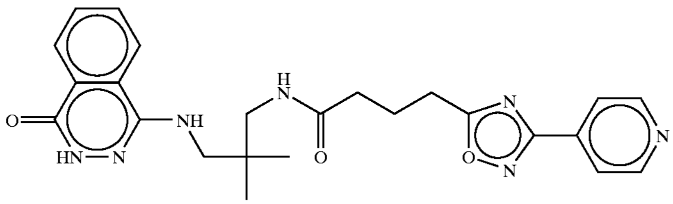 | N-[2,2-Dimethyl-3-(4-oxo-3,4-dihydro-phthalazin-1-ylamino)-propyl]-4-(3-pyridin-4-yl-[1,2,4]oxadiazol-5-yl)-butyramide |
| 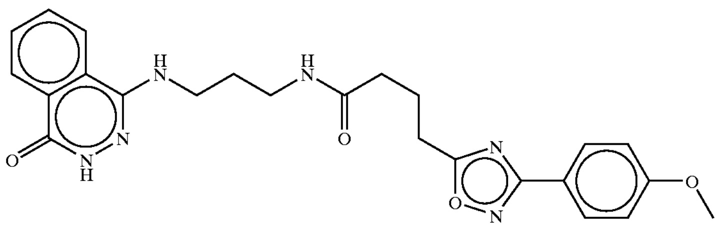 | 4-[3-(4-Methoxy-phenyl)-[1,2,4]oxadiazol-5-yl]-N-[3-(4-oxo-3,4-dihydro-phthalazin-1-ylamino)-propyl]-butyramide |
| 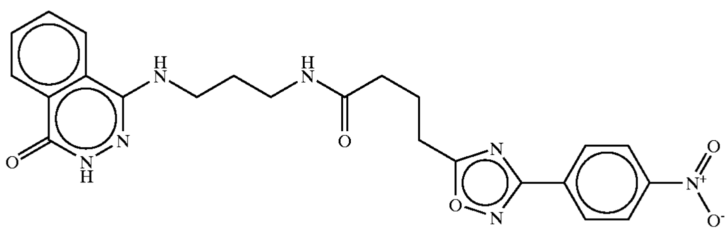 | 4-[3-(4-Nitro-phenyl)-[1,2,4]oxadiazol-5-yl]-N-[3-(4-oxo-3,4-dihydro-phthalazin-1-ylamino)-propyl]-butyramide |
| 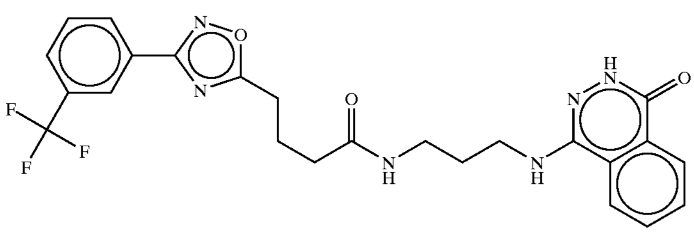 | N-[3-(4-Oxo-3,4-dihydro-phthalazin-1-ylamino)-propyl]-4-[3-(3-trifluoromethyl-phenyl)-[1,2,4]oxadiazol-5-yl]-butyramide |
| 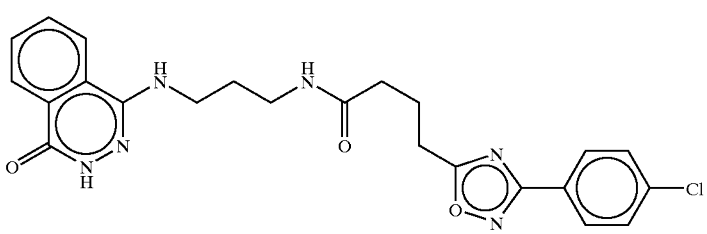 | 4-[3-(4-Chloro-phenyl)-[1,2,4]oxadiazol-5-yl]-N-[3-(4-oxo-3,4-dihydro-phthalazin-1-ylamino)-propyl]-butyramide |
| 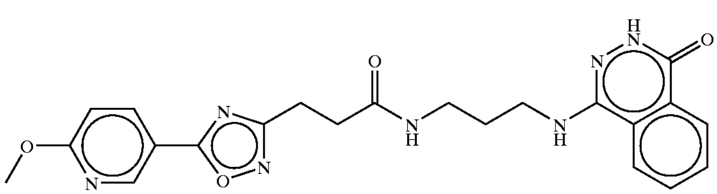 | 3-[5-(6-Methoxy-pyridin-3-yl)-[1,2,4]oxadiazol-3-yl]-N-[3-(4-oxo-3,4-dihydro-phthalazin-1-ylamino)-propyl]-propionamide |

TABLE 2-continued

Representative compounds of Formula I along with some nomenclatures.

| Structure | NAME |
|---|---|
| 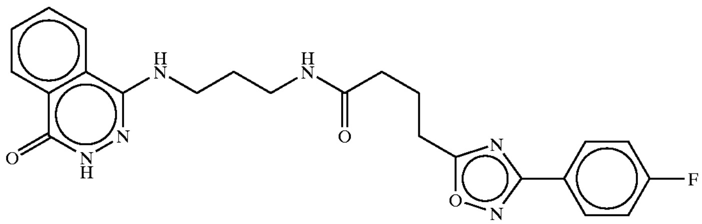 | 4-[3-(4-Fluoro-phenyl)-[1,2,4]oxadiazol-5-yl]-N-[3-(4-oxo-3,4-dihydro-phthalazin-1-ylamino)-propyl]-butyramide |
| 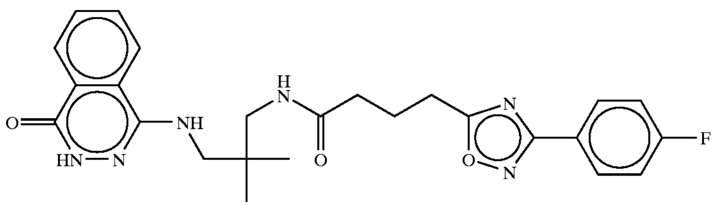 | N-[2,2-Dimethyl-3-(4-oxo-3,4-dihydro-phthalazin-1-ylamino)-propyl]-4-[3-(4-fluoro-phenyl)-[1,2,4]oxadiazol-5-yl]-butyramide |
| 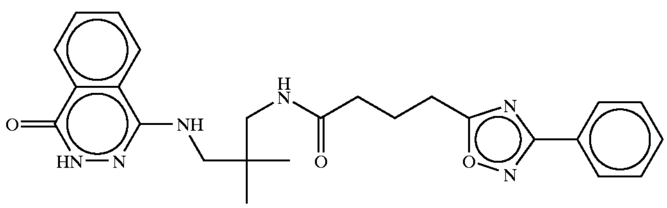 | N-[2,2-Dimethyl-3-(4-oxo-3,4-dihydro-phthalazin-1-ylamino)-propyl]-4-(3-phenyl-[1,2,4]oxadiazol-5-yl)-butyramide |
| 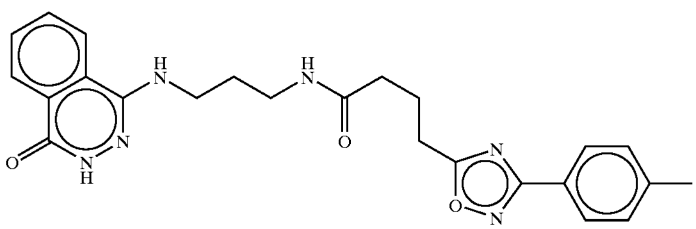 | N-[3-(4-Oxo-3,4-dihydro-phthalazin-1-ylamino)-propyl]-4-(3-p-tolyl-[1,2,4]oxadiazol-5-yl)-butyramide |
| 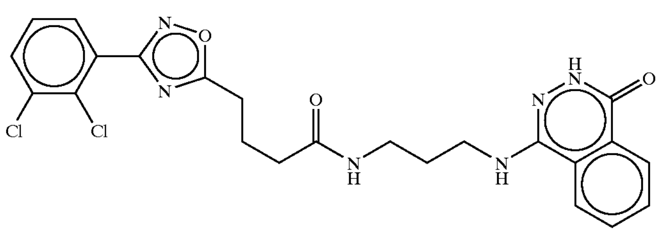 | 4-[3-(2,3-Dichloro-phenyl)-[1,2,4]oxadiazol-5-yl]-N-[3-(4-oxo-3,4-dihydro-phthalazin-1-ylamino)-propyl]-butyramide |
| 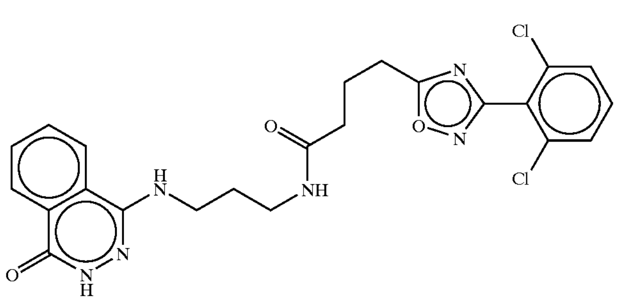 | 4-[3-(2,6-Dichloro-phenyl)-[1,2,4]oxadiazol-5-yl]-N-[3-(4-oxo-3,4-dihydro-phthalazin-1-ylamino)-propyl]-butyramide |

TABLE 2-continued

Representative compounds of Formula I along with some nomenclatures.

| Structure | NAME |
|---|---|
| 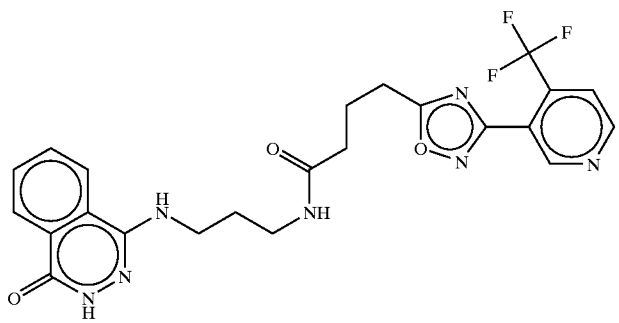 | N-[3-(4-Oxo-3,4-dihydro-phthalazin-1-ylamino)-propyl]-4-[3-(4-trifluoromethyl-pyridin-3-yl)-[1,2,4]oxadiazol-5-yl]-butyramide |
| 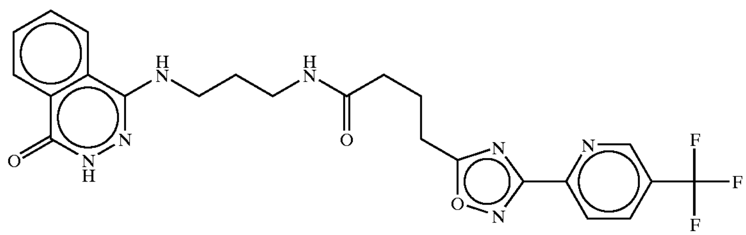 | N-[3-(4-Oxo-3,4-dihydro-phthalazin-1-ylamino)-propyl]-4-[3-(5-trifluoromethyl-pyridin-2-yl)-[1,2,4]oxadiazol-5-yl]-butyramide |
| 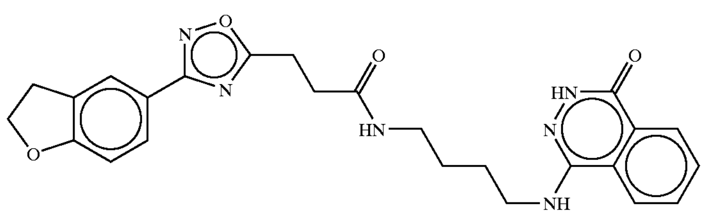 | 3-[3-(2,3-Dihydro-benzofuran-5-yl)-[1,2,4]oxadiazol-5-yl]-N-[4-(4-oxo-3,4-dihydro-phthalazin-1-ylamino)-butyl]-propionamide |
| 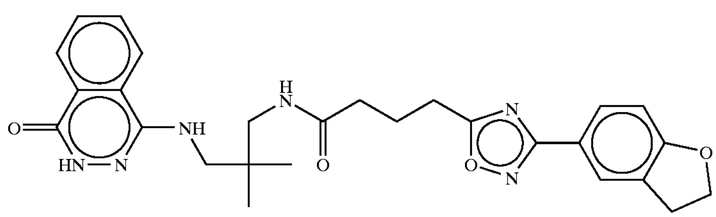 | 4-[3-(2,3-Dihydro-benzofuran-5-yl)-[1,2,4]oxadiazol-5-yl]-N-[2,2-dimethyl-3-(4-oxo-3,4-dihydro-phthalazin-1-ylamino)-propyl]-butyramide |
| 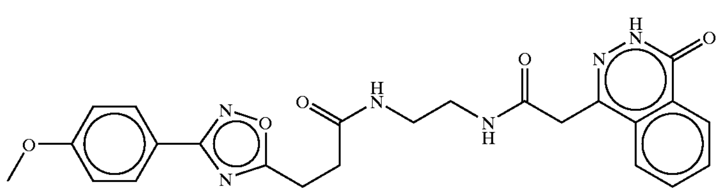 | 3-[3-(4-Methoxy-phenyl)-[1,2,4]oxadiazol-5-yl]-N-{2-[2-(4-oxo-3,4-dihydro-phthalazin-1-yl)-acetylamino]-ethyl}-propionamide |
| 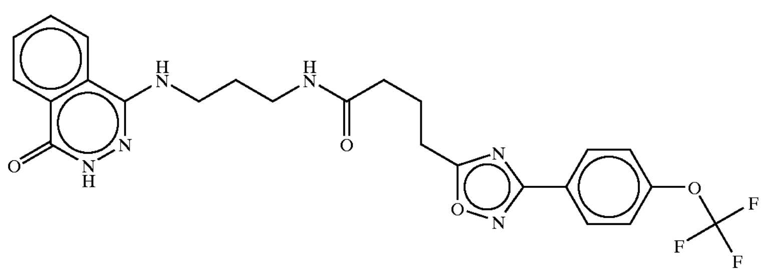 | N-[3-(4-Oxo-3,4-dihydro-phthalazin-1-ylamino)-propyl]-4-[3-(4-trifluoromethoxy-phenyl)-[1,2,4]oxadiazol-5-yl]-butyramide |

TABLE 2-continued

Representative compounds of Formula I along with some nomenclatures.

| Structure | NAME |
|---|---|
| 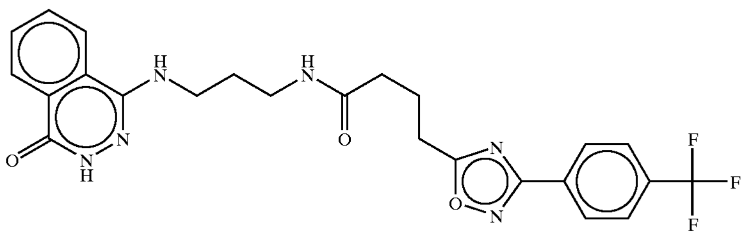 | N-[3-(4-Oxo-3,4-dihydro-phthalazin-1-ylamino)-propyl]-4-[3-(4-trifluoromethyl-phenyl)-[1,2,4]oxadiazol-5-yl]-butyramide |
| 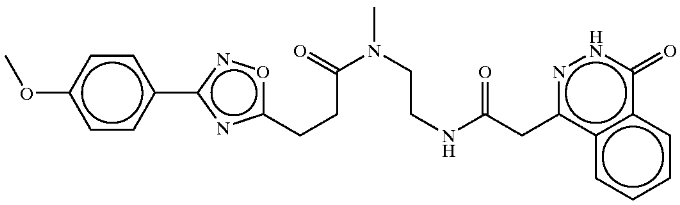 | 3-[3-(4-Methoxy-phenyl)-[1,2,4]oxadiazol-5-yl]-N-methyl-N-{2-[2-(4-oxo-3,4-dihydro-phthalazin-1-yl)-acetylamino]-ethyl}-propionamide |
| 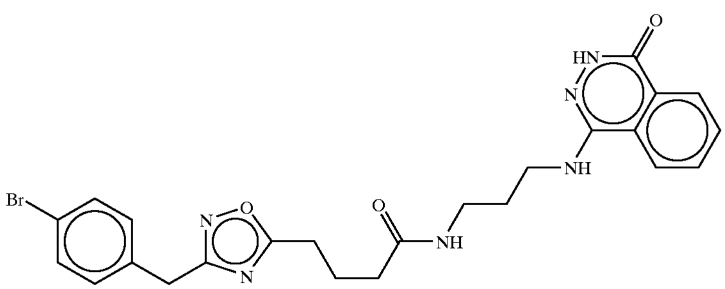 | 4-[3-(4-Bromo-benzyl)-[1,2,4]oxadiazol-5-yl]-N-[3-(4-oxo-3,4-dihydro-phthalazin-1-ylamino)-propyl]-butyramide |
| 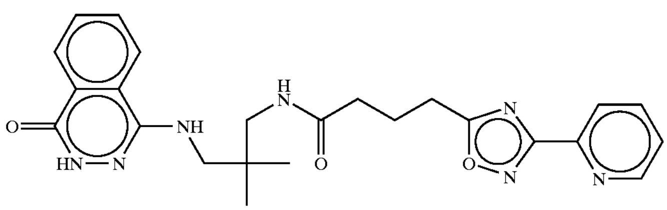 | N-[2,2-Dimethyl-3-(4-oxo-3,4-dihydro-phthalazin-1-ylamino)-propyl]-4-(3-pyridin-2-yl-[1,2,4]oxadiazol-5-yl)-butyramide |
| 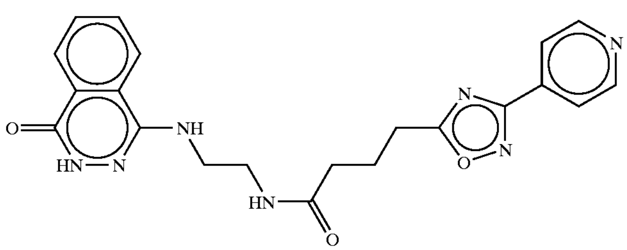 | N-[2-(4-Oxo-3,4-dihydro-phthalazin-1-ylamino)-ethyl]-4-(3-pyridin-4-yl-[1,2,4]oxadiazol-5-yl)-butyramide |
| 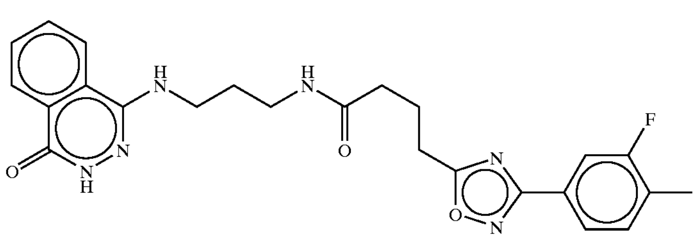 | 4-[3-(3-Fluoro-4-methyl-phenyl)-[1,2,4]oxadiazol-5-yl]-N-[3-(4-oxo-3,4-dihydro-phthalazin-1-ylamino)-propyl]-butyramide |

TABLE 2-continued

Representative compounds of Formula I along with some nomenclatures.

| Structure | NAME |
|---|---|
| 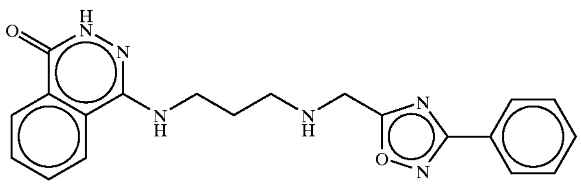 | 4-{3-[(3-Phenyl-[1,2,4]oxadiazol-5-ylmethyl)-amino]-propylamino}-2H-phthalazin-1-one |
| 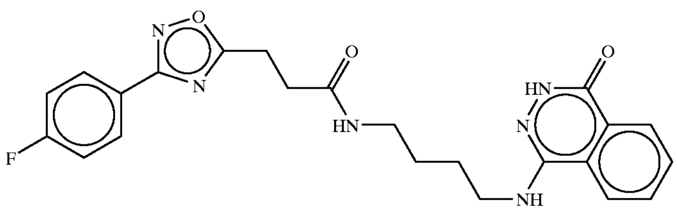 | 3-[3-(4-Fluoro-phenyl)-[1,2,4]oxadiazol-5-yl]-N-[4-(4-oxo-3,4-dihydro-phthalazin-1-ylamino)-butyl]-propionamide |
| 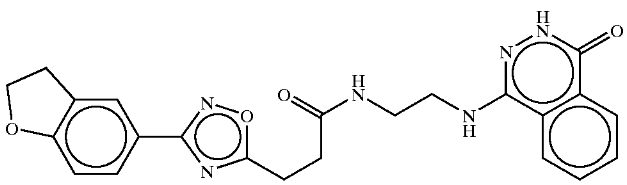 | 3-[3-(2,3-Dihydro-benzofuran-5-yl)-[1,2,4]oxadiazol-5-yl]-N-[2-(4-oxo-3,4-dihydro-phthalazin-1-ylamino)-ethyl]-propionamide |
| 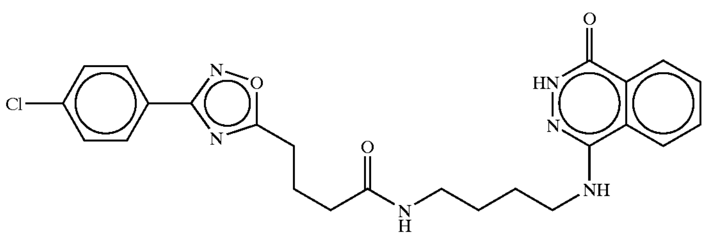 | 4-[3-(4-Chloro-phenyl)-[1,2,4]oxadiazol-5-yl]-N-[4-(4-oxo-3,4-dihydro-phthalazin-1-ylamino)-butyl]-butyramide |
| 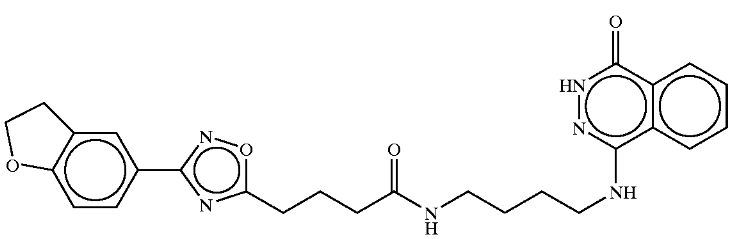 | 4-[3-(2,3-Dihydro-benzofuran-5-yl)-[1,2,4]oxadiazol-5-yl]-N-[4-(4-oxo-3,4-dihydro-phthalazin-1-ylamino)-butyl]-butyramide |
| 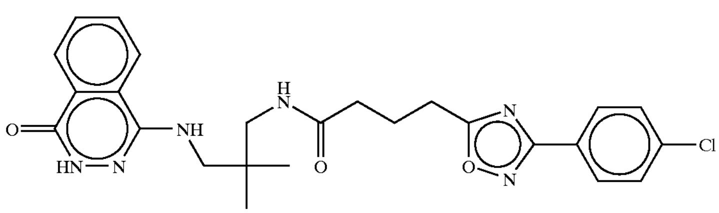 | 4-[3-(4-Chloro-phenyl)-[1,2,4]oxadiazol-5-yl]-N-[2,2-dimethyl-3-(4-oxo-3,4-dihydro-phthalazin-1-ylamino)-propyl]-butyramide |
| 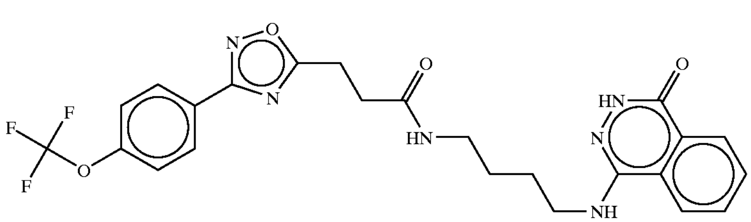 | N-[4-(4-Oxo-3,4-dihydro-phthalazin-1-ylamino)-butyl]-3-[3-(4-trifluoromethoxy-phenyl)-[1,2,4]oxadiazol-5-yl]-propionamide |

TABLE 2-continued

Representative compounds of Formula I along with some nomenclatures.

| Structure | NAME |
|---|---|
| 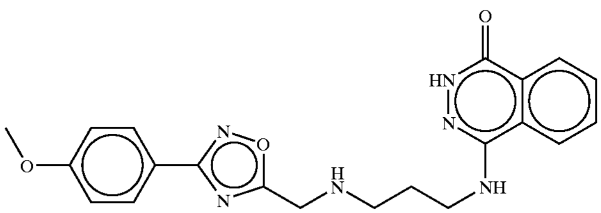 | 4-(3-{[3-(4-Methoxy-phenyl)-[1,2,4]oxadiazol-5-ylmethyl]-amino}-propylamino)-2H-phthalazin-1-one |
| 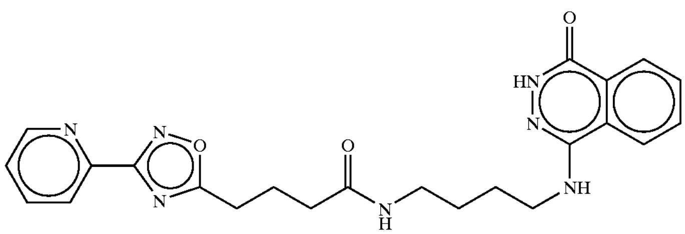 | N-[4-(4-Oxo-3,4-dihydro-phthahzin-1-ylamino)-butyl]-4-(3-pyridin-2-yl-[1,2,4]oxadiazol-5-yl)-butyramide |
| 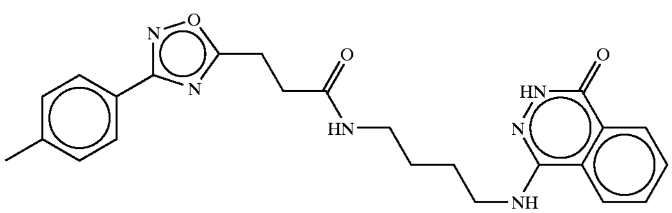 | N-[4-(4-Oxo-3,4-dihydro-phthalazin-1-ylamino)-butyl]-3-(3-p-tolyl-[1,2,4]oxadiazol-5-yl)-propionamide |
| 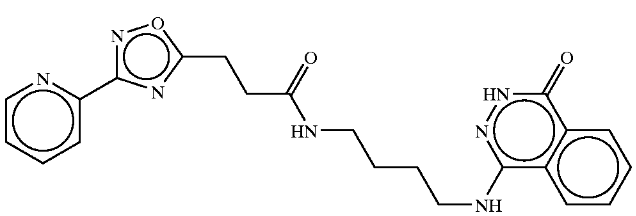 | N-[4-(4-Oxo-3,4-dihydro-phthalazin-1-ylamino)-butyl]-3-(3-pyridin-2-yl-[1,2,4]oxadiazol-5-yl)-propionamide |
| 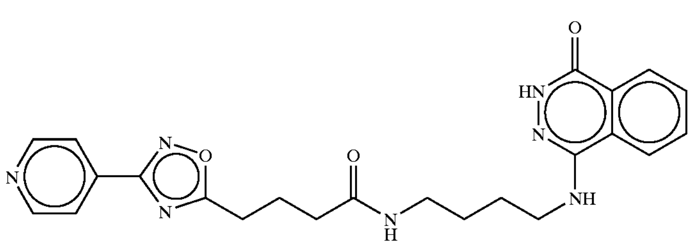 | N-[4-(4-Oxo-3,4-dihydro-phthalazin-1-ylamino)-butyl]-4-(3-pyridin-4-yl-[1,2,4]oxadiazol-5-yl)-butyramide |
| 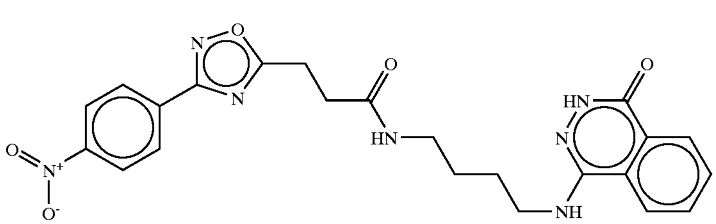 | 3-[3-(4-Nitro-phenyl)-[1,2,4]oxadiazol-5-yl]-N-[4-(4-oxo-3,4-dihydro-phthalazin-1-ylamino)-butyl]-propionamide |

TABLE 2-continued

Representative compounds of Formula I along with some nomenclatures.

| Structure | NAME |
|---|---|
| 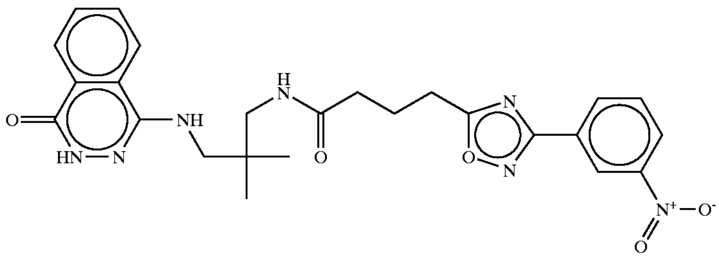 | N-[2,2-Dimethyl-3-(4-oxo-3,4-dihydro-phthalazin-1-ylamino)-propyl]-4-[3-(3-nitro-phenyl)-[1,2,4]oxadiazol-5-yl]-butyramide |
| 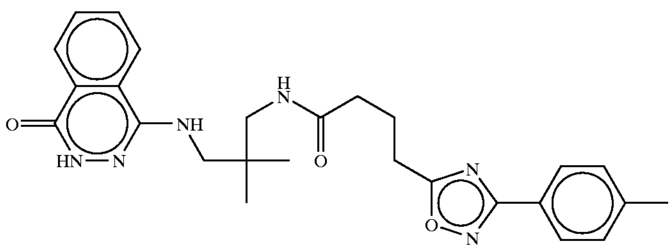 | N-[2,2-Dimethyl-3-(4-oxo-3,4-dihydro-phthalazin-1-ylamino)-propyl]-4-(3-p-tolyl-[1,2,4]oxadiazol-5-yl)-butyramide |
| 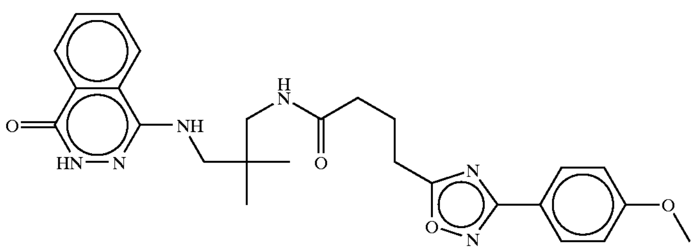 | N-[2,2-Dimethyl-3-(4-oxo-3,4-dihydro-phthalazin-1-ylamino)-propyl]-4-[3-(4-methoxy-phenyl)-[1,2,4]oxadiazol-5-yl]-butyramide |
| 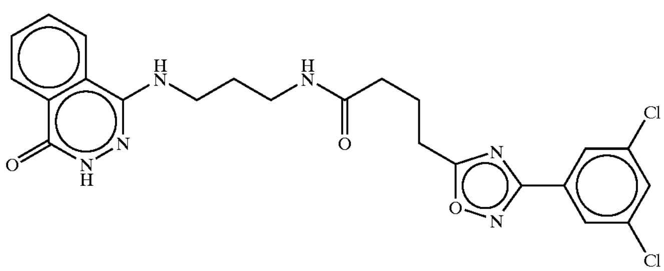 | 4-[3-(3,5-Dichloro-phenyl)-[1,2,4]oxadiazol-5-yl]-N-[3-(4-oxo-3,4-dihydro-phthalazin-1-ylamino)-propyl]-butyramide |
| 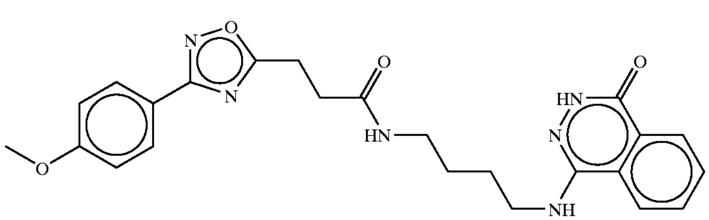 | 3-[3-(4-Methoxy-phenyl)-[1,2,4]oxadiazol-5-yl]-N-[4-(4-oxo-3,4-dihydro-phthalazin-1-ylamino)-butyl]-propionamide |
| 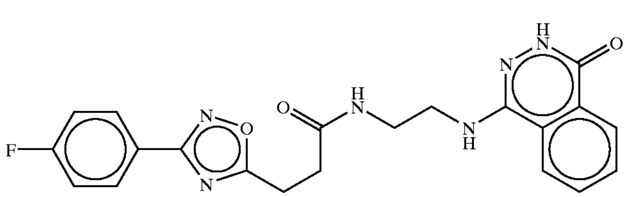 | 3-[3-(4-Fluoro-phenyl)-[1,2,4]oxadiazol-5-yl]-N-[2-(4-oxo-3,4-dihydro-phthalazin-1-ylamino)-ethyl]-propionamide |

TABLE 2-continued

Representative compounds of Formula I along with some nomenclatures.

| Structure | NAME |
|---|---|
| 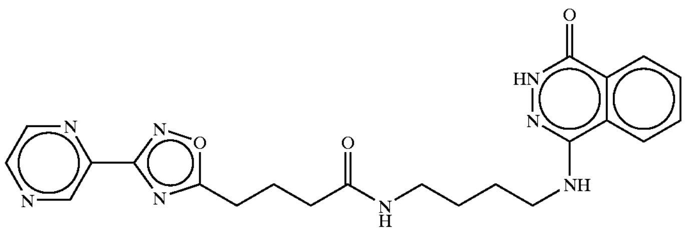 | N-[4-(4-Oxo-3,4-dihydro-phthalazin-1-ylamino)-butyl]-4-(3-pyrazin-2-yl-[1,2,4]oxadiazol-5-yl)-butyramide |
| 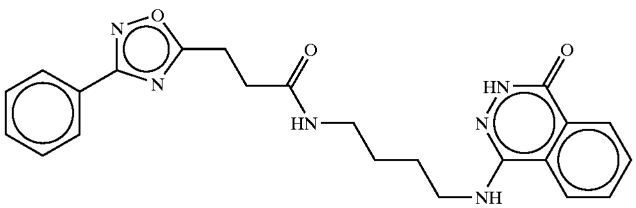 | N-[4-(4-Oxo-3,4-dihydro-phthalazin-1-ylamino)-butyl]-3-(3-phenyl-[1,2,4]oxadiazol-5-yl)-propionamide |
| 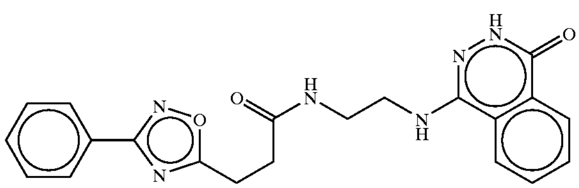 | N-[2-(4-Oxo-3,4-dihydro-phthalazin-1-ylamino)-ethyl]-3-(3-phenyl-[1,2,4]oxadiazol-5-yl)-propionamide |
| 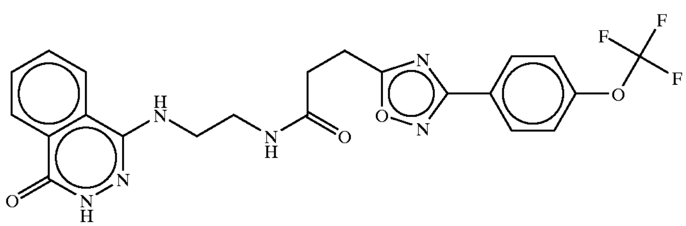 | N-[2-(4-Oxo-3,4-dihydro-phthalazin-1-yl ylamino)-ethyl]-3-[3-(4-trifluoromethoxy-phenyl)-[1,2,4]oxadiazol-5-yl]-propionamide |
| 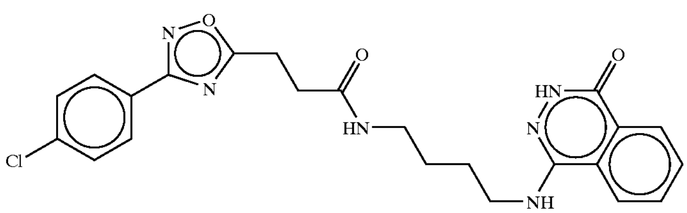 | 3-[3-(4-Chloro-phenyl)-[1,2,4]oxadiazol-5-yl]-N-[4-(4-oxo-3,4-dihydro-phthalazin-1-ylamino)-butyl]-propionamide |
| 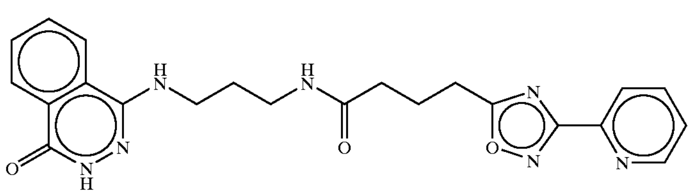 | N-[3-(4-Oxo-3,4-dihydro-phthalazin-1-ylamino)-propyl]-4-(3-pyridin-2-yl-[1,2,4]oxadiazol-5-yl)-butyramide |
| 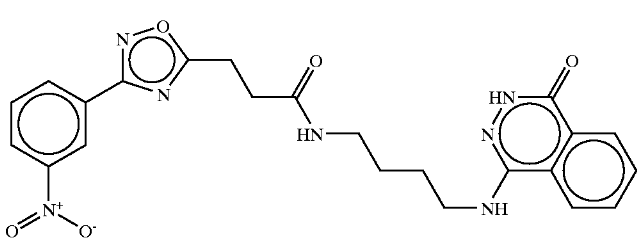 | [3-(3-Nitro-phenyl)-[1,2,4]oxadiazol-5-yl]-N-[4-(4-oxo-3,4-dihydro-phthalazin-1-ylamino)-butyl]-propionamide |

TABLE 2-continued

Representative compounds of Formula I along with some nomenclatures.

| Structure | NAME |
|---|---|
| 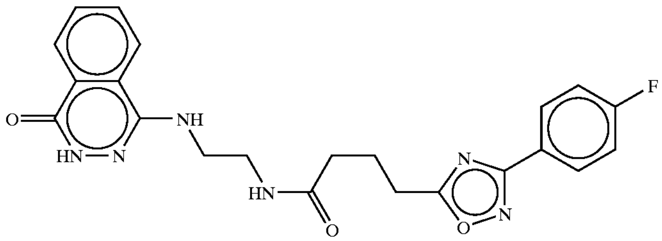 | 4-[3-(4-Fluoro-phenyl)-[1,2,4]oxadiazol-5-yl]-N-[2-(4-oxo-3,4-dihydro-phthalazin-1-ylamino)-ethyl]-butyramide |
| 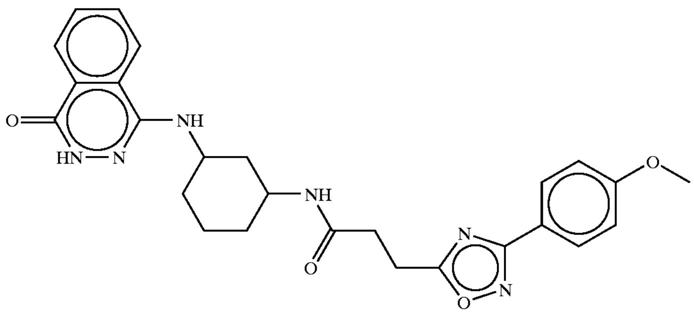 | 3-[3-4-Methoxy-phenyl)-[1,2,4]oxadiazol-5-yl]-N-[3-(4-oxo-3,4-dihydro-phthalazin-1-ylamino)-phenyl]-propionamide |
| 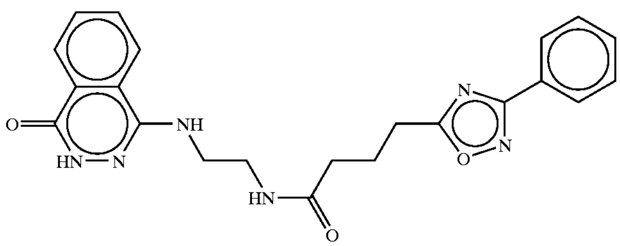 | N-[2-(4-Oxo-3,4-dihydro-phthalazin-1-ylamino)-ethyl]-4-(3-phenyl-[1,2,4]oxadiazol-5-yl)-butyramide |
| 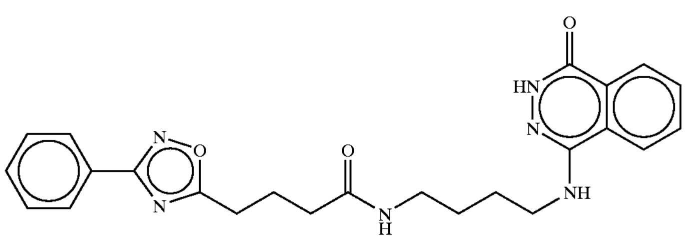 | N-[4-(4-Oxo-3,4-dihydro-phthalazin-1-yl ylamino)-butyl]-4-(3-phenyl-[1,2,4]oxadiazol-5-yl)-butyramide |
| 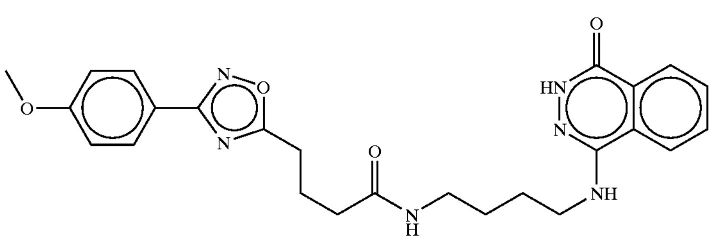 | 4-[3-(4-Methoxy-phenyl)-[1,2,4]oxadiazol-5-yl]-N-[4-(4-oxo-3,4-dihydro-phthalazin-1-ylamino)-butyl]-butyramide |
| 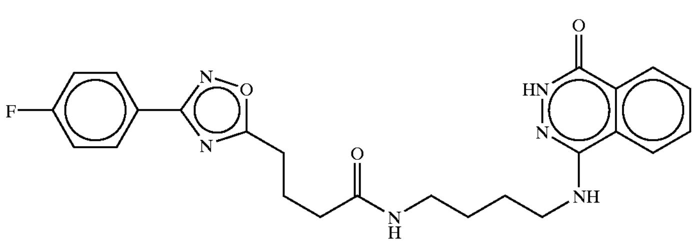 | 4-[3-(4-Fluoro-phenyl)-[1,2,4]oxadiazol-5-yl]-N-[4-(4-oxo-3,4-dihydro-phthalazin-1-ylamino)-butyl]-butyramide |

TABLE 2-continued

Representative compounds of Formula I along with some nomenclatures.

| Structure | NAME |
|---|---|
| 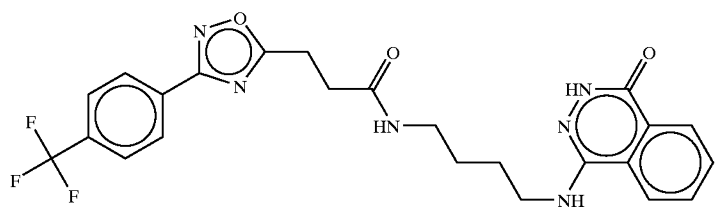 | N-[4-(4-Oxo-3,4-dihydro-phthalazin-1-ylamino)-butyl]-3-[3-(4-trifluoromethyl-phenyl)-[1,2,4]oxadiazol-5-yl]-propionamide |
| 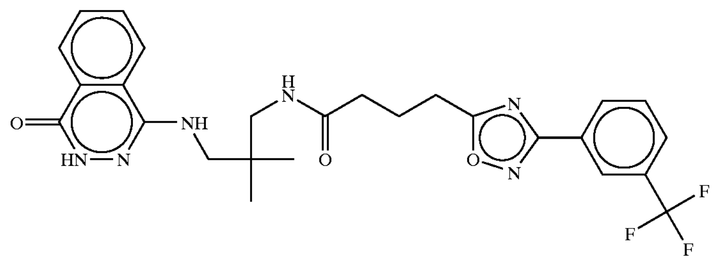 | N-[2,2-Dimethyl-3-(4-oxo-3,4-dihydro-phthalazin-1-ylamino)-propyl]-4-[3-(3-trifluoromethyl-phenyl)-[1,2,4]oxadiazol-5-yl]-butyramide |
| 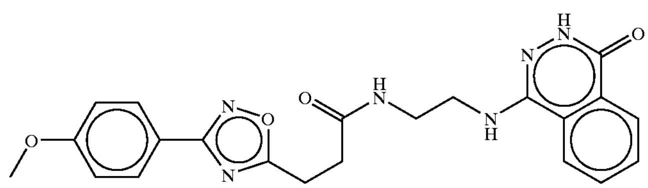 | 3-[3-(4-Methoxy-phenyl)-[1,2,4]oxadiazol-5-yl]-N-[2-(4-oxo-3,4-dihydro-phthalazin-1-ylamino)-ethyl]-propionamide |
| 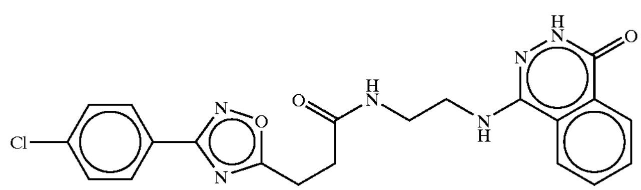 | 3-[3-(4-Chloro-phenyl)-[1,2,4]oxadiazol-5-yl]-N-[2-(4-oxo-3,4-dihydro-phthalazin-1-ylamino)-ethyl]-propionamide |
| 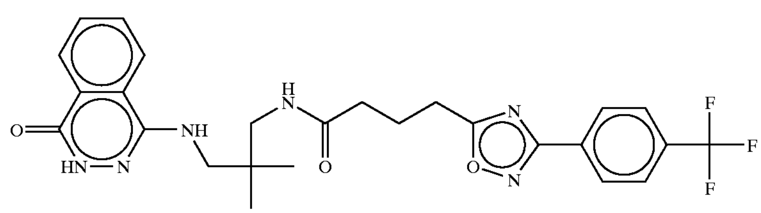 | N-[2,2-Dimethyl-3-(4-oxo-3,4-dihydro-phthalazin-1-ylamino)-propyl]-4-[3-(4-trifluoromethyl-phenyl)-[1,2,4]oxadiazol-5-yl]-butyramide |
| 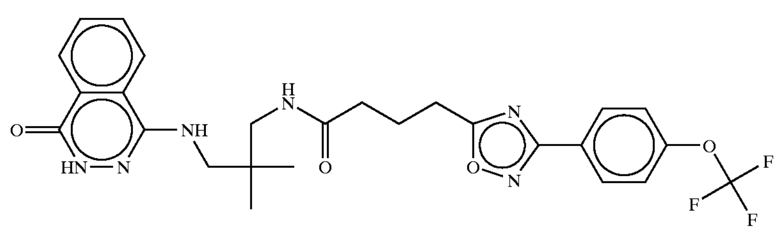 | N-[2,2-Dimethyl-3-(4-oxo-3,4-dihydro-phthalazin-1-ylamino)-propyl]-4-[3-(4-trifluoromethoxy-phenyl)-[1,2,4]oxadiazol-5-yl]-butyramide |

TABLE 2-continued

Representative compounds of Formula I along with some nomenclatures.

| Structure | NAME |
|---|---|
| 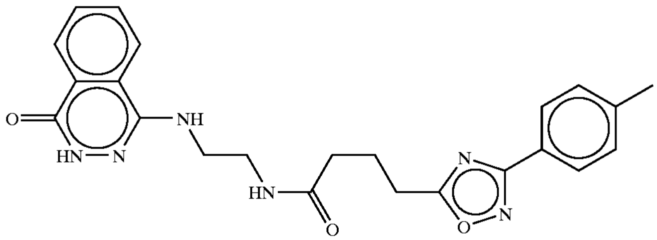 | N-[2-(4-Oxo-3,4-dihydro-phthalazin-1-ylamino)-ethyl]-4-(3-p-tolyl-[1,2,4]oxadiazol-5-yl)-butyramide |
| 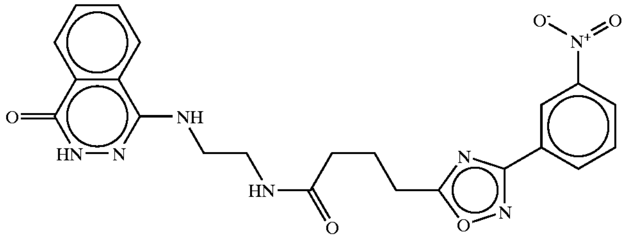 | 4-[3-(3-Nitro-phenyl)-[1,2,4]oxadiazol-5-yl]-N-[2-(4-oxo-3,4-dihydro-phthalazin-1-ylamino)-ethyl]-butyramide |
| 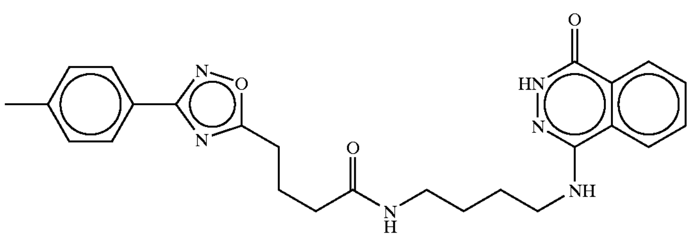 | N-[4-(4-Oxo-3,4-dihydro-phthalazin-1-ylamino)-butyl]-4-(3-p-tolyl-[1,2,4]oxadiazol-5-yl)-butyramide |
| 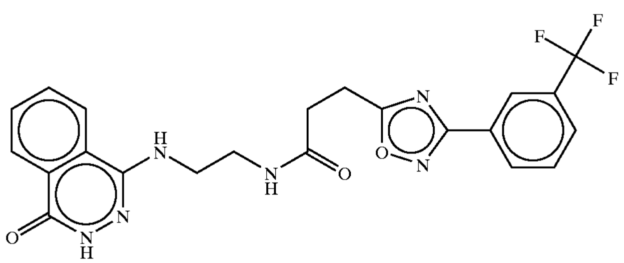 | N-[2-(4-Oxo-3,4-dihydro-phthalazin-1-ylamino)-ethyl]-3-[3-(3-trifluoromethyl-phenyl)-[1,2,4]oxadiazol-5-yl]-propionamide |
| 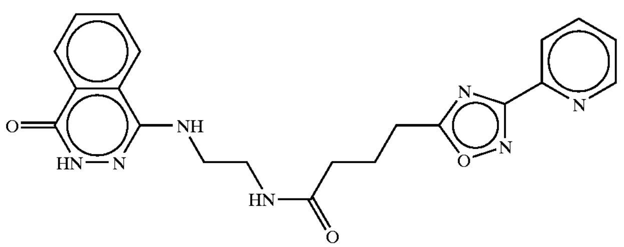 | N-[2-(4-Oxo-3,4-dihydro-phthalazin-1-ylamino)-ethyl]-4-(3-pyridin-2-yl-[1,2,4]oxadiazol-5-yl)-butyramide |
| 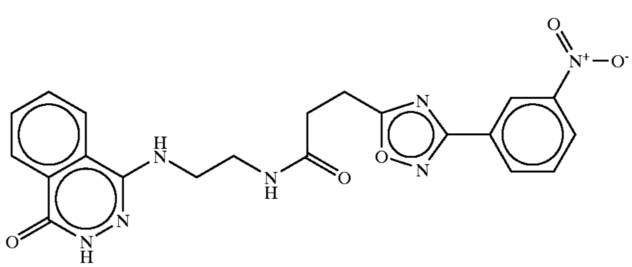 | 3-[3-(3-Nitro-phenyl)-[1,2,4]oxadiazol-5-yl]-N-[2-(4-oxo-3,4-dihydro-phthalazin-1-ylamino)-ethyl]-propionamide |

TABLE 2-continued

Representative compounds of Formula I along with some nomenclatures.

| Structure | NAME |
|---|---|
| 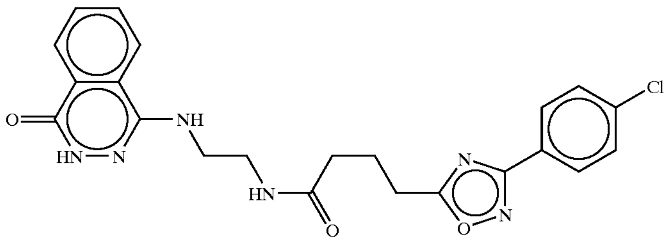 | 4-[3-(4-Chloro-phenyl)-[1,2,4]oxadiazol-5-yl]-N-[2-(4-oxo-3,4-dihydro-phthalazin-1-ylamino)-ethyl]-butyramide |
| 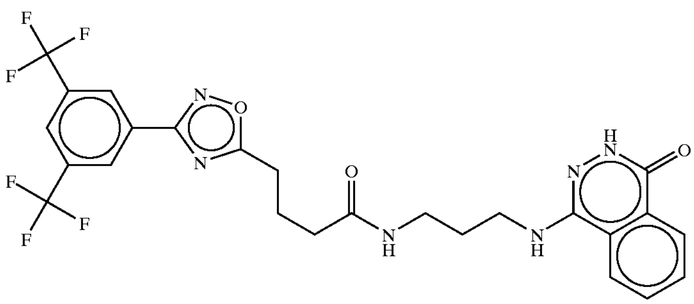 | 4-[3-(3,5-Bis-trifluoromethyl-phenyl)-[1,2,4]oxadiazol-5-yl]-N-[3-(4-oxo-3,4-dihydro-phthalazin-1-ylamino)-propyl]-butyramide |
| 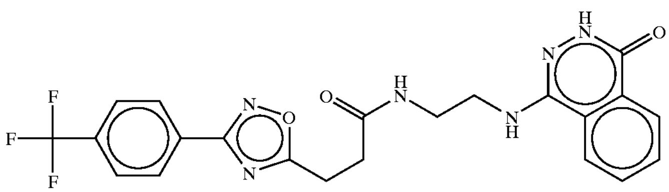 | N-[2-(4-Oxo-3,4-dihydro-phthalazin-1-ylamino)-ethyl]-3-[3-(4-trifluoromethyl-phenyl)-[1,2,4]oxadiazol-5-yl]-propionamide |
| 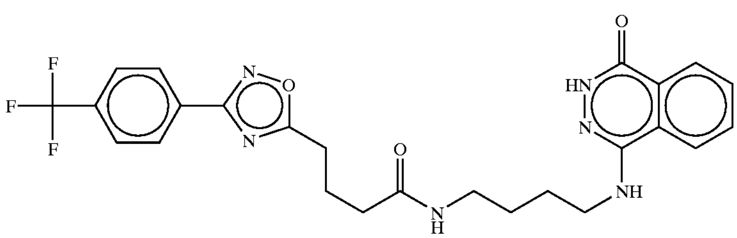 | N-[4-(4-Oxo-3,4-dihydro-phthalazin-1-ylamino)-butyl]-4-[3-(4-trifluoromethyl-phenyl)-[1,2,4]oxadiazol-5-yl]-butyramide |
| 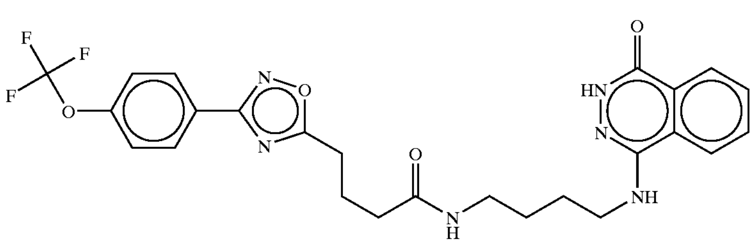 | N-[4-(4-Oxo-3,4-dihydro-phthalazin-1-ylamino)-butyl]-4-[3-(4-trifluoromethoxy-phenyl)-[1,2,4]oxadiazol-5-yl]-butyramide |
| 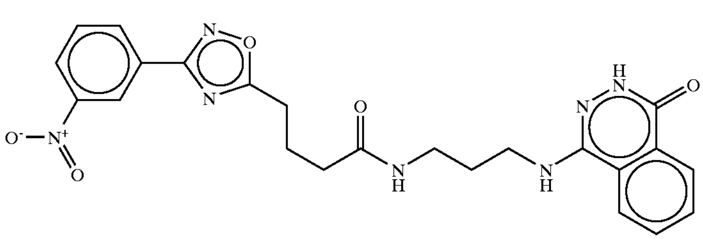 | 4-[3-(3-Nitro-phenyl)-[1,2,4]oxadiazol-5-yl]-N-[3-(4-oxo-3,4-dihydro-phthalazin-1-ylamino)-propyl]-butyramide |

TABLE 2-continued

Representative compounds of Formula I along with some nomenclatures.

| Structure | NAME |
| --- | --- |
| 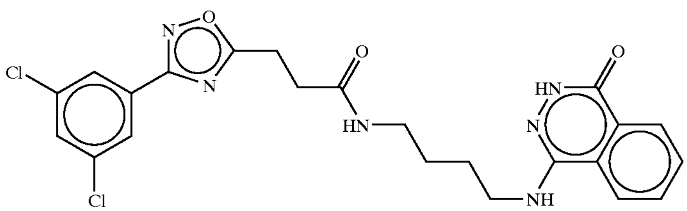 | 3-[3-(3,5-Dichloro-phenyl)-[1,2,4]oxadiazol-5-yl]-N-[4-(4-oxo-3,4-dihydro-phthalazin-1-ylamino)-butyl]-propionamide |
| 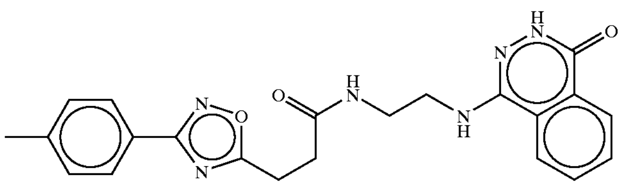 | N-[2-(4-Oxo-3,4-dihydro-phthalazin-1-ylamino)-ethyl]-3-(3-p-tolyl-[1,2,4]oxadiazol-5-yl)-propionamide |
| 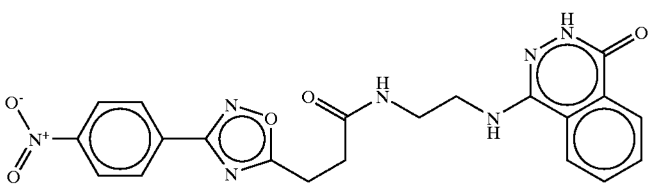 | 3-[3-(4-Nitro-phenyl)-[1,2,4]oxadiazol-5-yl]-N-[2-(4-oxo-3,4-dihydro-phthalazin-1-ylamino)-ethyl]-propionamide |
| 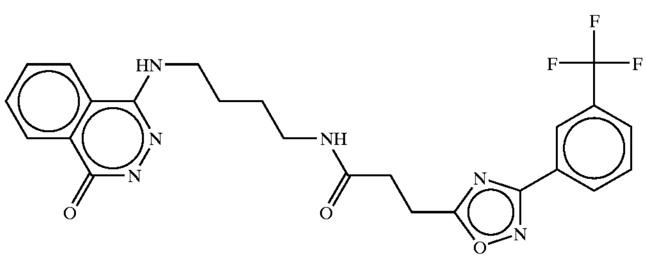 | N-[4-(4-Oxo-3,4-dihydro-phthalazin-1-ylamino)-butyl]-3-[3-(3-trifluoromethyl-phenyl)-[1,2,4]oxadiazol-5-yl]-propionamide |
| 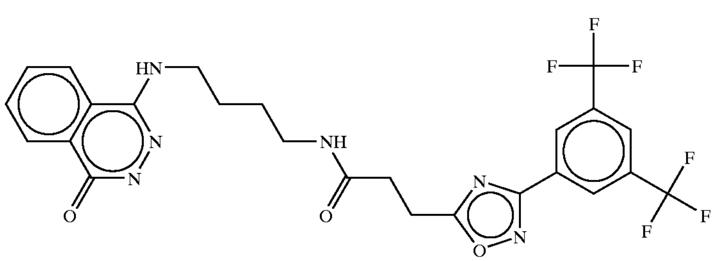 | 3-[3-(3,5-Bis-trifluoromethyl-phenyl)-[1,2,4]oxadiazol-5-yl]-N-[4-(4-oxo-3,4-dihydro-phthalazin-1-ylamino)-butyl]-propionamide |
| 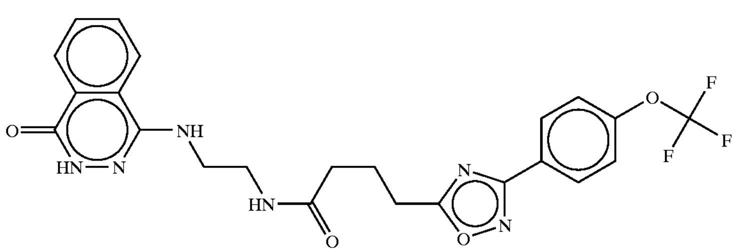 | N-[2-(4-Oxo-3,4-dihydro-phthalazin-1-ylamino)-ethyl]-4-[3-(4-trifluoromethoxy-phenyl)-[1,2,4]oxadiazol-5-yl]-butyramide |

TABLE 2-continued

Representative compounds of Formula I along with some nomenclatures.

| Structure | NAME |
|---|---|
| 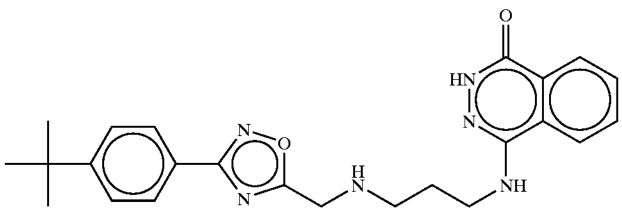 | 4-(3-{[3-(4-tert-Butyl-phenyl)-[1,2,4]oxadiazol-5-ylmethyl]-amino}-propylamino)-2H-phthalazin-1-one |
| 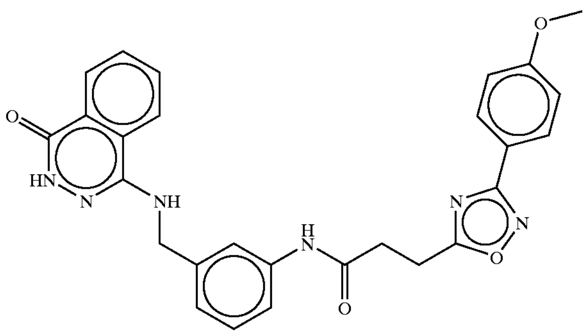 | 3-[3-(4-Methoxy-phenyl)-[1,2,4]oxadiazol-5-yl]-N-{3-[(4-oxo-3,4-dihydro-phthalazin-1-ylamino)-methyl]-phenyl}-propionamide |
| 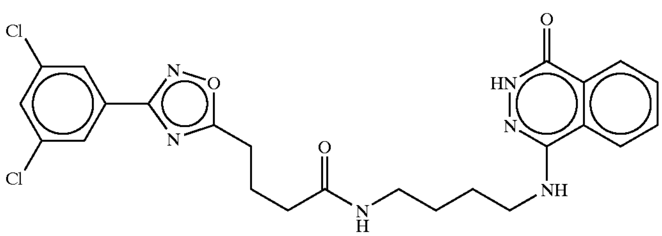 | 4-[3-(3,5-Dichloro-phenyl)-[1,2,4]oxadiazol-5-yl]-N-[4-(4-oxo-3,4-dihydro-phthalazin-1-ylamino)-butyl]-butyramide |
| 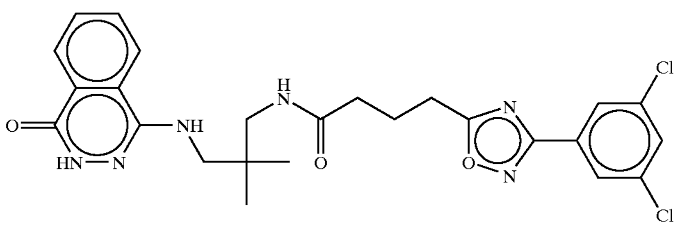 | 4-[3-(3,5-Dichloro-phenyl)-[1,2,4]oxadiazol-5-yl]-N-[2,2-dimethyl-3-(4-oxo-3,4-dihydro-phthalazin-1-ylamino)-propyl]-butyramide |
| 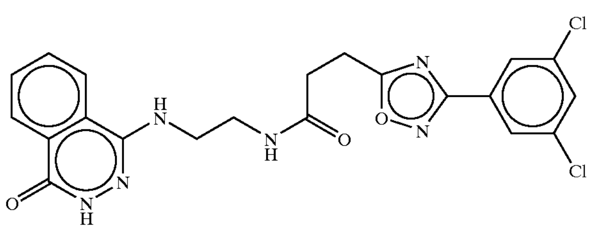 | 3-[3-(3,5-Dichloro-phenyl)-[1,2,4]oxadiazol-5-yl]-N-[2-(4-oxo-3,4-dihydro-phthalazin-1-ylamino)-ethyl]-propionamide |
| 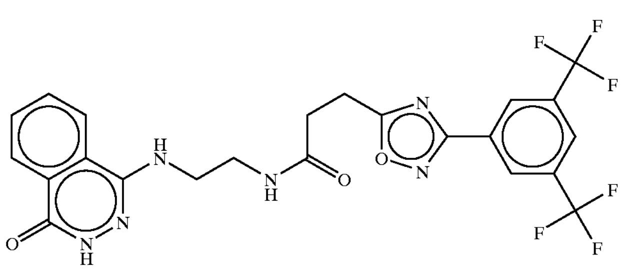 | 3-[3-(3,5-Bis-trifluoromethyl-phenyl)-[1,2,4]oxadiazol-5-yl]-N-[2-(4-oxo-3,4-dihydro-phthalazin-1-ylamino)-ethyl]-propionamide |

TABLE 2-continued

Representative compounds of Formula I along with some nomenclatures.

| Structure | NAME |
|---|---|
| 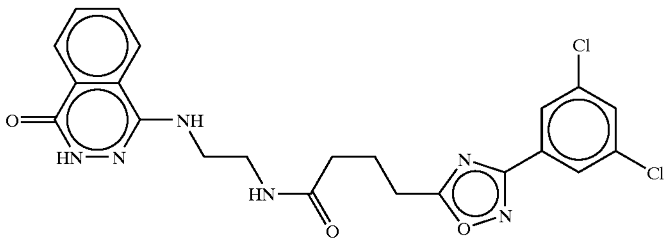 | 4-[3-(3,5-Dichloro-phenyl)-[1,2,4]oxadiazol-5-yl]-N-[2-(4-oxo-3,4-dihydro-phthalazin-1-ylamino)-ethyl]-butyramide |

Compounds of Tables 1 and 2 have PARP1 $IC_{50}$ in the range of from about 1 mM to about 1 nM. In addition, Compounds of Tables 1 and 2 have PARP2 $IC_{50}$ in the range of from about 1 mM to about 1 nM. Preferably, PARP1 $IC_{50}$ activity of compounds of Formula I is about 100 μM or less, more preferably about 50 μM or less, still more preferably about 10 μM or less, yet more preferably about 1 μM or less, still further preferably about 500 nM or less, and most preferably about 200 nM or less. Alternatively or in addition, PARP2 $IC_{50}$ activity of compounds of Formula I is preferably about 100 μM or less, more preferably about 10 μM or less, yet more preferably 1 μM or less, still more preferably about 500 nM or less, and most preferably about 150 nM or less.

Compounds of the present invention have activity in cellular assays in which the compounds augment the activity of some DNA damaging agents. Some DNA damaging agents including, but not limited to, alkylating agents, ionizing radiation, and inhibitors of DNA metabolism are useful clinically as cancer therapeutics. Many of the compounds in Tables 1 and 2 have activity as sensitizers to DNA damage in cell based assays. This activity is measured as the concentration of PARP inhibitor required such that 90% of cells are killed at ½ the concentration of chemotherapy compound required to kill 90% of the cells in the absence of the PARP inhibitor. This is termed the effective concentration for a two fold sensitization or $EC_{TFS}$. Preferably, $EC_{TFS}$ activity of compounds of Formula I against cultured tumor cell lines is about 50 μM of less, and more preferably about 10 μM or less.

While the forms of the invention herein constitute presently preferred embodiments, many others are possible. It is not intended herein to mention all of the possible equivalent forms or ramifications of the invention. It is understood that the terms used herein are merely descriptive rather than limiting, and that various changes can be made without departing from the spirit or scope of the invention.

Synthesis of Compounds of Formula I

The compounds of the present invention can be prepared by a variety of methods, including solid-phase, solution-phase and combinatorial synthesis. It should be appreciated that although the following schemes for producing compounds of Formula I often indicate exact structures, methods of the present invention apply widely to analogous compounds of Formula I, given an appropriate consideration to protection and deprotection of reactive functional groups by methods standard to the art of organic chemistry. For example, hydroxy groups, in order to prevent unwanted side reactions, sometimes need to be converted to ethers or esters during chemical reactions at other sites in the molecule. The hydroxy protecting group is then removed to provide the free hydroxy group. Similarly, amino groups and carboxylic acid groups can be derivatized to protect them against unwanted side reactions. Typical protecting groups, and methods for attaching and cleaving them, are described fully in the above incorporated references by T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1–8 (John Wiley and Sons, 1971–1996).

One particular aspect of the present invention provides a process for producing a compound of Formula I. In particular, the process comprises contacting an amine compound of the formula:

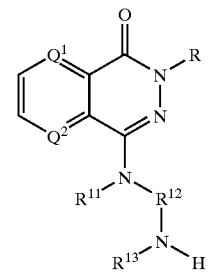

with a carboxylic acid derivative of the formula W—[C(=O)]$_c$—[NR$^{14}$]$_d$—[R$^{15}$]$_e$—[C(=O)]$_f$—R$^{16}$ under conditions sufficient to produce the Compound of Formula I, wherein Q$^1$, Q$^2$, R, R$^{11}$, R$^{12}$, R$^{13}$, R$^{14}$, R$^{15}$, R$^{16}$, c, d, e and f are as defined herein; and W is a carboxylic acid.

While the amine compound can be produced by a wide variety of methods, in on particular embodiment, the amine compound is produced by contacting a cyanoester aryl compound of the formula:

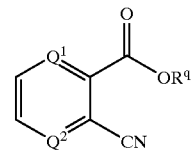

or an anhydride of the formula:

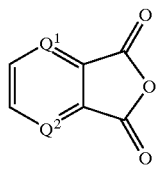

with an amine compound of the formula HR$^{11}$N—R$^{12}$—NR$^{13}$H under conditions sufficient to produce an intermediate product; and contacting the intermediate product with hydrazine under conditions sufficient to produce the amine compound, where Q$^1$, Q$^2$, R$^{11}$, R$^{12}$, and R$^{13}$ are as defined herein; and R$^q$ is alkyl, aryl, cycloalkyl, or aralkyl.

Another aspect of the present invention produces a process for producing a bicyclic aryl compound of the formula:

IA

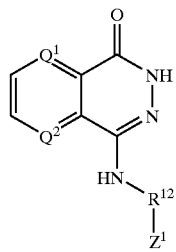

comprising:
(a) contacting a cyanoester aryl compound of the formula:

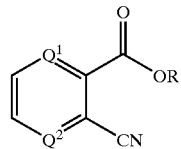

or an anhydride of the formula:

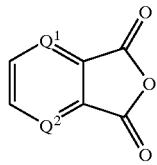

with an amine compound of the formula H$_2$N—R$^{12}$—Z$^1$ under conditions sufficient to produce an intermediate product; and
(b) contacting said intermediate product with hydrazine under conditions sufficient to produce said bicyclic aryl compound, wherein
each of Q$^1$ and Q$^2$ is independently N or CR$^a$, where R$^a$ is hydrogen, halo, nitro, or alkyl;
R is an alkyl;
R$^{12}$ is selected from the group consisting of:
(a) alkylene,
(b) cycloalkylene,
(c) heteroalkylene,
(d) aralkylene
Z$^1$ is selected from the group consisting of:
(a) optionally substituted heterocycloalkyl comprising at least one nitrogen atom;
(b) optionally substituted heterocyclyl comprising at least one nitrogen atom;
(c) —NR$^{28}$R$^{29}$, where
R$^{28}$ is selected from the group consisting of hydrogen and alkyl; and
R$^{29}$ is selected from the group consisting of hydrogen, alkyl, and an amine protecting group;
(d) alkyl;
(e) heteroalkyl;
(f) optionally substituted aryl; and
(g) cycloalkyl.

Preferably, Z$^1$ is selected from the group consisting of optionally substituted heterocycloalkyl comprising at least one nitrogen atom; optionally substituted heterocyclyl comprising at least one nitrogen atom; and —NR$^{28}$R$^{29}$, where R$^{28}$ and R$^{29}$ are those defined above. This method is particularly useful for producing compounds of Formula I that comprise a diamine substituent. The second amine moiety can be protected prior to reaction or it can be a non-protected amine moiety. When the second amine moiety is a protected amine, the resulting intermediate is of the formula:

IIA

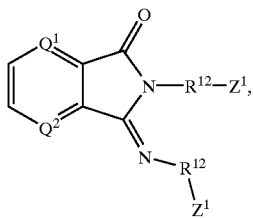

IIB

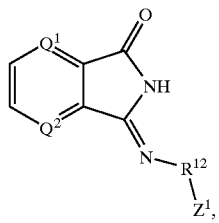

or mixtures thereof. When phthalic anhydride is used, the intermediate is of Formula IIA (where Q$^1$ and Q$^2$ are CH). However, when the second amine moiety is a non-protected amine, the resulting intermediate is typically of the formula:

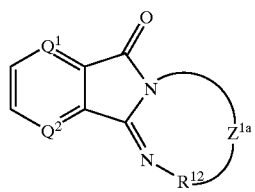

where —Z$^1$—NH$_2$ represents the —Z$^1$ moiety. For example, when the amine compound H$_2$N—R$^{12}$—Z$^1$ is ethylenediamine (H$_2$H—(CH$_2$)$_2$—NH$_2$), the resulting intermediate is:

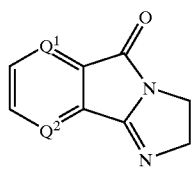

And when the amine compound is BOC-protected (i.e., tert-butylcarbamate) ethylenediamine (H$_2$N—(CH$_2$)$_2$—NHBOC), the resulting intermediate is:

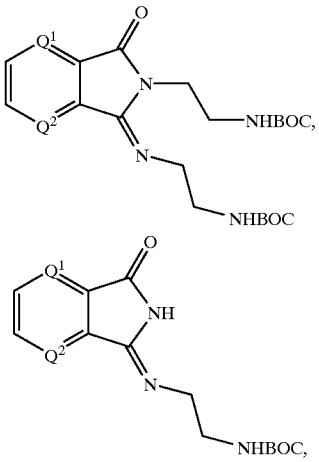

or mixtures thereof, depending on whether a cyanobenzoate or phthalic anhydride is used.

The reaction between a diamine and cyanobenzoate or phthalic anhydride (hereinafter the "aryl moiety reagent") is typically carried out in an alcoholic solvent or a polar aprotic solvent such as dimethylformamide (DMF), dimethylsulfoxide (DMSO), or dimethylacetamide (DMA). The reaction temperature depends on a variety of factors such as the particular solvent used, concentration of each reagents, and other reaction factors. Typically, when a polar aprotic solvent such as DMF is used, the reaction is conveniently carried out in the range of from about 60° C. to about 100° C., and generally the reaction temperature is about 80° C. When an alcoholic solvent is used, the reaction temperature is generally in the range of from about room temperature to about 80° C., with room temperature being a typical reaction temperature.

The reaction time depends on a variety of factors including, but not limited to, the concentration of each reagents, reaction temperature and the solvent used. When the reaction is conducted at room temperature in methanol or ethanol as a solvent, a typical reaction time ranges from about 1.5 h to about 20 hrs. While not necessary, a base can be added to the reaction mixture to facilitate the coupling reaction between the diamine and the aryl moiety reagent. The addition of base is particularly useful when using an alcoholic solvent. Generally, the corresponding alkoxide is used as the base. For example, when the reaction solvent is methanol, the base used is a methoxide and when the reaction solvent is ethanol, the base used is an ethoxide.

The intermediate can be purified prior to reaction with hydrazine; however, it is typically subjected to an aqueous work-up, concentrated and used without further purification.

The reaction between the intermediate and hydrazine is conveniently carried out in an alcoholic solvent such as methanol or ethanol. Typically, the intermediate is combined with hydrazine hydrate in an alcoholic solvent. The mixture is then heated, generally in the temperature range of from about 60° C. to about 90° C. for about 3 hrs to about 20 hrs to produce the 2H-phthalazin-1-one compound of Formula IA.

The bicyclic aryl compound of Formula 1A can be derivatized (i.e., converted) to produce a bicyclic aryl amide of the formula:

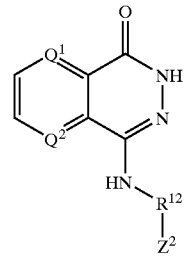

IB by contacting the bicyclic aryl compound of Formula IA with a carboxylic acid derivative of the formula W—[C(=O)]$_c$—R$^{15}$—[C(=O)]$_f$—R$^{16}$ under conditions sufficient to produce the bicyclic aryl amide of Formula IB, wherein W is a carboxylic acid activating group or —OR$^{30}$, where R$^{30}$ is hydrogen, alkyl, aralkyl, or aryl;

Z$^2$ is —NR$^{13}$—[C(=O)]$_c$—R$^{15}$—[C(=O)]$_f$—R$^{16}$ where
c is 1 or 2;
each of d, e, and f is independently 0 or 1;
X$^3$ is as defined herein;
R$^{13}$ is as defined herein, preferably selected from the group consisting of hydrogen and alkyl;
R$^{15}$ is as defined herein, preferably optionally substituted alkylene or optionally substituted heteroalkylene; and
R$^{16}$ is as defined herein.

As used herein, a "carboxylic acid activating group" refers to a moiety which renders the carboxylic acid reactive to substitution reactions. Exemplary carboxylic acid activating groups include halides, such as chloride and bromide; anhydrides of the formula R'—C(=O)—O—, where R' is hydrogen, optionally substituted alkyl, optionally substituted aryl, or optionally substituted aralkyl.

Preferably, R$^{16}$ is selected from the group consisting of optionally substituted heteroalkyl; alkoxy; optionally substituted aryloxy; substituted aralkoxy; alkenyl; optionally substituted aralkenyl; heterocycloalkyl; arylsulfonylalkyl; optionally substituted arylamino; optionally substituted cycloalkylamino; optionally substituted aralkylamino; —NHPO$_3$R$^{17}$R$^{18}$, where R$^{17}$ and R$^{18}$ are alkyl; —NHSO$_2$Ar$^2$, where Ar$^2$ is substituted aryl or aralkenyl; substituted heteroarylamino; heteroaralkylamino; substituted heteroalkylamino; alkylcarbamate; —SO$_2$R$^{19}$, where R$^{19}$ is optionally substituted aryl, substituted heteroaryl, optionally substituted heteroaralkyl, alkyl, aralkenyl, substituted heterocycloalkylalkyl, or substituted heteroaryl; optionally substituted cycloalkylalkyl; cycloalkenylalkyl; optionally substituted heterocycloalkylalkyl; cycloalkenyl; and alkylsulfonylalkyl.

It should be appreciated that when —Z$^1$ moiety comprises a protected amino group, the process further requires deprotection of the amino group prior to derivatization. For example, when —Z$^1$ moiety comprises a BOC-protected amino group, the BOC group is typically removed by contacting with an acid, e.g., trifluoroacetic acid, to liberate a free amino group prior to derivatization.

Conveniently, carboxylic acid is typically used to couple to the bicyclic aryl (e.g., 2H-phthalazin-1-one) compound of Formula IA, i.e., W of the carboxylic acid derivative is —OH. Such coupling of a carboxylic acid to an amine group to produce an amide linkage is well known to one of ordinary skill in the art. Generally, the reaction is conducted in the presence of a carboxylic acid activating agent, e.g., HOBt/EDC or HATU/HOBt mixture in the presence of a trialkylamine such as triethylamine or diisopropylethylamine. While a wide range of reaction temperature can be used, the coupling reaction is typically conducted at room temperature for about 2 hours to about 16 hrs.

The bicyclic aryl compound of Formula IA can be also be converted a bicyclic aryl (e.g., 2H-phthalazin-1-one) urea derivative of the formula:

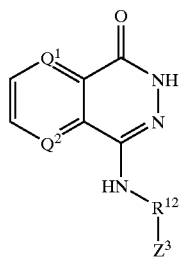

IC by contacting the bicyclic aryl compound of Formula IA with an isocyanate compound of the formula $X^3$=C=N—$R^{15}$—[C(=O)]$_f$—$R^{16}$ under conditions sufficient to produce the bicyclic aryl urea derivative of Formula IC, wherein X is O or S;
$Z^3$ is —$NR^{13}$—C(=$X^3$)—NH—$R^{15}$—[C(=O)]$_f$—$R^{16}$
where
  f is 0 or 1;
  $X^3$ is as defined herein;
  $R^{15}$ is as defined herein, preferably optionally substituted alkylene or optionally substituted heteroalkylene; and
  $R^{16}$ is as defined herein.

The coupling reaction between the bicyclic aryl compound of Formula IA and the isocyanate compound of the formula $X^3$=C=N—$R^{15}$—[C(=O)]$_f$—$R^{16}$ is generally conveniently conducted at room temperature with a typical reaction time in the range of from about 2 hrs to about 16 hrs. Many isocyanate compounds of the formula $X^3$=C=N—$R^{15}$—[C(=O)]$_f$—$R^{16}$ can be obtained commercially from recognized sources. Alternatively these compounds can readily be prepared by procedures described by Ozaki et al. in *Chemical Reviews*, 1972, 72, 457–460.

The bicyclic aryl compound of Formula IA can be also be converted a bicyclic aryl amine of the formula:

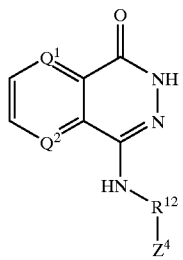

ID by contacting the bicyclic aryl compound of Formula IA with a carbonyl compound of the formula $R^{31}$—C(=O)—$R^{15}$—[C(=$X^3$)]$_f$—$R^{16}$ in the presence of a reducing agent under conditions sufficient to produce said bicyclic aryl amine of Formula ID, wherein $R^{31}$ is hydrogen or alkyl, preferably hydrogen;
$Z^4$ is —$NR^{13}$—CH($R^{31}$)—$R^{15}$—[C(=O)]$_f$—$R^{16}$
where
  f is 0 or 1;
  $X^3$ is as defined herein, preferably O;
  $R^{15}$ is as defined herein, preferably optionally substituted alkylene or optionally substituted heteroalkylene; and
  $R^{16}$ is as defined herein.

Such a reductive amination reaction between an amine compound and a carbonyl group can be typically carried out using a variety of reducing agents including, but not limited to, boronhydrides, such as $NaBH_4$, $NaCNBH_3$, $NaBH(OAc)_3$ and the like, in the presence of a carboxylic acid such as acetic acid. In the absence of the reducing agent, the resulting product is typically an imine compound in which $Z^4$ moiety of the compound of Formula ID is of the formula —$NR^{13}$=CH($R^{31}$)—$R^{15}$—[C(=C(=$X^3$))]$_f$—$R^{16}$.

The compounds of Formula I where Y is of the formula —$R^{22}$—$NR^{23}$—$R^{24}$—[$NR^{25}$]$_g$—[$R^{26}$]$_h$—[C(=$X^4$)]$_i$—[$R^{27}$]$_j$—$Ar^3$, where x is 1, e.g., a 4-substituted 2H-phthalazin-1-one compound of the formula:

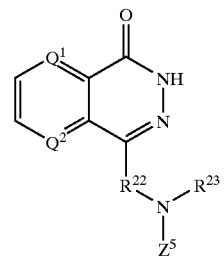

IE can be produced by reacting a bicyclic aryl compound of the formula:

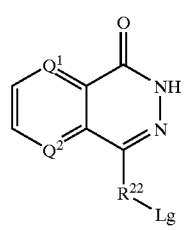

IF with an amine compound of the formula $HNR^{23}$—$Z^5$ under conditions sufficient to produce a 4-substituted bicyclic aryl compound of Formula IE, where Lg is a leaving group;
$R^{22}$ is alkylene;
$Z^5$ is —$R^{24}$—[$NR^{25}$]$_g$—[$R^{26}$]$_h$—[C(=$X^4$)]$_i$—[$R^{27}$]$_j$—$Ar^3$
wherein
  each of g, h, i, and j is independently 0 or 1;
  $X^4$ is selected from the group consisting of O and S;
  each of $R^{24}$, and $R^{26}$ is independently alkylene;
  $R^{23}$ is selected from the group consisting of hydrogen and heteraralkyl;
  $R^{25}$ is selected from the group consisting of hydrogen and alkyl;

R²⁷ is selected from the group consisting of —NH— and alkylene; and

Ar³ is selected from the group consisting of optionally substituted aryl and substituted heteroaryl.

The bicyclic aryl compound of Formula IF where R²² is methylene, Q¹ and Q² are CH, and Lg is chloride is commercially available and can be used to produce other derivatives of compound of Formula IF. The substitution reaction is typically performed under a polar aprotic solvent such as DMF or DMSO at room temperature.

Compounds of Formula I where Y is R³—C(=X¹)—Y¹ can be synthesized from a compound of the formula:

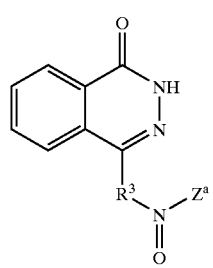

IG by contacting with an amine compound of the formula —NR⁴R⁵ under conventional amide synthesis procedures, where R³, R⁴, R⁵, X¹ and Y¹ are those defined herein and Z$^a$ is —OH, halide or an alkoxide. A compound of Formula IG where R³ is methylene and Z$^a$ is —OH is commercially available from a variety of sources.

Pharmaceutical Composition

The compounds of Formula I can be administered to a patient to achieve a desired physiological effect. Preferably, the patient is a mammal, and more preferably a human. Preferably, the compound of Formula I is administered as a pharmaceutical composition comprising a compound of Formula I or a pharmaceutically acceptable salt, prodrug, stereoisomer, or mixtures (hereafter, "a compound of Formula I"). Typically, the compounds of Formula I in the pharmaceutical composition of the present invention have an IC$_{50}$ for inhibiting PARP in vitro of 10 μM or lower, preferably 1 μM or lower, more preferably 500 nM or lower, and most preferably 200 nM or lower.

The composition of the present invention can be administered in a variety of forms adapted to the chosen route of administration, i.e., orally or parenterally. Parenteral administration in this respect includes, but not limited to, administration by the following routes: intravenous; intramuscular; subcutaneous; intraocular; intrasynovial; transepithelially including transdermal, ophthalmic, sublingual and bucal; topically including ophthalmic, dermal, ocular, rectal and nasal inhalation via insufflation and aerosol; intrapertioneal; and rectal systemic.

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound can be incorporated with excipient and used in the form of ingestible tablets, buccal tablets, troches, capsules, lozenges, elixirs, suspensions, syrups, wafers, and the like. Such compositions and preparation can contain at least 0.1% of active compound. The percentage of the compositions and preparation can, of course, be varied and can conveniently be between about 0.1 to 75% by weight of the active ingredient, preferably about 1 to 50% of the same, and more preferably about 1 to about 10%. The amount of active compound in such therapeutically useful compositions is such that a suitable dosage is obtained. Preferred compositions or preparations according to the present invention are prepared such that an oral dosage unit form contains from about 1 to about 1000 mg of active compound. The active ingredient can be in the form of a powder or granules; in the form of a solution or a suspension in an aqueous liquid or nonaqueous liquid; or in the form of an oil-in-water emulsion or a water-in-oil emulsion. The active ingredient can also be in the form of a bolus, electuary, or paste.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or succharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl or propylparabens a preservatives, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulation.

Typically, the composition is usually formulated into a unit dosage form, such as a tablet, capsule, aqueous suspension or solution. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, corn starch and the like.

Particularly preferred formulations include tablets and gelatin capsules comprising the active ingredient together with (a) diluents, such as lactose, dextrose, sucrose, mannitol, sorbitol, cellulose, dried corn starch, and glycine; and/or (b) lubricants, such as silica, talcum, stearic acid, its magnesium or calcium salt, and polyethylene glycol.

Tablets can also contain binders, such as magnesium aluminum silicate, starch paste, gelatin, tragacanth, methylcellulose, sodium carboxymethylcellulose and polyvinylpyrrolidone; disintegrants, such as starches, agar, alginic acid or its sodium salt, and effervescent mixtures; and/or absorbents, colorants, flavors, and sweeteners. The compositions of the invention may be sterilized and/or contain adjuvants, such as preserving, stabilizing, swelling or emulsifying agents, solution promoters, salts for regulating osmotic pressure, and/or buffers. In addition, the composition may also contain other therapeutically valuable substances. Aqueous suspensions can contain emulsifying and suspending agents combined with the active ingredient. All oral dosage forms can further contain sweetening and/or flavoring and/or coloring agents.

These compositions are prepared according to conventional mixing, granulating, or coating methods, respectively.

Tablet can be made by compressing or molding the active ingredient optionally with one or more accessory ingredients. Compressed tablets can be prepared by compressing, in a suitable machine, the active ingredient in a free-flowing form such as a powder or granules, optionally mixed with a binder, lubricant, inert diluent, surface active, or dispersing agent. Molded tablets can be made by molding, in a suitable machine, a mixture of the powdered active ingredient and a suitable carrier moistened with an inert liquid diluent.

The active compound can also be administered parenterally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and preferably is preserved against the contaminating action of microorganisms such as bacterial and fungi.

When administered parenterally, the composition normally is in a unit dosage, sterile injectable form (aqueous isotonic solution, suspension or emulsion) with a pharmaceutically acceptable carrier. Such carriers are preferably non-toxic and parenterally-acceptable. Exemplary carriers include, but are not limited to, water; aqueous solutions, such as saline (isotonic sodium chloride solution), Ringer's solution, dextrose solution, and Hanks' solution; ethanol, polyol (e.g., glycerol, propylene glycol, 1,3-butanediol, and liquid polyethylene glycol, and the like); vegetable oils or fixed oils (e.g., corn, cottonseed, peanut, sesame oil, and synthetic mono- or di-glyceride), ethyl oleate, and isopropyl myristate; and suitable mixtures thereof.

The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, e.g., sugars or sodium chloride.

Sterile injectable solutions are prepared by incorporating the active compound in the required amount in the appropriate solvent with various other ingredients enumerated above, as required, optionally followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

Oleaginous suspensions can be formulated according to techniques known in the art using suitable dispersing or wetting agents and suspending agents. Among the acceptable solvents or suspending mediums are sterile fixed oils. For this purpose, any bland fixed oil an be used. Fatty acids, such as oleic acid and its glyceride derivatives, including olive oil and castor oil, especially in their polyoxyethylated forms, are also useful in the preparation of injectables. These oil solutions or suspensions can also contain long-chain alcohol diluents or dispersants.

When administered rectally, the composition will usually be formulated into a unit dosage form such as a suppository or cachet. These compositions can be prepared by mixing the compound with suitable non-irritating excipients that are solid at room temperature, but liquid at rectal temperature, such that they will melt in the rectum to release the compound, common excipients include cocoa butter, beeswax and polyethylene glycols or other fatty emulsions or suspensions.

The compounds of Formula I can also be administered topically, especially when the conditions addressed for treatment involve areas or organs readily accessible by topical application, including neurological disorders of the eye, the skin or the lower intestinal tract. Such composition can comprise a topical carrier. The term "topical carrier", as used herein, is well-known to one of ordinary skill in the art, and means one or more compatible solid or liquid filler diluents or vehicles which are suitable for facilitating topical application of an active compound to a patient. The topical carrier can be a pharmaceutically acceptable carrier of sufficiently high purity and suitable for use in contact with the areas or organs of a patient without undue toxicity, incompatibility, instability, allergic response, and the like.

For topical application to the eye, or ophthalmic use, the compounds can be formulated as micronized suspensions in isotonic, pH-adjusted sterile saline or, preferably, as a solution in isotonic, pH-adjusted sterile saline, either with or without a preservative such as benzyalkonium chloride. Alternatively, the compounds can be formulated into ointments, such as petrolatum.

The composition for topical application (i.e., topical composition) useful in the present invention can be made into a variety of product types. These include, but are not limited to, lotions, creams, gels, sticks, sprays, ointments, and pastes. These product types can comprise several types of carrier systems including, but not limited to, solutions, emulsions, gels, solids, and liposomes. For example, for topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene compound, polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

A topical composition useful in the present invention formulated as a solution carrier system typically includes a pharmaceutically-acceptable aqueous or organic solvent. Water is a preferred solvent. Exemplary suitable organic solvents include ethanol, propylene glycol, polyethylene glycol, polypropylene glycol, glycerol, 1,2,4-butanetriol, sorbitol esters, 1,2,6-hexanetriol, isopropanol, butanediol, and mixtures thereof.

If the topical composition useful in the present invention is formulated as an aerosol carrier system and applied to the skin as a spray-on, a propellant is added to a solution composition. Exemplary propellants include chlorofluorinated lower molecular weight hydrocarbons. Other useful propellants include chloro-fluorinated lower molecular weight hydrocarbons. Other useful propellants are discussed in Sagarin, *Cosmetics Science and Technology*, 2nd Ed., 1972, Vol. 2, ("Sagarin volume 2"), which is incorporated herein in its entirety. Useful propellants are disclosed in pages 443–465 of Sagarin, volume 2.

The topical composition of the present invention can be formulated as a solution carrier system comprising an emollient. Such compositions contain from about 2% to about 50% of a topical pharmaceutically-acceptable emollient. A wide variety of suitable emollients are known and can be used herein.

A lotion can be made from a solution carrier system. Lotions comprise from about 1% to about 20% emollient, and from about 50% to about 90% water.

Another type of product that can be formulated from a solution carrier system is a cream. A cream typically comprises from about 5% to about 50% of an emollient, and from about 45% to about 85% water.

Yet another type of product that can be formulated from a solution carrier system is an ointment. An ointment can comprise a simple base of animal or vegetable oils or semi-solid hydrocarbons (oleaginous). Ointments can also comprise absorption ointment bases which absorb water to form emulsions. Ointment carriers can also be water soluble. An ointment can comprise from about 2% to about 10% of emollient and from about 0.1% to about 2% of a thickening agent.

The composition for topical application of the present invention can further comprise ancillary components. The ancillary components, whose use is optional but preferably, impart additional desirable properties to the composition for topical application of the present invention. These ancillary components can include a thickener component, a preservative component, a lipid-soluble component, and coloring.

The topical composition can further comprise a preservative component to retard microbial and mold growth in the composition. A useful preservative component includes propylene glycol, phonoxyethanol, chlorphenesin, methylparaben, ethylparaben, butylparaben, propylparaben, and mixtures thereof.

The composition for topical application can further include a lipid-soluble component that provide added smoothness. The lipid-soluble component include, but are not limited to, steareth-2-steareth-21, dimethicone and a branched chain neopentanoate ester such as °Ctyldodecyl neopentanoate, heptyldodecyl neopentanoate, nonyldodecyl neopentanoate, °Ctylundecyl neopentanoate, heptylundecyl neopentanoate, nonylundecyl neopentanoate, °Ctyltridecyl neopentanoate, heptyltridecyl neopentanoate, and nonyltridecyl neopentanoate. Steareth-2 is polyoxyethylene (2) stearyl ether with 0.01% butylated hydroxyanisole and 0.005% citric acid added as preservatives. Similarly, steareth-21 is polyoxyethylene (21) stearylether with 0.01% butylated hydroxyanisole and 0.005% citric acid added as preservatives.

Topical application to the lower intestinal tract can be effected in rectal suppository formulations (see above) or in suitable enema formulations.

Formulations suitable for nasal or buccal administration, (such as self-propelling powder dispensing formulations), can comprise about 0.1% to about 5% w/w of the active ingredient or, for example, about 1% w/w of the same. In addition, some formulations can be compounded into a sublingual troche or lozenge.

The formulations can conveniently be presented in unit dosage form and can be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

In a preferred embodiment, the carrier is a solid biodegradable polymer or mixture of biodegradable polymers with appropriate time release characteristics and release kinetics. The composition of the invention can then be molded into a solid implant suitable for providing efficacious concentrations of the compounds of the invention over a prolonged period of time without the need for frequent re-dosing. The composition of the present invention can be incorporated into the biodegradable polymer or polymer mixture in any suitable manner known to one of ordinary skill in the art and can form a homogeneous matrix with the biodegradable polymer, or can be encapsulated in some way within the polymer, or can be molded into a solid implant. In one embodiment, the biodegradable polymer or polymer mixture is used to form a soft "depot" containing the pharmaceutical composition of the present invention that can be administered as a flowable liquid, for example, by injection, but which remains sufficiently viscous to maintain the pharmaceutical composition within the localized area around the injection site. The degradation time of the depot so formed can be varied from several days to a few years, depending upon the polymer selected and its molecular weight. By using a polymer composition in injectable form, even the need to make an incision can be eliminated. In any event, a flexible or flowable delivery "depot" will adjust to the shape of the space it occupies within the body with a minimum of trauma to surrounding tissues.

The pharmaceutical composition of the present invention is used in amounts that are therapeutically effective, and can depend upon the desired release profile, the concentration of the pharmaceutical composition required for the sensitizing effect, and the length of time that the pharmaceutical composition has to be released for treatment. The physician can determine the dosage of the present therapeutic agents which will be most suitable for treatment and it can vary with the form of administration and the particular compound chosen, and also, it can vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2X to about 4X, can be required for oral administration.

The composition of the invention is preferably administered as a capsule or tablet containing a single or divided dose of the compound, or as a sterile solution, suspension, or emulsion, for parenteral administration in a single or divided dose.

The compounds of the invention are used in the composition in amounts that are therapeutically effective. The effective amount of the PARP inhibitor depends on the particular compound being used.

The pharmaceutical excipient or carrier are capable of being commingled with the other components of the composition of the present invention, and with each other, in a manner such that there is no interaction which would substantially reduce the therapeutic efficacy of the composition under ordinary use situations.

The therapeutic compounds of the present invention can be administered to a patient alone or in combination with pharmaceutically acceptable carriers, as noted above, the proportion of which is determined by the solubility and chemical nature of the compound, chosen route of administration and standard pharmaceutical practice.

Utility

An effective therapeutic amount of the compounds and compositions described above are administered to a patient, preferably a mammal and more preferably a human, to effect a pharmacological activity involving inhibition of a PARP enzyme. As such, compounds of the present invention are useful in treating or preventing a variety of diseases and illnesses including neural tissue damage resulting from cell damage or death due to necrosis or apoptosis, cerebral ischemia and reperfusion injury or neurodegenerative diseases in an animal. In addition, compounds of the present invention can also be used to treat a cardiovascular disorder in an animal, by administering an effective amount of the compound of formula to the animal. Further still, the compounds of the invention can be used to treat cancer and to radiosensitize or chemosensitize tumor cells.

In one particular embodiment of the present invention, compounds of Formula I can be used to stimulate damaged neurons, promote neuronal regeneration, prevent neurodegeneration and/or treat a neurological disorder. Accordingly, the present invention further relates to a method of effecting a neuronal activity in a patient, comprising administering an effective amount of the compound of Formula I to the patient. As stated above, the compounds of Formula I inhibit PARP activity and, thus, are useful for treating neural tissue damage, particularly damage resulting from cerebral ischemia and reperfusion injury or neurodegenerative diseases in animals.

Examples of neurological disorders that are treatable by the compounds of using the present invention include, without limitation, trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet descruction syndromes; peripheral neuropathies such as those caused by lead, dapsone, ticks, prophyria, or Guillain-Barre syndrome; Alzeheimer's disease; Huntington's Disease and Parkinson's disease.

The compounds of the present invention is particularly useful for treating a neurological disorder selected from the group consisting of: peripheral neuropathy caused by physical injury or disease state; head trauma, such as traumatic brain injury; physical damage to the spinal cord; stroke associated with brain damage, such as vascular stroke associated with hypoxia and brain damage, focal cerebral ischemia, global cerebral ischemia, and cerebral reperfusion injury; demyelinating diseases, such as multiple sclerosis; and neurological disorders related to neurodegeneration, such as Alzheimer's Disease, Parkinson's Disease, Huntington's Disease and amyotrophic lateral sclerosis.

The compounds, compositions and methods of the invention can also be used to treat a cardiovascular disorder in a patient, by administering an effective amount of the compound of formula to the patient.

As used herein, the term "cardiovascular disorders" refers to those disorders that can either cause ischemia or are caused by reperfusion of the heart. Examples include, but are not limited to, coronary artery disease, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to PARP activation.

The compounds of the present invention are useful for treating cardiac tissue damage, particularly damage resulting from cardiac ischemia or caused by reperfusion injury in a patient. The compounds of the invention are particularly useful for treating cardiovascular disorders selected from the group consisting of: coronary artery disease, such as atherosclerosis; angina pectoris; myocardial infarction; myocardial ischemia and cardiac arrest; cardiac bypass; and cardiogenic shock.

Further, the compounds of the present invention can be used to treat tissue damage resulting from cell damage or death due to necrosis or apoptosis, neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic obstructive pulmonary disease, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize tumor cells.

In another aspect, the compounds of the present invention can be used to treat cancer, and to radiosensitize and/or chemosensitize tumor cells. The term "cancer" is interpreted broadly. The compounds of the present invention can be "anti-cancer agents," which term also encompasses "anti-tumor cell growth agents" and "anti-neoplastic agents." For example, the compounds of the invention are useful for treating cancers, and radiosensitizing and/or chemosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant pertioneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor.

Radiosensitizers are known to increase the sensitivity of cancerous cells to the toxic effects of electromagnetic radiation. Many cancer treatment protocols currently employ radiosensitizers activated by the electromagnetic radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: Hematoporphyrin derivatives, Photofrin, benzoporphyrin derivatives, NPe6, tin etioporphyrin SnET2, pheoborbide-α, bacteriochlorophyll-α, naphthalocyanines, phthalocyanines, zinc phthalocyanine, and therapeutically effective analogs and derivatives of the same.

Radiosensitizers can be administered in conjunction with a therapeutically effective amount of one or more other compounds, including but not limited to: compounds which promote the incorporation of radiosensitizers to the target cells; compounds which control the flow of therapeutics, to nutrients, and/or oxygen to the target calls.

Similarly, chemosensitizers are also known to increase the sensitivity of cancerous cells to the toxic effects of chemotherapeutic compounds. Exemplary chemotherapeutic agents that can be used in conjunction with a compound of Formula I include, but are not limited to, adriamycin, camptothecin, dacarbazine, carboplatin, cisplatin, daunorubicin, docetaxel, doxorubicin, interferon (alpha, beta, gamma), interleukin 2, innotecan, paclitaxel, streptozotocin, temozolomide, topotecan, and therapeutically effective analogs and derivatives of the same. In addition, other therapeutic agents which can be used in conjunction with a compound of Formula I include, but are not limited to, 5-fluorouracil, leucovorin, 5'-amino-5'-deoxythymidine, oxygen, carbogen, red cell transfusions, perfluorocarbons (e.g., Fluosol-DA), 2,3-DPG, BW12C, calcium channel blockers, pentoxyfylline, antiangiogenesis compounds, hydralazine, and L-BSO.

The compounds of the present invention can also be used to treat benign hyperplastic diseases such as benign prostatic hypertrophy, arterial hyperplastic diseases or Cushing's syndrome.

Administration

The amount of a compound of Formula I required to achieve a therapeutic effect depends on a variety of factors such as the particular compound administered, the route of administration, the animal under treatment, and the particular disorder or disease concerned. A suitable systemic dose of a compound of Formula I for a patient suffering from, or likely to suffer from, a condition described herein is typically in the range of about 0.1 to about 100 mg of base per kilogram of body weight, preferably from about 1 to about 10 mg/kg of patient body weight. The physician can determine the dosage of the present therapeutic agents which is suitable for treatment.

In so proceeding, the physician or veterinarian can employ an intravenous bolus followed by an intravenous infusion and repeated administrations, as considered appropriate. As stated above, compounds of the present invention can be administered, for example, orally, parenterally, by inhalation spray, topically, rectally, nasally, buccally, sublingually, vaginally, intraventricularly, or via an implanted reservoir in dosage formulations containing conventional non-toxic pharmaceutically-acceptable carriers, adjuvants and vehicles.

To be effective therapeutically as central nervous system targets, the compounds used in the methods of the present invention should readily penetrate the blood-brain barrier when peripherally administered. Compounds which cannot penetrate the blood-brain barrier, however, can still be effectively administered by an intraventricular route.

For the methods of the present invention, any effective administration regimen regulating the timing and sequence of doses can be used. Doses of the compounds preferably include pharmaceutical dosage units comprising an efficacious quantity of active compound. By an efficacious quantity is meant a quantity sufficient to inhibit PARP activity and/or derive the desired beneficial effects therefrom through administration of one or more of the pharmaceutical dosage units. In a particularly preferred embodiment, the dose is sufficient to prevent or reduce the effects of vascular stroke or other neurodegenerative diseases.

In methods of treating nervous insult (particularly acute ischemic stroke and global ischemia caused by drowning or head trauma), the compounds of the invention can be co-administered with one or more other therapeutic agents, preferably agents which can reduce the risk of stroke (such as aspirin) and, more preferably, agents which can reduce the risk of a second ischemic event (such as ticlopidine).

The compounds and compositions can be co-administered with one or more therapeutic agents either (i) together in a single formulation, or (ii) separately in individual formulations designed for optimal release rates of their respective active agent. Each formulation can contain from about 0.01% to about 99.99% by weight, preferably from about 3.5% to about 60% by weight, of the compound of the invention, as well as one or more pharmaceutical excipients, such as wetting, emulsifying and pH buffering agents. When the compounds used in the methods of the invention are administered in combination with one or more other therapeutic agents, specific dose levels for those agents will depend upon considerations such as those identified above for compositions and methods of the invention in general.

For the methods of the present invention, any administration regimen regulating the timing and sequence of delivery of the compound can be used and as necessary to effect treatment. Such regimen can include pretreatment and/or co-administration with additional therapeutic agents. To maximize protection of nervous tissue for nervous insult, the compounds of the invention is administered to the affected cells as soon as possible. In situations where nervous insult is anticipated, the compounds are advantageously administered before the expected nervous insult. Such situations of increased likelihood of nervous insult include surgery, such as carotid endarterectomy, cardiac, vascular, aortic, orthopedic surgery; endovascular procedures, such as arterial catheterization (carotid, vertebral, aortic, cardiac, renal, spinal, Adamkiewicz); injections of embolic agents; the use of coils or balloons for hemostasis; interruptions of vascularity for treatment of brain lesions; and predisposing medical conditions such as crescendo transient ischemic attacks, emboli and sequential strokes.

EXAMPLES

Additional objects, advantages, and novel features of this invention will become apparent to those skilled in the art upon examination of the following examples thereof, which are not intended to be limiting.

Example 1

This example illustrate a method of producing a 4-diamine substituted 2H-phthalazin-1-one.

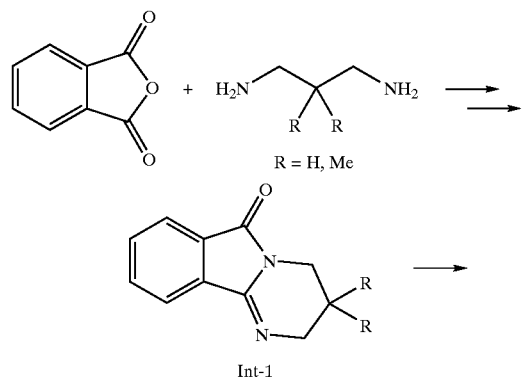

4-(3-amino-propylamino)-2H-phthalazin-1-one (R=H)

A 2-L, three-neck, round bottomed flask equipped with a mechanical stirrer and a thermometer was charged with 1,3-propanediamine (66.0 g, 0.890 mol) and ethanol (450 mL). Phthalic and anhydride (120 g, 0.811 mol) was then added portion-wise over 20 min. An exothermic reaction occurred, and a thick white precipitate formed. Stirring was continued for another 1 h, and the resulting precipitate was vacuum filtered. The cake was washed with ethanol (2×100 mL) affording 178 g of a white solid which was used directly. A 1-L, three-neck round bottomed flask equipped with a mechanical stirrer and a thermoregulator was charged with the above solid (50.0 g) and ethylene glycol (200 mL), and the reaction mixture was refluxed at 170° C. for 1 h. The volatiles were then distilled off until the temperature inside the flask reached 210° C. The heating mantle was removed, the flask cooled to room temperature, and the distillate poured back into the flask. The resulting solution was treated with hydrazine monohydrate (36.1 g, 0.721 mol) and the mixture heated at 90° C. for 16 h. After cooling to ambient temperature, water (500 mL) was added, and the resulting yellow precipitate was vacuum filtered and washed with water (3×100 mL). This material was transferred to a 1-L beaker equipped with a magnetic stirrer, and a mixture of 37% hydrochloric acid (15 mL) and water (200 mL) was added to form a clear solution. The product was then precipitated by addition of 29% aqueous ammonium hydroxide (75 mL). The resulting solids were filtered and washed on the filter with water (3×100 mL). Drying overnight under vacuum at 45° C. afforded a 51% yield of the title compound as a yellow solid. m.p. 147–148° C.; $^1$H NMR (DMSO-$d_6$) δ (ppm) 8.24 (d, 1H, J=0.9 Hz), 8.21 (d, 1H, J=0.9 Hz); 7.91–7.77 (m, 4H), 6.74 (bs, 1H), 3.29 (dd, 2H, J=11.8, 6.6 Hz), 2.67 (t, 2H, J=6.6 Hz), 1.72 (quin, 2H, J=6.7 Hz); m/z=219 (M+H).

4-(3-amino-2,2-dimethyl-propylamino)-2H-phthalazin-1-one (R=Me)

This compound was prepared from 2,2-dimethyl-propane-1,3-diamine according to the procedure described above with few modifications:

Phthalic anhydride (10 g, 67.5 mmol) and the 2,2-dimethyl-propylamine (8.5 mL, 70.8 mmol) (R=Me) were dissolved in 40 mL of ethanol (EtOH). After the reaction was complete, the mixture was concentrated in vacuo. The crude material (5 g, 0.02 mmol) was cyclized as described by Gaozza et al. Precipitated product was filtered and dried (3.36 g, 78%).

To 2,2-dimethyl-2,3-dihydro-1H-4,9a-diaza-fluoren-9-one (1.5 g, 7.0 mmol) in EtOH (17.5 mL), hydrazine hydrate (0.98 mL) was added and the mixture was heated at reflux for 3½ h. Crystallization provided 0.994 g (58%) of 4-(3-amino-2,2-dimethyl-propylamino)-2H-phthalazin-1-one.

Example 2

This example illustrates a method for producing a diamine substituted 2H-phthalazin-1-one using a cyanobenzoate compound.

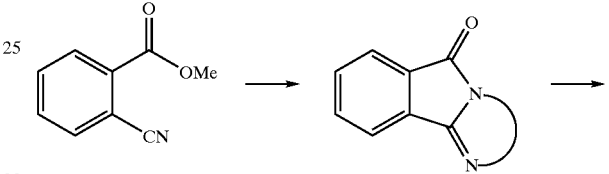

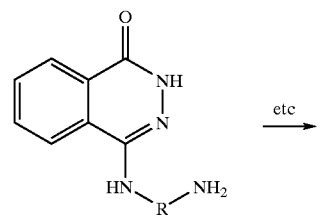

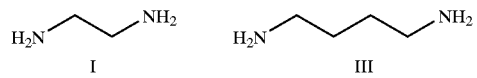

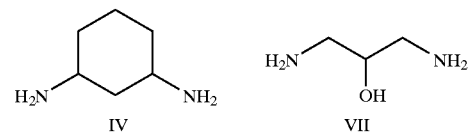

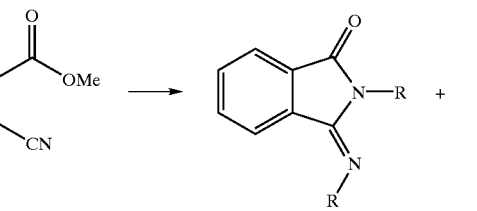

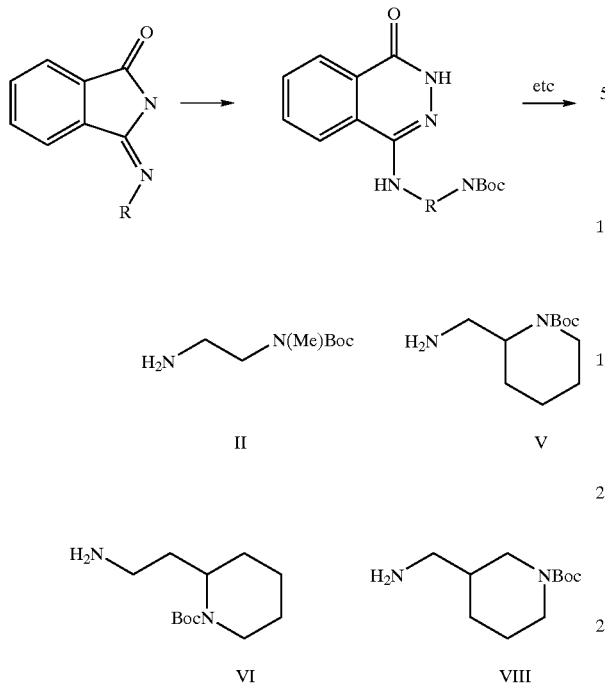

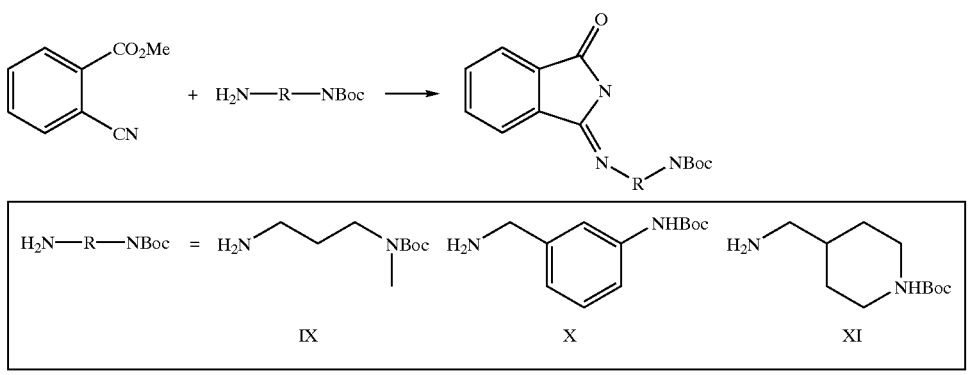

Procedure of I and III:

A mixture of 2-cyano-benzoic acid methyl ester (2 g, 12.4 mmol) and butane-1,4-diamine (1.09 g, 12.4 mmol) was heated at 80° C. in DMF (10 mL) overnight. Dichloromethane (i.e., DCM) was added and the organic layer was washed with saturated $NaHCO_3$, 10% citric acid and brine, dried over $MgSO_4$, filtered and concentrated. Purification using silica gel column chromatography (gradient of $CH_2Cl_2$ to $CH_2Cl_2$/MeOH, 98/2) afforded 600 mg of cyclized material (24% yield). This material was treated with hydrazine hydrate as described in Example 1 to provide 4-(4-Aminobutylamino)-2H-phthalazin-1-one.

Procedure for IV and VII (1,3-cyclohexanediamine and 1,3-diamino-2-propanol):

To a solution of methyl 2-cyanobenzoate (322 mg, 2.00 mmol) in DMF (1 mL), 1,3-cyclohexanediamine (285 mg, 2.50 mmol) was added. The reaction mixture was heated at 85° C. for 16 h, cooled, extracted with ether, and concentrated to yield 320 mg of the cyclic intermediate as a light yellow solid (71%). This product was treated with hydrazine hydrate (2.80 mmol) in EtOH (2 mL) and heated at 85° C. for 10 hours. The product was isolated by filtration, washed with MeOH, and dried to yield 318 mg of a yellow solid.

Procedure for II, V, VI and VIII: (Boc-protected Diamines)

To a solution of methyl 2-cyanobenzoate (322 mg, 2.00 mmol) in DMF (1 mL) 3-(aminomethyl)-1-N-boc-piperidine (0.96 g, 4.50 mmol) was added. The reaction mixture was heated at 85° C. for 16 h, cooled and extracted into DCM to yield 550 mg of the cyclic intermediate as a yellow oil (51%). This product was treated with hydrazine hydrate (1.50 mmol) in EtOH (2 mL) and heated at 85° C. for 10 hours. The product was isolated by flash chromatography (EtOAc/hexanes), to yield 310 mg of a white solid. This product was suspended in 50% TFA/DCM (5 mL) and stirred for 1 h. The solvent was removed under vacuum to yield 223 mg of a yellow oil.

Example 3

Procedure for IX, X, XI

This example illustrates a method for producing a diamine substituted 2H-phthalazin-1-one using a mono-protected diamine compound.

Combined 2-cyano-benzoic acid methyl ester (0.40 g, 2.48 mmol) and 2.48 mmol of amine ((3-aminomethyl-phenyl)-carbamic acid tert-butyl ester or (3-amino-propyl)-methyl-carbamic acid tert-butyl ester or 4-Aminomethyl-piperidine-1-carboxylic acid tert-butyl ester) in 5 mL MeOH at 0° C. Added 2.73 mmol NaOMe (as 0.5M solution) and stirred 3–18 h at RT. Removed solvent in vacuo and extracted with EtOAc (100 mL) and 0.5M $NaHSO_4$ (2×15 mL) then brine (1×15 mL). Organic layer was dried ($MgSO_4$) and concentrated in vacuo.

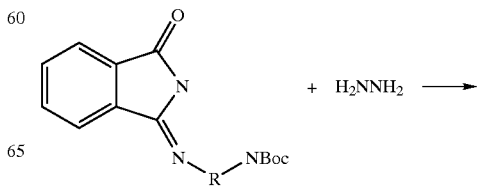

421
-continued

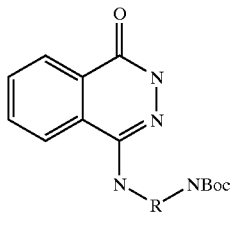

Combined the crude 3-alkylimino-2,3-dihydro-isoindol-1-one (1.22 mmol) produced above with hydrazine hydrate (3.65 mmol) in 5 mL of MeOH and heated to 85° C. for 18 h. Filtered product and washed with $H_2O$.

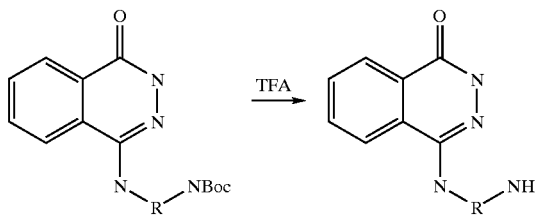

Combined the crude Boc-protected compound produced above (1.2 mmol) with trifluoroacetic acid (i.e., TFA) (36.1 mmol) in 5 mL of DCM. Stirred at rt for 2h. Removed solvent in vacuo with toluene addition to facilitate removal of TFA.

Example 4

This example illustrates a method for coupling an aryl diamine 2H-phthalazin-1-one and a method for further derivatizing the resulting 4-(amino-substituted arylamino)-2H-phthalazin-1-one.

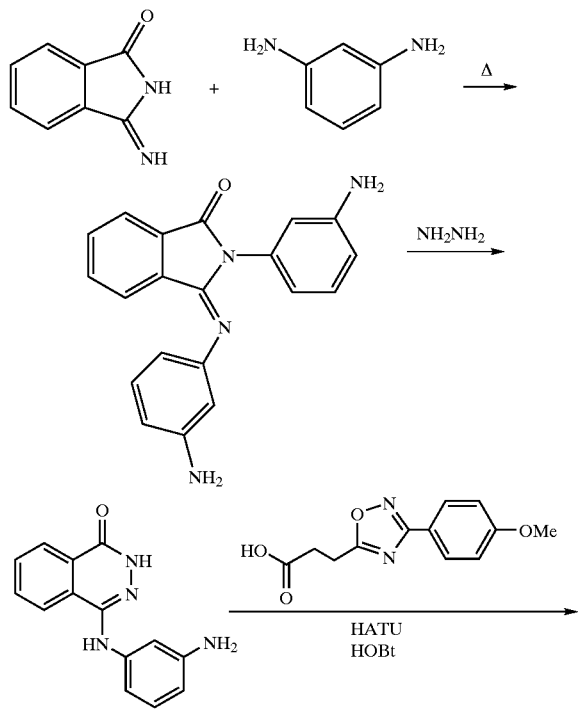

422
-continued

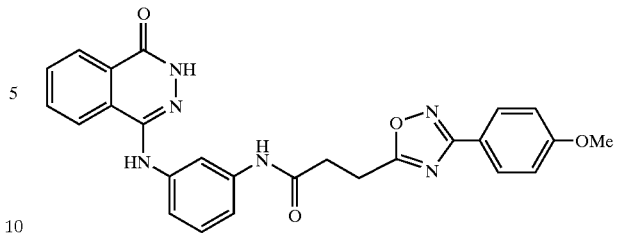

Synthesis of 3-[3-(4-Methoxy-phenyl)-[1,2,4]oxadiazol-5-yl]-N-[3-(4-oxo-3,4-dihydro-phthalazin-1-ylamino)-phenyl]-propionamide 3-Imino-2,3-dihydro-isoindol-1-one (50 mg, 0.34 mmol) and benzene-1,3-diamine (110 mg, 0.102 mmol) were heated at 200° C. for 16 hrs. The resulting mixture was dissolved in EtOH (600 μL) and hydrazine hydrate (200 μL) was added. After heating for 2 hours at 80° C. the mixture was concentrated in vacuo and dissolved in 1500 μL DMSO and directly applied to preparative HPLC to afford 4-(3-amino-phenylamino)-2H-phthalazin-1-one.

4-(3-Amino-phenylamino)-2H-phthalazin-1-one (13.8 mg, 0.055 mmol) and 3-[3-(4-methoxy-phenyl)-[1,2,4] oxadiazol-5-yl]-propionic acid (20 mg, 0.081 mmol) were dissolved in DMA (400 μL). HOBt (15 mg, 0.11 mmol), HATU (42 mg, 0.11 mmol) and diisopropylethylamine (i.e. DIPEA) (39 μL, 0.22 mmol) were added and the mixture was stirred overnight at rt. The mixture was stirred overnight at rt and directly applied to preparative HPLC. The purity was determined by RPLC/MS.

Example 5

This example illustrates a method for producing 6H-pyrido[2,3-d]pyridazin-5-one and its derivatives.

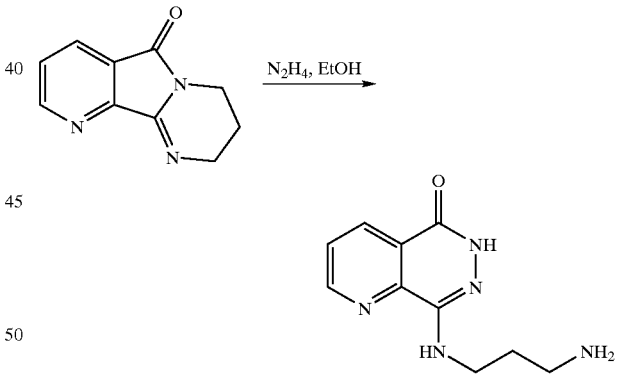

Methyl 2-cyanonicotinate was prepared using a procedure similar to those described by Carpino, L. A. in *J. Am. Chem. Soc.*, 1962, 17, 2266.

A solution of 2-carbamylnicotinic acid (2.00 g, 12.04 mmol) in pyridine (10 mL) and methanol (3 mL) was cooled to 0° C. and methanesulfonyl chloride (3.00 g, 26.3 mmol) was added over 10 min. The solution was slowly warmed to RT and allowed to stir for 6 h. The reaction mixture was treated with water (20 mL) and the organic solvents were removed under vacuum. The aqueous mixture was cooled to −10° C. Precipitated methyl 2-cyanonicotinate was collected by filtration (1.70 g, 10.49 mmol). To a mixture of methyl 2-cyanonicotinate (2.00 mmol), DMF (1 mL), and Sc(OTf)$_3$ (0.20 mmol) was added 1,3-diaminopropane (2.50 mmol).

The reaction mixture was heated at 85° C. for 1 h, cooled, and triturated from ether to yield 260 mg of the cyclic intermediate 7,8-Dihydro-6H-4,5,8a-triazafluoren-9-one as a yellow solid (70%). This product was treated with hydrazine hydrate (2.80 mmol) in EtOH (2 mL) and heated at 50° C. for 10 hours. The solution was cooled and compound 8-(3-amino-propylamino)-6H-pyrido[2,3-d]pyridazin-5-one was isolated by filtration, washed with MeOH, and dried to yield 244 mg of a yellow solid. The purity was determined by RPLC/MS (98%).

This compound can be further derivatized similar to 2H-phthalazin-1-one compounds as described herein.

Example 6

This example illustrates a method for producing 6H-pyrazino[2,3-d]pyridazin-5-one and its derivatives.

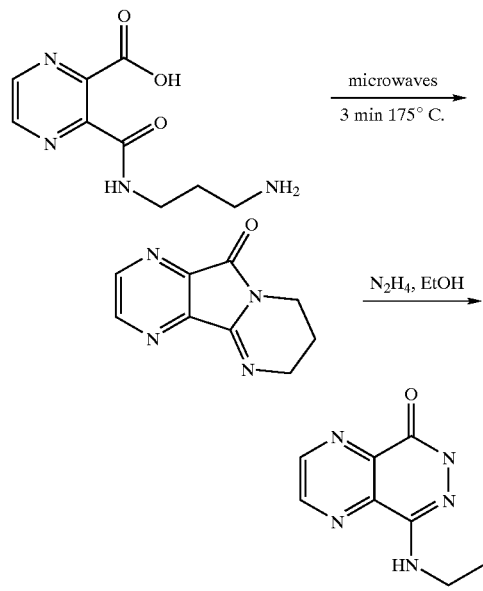

To a solution of 2,3-pyrazinedicarboxylic anhydride (6.50 g, 43.3 mmol) in ethanol (25 mL) was added 1,3-propanediamine (3.42 g, 46.0 mmol) dropwise over 5 min. The reaction was stirred over night at RT and the precipitated product was collected by filtration to yield 9.15 g of 3-(3-Amino-propylcarbamoyl)-pyrazine-2-carboxylic acid as a white solid (94%). This intermediate (200 mg) was dissolved in DMF (3 mL) and heated in a microwave reactor for 3 min at 175° C. to produce 7,8-Dihydro-6H-1,4,5,8a-tetraaza-fluoren-9-one, which was used without further purification.

7,8-Dihydro-6H-1,4,5,8a-tetraaza-fluoren-9-one (0.53 mmol) was treated with hydrazine hydrate (3.0 mmol) in ethanol (3 mL) for 20 h at RT. Ethanol was removed under vacuum and the crude produce was purified by flash chromatography (MeOH/DCM/Et$_3$N) to yield 8-(3-amino-propylamino)-6H-pyrazino[2,3-d]pyridazin-5-one.

This compound can be further derivatized similar to 2H-phthalazin-1-one compounds as described herein.

Example 7

This example illustrates a method for producing 5-methyl-2H-phthalazin-1-one and its derivatives.

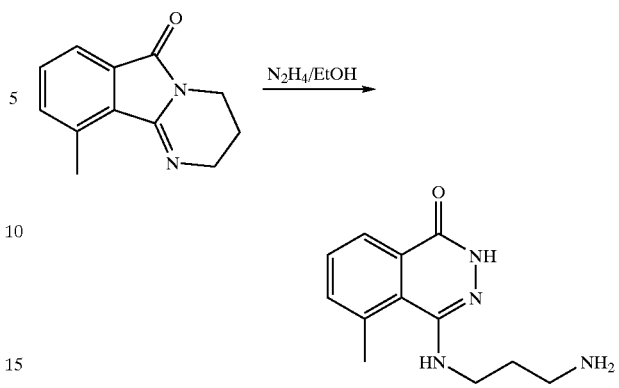

2-Iodo-3-methylbenzoic acid (1.50 g, 5.70 mmol) was dissolved in DMF (15 mL) and treated with CuCN (0.625 g, 7.0 mmol). The solution was heated at 85° C. for 1 h, cooled and poured into water (25 mL). The solution was cooled to 0° C. and 2-cyano-3-methylbenzoic acid precipitated from the solution was isolated by filtration to yield 0.651 mg of a white solid (71%). Crude 2-cyano-3-methylbenzoic acid (0.50 g, 3.1 mmol) was dissolved in MeOH (10 mL) and cooled to 0° C. This solution was treated with excess trimethylsilyl chloride (5.0 mmol) and allowed to warm to RT where it was stirred for 5 h. The methanol was removed under vacuum and the residue was treated with water (20 mL) and extracted with ethyl acetate and concentrated to yield methyl 2-cyano-3-methylbenzoate (0.44 g, 2.52 mmol). To this solid was added DMF (5 mL), Sc(OTf)$_3$ (0.01 g, 0.02 mmol), and diaminopropane (0.22 g, 3.0 mmol). The resulting mixture was heated at 85° C. for 0.5 h, cooled and the cyclic intermediate 5-Methyl-2,3-dihydro-1H-4,9a-diaza-fluoren-9-one was isolated by trituration with ether. This compound (0.112 g, 0.5 mmol) was dissolved in ethanol containing excess hydrazine hydrate (3.0 mmol). This solution was stirred at RT for 20 h and 4-(3-amino-propylamino)-5-methyl-2H-phthalazin-1-one was isolated by flash chromatography (MeOH/DCM/Et$_3$N).

This compound can be further derivatized similar to 2H-phthalazin-1-one compounds as described herein.

Example 8

This example illustrates a method for producing 5-methyl-2H-phthalazin-1-one and its derivatives.

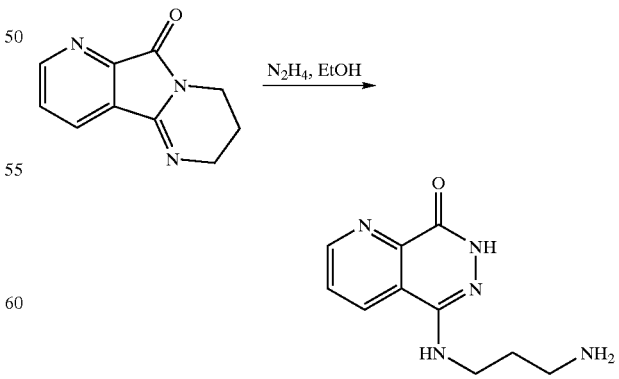

Using a procedure similar to that described for 6H-pyrido[2,3-d]pyridazin-5-one derivatives (Examples 5), 3-carbamoylpicolinic acid (1.5 mmol) was reacted with excess MsCl (4.0 mmol) to yield methyl 3-cyanopicolinate (1.2 mmol). Methyl 3-cyanopicolinate (1.2 mmol), Sc(OTf)$_3$ (0.02 mmol), and diaminopropane (3.0 mmol) were combined and heated at 80° C. for 1 h to yield 7,8-dihydro-6H-1,5,8a-triaza-fluoren-9-one, which was treated with excess hydrazine hydrate (5.0 mmol) in EtOH at RT to yield compound 5-(3-amino-propylamino)-7H-pyrido[2,3-d]pyrido[2,3-d]pyridazin-8-one (0.75 mmol) as a yellow solid.

This compound can be further derivatized similar to 2H-phthalazin-1-one compounds as described herein.

Example 9

This example illustrates a variety of methods for derivatizing a diamine substituted 2H-phthalazin-1-one compound.

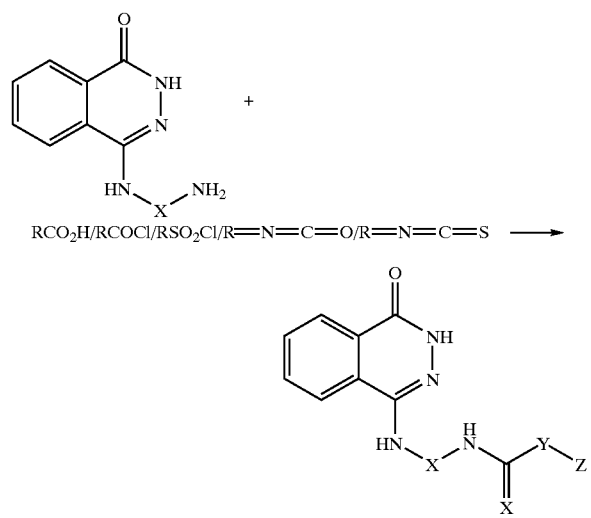

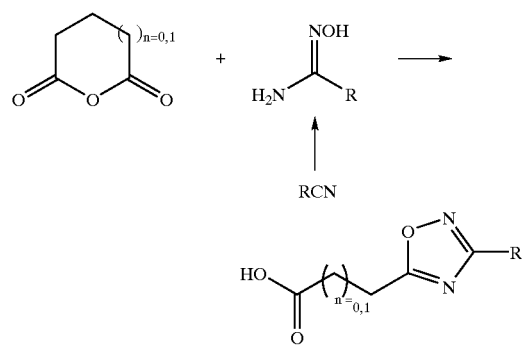

N-[3-(4-Oxo-3,4-dihydro-phthalazin-1-ylamino)-propyl]-substituted amides

General procedure A for synthesis of amides:

To a solution of starting amine (10 mg, 0.046 mmol) in DMA (300 µL), DIPEA (8.8 µL, 0.51 mmol) was added followed by an acyl chloride, e.g., benzoyl chloride (6.4 µL, 0.055 mmol). The mixture was stirred overnight at rt. DMSO (300 µL) was added and the mixture was filtered if a precipitate was present. Mass directed preparative LC/MS of the crude mixture afforded the desired material.

General procedure B for synthesis of amides:

To a solution of an amine, e.g., 4-(3-amino-propylamino)-2H-phthalazin-1-one (8.5 mg, 0.039 mmol) and acid (0.039 mmol) in DMA (400 µL), HOBt (5.8 mg, 0.043 mmol), EDC (8.1 mg, 0.043 mmol) and DIPEA (7.7 µL, 0.043 mmol) were added. The mixture was stirred overnight at rt. DMSO (400 µL) was added and if necessary filtered. Mass directed preparative LC/MS of the crude mixture afforded the desired material.

General procedure C for synthesis of amides:

Combined 0.05 mmol of 4-(3-amino-benzylamino)-2H-phthalazin-1-one with 0.075 mmol of a carboxylic acid, HATU (13.5 mg, 0.10 mmol), HOBt (17 mg, 0.125 mmol) and DIEA (36 µl, 0.20 mmol) in 800 µl DMA. Stirred 18 at RT. Mass directed preparative LC/MS of the crude mixture afforded the desired material.

Example 10

This example illustrates a method for synthesizing carboxylic acid compounds comprising an optionally substituted heteroaryl moiety.

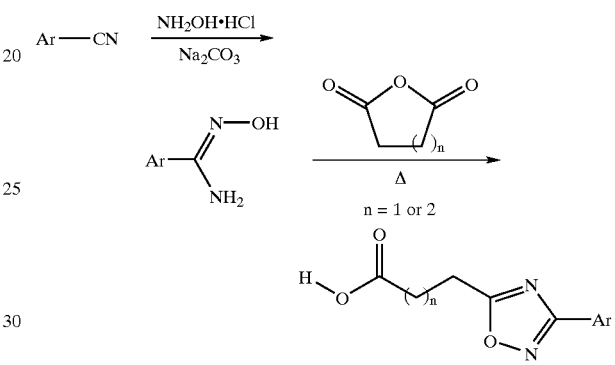

where Ar is optionally substituted aryl or optionally substituted heteroaryl.

Synthesis of amidoximes:

Amidoxime derivatives were prepared according to the modified procedures of Swain, C. J. et al., *J. Med. Chem.* 1991, 34, 140–151. Briefly, hydroxylamine hydrochloride (0.15 g, 2.1 mmol) and Na$_2$CO$_3$ (0.11 g, 1.05 mmol) were dissolved in 20% H$_2$O in EtOH, followed by addition of the nitrile compound (2.1 mmol). The mixture was heated to reflux 4–18 h. After removal of the solvent the amide oxime was purified via silica gel (0–5% MeOH/CH$_2$Cl$_2$) if necessary.

Synthesis of the corresponding acids:

The corresponding acids were prepared according to the procedure described by R. M. Srivastava et al., in *J. Het. Chem,* 1984, 21, 1193–1195.

Briefly, equimolar amounts of anhydride and amidoxime were heated at 120° C. for 3 h. The reaction mixtures were allowed to cool to rt and directly used for coupling with the template amines without further purification.

Example 11

This examples illustrates another method for synthesizing carboxylic acid compounds comprising an optionally substituted heteroaryl moiety and methods for further derivatizing the same or coupling the same to a 2H-phthalazin-1-one compound or its derivatives.

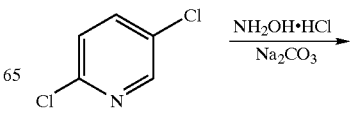

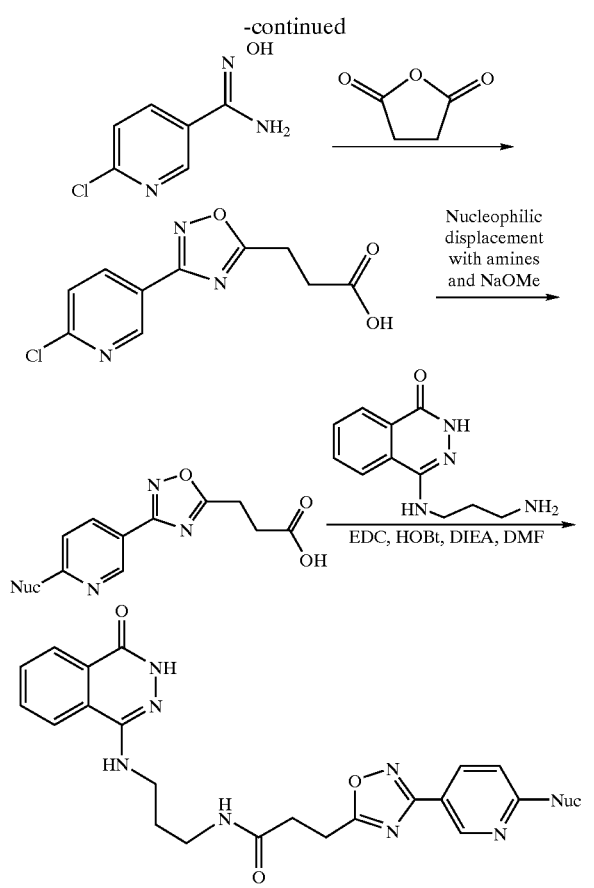

6-Chloro-N-hydroxy-nicotinamidine:

Hydroxylamine hydrochloride (0.50 g, 7.22 mmol) and $Na_2CO_3$ (0.38 g, 3.61 mmol) were dissolved in 2.5 mL water. A solution of 6-chloronicotinonitrile (1.00 g, 7.22 mmol) in 20 mL methanol was added and the combined solution was stirred 48 h at room temperature. The precipitate was filtered and dried to give 0.668 g (54%) of the product as a colorless solid.

3-[3-(6-Chloro-pyridin-3-yl)-[1,2,4-]oxadiazol-5-yl]-propionic acid:

Succinic anhydride (0.39 g, 3.89 mmol) and 6-chloro-N-hydroxy-nicotinamidine (0.67 g, 3.89 mmol) were dissolved in 2 mL of DMF and heated at 120° C. for 2 h. The cooled solution was filtered and the precipitate was washed with water, and dried to give the product as 0.70 g (71%) of colorless solid which was used without further purification. Displacement of the chloro group with an amine nucleophile, e.g., synthesis of 3-[3-(6-Methylamino-pyridin-3-yl)-[1,2,4]oxadiazol-5-yl]-propionic acid Methyl amine (2M, 1.5 mL, 3.0 mmol) was combined with 3-[3-(6-chloro-pyridin-3-yl)-[1,2,4]oxadiazol-5-yl]-propionic acid (76 mg, 0.3 mmol) in 2 mL ethanol and the solution was heated to 100° C. in a sealed overnight. After cooling, the solvent was removed and the residue was purified via RP-HPLC.

Displacement with sodium methoxide, e.g., synthesis of 3-[3-(6-Methoxy-pyridin-3-yl)-[1,2,4]oxadiazol-5-yl]-propionic acid Sodium methoxide (0.5 M, 3.94 mL, 1.97 mmol) was combined with 3-[3-(6-chloro-pyridin-3-yl)-[1,2,4] oxadiazol-5-yl]-propionic acid (100 mg, 0.394 mmol) and the solution was heated to 85° C. in a sealed tube 1 h. After cooling, the solvent was removed and the residue was extracted with ethyl acetate and $NaHSO_4$. After removal of the solvent from the organic layer the product was isolated as a colorless solid and used without further purification.

The acids were coupled to 4-(3-amino-propylamino)-2H-phthalazin-1-one according to the procedures described herein.

Example 12

This example illustrates a method for synthesizing 3-(3-amino-phenyl)-[1,2,4]oxadiazole and a method for coupling the same to 4-(3-amino-propylamino)-2H-phthalazin-1-one.

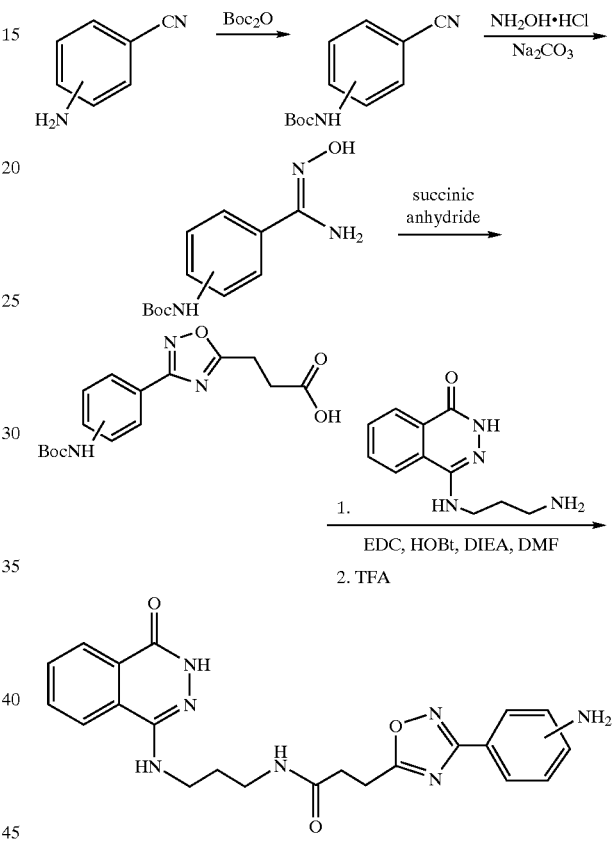

Synthesis of (3-Cyano-phenyl)-carbamic acid tert-butyl ester:

A solution of 3-amino-benzonitrile (118 mg, 1.00 mmol) and $Boc_2O$ (871 mg, 4.00 mmol) in 2.5 mL of THF was stirred at 60° C. under $N_2$ for 24 h. After removal of solvent, the residue was extracted with diethyl ether and $NaHSO_4$. The organic layer was dried over $MgSO_4$ and evaporated to yield (3-Cyano-phenyl)-carbamic acid tert-butyl ester (175 mg, 80%) which was used without further purification.

Synthesis of [3-(N-Hydroxycarbamimidoyl)-phenyl]-carbamic acid tert-butyl ester:

Hydroxylamine hydrochloride (179 mg, 2.60 mmol) and $Na_2CO_3$ (138 mg, 1.30 mmol) was dissolved in 1 mL water. A solution of (3-cyano-phenyl)-carbamic acid tert-butyl ester (560 mg, 2.60 mmol) in 10 mL of methanol was added and the combined solution was stirred at reflux overnight. The solvent was removed and the resulting precipitate was extracted with water and ethyl acetate to yield [3-(N-hydroxycarbamimidoyl)-phenyl]-carbamic acid tert-butyl ester which was used without further purification.

Synthesis of 3-[3-(3-tert-Butoxycarbonylamino-phenyl)-[1,2,4]oxadiazol-5-yl]-propionic acid:

Succinic anhydride (14 mg, 0.14 mmol) and [3-(N-hydroxycarbamimidoyl)-phenyl]-carbamic acid tert-butyl ester (35 mg, 0.14 mmol) were dissolved in 0.25 mL DMF and heated at 120° C. for 2 h. The cooled solution was evaporated and dried to yield 3-[3-(3-tert-butoxycarbonylamino-phenyl)-[1,2,4]oxadiazol-5-yl]-propionic acid which was used without further purification.

The acid was coupled to 4-(3-amino-propylamino)-2H-phthalazin-1-one according to the procedures described herein.

Example 13

This example illustrates a method for synthesizing 3-[3-(4-methylsulfanyl-phenyl)-[1,2,4]oxadiazol-5-yl]-propionic acid and 3-[3-(4-methanesulfonyl-phenyl)-[1,2,4]oxadiazol-5-yl]-propionic acid and a method for coupling the same to 4-(3-amino-propylamino)-2H-phthalazin-1-one.

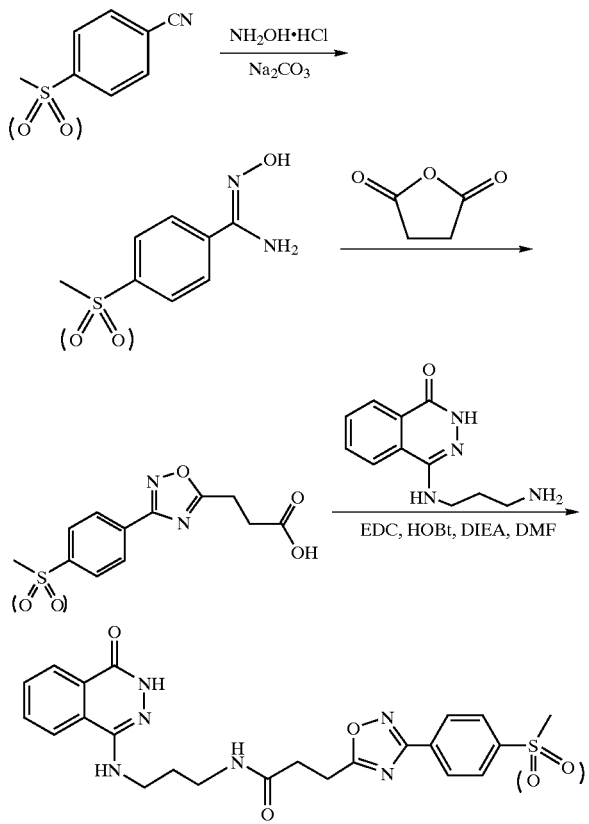

Synthesis of N-hydroxy-4-methylsulfanyl-benzamidine:

Hydroxylamine hydrochloride (104 mg, 1.5 mmol) and Na$_2$CO$_3$ (80 mg, 0.75 mmol) were dissolved in 0.5 mL of water. A solution of 4-methylsulfanyl-benzonitrile (223 mg, 1.5 mmol) in 4 mL of methanol was added and the combined solution was stirred at RT for about 48 h. After removal of the solvent, the precipitate was washed with water, filtered and dried to give N-hydroxy-4-methylsulfanyl-benzamidine (203 mg, 75%) which was used without further purification.

Synthesis of 3-[3-(4-methylsulfanyl-phenyl)-[1,2,4]oxadiazol-5-yl]-propionic acid:

Succinic anhydride (112 mg, 1.12 mmol) and N-hydroxy-4-methylsulfanyl-benzamidine (203 mg, 1.12 mmol) were dissolved in 2.0 mL of DMF and heated at 120° C. overnight. The cooled solution was evaporated and dried to give 3-[3-(4-methylsulfanyl-phenyl)-[1,2,4]oxadiazol-5-yl]-propionic acid which was used without further purification.

Synthesis of 4-methanesulfonyl-benzonitrile:

4-Methylsulfanyl-benzonitrile (250 mg, 1.68 mmol) was dissolved in 12 mL of HOAc. Potassium permanganate (531 mg, 3.36 mmol) was added as an aqueous solution (7–8 mL). After stirring 30 min at RT, NaHSO$_3$ was added with stirring until the brown color of the solution disappeared. The mixture was concentrated and diluted with water. The precipitate was filtered and dried in vacuo to yield 4-methanesulfonyl-benzonitrile (250 mg, 82%) which was used without further purification.

Synthesis of N-hydroxyl-4-methanesulfonyl-benzamidine:

Hydroxylamine hydrochloride (100 mg, 1.44 mmol) and Na$_2$CO$_3$ (76 mg, 0.72 mmol) were dissolved in 0.5 mL of water. A solution of 4-methanesulfanoyl-benzonitrile (260 mg, 1.44 mmol) in 4 mL of methanol was added and the combined solution was stirred at RT for about 48 h. After removal of the solvent, the precipitate was washed with water, filtered and dried to yield N-hydroxy-4-methanesulfonyl-benzamidine (180 mg, 59%) which was used without further purification.

Synthesis of 3-[3-(4-methanesulfonyl-phenyl)-[1,2,4]oxadiazol-5-yl]-propionic acid:

Succinic anhydride (85 mg, 0.85 mmol) and N-hydroxy-4-methanesulfonyl-benzamidine (180 mg, 0.85 mmol) were dissolved in 2.0 mL of DMF and heated at 120° C. overnight. The cooled solution was evaporated and dried to yield 3-[3-(4-methanesulfonyl-phenyl)-[1,2,4]oxadiazol-5-yl]-propionic acid which was used without further purification.

The acids were coupled to 4-(3-amino-proypylamino)-2H-phthalazin-1-one using the procedures disclosed herein.

Example 14

This example illustrates a method for synthesizing 2-[5-aryl-1,3,4-oxadiazol-2-yl]propionic acids and a method for coupling the same to 4-(3-amino-propylamino)-2H-phthalazin-1-one.

Method A:

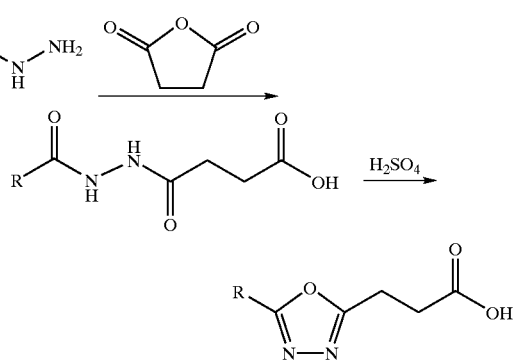

Method B:

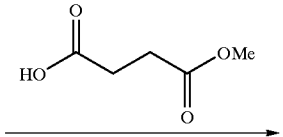

431

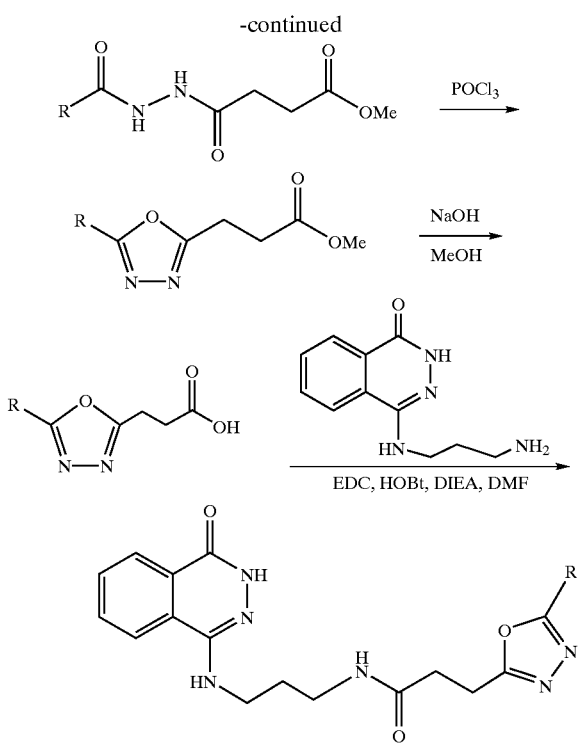

Method A
Synthesis of N-benzoyl succinic hydrazide:

Succinic anhydride (70 mg, 0.7 mmol) was dissolved in 3 mL of DMA with DIEA (183 µL, 1.05 mmol). Benzoyl hydrazide (95 mg, 0.7 mmol) was added and the solution was stirred at RT overnight. The solvent was removed in vacuo to yield N-benzoyl succinic hydrazide which was used without further purification.

Synthesis of 2-[5-phenyl-1,3,4-oxadiazol-2-yl]propionic acid:

The crude benzoyl succinic hydrazide (50 mg, 0.21 mmol) was dissolved in 1 mL conc. $H_2SO_4$ and heated to 80° C. for 30 min. The mixture was added to crushed ice and extracted with DCM. The organic layers were dried over $MgSO_4$ and evaporated to yield 2-[5-phenyl-1,3,4-oxadiazol-2-yl]propionic acid (40 mg, 87%) which was used without further purification.

For some oxadiazoles the product was not extracted, but simply filtered from the aqueous solution and dried. For many products this reaction sequence resulted in an undesired phthalimide product. In such instances method B described below can be utilized to yield a desired oxadiazoles.

Method B
Synthesis of N-(4-chlorobenzoyl)-methyl succinic hydrazide:

Combined monomethyl succinate (79 mg, 0.6 mmol) and EDC (134 mg, 0.7 mmol), HOBt (108 mg, 0.8 mmol) and DIEA (261 µL, 1.5 mmol) in 3 mL of DMF. Added 4-chlorobenzoyl hydrazide (85 mg, 0.5 mmol) and stirred overnight at RT. The solvent was removed in vacuo and the resulting residue was extracted with EtOAc, $NaHCO_3$, $NaHSO_4$, and brine. The organic layer was dried over $MgSO_4$ and evaporated to yield crude N-(4-chlorobenzoyl)-methyl succinic hydrazide (139 mg, 98%) which was used without further purification.

432

Synthesis of 2-[5-(4-chlorophenyl-1,3,4-oxadiazol-2-yl] methyl propionate:

N-(4-Chlorobenzoyl)-methyl succinic hydrazide (57 mg, 0.2 mmol) was combined with $POCl_3$ (186 µL, 2.0 mmol) and heated at 85° C. for 2 h. The solvent was removed in vacuo and the resulting mixture of methyl ester and free acid was used without further purification.

Synthesis of 2-[5-(4-Chlorophenyl-1,3,4-oxadiazol-2-yl] propionic acid:

The crude mixture from above was treated with 1N NaOH (300 µL, 0.3 mmol) in 2 mL of 10% $H_2O$/dioxane at 0° C. until all of the ester is consumed (1–3 h). The solvent was removed and the resulting residue was acidified with 10% $NaHSO_4$ and extracted with EtOAc. The organic layer was dried over $MgSO_4$ and evaporated to give the crude product (48 mg, 95%) which was used without further purification.

The acids from Method A and Method B were coupled to 4-(3-amino-proppylamino)-2H-phthalazin-1one according to procedures described herein (e.g., EDC/HOBt coupling protocol).

Example 15

This example illustrates a method for synthesizing 3-(5-aryl-2-tetrazolyl)propionic acids and a method for coupling the same to 4-(3-amino-propylamino)-2H-phthalazin-1-one.

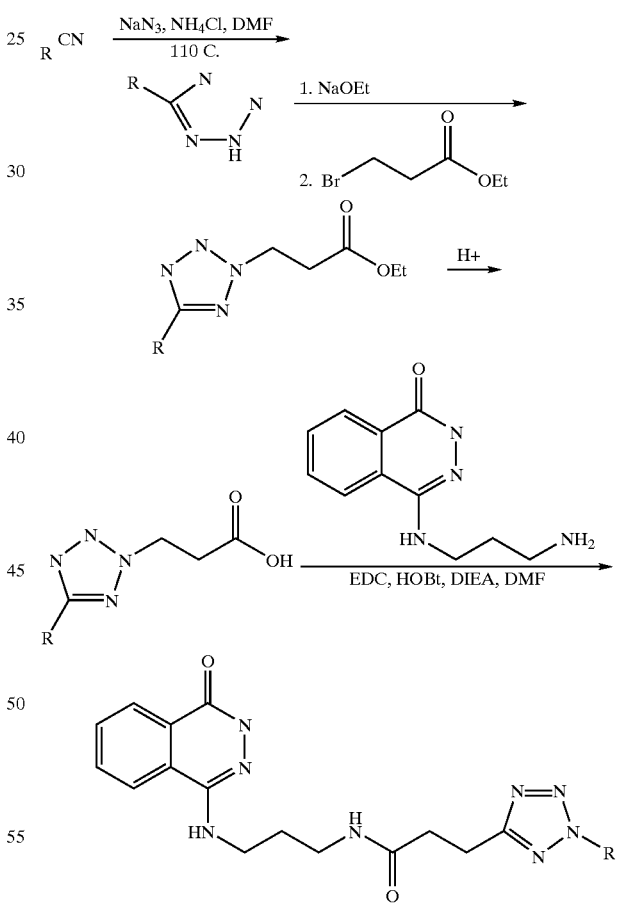

Tetrazoles were synthesized from nitrile compounds using a modified procedures of R. T. Buckler, S. Hayao, O. J. Lorenzetti, L. F. Sancilio, H. E. Hartzier, W. G. Strycker, *J. Med. Chem.*, 1970, 13, 725.

Synthesis of 5-p-tolyl tetrazole:

Tolunitrile (103 mg, 1.0 mmol) was refluxed with $NH_4Cl$ (70 mg, 1.3 mmol), and $NaN_3$ (85 mg, 1.3 mmol) in 3 mL of DMF overnight. The resulting 5-p-tolyl tetrazole was purified via RP-HPLC.

433

Synthesis of ethyl-3-(5-p-tolyl-2-tetrazolyl)propionate:

Sodium ethoxide (21%, 173 μL, 0.536 mmol) was dissolved in 650 μL absolute ethanol along with 5-p-tolyl tetrazole (65.9 mmol) at reflux. Ethyl 3-bromo-propionate (69 μL, 0.536 mmol) was added at reflux and the mixture was maintained at reflux overnight. The crude mixtures were filtered, concentrated and extracted with diethyl ether and sat. NaHCO$_3$. The organic layers were dried and evaporated. When necessary, further purification was performed by RP-HPLC to provide ethyl-3-(5-p-tolyl-2-tetrazolyl) propionate.

Synthesis of 3-(5-p-tolyl-2-tetrazolyl)propionic acid:

Ethyl-3-(5-p-tolyl-2-tetrazolyl)propionate (11.5 mg, 0.044 mmol) was dissolved in 120 μL of conc. HCl and 120 μL glacial acetic acid and heated to 85° C. overnight. The pure acid was precipitated by dilution with water, then filtered and dried to give 10 mg (97%) of colorless solid.

Tetrazole acids were then coupled to 4-(3-amino-propylamino)-2H-phthalazin-1-one using procedures described herein.

Example 16

This example illustrates a method for synthesizing 1-(3-aryl-1,2,4-oxadiazol-5-yl)acetamides and a method for coupling the same to 4-(3-amino-proypylamino)-2H-phthalazin-1-one.

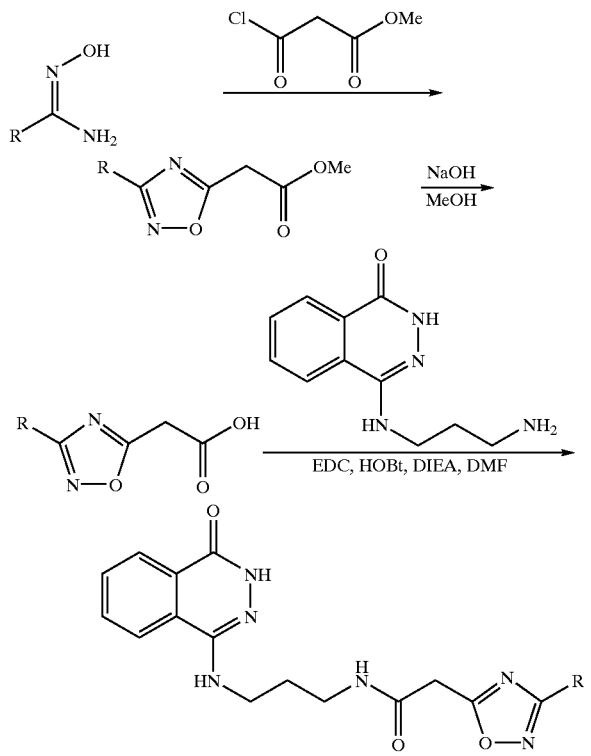

Synthesis of ethyl-1-[3-(4-methoxyphenyl)-1,2,4-oxadiazol-5-yl]acetate:

A solution of ethyl malonyl chloride (77 μL, 0.60 mmol), DIEA (209 μL, 1.2 mmol) and p-methoxy-benzamidoxime (100 mg, 0.60 mmol) in 5 mL of THF was stirred at RT for 1.5 h. An additional 77 μL of ethyl malonyl chloride was added and the mixture was stirred 1 h. The solvent was removed and the residue was heated at 110° C. under vacuum for 30 min, then RT under vacuum overnight. The desired product was purified via RP-HPLC to give 46 mg (30%) of a colorless oil.

434

Synthesis of 1-[3-(4-methoxyphenyl)-1,2,4-oxadiazol-5-yl] acetic acid:

A solution of ethyl-1-[3-(4-methoxyphenyl)-1,2,4-oxadiazol-5-yl]acetate (46 mg, 0.17 mmol) in 2 mL dioxane and 0.2 mL of water was cooled to 0° C. Sodium hydroxide (1H, 210 μL, 0.21 mmol) was added and the mixture was stirred at 0° C. 2 h. The solution was neutralized with 10% NaHSO$_4$ and concentrated, then extracted with EtOAc and 10% NaHSO$_4$. The organic layer was dried over MgSO$_4$ and evaporated to give the product (30 mg, 75%) as a colorless solid which was used without further purification.

The acid was coupled to 4-(3-amino-propylamino)-2H-phthalazin-1-one using the procedures described herein.

Example 16

This example illustrates a method for synthesizing 3-(5-aryl-[1,2,4]oxadiazol-3-yl)-propionic acid derivatives and method for coupling the same to 4-(3-amino-propylamino)-2H-phthalazin-1-one.

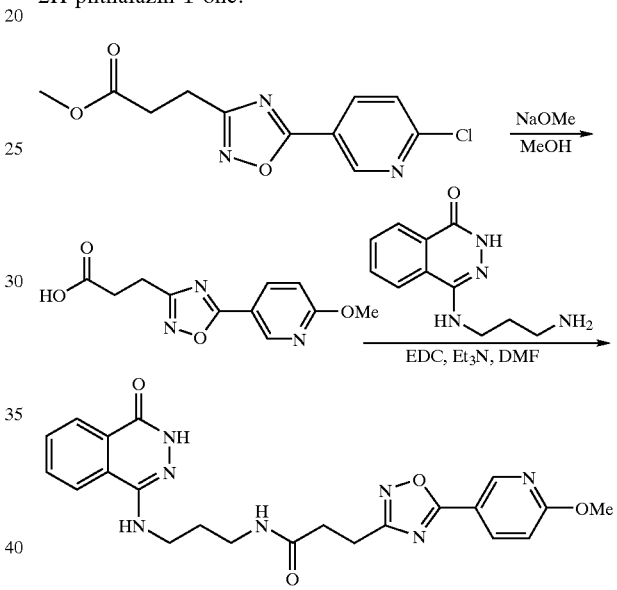

The oxadiazole moiety was prepared using a procedure similar to that described by Diaz-Ortiz, A.; Diez-Barra, E.; De La Hoz, A.; Moreno, A.; Gomez-Escalonilla, M. J.; Loupy, A.; *Heterocycles*, 1996, 43(5), 1021–1030.

Methyl 4-nitrobutyrate (200 mg, 1.36 mmol) and 6-chloronicotinonitrile (226 mg, 1.63 mmol) were dissolved in dioxane (3 mL) and treated with 1,4-phenylene diisocyanate (435 mg, 2.72 mmol) and triethylamine (2.0 mg, 0.02 mmol). The reaction mixture was heated in a microwave reactor for 4 min at 175° C. The reaction mixture was filtered and the filtrate was concentrated. 3-[5-(6-Methoxy-pyridin-3-yl)-[1,2,4]oxadiazol-3-yl]-propionic acid methyl ester was treated with excess NaOMe (5 mmol) in methanol (3 mL) and stirred at RT for 5 h. The methanol was removed under vacuum and the residue was dissolved in dioxane (5 mL) and treated with concentrated HCl dropwise until a precipitate formed. The resulting 3-[5-(6-methoxy-pyridin-3-yl)-[1,2,4] oxadiazol-3-yl]-propionic acid was collected by filtration and the purity was measured by RPLC (95%).

The acid (125 mg, 0.50 mmol) and 4-(3-amino-propylamino)-2H-phthalazin-1-one (100 mg, 0.46 mmol) were dissolved in DMF (2 mL) and treated with EDC (95 mg, 0.50 mmol) and triethylamine (76 mg, 0.75 mmol). Compound 3-[5-(6-methoxy-pyridin-3-yl)-[1,2,4]

oxadiazol-3-(4-oxo-3,4-dihydro-phthalazin-1-ylamino)-propyl]-propionamide was isolated by preparative RPLC.

Example 17

This example illustrates a method for synthesizing 3-(4-aryl-[1,2,3]triazol-1-yl)-propionic acid derivatives and a method for coupling the same to 4-(3-amino-propylamino)-2H-phthalazin-1-one.

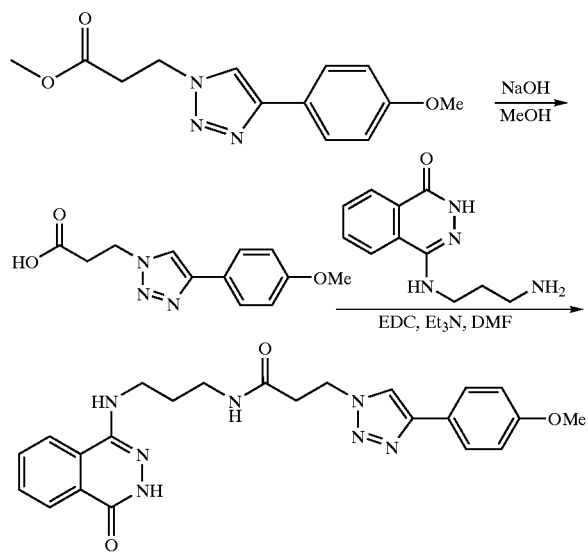

Methyl 4-azidobutyrate (200 mg, 1.40 mmol) and 1-ethynyl-4-methoxybenzene (277 mg, 210 mmol) were dissolved in dioxane (3 mL) and heated in a microwave reactor for 5 min at 175° C. The reaction mixture was filtered and the filtrate was concentrated under vacuum. Compound 3-[4-(4-methoxy-phenyl)-[1,2,3]triazol-1-yl]-propionic acid methyl ester was treated with aqueous 2M NaOH (5 mL) in THF (3 mL) and stirred at RT for 5 h. The methanol was removed under vacuum and the residue was dissolved in dioxane (5 mL) and treated with concentrated HCl dropwise until a precipitate formed. The resulting acid was collected by filtration and the purity was measured by RPLC (78%). Compound 3-[4-(4-methoxy-phenyl)-[1,2,3]triazol-1-yl]-propionic acid (125 mg, 0.50 mmol) and 4-(3-amino-propylamino)-2H-phthalazin-1-one (100 mg, 0.46 mmol) were dissolved in DMF (2 mL) and treated with EDC (95 mg, 0.50 mmol) and triethylamine (76 mg, 0.75 mmol). 3-[4-(4-Methoxy-phenyl)-[1,2,3]triazol-1-yl]-N-[3-(4-oxo-3,4-dihydro-phthalazin-1-ylamino)-propyl]-propionamide was isolated by preparative RPLC.

Example 18

This example illustrates a method for synthesizing 3-(5-aryl-isoxazol-3-yl)-propionic acid derivatives and a method for coupling the same to 4-(3-amino-propylamino)-2H-phthalazin-1-one.

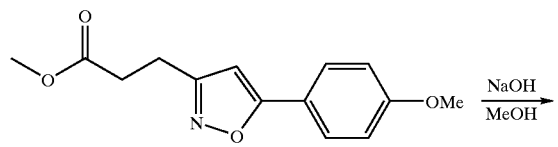

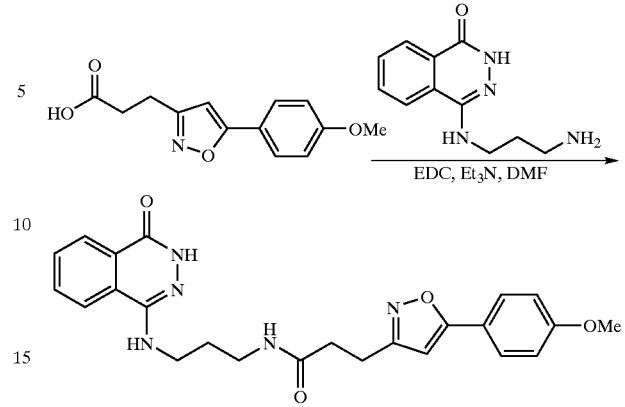

Isoxazole moiety was prepared using a procedure similar to that described by Dondoni, A.; Barbaro, G.; *J. Chem. Soc. Perkins* 2, 1974, 1591.

Methyl 4-nitrobutyrate (200 mg, 1.36 mmol) and 1-ethynyl-4-methyoxybenzene (264 mg, 2.00 mmol) were dissolved in dioxane (3 mL) and treated with 1,4-phenylene diisocyanate (435 mg, 2.72 mmol) and triethylamine (2.0 mg, 0.02 mmol). The reaction mixture was heated in a microwave reactor for 5 min at 185° C. The reaction mixture was filtered and the filtrate was concentrated under vacuum.

3-[5-(4-Methoxy-phenyl)-isoxazol-3-yl]-propionic acid methyl ester was treated with excess 4M NaOH in methanol (3 mL) and stirred at RT for 5 h. The methanol and water were removed under vacuum and the residue was dissolved in dioxane (5 mL) and treated with concentrated HCl dropwise until a precipitate formed. The resulting 3-[5-(4-methoxy-phenyl)-isoxazol-3-yl]-propionic acid was collected by filtration and the purity was measured by RPLC (91%).

3-[5-(4-Methoxy-phenyl)-isoxazol-3-yl]-propionic acid (124 mg, 0.50 mmol) and 4-(3-amino-propylamino)-2H-phthalazin-1-one (100 mg, 0.46 mmol) were dissolved in DMF (2 mL) and treated with 1-ethyl-3-(3-dimethylaminopropyl)carbodiimide hydrochloride (95 mg, 0.50 mmol) and triethylamine (76 mg, 0.75 mmol). 3-[5-(4-Methoxy-phenyl)-isoxazol-3-yl]-N-[3-(4-oxo-3,4-dihydro-phthalazin-1-ylamino)-propyl]-propionamide was isolated by preparative RPLC.

Example 19

This example illustrates a method for producing compounds of Formula I comprising a diaryl substituent.

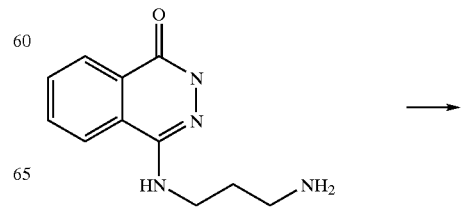

437
-continued

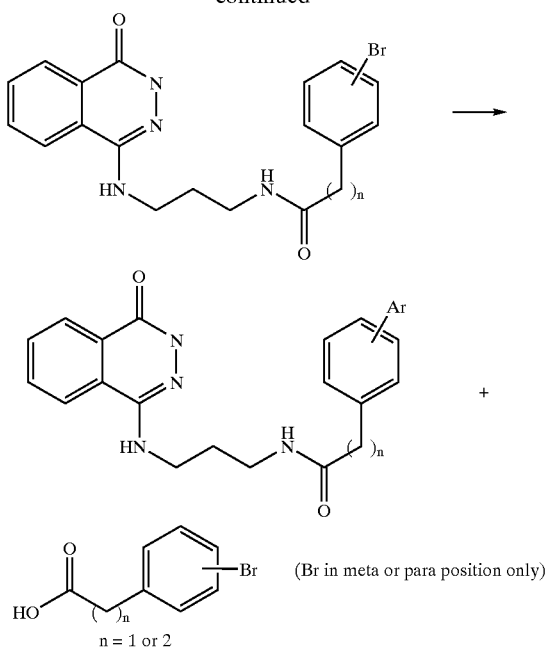

(Br in meta or para position only)

n = 1 or 2

Combined 4-(3-amino-propylamino)-2H-phthalazin-1-one (678 mg, 3.11 mmol) with 6.21 mmol acid, EDC (1.42 g, 7.46 mmol), HOBt (1.26 g, 9.33 mmol), and DIEA (2.2 ml, 12.4 mmol) in 50 mL DMA. Stirred 18 h at rt. Removed solvent and extracted with 150 mL of EtOAc and 50 mL of 10% $NaHSO_4$. Filtered the precipitate that formed on extraction. This material was used without further purification. Combined 0.05 mmol of the aryl bromide, 0.10 mmol LiCl, 1 mg Pd(OAc)$_2$, 16 mg PPh$_3$, and 0.06 mmol of an aryl boronic acid in 300 mL of DMA, 300 ml of MeOH, and 150 mL of 1M $Na_2CO_3$. Sealed the reaction vial and heated to 85° C. 18 h. Mass directed preparative LC/MS of the crude mixture afforded the desired material.

Example 20

This example illustrates a method for producing compounds of Formula I comprising a (thio)urea moiety.

To a solution of starting amine, e.g., 4-(3-amino-propylamino)-2H-phthalazin-1-one (17.5 mg, 0.08 mmol), in DMA (400 μL), DIPEA (17 μL, 0.095 mmol) was added followed by an (thio)isocyanate, e.g. 2-Isocyanato-1,4-dimethoxy-benzene (17.2 mg, 0.096 mmol). The mixture was stirred overnight at rt. DMSO (400 μL) was added and if necessary filtered. Mass directed preparative LC/MS of the crude mixture afforded the desired material.

Example 21

This example illustrates a method for producing compounds of Formula I comprising a sulfonamide moiety.
Synthesis of N-[3-(4-oxo-3,4-dihydro-phthalazin-1-ylamino)-propyl]-substituted sulfonamides:

To a solution of a starting amine (10 mg, 0.046 mmol) in DMA (300 μL), DIPEA (8.8 μL, 0.51 mmol) was added followed by sulfonyl chloride, e.g. benzoyl sulfonyl chloride (7 μL, 0.055 mmol). The mixture was stirred overnight at rt. DMSO (300 μL) was added and if necessary filtered. Mass directed preparative LC/MS of the crude mixture afforded the desired material.

438

Example 22

This example illustrates a method for coupling a carbonyl compound to diamine derivatives of compounds of Formula I using a reductive amination process.

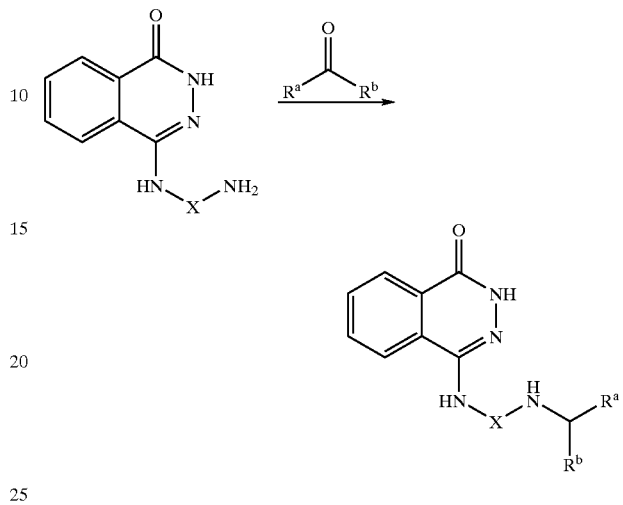

Synthesis of 4-(3-Benzylamino-propylamino)-2H-phthalazin-1-one:

To a mixture of 4-(3-amino-propylamino)-2H-phthalazin-1-one (22 mg, 0.10 mmol), DMF (1 mL), and AcOH (0.01 mL) was added benzaldehyde (11 mg, 0.10 mmol) and NaCNBH$_3$ (12 mg, 0.20 mmol). The reaction mixture was stirred at rt for 15 h, filtered, and purified by mass directed preparative LC/MS.

Example 23

This example illustrates a method for coupling compounds of Formula I comprising an imine moiety.

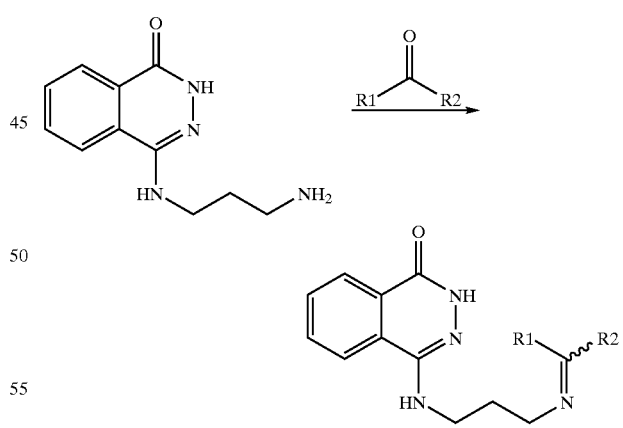

Synthesis of 4-{3-[(1,5-dimethyl-3-oxo-2-phenyl-2,3-dihydro-1H-pyrazol-4-ylmethylene)-amino]-propylamino}-2H-phthalazin-1-one To a mixture of 4-(3-Amino-propylamino)-2H-phthalazin-1-one (22 mg, 0.10 mmol), DMF (1 mL), and AcOH (0.01 mL) was added 4-antipyrinecarboxaldehyde (22 mg, 0.10 mmol). The reaction mixture was stirred at RT for 15 h, filtered, and isolated by mass directed preparative LC/MS. The purity was determined by RPLC/MS (95%).

Example 24

This example illustrates a method for producing 4-[3-(4-oxo-2-phenyl-3,4-dihydro-2H-pyridin-1-yl)-propylamino]-2H-phthalazin-1-one.

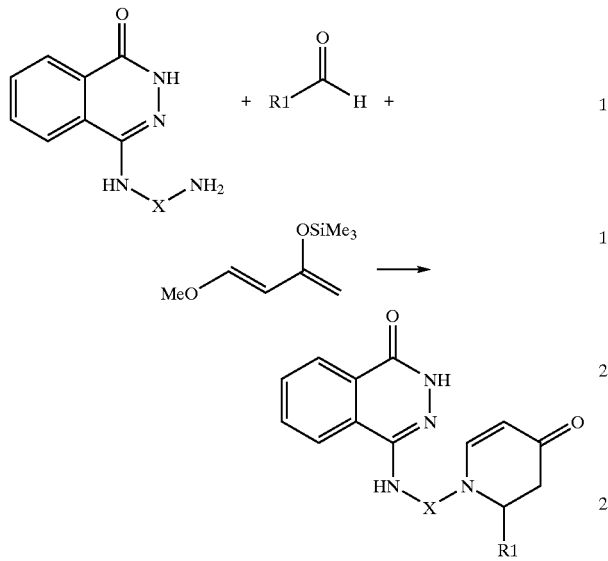

To a mixture of 4-(3-amino-propylamino)-2H-phthalazin-1-one (22 mg, 0.10 mmol), acetonitrile (i.e., ACN) (1 mL), Sc(OTf)$_3$ (5 mg, 0.01 mmol), and (3-Methoxy-1-methylene-allyloxy)-trimethylsilane (17 mg, 0.10 mmol) was added benzaldehyde (11 mg, 0.10 mmol). The reaction mixture was stirred at rt for 20 h, filtered, and purified by mass directed preparative LC/MS.

Example 24

This example illustrates a method for producing 2,2-Dimethyl-3-[3-(4-oxo-3,4-dihydro-phthalazin-1-ylamino)-propylamino]-3-phenyl-propionic acid methyl ester.

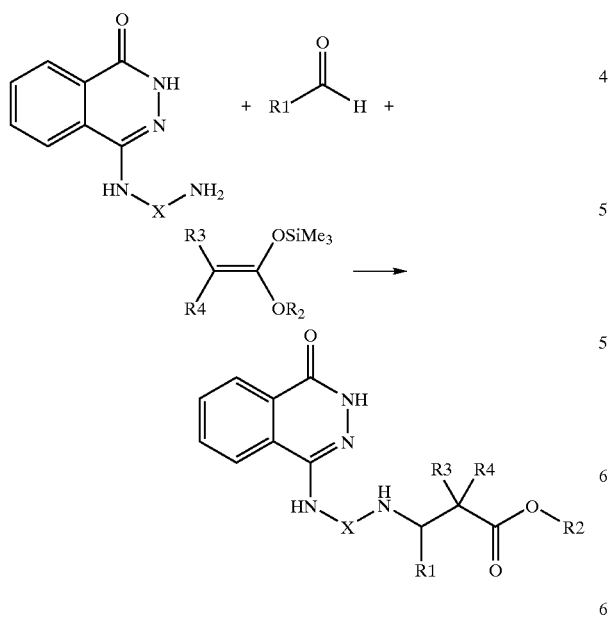

To a mixture of 4-(3-amino-propylamino)-2H-phthalazin-1-one (22 mg, 0.10 mmol), ACN (1 mL), Sc(OTf)$_3$ (5 mg, 0.01 mmol), and (1-methoxy-2-methyl-propenyloxy)-trimethylsilane (17 mg, 0.10 mmol) was added benzaldehyde (11 mg, 0.10 mmol). The reaction mixture was stirred at rt for 20 h, filtered, and purified by mass directed preparative LC/MS. The purity was determined by RLPC/MS (95%).

Example 25

This example illustrates a reductive alkylation of 4-aminophthalazinone to produce a various amino derivative.

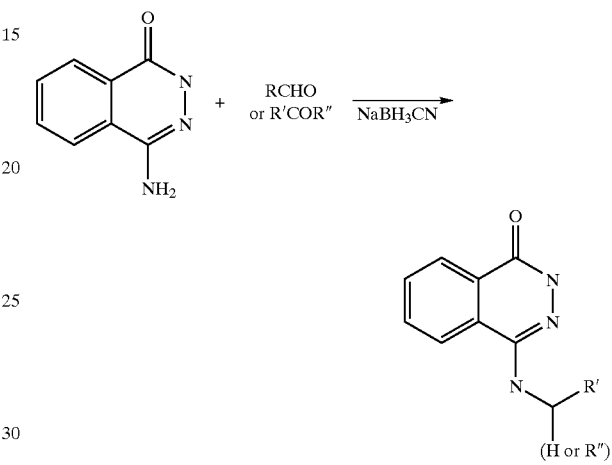

Combined 4-amino phthalazinone (0.0085 g, 0.05 mmol) and 50 µL acetic acid in 200 µL DMA. Added aldehyde or ketone (0.10 mmol) and shook 1 h at RT. Added NaBH$_3$CN (0.0079 g, 0.75 mmol) in 200 mL of DMA and shook 18 h at RT. Mass directed preparative LC/MS of the crude mixture afforded the desired material. The purity was determined by RPLC/MS.

Example 26

This example illustrates a method for alkylating a 4-aminophthalazinone derivatives.

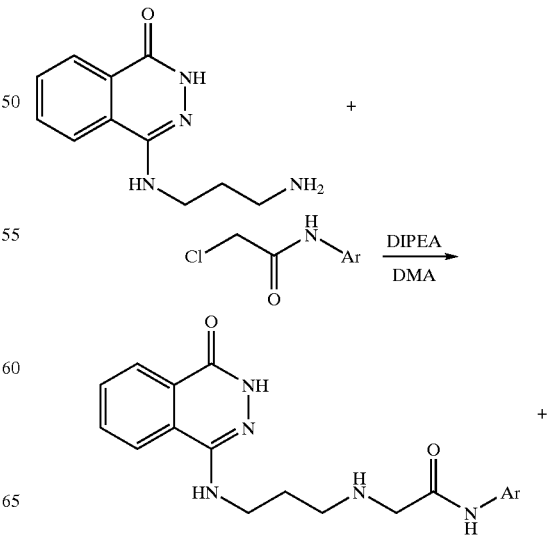

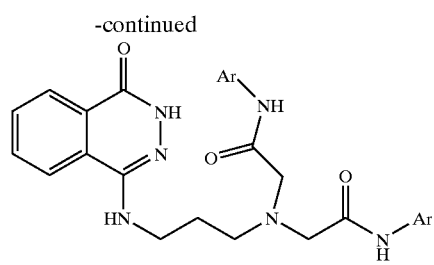

To a solution of 4-(3-amino-propylamino)-2H-phthalazin-1-one (15 mg, 0.07 mmol) in DMA (500 μL) a chloro or bromo acetamide, e.g. 2-chloro-N-(5-methyl-1-phenyl-1H-pyrazol-3-yl)-acetamide (17.5 mg, 0.07 mmol), and DIPEA (15 μL, 0.084 mmol) were added. The mixture was stirred and heated to 80° C. overnight, diluted with DMSO (400 μL) and purified by preparative HPLC. The mono and dialkylated products were isolated. The purity was determined by RPLC/MS.

Example 27

This example illustrates a method for synthesizing 4-alkylaminomethyl-2H-phthalazin-1-ones and derivatives thereof.

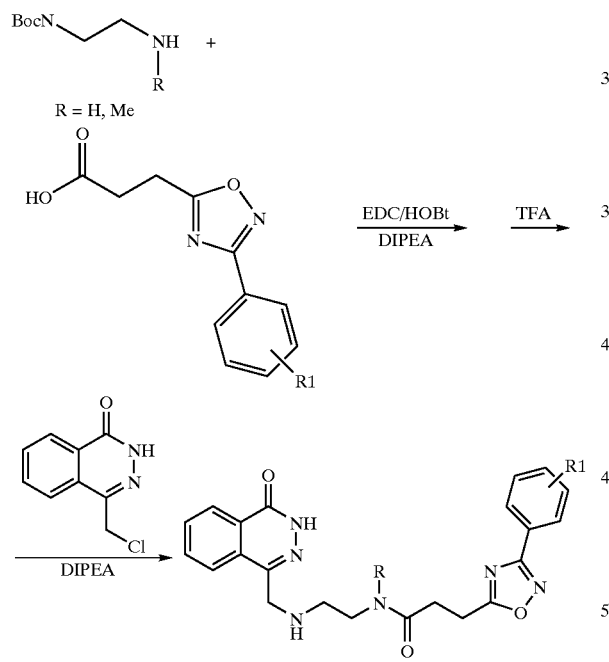

Synthesis of (2-{3-[3-(4-methoxy-phenyl)-[1,2,4]oxadiazol-5-yl]-propionylainino}-ethyl)-carbamnic acid tert-butyl ester 3-[3-(4-Methoxy-phenyl)-[1,2,4]oxadiazol-5-yl]-propionic acid (100 mg, 0.40 mmol) and (2-amino-ethyl)-carbamic acid tert-butyl ester (71.4 mg, 0.41 mmol) were dissolved in DMF (1 mL). HOBt (59 mg, 0.44 mmol), EDC (84 mg, 0.44 mmol) and DIPEA (78 μL, 0.44 mmol) were added. The mixture was stirred at rt overnight. CH$_2$Cl$_2$ was added and the organic layer was washed with sat NaHCO$_3$, 10% citric acid and brine. Dried (MgSO$_4$) and concentrated in vacuo. The resulting product can be purified on silica gel column chromatography (gradient CH$_2$Cl$_2$ to CH$_2$Cl$_2$MeOH 95/5). Yield 68%.

Synthesis N-(2-Amino-ethyl)-3-[3-(4-methoxy-phenyl)-[1,2,4]oxadiazo-1-5-yl]-propionamide The Boc group of (2-{3-[3-(4-methoxy-phenyl)-[1,2,4]oxadiazol-5-yl]-propionylamino}-ethyl)-carbamic acid tert-butyl was removed by treatment with CH$_2$Cl$_2$/TFA (1/1) for 1 hour at rt followed by concentration in vacuo. The residue was dissolved in MeOH/water (5/1) and Dowex OH$^-$ was added until the pH was about 8. The ion exchange resin was removed by filtration and the residue was concentrated in vacuo.

Synthesis of 3-[3-(4-methoxy-phenyl)-[1,2,4]oxadiazol-5-yl]-N-{2-[(4-oxo-3,4-dihydro-phthalazin-1-ylmethyl)-amino]-ethyl}-propionamide To a solution of 4-chloromethyl-2H-phthalazin-1-one (9.7 mg, 0.05 mmol) in DMF (200 μL), N-(2-amino-ethyl)-3-[3-(4-methoxy-phenyl)-[1,2,4]oxadiazol-5-yl]-propionamide (14.4 mg, 0.05 mmol) and DIPEA (9 μL, 0.05 mmol) were added. The mixture was stirred overnight at rt and directly applied to preparative HPLC. The purity was determined by RPLC/MS.

Example 28

This example illustrates another method for synthesizing 4-alkylaminomethyl-2H-phthalazin-1-ones and derivatives thereof.

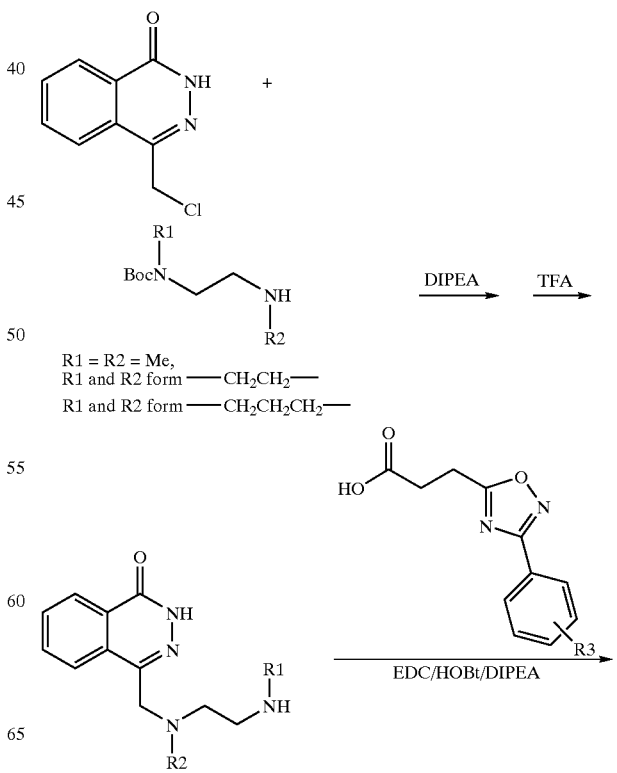

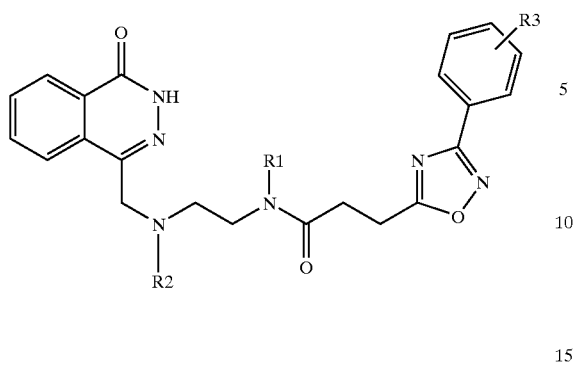

Synthesis of 4-(4-{3-[3-(4-methoxy-phenyl)-[1,2,4]oxadiazol-5-yl]-propionyl}-piperazin-1-ylmethyl)-2H-phthalazin-1-one To a solution of 4-chloromethyl-2H-phthalazin-1-one (40 mg, 0.21 mmol) in DMA (800 µL), piperazine-1-carboxylic acid tert-butyl ester (39 mg, 0.21 mmol) and DIPEA (37 µL, 0.21 mmol) were added. The mixture was stirred overnight at rt and concentrated in vacuo. TFA (1 mL) was added and the mixture was stirred for 1 hr at rt. The solvent was removed in vacuo followed by coevaporation with dioxane. To 400 µL of a stock solution of the residue in DMA (0.25 mM), 3-[3-(4-methoxy-phenyl)-[1,2,4]oxadiazol-5-yl]-propionic acid (26 mg, 0.11 mmol), EDC (22 mg, 0.12 mmol), HOBt (16 mg, 0.12 mmol) were added. Followed by DIPEA addition until neutral pH. The mixture was stirred overnight at rt and directly applied to preparative HPLC. The purity was determined by RPLC/MS.

Example 29

This example illustrates yet another method for synthesizing 4-alkylaminomethyl-2H-phthalazin-1-ones and derivatives thereof.

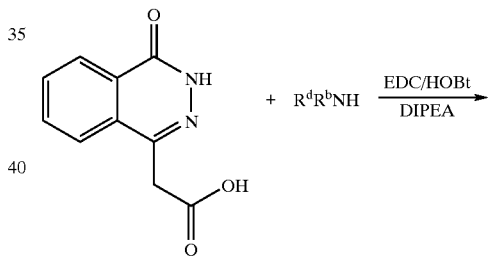

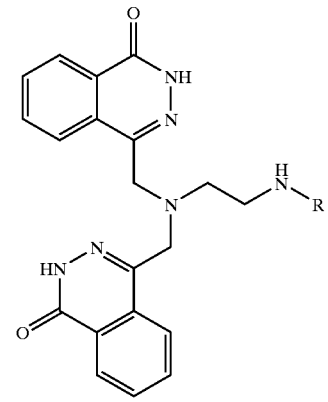

To a solution 4-chloromethyl-2H-phthalazin-1-one (13 mg, 0.067 mmol) in DMA (400 µL) were added the amine (e.g., N-(2-amino-ethyl)-acetamide (8 mg, 0.08 mmol)) and DIPEA (14.3 µL, 0.08 mmol). The mixture was stirred overnight at RT, diluted with DMSO (400 µL) and purified by preparative HPLC to yield 4-[(2-amino-ethylamino)-methyl]-2H-phthalazin-1-one and the dialkylated compound. The purity was determined by RPLC/MS.

Example 30

This example illustrates a method for producing N-substituted-2-(4-oxo-3,4-dihydro-phthalazin-1-yl)-acetamides.

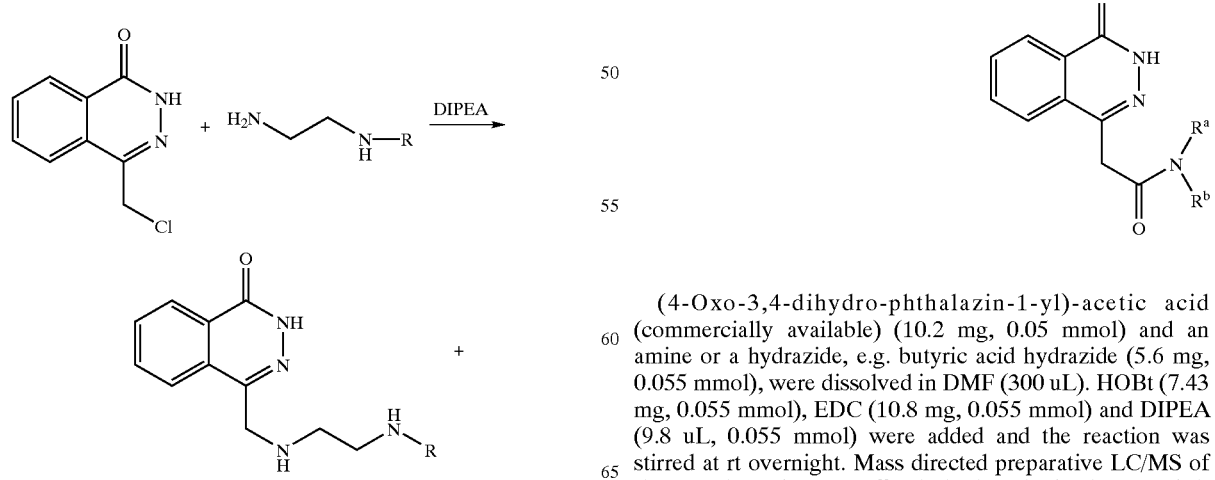

(4-Oxo-3,4-dihydro-phthalazin-1-yl)-acetic acid (commercially available) (10.2 mg, 0.05 mmol) and an amine or a hydrazide, e.g. butyric acid hydrazide (5.6 mg, 0.055 mmol), were dissolved in DMF (300 uL). HOBt (7.43 mg, 0.055 mmol), EDC (10.8 mg, 0.055 mmol) and DIPEA (9.8 uL, 0.055 mmol) were added and the reaction was stirred at rt overnight. Mass directed preparative LC/MS of the crude mixture afforded the desired material.

Example 31

This example illustrates a method for producing 8-(cis-3-aminocyclohexyl-amino)-6H-pyrido[2,3-d]pyridazin-5-one and 5-(cis-3-aminocyclohexylamino)-7H-pyrido[2,3-d]pyridazin-8-one.

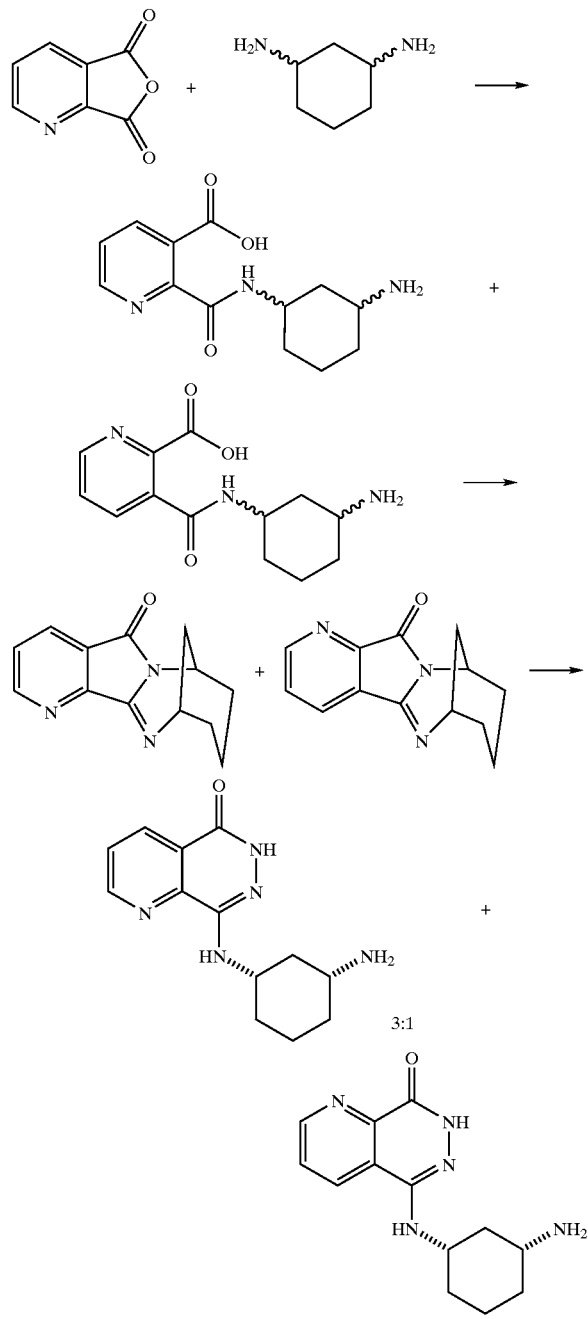

A 500 mL, four-neck, round bottomed flask equipped with a magnetic stirrer, an addition funnel, a thermometer, and a distillation condenser was charged with 2,3-pyridinedicarboxylic anhydride (26.1 g, 175 mmol) and ethanol (90 mL). To the resulting suspension, a solution of 1,3-cyclohexanediamine (mixture of cis- and trans-isomers, 21.0 g, 184 mmol) in ethanol (10 mL) was added dropwise over 30 min. An exothermic reaction was observed, and the reaction mixture gently refluxed during the addition. After stirring for 2.5 h at ambient temperature, the reaction mixture was heated to reflux, then evaporated to dryness. The resulting residue was heated to 210° C. for 1.5 h, the reaction mixture was cooled to ambient temperature and purified by column chromatography. This afforded a 50% yield of a mixture of 6,10-methano-7,8,9,10-tetrahydro-6H-1,5,10a-triazacycloocta[a]inden-11-one and 6,10-methano-7,8,9,10-tetrahydro-6H-4,5,10a-triazacycloocta[a]inden-11-one. Major isomer: white solid; m.p. 141–143° C., $^1$H NMR (CDCl$_3$) δ (ppm) 8.79 (dd, 1H, J=1.3, 4.9 Hz), 8.04 (dd, 1H, J=1.3, 7.6 Hz), 7.45 (dd, 1H, J=4.9, 7.6 Hz), 4.48 (bs, 1H), 4.25 (bs, 1H), 1.16–1.99 (m, 8H). Minor isom: pale yellow solid; m.p. 165–167° C., $^1$H NMR (CDCl$_3$) δ (ppm) 8.78 (dd, 1H, J=1.2, 4.8 Hz), 8.10 (dd, 1H, J=1.2, 7.7 Hz), 7.49 (dd, 1H, J=4.8, 7.7 Hz), 4.49 (bs, 1H), 4.15 (bs, 1H), 1.13–1.95 (m, 8H).

A 50 mL round bottomed flask equipped with a magnetic stirrer was charged with this mixture of isomers (2.50 g, 11.0 mmol), hydrazine monohydrate (1.49 g, 29.8 mmol) and 1-butanol (5 mL). The reaction mixture was heated to reflux and was stirred at reflux for 13.5 h. After cooling to ambient temperature, the reaction mixture was evaporated to dryness and the residue was purified by column chromatography to give a 68% yield of 8-(cis-3-aminocyclohexylamino)-6H-pyrido[2,3-d]pyridazin-5-one and a 23% yield of 5-(cis-3-aminocyclohexylamino)-7H-pyrido[2,3-d]pyridazin-8-one.

8-(cis-3-Aminocyclohexylamino)-6H-pyrido[2,3-d]pyridazin-5-one, yellow solid; $^1$H NMR (CD$_3$OD) δ (ppm) 9.01 (dd, 1H, J=1.6, 4.6 Hz), 8.60 (dd, 1H, J=1.6, 8.1 Hz), 7.80 (dd, 1H, J=4.6, 8.1 Hz), 3.76 (tt, 1H, J=3.7, 11.4 Hz), 2.78 (tt, 1H, J=3.7, 11.2 Hz), 2.37 (bd, 1H, J=11.8 Hz), 2.13 (bd, 1H, J=11.8 Hz), 1.80–2.03 (m, 2H), 1.42 (ddt, 1H, J=3.3, 13.2, 26.4 Hz), 1.06–1.27 (m, 3H); m/z=260 (M+H).

5-(cis-3-aminocyclohexylamino)-7H-pyrido[2,3-d]pyridazin-8-one, yellow solid; $^1$H NMR (CD$_3$OD) δ (ppm) 9.02 (dd, 1H, J=1.5,4.5 Hz), 8.55 (dd, 1H, J=1.5, 8.4 Hz), 7.86 (dd, 1H, J=4.5, 8.4 Hz), 3.78 (tt, 1H, J=3.7, 11.4 Hz), 2.79 (tt, 1H, J=3.7, 11.3 Hz), 1.79–2.38 (m, 4H), 1.10–1.43 (m, 4H); m/z=260 (M+H).

Other amines prepared by this method are listed below. Yields in the range of 9–87% were observed:

4-(3-Aminopropylamino)-5,8-difluoro-2H-phthalazin-1-one;

4-(3-Aminopropylamino)-5-nitro-2H-phthalazin-1-one;

4-(3-Amino-2,2-dimethylpropylamino)-2H-phthalazin-1-one;

4-(3-Amino-2-hydroxypropylamino)-2H-phthalazin-1-one; and 4-(cis-3-Aminocyclohexylamino)-2H-phthalazin-1-one.

Example 32

This example illustrates a method for producing 4-(2-dimethylaminoethoxy)-benzonitrile.

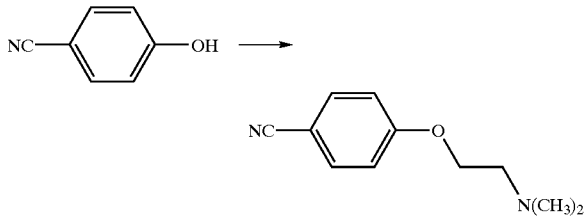

This material was prepared by a procedure adapted from U.S. Pat. No. 2,970,149 as follows.

A 1-L, three-neck, round bottomed flask equipped with a magnetic stirrer, a thermometer and a distillation condenser was charged with 4-cyanophenol (23.8 g, 0.200 mol) and toluene (230 mL). To the resulting suspension, a 25% solution of sodium methoxide in methanol (4.38 M, 68 mL, 0.300 mol) was added. The reaction was heated, and an azeotrope of methanol and toluene was distilled until the internal temperature reached 100° C. The reaction was then cooled to ambient temperature. In a second 1-L, one-neck, round bottomed flask equipped with a magnetic stirrer, 2-dimethylaminoethylchloride hydrochloride (13.2 g, 0.300 mol) was slurried in toluene (200 mL), and saturated aqueous potassium carbonate (400 mL) added. The mixture was cooled to −5° C., stirred for 4 h, and the organic layer was separated and transferred to a 1-L flask placed in an ice water bath. This toluene solution of 2-dimethylaminoethyl chloride was transferred via a cannula from this flask slowly over 45 min into the above suspension of sodium 4-cyanophenolate in toluene, maintaining the reaction temperature between 15–20° C. After the addition was finished, the mixture was refluxed for 65 h. The reaction mixture was then cooled to ambient temperature, the inorganic salts removed by vacuum filtration, and the filtrate washed with water and dried over sodium sulfate. Evaporation of the filtrate to dryness afforded an 83% yield of the title compound as a yellow oil. $^1$H NMR (DMSO-$d_6$) δ (ppm) 7.65 (d, 2H, J=8.8 Hz), 7.09 (d, 2H, J=8.8 Hz), 4.18 (t, 2H, J=5.4 Hz), 2.79 (t, 2H, J=5.4 Hz), 2.34 (s, 6H); m/z=191 (M+H).

Other benzonitriles compounds prepared by this method are listed below. Yields in the range of 59–93% were observed:

3-(2-Dimethylaminoethoxy)benzonitrile

4-[2-(4-Morpholinyl)ethoxy]benzonitrile

Example 33

This example illustrates a method for producing 4-dimethylaminomethyl-benzonitrile.

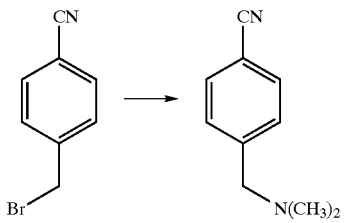

A 500-mL, three-neck, round bottomed flask equipped with a magnetic stirrer, an addition funnel, a thermometer, and a reflux condenser was charged with 4-bromomethylbenzonitrile (7.84 g, 40.0 mmol) and THF (50 mL). A 2 M solution of dimethylamine in THF (60 mL, 120 mmol) was added dropwise over 10 min at ambient temperature. An exothermic reaction was observed. After stirring at ambient temperature for 24 h, the reaction mixture was partitioned between 1 N hydrochloric acid (150 mL) and diethyl ether (200 mL). The ether layer was separated and the aqueous phase basified with saturated aqueous potassium carbonate solution to pH 9. The resulting mixture was extracted with diethyl ether (3×100 mL). The combined organic phase was dried over sodium sulfate and filtered. Evaporation of the filtrate to dryness gave a 97% yield of the title compound as a tan oil. $^1$H NMR (CDCl$_3$) δ (ppm) 7.60 (d, 2H, J=8.2 Hz), 7.44 (d, 2H, J=8.2 Hz), 3.47 (s, 2H), 2.24 (s, 6H); m/z=161 (M+H).

3-Dimethylaminomethylbenzonitrile was also prepared by this method in 94% yield.

Example 34

This example illustrates a method for producing 5-di-tert-butyloxycarbonylamino-1-methyl-1H-pyrazole-4-carbonitrile.

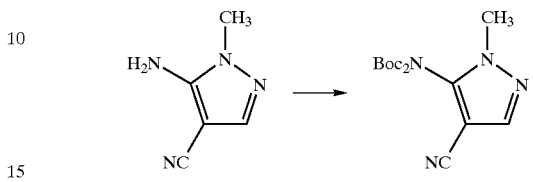

A 500-mL, one-neck, round bottomed flask equipped with a magnetic stirrer was charged with 5-amino-1-methyl-1H-pyrazole-4-carbonitrile (2.00 g, 16.4 mmol), triethylamine (5.02 g, 49.1 mmol), DMAP (0.20 g, 1.64 mmol), and THF (100 mL). To the resulting mixture was added di-tert-butyl dicarbonate (7.87 g, 36.1 mmol). After stirring for 4 h at ambient temperature, the reaction mixture was partitioned between saturated aqueous ammonium chloride solution (100 mL) and methylene chloride (200 mL). The organic phase was separated, dried over sodium sulfate and filtered. Concentration of the filtrate followed by column chromatography gave a 100% yield of the title compound as a light yellow oil. $^1$H NMR (CDCl$_3$) δ (ppm) 7.75 (s, 1H), 3.72 (s, 3H), 1.47 (s, 18H).

Other protected amines prepared by this method are listed below; yields in the range of 41–100% were observed:

3-Di-tert-Butyloxycarbonylaminobenzonitrile;

4-Di-tert-Butyloxycarbonylamino-2-methylsulfanylthiazole-5-carbonitrile;

5-Di-tert-Butyloxycarbonylaminothiophene-3-carbonitrile;

tert-Butyl 4-Di-tert-Butyloxycarbonylamino-5-cyanoimidazole-1-carboxylate;

tert-Butyl 5-Di-tert-Butyloxycarbonylamino-4-cyanoimidazole-1-carboxylic;

5-Di -tert-Butyloxycarbonylamino-3-methylisoxazole-4-carbonitrile;

5-Di-tert-Butyloxycarbonylaminothiophene-2-carbonitrile; and tert-Butyl 3-Di-tert-Butyloxycarbonylamino-4-cyanopyrazole-1-carboxylate

Example 35

This example illustrates a method for producing tert-Butyl (4-Cyano-1H-pyrazol-3-yl)carbamate.

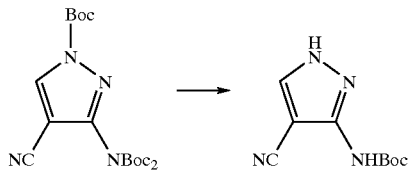

A 500-mL, one-neck, round bottom flask equipped with a magnetic stirrer and a reflux condenser was charged with tert-butyl 3-di-tert-butyloxycarbonylamino-4-cyanopyrazole-1-carboxylate (25.5 g, 62.4 mmol), potassium carbonate (19.2 g, 137 mmol), ethanol (200 mL) and water (190 mL). The reaction was then heated to reflux for 5 h. After this time the reaction was cooled to room temperature and the ethanol was removed under reduced pressure. Ethyl acetate (200 mL) was added to the resulting mixture, and the layers separated. The aqueous layer was extracted with ethyl acetate (2×200 mL) and the combined organic extracts washed with saturated sodium chloride solution (2×150 mL) and dried over sodium sulfate. Filtration and concentration under reduced pressure afforded a crude solid. Recrystallization of this material from ethyl acetate afforded a 60% yield of the title compound as a white solid. m.p. 167–170° C.; $^1$H NMR (DMSO), δ (ppm)=13.30 (bs, 1H), 9.50 (bs, 1H), 8.43 (bs, 1H), 1.40 (s, 9H).

A mixture of tert-butyl (5-cyano-1H-imidazol-4-yl) carbamate and tert-butyl (4-cyano-1H-imidazol-5-yl) carbamate was also prepared by this method in 49% yield.

Example 36

This example illustrates a method for producing tert-butyl [4-cyano-1-(2-trimethylsilylethoxymethyl)-1H-pyrazol-3-yl]carbamate.

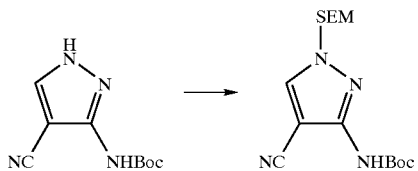

A 200-mL, one-neck, round bottomed flask equipped with a magnetic stirrer and a digital thermometer was charged with tert-butyl (4-cyano-1H-pyrazol-3-yl)carbamate (196 mg, 0.94 mmol) and anhydrous THF (10 mL). The reaction mixture was cooled to –25° C. and a 1 M solution of sodium hexamethyldisilazide in THF (1.0 mL, 1.0 mmol) was added in one portion. After stirring for 20 min the reaction was allowed to warm to room temperature. 2-Chloromethoxyethyltrimethylsilane (0.2 mL, 1.1 mmol) was added in one portion and stirring continued for 1 h. Ethyl acetate (15 mL) and water (10 mL) were then added to the reaction mixture. The layers were separated and the aqueous layer extracted with ethyl acetate (2×10 mL). The combined organic extracts were washed with saturated sodium chloride solution (2×15 mL), dried over sodium sulfate, filtered, and concentrated under reduced pressure. Purification of the resulting residue by column chromatography afforded a 100% yield (318 mg) of the title compound as colorless oil. $^1$H NMR (CDCl$_3$), δ (ppm)=6.72 (bs, 1H), 5.33 (s, 2H), 3.60 (t, 2H, J=8.2 Hz), 1.54 (s, 9H), 0.93 (t, 2H, J=8.2 Hz), 0.00 (s, 9H).

A mixture of tert-butyl [5-cyano-1-(2-trimethylsilylethoxymethyl)-1H-imidazol-4-yl]carbamate and tert-butyl [4-cyano-1-(2-trimethylsilylethoxymethyl)-1H-imidazol-5-yl]carbamate was also prepared by this method in 75% yield using potassium carbonate as a base and dimethylformamide as a solvent.

Example 37

This example illustrates a method for producing 2-ethanesulfonylthiophene-5-carbonitrile.

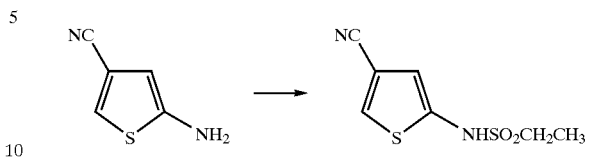

A 100 mL, one-neck, round bottomed flask equipped with a magnetic stirrer and a digital thermometer was charged with 5-aminothiophene-3-carbonitrile (300 mg, 2.42 mmol), pyridine (0.28 g, 3.59 mmol), and methylene chloride (10 mL). A solution of ethanesulfonyl chloride (0.34 g, 2.64 mmol) in methylene chloride (5 mL) was then added dropwise over 5 min at 0° C. under nitrogen. After stirring at 0° C. for 1 h, the reaction mixture was warmed to ambient temperature, then stirred at ambient temperature for another 20 h. The reaction mixture was diluted with methylene chloride (50 mL) then washed with 1 N hydrochloric acid (2×20 mL) and saturated sodium chloride solution (20 mL). The organic phase was dried over sodium sulfate and filtered. Concentration of the filtrate followed by column chromatography afforded a 75% yield of the title compound as a brown solid. $^1$H NMR (CDCl$_3$) δ (ppm) 7.83 (bs, 1H), 7.68 (d, 1H, J=1.5 Hz), 7.02 (d, 1H, J=1.5 Hz), 3.19 (q, 2H, J=7.4 Hz), 1.42 (t, 3H, J=7.4 Hz).

Example 38

This example illustrates a method for producing 1-(4-cyanothiophen-2-yl)-3-isobutylurea.

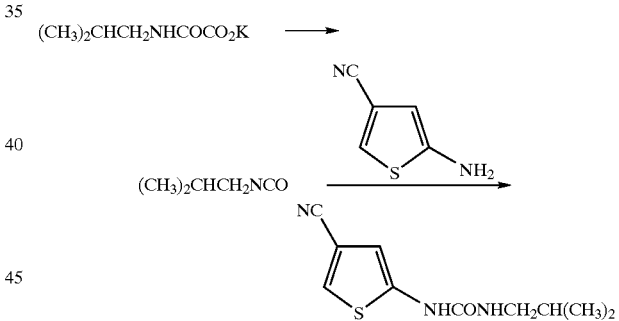

A 500-mL, one-neck, round bottomed flask equipped with a magnetic stirrer was charged with potassium isobutylcarbamoylmethanoate (2.75 g, 15.0 mmol), ammonium persulfate (5.13 g, 22.5 mmol), silver nitrate (255 mg, 1.50 mmol), copper(II) acetate (27 mg, 0.15 mmol), methylene chloride (90 mL), and water (90 mL). The mixture was heated to 40° C. then stirred at 40° C. for 3 h. After this time, the reaction mixture was cooled to ambient temperature. The organic phase was separated, dried with sodium sulfate, filtered and concentrated to half the volume. 5-Aminothiophene-3-carbonitrile (500 mg, 4.03 mmol) was added to the resulting solution. After stirring at ambient temperature for 24 h, the reaction mixture was heated to 40° C. and was then stirred at 40° C. for another 14 h. Concentration of the reaction mixture followed by column chromatography afforded a 50% yield of the title compound as a light yellow solid. $^1$H NMR (CDCl$_3$) δ (ppm) 7.86 (bs, 1H), 7.40 (d, 1H, J=1.4 Hz), 6.54 (d, 1H, J=1.5 Hz), 5.24 (t, 1H, J=5.6 Hz), 3.10 (t, 2H, J=6.3 Hz), 1.79 (m, 1H), 0.92 (d, 6H, J=6.7 Hz).

Example 39

This example illustrates a method for producing 2,6-dimethoxy-4-methylnicotinonitrile.

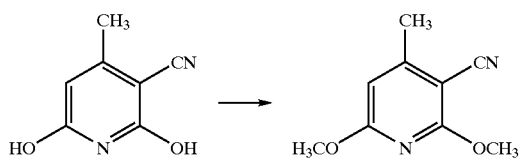

A 2-L, one-neck, round bottomed flask equipped with a magnetic stirrer was charged with 2,6-dihydroxy-4-methylnicotinonitrile (4.50 g, 30.0 mmol), dimethylformamide (180 mL), silver oxide (9.73 g, 42.0 mmol) and iodomethane (14.9 g, 105 mmol), and the mixture was stirred at ambient temperature for 18 h. Methylene chloride (400 mL) and methanol (400 mL) were then added, and the resulting suspension filtered through a pad of Celite 521. The filtrate was evaporated to dryness under reduced pressure, and the residue was purified by column chromatography to afford a 45% yield of the title compound as a white solid. m.p. 92–94° C.; $^1$H NMR (DMSO-$d_6$) δ (ppm) 6.23 (s, 1H), 4.02 (s, 3H), 3.95 (s, 3H), 2.42 (s, 3H); m/z=179 (M+H).

Example 40

This example illustrates a method for producing 4-(triisopropylsilyloxymethyl)benzonitrile.

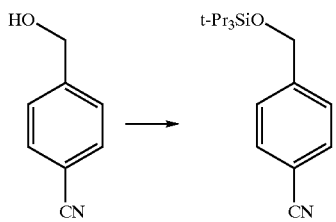

A 250 mL, three-neck, round bottomed flask equipped with a magnetic stirrer and a digital thermometer was charged with 4-hydroxymethylbenzonitrile (10.0 g, 75.2 mmol), methylene chloride (80 mL) and imidazole (7.20 g, 106 mmol), and the reaction mixture was cooled to 0° C. Triisopropylchlorosilane (15.9 g, 82.4 mmol) was added dropwise over 15 min, and the mixture was stirred at ambient temperature for 1 h. The mixture was then added to water (100 mL), the organic layer separated, then washed with 10% aqueous citric acid (100 mL). Drying over sodium sulfate, filtration, and concentration under reduced pressure afforded a quantitative yield of the title compound as a colorless oil. This material was used without further purification. $^1$H NMR (CDCl$_3$) δ (ppm) 7.62 (d, 2H, J=8.3 Hz), 7.46 (d, 2H, J=8.4 Hz), 4.88 (s, 2H), 1.03–1.28 (m, 21H); m/z=290 (M+H).

3-(Triisopropylsilyloxymethyl)benzonitrile was also prepared in quantitative yield using this method.

Example 41

This example illustrates a method for producing 2-methylthiophene-3-carbonitrile.

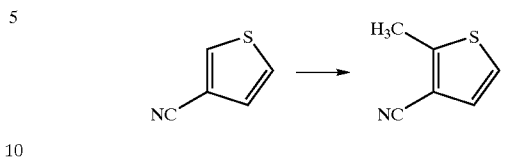

A 100-mL, three-neck, round bottomed flask equipped with a magnetic stirrer and a digital thermometer was purged with nitrogen and charged with thiophene-3-carbonitrile (2.91 g, 26.7 mmol) and anhydrous tetrahydrofuran (15 mL). The solution was cooled to −73° C., and 2 M solution of lithium diisopropylamide in heptane/tetrahydrofuran (14.8 mL, 29.6 mmol) was added dropwise, maintaining the temperature between −73° C. and −65° C. Once the addition was complete, the reaction was stirred at −73° C. for 30 min. Iodomethane (4.10 g, 28.9 mmol) was then added dropwise, again maintaining the temperature between −73° C. and −65° C. The mixture was then slowly warmed to ambient temperature. A 25% aqueous solution of ammonium chloride (5 mL) was added to the reaction mixture, and the resulting suspension filtered and evaporated to dryness. In order to separate inorganic impurities, the residue was triturated with methyl tert-butyl ether (150 mL) and filtered. The filtrate was concentrated under reduced pressure to afford the title compound in 90% yield as a brown oil. $^1$H NMR (DMSO-$d_6$) δ (ppm) 7.54 (d, 1H, J=5.4 Hz), 7.31 (d, 1H, J=5.4 Hz), 2.61 (s, 3H); m/z=124 (M+H).

2-Ethylthiophene-3-carbonitrile was also prepared using this method in 47% yield.

Example 42

This example illustrates a method for producing 1-(2-dimethylaminoethyl)-1H-pyrrole-2-carbonitrile.

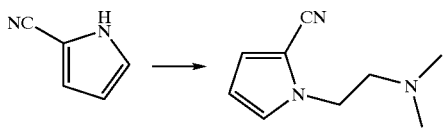

This material was prepared by a procedure adapted from U.S. Pat. No. 2,970,149 as described below.

A 250-mL, three-neck, round bottomed flask equipped with a magnetic stirrer, a thermometer and a reflux condenser was purged with nitrogen and charged with pyrrole-2-carbonitrile (1.84 g, 20.0 mmol) and anhydrous dimethylformamide (20 mL). The resulting solution was cooled to 0° C., and 60% sodium hydride in mineral oil (1.20 g, 30.0 mmol) was added portion-wise at 0–5° C. Once the addition was complete, the reaction was stirred at 0–5° C. for an additional 40 min.

In a second 100-mL, one-neck, round bottomed flask equipped with a magnetic stirrer, 2-dimethylaminoethylchloride hydrochloride (4.32 g, 30.0 mmol) was slurried in toluene (20 mL), and saturated aqueous potassium carbonate (35 mL) added. The mixture was cooled to 0° C., stirred for 1.5 h, and the organic layer was separated, dried over potassium carbonate and transferred to a 100-mL flask placed in an ice water bath. This toluene solution of 2-dimethylaminoethyl chloride was transferred via a cannula into the above solution of the sodium salt of pyrrole-2-carbonitrile, maintaining the reaction temperature between 0–5° C. After the addition was complete, the mixture was heated at 110° C. for 18 h. The reaction mixture was then cooled to ambient temperature, evaporated to dryness under reduced pressure, and methylene chloride (50 mL) added. The inorganic salts were removed by vacuum filtration, and the filtrate was washed with water (3×20 mL) and dried over sodium sulfate. Evaporation of the filtrate to dryness afforded a quantitative yield of 1-(2-dimethylaminoethyl)-1H-pyrrole-2-carbonitrile as a yellow oil. This material was used without further purification. $^1$H NMR (CDCl$_3$) δ (ppm) 6.91 (t, 1H, J=2.2 Hz), 6.78 (dd, 1H, J=3.9, 1.5 Hz), 6.16 (dd, 1H, J=2.8, 3.9 Hz), 4.11 (t, 2H, J=6.6), 2.67 (t, 2H, J=6.6 Hz), 2.27 (s, 6H); m/z=164 (M+H).

Example 43

This example illustrates a method for producing 4-(2-dimethylaminoethoxy)-N-hydroxybenzamidine.

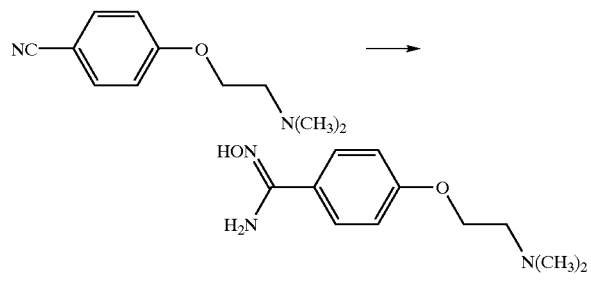

A 500-mL, one-neck, round bottomed flask equipped with a magnetic stirrer and a reflux condenser was charged with 4-(2-dimethylaminoethoxy)benzonitrile (31.5 g, 0.17 mol), ethanol (200 mL), hydroxylamine hydrochloride (17.2 g, 0.25 mol) and potassium carbonate (34.8 g, 0.25 mol). The resulting mixture was refluxed for 18 h. After cooling to ambient temperature, the reaction mixture was filtered, and the filtrate was concentrated to dryness affording a 49% yield of the title compound as a brown oil. $^1$H NMR (CD$_3$OD) δ (ppm) 7.87 (d, 2H, J=8.9 Hz), 7.04 (d, 2H, J=8.9 Hz), 4.36 (t, 2H, J=5.1 Hz), 3.37 (t, 2H, J=5.1 Hz), 2.79 (s, 6H); m/z=224 (M+H).

Sodium acetate could be substituted for potassium carbonate in the above procedure. Other hydroxyamidines prepared by this method are listed below. Yields in the range of 25–99% were observed.

N-Hydroxybenzamidine; 4-Chloro-N-hydroxybenzamidine; 4-Bromo-N-hydroxybenzamidine; 4-Fluoro-N-hydroxybenzamidine; 4-Trifluoromethoxy-N-hydroxybenzamidine; 4-Hydroxy-N-hydroxybenzamidine; 3-Hydroxy-N-hydroxybenzamidine; 3-Nitro-N-hydroxybenzamidine; 4-Methyl-N-hydroxybenzamidine; 3-Methyl-N-hydroxybenzamidine; 3-Ethyl-N-hydroxybenzamidine; 2,3-Dichloro-N-hydroxybenzamidine; 3,4-Difluoro-N-hydroxybenzamidine; N-Hydroxy-4-triisopropylsilyloxymethyl- benzamidine; N-Hydroxy-3-triisopropylsilyloxymethylbenzamidine; 3-Chloro-2-fluoro-N-hydroxybenzamidine; 3-Chloro-4 methyl-N-hydroxybenzamidine; 4-Methylsulfanyl-N-hydroxybenzamidine; 4-Dimethylaminomethyl-N-hydroxybenzamidine; 3-Dimethylaminomethyl-N-hydroxybenzamindine; 4-[2-(4-Morpholinyl)ethoxy]-N-hydroxybenzamidine; 6-Methoxy-N-hydroxynicotinamidine; 3-(2-Dimethylaminoethoxy)-N-hydroxybenzamidine; 4-Methoxy-N-hydroxybenzamidine; 2,4-Dimethoxy-N-hydroxybenzamidine; 3,5-Dimethoxy-N-hydroxybenzamidine; 2,3-Dimethoxy-N-hydroxybenzamidine; 2,5-Dimethoxy-N-hydroxybenzamidine; 2,6-Dimethoxy-N-hydroxybenzamidine; 2-Chloro-N-hydroxynicotinamidine; 2,6-Dimethoxy-4-methyl-N-hydroxynicotinamidine; N-Hydroxy-1H-pyrrole-2-carboxamidine; 1-(2-Dimethylaminoethyl)-N-hydroxy-1H-pyrrole-2-carboxamindine; 1-Methyl-N-hydroxy-1H-pyrrole-2-carboxamidine; 4-Difluoromethoxy-N-hydroxybenzarmidine; 2-Nitro-N-hydroxythiophene-4-carboxamidine; 3,4-Methylenedioxy-N-hydroxybenzamidine; 1,5-Dimethyl-N-hydroxy-1H-pyrrole-2-carboxamidine; N-Hydroxythiophene-2-carboxamidine; N-Hydroxythiophene-3-carboxamidine; N-Hydroxy-2,3-dihydrobenzofuran-5-carboxamidine; N-Hydroxy-2-methylthiazole-4-carboxamidine; tert-Butyl [5-(N-Hydroxycarbamimidoyl)thiophen-2-yl]carbamate; tert-Butyl [4-(N-Hydroxycarbamimidoyl)thiophen-2-yl]carbamate; tert-Butyl 4-(N-Hydroxycarbamimidoyl) piperidine-1-carboxylate; tert-Butyl 3-(N-Hydroxycarbamimidoyl)piperidine-1-carboxylate; tert-Butyl 2-(N-Hydroxycarbamimidoyl)piperidine-1-carboxylate; and tert-Butyl 2-(N-Hydroxycarbamimidoyl) pyrrolidine-1-carboxylate.

Example 44

This example illustrates a method for producing tert-butyl [4-(N-hydroxycarbamimidoyl)-1-(2-trimethylsilylethoxymethyl)-1H-pyrazol-3-yl]carbamate.

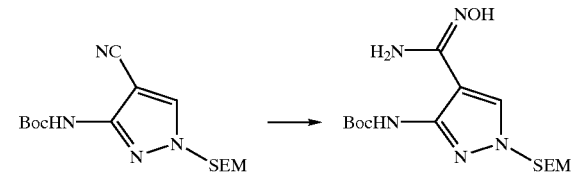

A 25-mL, one-neck, round bottomed flask equipped with a magnetic stirrer was charged with tert-butyl [4-cyano-1-(2-trimethylsilylethoxymethyl)-1H-pyrazol-3-yl]carbamate (203 mg, 0.6 mmol), methanol (10 mL) and 50% aqueous hydroxylamine (0.2 mL). The reaction mixture was stirred at room temperature for 18 h. The mixture was then concentrated to a viscous oil. This oil was dried under high vacuum affording a 94% yield of the title compound as a white solid. m.p. 157–158° C.; $^1$H NMR (DMSO-d$_6$) δ (ppm) 9.47 (s, 1H), 9.03 (s, 1H), 8.10 (s, 1H), 5.85 (bs, 2H), 5.27 (s, 2H), 3.53 (t, 2H, J=8.0 Hz), 1.43 (s, 9H), 0.84 (t, 2H, J=8.0 Hz), 0.07 (s, 9H); m/z=372 (M+H).

Ethanol can be substituted for methanol with similar yield. Other hydroxyamidines prepared by this method are listed below, and yields in the range of 32–99% were observed.

5-tert-Butyloxycarbonylamino-N-hydroxy-1-methyl-1H-pyrazole-4-carboxamidine; tert-Butyl [4-(N-Hydroxycarbamimidoyl)thiophen-2-yl]carbamate; tert-Butyl [5-(N-Hydroxycarbamimidoyl)-1-(2-trimethylsilylethoxymethyl)-1H-imidazol-4-yl]carbamate; tert-Butyl [4-(N-Hydroxycarbamimidoyl)-1-(2-trimethylsilylethoxymethyl)-1H-imidazol-5-yl]carbamate; tert-Butyl [4-(N-Hydroxycarbamimidoyl)-3-methylisoxazol-5-yl]carbamate; tert-Butyl [3-(N-Hydroxycarbamimidoyl)phenyl]carbamate; 3-Fluoro-N-hydroxy-4-methylbenzamidine; 2-Methyl-N-hydroxythiophene-3-carboxamidine; 2-Ethyl-N- hydroxythiophene-3-carboxamidine; 5-Ethanesulfonylamino-N-hydroxythiophene-3-carboxamidine; 3-[4-(N-Hydroxycarbamimidoyl)thiophen-2-yl]-1-isobutylurea; tert-butyl [5-(N-Hydroxycarbamimidoyl)-2-methylsulfanylthiazol-4-yl] carbamate; and 2-Chloro-N-hydroxyacetamidine.

Example 45

This example illustrates a method for producing 3-{3-[4-(2-dimethylaminoethoxy)phenyl]-1,2,4-oxadiazol-5-yl}propionic acid.

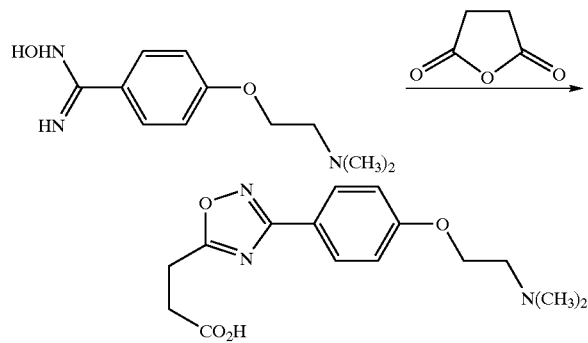

A 100-mL, one-neck, round bottomed flask equipped with a magnetic stirrer was charged with 4-(2-dimethylaminoethoxy)-N-hydroxybenzamidine (18.0 g, 81.0 mmol) and succinic anhydride (20.0 g, 200 mmol) and the flask purged with nitrogen. The reaction was then heated in an oil bath to 120° C. for 3 h. After cooling to ambient temperature, water (50 mL) was added, and the mixture was refluxed for 10 min in order to decompose excess succinic anhydride. The resulting solution was then cooled to ambient temperature, basified with 29% ammonium hydroxide to pH 5 and evaporated to dryness under reduced pressure. The residue was dissolved in methanol and passed through a silica gel column eluting with methanol. The fractions containing pure material were combined and evaporated to dryness under reduced pressure affording a 40% yield of the title acid as a white solid. m.p. 81–84° C.; $^1$H NMR (CD$_3$OD) δ (ppm) 7.98 (d, 2H, J=8.9 Hz), 7.06 (d, 2H, J=8.9 Hz), 4.38 (t, 2H, J=5.1 Hz), 3.49 (t, 2H, J=5.1 Hz), 3.18 (t, 2H, J=7.1 Hz), 2.88 (s, 6H), 2.82 (t, 2H, J=7.1 Hz); m/z=306 (M+H).

Other oxadiazolylpropionic acids prepared by this method are listed below. Yields in the range of 14–85% were observed.

3-(3-Phenyl-1,2,4-oxadiazol-5-yl)propionic acid; 3-[3-(4-Chlorophenyl-1,2,4-oxadiazol-5-yl)]propionic acid; 3-[3-(4-Bromophenyl-1,2,4-oxadiazol-5-yl)]propionic acid; 3-[3-(4-Fluorophenyl-1,2,4-oxadiazol-5-yl)]propionic acid; 3-[3-(3-Nitrophenyl-1,2,4-oxadiazol-5-yl)]propionic acid; 3-[3-(4-Trifluoromethoxyphenyl-1,2,4-oxadiazol-5-yl)]propionic acid; 3-[3-(4-Difluoromethoxyphenyl-1,2,4-oxadiazol-5-yl)]propionic acid; 3-[3-(4-Hydroxyphenyl-1,2,4-oxadiazol-5-yl)]propionic acid; 3-[3-(3-Hydroxyphenyl-1,2,4-oxadiazol-5-yl)]propionic acid; 3-[3-(4-Methylphenyl-1,2,4-oxadiazol-5-yl)]propionic acid; 3-[3-(3-Methylphenyl-1,2,4-oxadiazol-5-yl)]propionic acid; 3-[3-(3-Ethylphenyl-1,2,4-oxadiazol-5-yl)]propionic acid; 3-[3-(4-Dimethylaminomethylphenyl-1,2,4-oxadiazol-5-yl)]propionic acid; 3-[3-(3-Dimethylaminomethylphenyl-1,2,4-oxadiazol-5-yl)]propionic acid; 3-{3-[3-(2-Dimethylaminoethoxy)phenyl]-1,2,4-oxadiazol-5-yl}propionic acid; 3-{3-[4-(2-Morpholin-4-ylethoxy)phenyl]-1,2,4-oxadiazol-5-yl}propionic acid; 3-[3-(2,3-Dichlorophenyl-1,2,4-oxadiazol-5-yl)]propionic acid; 3-[3-(3,4-Difluorophenyl-1,2,4-oxadiazol-5-yl)]propionic acid; 3-[3-(3-Chloro-4-methylphenyl-1,2,4-oxadiazol-5-yl)] propionic acid; 3-[3-(3-Fluoro-4-methylphenyl-1,2,4-oxadiazol-5-yl)]propionic acid; 3-[3-(4-Chloro-3-fluorophenyl-1,2,4-oxadiazol-5-yl)]propionic acid; 3-[3-(3,4-Methylenedioxyphenyl-1,2,4-oxadiazol-5-yl)]propionic acid; 3-[3-(4-Methylsulfanylphenyl-1,2,4-oxadiazol-5-yl)] propionic acid; 3-[3-(4-Methoxyphenyl-1,2,4-oxadiazol-5-yl)]propionic acid; 3-[3-(2,3-Dimethoxyphenyl-1,2,4-oxadiazol-5-yl)]propionic acid; 3-[3-(2,4-Dimethoxyphenyl-1,2,4-oxadiazol-5-yl)]propionic acid; 3-[3-(2,5-Dimethoxyphenyl-1,2,4-oxadiazol-5-yl)] propionic acid; 3-[3-(2,6-Dimethoxyphenyl-1,2,4-oxadiazol-5-yl)]propionic acid; 3-[3-(3,5-Dimethoxyphenyl-1,2,4-oxadiazol-5-yl)]propionic acid; 3-[3-(Thiophen-2-yl)-1,2,4-oxadiazol-5-yl]propionic acid; 3-[3-(Thiophen-3-yl)-1,2,4-oxadiazol-5-yl]propionic acid; 3-[3-(2,3-Dihydrobenzofuran-5-yl)-1,2,4-oxadiazol-5-yl] propionic acid; 3-[3-(2-Methylthiazol-4-yl)-1,2,4-oxadiazol-5-yl]propionic acid; 3-[3-(6-Methoxypyridin-3-yl)-1,2,4-oxadiazol-5-yl]propionic acid; 3-[3-(6-Hydroxypyridin-3-yl)-1,2,4-oxadiazol-5-yl]propionic acid; 3-[3-(5-Nitrothiophen-3-yl)-1,2,4-oxadiazol-5-yl]propionic acid; 3-[3-(2-Methylthiophen-3-yl)-1,2,4-oxadiazol-5-yl] propionic acid; and 3-[3-(2-Ethylthiophen-3-yl)-1,2,4-oxadiazol-5-yl]propionic acid.

Example 46

This example illustrates a method for producing 3-[3-(5-tert-butyloxycarbonylaminothiophen-3-yl)-1,2,4-oxadiazol-5-yl]propionic acid.

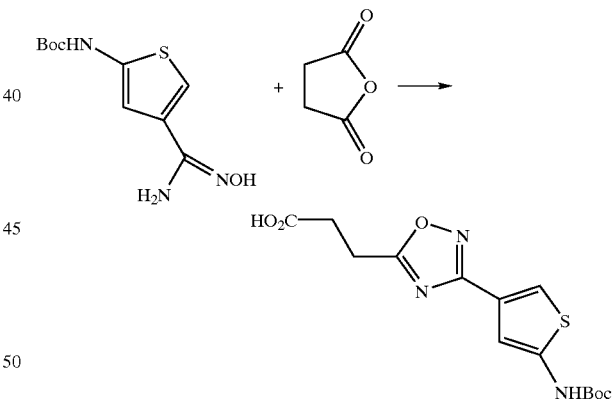

A 100-mL, three-neck, round bottomed flask equipped with a magnetic stirrer and a reflux condenser was purged with nitrogen and charged with 5-tert-butyloxycarbonylamino-N-hydroxythiophene-3-carboxamidine (2.96 g, 11.5 mmol), succinic anhydride (1.16 g, 11.6 mmol), anhydrous 1,2-dimethoxyethane (17 mL) and N,N-diisopropylethylamine (1.62 g, 12.6 mmol). The resulting solution was stirred for 30 min at ambient temperature and then refluxed for 18 h. After evaporating the reaction mixture to dryness under vacuum, a solution of potassium carbonate (5.0 g, 36.2 mmol) in water (85 mL) was added to the residue. The resulting suspension (pH=10) was stirred for 30 min, filtered through a pad of Celite 521 and the filtrate acidified with 2N hydrochloric acid to pH 3.

The mixture was extracted with methylene chloride (100 mL) and the extract dried over sodium sulfate. Filtration and concentration under reduced pressure afforded a 26% yield of the title compound as a brown solid. m.p. 104–110° C.; $^1$H NMR (DMSO-$d_6$) δ (ppm) 12.51 (1H, bs), 10.67 (s, 1H), 7.59 (s, 1H), 6.92 (s, 1H), 3.14 (t, 2H, J=6.9), 2.81 (t, 2H, J=6.8 Hz), 1.49 (s, 9H); m/z=338 (M−H).

Other oxadiazolylpropionic acids prepared by this method are listed below. Yields in the range of 28–67% were observed.

3-[3-(2,6-Dimethoxyphenyl)-1,2,4-oxadiazol-5-yl] propionic acid; 3-[3-(1-Methyl-1H-pyrrol-2-yl)-1,2,4-oxadiazol-5-yl]propionic acid; 3-[3-(1,5-Dimethyl-1H-pyrrol-2-yl)-1,2,4-oxadiazol-5-yl]propionic acid; 3-{3-[1-(2-Dimethylaminoethyl)-1H-pyrrol-2-yl]-1,2,4-oxadiazol-5-yl}propionic acid; 3-[3-(2-Chloropyridin-3-yl)-1,2,4-oxadiazol-5-yl]propionic acid; 3-[3-(2,6-Dimethoxy-4-methylpyridin-3-yl)-1,2,4-oxadiazol-5-yl]propionic acid; and 3-[3-(4-tert-Butyloxycarbonylamino-2-methylsulfanylthiazol-5-yl)-1,2,4-oxadiazol-5-yl]propionic acid.

Example 47

This example illustrates a method for producing 3-tert-butyloxycarbonylamino-N-(3-carbomethoxypropionyloxy)benzamidine.

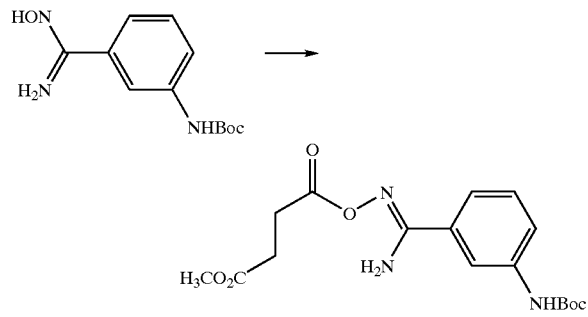

A 50-mL, one-neck, round bottomed flask equipped with a magnetic stirrer and a digital thermometer was charged with tert-butyl [3-(N-hydroxycarbamimidoyl)phenyl]carbamate (5.56 g, 22.1 mmol), diisopropylethylamine (4.29 g, 33.2 mmol) and THF (25 mL). The reaction mixture was then cooled to 0° C. in an ice/salt bath. 3-Carbomethoxypropionyl chloride (3.99 g, 26.6 mmol) was then added dropwise to the reaction mixture. Once the addition was complete, the cooling bath was removed and the mixture stirred at room temperature for an additional 3 h. The reaction was then concentrated under reduced pressure, the residue dissolved in ethyl acetate (60 mL), and the resulting solution washed with 2 M aqueous potassium carbonate solution (2×60 mL). Drying over sodium sulfate, filtration and concentration under reduced pressure afforded a quantitative yield of 3-tert-butyloxycarbonylamino-N-(3-carbomethoxypropionyloxy)benzamidine as a white solid that was used directly. $^1$H NMR (CDCl$_3$) δ (ppm) 7.71 (s, 1H), 7.50 (m, 2H,), 7.33 (m, 2H), 6.58 (bs, 1H), 5.19 (bs, 2H), 3.71 (s, 3H), 2.83 (m, 2H), 2.75 (m, 2H), 1.52 (s, 9H).

Other N-(3-carbomethoxypropionyloxy)amidines prepared by this method are listed below. Yields in the range of 80% to quantitative were observed.

tert-Butyl 4-[N-(3-Carbomethoxypropionyloxy) carbamimidoyl]piperidine-1-carboxylate; tert-Butyl 3-[N-(3-Carbomethoxypropionyloxy)carbamimidoyl]-piperidine-1-carboxylate; tert-Butyl 2-[N-(3-Carbomethoxypropionyloxy)carbamamidoyl]piperidine-1-carboxylate; tert-Butyl 2-[N-(3-Carbomethoxypropionyloxy)carbamimidoyl]pyrrolidine-1-carboxylate; tert-Butyl 4-[N-(3-Carbomethoxypropionyloxy)carbamimidoyl]thiophen-2-ylcarbamate; tert-Butyl 5-[N-(3-Carbomethoxypropionyloxy)carbamimidoyl]thiophen-2-ylcarbamate; tert-Butyl 5-[N-(3-Carbomethoxypropionyloxy)carbamimidoyl]thiophen-2-ylcarbamate; tert-Butyl 4-[N-(3-Carbomethoxypropionyloxy)carbamimidoyl]-2-methyl-2H-pyrazol-3-ylcarbamate; tert-Butyl 5-[N-(3-Carbomethoxypropionyloxy)carbamimidoyl]-1-(2-trimethylsilyl)ethoxymethyl-1H-imidazol-4-ylcarbamate; tert-Butyl 4-[N-(3-Carbomethoxypropionyloxy)carbamimidoyl]-1-(2-trimethylsilyl)-ethoxymethyl-1H-imidazol-5-ylcarbamate; N-(3-Carbomethoxypropionyloxy)-1H-pyrrole-2-carboxamidine; N-(3-Carbomethoxypropionyloxy)-1-methyl-1H-pyrrole-2-carboxamidine; tert-Butyl 4-[N-(3-Carbomethoxypropionyloxy)carbamimidoyl]-1-(2-trimethylsilyl)ethoxymethyl-1H-pyrazol-3-ylcarbamate; N-(3-Carbomethoxypropionyloxy)-3-triisopropylsilyloxymethylbenzamidine; N-(3-Carbomethoxypropionyloxy)-4-triisopropylsilyloxymethylbenzamidine; 3-{4-[N-(3-Carbomethoxypropionyloxy)carbamimidoyl]thiophen-2-yl}-1-isobutylurea.; 5-Ethanesulfonyl-amino-N-(3-carbomethoxypropionyloxy)thiophene-3-carboxamidine; 2-Chloro-N-(3-carbomethoxypropionyloxy)acetamidine; and tert-Butyl [4-(N-(3-Carbomethoxypropionyloxy)carbamimidoyl)-3-methylisoxazol-5-yl]carbamate.

Example 48

This example illustrates a method for producing methyl 3-[3-(3-tert-butyloxycarbonylaminophenyl)-1,2,4-oxadiazol-5-yl]propionate

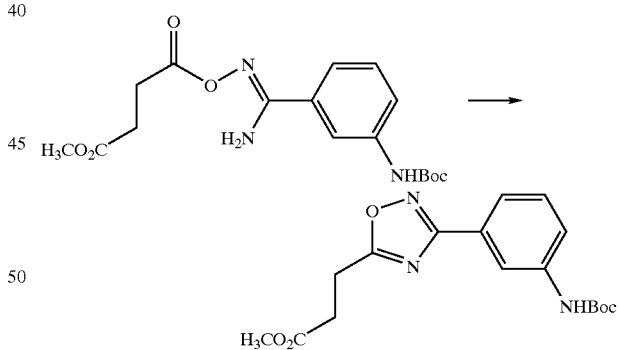

A suspension of 3-tert-butyloxycarbonylamino-N-(3-carbomethoxypropionyloxy) benzamidine (8.25 g, 22.6 mmol) in toluene (120 mL) was added to a 250-mL round bottomed flask equipped with a magnetic stirrer and a reflux condenser, and the contents heated to reflux for 5 h. The reaction was then cooled, and the resulting solution concentrated under vacuum. This afforded a quantitative yield of methyl 3-[3-(3-tert-butyloxycarbonylaminophenyl)-1,2,4-oxadiazol-5-yl]propionate as a yellow solid. m.p. 90–91° C.; $^1$H NMR (CDCl$_3$) δ (ppm) 7.97 (s, 1H), 7.72 (d, 1H,J=7.6 Hz), 7.61 (d, 1H,J=7.6 Hz), 7.39 (m, 2H), 6.57 (bs, 1H), 3.73 (s, 3H), 3.26 (t, 2H,J=7.3 Hz), 2.94 (t, 2H,J=7.3 Hz), 1.53 (s, 9H); m/z=346 (M−H).

1,2-Dimethoxyethane could be substituted for toluene. Other oxadiazole esters prepared by this method are listed below. Yields in the range of 54% to quantitative were observed.

Methyl 3-[3-(1-tert-Butyloxycarbonylpiperidin-4-yl)-1,2,4-oxadiazol-5-yl]propionate; Methyl 3-[3-(1-tert-Butyloxycarbonylpiperidin-3-yl)-1,2,4-oxadiazol-5-yl]propionate; Methyl 3-[3-(1-tert-Butyloxycarbonylpiperidin-2-yl)-1,2,4-oxadiazol-5-yl]propionate; Methyl 3-[3-(1-tert-Butyloxycarbonylpyrrolidin-2-yl)-1,2,4-oxadiazol-5-yl] propionate; Methyl 3-[3-(2-tert-Butyloxycarbonylaminothiophen-4-yl)-1,2,4-oxadiazol-5-yl]propionate; Methyl 3-[3-(2-tert-Butyloxycarbonylaminothiophen-5-yl)-1,2,4-oxadiazol-5-yl]propionate; Methyl 3-[3-(3-tert-Butyloxycarbonylamino-2-methyl-2H-pyrazol-4-yl)-1,2,4-oxadiazol-5-yl]propionate; Methyl 3-[3-(3-tert-Butyloxycarbonylamino-1-(2-trimethylsilyl)ethoxymethyl-1H-pyrazol-4-yl)-1,2,4-oxadiazol-5-yl]propionate; Methyl 3-[3-(4-tert-Butyloxycarbonylamino-1-(2-trimethylsilyl)ethoxymethyl-1H-imidazol-5-yl)-1,2,4-oxadizaol-5-yl]propionate; Methyl 3-[3-(5-tert-Butyloxycarbonylamino-1-(2-trimethylsilyl)ethoxymethyl-1H-imidazol-4-yl)-1,2,4-oxadiazol-5-yl]propionate; Methyl 3-[3-(1H-Pyrrol-2-yl)-1,2,4-oxadiazol-5-yl]propionate; Methyl 3-[3-(1-Methyl-1H-pyrrol-2-yl)-1,2,4-oxadiazol-5-yl]propionate; Methyl 3-[3-(3-Triisopropylsilyloxymethylphenyl)-1,2,4-oxadiazol-5-yl] propionate; Methyl 3-[3-(4-Triisopropylsilyloxymethylphenyl)-1,2,4-oxadiazol-5-yl]propionate; 3-{4-[(5-(2-Carbomethyoxy)ethyl)-1,2,4-oxadiazol-3-yl]thiophen-2-yl}-1-isobutylurea; Methyl-3-(2-Ethanesulfonylaminothiophene-4-yl-1,2,4-oxadiazol-5-yl)propionate; Methyl-3-(3-Chloromethyl-1,2,4-oxadiazol-5-yl)propionate; and Methyl-3-[3-(5-tert-Butyloxycarbonylamino-3-methylisoxazol-4-yl)-1,2,4-oxadizol-5-yl]propionate.

Example 49

This example illustrates a method for producing methyl 3-[3-(4-hydroxyphenyl)-1,2,4-oxadiazol-5-yl]propionate.

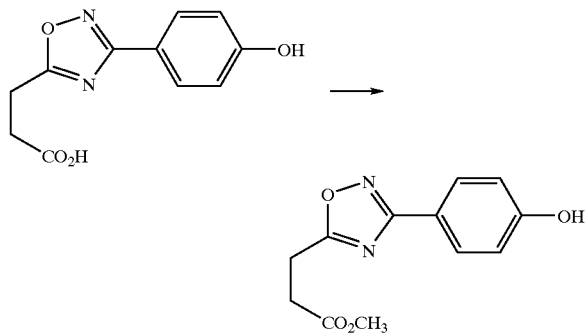

A 100-mL, one-neck, round bottomed flask equipped with a magnetic stirrer was charged with 3-[3-(4-hydroxyphenyl)-1,2,4-oxadiazol-5-yl]propionic acid (7.62 g, 32.4 mmol) and anhydrous methanol (130 mL). The reaction mixture was cooled to 0° C., and thionyl chloride (13.3 g, 112 mmol) added dropwise over 15 min. The ice bath was removed and stirring continued for 16 h at room temperature. The solvent was then removed under reduced pressure. The residue was dissolved in ethyl acetate (60 mL) and the solution washed with water (2×40 mL), 10% aqueous sodium hydrogen carbonate (2×40 mL) and saturated sodium chloride solution (20 mL). The organic layer was then dried over sodium sulfate, filtered and concentrated under reduced pressure. Purification of the crude product by column chromatography afforded a 91% yield of the title compound as a white solid. m.p. 90–92° C.; $^1$H NMR (DMSO-$d_6$), δ (ppm)=10.1 (s, 1H), 7.81 (d, 2H,J=9.6 Hz), 6.90 (d, 2H,J=8.6 Hz,), 3.62 (s, 3H), 3.20 (t, 2H,J=7.0 Hz,), 2.91 (t, 2H,J=7.0 Hz); m/z=249 (M+H).

Methyl 3-[3-(3hydroxyphenyl)-1,2,4-oxadiazol-5-yl]propionate was also prepared using this method in 83% yield.

Example 50

This example illustrates a method for producing methyl 3-[3-(4-isopropoxyphenyl)-1,2,4-oxadiazol-5-yl]propionate.

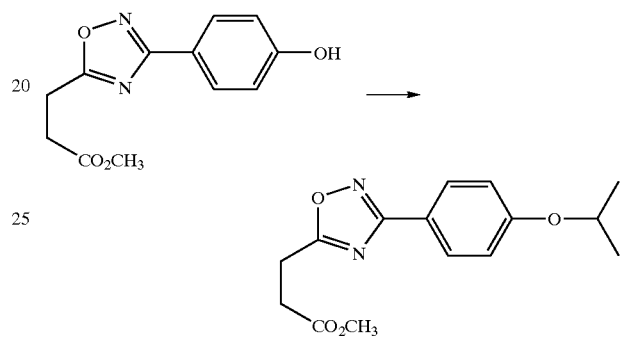

A 500-mL, one-neck, round bottomed flask equipped with a magnetic stirrer was charged with methyl 3-[3-(4-hydroxyphenyl)-1,2,4-oxadizol-5-yl]propionate (768 mg, 3.09 mmol), potassium carbonate (560 mg, 4.0 mmol) and anhydrous DMF (130 mL). The reaction was then stirred at room temperature for 20 min. 2-Bromopropane (455 mg, 3.70 mmol) was then added in one portion and stirring continued for 18 h. The solvent was then removed under reduced pressure and water (20 mL) added to the residue. The mixture was then extracted with a 1:1 mixture of ethyl acetate and hexanes (3×20 mL). The combined organic extracts were washed water (2×20 mL) and saturated sodium chloride sodium (20 mL) and dried over sodium sulfate. Filtration and concentration in vacuum afforded a 92% yield of the title compound as a colorless oil. $^1$H NMR (CDCl$_3$), δ (ppm)=7.97 (d, 2H,J=7.0 Hz), 6.94 (d, 2H,J=7.0 Hz), 4.83 (hept, 1H,J=6.1 Hz), 3.73 (s, 3H), 3.25 (t, 2H,J=7.3 Hz), 2.94 (t, 2H,J=7.5 Hz), 1.36 (d, 6H,J=6.1 Hz); m/z=291 (M+H).

Alkyl iodides can be substituted for the alkylbromides in the above procedure.

Other methyl 4-alkoxyphenyloxadiazol-5-ylpropionate esters prepared by this method are listed below. Yields in the range of 58–98% were observed.

Methyl 3-[3-(3-Methoxyphenyl)-1,2,4-oxadiazol-5-yl]propionate; Methyl 3-[3-(4-Ethoxyphenyl)-1,2,4-oxadiazol-5-yl]propionate; Methyl 3-[3-(3-Ethoxyphenyl)-1,2,4-oxadiazol-5-yl]propionate; Methyl 3-[3-(4-Propyloxyphenyl)-1,2,4-oxadizol-5-yl]propionate; Methyl 3-[3-(3-Propyloxyphenyl)-1,2,4-oxadiazol-3-yl]propionate; Methyl 3-[3-(3-Isopropyloxyphenyl)-1,2,4-oxadiazol-5-yl]propionate; and Methyl 3-[3-(4-Cyclopropylmethoxyphenyl)-1,2,4-oxadizol-5-yl]propionate.

Methyl 3-{3-[4-(2,2,2-Trifluoroethoxy)phenyl]-1,2,4-oxadiazol-5-yl}propionate and Methyl 3-{3-[3-(2,2,2-

Trifluoroethoxy)phenyl]-1,2,4-oxadiazol-5-yl}propionate were prepared in similar fashion, employing the para-toluenesulfonate ester of 2,2,2-trifluoroethanol at 100° C.

Example 51

This example illustrates a method for producing methyl 3-[3-(5-dimethylaminomethyl-1-methyl-1H-pyrrol-2-yl-1,2,4-oxadiazol-5-yl]propionate.

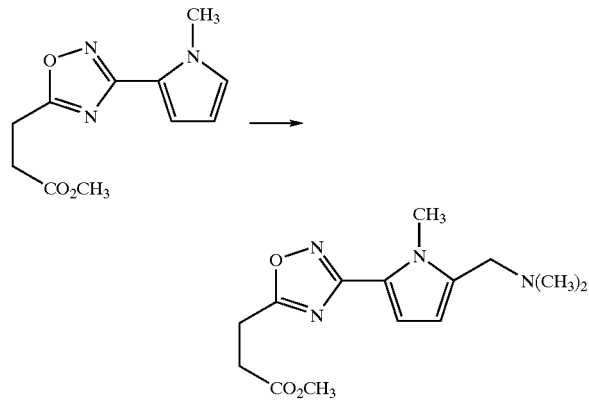

A 250-mL, three-neck, round bottom flask equipped with a magnetic stirrer and reflux condenser was charged with methyl 3-[3-(1-methyl-1H-pyrrol-2-yl)-1,2,4-oxadizol-5-yl] propionate (2.14 g, 9.10 mmol), dimethylamine hydrochloride (2.20 g, 27.0 mmol), paraformaldehyde (0.82 g 27.0 mmol) and n-butanol (80 mL). The mixture was heated to 100° C. for 16 h. After this time, additional dimethylamine hydrochloride (1.10 g, 13.5 mmol) and paraformaldehyde (0.41 g, 13.5 mmol) were added and heating continued for 8 h. The reaction was cooled to room temperature and the butanol removed under reduced pressure. Ethyl acetate (80 mL) and a 2M aqueous solution of potassium carbonate (80 mL) were added to the residue and the biphasic mixture was stirred for 15 min at ambient temperature. The layers were then separated. The aqueous layer was extracted with ethyl acetate (2×50 mL) and the combined organic extracts washed with saturated sodium chloride solution (2×50 mL), dried over sodium sulfate, filtered, and concentrated in vacuum. Purification of the resulting residue by column chromatography afforded at 71% yield of the title compound as a yellow oil. $^1$H NMR (CDCl$_3$) δ (ppm)=6.77 (d, 1H,J=3.8 Hz), 6.01 (d, 1H,J=3.8 Hz), 3.88 (s, 3H), 3.65 (s,3H), 3.31 (s, 2H), 3.14 (t, 2H,J=7.3 Hz), 2.84 (t, 2H,J=7.4 Hz), 2.14 (s, 6H).

Example 51

This example illustrates a method for producing methyl 3-{3-[1-(2-ethoxyethyl)-1H-pyrrol-2-yl]-1,2,4-oxadiazol-5-yl}propionate.

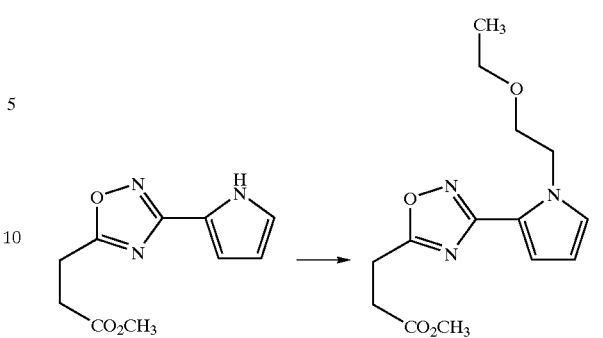

A 50-mL, one-neck, round bottomed flask equipped with a magnetic stirrer was charged with methyl 3-[3-(1H-pyrrol-2-yl)-1,2,4-oxadiazol-5-yl]propionate 700 mg, 3.16 mmol) and anhydrous DMF (10 mL). The reaction mixture was cooled to −40° C. and a 1 M solution of sodium hexamethyldisilazide in THF (3.80 mL, 3.80 mmol) was added in one portion. After stirring at this temperature for 20 min, the mixture was allowed to warm to room temperature. 1-Bromo-2-ethoxyethane (735 mg, 4.80 mmol) was then added in one portion and stirring continued for 16 h. The solvents were then removed under reduced pressure. Ethyl acetate (40 mL) and water (30 mL) were added to the residue. The organic layer was separated and the aqueous layer extracted with ethyl acetate (2×25 mL). The combined organic extracts were washed with saturated sodium chloride solution (2×30 mL), dried over sodium sulfate, filtered, and concentrated under reduced pressure. Purification of the resulting residue by column chromatography afforded a 61% yield of the title compound as yellow semi-solid. $^1$H NMR (CDCl$_3$), δ (ppm)=6.94 (d, 1H,J=3.3 Hz), 6.21 (t, 1HJ=3.3 Hz), 4.50 (t, 2H,J=5.7 Hz), 3.73 (s, 3H), 3.71 (d, 2H,J=5.4 Hz), 3.44 (qt, 2H,J=7.0 Hz), 3.22 (t, 2H,J=7.2 Hz), 2.91 (t, 2H,J=7.5 Hz), 1.14 (t, 3H,J=7.0 Hz).

Sodium hydride can be substituted for the sodium hexamethyldisilazide in the above procedure. Other N-alkylpyrrole esters prepared by this method are listed below. Yields ranging from 72–39% were observed.

Methyl 3-[3-(1-Ethyl-1H-pyrrol-2-yl)-1,2,4-oxadiazol-5-yl]propionate; and Methyl 3-[3-methyl(1-triisopropylsilyloxymethyl-1H-pyrrol-2-yl)-1,2,4-oxadiazol-5-yl]propionate.

Example 52

This example illustrates a method for producing methyl 3-{3-[4-(hydroxymethyl)phenyl]-1,2,4-oxadiazol-5-yl}propionate

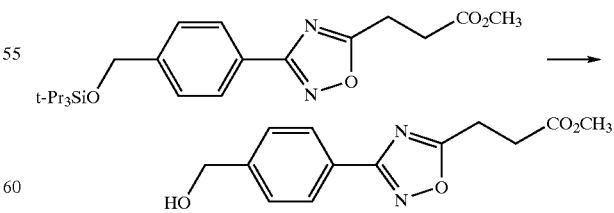

In a 500-mL, one-neck, round bottomed flask equipped with a magnetic stirrer, methyl 3-{3-[4-(triisopropylsilyloxymethyl)phenyl]-1,2,4-oxadiazol-5-yl}propionate (17.0 g, 40.6 mmol) was dissolved in tetrahydrofuran (250 mL). Tetrabutylammonium fluoride trihydrate (30.5 g, 117 mmol) was added, and the reaction mixture was stirred for 17 h at ambient temperature. The mixture was then evaporated to dryness under reduced pressure and purified by column chromatography on silica gel to provide a 75% yield of the title compound as a yellow solid. m.p. 56–57° C.; $^1$H NMR (DMSO-d$_6$) δ 7.94 (d, 2H,J=8.0 Hz), 7.49 (d, 2H,J=8.0 Hz), 5.35 (t, 1H,J=5.7 Hz), 4.57 (d, 2H,J=5.7 Hz), 2.93 (t, 2H,J=6.9 Hz), 3.62 (s, 3H), 3.24 (t, 2H,J=7.1 Hz); m/z=245 (M−OH).

Methyl 3-{3-[3-(hydroxymethyl)phenyl]-1,2,4-oxadiazol-5-yl}propionate was also prepared using this method in 66% yield.

Example 53

This example illustrates a method for producing methyl 3-{3-[4-(methoxymethyl)phenyl]-1,2,4-oxadiazol-5-yl}propionate

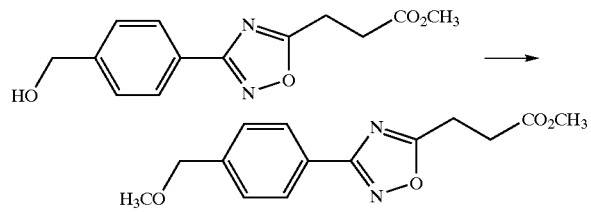

A 25-mL, one-neck, round bottomed flask equipped with a magnetic stirrer was charged with methyl 3-{3-[4-(hydroxymethyl)phenyl]-1,2,4-oxadiazol-5yl}propionate (262 mg, 1.00 mmol), dimethylformamide (2 mL), silver oxide (464 mg, 2.00 mmol) and methyl iodide (284 mg, 2.00 mmol). The reaction mixture was stirred for 17 h at ambient temperature, then diluted with methanol (2 mL) and filtered through a pad of Celite 521. Evaporation of the filtrate to dryness under reduced pressure afforded an oil which was purified by column chromatography on silica gel. This provided a 42% yield of the title compound as a white solid. m.p. 38–39° C.; $^1$H NMR (CDCl$_3$) δ 8.04 (d, 2H,J=8.3 Hz), 7.44 (d, 2H,J=8.1 Hz), 4.52 (s, 2H), 3.74 (s, 3H), 3.42 (s, 3H), 3.27 (t, 2H,J=7.4 Hz), 2.95 (t, 2H,J=7.4 Hz); m/z=245 (M−OCH$_3$).

Methyl 3-{3-[4-(ethoxymethyl)phenyl]-1,2,4-oxadiazol-5-yl}propionate and methyl 3-{3-[3-(ethoxymethyl)phenyl]-1,2,4-oxadiazol-5-yl}propionate were also prepared using this method in yields of 22 and 23%, respectively.

Example 54

This example illustrates a method for producing methyl 3-{3-[4-(difluoromethoxymethyl)phenyl]-1,2,4-oxadiazol-5-yl}propionate.

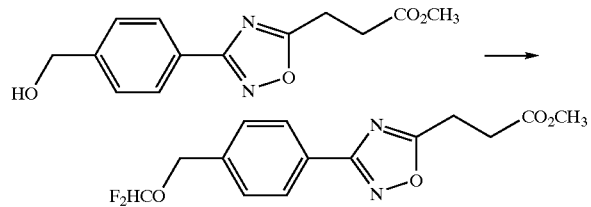

A 100-mL, one-neck, round bottomed flask equipped with a magnetic stirrer and digital thermometer was charged with methyl 3-{3-[4-(hydroxymethyl)phenyl]-1,2,4-oxadiazol-5-yl}propionate (2.50 g, 9.54 mmol), acetonitrile (20 mL), 2-(fluorosulfonyl)difluoroacetic acid (2.04 g, 11.4 mmol) and 4 Å molecular sieves (2 g). The mixture was stirred under a nitrogen atmosphere for 1 h at ambient temperature. The reaction mixture was then cooled to 0° C. and triethylamine (3.45 g, 34.2 mmol) added dropwise. Stirring was continued at 0–5° C. for 2 h. After warming to ambient temperature, the mixture was poured into water (20 mL) and extracted with methylene chloride (3×20 mL). The organic extracts were combined, washed with water, dried over sodium sulfate and evaporated to dryness under reduced pressure. The resulting material was purified by column chromatography on silica gel to provide a 10% yield of the title compound as a white solid. m.p. 34–35° C.; $^1$H NMR (CDCl$_3$) δ 8.08 (d, 2H,J=8.3 Hz), 7.47 (d, 2H,J=8.2 Hz), 6.34 (t, 1H,J=74.0 Hz), 4.95 (s, 2H), 3.73 (s, 3H), 3.27 (t, 2H,J=7.4 Hz), 2.95 (t, 2H,J=7.3 Hz); m/z=313 (M+H).

Methyl 3-{3-[3-(difluoromethoxymethyl)phenyl]-1,2,4-oxadiazol-5-yl}propionate was also prepared using this method in 4% yield.

Example 55

This example illustrates a method for producing methyl 3-[3-(1-methylpiperidin-4-yl)-1,2,4-oxadiazol-5-yl]propionate.

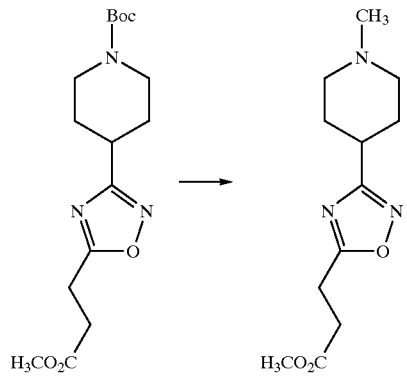

A 25-mL round bottomed flask equipped with a magnetic stirrer was charged with tert-butyl 4-[5-(2-methoxycarbonylethyl)-1,2,4-oxadiazol-3-yl]piperidine-1-carboxylate (620 mg, 1.83 mmol) and a 4 M solution of hydrogen chloride in 1,4-dioxane (6 mL). After stirring for 1.5 h at ambient temperature, the reaction mixture was poured into a 10% aqueous solution of potassium carbonate (50 mL). The resulting mixture was extracted with methylene chloride (3×30 mL). The combined organic phase was washed with water, dried over sodium sulfate, and filtered. Evaporation of the filtrate to dryness gave a light yellow oil which was charged directly into a 50-mL round bottomed flask equipped with a magnetic stirrer and containing a methylene chloride (8 mL) solution of methyltrimethoxyphosphonium tertrafluoborate (402 mg, 1.78 mmol). The resulting reaction mixture was stirred at ambient temperature for 16 h then quenched with methanol (5 mL). After stirring for another 30 min, the reaction mixture was partitioned between methylene chloride (20 mL) and a 10% aqueous potassium carbonate (20 mL). The combined organic phases were dried with sodium sulfate and filtered. Concentration of the filtrate followed by column chromatography gave a 35% yield of the title compound as a light yellow oil; $^1$H NMR (DMSO-d$_6$) δ (ppm) 3.71 (s, 3H), 3.18 (t, 2H,J=7.2 Hz), 2.67–2.93 (m, 5H), 2.30 (s, 3H), 1.82–2.12 (m, 6H); m/z=254 (M+H).

Other oxadiazole esters prepared by this method are listed below. Yields in the range of 38–56% were observed.

Methyl 3-[3-(1-Methylpiperidin-2-yl)-1,2,4-oxadiazol-5-yl]propionate; Methyl 3-[3-(1-Methylpiperidin-3-yl)-1,2,4-oxadizol-5-yl]propionate; and Methyl 3-[3-(1-Methylpyrrolidin-2-yl)-1,2,4-oxadiazol-5-yl]propionate.

Example 56

This example illustrates a method for producing methyl 3-[3-(5-benzyloxycarbonylaminothiophen-2-yl)-1,2,4-oxadiazol-5-yl]propionate.

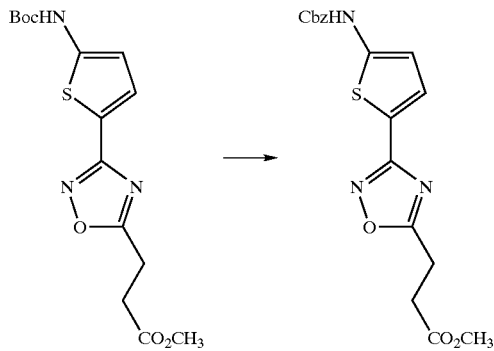

A 50-mL round bottomed flask equipped with a magnetic stirrer was charged with methyl 3-[3-(5-tert-butyloxycarbonylaminothiophen-2-yl)-[1,2,4]oxadiazol-5-yl]propionate (0.20 g, 0.57 mmol), triethylamine (0.47 g, 4.52 mmol), DMAP (0.061 g, 0.50 mmol) and THF (6 mL). A solution of benzyl chloroformate (0.39 g, 2.28 mmol) in THF (1 mL) was added at ambient temperature. After stirring for 3 h, the reaction mixture was partitioned between saturated aqueous ammonium chloride solution (20 mL) and methylene chloride (20 mL). The organic phase was separated, dried over sodium sulfate and filtered. The filtrate was concentrated to dryness and the resulting material was dissolved in a mixture of methylene chloride (4 mL) and trifluoroacetic acid (2 mL). After stirring at ambient temperature for 0.5 h, toluene (5 mL) was added to the reaction mixture. Concentration and purification by column chromatography gave a 83% yield of the title compound as a light yellow solid; m.p. 146–148° C.; $^1$H NMR (DMSO-d$_6$) δ (ppm) 11.28 (s, 1H), 7.49 (d, 1H,J=4.0 Hz), 7.33–7.45 (m, 5H), 6.62 (d, 1H,J=4.0 Hz), 5.22 (s, 2H), 3.62 (s, 3H), 3.19 (t, 2H,J=7.0 Hz), 2.90 (t, 2H,J=6.9 Hz).

Other propionic acid methyl esters prepared by this method are listed below. Yields in the range of 93–100% were observed.

3-[3-(5-Ethoxycarbonylaminothiophen-3-yl)-1,2,4-oxadiazol-5-yl]propionic acid methyl ester; 3-[3-(5-Propionylaminothiophen-3-yl)-1,2,4-oxadiazol-5-yl] propionic acid methyl ester; 3-{3-[5-(3-Methylbutyrylamino)thiophen-3-yl]-1,2,4-oxadiazol-5-yl}propionic acid methyl ester; and 3-[3-(5-Benzyloxycarbonylaminothiophen-3-yl)-1,2,4-oxadiazol-5-yl]propionic acid methyl ester.

Example 57

This example illustrates a method for producing 3-[3-(3-tert-butyloxycarbonylaminophenyl)-1,2,4-oxadiazol-5-yl] propionic Acid.

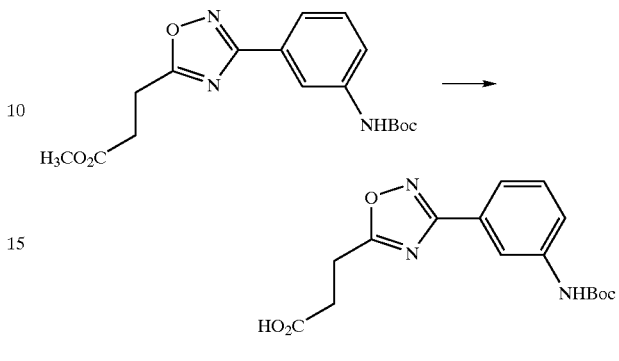

A 100-mL round bottomed flask was charged with methyl 3-[3-(3-tert-butyloxycarbonylaminophenyl)-1,2,4-oxadiazol-5-yl]propionate (4.04 g, 11.6 mmol), lithium hydroxide (1.39 g, 58.2 mmol), methanol (15 mL), water (15 mL) and THF (15 mL). The resulting solution was then stirred for 2 h at room temperature. The solvents were then removed under reduced pressure and the residue dissolved into water (60 mL). The resulting solution was cooled to 0° C. and acidified to pH 5 by the addition of 2 N hydrochloric acid. The mixture was then extracted with ethyl acetate (4×50 mL) and the combined extracts dried over sodium sulfate. Filtration and concentration under reduced pressure afforded an 83% yield of 3-[3-(3-tert-butyloxycarbonylaminophenyl)-1,2,4-oxadiazol-5-yl] propionic acid as a white solid. m.p. 143–144° C.; $^1$H NMR (DMSO-d$_6$) δ (ppm) 12.42 (bs, 1H), 9.60 (s, 1H), 8.24 (s, 1H), 7.57 (m, 2H), 7.42 (t, 1H,J=7.9 Hz), 3.26 (t, 2H,J=6.9 Hz), 2.84 (t, 2H,J=6.9 Hz), 1.49 (s, 9H); m/z=332 (M−H).

Other oxadiazolylpropionic acids prepared by this method are listed below. Yields in the range of 55–99% were observed.

3-[3-(1-tert-Butyloxycarbonylpiperidin-4-yl)-1,2,4-oxadiazol-5-yl]propionic acid; 3-[3-(1-tert-Butyloxycarbonylpiperidin-3-yl)-1,2,4-oxadiazol-5-yl] propionic acid; 3-[3-(1-tert-Butyloxycarbonylpipidin-2-yl)-1,2,4-oxadiazol-5-yl]propionic acid; 3-[3-(1-tert-Butyloxycarbonylpyrrolidin-2-yl)-1,2,4-oxadiazol-5-yl] propionic acid; 3-[3-(2-Propionylaminothiophene-4-yl)-1,2,4-oxadiazol-5-yl]propionic acid; 3-{3-[2-(3-Methylbutyrylamino)thiophen-4-yl]-1,2,4-oxadiazol-5-yl}propionic acid; 3-[3-(2-Benzyloxycarbonylaminothiophene-5-yl)-1,2,4-oxadiazol-5-yl]propionic acid; 3-[3-(2-Benzyloxycarbonylaminothiophene-4-yl)-1,2,4-oxadiazol-5-yl]propionic acid; 3-[3-tert-Butyloxycarbonylamino-2-methyl-2H-pyrazol-4-yl)-1,2,4-oxadiazol-5-yl]propionic acid; 3-[3-(3-tert-Butyloxycarbonylamino-1-(2-trimethylsilyl)ethoxy-methyl-1H-pyrazol-4-yl)-1,2,4-oxadiazol-5-yl]propionic acid; 3-[3-(4-tert-Butyloxycarbonylamino-1-(2-trimethylsilyl)ethoxymethyl-1H-imidazol-5-yl)-1,2,4-oxadiazol-5-yl]propionic acid; 3-[3-(5-tert-Butyloxycarbonylamino-1-(2-trimethylsilyl) ethoxymethyl-1H-imidazol-4-yl)-1,2,4-oxadiazol-5-yl] propionic acid; 3-[(3-Methyl-1-triisopropylsilyloxymethyl-1H-pyrrol-2-yl)-1,2,4-oxadiazol-5-yl]propionic acid; 3-{3-[1-(2-Ethoxyethyl)-1H-pyrrol-2-yl]-1,2,4-oxadiazol-5-yl}propionic acid; 3-[3-(3-Difluoromethoxymethylphenyl)-

1,2,4-oxadiazol-5-yl]propionic acid; 3-[3-(4-Difluoromethoxymethylphenyl)-1,2,4-oxadiazol-5-yl] propionic acid; 3-[3-(4-Ethoxymethylphenyl)-1,2,4-oxadiazol-5-yl]propionic acid; 3-[3-(3-Ethoxymethylphenyl)-1,2,4-oxadiazol-5-yl]propionic acid; 3-[3-(4-Methoxymethylphenyl)-1,2,4-oxadiazol-5-yl] propionic acid; 3-[3-(3-Methoxyphenyl)-1,2,4-oxadiazol-5-yl]propionic acid; 3-[3-(4-Isopropoxyphenyl)-1,2,4-oxadiazol-5-yl]propionic acid; 3-[3-(3-Isopropoxyphenyl)-1,2,4-oxadiazol-5-yl]propionic acid; 3-[3-(4-Propoxyphenyl)-1,2,4-oxadiazol-5-yl]propionic acid; 3-[3-(3-Propoxyphenyl)-1,2,4-oxadiazol-5-yl]propionic acid; 3-[3-(3-Ethoxyphenyl)-1,2,4-oxadiazol-5-yl]propionic acid; 3-[3-(4-Ethoxyphenyl)-1,2,4-oxadiazol-5-yl]propionic acid; 3-{3-[4-(2,2,2-Trifluoroethoxy)phenyl]-1,2,4-oxadiazol-5-yl}propionic acid; 3-{3-[3-(2,2,2-Trifluoroethoxy)phenyl]-1,2,4-oxadiazol-5-yl}propionic acid; 3-[3-(4-Cyclopropylmethoxyphenyl)-1,2,4-oxadiazol-5-yl] propionic acid; 3-[3-(1-Ethyl-1H-pyrrol-2-yl)-1,2,4-oxadiazol-5-yl]propionic acid; 3-[3-(5-Ethoxycarbonylaminothiophen-3-yl)-1,2,4-oxadiazol-5-yl] propionic acid; 3-[3-(2-tert-Butyloxycarbonylaminothiophen-5-yl)-1,2,4-oxadiazol-5-yl]propionic acid; 3-{4-[(5-(2-Carboxy)ethyl)-1,2,4-oxadiazol-3-yl]thiophen-2-yl}-1-isobutylurea, 3-(2-Ethanesulfonylaminothiophene-4-yl-1,2,4-oxadiazol-5-yl) propionic acid; 3-(3-Chloromethyl-1,2,4-oxadiazol-5-yl) propionic acid; 3-[3-(5-tert-Butyloxycarbonylamino-3-methylisoxazol-4-yl)-1,2,4-oxadiazol-5-yl]propionic acid; 3-[3-(5-Dimethylaminomethyl-1-methyl-1H-pyrrol-2-yl)-1,2,4-oxadiazol-5-yl]propionic acid; 3-[3-(1-Methylpiperidin-2-yl)-1,2,4-oxadiazol-5-yl]propionic acid; 3-[3-(1-Methylpiperidin-3-yl)-1,2,4-oxadiazol-5-yl]propionic acid; 3-[3-(1-Methylpiperidin-2-yl)-1,2,4-oxadiazol-5-yl] propionic acid; and 3-[3-(1-Methylpiperidin-4-yl)-1,2,4-oxadiazol-5-yl]propionic acid.

Example 58

This example illustrates a method for producing 3-[3-(2,4-dihydroxyphenyl)-1,2,4-oxadiazol-5-yl]propionic acid.

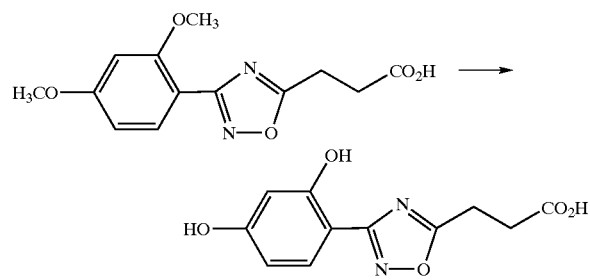

A 50-mL, one-neck, round bottomed flask equipped with a magnetic stirrer and digital thermometer was charged with 3-[3-(2,4-dimethoxyphenyl)-1,2,4-oxadiazol-5-yl]propionic acid (835 mg, 3.00 mmol), the flask purged with nitrogen, then anhydrous methylene chloride (10 mL) added. After cooling the resulting solution to −70° C., a 1 M solution of boron tribromide in methylene chloride (9.0 mL, 9.0 mmol) was added, and the reaction mixture slowly warmed to ambient temperature. After stirring for an additional 1 h at ambient temperature, the mixture was quenched with water (50 mL) and heated to reflux. The resulting suspension was then cooled to ambient temperature, and the solid filtered. The filter cake was triturated with water (20 mL) in order to remove boric acid, and dried overnight at 45° C. under reduced pressure affording a 71% yield of the title compound as a brown solid. m.p. 177–179° C.; $^1$H NMR (DMSO-d$_6$) δ (ppm) 12.40 (bs, 1H), 9.95 (s, 1H), 9.75 (s, 1H), 7.65 (d, 1H,J=9.2 Hz), 6.38 (m, 2H), 3.16 (t, 2H,J=7.0 Hz), 2.82 (t, 2H,J=6.8 Hz); m/z=2.49 (M−H).

Other substituted propionic acids prepared by this method are listed below. Yields in the range of 29–100% were observed.

3-[3-(2,3-Dihydroxyphenyl)-1,2,4-oxadiazol-5-yl] propionic acid; 3-[3-(3,5-Dihydroxyphenyl)-1,2,4-oxadiazol-5-yl]propionic acid; 3-[3-(2,5-Dihydroxyphenyl)-1,2,4-oxadiazol-5-yl]propionic acid; 3-[3-(2,6-Dihydroxyphenyl)-1,2,4-oxadiazol-5-yl]propionic acid; and 3-[3-(2-Hydroxy-6-methoxy-4-methylpyridin-3-yl)-1,2,4-oxadiazol-5-yl]propionic acid.

Example 59

This example illustrates a method for producing 3-[3-(3,4-dihydroxyphenyl)-1,2,4-oxadiazol-5-yl]propionic acid.

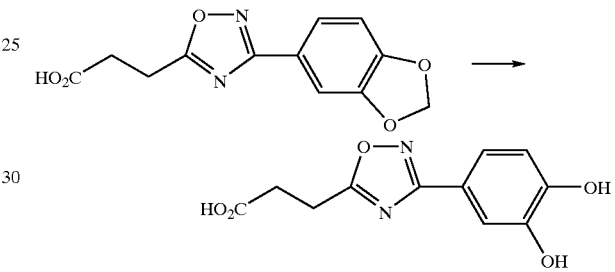

A 500-mL, one-neck, round bottomed flask equipped with a magnetic stirrer was charged with 3-[3-(3,4-methylenedioxyphenyl-1,2,4-oxadiazol-5-yl)]propionic acid (2.74 g, 10.4 mmol), the flask purged with nitrogen, then anhydrous methylene chloride (110 mL) and a 1 M solution of boron trichloride in methylene chloride (31 mL, 31 mmol) were added. After 2 h at ambient temperature, the reaction mixture was quenched with water (20 mL) and heated to reflux. The reaction mixture was then cooled to ambient temperature, and the dichloromethane was evaporated under vacuum. The resulting aqueous suspension was filtered; the filter cake was washed with water (20 mL), then dried for 6 h at 45° C. under reduced pressure. This afforded a 71% yield of the title compound as a brown solid. m.p. 151–155° C., $^1$H NMR (DMSO-d$_6$) δ (ppm) 12.3 (bs, 1H), 9.4 (bs, 2H), 7.38 (s, 1H), 7.29 (d, 1H),J=8.2 Hz), 6.85 (d, 1H,J=8.2 Hz), 3.14 (t, 2H,J=6.8 Hz), 2.81 (t, 2H,J=6.8 Hz); m/z=149 (M−H).

Example 60

This example illustrates a method for producing 3-{3-[2-(4-methylpiperazin-1-yl)-pyridin-3-yl]-1,2,4-oxadiazol-5yl}propionic acid

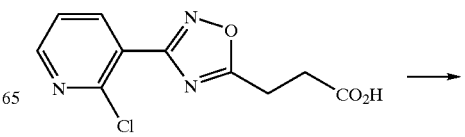

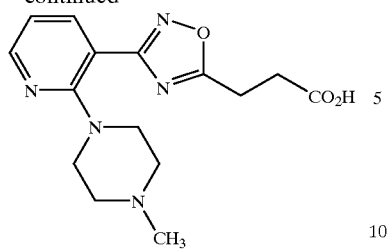

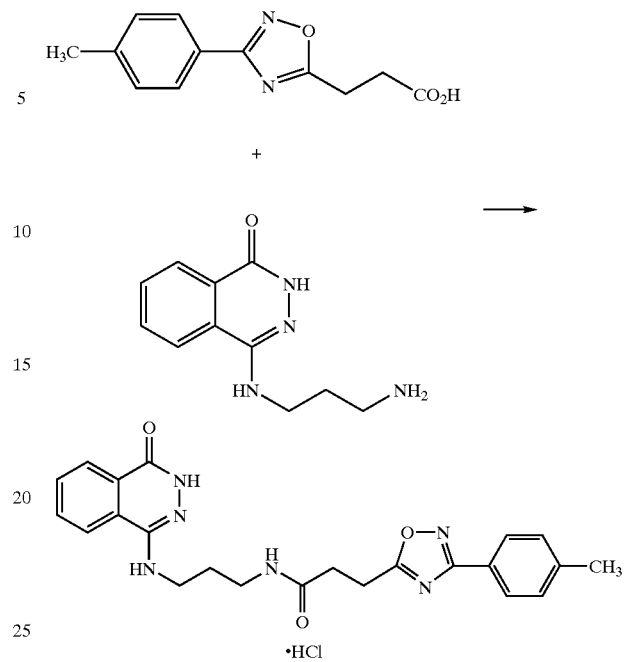

A 25-mL, one-neck, round bottomed flask equipped with a magnetic stirrer was charged with 3-[3-(2-chloropyridin-3-yl)-1,2,4-oxadiazol-5-yl]propionic acid (500 mg, 2.00 mmol), 1-methylpiperazine (200 mg, 2.20 mmol), dimethylformamide (7 mL) and potassium carbonate (690 mg, 5.00 mmol). The flask was purged with nitrogen and heated at 100° C. for 27 h. The reaction mixture was then evaporated to dryness under vacuum, and the resulting solids were purified by column chromatography on silica gel to provide a 59% yield of the title compound as a brown oil. $^1$H NMR (CDCl$_3$) δ (ppm) 8.22 (dd, 1H,J=4.6, 1.6 Hz), 7.93 (dd, 1H, dd,J=7.6, 1.7 Hz), 6.76 (dd, 1H,J=7.4, 4.8 Hz), 3.20–3.30 (m, 4H), 3.04 (t, 2H,J=7.3 Hz), 2.48 (t, 2H,J=6.7), 2.35–2.45 (m, 4H), 2.21 (s, 3H); m/z=316 (M−H).

Example 61

This example illustrates a method for producing sodium 3-[3-(morpholin-4-ylmethyl)-1,2,4-oxadiazol-5-yl] propionate.

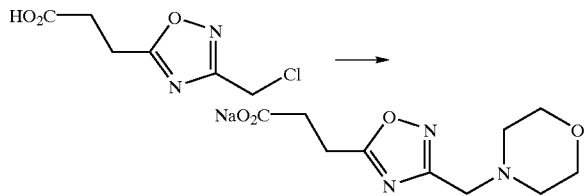

A 25 mL, one-neck, round bottomed flask equipped with a magnetic stirrer was charged with 3-(3-chloromethyl-1,2,4-oxadiazol-5-yl)propionic acid (1.48 g, 7.77 mmol), dimethylformamide (4 mL) and morpholine (2.0 g, 22.9 mmol). The reaction mixture was then stirred for 4 h at ambient temperature. The resulting suspension was filtered, and the filter cake was washed with ether and dried to afford 2.52 g of the crude product. A portion (1.49 g) of this material was dissolved in methanol (6 mL) and treated with sodium hydroxide (399 mg, 9.98 mmol). After 1 h, the reaction mixture was concentrated to dryness under vacuum, and then triturated with ethyl acetate. The precipitate was filtered and dried under reduced pressure affording a 68% yield of sodium 3-[3-(morpholin-4-ylmethyl)-1,2,4-oxadiazol-5yl] propionate, contaminated with a small amount of sodium acetate, as a white solid. This material was used directly. m.p. 155–161° C. (dec.); $^1$H NMR (DMSO-d$_6$) δ (ppm) 3.56 (m, 6H), 2.98 (t, 2H,J=7.2 Hz), 2.46 (t, 4H,J=4.3 Hz), 2.36 (t, 2H,J=7.2 Hz): m/z=263 (M−Na).

Example 62

This example illustrates a method for producing hydrochloride salt of N-[3-(4-oxo-3,4-dihydro-phthalazin-1-ylamino)-propyl]-3-(3-p-tolyl-[1,2,4]oxadiazol-5-yl)-propionamide.

A 10-mL round bottomed flask equipped with a magnetic stirrer was purged with nitrogen and charged with 4-(3-aminopropylamino)-2H-phthalazin-1-one (152 mg, 0.65 mmol), 3-{3-[4-methylphenyl]-1,2,4-oxadiazol-5-yl}propionic acid (163 mg, 0.65 mmol), anhydrous DMF (4 mL), 1-(3-dimethylamino-propyl)-3-ethylcarbodiimide hydrochloride (150 mg, 0.78 mmol), 1-hydroxybenzotriazole (84 mg, 0.78 mmol) and diisopropylethylamine (85 mg, 0.78 mmol). After stirring for 22 h at ambient temperature, the mixture was filtered and the filtrate was concentrated to dryness under reduced pressure. The residue was purified by column chromatography and converted to the corresponding hydrochloride salt by treatment of a methanol (2 mL) suspension of the free base with one equivalent of a 1 M solution of hydrogen chloride in dioxane. Concentration of the resulting solution under reduced pressure and drying under high vacuum gave a 54% yield of the title compound as a white solid. m.p. 194–196° C., $^1$H NMR (DMSO-d$_6$) δ (ppm) 11.54 (s, 1H), 8.21 (d, 1H,J=7.7 Hz), 8.10 (m, 1H), 7.80–7.91 (m, 4H), 7.30 (d, 2H,J=8.0 Hz), 3.13–3.24 (m, 6H), 2.69 (t, 2H,J=7.2 Hz), 2.33 (s, 3H), 1.71–1.80 (m, 2H); m/z=433 (M+H).

A solution of 1 M hydrogen chloride in diethyl ether can be substituted for 1 M hydrogen chloride in dioxane. Examples that were prepared by this method, including the observed yield and analytical data, are listed below.

Hydrochloride salt of 3-[3-(4-Chloro-phenyl)-[1,2,4] oxadiazol-5-yl]-N-[3-(4-oxo-3,4-dihydro-phthalazin-1-ylamino)-propyl]propionamide, 84%, white solid; m.p. 198–200° C.; $^1$H NMR (DMSO-d$_6$) δ (ppm) 11.55 (s, 1H), 8.20 (d, 1H,J=6.9 Hz), 8.10 (m, 2H), 7.96 (d, 2H,J=8.4 Hz), 7.85 (m, 2H), 7.59 (d, 2H,J=8.5 Hz), 3.10–3.30 (m, 7H), 2.70 (t, 2H,J=7.2 Hz), 1.76 (m, 2H); m/z=453 (M+H).

Hydrochloride salt of N-[3-(4-Oxo-3,4-dihydro-phthalazin-1-ylamino)-propyl]-3-(3-phenyl-[1,2,4] oxadiazol-5-yl) propionamide, 62%, white solid; m.p. 179–181° C.; $^1$H NMR (DMSO-d$_6$) δ (ppm) 11.55 (s, 1H), 8.20 (d, 1H,J=7.5 Hz), 8.10 (m, 2H), 7.97 (m, 2H), 7.84 (m, 2H), 7.53 (m, 3H), 3.10–3.30 (m, 7H), 2.70 (t, 2H,J=7.2 Hz), 1.76 (m, 2H); m/z=419 (M+H);

Hydrochloride salt of N-[3-(4-Oxo-3,4-dihydro-phthalazin-1-ylamino)-propyl]-3-(3-p-tolyl-[1,2,4]oxadiazol-5-yl)-propionamide, 53%, white solid; m.p. 194–196° C.; $^1$H NMR (DMSO-d$_6$) δ (ppm) 11.54 (s, 1H), 8.21 (d, 1H,J=7.7 Hz), 8.10 (m, 1H), 7.80–7.91 (m, 4H), 7.30 (d, 2H,J=8.0 Hz), 3.13–3.24 (m, 6H), 2.69 (t, 2H,J=7.2 Hz), 2.33 (s, 3H), 1.75 (m, 2H); m/z=433 (M+H);

Hydrochloride salt of 3-[3-(4-Methoxy-phenyl)-[1,2,4]oxadiazol-5-yl]-N-[3-(4-oxo-3,4-dihydro-phthalazin-1-ylamino)-cyclohexyl]-propionamide, 79%, off-white solid; m.p. 155° C. (dec.); $^1$H NMR (DMSO-d$_6$) δ (ppm) 11.52 (s, 1H), 8.18 (m, 2H), 8.00 (d, 1H,J=9.0 Hz), 7.85 (m, 2H), 7.05 (d, 2H,J=9.0 Hz), 3.79 (s, 3H), 3.60 (m, 2H), 3.16 (m, 2H), 2.64 (t, 2H,J=6.9 Hz), 2.21 (d, 1H,J=11.1 Hz), 1.97 (d, 1H,J=9.3 Hz), 1.75 (d, 2H,J=10.3 Hz), 1.30–1.40 (m, 5H); m/z=489 (M+H);

Hydrochloride salt of N-[3-(4-Oxo-3,4-dihydro-phthalazin-1-ylamino)-propyl]-3-[3-(4-trifluoromethoxy-phenyl)-[1,2,4]oxadiazol-5-yl]-propionamide, 25%, white solid; m.p. 176–179° C.; $^1$H NMR (DMSO-d$_6$) δ (ppm) 11.55 (s, 1H), 8.22 (d, 1H,J=7.0 Hz), 8.08–8.10 (m, 4H), 7.88 (t, 1H,J=7.0 Hz), 7.80 (t, 1H,J=7.5 Hz), 7.51 (d, 2H,J=8.3 Hz), 3.13–3.26 (m, 6H), 2.71 (t, 2H,J=7.1 Hz), 1.72–1.81 (m, 2H); m/z=503 (M+H);

Hydrochloride salt of 3-[3-(4-Fluoro-phenyl)-[1,2,4]oxadiazol-5-yl]-N-[3-(4-oxo-3,4-dihydro-phthalazin-1-ylamino)-propyl]-propionamide, 30%, white solid; m.p. 284–287° C.; $^1$H MMR (DMSO-d$_6$) δ (ppm) 8.24 (d, 1H,J=7.1 Hz), 7.82–8.05 (m, 5H), 7.30 (t, 2H,J=8.8 Hz), 3.16–3.25 (m, 6H), 2.70 (t, 2H,J=6.9 Hz), 1.78 (m, 2H); m/z=437 (M+H);

Hydrochloride salt of 3-[3-(2,3-Dihydro-benzofuran-5-yl)-[1,2,4]oxadiazol-5-yl]-N-[2,2-dimethyl-3-(4-oxo-3,4-dihydro-phthalazin-1-ylamino)-propyl]-propionamide, 82%, white solid; m.p. 115–118° C.; $^1$H NMR (CDCl$_3$) δ (ppm) 9.28 (bs, 1H), 8.42 (m, 2H), 8.02 (m, 2H), 7.58 (m, 2H), 6.70 (d, 1H,J=8.2 Hz, 4.54 (t, 2H,J=8.7 Hz), 3.67 (m, 2H), 3.18–3.31 (m, 8H), 1.18 (s, 6H); m/z=489 (M+H);

Hydrochloride salt of 2-Hydroxy-N-[2-hydroxy-3-(4-oxo-3,4-dihydro-phthalazin-1-ylamino)-propyl]-4-methylsulfanyl-butyramide, 66%, white solid; m.p. 165–170° C.; $^1$H NMR (DMSO-d$_6$) δ (ppm) 11.56 (s, 1H), 8.22 (dd, 1H,J=0.9, 7.7 Hz), 8.11 (d, 1H,J=8.1 Hz), 7.91 (dt, 1H,J=1.2,7.1 Hz), 7.82 (t, 1H,J=7.4 Hz), 7.72 (bs, 1H), 6.58 (t, 1H,J=5.4 Hz), 5.70 (dd, 1H,J=1.9, 5.5 Hz), 5.08 (dd, 1H,J=3.3, 4.9 Hz), 3.94 (m, 2H), 3.28 (m, 1H), 3.24 (t, 2H,J=5.6 Hz), 3.12 (m, 1H), 2.01 (s, 3H), 1.79 (m, 2H); m/z=367 (M+H);

Hydrochloride salt of 3-(3-Benzo[1,3]dioxol-5-yl-[1,2,4-oxadiazol-5-yl)-N-[3-(4-oxo-3,4-dihydro-phthalazin-1-ylamino)-propyl]-propionamide, 69%, white solid; m.p. 236–242° C.; $^1$H NMR (DMSO-d$_6$) δ (ppm) 11.53 (s, 1H), 8.21 (d, 1H,J=7.1 Hz), 8.03–8.09 (m, 2H), 7.90 (t, 1H,J=7.0 Hz), 7.79 (t, 1H,J=7.4 Hz), 7.52 (d, 1H,J=8.1 Hz), 7.39 (s, 1H), 7.02 (d, 1H,J=8.1 Hz), 6.52 (t, 1H,J=5.2 Hz), 6.10 (s, 2H), 3.14–3.62 (m, 6H), 2.68 (t, 2H,J=7.0 Hz), 1.71–1.80 (m, 2H); m/z=463 (M+H)

Hydrochloride salt of N-[3-(4-Oxo-3,4-dihydro-phthalazin-1-ylamino)-propyl]-3-(3-thiophen-2-yl-[1,2,4]oxadiazol-5yl)-propionamide, 83%, tan solid; m.p. 193–196° C.; $^1$H NMR (DMSO-d$_6$) δ (ppm) 11.57 (s, 1H), 8.20 (d, 1H,J=7.8 Hz), 8.06 (m, 2H), 7.68–7.95 (m, 4H), 7.23 (m, 1H), 3.08–3.30 (m, 7H), 2.68 (t, 2H,J=7.2 Hz), 1.76 (m, 2H); m/z=425 (M+H);

Hydrochloride salt of 3-[3-(2,3-Dichloro-phenyl)-[1,2,4]oxadiazol-5-yl]-N-[3-(4-oxo-3,4-dihydro-phthalazin-1-ylamino)-propyl]propionamide, 79%, off-white solid; m.p. 178–184° C.; $^1$H NMR (DMSO-d$_6$) δ (ppm) 11.55 (s, 1H), 8.21 (d, 1H,J=6.6 Hz), 8.10 (m, 2H), 7.80–7.91 (m, 4H), 7.51 (t, 1H,J=8.0 Hz), 3.08–3.25 (m, 6H), 2.70 (t, 2H,J=7.0 Hz), 1.75 (m, 2H); m/z=487 (M+H).

Hydrochloride salt of 3-[3-(4-Methylsulfanyl-phenyl)-[1,2,4]oxadiazol-5-yl]-N-[3-(4-oxo-3,4-dihydro-phthalazin-1-ylamino)-propyl]-propionamide, 77%, white solid; m.p. 190–191° C.; $^1$H NMR (CD$_3$OD) δ (ppm) 8.28 (m, 2H), 8.02 (m, 2H), 7.77 (d, 2H,J=8.5 Hz), 7.08 (d, 2H,J=8.4 Hz), 3.36 (m, 2H), 2.85 (t, 2H,J=6.4 Hz), 2.38 (m, 3H), 1.98 (m, 2H); m/z=465 (M+H);

Hydrochloride salt of 3-[3-(2,3-Dihydro-benzofuran-5-yl)-[1,2,4]oxadiazol-5-yl]-N-[2-hydroxy-3-(4-oxo-3,4-dihydro-phthalazin-1-ylamino)-propyl]-propionamide, 33%, white solid; m.p. 174–177° C.; $^1$H NMR (DMSO-d$_6$) δ (ppm) 11.55 (s, 1H), 8.21 (dd, 1H,J=1.3, 7.7 Hz), 8.07 (m, 2H), 7.88 (dt, 1H,J=1.4, 7.3 Hz), 7.80 (m, 2H), 7.71 (dd, 1H,J=1.8, 8.3 Hz), 6.85 (d, 1H,J=8.3 Hz), 6.46 (t, 1H,J=5.6 Hz), 4.99 (d, 1H,J=5.0 Hz), 4.59 (t, 2H,J=8.8 Hz), 3.84 (m, 1H), 3.09–3.28 (m, 8H), 2.72 (t, 2H,J=7.3 Hz); m/z=477 (M+H).

Hydrochloride salt of 3-[3-(6-Methoxy-pyridin-3-yl)-[1,2,4]-oxadiazol-5-yl]-N-[3-(4-oxo-3,4-dihydro-phthalazin-1-ylamino)-propyl]propionamide, 49%, pink solid; m.p. 150° C. (dec.); $^1$H NMR (CD$_3$OD) δ (ppm) 8.68 (d, 1H,J=2.2 Hz), 8.46 (d, 1H,J=8.1 Hz), 8.28 (m, 2H), 8.06 (m, 2H), 6.93 (d, 1H,J=8.8 Hz), 3.92 (s, 3H), 3.28–3.48 (m, 6H), 2.88 (t, 2H,J=6.9 Hz), 2.03 (m, 2H); m/z=450 (M+H);

Hydrochloride salt of N-[3-(4-Oxo-3,4-dihydro-phthalazin-1-ylamino)-propyl]-3-(3-thiophen-3-yl-[1,2,4]oxadiazol-5yl)-propionamide, 64%, white solid; m.p. 195–198° C.; $^1$H NMR (DMSO-d$_6$) δ (ppm) 11.57 (s, 1H), 8.23 (m, 2H), 8.09 (m, 2H), 7.88 (t, 1H,J=8.1 Hz), 7.80 (t, 1H,J=7.8 Hz), 7.73 (dd, 1H,J=5.1,3.0 Hz), 7.54 (dd, 1H,J=5.1, 1.2 Hz), 6.56 (t, 1H,J=5.3 Hz), 3.10–3.30 (m, 6H), 2.68 (t, 2H,J=8.7 Hz), 1.77 (m, 2H); m/z=425 (M+H);

Hydrochloride salt of 3-{3-[4-(2-Dimethylamino-ethoxy)-phenyl]-[1,2,4]oxadiazol-5-yl}-N-[3-(4-oxo-3,4-dihydro-phthalazin-1-ylamino)-propyl]-propionamide, 17%, white solid; m.p. 65–67° C.; $^1$H NMR (DMSO-d$_6$) δ (ppm) 11.54 (s, 1H), 10.10 (s, 1H), 8.21 (dd, 1H,J=7.8, 1.2 Hz), 8.10 (m, 2H), 7.93 (d, 2H,J=8.8 Hz), 7.83 (m, 2H), 7.12 (d, 2H,J=8.8 Hz), 4.40 (t, 2H,J=5.0 Hz), 3.57 (m, 2H), 3.10–3.30 (m, 6H), 2.87 (s, 3H), 2.86 (s, 3H), 2.69 (t, 2H,J=7.1 Hz), 1.78 (m, 2H); m/z=506 (M+H);

Hydrochloride salt of 3-[3-(4-Hydroxy-phenyl)-[1,2,4]oxadiazol-5-yl]-N-[3-(5-oxo-5,6-dihydro-pyrido[2,3-d]pyridazin-8-ylamino)-cyclohexyl]-propionamide, 14%, yellow solid; m.p. 74° C. (dec.); $^1$H NMR (CD$_3$OD) δ (ppm) 9.02 (dd, 1H,J=1.6, 4.6 Hz), 8.60 (dd, 1H,J=1.6, 8.1 Hz), 7.77–7.84 (m, 3H), 6.79 (m, 2H), 3.79 (m, 2H), 3.23 (m, 2H), 2.76 (t, 2H,J=7.0 Hz), 2.37 (bd, 1H,J=11.7 Hz), 2.11 (bd, 1H,J=10.8 Hz), 1.88 (m, 2H), 1.15–1.53 (m, 4H); m/z=476 (M+H).

Hydrochloride salt of 3-[3-(4-Difluoromethoxy-phenyl)-[1,2,4]oxadiazol-5-yl]-N-[3-(4-oxo-3,4-dihydro-phthalazin-1-ylamino)-propyl]-propionamide, 49%, off-white solid; m.p. 189–196° C.; $^1$H NMR (DMSO-d$_6$) δ (ppm) 11.55 (s, 1H), 8.30–7.70 (m, 7H), 7.60–7.49 (m, 3H), 3.26–3.13 (m, 6H), 2.70 (m, 2H), 1.76 (m, 2H); m/z=485 (M+H);

Hydrochloride salt of 3-[3-(4-Bromo-phenyl)-[1,2,4]oxadiazol-5yl]-N-[3-(4-oxo-3,4-dihydro-phthalazin-1-ylamino)-propyl]-propionamide, 24%, white solid; m.p. 188–195°60 C.; $^1$H NMR (DMSO-d$_6$) δ (ppm) 11.57 (bs, 1H), 8.08–8.34 (m, 3H), 7.88–7.95 (m, 4H), 7.78 (m, 2H), 3.14–3.27 (m, 6H), 2.71 (m, 2H), 1.77 (t, 2H,J=6.8 Hz); m/z=497 (M+H);

Hydrochloride salt of N-[3-(5,8-Difluoro-4-oxo-3,4-dihydro-phthalazin-1-ylamino)-propyl]-3-[3-(4-methoxy-phenyl)-[1,2,4]oxadiazol-5yl]-propionamide, 14%, pale yellow solid; m.p. 174–176° C.; $^1$H NMR (DMSO-d$_6$) δ (ppm) 11.66 (s, 1H), 8.10 (t, 1H,J=5.6 Hz), 7.89 (d, 2H,J=8.8 Hz), 7.77 (m, 1H), 7.61 (dt, 1H,J=3.9, 10.4 Hz), 7.05 (d, 2H,J=8.8 Hz), 6.07 (bs,1H), 3.81 (s, 3H), 3.11–3.22 (M, 6H), 2.69 (t, 2H,J=7.0 Hz), 1.70 (m, 2H), m/z=485 (M+H).

Hydrochloride salt of 3-{3-[3-(2-Dimethylamino-ethoxy) phenyl]-[1,2,4]oxadiazol-5-yl }-N-[3-(4-oxo-3,4-dihydro-phthalazin-1-ylamino)-propyl]-propionamide, 32%, white solid; m.p. 68–70° C.; $^1$H NMR (DMSO-d$_6$) δ (ppm) 11.57 (s, 1H), 10.32 (s, 1H), 8.10 (m, 3H), 7.88 (t, 1H,J=7.0 Hz), 7.80 (t, 1H,J=7.2 Hz), 7.61 (d, 1H,J=7.7 Hz), 7.54 (m, 1H), 7.48 (t, 1H,J=7.8 Hz), 7.20 (d, 1H,J=8.2 Hz), 4.42 (t, 2H,J=4.9 Hz), 3.10–3.26 (m, 7H), 2.86 (s, 3H), 2.84 (s, 3H), 2.70 (t, 2H,J=7.1 Hz), 1.75 (m, 2H); m/z=506 (M+H).

Hydrochloride salt of 3-[3-(4-dimethylaminomethyl-phenyl)-1,2,4]-oxadiazol-5-yl]-N-[3-(4-oxo-3,4-dihydro-phthalazin-1-ylamino)-propyl]-propionamide, 55%, white solid; m.p. 98° C. (dec.); $^1$H NMR (DMSO-d$_6$) δ (ppm) 11.56 (s, 1H), 11.26 (s, 1H), 8.21–8.26 (m, 3H), 8.03 (d, 2H,J=7.9 Hz), 7.69–7.89 (m, 4H), 4.35 (d, 2H,J=4.6 Hz), 3.17–3.40 (m, 6H), 2.70–2.76 (m, 8H), 1.78 (m, 2H); m/z=476 (M+H);

Hydrochloride salt of 3-[3-(3-Dimethylaminomethyl-phenyl)-[1,2,4]oxadiazol-5-yl]-N-[3-(4-oxo-3,4-dihydro-phthalazin-1-ylamino)-propyl]-propionamide, 24%, white solid; m.p. 90° C. (dec.); $^1$H NMR (DMSO-d$_6$) δ (ppm) 11.54 (s, 1H), 10.74 (s, 1H), 7.61–8.18 (m, 9H), 4.38 (bs, 2H), 3.19–3.21 (m, 6H), 2.71 (bs, 8H), 1.77 (bs, 2H); m/z=476 (M+H);

Hydrochloride salt of 3-[3-(3-Hydroxy-phenyl)-[1,2,4]oxadiazol-5-yl]-N-[3-(4-oxo-3,4-dihydro-phthalazin-1-ylamino)-propyl]-propionamide, 31%, white solid; m.p. 250–251° C.; $^1$H NMR (DMSO-d$_6$) δ (ppm) 11.54 (s, 1H), 8.21 (d, 1H,J=6.6 Hz), 8.20 (bs, 2H), 7.80–7.90 (m, 2H), 7.29–7.42 (m, 3H), 6.95 (m, 1H), 3.13–3.25 (m, 6H), 2.69 (t, 2H,J=7.2 Hz), 1.77 (m, 2H); m/z=4.35 (M+H);

Hydrochloride salt of 3-[3-(3,4-Difluoro-phenyl)-[1,2,4]-oxadiazol-5-yl]-N-[3-(4-oxo-3,4-dihydro-phthalazin-1-ylamino)-propyl]-propionamide, 55%, off-white solid; m.p. 195–200° C.; $^1$H NMR (DMSO-d$_6$) δ (ppm) 11.53 (s, 1H), 8.20 (d, 1H,J=6.7 Hz), 8.06 (m, 2H), 7.80–7.92 (m, 4H), 7.56–7.60 (m, 1H), 3.15–3.23 (m, 6H), 2.70 (t, 2H,J=7.1 Hz), 1.75 (m, 2H); m/z=455 (M+H);

Hydrochloride salt of 3-[3-(3,4-Dihydroxy-phenyl)-[1,2,4]oxadiazol-5-yl]-N-[3-(4-oxo-3,4-dihydro-phthalazin-1-ylamino)-propyl]-propionamide, 45%, light brown solid; m.p. 178–185° C.; $^1$H NMR (DMSO-d$_6$) δ (ppm) 11.54 (s, 1H), 8.20 (d, 1H,J=6.6 Hz), 8.05 (m, 2H), 7.88 (t, 1H,J=10.6 Hz), 7.77 (t, 1H,J=12.3 Hz), 7.37 (d, 1H,J=2.0 Hz), 7.28 (dd, 1H,J=9.9, 8.2 Hz), 6.84 (d, 1H,J=8.2 Hz), 3.24 (t, 2H,J=7.1 Hz), 3.11–3.19 (m, 5H), 2.66 (t, 2H,J=7.3 Hz); m/z=451 (M+H);

Hydrochloride salt of 3-[3-(3,5-Dihydroxy-phenyl)-[1,2,4]oxadiazol-5-yl]-N-[3-(4-oxo-3,4-dihydro-phthalazin-1-ylamino)-propyl]-propionamide, 39%, off-white solid; m.p. 189–195° C.; $^1$H NMR (DMSO-d$_6$) δ (ppm) 11.52 (s, 1H), 8.22 (d, 1H,J=9.4 Hz), 8.19 (d, 1H,J=1.3 Hz), 8.08 (t, 1H,J=6.7 Hz), 7.88 (t, 1H,J=7.2 Hz), 7.82 (t, 1H,J=7.2 Hz), 6.96 (s, 2H), 6.37 (s, 1H), 3.13–3.24 (m, 6H), 2.70 (t, 2H,J=7.3 Hz), 1.82 (m, 2H); m/z=451 (M+H);

Hydrochloride salt of 3-[3-(2,3-Dihydroxy-phenyl)-[1,2,4]oxadiazol-5-yl]-N-[3-(4-oxo-3,4-dihydro-phthalazin-1-ylamino)-propyl]-propionamide, 41%, off-white solid; m.p. 178–182° C.; $^1$H NMR (DMSO-d$_6$) δ (ppm) 11.55 (s, 1H), 8.20 (d, 1H,J=7.1 Hz), 8.10 (d, 2H,J=7.5 Hz), 7.88 (t, 1H,J=7.4 Hz), 7.80 (t, 1H,J=7.4 Hz), 7.24 (d, 1H,J=6.4 Hz), 6.95 (d, 1H,J=1.2 Hz), 6.76 (t, 1H,J=7.9 Hz), 3.15–3.27 (m, 6H), 2.70 (t, 2H,J=7.2 Hz), 1.74–1.79 (m, 2H); m/z=451 (M+H).

Hydrochloride salt of 3-[3-(2,5-Dihydro-phenyl)-[1,2,4] oxadiazol-5-yl]-N-[3-(4-oxo-3,4-dihydro-phthalazin-1-ylamino)-propyl]-propionamide, 60%, white solid; m.p. 200–206° C.; $^1$H NMR (DMSO-d$_6$) δ (ppm) 11.55 (s, 1H), 8.21 (d, 1H,J=6.8 Hz), 8.09 (bs, 2H), 7.88 (t, 1H,J=7.3 Hz), 7.82 (t, 1H,J=3.6 Hz), 7.22 (d, 1H,J=1.1 Hz), 6.84 (s, 2H), 3.13–3.26 (m, 6H), 2.70 (t, 2H,J=7.2 Hz), 1.77 (m, 2H); m/z=451 (M+H);

Hydrochloride salt of 3-[3-(2,4-Dihydroxy-phenyl)-[1,2,4]oxadiazol-5-yl]-N-[3-(4-oxo-3,4-dihydro-phthalazin-1-ylamino)-propyl]-propionamide, 28%, white solid; m.p. 202° C. (dec.); $^1$H NMR (DMSO-d$_6$) δ (ppm) 11.57 (s, 1H), 8.10–8.20 (m, 3H), 7.83 (m, 2H), 7.64 (d, 1H,J=9.3 Hz), 6.40 (m, 2H), 3.27 (m, 2H), 3.10–3.21 (m, 6H), 2.68 (t, 2H,J=7.2 Hz), 1.75 (m, 2H); m/z=451 (M+H);

Hydrochloride salt of 3-[3-(2,6-Dihydroxy-phenyl)-[1,2,4]oxadiazol-5-yl]-N-[3-(4-oxo-dihydro-phthalazin-1-ylamino)-propyl]-propionamide, 57%, white solid; m.p. 170–172° C.; $^1$H NMR (DMSO-d$_6$) δ (ppm) 11.56 (s, 1H), 10.82 (s, 1H), 10.20 (s, 1H), 8.21 (d, 1H,J=7.7 Hz), 7.81–8.15 (m, 4H), 7.41 (t, 1H,J=8.1 Hz), 7.05 (d, 1H,J=8.4 Hz), 6.68 (d, 1H,J=7.8 Hz), 3.25 (m, 2H), 3.16 (m, 2H), 2.72 (t, 2H,J=6.9 Hz), 2.46 (t, 2H,J=7.2 Hz), 1.71–1.80 (m, 2H); m/z=451 (M+H);

Hydrochloride salt of 3-[3-(1-Methyl-1H-pyrrol-2-yl)-[1,2,4]oxadiazol-5-yl]-N-[3-(4-oxo-3,4-dihydro-phthalazin-1-ylamino)-propyl]-propionamide, 74%, yellow solid; m.p. 173–177° C. (dec.); $^1$H NMR (DMSO-d$_6$) δ (ppm) 11.56 (bs, 1H), 8.10–8.20 (m, 3H), 7.87 (m, 2H), 7.03 (t, 2.1 Hz), 6.75 (dd, 1H, 3.8, 1.8 Hz), 6.11 (dd, 1H,J=3.8, 2.7 Hz), 3.87 (s, 3H), 3.09–3.26 (m, 6H), 2.67 (t, 2H,J=7.1 Hz), 1.77 (m, 2H); m/z=422 (M+H);

Hydrochloride salt of 3-[3-[4-(2-Morpholin-4-yl-ethoxy)-phenyl]-[1,2,4]oxadiazol-5-yl]-N-[3-(4-oxo-3,4-dihydro-phthalazin-1-ylamino)-propyl]-propionamide, 63%, tan solid; m.p. 114–116° C.; $^1$H NMR (CD$_3$OD) δ (ppm) 7.84–8.29 (m, 6H), 6.94 (d, 2H,J=8.9 Hz), 4.38 (t, 2H,J=4.5 Hz), 4.09 (d, 2H,J=11.7 Hz), 3.89 (t, 2H,J=12.6 Hz), 3.61–3.69 (m, 4H), 3.25–3.39 (m, 8H), 2.84 (t, 2H,J=6.9 Hz), 1.90 (m, 2H); m/z=548 (M+H);

Hydrochloride salt of 3-[3-(6-Hydroxy-pyridin-3-yl)-[1,2,4]oxadiazol-5-yl]-N-[3-(4-oxo-3,4-dihydro-phthalazin-1-ylamino)-propyl]-propionamide, 41%, tan solid; m.p. 153° C. (dec.); $^1$H NMR (DMSO-d$_6$) δ (ppm) 8.15–8.23(m, 3H), 7.97 (d, 1H,J=2.3 Hz), 7.84–7.93 (m, 3H), 6.47 (d, 1H,J=9.6 Hz), 6.23 (bs, 1H), 5.75 (s, 1H), 3.12–3.29 (m, 6H), 2.68 (t, 2H,J=7.0 Hz), 1.77 (m, 2H); m/z=436 (M+H);

Hydrochloride salt of 3-[3-(2,3-Dimethoxy-phenyl)-[1,2,4]oxadiazol-5yl]-N-[3-(4-oxo-3,4-dihydro-phthalazin-1-ylamino)-propyl]-propionamide, 45%, white solid; m.p. 137–144° C.; $^1$H NMR (DMSO-d$_6$) δ (ppm) 11.54 (s, 1H), 8.08 (t, 2H,J=9.0 Hz), 7.88 (t, 1H,J=7.4 Hz), 7.80 (t, 1H,J=7.2 Hz), 7.33 (dd, 1H,J=7.2,2.0 Hz), 7.18 (m, 2H), 3.85 (s, 3H), 3.75 (s, 3H), 3.13–3.24 (m, 6H), 2.69 (t, 2H,J=7.2 Hz), 1.77 (m, 2H); m/z=4.79 (M+H);

Hydrochloride salt of 3-[3-(2,4-Dimethoxy-phenyl)-[1,2,4]oxadiazol-5-yl]-N-[3-(4-oxo-3,4-dihydro-phthalazin-1-ylamino)-propyl]-propionamide, 58%, white solid; m.p. 120° C. (dec.); $^1$H NMR (DMSO-d$_6$) δ (ppm) 11.55 (s, 1H), 8.21 (d, 1H,J=7.5 Hz), 7.97 (m, 1H), 7.86 (m, 2H), 7.76 (d, 1H,J=8.7 Hz), 6.69 (d, 1H,J=2.3 Hz), 6.62 (dd, 1H,J=9.0, 2.3 Hz), 3.84 (s, 3H), 3.81 (s, 3H), 3.10–3.35 (m, 7H), 2.67 (t, 2H,J=7.2 Hz), 1.76 (m, 2H); m/z=479 (M+H).

Hydrochloride salt of 3-[3-(2,5-Dimethoxy-phenyl)-[1,2,4]oxadiazol-5-yl]-N-[3-(4-oxo-3,4-dihydro-phthalazin-1-ylamino)-propyl]-propionamide, 66%, off-white solid; m.p. 198–201° C.; $^1$H NMR (DMSO-$d_6$) δ (ppm) 11.61 (s, 1H), 8.20 (d, 1H J=7.8 Hz), 8.06 (m, 2H), 7.86 (t, 1H,J=7.7 Hz), 7.80 (t, 1H,J=7.2 Hz), 7.33 (d, 1H,J=2.8 Hz), 7.11 (m, 2H), 3.79 (s, 3H), 3.74 (s, 3H), 3.13–3.26 (m, 6H), 2.68 (t, 1H,J=7.2 Hz), 1.76 (m, 2H); m/z=479 (M+H);

Hydrochloride salt of 3-[3-(2,6-Dimethoxy-phenyl)-[1,2,4]oxadiazol-5-yl]-N-[3-(4-oxo-3,4-dihydro-phthalazin-1-ylamino)-propyl]-propionamide, 39%, off-white solid; m.p. 171–176° C.; $^1$H NMR (DMSO-$d_6$) δ (ppm) 11.71 (s, 1H), 8.20 (d, 1H,J=1.3 Hz), 8.11 (bs, 2H), 7.46 (t, 1H,J=8.4 Hz), 6.76 (d, 2H,J=8.5 Hz), 3.16–3.25 (m, 6H), 2.65 (t, 2H,J=7.3 Hz), 2.51 (s, 3H), 1.76 (m, 2H); m/z=479 (M+H);

Hydrochloride salt of 3-[3-(2,6-Dimethoxy-4-methyl-pyridin-3-yl)-[1,2,4]oxadiazol-5-yl]-N-[3-(4-oxo-3,4-dihydro-phthalazin-1-ylamino)-propyl]-propionamide, 49%, white solid; m.p. 105° C. (dec.); $^1$H NMR (DMSO-$d_6$) δ (ppm) 11.55 (s, 1H), 8.21 (d, 1H,J=7.8 Hz), 8.05–8.12 (m, 2H), 7.78–7.91 (m, 2H), 6.37 (s, 1H), 3.88 (s, 3H), 3.81 (s, 3H), 3.14–3.23 (m, 7H), 2.66 (t, 2H,J=7.2 Hz), 2.07 (s, 3H), 1.75 (m, 2H); m/z=494 (M+H);

Hydrochloride salt of 3-{3-[1-(2-Dimethylamino-ethyl)-1H-pyrrol-2-yl]-[1,2,4]oxadiazol-5-yl}-N-[3-(4-oxo-3,4-dihydro-phthalazin-1-ylamino)-propyl]-propionamide, 77%, white solid; m.p. 110–111° C.; $^1$H NMR (CD$_3$OD) δ (ppm) 8.31 (d, 1H,J=7.6 Hz), 8.00 (d, 1H,J=7.7 Hz), 7.85 (m, 2H), 7.03 (dd, 1H,J=2.6, 1.8 Hz), 6.91 (dd, 1H, J=3.9, 1.7 Hz), 6.17 (dd, 1H,J=3.8, 2.7 Hz), 4.81 (s, 6H), 4.70 (t, 2H,J=7.2 Hz), 3.53 (t, 2H,J=6.9 Hz), 3.28–3.45 (m, 6H), 3.24 (t, 2H,J=6.6 Hz), 2.82 (t, 2H,J=7.2 Hz), 1.88 (m, 2H); m/z=479 (M+H);

CF$_3$CO$_2$H salt of 3-[3-(2-Hydroxy-6-methoxy-4-methyl-pyridin-3-yl)-[1,2,4]oxadiazol-5yl]-N-[3-(4-oxo-3,4-dihydro-phthalazin-1-ylamino)-propyl]-propionamide, 19%, yellow solid; m.p. 86° C. (dec.); $^1$H NMR (DMSO-$d_6$) δ (ppm) 11.54 (s, 1H), 8.21 (dd, 1H,J=7.8, 1.4 Hz), 8.08 (d, 1H,J=8.1 Hz), 8.02 (t, 1H,J=5.7 Hz), 7.88 (t, 1H,J=8.1 Hz), 7.80 (t, 1H,J=7.1 Hz), 6.14 (s, 1H), 3.83 (s, 3H), 3.12–3.26 (m, 7H), 2.66 (t, 2H,J=7.2 Hz), 2.07 (s, 3H), 1.76 (m, 2H); m/z=480 (M+H) (This sample was purified by preparative HPLC and obtained as the trifluoroacetate salt);

3-(3-Morpholin-4-yl-[1,2,4]oxadiazol-5-yl)-N-[3-(4-oxo-3,4-dihydro-phthalazin-1-ylamino)-propyl]-propionamide·1.5 CF$_3$COOH salt, 11%, white solid; m.p. 80–85° C.; $^1$H NMR (CD$_3$OD) δ (ppm) 8.33 (d, 1H,J=6.7 Hz), 8.03 (d, 1H,J=7.8 Hz), 7.91 (t, 1H,J=7.8 Hz), 7.84 (t, 1H,J=8.8 Hz), 4.50 (s, 2H), 3.88 (t, 4H,J=4.5 Hz), 3.22–3.43 (m, 10H), 2.83 (t, 2H,J=7.0 Hz), 1.88 (m, 2H); m/z=442 (M+H). Elemental analysis: Calculated C, 47.06%; H, 4.69%; N, 16.0%; Found C, 47.02%; H, 4.95%; N, 16.30%. (This sample was purified by preparative HPLC and obtained as the 1.5 trifluoroacetate salt).

Hydrochloride salt of N-[3-(4-Oxo-3,4-dihydro-phthalazin-1-ylamino)-propyl]-3-(3-piperidin-4-yl-[1,2,4]oxadiazol-5-yl)-propionamide, 80%, white solid, m.p. 107–109° C.; $^1$H NMR (CD$_3$OD) δ (ppm) 8.32 (dd, 1H,J=1.4, 8.0 Hz), 8.13 (bs, 1H), 7.92 (m, 2H), 3.59 (m, 2H), 3.43 (t, 2H,J=6.4 Hz), 3.05–3.32 (m, 7H), 2.75–2.89 (m, 5H), 1.85–2.39 (m, 6H); m/z=440 (M+H);

Hydrochloride salt of 3-[3-(5-Dimethylaminomethyl-1-methyl-1H-pyrrol-2-yl)-[1,2,4]oxadiazol-5-yl]-N-[3-(4-oxo-3,4-dihydro-phthalazin-1-ylamino)-propyl]-propionamide, 33%, Orange solid; m.p. 87–91 (dec.); $^1$H-NMR (DMSO-$d_6$) δ (ppm) 11.54 (s, 1H), 8.21 (d, 1H,J=7.7 Hz), 8.12 (m, 2H), 7.84 (m,2H), 6.78 (d, 2H,J=3.8 Hz), 6.62 (t, 1H,J=5.2 Hz), 6.38 (bs, 1H), 3.94 (s, 3H), 3.12–3.32 (m, 6H), 2.67 (t, 2H,J=7.0 Hz), 2.54 (bs, 2H), 1.76 (t, 2H,J=6.9 Hz); m/z=479 (M+H).

Hydrochloride salt of 3-{3-[2-(4-Methyl-piperazin-1-yl)-pyridin-3-yl]-[1,2,4]oxadiazol-5-yl}-N-[3-(4-oxo-3,4-dihydro-phthalazin-1-ylamino)-propyl]-propionamide, 65%, yellow solid; m.p. 75° C. (dec.); $^1$H NMR (CD$_3$OD) δ (ppm) 8.26–8.33 (m, 3H), 7.81–7.97 (m, 3H), 7.06 (dd, 1H,J=7.6, 4.9 Hz), 3.20–3.80 (m, 14H), 2.92 (s, 3H), 2.85 (t, 2H,J=6.6 Hz), 1.85 (m, 2H); m/z=581 (M+H);

Hydrochloride salt of 3-[3-(1-Methyl-piperidin-2-yl)-[1,2,4]oxadiazol-5-yl]-N-[3-(4-oxo-3,4-dihydro-phthalazin-1-ylamino)-propyl]-propionamide, 59%, yellow solid; m.p. 125° C. (dec.); $^1$H NMR (CD$_3$OD) δ (ppm) 8.33 (d, 1H,J=7.5 Hz), 8.03 (d, 1H,J=7.5 Hz), 7.88 (m, 2H), 4.49 (d, 1H,J=8.7 Hz), 3.55 (d, 1H,J=7.2 Hz), 3.10–3.42 (m, 7H), 2.82 (t, 2H,J=6.8 Hz), 2.70 (s, 3H), 2.20–1.60 (m, 8H): m/z=440 (M+H).

Hydrochloride salt of 3-[3-(1-Methyl-pyrrolidin-2-yl)-[1,2,4]oxadiazol-5-yl]-N-[3-(4-oxo-3,4-dihydro-phthalazin-1-ylamino)-propyl]-propionamide, 10%, white solid; m.p. 65–67° C.; $^1$H NMR (CD$_3$OD) δ (ppm) 8.30 (m, 2H), 7.97 (m, 2H), 3.86 (bs, 1H), 3.49 (t, 2H,J=6.7 Hz), 3.30–3.42 (m, 4H), 3.27 (t, 2H,J=7.0 Hz) 3.07 (s, 3H), 2.84 (t, 2H,J=7.0 Hz), 2.60–2.69 (m, 1H), 2.23–2.46 (m, 3H), 1.95 (m, 2H); m/z=426 (M+H);

Hydrochloride salt of 3-[3-(1-Methyl-piperidin-3-yl)-[1,2,4]oxadiazol-5-yl]-N-[3-(4-oxo-3,4-dihydro-phthalazin-1-ylamino)-propyl]-propionamide, 20%, yellow solid; m.p. 135° C. (dec.); $^1$H NMR (CD$_3$OD) δ (ppm) 8.33 (d, 1H,J=7.2 Hz), 8.03 (d, 1H,J=7.7 Hz), 7.80–7.95 (m, 2H), 3.77; (d, 1H,J=11 Hz), 3.53 (d, 1H,J=12 Hz), 2.95–3.45 (m, 9H), 2.91 (s, 3H), 2.77 (t, 2H,J=6.6 Hz), 2.05 (d, 1H,J=13.4 Hz), 1.48–2.12 (m, 5H); m/z=440 (M+H);

Hydrochloride salt of N-[3-(4-Oxo-3,4-dihydro-phthalazin-1-ylamino)-propyl]-3-{3-[3-(2,2,2-trifluoro-ethoxy)-phenyl]-[1,2,4]-oxadiazol-5-yl}propionamide, 84%, off-white solid; m.p. 152–158° C.; $^1$H NMR (DMSO-$d_6$) δ (ppm) 11.55 (s, 1H), 8.22 (d, 1H,J=1.2 Hz), 8.10 (m, 2H), 8.77 (m, 2H), 7.65 (d, 1H,J=7.7 Hz), 7.57 (s, 1H), 7.50 (t, 1H,J=8.1 Hz), 7.25 (m, 1H), 4.85 (q, 2H,J=8.9 Hz), 3.20 (m, 6H), 2.71 (t, 2H,J=8.9 Hz), 1.76 (q, 2H,J=6.9 Hz); m/z=517 (M+H);

Hydrochloride salt of N-[3-(4-Oxo-3,4-dihydro-phthalazin-1-ylamino)-propyl]-3-[3-[4-(2,2,2-trifluoro-ethoxy)-phenyl]-[1,2,4]oxadiazol-5-yl]-propionamide, 67%, Off-white solid; m.p. 192–196° C. (dec.); $^1$H-NMR (DMSO-$d_6$) δ (ppm) 11.56 (s, 1H), 8.20 (d, 1H,J=7.8 Hz), 8.12 (m, 2H), 7.81–7.92 (m, 4H), 7.19 (d, 2H,J=8.8 Hz), 4.83 (q, 2H,J=8.8 Hz), 3.13–3.25 (m, 6H), 2.69 (t, 2H,J=7.0 Hz), 1.76 (t, 2H,J=6.8 Hz); m/z=517 (M+H);

Hydrochloride salt of 3-[3-(3-Fluoro-4-methyl-phenyl)-[1,2,4]oxadiazol-5-yl]-N-[3-(4-oxo-3,4-dihydro-phthalazin-1ylamino)-propyl]-propionamide, 46%, off-white solid; m.p. 185–190° C.; $^1$H NMR (DMSO-$d_6$) δ (ppm) 11.54 (bs, 1H), 8.22–8.17 (m, 3H), 7.87 (m, 2H), 7.71 (d, 1H,J=1.3 Hz), 7.62 (d, 1H,J=10.3 Hz), 7.39 (t, 1H J=7.9 Hz), 6.98 (bs, 2H), 3.25–3.13 (m, 6H), 2.70 (t, 2H,J=7.0 Hz), 2.26 (s, 3H), 1.77 (quin., 2H,J=6.9 Hz); m/z=451 (M+H);

Hydrochloride salt of 3-[3-(4-Isopropoxy-phenyl)-[1,2,4]oxadiazol-5-yl]-N-[3-(4-oxo-3,4-dihydro-phthalazin-1-ylamino)-propyl]-propionamide, 87%, off-white solid; m.p.

183–186° C. (dec.); $^1$H-NMR (DMSO-d$_6$) δ (ppm) 11.56 (bs, 1H), 8.21 (d, 1H,J=7.7 Hz), 8.10 (m, 2H), 7.81–7.91 (m, 4H), 7.01 (d, 2H,J=8.8 Hz), 4.65 (hep, 1H,J=6.1 Hz), 3.14–3.27 (m, 6H), 2.68 (t, 2H,J=7.0 Hz), 1.77 (t, 2H,J=6.9 Hz), 1.27 (d, 6H,J=6.0 Hz); m/z=477 (M+H);

Hydrochloride salt of 3-[3-(4-Cyclopropylmethoxy-phenyl)-[1,2,4]oxadiazol-5-yl]-N-[3-(4-oxo-3,4-dihydro-phthalazin-1-ylamino)-propyl]-propionamide, 97%, off-white solid; m.p. 178–180° C. (dec.); $^1$H-NMR (DMSO-d$_6$) δ (ppm) 11.56 (bs, 1H), 8.14–8.22 (m, 3H), 7.82–7.95 (m, 4H), 7.02 (d, 2H,J=8.7 Hz), 3.84 (d, 2H,J=7.0 Hz), 3.14–3.83 (m, 6H), 2.69 (t, 2H,J=7.1 Hz), 1.77 (t, 2H,J=6.7 Hz), 1.23 (m, 1H), 0.57 (m, 2H), 0.33 (m, 2H); m/z=489 (M+H);

Hydrochloride salt of 3-[3-(3-Isopropoxy-phenyl)-[1,2,4]oxadiazol-5-yl]-N-[3-(4oxo-3,4-dihydro-phthalazin-1ylamino)-propyl]-propionamide, 86%, off-white solid; m.p. 135–141° C.; $^1$H NMR (DMSO-d$_6$) δ (ppm) 8.30–8.19 (m, 3H), 7.86 (m, 2H), 7.59–7.39 (m, 3H), 7.10 (m, 1H), 4.65 (m, 1H), 3.28–3.16 (m, 6H), 2.71 (t, 2H,J=7.1 Hz), 1.78 (p, 2H,J=6.8 Hz), 1.27 (d, 6H,J=6.0 Hz); m/z=477 (M+H);

Hydrochloride salt of N-[3-(4-Oxo-3,4-dihydro-phthalazin-1-ylamino)-propyl]-3-[3-(5-propionylamino-thiophen-3-yl)-[1,2,4]oxadiazol-5-yl]-propionamide, 71%, off-white solid; m.p. 112–114° C.; $^1$H NMR (DMSO-d$_6$) δ (ppm) 11.56 (s, 1H), 11.33 (s, 1H), 8.21 (dd, 1H,J=1.2, 7.8 Hz), 8.10 (m, 2H), 7.88 (t, 1H,J=7.5 Hz), 7.80 (t, 1H,J=7.7 Hz), 7.59 (d, 1H,J=1.4 Hz), 7.02 (d, 1H,J=1.6 Hz), 3.24 (t, 2H,J=6.9 Hz), 3.12–3.19 (m, 4H), 2.67 (t, 2H,J=7.1 Hz), 2.37 (q, 2H,J=7.5 Hz), 2.37 (q, 2H,J=7.5 Hz), 1.74–1.81 (m, 2H), 1.10 (t, 3H,J=7.5 Hz); m/z=496 (M+H);

Hydrochloride salt of 3-Methyl-N-[4-(5-[2-[3-(4-oxo-3,4-dihydro-phthalazin-1-ylamino)-propylcarbamoyl]-ethyl]-[1,2,4]oxadiazol-3-yl)-thiophen-2-yl]-butyramide, 66%, white solid; m.p. 137–139° C.; $^1$H NMR (DMSO-d$_6$) δ (ppm) 11.56 (s, 1H), 11.34 (s, 1H), 8.21 (dd, 1H,J=1.3, 7.7 Hz), 8.08 (m, 2H), 7.88 (t, 1H,J=7.7 Hz), 7.80 (t, 1H,J=8.0 Hz), 7.59 (d, 1H,J=1.5 Hz), 7.03 (d, 1H,J=1.6 Hz), 3.24 (t, 2H,J=6.7 Hz), 3.12–3.19 (m, 4H), 2.68 (t, 2H,J=7.1 Hz), 2.24 (d, 2H,J=7.1 Hz), 2.01–2.15 (m, 1H), 1.77 (m, 2H), 0.93 (d, 6H,J=6.6 Hz; m/z=524 (M+H);

Hydrochloride salt of 3-[3-(4-Methoxymethyl-phenyl)-[1,2,4]oxadiazol-5-yl]-N-[3-(4-oxo-3,4-dihydro-phthalazin-1-ylamino)-propyl]-propionamide, 73%, white solid; m.p. 183° C. (dec.); $^1$H NMR (DMSO-d$_6$) δ (ppm) 11.55 (s, 1H), 8.21 (d, 1H,J=7.5 Hz), 8.07 (m, 2H), 7.94 (d, 2H,J=8.1 Hz), 7.88 (t, 1H,J=6.0 Hz), 7.80 (t, 1H,J=7.8 Hz), 4.40 (d, 2H,J=8.1 Hz), 4.45 (s, 2H), 3.31 (s, 3H), 3.07–3.26 (m, 6H), 2.66 (t, 2H,J=7.2 Hz), 1.76 (m, 2H); m/z=463 (M+H);

Hydrochloride salt of 3-[3-(3-Methoxy-phenyl)-[1,2,4]oxadiazol-5-yl]-N-[3-(4-oxo-3,4-dihydro-phthalazin-1-ylamino)-propyl]-propionamide, 62%, off-white solid, m.p. 166–172° C.; $^1$H NMR (DMSO-d$_6$) δ (ppm) 11.56 (s, 1H), 8.21 (d, 1H,J=6.5 Hz), 8.13 (bs, 2H), 7.85 (m, 2H), 7.55 (d, 1H,J=7.7 Hz), 7.45 (t, 2H,J=4.5 Hz), 7.12 (d, 1H,J=5.9 Hz), 3.81 (s, 3H), 3.13–3.25 (m, 6H), 2.71 (t, 2H,J=7.2 Hz), 1.77 (m, 2H); m/z=449 (M+H);

Hydrochloride salt of 3-[3-(3-Ethoxy-phenyl)-[1,2,4]oxadiazol-5-yl]-N-[3-(4-oxo-3,4-dihydro-phthalazin-1-ylamino)-propyl]-propionamide, 54%, off-white solid; m.p. 166–171° C.; $^1$H NMR (DMSO-d$_6$) δ (ppm) 11.55 (bs, 1H), 8.21 (d, 1H,J=6.4 Hz), 8.15 (bs, 1H), 7.88 (m, 2H), 7.54 (d, 1H,J=7.7 Hz), 7.42 (m, 2H), 7.11 (d, 1H,J=5.6 Hz), 4.07 (m, 2H), 3.16–3.22 (m, 6H), 2.71 (t, 2H,J=7.2 Hz), 1.77 (m, 2H), 1.33 (t, 3H,J=7.0 Hz); m/z=463 (M+H);

Hydrochloride salt of 3-[3-(3-Chloro-4-methyl-phenyl)-[1,2,4]oxadiazol-5-yl]-N-[3-(4-oxo-3,4-dihydro-phthalazin-1-ylamino)-propyl]-propionamide, 49%, yellow solid; m.p. 185–187° C.; $^1$H NMR (DMSO-d$_6$) δ (ppm) 11.53 (s, 1H), 8.20 (d, 1H,J=7.7 Hz), 8.07 (m, 3H), 7.80–7.90 (m, 4H), 7.47 (d, 1H,J=8.1 Hz), 3.12–3.25 (m, 7H), 2.69 (t, 2H,J=7.2 Hz), 2.35 (s, 3H), 1.75 (m, 2H); m/z=467 (M+H);

Hydrochloride salt of 3-[3-(1-Ethyl-1H-pyrrol-2-yl)-[1,2,4]oxadiazol-5yl]-N-[3-(4-oxo-3,4-dihydro-phthalazin-1-ylamino)-propyl]-propionamide, 57%, off-white solid; m.p. 148–150 (dec.); $^1$H-NMR (DMSO-d$_6$) δ (ppm) 11.55 (bs, 1H), 8.21 (d, 1H,J=7.8 Hz), 8.12 (m, 2H), 7.81–7.92 (m, 4H), 7.19 (d, 2H,J=8.8 Hz), 4.83 (q, 2H,J=8.8 Hz), 3.13–3.25 (m, 6H), 2.69 (t, 2H,J=7.0 Hz), 1.76 (t, 2H,J=6.8 Hz); m/z=436 (M+H);

Hydrochloride salt of N-[3-(4-Oxo-3,4-dihydro-phthalazin-1-ylamino)-propyl]-3-[3-(3-propoxy-phenyl)-[1,2,4]oxadiazol-5-yl]-propionamide, 64%, off-white solid; m.p. 141–149 (dec.); $^1$H NMR (DMSO-d$_6$) δ (ppm) 11.55 (s, 1H), 8.22 (d, 1H,J=1.3 Hz), 8.09 (m, 2H), 8.7.88 (m, 2H), 7.55–7.40 (m, 3H), 7.10 (m, 1H), 3.97 (t, 2H,J=6.5 Hz), 3.24–3.12 (m, 6H), 2.70 (t, 2H,J=7.2 Hz), 1.77–1.72 (m, 4H), 0.98 (t, 3H,J=7.4 Hz); m/z=477 (M+H);

Hydrochloride salt of N-[3-(4-Oxo-3,4-dihydro-phthalazin-1-ylamino)-propyl]-3-[3-(4-propoxy-phenyl)-[1,2,4]oxadiazol-5-yl]-propionamide, 87%, off-white solid; m.p. 193–196° C. (dec.), $^1$H NMR (DMSO-d$_6$) δ (ppm) 11.56 (bs, 1H), 8.21 (d, 1H,J=7.7 Hz), 8.13 (m, 2H), 7.82–7.89 (m, 4H), 7.03 (d, 2H,J=8.9 Hz), 3.95 (t, 2H,J=7.0 Hz), 3.14–3.25 (m, 6H), 2.69 (t, 2H,J=7.0 Hz), 1.72–1.80 (m, 4H), 0.98 (t, 3H,J=7.44 Hz); m/z=477 (M+H);

Hydrochloride salt of 3-[3-(4-Ethoxy-phenyl)-[1,2,4]oxadiazol-5-yl]-N-[3-(4-oxo-3,4-dihydro-phthalazin-1-ylamino)-propyl]propionamide, 45%, off-white solid; m.p. 196–199° C. (dec.); $^1$H-NMR (DMSO-d$_6$) δ (ppm) 11.55 (bs, 1H), 8.20 (d, 1H,J=7.7 Hz), 8.12 (m, 2H), 7.81–7.89 (m, 4H), 7.02 (d, 2H,J=8.8 Hz), 4.02 (q, 2H,J=7.0 Hz), 3.14–3.25 (m, 6H), 2.68 (t, 2H,J=7.0 Hz), 1.77 (t, 2H,J=6.9 Hz), 1.33 (t, 2H,J=7.0 Hz); m/z=463 (M+H);

Hydrochloride salt of 3-[3-(3-Chloro-2-fluoro-phenyl)-[1,2,4]oxadiazol-5-yl]-N-[3-(4-oxo-3,4-dihydro-phthalazin-1-ylamino)-propyl]-propionamide, 60%, off-white solid; m.p. 195–198° C. (dec.); $^1$H NMR (DMSO-d$_6$) δ (ppm) 11.55 (bs, 1H), 8.20 (d, 1H,J=7.8 Hz), 8.10 (m, 2H), 7.38–7.94 (m, 4H), 7.38 (t, 1H,J=7.8 Hz), 3.13–3.25 (m, 6H), 2.71 (t, 2H,J=7.0 Hz), 1.76 (t, 2H,J=6.8 Hz); m/z=471 (M+H);

Hydrochloride salt of 3-[3-(2-Ethyl-thiophen-3-yl)-[1,2,4]oxadiazol-5-yl]-N-[3-(4-oxo-3,4-dihydro-phthalazin-1-ylamino)-propyl]propionamide, 69%, off-white solid; m.p. 156–160° C.; $^1$H NMR (DMSO-d$_6$) δ (ppm) 11.57 (bs, 1H), 8.21 (d, 1H,J=7.8 Hz), 8.11 (m, 2H), 7.87 (m, 2H), 7.45 (d, 1H,J=5.3 Hz), 7.39 (d, 1H,J=5.3 Hz), 3.12–3.19 (m, 6H), 2.68 (t, 2H,J=7.1 Hz), 1.77 (m, 2H), 1.24 (t, 3HJ=7.4 Hz); m/z=453 (M+H);

Hydrochloride salt of 3-[3-(3-Ethoxymethyl-phenyl)-[1,2,4]oxadiazol-5-yl]-N-[3-(4-oxo-3,4-dihydro-phthalazin-1-ylamino)propyl]-propionamide, 61%, white solid; m.p. 155–157° C.; $^1$H NMR (DMSO-d$_6$) δ (ppm) 11.55 (s, 1H), 8.21 (d, 1H,J=8.4 Hz), 8.11 (m, 2H), 7.81–7.93 (m, 4H), 7.49 (d, 2H,J=5.5 Hz), 4.51 (s, 2H), 3.40–3.60 (m, 3H), 3.13–3.25 (m, 6H), 2.71 (t, 2H,J=7.1 Hz), 1.76 (m, 2H), 1.16 (t, 3H,J=6.9 Hz); m/z=477 (M+H);

Hydrochloride salt of 3-[3-[1-(2-Ethoxy-ethyl)-1H-pyrrol-2-yl]-[1,2,4]oxadiazol-5-yl]-N-[3-(4-oxo-3,4-dihydro-phthalazin-1-ylamino)-propyl]-propionamide, 54%, off-white solid; m.p. 139–143° C. (dec.); $^1$H-NMR (DMSO-d$_6$) δ (ppm) 8.18–8.23 (m, 3H), 7.92 (m, 2H), 7.07

(m, 1H), 6.77 (m, 1H), 6.13 (m, 1H), 4.43 (t, 1H,J=5.6 Hz), 3.60 (t, 1H,J=5.6 Hz), 3.30–3.40 (m, 4H), 3.11–3.18 (m, 4H), 2.67 (t, 2H,J=7.0 Hz), 1.78 (t, 2H,J=6.8 Hz), 1.02 (t, 3H,J=7.0 Hz); m/z=480 (M+H);

Hydrochloride salt of 3-[3-(3-Ethyl-phenyl)-[1,2,4]oxadiazol-5-yl]-N-[3-(4-oxo-3,4-dihydro-phthalazin-1-ylamino)-propyl]-propionamide, 23%, off-white solid; m.p. 168–170° C.; $^1$H NMR (DMSO-d$_6$) δ (ppm) 11.55 (s, 1H), 8.21 (dd, 1H,J=1.3, 7.7 Hz), 8.09–8.11 (m, 2H), 7.76–7.91 (m, 4H), 7.42 (m, 2H), 3.13–3.24 (m, 6H), 2.63–2.73 (m, 4H), 1.77 (m, 2H), 1.19 (t, 3H,J=7.6 Hz); m/z 447 (M+H);

Hydrochloride salt of 3-[3-(5-Ethanesulfonylamino-thiophen-3-yl)-[1,2,4]oxadiazol-5-yl]-N-[3-(4-oxo-3,4-dihydro-phthalazin-1ylamino)-propyl]-propionamide, 64%, white solid; m.p. 161° C. (dec.); $^1$H NMR (DMSO-d$_6$) δ (ppm) 11.56 (s, 1H), 10.57 (s, 1H), 8.21 (dd, 1H,J=1.2, 7.6 Hz), 8.10 (m, 2H), 7.78–7.91 (m, 3H), 7.08 (d, 1H,J=1.6 Hz), 3.24 (t, 2H,J=6.5 Hz), 3.09–3.17 (m, 6H), 2.68 (t, 2H,J=7.1 Hz), 1.76 (m, 2H), 1.23 (t, 3H,J=7.3 Hz); m/z=532 (M+H);

Hydrochloride salt of 3-[3-[5-(3-Isobutyl-ureido)-thiophen-3yl]-[1,2,4]oxadiazol-5yl]-N-[3-(4-oxo-3,4-dihydro-phthalazin-1-ylamino)-propyl]-propionamide, 60%, off-white solid; m.p. 143–145° C.; $^1$H NMR (DMSO-d$_6$) δ (ppm) 11.57 (bs, 1H), 9.89 (s, 1H), 8.21 (dd, 1H,J=1.2, 7.7 Hz), 8.10 (m, 2H), 7.85 (m, 2H), 7.43 (d, 1H,J=1.5 Hz), 6.77 (d, 1H,J=1.6 Hz), 6.57 (bs, 1H), 3.12–3.26 (m, 6H), 2.93 (d, 2H,J=5.5 Hz), 2.67 (t, 2H,J=7.1 Hz), 1.66–1.81 (m, 3H), 0.86 (d, 6H,J=6.7 Hz); m/z=539 (M+H).

Example 63

This example illustrates a method for producing hydrochloride salt of 3-{3-[1-(2-Hydroxy-ethyl)-1H-pyrrol-2-yl]-[1,2,4]oxadiazol-5-yl}-N-[3-(4-oxo-3,4-dihydro-phthalazin-1-ylamino)-propyl]-propionamide.

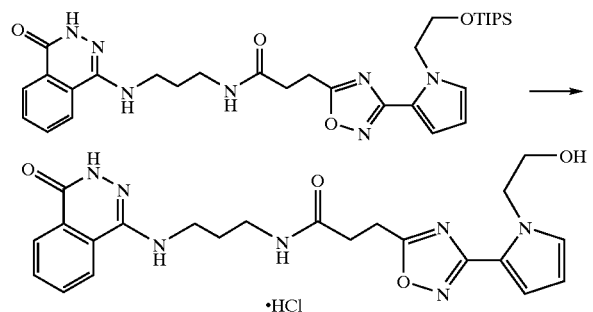

A 50-mL, one-neck, round bottomed flask equipped with a magnetic stirrer was charged with N-[3-(4-oxo-3,4-dihydrophthalazin-1-ylamino)propyl]-3-{3-[1-(2-triisopropylsilyloxyethyl)-1H-pyrrol-2-yl]-1,2,4-oxadiazol-5-yl}propionamide (243 mg, 0.40 mmol) and anhydrous THF (25 mL). A 1 M solution of TBAF in THF (1.2 mL, 1.2 mmol) was added in one portion and stirring continued for 2 h at ambient temperature. The reaction mixture was then filtered through a pad of silica eluting with a 1:1 mixture of methylene chloride and methanol. The solvents were removed under reduced pressure and the resulting solid purified by column chromatography. The resulting material was suspended in methanol (5 mL) and converted to the corresponding hydrochloride salt by treatment with one equivalent of a 1 M solution of hydrogen chloride in diethyl ether. Concentration of the resulting solution under reduced pressure and drying under high vacuum afforded a 97% yield of the title compound as a white solid. m.p. 115–119° C. (dec.); $^1$H NMR (DMSO-d$_6$), δ (ppm)=11.54 (s, 1H), 8.21 (d, 1H, J=7.7 Hz), 8.08 (m, 2H), 7.83 (m, 2H), 7.06 (t, 2H, J=5.4 Hz), 6.76 (m, 1H), 6.54 (t, 1H, J=5.4 Hz), 6.11 (m, 1H), 4.33 (t, 2H, J=5.8 Hz), 3.10–3.41 (m, 6H), 2.66 (t, 2H, J=7.1 Hz), 2.23 (t, 2H, J=7.5 Hz), 1.63 (m, 2H); m/z=452 (M+H)

Example 64

This example illustrates a method for producing [3-methyl-4-(5-{2-[3-(4-oxo-3,4-dihydro-phthalazin-1-ylamino)-propylcarbamoyl]-ethyl}-[1,2,4]oxadiazol-3-yl)-isoxazol-5-yl]-carbamic acid tert-butyl ester.

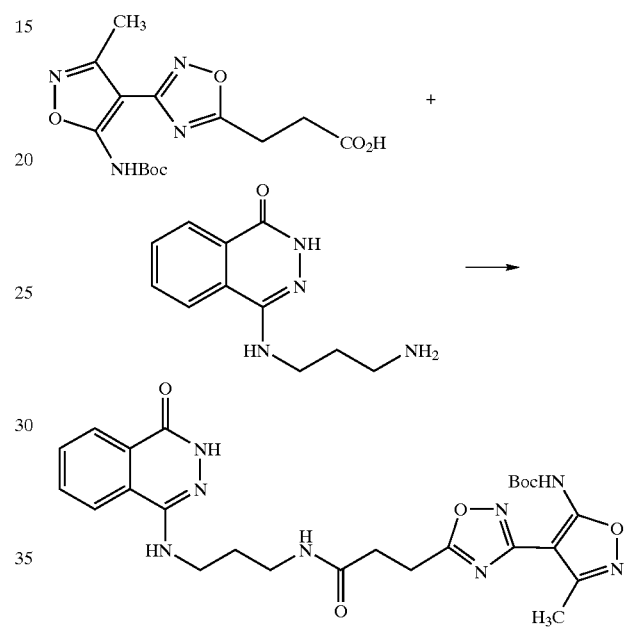

A 25-mL round bottomed flask equipped with a magnetic stirrer was purged with nitrogen and charged with 4-(3-aminopropylamino)-2H-phthalazin-1-one (451 mg, 2.07 mmol), 3-[3-(5-tert-butyloxycarbonylamino-3-methylisoxazol-4-yl)-1,2,4-oxadiazol-5-yl]propionic acid (699 mg, 2.07 mmol), anhydrous DMF (7 mL), 1-(3-dimethylaminopropyl)-3-ethylcarbodiimide hydrochloride (595 mg, 3.10 mmol), 1-hydroxybenzotriazole (221 mg, 2.07 mmol) and diisopropylethylamine (320 mg, 2.48 mmol). After stirring for 17 h at ambient temperature, the mixture was filtered and the filtrate was concentrated to dryness under vacuum. The residue was purified by column chromatography to give a 53% yield of the title compound as a white solid. m.p. 135–142° C.; $^1$H NMR (DMSO-d$_6$) δ (ppm) 11.55 (s, 1H), 10.27 (s, 1H), 8.22 (d, 1H, J=1.3 Hz), 8.07 (m, 2H), 7.85 (m, 2H), 6.54 (m, 1H), 3.24–3.13 (m, 6H), 2.65 (t, 2H, J=7.2 Hz), 2.35 (s, 3H), 1.76 (m, 2H), 1.38 (s, 9H); m/z=539 (M+H).

Other compounds that were prepared by this method using appropriate reagents, including the observed yield and analytical data, are listed below.

3-[3-(3-Nitro-phenyl)-[1,2,4]oxadiazolyl-5-yl]-N-[3-(4-oxo-3,4-dihydro-phthalazin-1-ylamino)-propyl]-propionamide, 81%, yellow solid: m.p. 205–208° C.; $^1$H NMR (DMSO-d$_6$) δ (ppm) 11.50 (s, 1H), 8.65 (s, 1H), 8.37 (d, 2H, J=6.4 Hz), 8.19 (d, 1H, J=6.6 Hz), 8.07 (m, 2H), 7.76–7.88 (m, 3H), 6.48 (t, 1H, J=5.3 Hz), 3.14–3.26 (m, 6H), 2.73 (t, 2H, J=7.1 Hz), 1.76 (m, 2H); m/z=464 (M+H).

3-[3-(2-Methyl-thioazol-4-yl)-[1,2,4]oxadiazol-5-yl]-N-[3-(4-oxo-3,4-dihydro-phthalazin-1-ylamino)-propyl]-propionamide, 88%, white solid; m.p. 183–187° C.; $^1$H NMR (DMSO-d$_6$) δ (ppm) 11.59 (s, 1H), 8.22 (m, 2H), 8.09 (m, 2H), 7.85 (m, 2H), 6.58 (t, 1H, J=5.2 Hz), 3.30–3.10 (m, 6H), 2.77–2.68 (m, 5H), 1.76 (quin., 3H, J=5.2 Hz); m/z= 440 (M+H).

N-[3-(4-Oxo-3,4-dihydro-phthalazin-1-ylamino)-propyl]-3-(3-m-tolyl-[1,2,4]oxadiazol-5-yl)-propionamide, 89%, white solid; m.p. 170–178° C.; $^1$H NMR (DMSO-d$_6$) δ (ppm) 11.55 (s, 1H), 8.22 (d, 1H, J=6.7 Hz), 8.19 (bs, 1H), 7.77–7.91 (m, 4H), 7.40 (t, 1H, J=7.6 Hz), 7.33 (t, 1H, J=11.9 Hz), 3.13–3.24 (m, 6H), 2.70 (t, 2H, J=7.2 Hz), 2.36 (s, 3H), 1.76 (m, 2H); m/z=433 (M+H).

3-[3-(1,5-Dimethyl-1H-pyrrol-2-yl)-[1,2,4]oxadiazol-5-yl]-N-[3-(4-oxo-3,4-dihydro-phthalazin-1-ylamino)-propyl]-propionamide, 81%, tan solid. m.p. 168–170° C. (dec.); $^1$H NMR (DMSO-d$_6$) δ (ppm) 11.59 (s, 1H), 8.21 (dd, 1H, J=7.8, 1.2 Hz), 8.06 (m, 2H), 7.81 (m, 2H), 6.65 (d, 1H, J=3.7 Hz), 6.53 (t, 1H, J=5.1 Hz), 5.91 (d, 1H, J=3.6 Hz), 3.76 (s, 3H), 3.08–3.40 (m, 6H), 2.65 (t, 2H, J=7.2 Hz), 2.22 (s, 3H), 1.76 (m, 2H); m/z=436 (M+H).

3-[3-(4-Hydroxy-phenyl)-[1,2,4]oxadiazol-5-yl]-N-[3-(4-oxo-3,4-dihydro-phthalazin-1-ylamino)-propyl]-propionamide, 13%, tan solid; m.p. 266–269° C.; $^1$H NMR (DMSO-d$_6$) δ (ppm) 11.66 (s, 1H), 10.08 (s, 1H), 8.21 (d, 1H, J=7.7 Hz), 8.07 (m, 2H), 7.88 (t, 1H, J=7.5 Hz), 7.75≅7.85 (m, 3H), 6.88 (d, 2H, J=6.8 Hz), 6.55 (t, 1H, J=5.3 Hz), 3.12–3.29 (m, 6H), 2.68 (t, 2H, J=7.2 Hz), 1.76 (m, 2H); m/z=435 (M+H).

3-[3-(5-Nitro-thiophen-3-yl)-[1,2,4]oxadiazol-5-yl]-N-[3-(4-oxo-3,4-dihydro-phthalazin-1-ylamino)-propyl]-propionamide, 79%, off-white solid; m.p. 240–245° C.; $^1$H NMR (DMSO-d$_6$) δ (ppm) 11.52 (s, 1H), 8.56 (d, 1H, J=1.9 Hz), 8.31 (d, 1H, J=1.9 Hz), 8.07 (t, 1H, J=4.5 Hz), 8.06 (t, 1H, J=4.5 Hz), 7.85 (t, 1H, J=5.1 Hz), 7.79 (t, 1H, J=6.9 Hz), 6.49 (t, 1H, J=5.3 Hz), 3.12–3.24 (m, 6H), 2.67 (t, 2H, J=7.2 Hz), 1.75 (m, 2H); m/z=470 (M+H).

3-[3-(4-Methoxy-phenyl)-[1,2,4]oxadiazol-5-yl]-N-[3-(8-nitro-4-oxo-3,4-dihydro-phthalazin-1-ylamino)-propyl]-propionamide, 45%, yellow solid; m.p. 171–173° C.; $^1$H NMR (DMSO-d$_6$) δ (ppm) 12.17 (s, 1H), 8.49 (dd, 1H, J=1.3, 8.0 Hz), 8.28 (dd, 1H, J=1.3, 7.8 Hz), 7.88–8.03 (m, 4H), 7.05 (m, 2H), 4.92 (t, 1H, J=5.1 Hz), 3.80 (s, 3H), 3.05–3.19 (m, 6H), 2.67 (t, 2H, J=7.1 Hz), 1.65 (m, 2H); m/z=494 (M+H).

3-[3-(3,5-Dimethoxy-phenyl)-[1,2,4]oxadiazol-5-yl]-N-[3-(4-oxo-3,4-dihydro-phthalazin-1-ylamino)-propyl]-propionamide, 72%, off-white solid; m.p. 189–197° C.; $^1$H NMR (DMSO-d$_6$) δ (ppm) 11.54 (s, 1H), 8.19 (d, 1H, J=7.6 Hz), 8.05 (m, 2H), 7.85 (t, 1H, J=1.4 Hz), 7.79 (t, 1H, J=7.6 Hz), 7.08 (d, 2H, J=2.3 Hz), 6.67 (t, 1H, J=2.3 Hz), 6.55 (t, 1H, J=5.3 Hz), 3.79 (s, 6H), 3.13–3.26 (m, 6H), 2.69 (t, 2H, J=7.2 Hz), 1.76 (m, 2H); m/z=479 (M+H).

[4-(5-{2-[3-(4-Oxo-3,4-dihydro-phthalazin-1-ylamino)-propylcarbamoyl]-ethyl}-[1,2,4]oxadiazol-3-yl)-thiophen-2-yl]-carbamic acid tert-butyl ester, 55%, off-white solid; m.p. 112–118° C.; $^1$H NMR (DMSO-d$_6$) δ (ppm) 10.63 (s, 1H), 11.53 (s, 1H), 8.21 (dd, 1H, J=1.4, 1.4 Hz), 8.08 (d, 1H, J=7.8 Hz), 8.02 (t, 1H, J=5.6 Hz), 7.87 (t, 1H, J=7.3 Hz), 7.79 (t, 1H, J=7.2 Hz), 7.55 (d, 1H, J=1.6 Hz), 6.90 (d, 1H, J=1.6 Hz), 6.53 (t, 1H, J=5.2 Hz), 3.11–3.30 (m, 6H), 2.67 (t, 2H, J=7.3 Hz), 1.74 (m, 2H), 1.49 (s, 9H); m/z=540 (M+H).

[2-Methylsulfanyl-5-(5-{2-[3-(4-oxo-3,4-dihydro-phthalazin-1-ylamino)-propylcarbamoyl]-ethyl}-[1,2,4] oxadiazol-3-yl)-thiazol-4-yl]-carbamic acid tert-butyl ester, 29%, white solid; m.p. 144–146° C.; $^1$H NMR (DMSO-d$_6$) δ (ppm) 11.54 (s, 1H), 9.41 (s, 1H), 8.21 (d, 1H, J=7.7 Hz), 8.08 (d, 1H, J=8.0 Hz), 8.03 (t, 1H, J=5.5 Hz), 7.88 (t, 1H, J=7.3 Hz), 7.80 (t, 1H, J=7.7 Hz), 6.53 (t, 1H, J=5.3 Hz), 3.11–3.26 (m, 6H), 2.71 (s, 3H), 2.65 (t, 2H, J=7.1 Hz), 1.77 (m, 2H), 1.38 (s, 9H); m/z=587 (M+H).

4-(5-{2-[3-(4-Oxo-3,4-dihydro-phthalazin-1-ylamino)-propylcarbamoyl]-ethyl}-[1,2,4]oxadiazol-3-yl)-piperidine-1-carboxylic acid tert-butyl ester, 90%, white solid; m.p. 86–88° C.; $^1$H NMR (CD$_3$OD) δ (ppm) 8.33 (dd, 1H, J=1.5, 7.6 Hz), 8.02 (dd, 1H, J=0.8, 7.4 Hz), 7.90 (dt, 1H, J=1.5, 7.3 Hz), 7.82 (dt, 1H, J=1.3, 7.8 Hz), 4.03 (t, 1H, J=3.3 Hz), 3.99 (t, 1H, J=3.1 Hz), 3.29 (t, 2H, J=6.7 Hz), 3.32 (m, 2H), 3.18 (t, 2H, J=7.0 Hz), 2.89–3.00 (m, 3H), 2.75 (t, 2H, J=7.0 Hz), 1.81–1.95 (m, 4H), 1.64 (m, 2H), 1.44 (s, 9H); m/z 526 (M+H).

2-(5-{2-[3-(4-Oxo-3,4-dihydro-phthalazin-1-ylamino)-propylcarbamoyl]-ethyl}-[1,2,4]oxadiazol-3-yl)-piperidine-1-carboxylic acid tert-butyl ester, 91%, yellow solid; m.p. 70–72° C.; $^1$H NMR (CD$_3$OD) δ (ppm) 8.33 (d, 1H, J=7.7 Hz), 7.80–8.04 (m, 3H), 5.48 (s, 1H), 5.37 (d, 1H, J=4.2 Hz), 3.94 (d, 1H, J=13.2 Hz), 3.39 (t, 2H, J=6.7 Hz), 3.20 (t, 2H, J=6.9 Hz), 2.93 (m, 2H), 2.75 (t, 2H, J=7.2 Hz), 2.20 (d, 1H, J=13.5 Hz), 1.75–1.90 (m, 3H), 1.58 (d, 2H, J=12.8 Hz), 1.20–1.55 (m, 11H); m/z=526 (M+H).

N-[3-(4-Oxo-3,4-dihydro-phthalazin-1-ylamino)-propyl]-3-[3-[1-(2-triisopropylsilanyloxy-ethyl)-1H-pyrrol-2-yl]-[1,2,4]oxadiazol-5-yl]-propionamide, 77%, Off-white solid; m.p. 137–145° C. (dec.); $^1$H-NMR (DMSO-d$_6$) δ (ppm) 11.55 (s, 1H), 8.20 (d, 1H, J=7.7 Hz), 8.07 (m, 2H), 7.85 (m, 2H), 7.05 (m, 1H), 6.76 (m, 1H), 6.55 (m, 1H), 6.12 (m, 1H), 4.41 (t, 2H, J=5.4 Hz), 3.88 (t, 1H, J=5.30 Hz), 3.09–3.24 (m, 6H), 2.65 (t, 2H, J=7.2 Hz), 1.76 (t, 2H, J=7.1 Hz), 0.88–0.94 (m, 21H); m/z=608 (M+H).

2-(5-{2-[3-(4-Oxo-3,4-dihydro-phthalazin-1-ylamino)-propylcarbamoyl]-ethyl}-[1,2,4]oxadiazol-3-yl)-pyrrolidine-1-carboxylic acid tert-butyl ester, 80%, white solid; m.p. 82–84° C.; $^1$H NMR (CDCl$_3$) δ (ppm) 10.25 (bs, 1H), 8.43 (d, 1H, J=7.6 Hz), 7.73–7.83 (m, 3H), 6.74 (t, 1H, J=6.1 Hz), 5.65 (bs, 1H), 4.97 (m, 1H), 3.22–3.57 (m, 9H), 2.75 (m, 2H), 1.82–2.23 (m, 5H), 1.28–1.44 (m, 9H); m/z=512 (M+H).

3-(5-{2-[3-(4-Oxo-3,4-dihydro-phthalazin-1-ylamino)-propylcarbamoyl]-ethyl}-[1,2,4]oxadiazol-3-yl)-piperidine-1-carboxylic acid tert-butyl ester, 98%, white solid; m.p. 95° C. (dec.); $^1$H NMR (CD$_3$OD) δ (ppm) 8.32 (dd, 1H, J=7.8, 1.4 Hz), 8.02 (d, 1H, J=7.8 Hz), 7.80–7.93 (m, 2H), 4.11 (m, 1H), 3.85 (d, 1H, J=12.3 Hz), 3.39 (t, 2H, J=6.6 Hz), 3.25–3.35 (m, 2H), 3.19 (t, 2H, J=7.1 Hz), 2.80–3.10 (m, 2H), 2.75 (t, 2H, J=6.9 Hz), 2.00–2.15 (m, 1H), 1.61–1.91 (m, 4H), 1.35–1.60 (m, 11H); m/z=526=(M+H).

[2-Methyl-4-(5-{2-[3-(4-oxo-3,4-dihydro-phthalazin-1-ylamino)-propylcarbamoyl]-ethyl}-[1,2,4]-oxadiazol-3-yl)-2H-pyrazol-3-yl]-carbamic acid tert-butyl ester, 90%, white solid; m.p. 106–108° C.; $^1$H NMR (CD$_3$OD) δ (ppm) 8.32 (dt, 1H, J=0.8, 7.9 Hz), 8.00 (d, 1H, J=7.8 Hz), 7.79–7.91 (m, 3H), 3.73 (s, 3H), 3.34–3.39 (m, 4H), 3.23 (t, 2H, J=7.0 Hz), 2.79 (t, 2H, J=7.0 Hz), 1.85 (m, 2H), 1.46 (s, 9H); m/z 538=(M+H).

[5-(5-{2-[3-(4-oxo-3,4-dihydro-phthalazin-1-ylamino)-propylcarbamoyl]-ethyl}-[1,2,4]oxadiazol-3-yl)-thiophen-2-yl]-carbamic acid tert-butyl ester, 81%, off-white solid; m.p. 177° C. (dec.); $^1$H NMR (DMSO-d$_6$) δ (ppm) 11.54 (s, 1H), 10.86 (s, 1H), 8.20 (d, 1H, J=6.6 Hz), 8.07 (m, 2H), 7.88 (t, 1H, J=7.3 Hz), 7.79 (t, 1H, J=7.4 Hz), 7.44 (d, 1H, J=4.0 Hz), 6.55 (m, 2H), 3.10–3.24 (m, 7H), 2.66 (t, 2H, J=7.4 Hz), 1.76 (m, 2H), 1.48 (s, 9H); m/z=540 (M+H).

[4-(5-{2-[3-(4-Oxo-3,4-dihydro-phthalazin-1-ylamino)-propylcarbamoyl]-ethyl}-[1,2,4]oxadiazol-3-yl)-thiophen-2-yl]-carbamic acid benzyl ester, 74%, white solid; m.p. 138–140° C.; $^1$H NMR (DMSO-d$_6$) δ (ppm) 11.56 (s, 1H), 11.03 (s, 1H), 8.20 (d, 1H, J=7.8 Hz), 8.07 (m, 2H), 7.88 (t, 1H, J=7.2 Hz), 7.79 (t, 1H, J=7.4 Hz), 7.61 (s, 1H), 7.35–7.45 (m, 5H), 6.93 (d, 1H, J=1.4 Hz), 6.55 (t, 1H, J=5.1 Hz), 5.20 (s, 2H), 3.12–3.27 (m, 6H), 2.67 (t, 2H, J=7.0 Hz), 1.76 (m, 2H); m/z 574=(M+H).

[5-(5-{2-[3-(4-Oxo-3,4-dihydro-phthalazin-1-ylamino)-propylcarbamoyl]-ethyl}-[1,2,4]oxadiazol-3-yl)-thiophen-2-yl]-carbamic acid benzyl ester, 65%, white solid; m.p. 158–160° C.; $^1$H NMR (DMSO-d$_6$) δ (ppm) 11.55 (s, 1H), 11.25 (s, 1H), 8.20 (d, 1H, J=6.6 Hz), 8.03–8.10 (m, 2H), 7.88 (t, 1H, J=7.2 Hz), 7.79 (t, 1H, J=7.4 Hz), 7.34–7.48 (m, 6H), 6.59 (d, 1H, J=4.0 Hz), 6.54 (t, 1H, J=5.2 Hz), 5.21 (s, 2H), 3.10–3.27 (m, 6H), 2.67 (t, 2H, J=7.2 Hz), 1.76 (m, 2H); m/z=574 (M+H).

3-[3-(4-Difluoromethoxy)methyl-phenyl)-[1,2,4]oxadiazol-5-yl]-N-[3-(4-oxo3,4-dihydro-phthalazin-1-ylamino)-propyl]-propionamide, 88%, white solid; m.p. 193–195°; $^1$H NMR (DMSO-d$_6$) δ (ppm) 11.54 (s, 1H), 8.20 (s, 1H, J=6.3 Hz), 8.04 (s, 1H), 8.07 (d, 1H, J=7.2 Hz), 7.98 (d, 1H, J=8.4 Hz), 7.79 (t, 1H, J=6.0 Hz), 7.88 (t, 1H, J=6.0 Hz), 7.51 (d, 2H, J=8.4 Hz), 6.82 (t, 1H, J=75.0 Hz), 6.53 (t, 1H, J=5.4 Hz), 4.96 (s, 2H), 3.10–3.26 (m, 6H), 2.70 (t, 2H, J=7.2 Hz), 1.76 (m, 2H); m/z=499 (M+H).

[4-(5-{2-[3-(4-Oxo-3,4-dihydro-phthalazin-1-ylamino)-propylcarbamoyl]-ethyl}-[1,2,4]oxadiazol-3-yl)-thiophen-2-yl]-carbamic acid ethyl ester, 87%, white solid; m.p. 184–186° C.; $^1$H NMR (DMSO-d$_6$) δ (ppm) 11.55 (s, 1H), 10.87 (s, 1H), 8.21 (dd, 1H, J=1.2, 7.7 Hz), 8.02–8.10 (m, 2H), 7.88 (dt, 1H, J=1.4, 7.4 Hz), 7.80 (t, 1H, J=7.2 Hz), 7.59 (d, 1H, J=1.6 Hz), 6.93 (d, 1H, J=1.7 Hz), 6.55 (t, 1H, J=5.1 Hz), 4.17 (q, 2H, J=7.1 Hz), 3.12–3.27 (m, 6H), 2.67 (t, 2H, J=7.1 Hz), 1.78 (m, 2H), 1.26 (t, 3H, J=7.1 Hz); m/z=512 (M+H).

3-[3-(3-Difluoromethoxymethyl-phenyl)-[1,2,4]oxadiazol-5-yl]-N-[3-(4-oxo-3,4-dihydro-phthalazin-1-ylamino)-propyl]-propionamide, 31%, white solid; m.p. 155–157° C.; $^1$H NMR (DMSO-d$_6$) δ (ppm) 11.54 (s, 1H), 7.77–8.22 (m, 7H), 7.62 (m, 2H), 6.83 (t, 1H, J=5.4 Hz), 6.53 (t, 1H, J=8.2 Hz), 5.00 (s, 2H), 3.10–3.25 (m, 6H), 2.71 (t, 2H, J=7.3 Hz), 1.76 (m, 2H); m/z=499 (M+H).

[4-(5-{2-[3-(4-Oxo-3,4-dihydro-phthalazin-1-ylamino)-propylcarbamoyl]-ethyl}-[1,2,4]oxadiazol-3-yl)-1-(2-trimethylsilanyl-ethoxymethyl)-1H-pyrazol-3-yl]-carbamic acid tert-butyl ester, 73%, White solid; m.p. 102–105° C.; $^1$H NMR (DMSO-d$_6$) δ (ppm) 11.56 (s, 1H), 8.88 (s, 1H), 8.84 (s, 1H), 8.20 (d, 1H, J=7.8 Hz), 8.09 (d, 1H, J=8.0 Hz), 8.03 (m, 2H), 7.78–7.90 (m, 4H), 6.55 (t, 1H, J=5.4 Hz), 5.36 (s, 2H), 3.55 (m, 2H), 3.11–3.28 (m, 6H), 2.65 (t, 2H, J=7.0 Hz), 1.79 (t, 2H, J=6.9 Hz), 1.33 (s, 9H), 0.81–0.87 (m, 2H), −0.03 (s, 9H); m/z=654 (M+H).

[3-(5-{2-[3-(4-Oxo-3,4-dihydro-phthalazin-1-ylamino)-propylcarbamoyl]-ethyl}-[1,2,4]oxadiazol-3-yl)-phenyl]-carbamic acid tert-butyl ester, 85%, White solid; m.p. 199–202° C. (dec.); $^1$H-NMR (DMSO-d$_6$) δ (ppm) 11.59 (s, 1H), 9.62 (s, 1H), 8.27 (s, 1H), 8.20 (d, 1H, J=7.7 Hz), 8.09 (m, 2H), 7.85 (m, 2H), 7.56 (t, 2H, J=7.8 Hz), 7.39 (t, 2H, J=7.9 Hz), 6.57 (t, 1H, J=5.2 Hz), 3.14–3.30 (m, 6H), 2.71 (t, 2H, J=7.5 Hz), 1.78 (t, 2H, J=6.9 Hz), 1.49 (s, 9H); m/z=534 (M+H).

N-[3-(4-oxo-3,4-dihydrophthalazin-1-ylamino)propyl]-3-(3-chloromethyl-1,2,4-oxadiazol-5-yl)propionamide, 32%

Yellow oil, $^1$H NMR (DMSO-d$_6$) δ (ppm) 11.56 (s, 1H), 8.20 (d, 1H, J=8.4 Hz), 8.06 (m, 2H), 7.90 (t, 1H, J=7.1 Hz), 7.80 (t, 1H, J=7.1 Hz), 6.55 (t, 1H, J=5.4 Hz), 5.77 (s, 2H), 3.12–3.26 (m, 6H), 2.61 (t, 2H, J=7.2 Hz), 1.76 (m, 2H).

Example 65

This example illustrates a method for producing 4-(N,N'-dicyclohexylcarbamimidoyloxy)-4-oxo-N-[3-(4-oxo-3,4-dihydro-phthalazin-1-ylamino)-propyl]-butyramide.

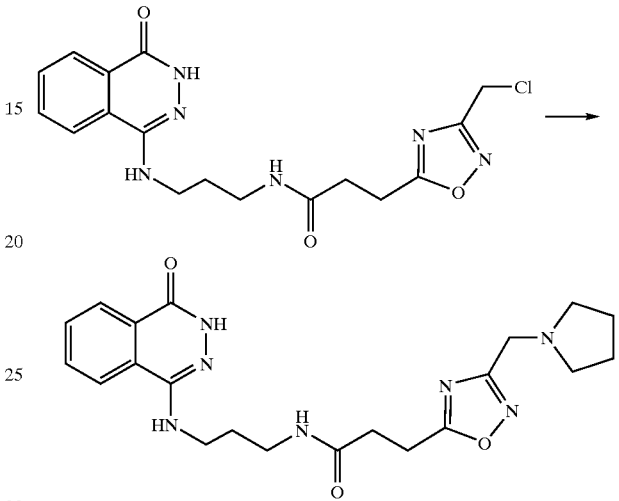

A 3-mL reaction vial equipped with a magnetic stirrer was charged with N-[3-(4-oxo-3,4-dihydrophthalazin-1-ylamino)propyl]-3-(3-chloromethyl-1,2,4-oxadiazol-5-yl) propionamide (300 mg, 0.77 mmol) and purged with nitrogen. Anhydrous dimethylformamide (1 mL) and pyrrolidine (170 mg, 2.40 mmol) were added, and the reaction mixture was stirred for 15 h at ambient temperature. The product was then purified by directly loading the reaction mixture on a preparative HPLC column (25 cm×2.18 cm, Luna 5 mm, C18(2) column) and eluting with a mixture of 83% of 0.2% solution of trifluoroacetic acid in water and 17% acetonitrile at a flow rate of 15 mL/min. The fractions containing the desired product were combined, treated with 10% aqueous potassium carbonate and evaporated to dryness under reduced pressure. The residue was additionally purified by column chromatography on silica gel to provide the free base as an off-white solid. This solid was dissolved in methanol (3 mL) and converted to the corresponding hydrochloride salt by treatment with one equivalent of a 1 M hydrogen chloride solution in ether and concentration of the resulting solution to dryness. This afforded a 6% yield of the title compound as a white solid. m.p. 98–103° C.; $^1$H NMR (DMSO-d$_6$) δ (ppm) 11.59 (s, 1H), 10.7 (bs, 1H), 8.20 (d, 1H, J=7.9 Hz), 8.10 (m, 2H), 7.88 (t, 1H, J=7.5 Hz), 7.80 (t, 1H, J=7.3 Hz), 6.62 (bs, 1H), 4.64 (s, 2H), 3.30–3.70 (m, 3H), 3.11–3.39 (m, 6H), 2.65 (t, 2H, J=7.0 Hz), 1.73–2.49 (m, 6H); m/z=426 (M+H).

N-[3-(4-Oxo-3,4-dihydro-phthalazin-1-ylamino)-propyl]-3-(3-piperidin-1-yl-[1,2,4]oxadiazol-5-yl)-propionamide, CF$_3$CO$_2$H salt hydrate was also prepared in a similar manner, but was only purified by preparative HPLC as described above in 23% yield, as a white solid. m.p. 92–98° C.; $^1$H NMR (DMSO-d$_6$) δ (ppm) 10.54 (s, 1H), 8.22 (d, 1H, J=6.4 Hz), 8.12 (d, 1H, J=7.6 Hz), 7.86 (t, 1H, J=8.1 Hz), 7.80 (t, 1H, J=6.9 Hz), 4.51 (s, 1H), 3.43 (bs, 2H), 3.11–3.26 (m, 6H), 2.98 (bs, 2H), 2.68 (t, 2H, J=7.1 Hz), 1.73–1.78 (m, 3H); m/z=400 (M+H); Elemental analysis: Calculated C, 49.04%; H, 5.80%; N, 16.68%; Found C, 48.91%; H, 5.62%; N, 16.68%.

Example 66

This example illustrates a method for producing hydrochloride salt of N-[3-(4-oxo-3,4-dihydro-phthalazin-1-ylamino)-propyl]-3-(3-piperidin-4-yl-[1,2,4]oxadiazol-5-yl)-propionamide.

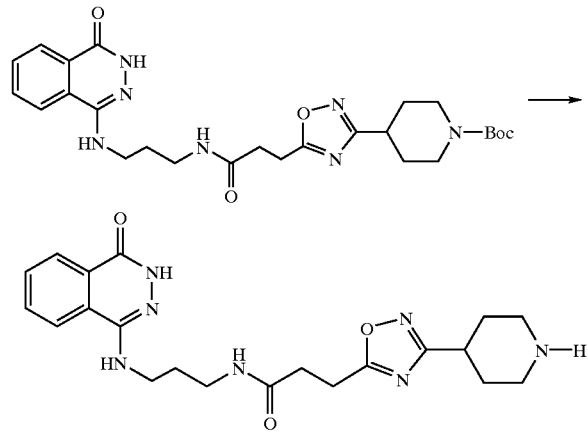

A 50-mL round bottomed flask equipped with a magnetic stirrer was charged with tert-butyl 4-(5-{2-[3-(4-oxo-3,4-dihydro-phthalazin-1-ylamino)propylcarbamoyl]ethyl}-1,2,4-oxadiazol-3-yl)piperidine-1-carboxylate (457 mg, 0.87 mmol), trifluoroacetic acid (2 mL), and methylene chloride (4 mL). After stirring at ambient temperature for 1 h, the toluene (5 mL) was added to the reaction mixture and the solution evaporated to dryness. The resulting solid was basified with 10% aqueous potassium carbonate solution and the mixture re-evaporated to dryness. The residue was purified by column chromatography and converted to the corresponding hydrochloride salt by treatment of a methanol (5 mL) solution of the free base with one equivalent of a 1 M solution of hydrogen chloride in diethyl ether. Concentration of the resulting solution and drying under high vacuum gave a 100% yield of the title compound as a white solid; m.p. 56–58° C.; $^1$H NMR (CD$_3$OD) δ (ppm) 8.32 (d, 1H, J=7.6 Hz), 8.10 (m, 1H), 7.92 (t, 1H, J=7.3 Hz), 7.85 (t, 1H, J=7.2 Hz), 3.39–3.43 (m, 4H), 3.28–3.35 (m, 3H), 3.10–3.22 (m, 5H), 2.77 (t, 2H, J=7.0 Hz), 1.85–2.26 (m, 6H); m/z=426 (M+H).

Other compounds that were prepared in a similar method using appropriate reagents, including the observed yield and analytical data, are listed below.

3-[3-(4-Amino-2-methylsulfanyl-thiazol-5-yl)-[1,2,4]oxadiazol-5-yl]-N-[3-(4-oxo-3,4-dihydro-phthalazin-1-ylamino)-propyl]-propionamide Hydrochloride, 99%, light yellow solid; m.p. 141° C. (dec.); $^1$H NMR (DMSO-d$_6$) δ (ppm) 11.61 (bs, 1H), 8.18–8.23 (m, 3H), 7.87 (m, 2H), 3.10–3.29 (m, 6H), 2.60–2.76 (m, 5H), 1.77 (m, 2H); m/z=487 (M+H).

Hydrochloride salt of N-[3-(4-Oxo-3,4-dihydro-phthalazin-1-ylamino)-propyl]-3-(3-piperidin-2-yl-[1,2,4]oxadiazol-5-yl)-propionamide, 71%, yellow solid; m.p. 130° C. (dec.), $^1$H NMR (CD$_3$OD) δ (ppm) 8.33 (d, 1H, J=7.4 Hz), 7.80–8.10 (m, 3H), 4.55 (dd, 1H, J=10.9, 3.3 Hz), 3.12–3.50 (m, 8H), 2.80 (t, 2H, J=7.0 Hz), 2.30 (d, 1H, J=12.0 Hz), 1.65–2.00 (m, 7H); m/z=426 (M+H).

Hydrochloride salt of N-[3-(4-Oxo-3,4-dihydro-phthalazin-1-ylamino)-propyl]-3-(3-pyrrolidin-2-yl-[1,2,4]oxadiazol-5-yl)-propionamide, 99%, white solid; m.p. 73–75° C.; $^1$H NMR (CD$_3$OD) δ (ppm) 8.33 (dd, 1H, J=1.1, 7.9 Hz), 8.06 (d, 1H, J=8.0 Hz), 7.91 (dt, 1H, J=1.3, 7.2 Hz), 7.84 (t, 1H, J=7.5 Hz), 4.90 (t, 1H, J=7.4 Hz), 3.39–3.53 (m, 4H), 3.28–3.33 (m, 3H), 3.24 (t, 2H, J=7.0 Hz), 2.81 (t, 2H, J=7.0 Hz), 2.50 (m, 1H), 2.10–2.33 (m, 3H), 1.89 (m, 2H); m/z=412 (M+H).

Hydrochloride salt of N-[3-(4-Oxo-3,4-dihydro-phthalazin-1-ylamino)-propyl]-3-(3-piperidin-3-yl-[1,2,4]oxadiazol-5-yl)-propionamide, 89%, yellow solid; m.p. 157° C. (dec.), $^1$H NMR (CD$_3$OD) δ (ppm) 7.92–8.40 (m, 4H), 3.25–3.65 (m, 8H), 3.23 (t, 2H, J=6.9 Hz), 3.20 (m, 1H), 2.78 (t, 2H, J=7.2 Hz), 2.19 (m, 1H), 1.75–2.05 (m, 5H); m/z=426 (M+H).

Hydrochloride salt of 3-[3-(5-Amino-1-methyl-1H-pyrazol-4-yl)-[1,2,4]oxadiazol-5-yl]-N-[3-(4-oxo-3,4-dihydro-phthalazin-1-ylamino)-propyl]-propionamide, 88%, white solid; m.p. 173°° C. (dec.); $^1$H NMR (DMSO-d$_6$) δ (ppm) 11.53 (bs, 1H), 8.16–8.23 (m, 3H), 7.84–7.91 (m, 2H), 7.61 (s, 1H), 3.61 (s, 3H), 3.10–3.28 (m, 6H), 2.67 (t, 2H, J=7.0 Hz), 1.77 (m, 2H); m/z=438 (M+H).

Hydrochloride salt of 3-[3-(5-Amino-3H-imidazol-4-yl)-[1,2,4]oxadiazol-5-yl]-N-[3-(4-oxo-3,4-dihydro-phthalazin-1-ylamino)-propyl]-propionamide was synthesized in a similar fashion, but an equal volume of 4 N hydrochloric acid and methanol was employed, 46%, white solid; m.p. 170° C. (dec.); $^1$H NMR (DMSO-d$_6$) δ (ppm) 11.56 (s, 1H), 8.28 (s, 1H), 8.20 (d, 1H, J=7.5 Hz), 8.10 (m, 2H), 7.88 (t, 1H, J=7.8 Hz), 7.80 (t, 1H, J=7.8 Hz), 6.57 (s, 1H), 3.08–3.25 (m, 6H), 2.69 (t, 2H, J=7.1 Hz), 1.71–1.80 (m, 2H); m/z=424 (M+H).

3-[3-(5-Amino-3-methyl-isoxazol-4-yl)-[1,2,4]oxadiazol-5-yl]-N-[3-(4-oxo-3,4-dihydro-phthalazin-1-ylamino)-propyl]-propionamide (free base), 8%, white solid. m.p. 110–118° C.; $^1$H NMR (DMSO-d$_6$) δ (ppm) 11.55 (s, 1H), 8.19 (m, 1H), 8.07 (m, 2H), 7.84 (m, 2H), 7.39 (s, 2H), 6.56 (m, 1H), 3.24–3.11 (m, 6H), 2.67 (m, 2H), 2.27 (s, 3H), 1.76 (m, 2H); m/z=439 (M+H).

Example 67

This example illustrates a method for producing N-[3-(4-oxo-3,4-dihydro-phthalazin-1-ylamino)-cyclohexyl]-acetamide.

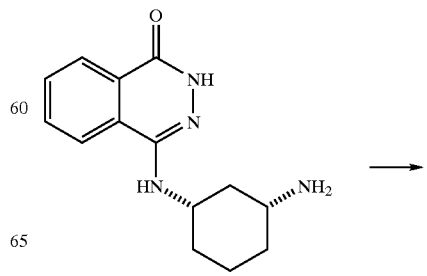

-continued

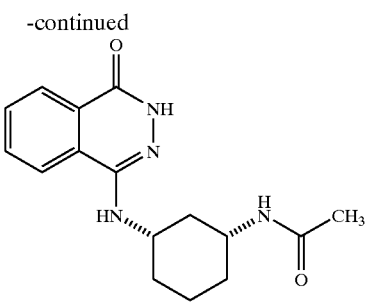

A 25-mL, one-neck, round bottomed flask equipped with a magnetic stirrer was charged with 4-(cis-3-aminocyclohexylamino)-2H-phthalazin-1-one (150 mg, 0.58 mmol) and the flask purged with nitrogen. Anhydrous dimethylformamide (4.5 mL), triethylamine (117 mg, 1.16 mmol) and acetic anhydride (71 mg, 0.70 mmol) were then added. After stirring at room temperature for 15 minutes the mixture was evaporated to dryness under reduced pressure. The resulting residue was triturated with water (20 mL) and filtered. Drying the filter cake under high vacuum for 18 h afforded in 88% yield of the title compound as a white solid. m.p. 312–315° C.; $^1$H NMR (DMSO-$d_6$) δ (ppm) 8.20 (m, 2H), 7.90–7.75 (m, 3H), 6.30 (d, 1H, J=7.4 Hz), 3.48 (m, 2H), 2.10 (m, 2H), 1.78 (s, 3H), 1.28–1.0 (m, 4H); m/z=301 (M+H).

Other compounds prepared by this method from the corresponding acid anhydrides or chlorides, including the observed yield and analytical data, are listed below. Compounds that were isolated as the hydrochloride salt, were obtained from the corresponding free base as described above.

Hydrochloride salt of N-[3-(4-Oxo-3,4-dihydro-phthalazin-1-ylamino)-cyclohexyl]-oxalamic acid ethyl ester, 62%, white solid; m.p. 178–182° C.; $^1$H NMR (CD$_3$OD) δ (ppm) 8.65 (d, 1H, J=8.1 Hz), 8.31 (d, 1H, J=7.7 Hz), 8.09 (m, 2H), 4.32 (q, 2H, J=7.1 Hz), 3.91 (m, 2H), 2.32 (bd, 1H, J=11.4 Hz), 2.12 (bs, 1H), 1.95 (m, 2H), 1.45–1.71 (m, 4H), 1.35 (t, 3H, J=7.1 Hz); m/z=359 (M+H).

N-[3-(5-Oxo-5,6-dihydro-pyrido[2,3-d]pyridazin-8-ylamino)-cyclohexyl]-acetamide, 78%, yellow solid; m.p. 258–259° C.; $^1$H NMR (CD$_3$OD/CDCl$_3$, 1:1, v/v) δ (ppm) 9.01 (dd, 1H, J=1.7, 4.6 Hz), 8.65 (dd, 1H, J=1.7, 8.1 Hz), 7.79 (dd, 1H, J=4.6, 8.1 Hz), 3.83 (m, 2H), 2.44 (bd, 1H, J=10.0 Hz), 2.19 (bd, 1H, J=12.1 Hz), 1.85–1.97 (m, 5H), 1.49 (m, 1H), 1.17–1.29 (m, 3H); m/z=302 (M+H).

N-[3-(5-Oxo-5,6-dihydro-pyrido[2,3-d]pyridazin-8-ylamino)-cyclohexyl]-propionamide, 91%, yellow solid; m.p. 206–261° C.; $^1$H NMR (CD$_3$OD/CDCl$_3$, 1:1 v/v) δ (ppm) 9.01 (dd, 1H, J=1.4, 4.5 Hz), 8.65 (dd, 1H, J=1.4, 8.1 Hz), 7.78 (dd, 1H, J=4.5, 8.1 Hz), 3.84 (m, 2H), 2.44 (bd, 1H, J=11.7 Hz), 2.16–2.23 (m, 3H), 1.92 (m, 2H), 1.50 (m, 1H), 1.21–1.28 (m, 3H), 1.14 (t, 3H, J=7.6 Hz); m/z=316 (M+H).

N-[3-(4-Oxo-3,4-dihydro-phthalazin-1-ylamino)-cyclohexyl]-acrylamide, 37%, off-white solid; m.p. 161–167° C.; $^1$H NMR (DMSO-$d_6$) δ (ppm) 8.19 (m, 2H), 7.80 (t, 1H, J=7.3 Hz), 6.20 (dd, 1H, J=17.3, 10.0 Hz), 6.07 (dd, 1H, J=17.3, 2.6 Hz), 6.31 (dd, 1H, J=9.7, 2.4 Hz), 3.10 (m, 1H), 2.23 (d, 1H, J=11.8 Hz), 1.99 (d, 1H, J=11.7 Hz), 1.80 (bs, 1H), 1.13–1.39 (m, 4H); m/z=313 (M+H).

Hydrochloride salt of N-[3-(4-Oxo-3,4-dihydro-phthalazin-1-ylamino)-cyclohexyl]-propionamide, 48%, off-white solid; m.p. 197–201° C.; $^1$H-NMR (DMSO-d6) δ (ppm) 8.25–7.70 (m, 4H), 3.60 (m, 2H), 2.18 (m, 1H), 2.10–1.90 (m, 4H), 1.77 (m, 2H), 1.45–1.05 (m, 6H), 1.01 (t, 3H, J=7.5 Hz); m/z=315 (M+H).

N-[3-(8-Oxo-7,8-dihydro-pyrido[2,3-d]pyridazin-5-ylamino)-cyclohexyl]-acetamide, 70%, yellow solid; m.p. 176° C. (dec.); $^1$H NMR (CD$_3$OD/CDCl$_3$, 1:1 v/v) δ (ppm) 9.05 (bs, 1H), 8.43 (d, 1H, J=8.3 Hz), 7.81 (dd, 1H, J=4.0, 7.9 Hz), 7.5 (s, 1H), 3.82 (m, 2H), 2.40 (bd, 1H, J=12.0 Hz), 2.16 (bd, 1H, J=11.1 Hz), 1.85–1.95 (m, 5H), 1.44–1.50 (m, 4H); m/z=302 (M+H).

N-[3-(8-Oxo-7,8-dihydro-pyrido[2,3-d]pyridazin-5-ylamino)-cyclohexyl]-propionamide, 71%, yellow solid; m.p. 182° C. (dec.); $^1$H NMR (CD$_3$OD/CDCl$_3$, 1:1, v/v) δ (ppm) 9.04 (bs, 1H), 8.47 (d, 1H, J=8.2 Hz), 7.88 (dd, 1H, J=4.3, 8.1 Hz), 3.77–3.89 (m, 2H), 2.40 (bd, 1H, J=10.8 Hz), 2.15–2.22 (m, 3H), 1.91 (m, 2H), 1.20–1.50 (m, 4H), 1.14 (t, 3H, J=7.6 Hz); m/z=316 (M+H).

Example 68

This example illustrates a method for producing 5-(3-bromopropyl)-3-(4-hydroxyphenyl)-1,2,4-oxadiazole.

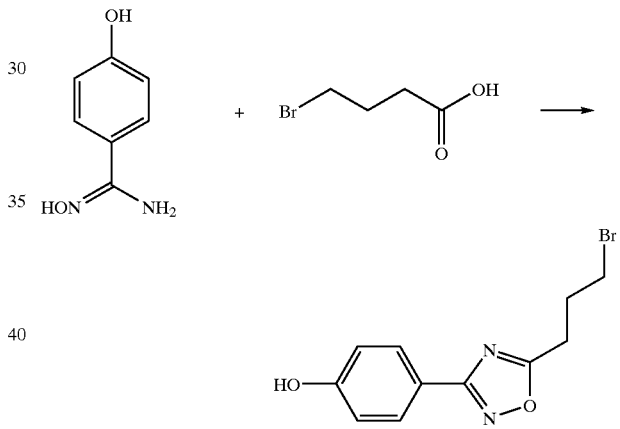

A 50-mL, one-neck, round bottomed flask equipped with a magnetic stirrer was charged with 4-hydroxybenzamidine (614 mg, 4.04 mmol) and dicyclohexylcarbodiimide (930 mg, 4.51 mmol), and the flask purged with nitrogen. Anhydrous diglyme (10 mL) and 4-bromobutyric acid (420 µL, 668 mg, 4.00 mmol) were added, and the reaction mixture was stirred for 1 h at ambient temperature and then heated in an oil bath at 90° C. for 18 h. After this time the reaction was cooled and the solvent removed under reduced pressure. The resulting solid was purified by column chromatography on silica gel, to give a 72% yield of the title compound as a yellow oil. $^1$H NMR (DMSO-$d_6$) δ 10.15 (s, 1H), 7.84 (d, 2H, J=7.7 Hz), 6.91 (d, 2H, J=7.7 Hz), 3.67 (t, 2H, J=6.7 Hz), 3.11 (t, 2H, J=7.2 Hz), 2.32 (m, 2H).

Example 69

This example illustrates a method for producing 4-(3-{3-[3-(4-hydroxyphenyl)-[1,2,4]oxadiazol-5-yl]-propylamino}-propylamino)-2H-phthalazin-1-one.

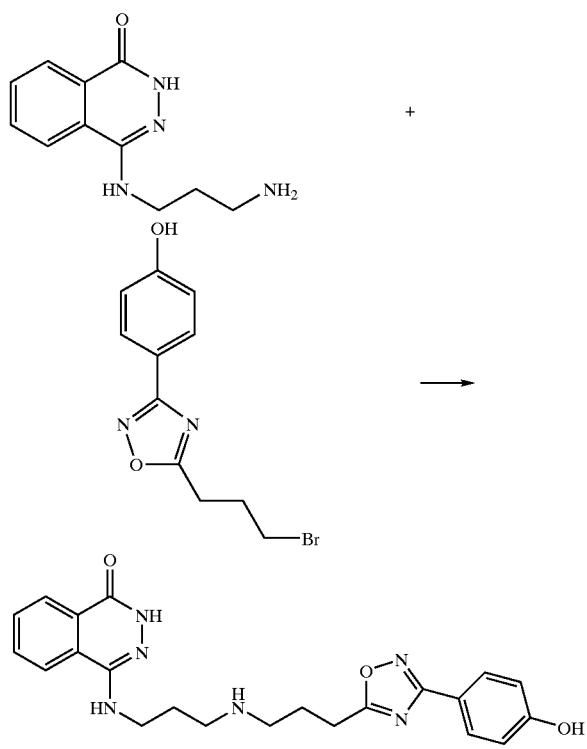

A 25-mL, one-neck, round bottomed flask equipped with a magnetic stirrer was charged with 4-(3-aminopropylamino)-2H-phthalazin-1-one (350 mg, 1.61 mmol), 5-(3-bromopropyl)-3-(4-hydroxyphenyl)-1,2,4-oxadiazole (346 mg, 1.23 mmol), dimethylformamide (2.4 mL) and triethylamine (137 mg, 1.32 mmol). The reaction mixture was stirred for 48 h at ambient temperature and then purified by direct loading on a preparative HPLC column (25 cm×2.18 cm, Luna 5 mm, C18(2) column), eluting with a gradient of 10% acetonitrile/90% 0.1% trifluoroacetic acid in water to 100% acetonitrile over 20 min at a flow rate of 15 mL/min. The fractions containing the desired product were combined and lyophilized to afford a 51% yield of a trifluoroacetate monohydrate salt of the title compound as a white solid. m.p. 164–167° C. (dec.); $^1$H NMR (CD$_3$OD) δ (ppm) 8.34 (d, 2H, J=7.2 Hz), 7.99 (d, 2H, J=7.7 Hz), 7.81–7.93 (m, 4H), 6.86 (d, 2H, J=9.0 Hz), 3.53 (t, 2H, J=6.5 Hz), 3.16–3.26 (m, 4H), 3.10 (t, 2H), J=7.3 Hz), 2.27 (m, 2H), 2.11 (m, 2H); m/z=421 (M+H); Elemental analysis: Calculated C, 52.17; H, 4.93%; N, 15.21%; Found C, 52.35%, H, 4.91%, N, 15.13%.

Example 70

This example illustrates an enzyme assay for determining the PARP inhibitory activity of compounds of Formula I.

PARP-1-enzyme was purified from HeLa cell extracts by conventional chromatography methods. The enzyme was incubated with 32P-NAD (Amersham Inc. or New England Nuclear) and sheared E. coli DNA (Sigma) in the presence of appropriate concentrations of inhibitor. Assay plates were typically incubated at room temperature for 30 minutes. Protein, including auto-ribosylated PARP, was precipitated by the addition of saturated ammonium sulfate and collected on Immobilon membranes (Millipore Inc.). Radioactivity incorporated into protein was determined by scintillation counting of the filters. Percent inhibition of enzyme activity was plotted as a function of inhibitor concentration and the concentration of inhibitor required for 50% inhibition was determined (IC$_{50}$).

A similar protocol was followed to determine inhibitory activity against PARP-2. Recombinant human PARP-2 enzyme was purified from insect cell lysates infected with baculovirus encoding expression of full length PARP-2 coupled to oligonucleotide sequences encoding epitope tags to facilitate purification.

Example 71

This example illustrates a cell based assay for determining the PARP inhibitory activity of compounds of Formula I.

The ability of PARP inhibitors to augment the cytotoxicity of the alkylating agent streptozotocin (ICN Pharmaceuticals, Cost Mesa, Calif.) was tested with the human colon carcinoma HCT116 cell line (American Type Culture Collection, Manassas, Va.). The assays were performed in 96-well plates (Corning Incorporated, Corning, N.Y.) with each assay well containing 100 µl of HCT116 cells at 10$^4$ cells/mL, 50 µl of streptozotocin, and 50 µl of PARP inhibitor or diluent (DMSO) control. Culture medium was composed of 90% RPMI 1640 (Gibco BRL/Life Technologies, Rockville, Md.), 10% fetal bovine serum (HyClone, Logan, Utah) 100 units penicillin/ml and 100 µg streptomycin/mL (Gibco BRL/Life Technologies). Briefly, appropriate concentrations of individual PARP inhibitors or DMSO control were diluted in culture medium. Aliquots of 100 µL of the individual PARP inhibitors or diluent control were placed in the second row of each of five 96-well plates and each sample was diluted by serial dilution in culture medium. Samples of 50 µL of either 0 µM, 475 µM, 950 µM, 1900 µM, or 3800 µM streptozotocin in culture medium were added to the five 96-well plates (one concentration of streptozotocin per plate). HCT116 cells grown to 50 to 80% confluency were harvested by trypsinization (Gibco BRL/Life Technologies) from a 100 mm culture plate (Corning Incorporated) and resuspended in 10 mL of culture medium. The cells were counted and diluted to 1×10$^4$ cells/mL in culture medium. An aliquot of 100 µL of the cell dilution was added to all the assay wells in the five plates. The plates were placed in a 37° C., 5% CO$_2$ incubator and incubated for four days. At the end of four days, 1 µL of [methyl-$^3$H]-thymidine (1 mCi/mL; NEN, Boston, Mass) diluted in 20 µL of culture medium was added to each assay well. The plates were incubated for an additional 24 hours at 37° C., 5% CO$_2$. The plates were frozen at −80° C. and subsequently thawed at 37° C. Labelled DNA was collected by filtration through a glass fiber filter (Packard, Meriden, Conn.) using a Filtermate 196 cell harvester (Packard). The filters were washed four times with distilled water and one time with methanol (EM Science, Gibbstown, N.J.) and allowed to dry. Incorporated $^3$H was determined using a Matrix 96 Direct Beta Counter (Packard). Relative growth inhibition was determined by comparing the amount of streptozotocin required to inhibit cell growth 90% in the absence of PARP inhibitor to the amount of streptozotocin required to induce 90% growth inhibition in the presence of PARP inhibitor. The concentration of PARP inhibitor which reduced the dose of streptozotocin required to induce 90% growth inhibition by half is termed the EC$_{tfs}$ (Effective Concentration two fold sensitization).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patenatable subject matter. All publications, patents, and patent applications cited herein are hereby incorporated by reference in their entirety for all purposes.

What is claimed is:

1. A compound of the formula:

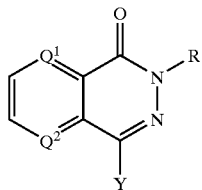

or a pharmaceutically acceptable salt thereof; wherein each of $Q^1$ and $Q^2$ is independently N or $CR^a$, where $R^a$ is hydrogen, halo, nitro, or alkyl;

R is hydrogen or alkyl; and

Y is -(alkylene)$_x$—$NR^{11}$—$NR^{12}$—$NR^{13}$—[C(=X$^3$)]$_c$—[$NR^{14}$]$_d$—[$R^{15}$]$_e$—[C(=X$^4$)]$_f$—$R^{16}$, wherein x is 0 or 1;

$R^{11}$ is selected from the group consisting of hydrogen, alkyl and optionally substituted heteroaralkyl; or $R^{11}$ together with the nitrogen atom to which it is attached to and at least a portion of $R^{12}$ form an optionally substituted heterocyclyl;

$R^{12}$ is selected from the group consisting of:
(a) alkylene,
(b) cycloalkylene,
(c) heteroalkylene,
(d) aralkylene, and
(e) arylene;

c is 0, 1, or 2;

each of d, e, and f is independently 0 or 1;

each of $X^3$ and $X^4$ is independently selected from the group consisting of O and S;

$R^{13}$ is selected from the group consisting of hydrogen, alkyl, a moiety of the formula
-(alkylene)—[C(=O)NR$^{40}$]$_y$—AR$^4$, where y is 0 or 1, $R^{40}$ is hydrogen or alkyl, and $Ar^4$ is optionally substituted aryl or optionally substituted heteroaryl; or $R^{11}$ and $R^{13}$ together with the nitrogen atoms to which they are attached to and $R^{12}$ form an optionally substituted heterocyclyl; or $R^{13}$ together with the nitrogen atom to which it is attached to and at least a portion of $R^{12}$ form an optionally substituted heterocyclyl; or $R^{13}$ and $R^{16}$ together with atoms to which they are attached to form an optionally substituted heterocyclic ring;

$R^{14}$ is hydrogen or alkyl;

$R^{15}$ is selected from the group consisting of:
(a) optionally substituted alkylene,
(b) optionally substituted heteroalkylene, and
(c) optionally substituted alkenylene, $R^{16}$ is selected from the group consisting of:
(a) hydrogen
(b) optionally substituted heteroaryl,
(c) optionally substituted aryl,
(d) optionally substituted heteroalkyl,
(e) alkoxy,
(f) optionally substituted cycloalkyl,
(e) optionally substituted alkyl,
(h) optionally substituted aryloxy,
(i) substituted aralkoxy,
(j) heterocycloalkyl,
(k) arylsulfonylalkyl,
(l) —NR$^{50}$R$^{51}$, wherein R$^{50}$ is hydrogen or alkyl and R$^{51}$ is optionally substituted aryl, optionally substituted cycloalkyl, optionally substituted aralkyl, optionally substituted heteroaryl, optionally substituted heteroaralkyl, or optionally substituted heteroalkyl,
(m) —NHPO$_3$R$^{17}$R$^{18}$, where R$^{17}$ and R$^{18}$ are alkyl,
(n) —NHSO$_2$Ar$^2$, where Ar$^2$ is substituted aryl or aralkenyl,
(o) alkylcarbamate;
(p) —SO$_2$R$^{19}$, where R$^{19}$ is optionally substituted aryl, substituted heteroaryl, optionally substituted heteroaralkyl, alkyl, aralkenyl, substituted heterocycloalkylalkyl, or substituted heteroaryl,
(q) alkylsulfonylalkyl,
(r) heterocyclyl, and
(s) a moiety of the formula -(alkylene)—[C(=O)NR$^{40}$]$_y$—Ar$^5$, where y is 0 or 1, R$^{40}$ is hydrogen or alkyl, and Ar$^5$ is optionally substituted aryl or optionally substituted heteroaryl.

2. The compound according to claim 1, wherein R is hydrogen.

3. The compound according to claim 1, wherein x is 0.

4. The compound according to claim 1, wherein $R^{12}$ is selected from the group consisting of alkylene, cycloalkylene, heteroalkylene, aralkylene, and arylene.

5. The compound according to claim 4, wherein $R^{12}$ is selected from the group consisting of propylene, 2,2-dimethylpropylene, ethylene, 1,3-cyclohexylene, 2-hydroxypropylene, 1,3-phenylene, butylene, and benz-3-ylene.

6. The compound according to claim 1, wherein $R^{13}$ together with the nitrogen atom to which it is attached to and at least a portion of $R^{12}$ form an optionally substituted heterocyclyl.

7. The compound according to claim 6, wherein $R^{10}$ together with the nitrogen atom to which it is attached to and at least a portion of $R^{12}$ form piperidinyl.

8. The compound according to claim 1, wherein $R^{11}$ together with the nitrogen atom to which it is attached to and at least a portion of $R^{12}$ form an optionally substituted heterocyclyl.

9. The compound according to claim 8, wherein $R^{11}$ together with the nitrogen atom to which it is attached to and at least a portion of $R^{12}$ form piperidinyl.

10. The compound according to claim 1, wherein $R^{11}$ and $R^{13}$ together with the nitrogen atoms to which they are attached to and $R^{12}$ form an optionally substituted heterocyclyl.

11. The compound according to claim 10, wherein $R^{11}$ and $R^{13}$ together with the nitrogen atoms to which they are attached to and $R^{12}$ form piperazinyl or diazepinyl.

12. The compound according to claim 1, wherein $R^{11}$ is hydrogen or alkyl.

13. The compound according to claim 12, wherein $R^{11}$ is hydrogen or methyl.

14. The compound according to claim 1, wherein $R^{11}$ is optionally substituted heteroaralkyl.

15. The compound according to claim 14, wherein $R^{11}$ is (4-oxo-3,4-dihydro-phthalazin-1-yl)methyl.

16. The compound according to claim 1, wherein $R^{13}$ is hydrogen or alkyl.

17. The compound according to claim 16, wherein $R^{13}$ is hydrogen or methyl.

18. The compound according to claim 1, wherein $R^{14}$ is hydrogen.

19. The compound according to claim 1, wherein c and e are 1, and d and f are 0.

20. The compound according to claim 19, wherein $R^{15}$ is ethylene or propylene.

21. The compound according to claim 19, wherein $R^{16}$ is selected from the group consisting of:
  (a) hydrogen;
  (b) optionally substituted heteroaryl,
  (c) optionally substituted aryl,
  (d) alkoxy,
  (e) optionally substituted cycloalkyl,
  (f) optionally substituted aryloxy,
  (g) substituted aralkoxy,
  (h) alkenyl,
  (i) optionally substituted aralkenyl,
  (j) optionally substituted heterocycloalkyl,
  (k) arylsulfonylalkyl,
  (l) —$NR^{50}R^{51}$, where $R^{50}$ is hydrogen or alkyl and $R^{51}$ is optionally substituted aryl, optionally substituted cycloalkyl, optionally substituted heteroaryl, heteroaralkyl, or optionally substituted aralkyl,
  (m) —$NHPO_3R^{17}R^{18}$, where $R^{17}$ and $R^{18}$ are alkyl,
  (n) —$NHSO_2Ar^2$, where $Ar^2$ is substituted aryl or aralkenyl, and
  (o) alkylcarbamate.

22. The compound according to claim 21, wherein $R^{16}$ is substituted heteroaryl.

23. The compound according to claim 22 of the formula:

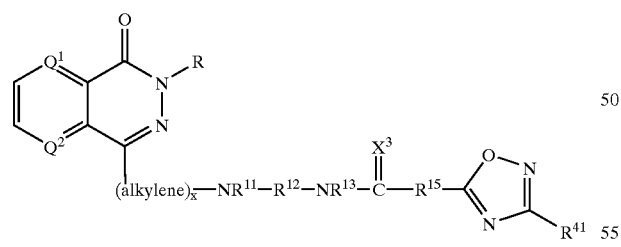

wherein
  $Q^1$, $Q^2$, R, x, $X^3$, $R^{11}$, $R^{12}$, $R^{13}$, and $R^{15}$ are as defined in claim 1; and
  $R^{41}$ is optionally substituted aryl, optionally substituted aralkyl, optionally substituted heteroaryl, optionally substituted heterocycloalkyl, or optionally substituted heterocyclylalkyl.

24. The compound according to claim 23, wherein x is 0.

25. The compound according to claim 23, wherein $R^{41}$ is selected from the group consisting of:

(a) optionally substituted pyrrolyl;
  (b) optionally substituted thienyl;
  (c) optionally substituted furyl;
  (d) optionally substituted phenyl;
  (e) optionally substituted imidazolyl;
  (f) optionally substituted thiazolyl;
  (g) optionally substituted pyrazolyl;
  (h) optionally substituted indolyl;
  (i) optionally substituted benzo[1,2,5]oxadiazolyl;
  (j) optionally substituted pyridinyl;
  (k) optionally substituted piperidinyl;
  (l) optionally substituted pyrazolo[1,5-a]pyrimidinyl;
  (m) optionally substituted pyrrolidinyl;
  (n) optionally substituted (piperidin-1-yl)methyl;
  (o) optionally substituted isoxazolyl;
  (p) optionally substituted (morpholin-4-yl)methyl;
  (q) optionally substituted benzyl; and
  (r) optionally substituted pyrazinyl.

26. The compound according to claim 1, wherein c, d, e, and f are 0.

27. The compound according to claim 26, wherein x is 0.

28. The compound of claim 26, wherein $R^{16}$ is selected from the group consisting of:
  (a) hydrogen,
  (b) optionally substituted heteroaralkyl,
  (c) —$SO_2R^{19}$, where $R^{19}$ is optionally substituted aryl, substituted heteroaryl, optionally substituted heteroaralkyl, alkyl, aralkenyl, substituted heterocycloalkylalkyl, or substituted heteroaryl,
  (d) optionally substituted cycloalkylalkyl,
  (e) alkyl,
  (f) optionally substituted heteroalkyl,
  (g) alkenyl,
  (h) optionally substituted aralkyl, and
  (i) optionally substituted heterocycloalkylalkyl.

29. The compound of claim 28, wherein $R^{16}$ is selected from the group consisting of:
  (a) —$SO_2R^{19}$, where $R^{19}$ is optionally substituted aryl, substituted heteroaryl, optionally substituted heteroaralkyl, alkyl, aralkenyl, substituted heterocycloalkylalkyl, or substituted heteroaryl,
  (b) optionally substituted cycloalkylalkyl,
  (c) optionally substituted heteroalkyl,
  (d) alkenyl,
  (e) substituted heterocycloalkylalkyl, and
  (f) optionally substituted heteroaralkyl.

30. The compound of claim 3, wherein c and d are 1.

31. The compound of claim 30, wherein $R^{16}$ is selected from the group consisting of:
  (a) optionally substituted aryl,
  (b) cycloalkylalkyl,
  (c) cycloalkyl,
  (d) heteroaryl,
  (e) heterocycloalkylalkyl,
  (f) optionally substituted aralkyl,
  (g) heteroaralkyl,
  (h) heteroalkyl,
  (i) alkyl,
  (j) alkylsulfonylalkyl, (k) heterocycloalkyl,
(l) aralkenyl,
(m) alkoxy, and
(n) alkenyl.

32. The compound of claim 30, wherein e and f are 0.

33. The compound of claim 32, wherein $R^{16}$ is selected from the group consisting of:
(a) optionally substituted aryl,
(b) cycloalkylalkyl,
(c) cycloalkyl,
(d) heteroaryl,
(e) heterocycloalkylalkyl,
(f) optionally substituted aralkyl,
(g) heteroarylalkyl,
(h) heteroalkyl,
(i) alkyl,
(j) alkylsulfonylalkyl, and
(k) heterocycloalkyl.

34. The compound of claim 30, wherein e is 0 and f is 1.

35. The compound of claim 34, wherein $R^{16}$ is selected from the group consisting of:
(a) substituted aryl,
(b) aralkenyl, and
(c) alkoxy.

36. The compound of claim 35, wherein $X^3$ is S.

37. The compound of claim 30, wherein e and f are 1.

38. The compound of claim 37, wherein $R^{16}$ is selected from the group consisting of:
(a) alkoxy, and
(b) alkenyl.

39. The compound of claim 3, wherein c and e are 1, and d and f are 0.

40. The compound of claim 39, wherein $R^{16}$ is optionally substituted heteroaryl.

41. The compound of claim 3, wherein c, e, and f are 1, and d is 0.

42. The compound of claim 41, wherein $R^{16}$ is selected from the group consisting of:
(a) $-NR^{50}R^{51}$, where $R^{50}$ is hydrogen or alkyl and $R^{51}$ is optionally substituted aryl, optionally substituted aralkyl, optionally substituted heteroaryl, or optionally substituted heteroalkyl,
(b) aryl,
(c) heteroaryl,
(d) alkoxy, and
(e) alkyl.

43. The compound of claim 42, wherein $X^3$ is O.

44. A composition comprising:
(i) a pharmaceutically acceptable excipient; and
(ii) a compound of claim 1.

45. The composition of claim 44, wherein x is 0.

46. The composition of claim 45, wherein $R^{16}$ is substituted heteroaryl.

47. The composition of claim 46, wherein $R^{16}$ is substituted [1,2,4]-oxadiazolyl.

48. The composition of claim 47, wherein $R^{16}$ is 3-(optionally substituted phenyl)-substituted [1,2,4]-oxadiazol-5-yl or 3-(optionally substituted heteroaryl)-substituted [1,2,4]-oxadiazol-5-yl.

49. The composition of claim 44, wherein said compound has $IC_{50}$ of 10 $\mu$M or less for inhibiting poly(ADP-ribose) polymerase in vitro.

50. The composition of claim 44, wherein said compound has $IC_{50}$ of 10 $\mu$M or less for inhibiting poly(ADP-ribose) polymerase in vivo.

51. A method for inhibiting PARP activity comprising the steps of administering an effective amount of a compound of claim 1.

52. A method for radiosensitizing tumor cells comprising the steps of administering an effective amount of a compound of claim 1 to the tumor cells.

53. A method for chemosensitizing tumor cells comprising the steps of administering an effective amount of a compound of claim 1 to the tumor cells.

54. A process for producing a compound of claim 1, said process comprising contacting an amine compound of the formula:

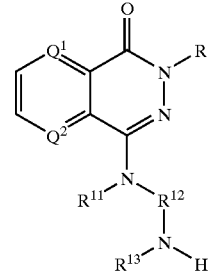

with a carboxy acid derivative of the formula W—[C(=O)]$_c$—[NR$^{14}$]$_d$—[R$^{15}$]$_e$—[C(=O)]$_f$—R$^{16}$ under conditions sufficient to produce the Compound of claim 1, wherein
$Q^1$, $Q^2$, R, $R^{11}$, $R^{12}$, $R^{13}$, $R^{14}$, $R^{15}$, $R^{16}$, c, d, e and f are as defined in claim 1; and
W is a carboxylic acid activating group or —OR$^{30}$, where $R^{30}$ is hydrogen, alkyl, cycloalkyl, aralkyl, or aryl.

55. The process of claim 54, wherein the amine compound is produced by:
(a) contacting a cyanoester aryl compound of the formula:

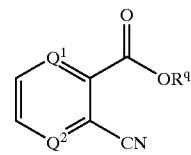

or an anhdyride of the formula:

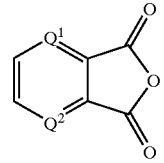

with an amine compound of the formula HR$^{11}$N—R$^{12}$—NR$^{13}$H under conditions sufficient to produce an intermediate product; and
(b) contacting the intermediate product with hydrazine under conditions sufficient to produce the amine compound, wherein
$Q^1$, $Q^2$, $R^{11}$, $R^{12}$, and $R^{13}$ are as defined in claim 1; and
$R^9$ is alkyl, aryl, cycloalkyl, or aralkyl.

* * * * *